US012686683B2

(12) United States Patent
Zhou et al.

(10) Patent No.: US 12,686,683 B2
(45) **Date of Patent: *Jul. 21, 2026**

(54) TRICYCLIC HETEROCYCLIC DERIVATIVES, COMPOSITIONS AND USES THEREOF

(71) Applicant: Danatlas Pharmaceuticals Co., Ltd., Beijing (CN)

(72) Inventors: Wenlai Zhou, Beijing (CN); Jincong Zhuo, Beijing (CN); Yao Zhang, Beijing (CN); Zhangqi Yu, Beijing (CN); Dan Yan, Beijing (CN)

(73) Assignee: DANATLAS PHARMACEUTICALS CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/308,305

(22) Filed: Aug. 24, 2025

(65) Prior Publication Data

US 2025/0388589 A1 Dec. 25, 2025

Related U.S. Application Data

(60) Division of application No. 18/499,097, filed on Oct. 31, 2023, which is a continuation of application No. PCT/CN2023/091076, filed on Apr. 27, 2023.

(30) Foreign Application Priority Data

| | | |
|---|---|---|
| Apr. 28, 2022 | (WO) | PCT/CN2022/000075 |
| Nov. 10, 2022 | (WO) | PCT/CN2022/131223 |
| Dec. 1, 2022 | (WO) | PCT/CN2022/135765 |
| Apr. 19, 2023 | (WO) | PCT/CN2023/089128 |

(51) Int. Cl.

| | |
|---|---|
| ***C07D 487/04*** | (2006.01) |
| ***A61K 45/06*** | (2006.01) |
| ***C07D 471/04*** | (2006.01) |
| ***C07D 519/00*** | (2006.01) |

(52) U.S. Cl.

CPC ............ *C07D 487/04* (2013.01); *A61K 45/06* (2013.01); *C07D 471/04* (2013.01); *C07D 519/00* (2013.01)

(58) Field of Classification Search

CPC .................................................... C07D 487/04

See application file for complete search history.

(56) References Cited

FOREIGN PATENT DOCUMENTS

| | | | |
|---|---|---|---|
| WO | 2011056739 | A1 | 5/2011 |
| WO | 2023205914 | A1 | 11/2023 |
| WO | 2024222842 | A1 | 10/2024 |

OTHER PUBLICATIONS

Wolff, Manfred E. "Burger's Medicinal Chemistry, 5ed, Part I", John Wiley & Sons, 1995, pp. 975-977.*

Banker, G.S. et al., "Modern Pharmaceutics, 3ed.", Marcel Dekker, New York, 1996, pp. 451 and 596.*

Rautio et al. "Prodrugs: design and clinical Applications" Nature Reviews Drug Discovery 2008, 7, 255-270.*

Beaumont "Design of Ester Prodrugs to Enhance Oral Absorption of Poorly Permeable Compounds: Challenges to the Discovery Scientist" Current Drug Metabolism, 2003, 4, 461-485.*

Malmborg "Predicting human exposure of active drug after oral prodrug administration, using a joined in vitro/in silico-in vivo extrapolation and physiologically-based pharmacokinetic modeling approach" Journal of Pharmacological and Toxicological Methods 67 (2013) 203-213.*

The extended European search report received in the counterpart European Application 23795524.0, mailed on Jan. 5, 2026.

The first office action issued in Russian corresponding application 202492752, mailed on Jan. 21, 2025.

* cited by examiner

*Primary Examiner* — David K O'Dell

(74) *Attorney, Agent, or Firm* — Kilpatrick Townsend & Stockton LLP

(57) ABSTRACT

The disclosure relates to tricyclic heterocyclic derivatives as shown in Formula (I), to pharmaceutical compositions comprising them, to a process for their preparation, and their use as therapeutic agents.

(I)

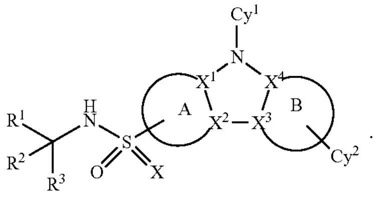

26 Claims, No Drawings

TRICYCLIC HETEROCYCLIC DERIVATIVES, COMPOSITIONS AND USES THEREOF

CROSS-REFERENCE TO RELATED APPLICATIONS

The present application is a division of U.S. patent application Ser. No. 18/499,097, filed on Oct. 31, 2023, which is a continuation of International Patent Application No. PCT/CN2023/091076, filed on Apr. 27, 2023, the contents of which are hereby incorporated by reference.

TECHNICAL FIELD

The present disclosure relates to tricyclic heterocyclic derivatives as inhibitor of PARG. The present disclosure also relates to methods for preparing the tricyclic heterocyclic derivatives, pharmaceutical compositions, and their uses in the treatment of diseases related to the activity of PARG including, e.g., cancers and other diseases.

BACKGROUND

DNA damage repair (DDR) is a collection of processes by which a cell identifies and corrects damage to the DNA molecules that encode its genome. But once a cancer has formed, DNA repair pathways become a double-edged sword because they promote the repair and survival of cancer cells in response to chemotherapies and radiotherapies. As a result, cancers with compromised DNA repair are susceptible to DNA damage and depend on complementary repair pathways which can be exploited therapeutically.

An aberrant DDR often can sensitize cancer cells to specific types of DNA damage, thus defective DDR can be developed into targeted cancer therapies. Targeting DNA repair deficiencies has become a proven and effective strategy in cancer treatment. For example, the success of poly (ADP-ribose) polymerase (PARP) inhibitors in treating BRCA-deficient breast, ovarian, prostate and pancreatic cancers (Audeh M W et al., 2010).

Poly(ADP-ribosyl)ation (PARylation) is a unique post-translational modification for maintaining genome stability through different molecular pathways, especially DNA repair (Kraus W L et al., 2015). The binding of PARP to the break and the rapid synthesis of poly ADP-ribose (PAR) on PARP itself is one of the earliest events during single strand DNA repair. Current PARP inhibitors primarily suppress PARP1 and PARP2 enzymatic activities, which inhibits PARP1/2-dependent DNA repair. Recently, clinical resistance to PARP inhibitors has been described (Drost and Jonkers, 2014) (Barber L J et al., 2013) (Tobalina L et al., 2021) and therefore alternative inhibitors targeting the DNA damage repair machinery are required.

PARylation is a transient posttranslational modification and is rapidly degraded by the enzyme PAR glycohydrolase (PARG) (Barkauskaite E et al., 2015). When PARP is bound to PAR, its catalytic activity is reduced and therefore PARG activity helps to restore PARP to its catalytically active form (Curtin and Szabo, 2013). Similar to PARPs, PARG also facilitates both DNA double-strand break (DSB) and single-strand break (SSB) repair (Mortusewicz O et al., 2011). Apart its primary role in DNA repair, PARG impacts PAR signaling in RNA splicing, transcriptional and epigenetic regulation (Ji and Tulin 2009) (Le May N et al., 2012) (Dahl M et al. 2014) (Guastafierro T et al., 2013) (Caiafa P et al., 2009). Some evidence suggests that PARG depletion inhibits SSB repair and reduces survival of BRCA2-deficient cells (Fathers C et al., 2012). However, other tumor mutations may give rise to deficiencies in DSB repair mechanisms (so-called "BRCA-ness") may also cause sensitizing tumor cells to PARG inhibition.

However, as deficiency in PARG doesn't sensitize to all agents (e.g. gemcitabine, camptothecin), it indicates that a specificity for PARG function with certain pathways of DDR and chemo- and radiotherapies (Fujihara H et al., 2009) (Shirai H et al., 2013) (Zhou Y et al., 2011). In humans, PARG knock-down or depletion can sensitize lung, cervical and pancreatic cancer cells to irradiation or experimental DNA damaging agents (e.g. hydrogen peroxide, Methylmethanesulfonate) (Ame J C et al., 2009) (Nakadate Y et al., 2013) (Shirai H et al., 2013).

Some studies suggest that PARG inhibition may provide a therapeutic advantage in PARP inhibitor resistant cells (Fisher A E et al., 2007). Furthermore, depletion of PARG has been reported to lead to a markedly different gene expression pattern to that of PARP in breast cancer cells (Frizzell K M et al., 2009). Ovarian cancer cells respond differently to PARP inhibitor and PARG inhibitor and sensitivity to the latter is due to persistent fork stalling and replication catastrophe (Pillay N et al., 2019) (Coulson-Gilmer C et al., 2021).

Recent research has also shown a mechanistic differentiation between PARG and PARP inhibition. Following a genotoxic stimulus depletion of PARG, in contrast to PARP depletion, leads to a drop in NAD levels and causes to lung cancer cell death that may be as a result of energy failure (Erdelyi K et al., 2009). PARG inhibition can also sequester NAD+ to potentiate the metabolic lethality of alkylating chemotherapy in IDH mutant tumor cells (Nagashima H et al., 2020).

Cell permeable PARG inhibitors have been limited to compounds such as Tannic acid or Gallotannin or PDD00017273 which have low specificity for PARG and limited bioavailability (Sun Y et al., 2012) (Fathers C et al., 2012) (Blenn C et al., 2011) (James D I et al., 2016).

An object of this disclosure is to provide cell permeable inhibitors of PARG.

SUMMARY

The present disclosure relates to, inter alia, compounds of Formula (I), (I)

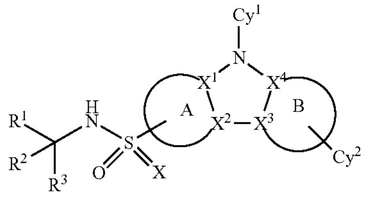

or a pharmaceutically acceptable salt, stereoisomer, solvate, N-oxide, tautomeric, isotopic variants, prodrugs or deuterated compound thereof; wherein the variables are as defined below.

In another aspect, provided herein is a pharmaceutical composition comprising a compound of formula (I), or pharmaceutically acceptable salt, stereoisomer, solvate, N-oxide, tautomeric, isotopic variants, prodrugs or deuterated compound thereof and at least one pharmaceutically acceptable carrier.

In another aspect, provided herein is a method of inhibiting PARG comprising:

contacting a PARG with a compound of formula (I), or pharmaceutically acceptable salt, stereoisomer, solvate, N-oxide, tautomeric, isotopic variants, prodrugs or deuterated compound thereof.

In another aspect, provided herein is a method of treating cancers and other diseases comprising administering to a patient a therapeutically effective amount of a compound of formula (I), or pharmaceutically acceptable salt, stereoisomer, solvate, N-oxide, tautomeric, isotopic variants, prodrugs or deuterated compound thereof.

The details of one or more embodiments are set forth in the description below. Other features, objects, and advantages will be apparent from the description and from the claims.

DETAILED DESCRIPTION

The present disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

Before the present disclosure is further described, it is to be understood that the disclosure is not limited to the particular embodiments set forth herein, and it is also to be understood that the terminology used herein is for the purpose of describing particular embodiments only, and is not intended to be limiting.

The present disclosure provides, inter alia, a compound of formula (I):

(I)

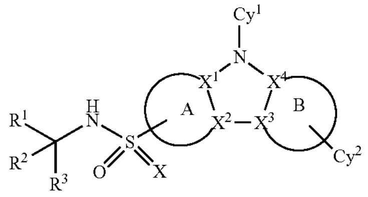

or a pharmaceutically acceptable salt, stereoisomer, solvate, N-oxide, tautomeric, isotopic variants, prodrugs or deuterated compound thereof, wherein:

X is O or $NR^5$;

$X^1$ is C;

$X^2$ is N or C;

$X^3$ is N or C;

$X^4$ is C;

and

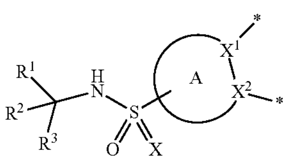

is

-continued

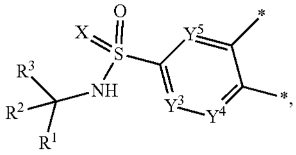

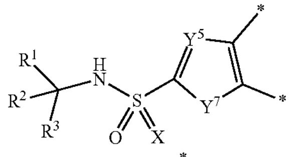

or

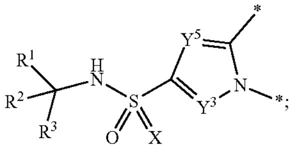

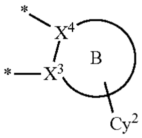

is

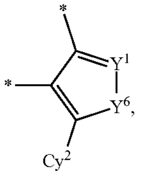

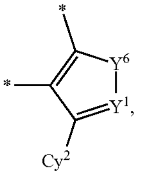

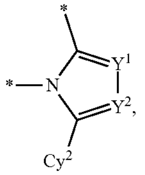

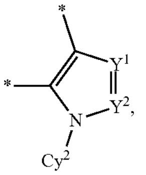

or

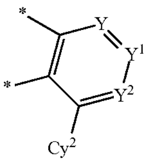

Y is N or $CR^{15}$;

$Y^1$ is N or $CR^6$;

$Y^2$ is N or $CR^7$;

$Y^3$ is N or $CR^8$;

$Y^4$ is N or $CR^4$;

$Y^5$ is N or $CR^4$;

$Y^6$ is S, O or $NR^{14}$.

$Y^7$ is S, O or $NR^{16}$;

$Cy^1$ is 5-10 membered heteroaryl optionally substituted by 1, 2, 3, 4, or 5 substituents independently selected from $R^9$;

$Cy^2$ is selected from $C_6$-$C_{10}$ aryl, $C_3$-$C_{10}$ cycloalkyl, 5-10 membered heteroaryl, or 4-14 membered heterocycloalkyl; wherein, the $C_6$-$C_{10}$ aryl, $C_3$-$C_{10}$ cycloalkyl, 5-10 membered heteroaryl, or 4-14 membered heterocycloalkyl is optionally substituted by 1, 2, 3, 4, or 5 substituents independently selected from $R^{10}$;

$R^1$, $R^2$ and $R^3$ are each independently selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl is optionally substituted by 1-5 substituents independently selected from D, halo, CN, OH, $C_1$-$C_6$ alkyl, $C_1$-$C_6$ haloalkyl, —O—$C_1$-$C_6$ alkyl, —$OC_1$-$C_6$ haloalkyl;

or $R^2$ and $R^3$ together with the carbon atom to which they are attached form $C_3$-$C_7$ cycloalkyl, or 4-7 membered heterocycloalkyl; wherein, the $C_3$-$C_7$ cycloalkyl, 4-7 membered heterocycloalkyl is optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —$OC_1$-$C_6$ haloalkyl;

$R^4$ is selected from H, D, halo, OH, CN, $NO_2$, $SF_5$, $C_1$-$C_3$ alkyl, $C_2$-$C_3$ alkenyl, $C_2$-$C_3$ alkynyl, —O—$C_1$-$C_3$ alkyl, or $NR^CR^D$; wherein, the $C_1$-$C_3$ alkyl, $C_2$-$C_3$ alkenyl, $C_2$-$C_3$ alkynyl is optionally substituted with halogen or CN;

$R^5$ is selected from H, D, CN, $OR^B$, or $C_1$-$C_4$ alkyl optionally substituted with at least one of $R^{5A}$; wherein, each $R^{5A}$ is independently selected from D, F, Cl, CN, $NH_2$, OH, —O—$C_1$-$C_6$ alkyl, —$OC_1$-$C_6$ haloalkyl, optionally substituted $C_3$-$C_7$ cycloalkyl, or optionally substituted 4-7 membered heterocycloalkyl; wherein, the optionally substituted substituent is selected from D, halo, CN, OH, $C_1$-$C_4$ alkyl, $C_1$-$C_4$haloalkyl, —O—$C_1$-$C_4$ alkyl, —$OC_1$-$C_4$haloalkyl;

or $R^1$ and $R^5$ together with the atoms to which they are attached form 5-7 membered partially saturated heterocycloalkyl optionally substituted by 1, 2, 3 or 4 substituents independently selected from D, halogen, CN, $CF_3$, $NO_2$, oxo, OH, $C_1$-$C_6$ alkyl, $C_1$-$C_6$ haloalkyl, —O—$C_1$-$C_6$ alkyl, —$OC_1$-$C_6$ haloalkyl;

$R^6$, $R^7$ and $R^{15}$ are each independently selected from H, D, halogen, CN, $NO_2$, $C_1$-$C_6$ alkyl, $C_1$-$C_6$ haloalkyl, $C_2$-$C_6$ alkenyl, $C_2$-$C_6$ alkynyl, $OR^A$, $SR^A$, $SF_5$, $NHOR^A$, $C(O)OR^A$, $C(O)R^B$, $C(O)NR^CR^D$, $OC(O)NR^CR^D$, $NR^CR^D$, $NR^CC(O)R^B$, $NR^CC(O)NR^CR^D$, $NR^CC(O)OR^A$, $NR^CS(O)_2R^B$, $B(OR^C)(OR^D)$, $C(=NR^C)NR^CR^D$, $NR^DC(=NR^C)NR^CR^D$, $NR^DC(=NR^C)R^B$, $P(O)R^ER^F$, $P(O)OR^EOR^F$, $OP(O)OR^EOR^F$, $S(O)(=NR^B)R^B$, $S(O)R^B$, $S(O)NR^CR^D$, $S(O)_2R^B$, $S(O)_2NR^CR^D$, $NR^CS(O)_2NR^CR^D$, or $NR^CS(O)(=NR^B)R^B$; wherein, the $C_1$-$C_6$ alkyl, $C_2$-$C_6$ alkenyl, or $C_2$-$C_6$ alkynyl is optionally substituted with 1, 2, or 3 substituents independently selected from $R^{11}$;

$R^8$ is selected from H, D, CN, halo, OH, $NH_2$, $C_1$-$C_3$ alkyl, $C_1$-$C_3$ haloalkyl, —O—$C_1$-$C_3$ alkyl, —$OC_1$-$C_3$ haloalkyl, $C_1$-$C_3$ cyanoalkyl, or $SF_5$;

each $R^9$ is independently selected from H, D, halo, $C_1$-$C_6$ alkyl, $C_2$-$C_6$ alkenyl, $C_2$-$C_6$ alkynyl, $C_1$-$C_6$ haloalkyl, $OC_1$-$C_6$ alkyl, $OC_1$-$C_6$ haloalkyl, $OC_3$-$C_7$ cycloalkyl, $C_3$-$C_7$ cycloalkyl, CN, $NO_2$, $N_3$, or $SF_5$; wherein, the $C_1$-$C_6$ alkyl, $C_2$-$C_6$ alkenyl, $C_2$-$C_6$ alkynyl or $C_3$-$C_7$ cycloalkyl is optionally substituted with 1, 2, or 3 substituents independently selected from $R^{11}$;

each $R^{10}$ is independently selected from H, D, halo, CN, $NO_2$, $N_3$, oxo, $C_1$-$C_6$ alkyl, $C_2$-$C_6$ alkenyl, $C_2$-$C_6$ alkynyl, $OR^A$, $SR^A$, $SF_5$, $NR^COR^A$, $C(O)R^B$, $C(=S)R^B$, $C(O)NR^CR^D$, $C(O)N(R^C)OR^A$, $C(O)OR^A$, $OC(O)R^B$, $OC(O)NR^CR^D$, $NR^CR^D$, $NR^CC(O)R^D$, $NR^CC(O)NR^CR^D$, $NR^CC(O)OR^A$, $B(OR^C)(OR^D)$, $C(=NR^C)NR^CR^D$, $NR^DC(=NR^C)NR^CR^D$, $NR^DC(=NR^C)R^B$, $SiR^GR^HR^I$, $P(O)R^ER^F$, $P(O)OR^EOR^F$, $OP(O)OR^EOR^F$, $S(O)(=NR^B)R^B$, $S(O)R^B$, $S(O)NR^CR^D$, $S(O)_2R^B$, $NR^CS(O)_2R^B$, $S(O)_2NR^CR^D$, $NR^CS(O)_2NR^CR^D$, $NR^CS(O)(=NR^B)R^B$, $Cy^3$, $C_1$-$C_6$ alkyl-$Cy^3$, $OCy^3$, or O—$C_1$-$C_6$ alkyl-$Cy^3$; wherein, the $C_1$-$C_6$ alkyl, $C_2$-$C_6$ alkenyl, $C_2$-$C_6$ alkynyl is optionally substituted with 1, 2, 3, 4 or 5 substituents independently selected from $R^{11}$; or two $R^{10}$, together with the atom(s) to which they are attached form oxo, $C_3$-$C_{10}$ cycloalkyl or 4-10 membered heterocycloalkyl; wherein, the $C_3$-$C_{10}$ cycloalkyl or 4-10 membered heterocycloalkyl optionally substituted by 1, 2, or 3 substituents independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$-cyanoalkyl, CN, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $OP(O)OR^eOR^f$, $P(O)OR^eOR^f$, $S(O)(=NR^b)R^b$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^eS(O)(=NR^b)R^b$, $Cy^4$; wherein, $Cy^4$ is $C_6$-$C_{10}$ aryl, $C_3$-$C_{10}$ cycloalkyl, 5-10 membered heteroaryl, and 4-10 membered heterocycloalkyl; wherein the $C_6$-$C_{10}$ aryl, $C_3$-$C_{10}$ cycloalkyl, 5-10 membered heteroaryl, 4-10 membered heterocycloalkyl is optionally substituted by 1, 2, 3 or 4 substituents independently selected from D, halo, CN, $NO_2$, OH, oxo, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$;

$Cy^3$ is independently selected from $C_6$-$C_{10}$ aryl, $C_3$-$C_{10}$ cycloalkyl, 5-10 membered heteroaryl, or 4-10 membered heterocycloalkyl; wherein the $C_6$-$C_{10}$ aryl, $C_3$-$C_{10}$ cycloalkyl, 5-10 membered heteroaryl, 4-10 membered heterocycloalkyl can be unsubstituted or substituted with 1, 2, 3, 4 or 5 substituents independently selected from $R^{12}$;

each $R^{11}$ is independently selected from H, D, halo, CN, $NO_2$, $N_3$, $C_1$-$C_6$ alkyl, $C_2$-$C_6$ alkenyl, $C_2$-$C_6$ alkynyl, $C_1$-$C_6$ haloalkyl, $OC_1$-$C_6$ alkylOH, $OC_1$-$C_6$ alkyl-O—$C_1$-$C_6$ alkyl, $OR^{a1}$, $SR^{a1}$, $SF_5$, $NHOR^{a1}$, $C(O)R^{b1}$, $C(O)NR^{c1}R^{d1}$, $C(O)OR^{a1}$, $OC(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b1}$, $P(O)OR^{e1}OR^{f1}$, $OP(O)OR^{e1}OR^{f1}$, $S(O)(=NR^{b1})R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl, wherein, the $C_6$-$C_{10}$ aryl, $C_3$-$C_{10}$ cycloalkyl, 5-10 membered heteroaryl, 4-10 membered heterocycloalkyl can be unsubstituted or substituted by 1, 2, 3, 4 or 5 substituents independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$;

each $R^{12}$ is independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$ alkylOH, $C_1$-$C_6$ alkyl-O—$C_1$-$C_6$ alkyl, CN, $NO_2$, $N_3$, $OR^{a1}$, $SR^{a1}$, $SF_5$, $NHOR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b1}$, $P(O)R^{e1}R^{f1}$, $P(O)OR^{e1}OR^{f1}$, $OP(O)OR^{e1}OR^{f1}$, $S(O)(=NR^{b1})R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl; wherein, the $C_6$-$C_{10}$ aryl, $C_3$-$C_{10}$ cycloalkyl, 5-10 membered heteroaryl, 4-10 membered heterocycloalkyl can be unsubstituted or substituted by 1, 2, 3, 4 or 5 substituents independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$;

each $R^{13}$ is independently selected from H, D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_1$-$C_4$ alkylOH, $OC_1$-$C_4$ alkyl-O—$C_1$-$C_4$ alkyl, $OC_1$-$C_4$ alkyl-O—$C_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, optionally substituted $C_3$-$C_7$ cycloalkyl, or optionally substituted 4-7 membered heterocycloalkyl, $SF_5$, $OR^a$, $SR^a$, $C(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$; wherein, the optionally substituted substituent is selected from D, halo, CN, OH, $C_1$-$C_4$ alkyl, $C_1$-$C_4$haloalkyl, —O—$C_1$-$C_4$ alkyl, —$OC_1$-$C_4$haloalkyl;

$R^{14}$ and $R^{16}$ are each selected from H, D, $C_1$-$C_6$ alkyl, $C_1$-$C_6$ haloalkyl, $C_2$-$C_6$ alkenyl, $C_2$-$C_6$ alkynyl, $C_1$-$C_6$ alkyl-OH, $C_1$-$C_6$ alkyl-CN, $C_1$-$C_6$ alkyl-O—$C_1$-$C_6$ alkyl;

$R^A$ is independently selected from H, D, $C_1$-$C_6$ alkyl, $C_2$-$C_4$ alkenyl, $C_2$-$C_4$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein, the $C_1$-$C_6$ alkyl, $C_2$-$C_4$ alkenyl, $C_2$-$C_4$ alkynyl, $C_3$-$C_{10}$ cycloalkyl, 4-10 membered heterocyclalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $NR^cS(O)(=NR^b)R^b$;

$R^B$ is independently selected from H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from $R^{13}$;

$R^C$ and $R^D$ are each independently selected from H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl is optionally substituted with 1, 2, 3, 4 or 5 substituents independently selected from D, OH, CN, halo, oxo, $C_1$-$C_4$ alkyl, $C_1$-$C_4$haloalkyl, $C_1$-$C_4$ cyanoalkyl, $OC_1$-$C_4$ alkyl, $OC_1$-$C_4$haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, $C_1$-$C_4$ alkyl-O—$C_1$-$C_4$ alkyl, $C_1$-$C_4$alkyl-O—$C_1$-$C_4$haloalkyl, $SF_5$, $OC(O)NR^cR^d$, $NR^cR^d$, $NR^cC(O)R^b$, $S(O)NR^cR^d$, $S(O)_2R^b$, $NR^eS(O)_2R^b$, $S(O)_2NR^cR^d$, $NR^eS(O)_2NR^cR^d$, or $B(OR^c)(OR^d)$;

or $R^C$ and $R^D$ together with the N atom to which they are attached form a 4-7 membered heterocycloalkyl optionally substituted with 1, 2, 3, 4 or 5 substituents independently selected from D, OH, oxo, CN, —$NH_2$, —$NH(C_1$-$C_4$ alkyl), —$N(C_1$-$C_4$ alkyl$)_2$, halo, or $C_1$-$C_4$ alkyl, $C_1$-$C_4$ haloalkyl, $C_1$-$C_4$ cyanoalkyl, $OC_1$-$C_4$ alkyl, or $OC_1$-$C_4$haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$haloalkyl;

$R^a$ and $R^{a1}$ are each independently selected from H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl is optionally substituted with 1, 2, or 3 substituents independently selected from D, OH, CN, —$NH_2$, —$NH(C_1$-$C_4$ alkyl), —$N(C_1$-$C_4$ alkyl$)_2$, halo, $C_1$-$C_4$ alkyl, $C_1$-$C_4$ alkoxy, $C_1$-$C_4$haloalkyl, or $C_1$-$C_4$haloalkoxy;

$R^b$ and $R^{b1}$ are each independently selected from H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, arylalkyl, heteroarylalkyl, cycloalkylalkyl, or heterocycloalkylalkyl; wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, arylalkyl, heteroarylalkyl, cycloalkylalkyl, or heterocycloalkylalkyl is optionally substituted with 1, 2, or 3 substituents independently selected from D, OH, CN, —$NH_2$, —$NH(C_1$-$C_4$ alkyl), —$N(C_1$-$C_4$ alkyl$)_2$, halo, $C_1$-$C_4$ alkyl, $C_1$-$C_4$ alkoxy, $C_1$-$C_4$haloalkyl, $C_1$-$C_4$haloalkoxy, $C_6$-$C_{10}$ aryl, $C_3$-$C_{10}$ cycloalkyl, 5-10 membered heteroaryl, or 4-10 membered heterocycloalkyl;

$R^c$ and $R^d$ are each independently selected from H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl; wherein the $C_{1-4}$ alkyl, $C_{2-4}$ alkenyl, $C_{2-4}$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl is optionally substituted with 1, 2, or 3 substituents independently selected from D, OH, CN, —$NH_2$, —$NH(C_1$-$C_4$ alkyl), —$N(C_1$-$C_4$ alkyl$)_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkyl-O—$C_1$-$C_4$ alkyl, and $C_1$-$C_4$ alkyl-O—$C_1$-$C_4$ alkyl-O—;

or $R^c$ and $R^d$ together with the N atom to which they are attached form a 4-7 membered heterocycloalkyl optionally substituted with 1, 2, or 3 substituents independently selected from D, OH, CN, —$NH_2$, —$NH(C_1$-$C_4$ alkyl), —$N(C_1$-$C_4$ alkyl$)_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkoxy-$C_1$-$C_4$ alkyl, and $C_1$-$C_4$ alkoxy-$C_1$-$C_4$ alkoxy;

$R^{c1}$ and $R^{d1}$ are each independently selected from H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl or heterocycloalkylalkyl; wherein the $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl or heterocycloalkylalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, or $C_1$-$C_4$haloalkoxy;

or $R^{c1}$ and $R^{d1}$ together with the N atom to which they are attached form a 4-7 membered heterocycloalkyl optionally substituted with 1, 2, or 3 substituents independently selected from D, OH, CN, —$NH_2$, —NH ($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, and $C_{1-4}$haloalkoxy;

$R^E$, $R^e$ and $R^{e1}$ are each independently selected from H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 3-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl;

$R^F$, $R^f$ and $R^{f1}$ are each independently selected from H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl;

$R^G$, $R^H$ and $R^I$ are each independently selected from $C_1$-$C_4$ alkyl or phenyl.

In some embodiments, the compounds of Formula (I) are represented by compounds of Formula (Ia), (Ib), (Ic), (Id), (Ie), (If), (Ig), (Ih), (Ii), (Ij), (Ik), (Il), (Im), (In), (Io), (Ip) or (Iq):

(Ia)

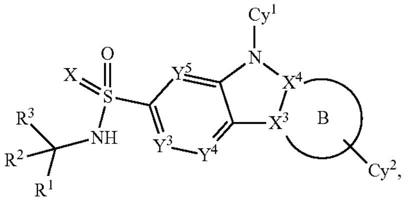

(Ib)

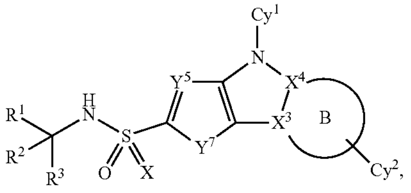

(Ic)

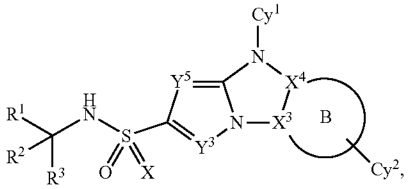

-continued (Id)

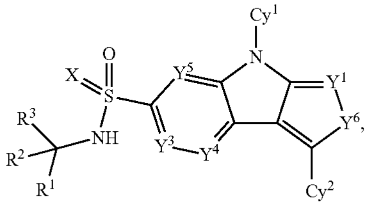

(Ie)

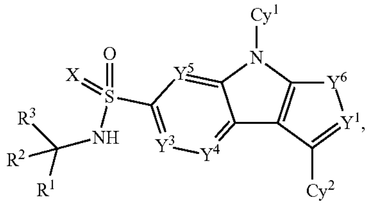

(If)

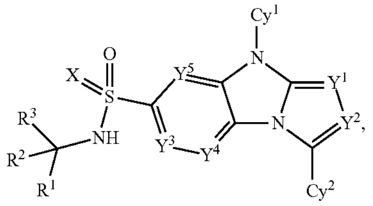

(Ig)

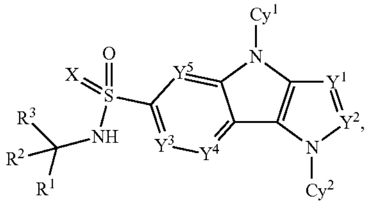

(Ih)

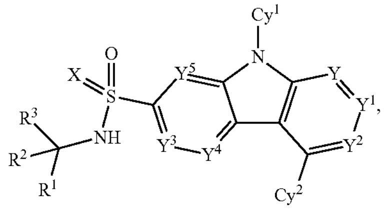

(Ii)

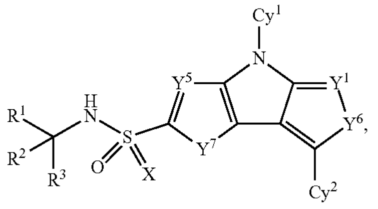

(Ij)

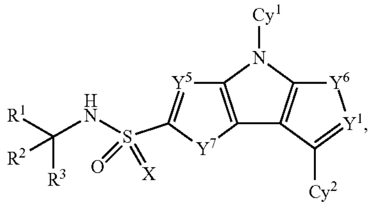

-continued (Ik)

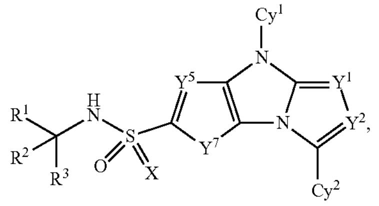

(Il)

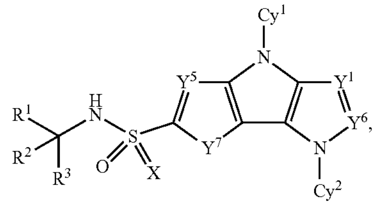

(Im)

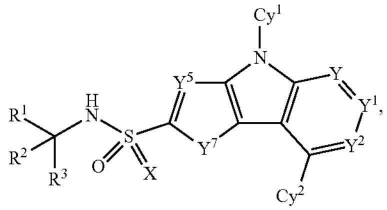

(In)

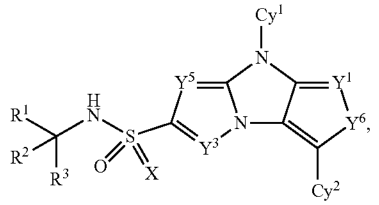

(Io)

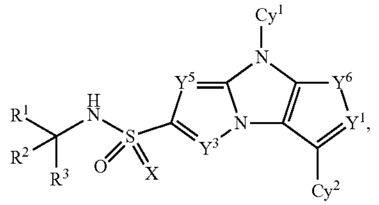

(Ip)

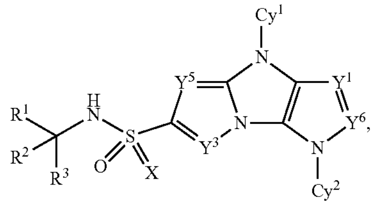

(Iq)

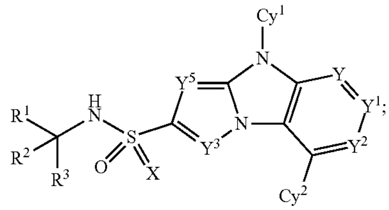

or a pharmaceutically acceptable salt, stereoisomer, solvate, N-oxide, tautomeric, isotopic variants, prodrugs or deuterated compound thereof;

wherein, $R^1$, $R^2$, $R^3$, X, $X^1$, $X^2$, $X^3$, $X^4$, Y, $Y^1$, $Y^2$, $Y^3$, $Y^4$, $Y^5$, $Y^6$, $Y^7$, $Cy^1$, and $Cy^2$ are defined with respect to Formula (I).

In some embodiments, the compounds of Formula (I) are represented by compounds of Formula (Ia), (Id), (Ie), (If), (Ig), (Ih):

(Ia)

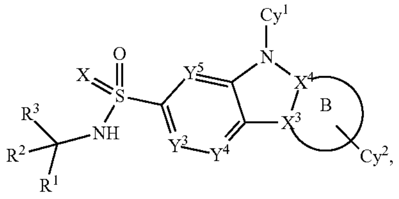

(Id)

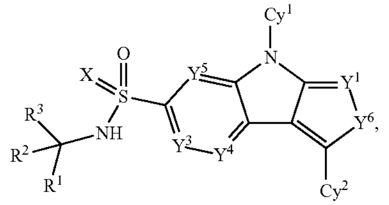

(Ie)

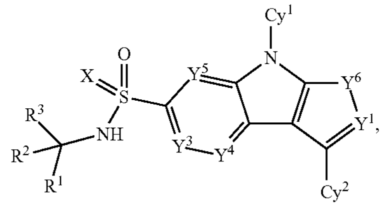

(If)

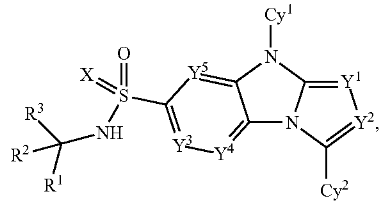

(Ig)

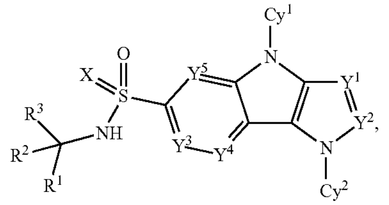

(Ih)

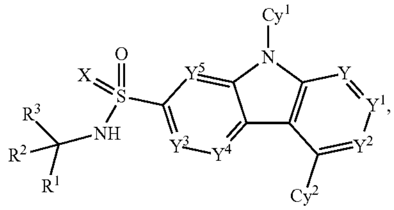

or a pharmaceutically acceptable salt, stereoisomer, solvate, N-oxide, tautomeric, isotopic variants, prodrugs or deuterated compound thereof;

wherein, $R^1$, $R^2$, $R^3$, X, $X^3$, $X^4$, Y, $Y^1$, $Y^2$, $Y^3$, $Y^4$, $Y^5$, $Y^6$, $Cy^1$, and $Cy^2$ are defined with respect to Formula (I).

In some embodiments, the compounds of Formula (I) are represented by compounds of Formula (Ib), (Ii), (Ij), (Ik), (Il), (Im):

(Ib)

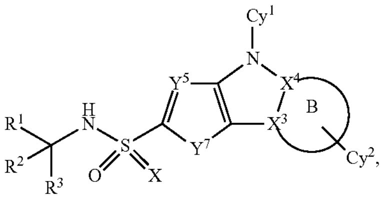

(Ii)

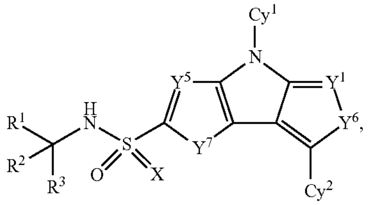

(Ij)

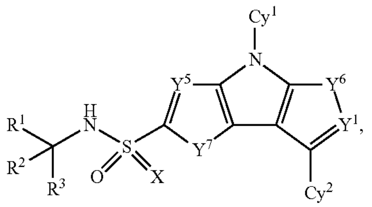

(Ik)

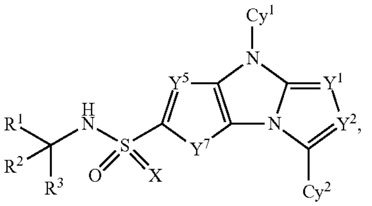

(Il)

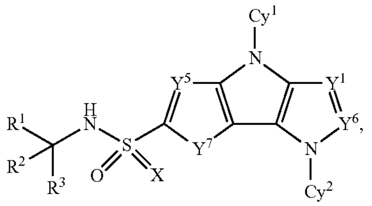

(Im)

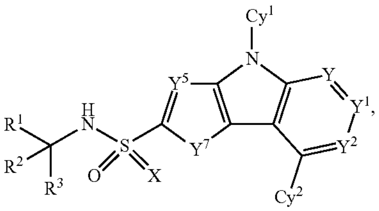

or a pharmaceutically acceptable salt, stereoisomer, solvate, N-oxide, tautomeric, isotopic variants, prodrugs or deuterated compound thereof;

wherein, $R^1$, $R^2$, $R^3$, X, $X^3$, $X^4$, Y, $Y^1$, $Y^2$, $Y^5$, $Y^6$, $Y^7$, $Cy^1$, and $Cy^2$ are defined with respect to Formula (I).

In some embodiments, the compounds of Formula (I) are represented by compounds of Formula (Ic), (In), (Io), (Ip) or (Iq):

(Ic)

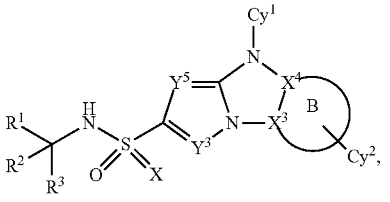

(In)

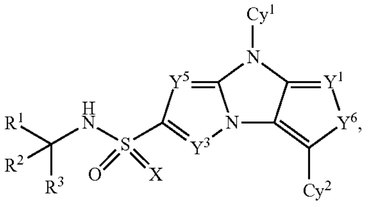

(Io)

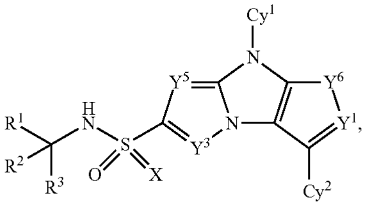

(Ip)

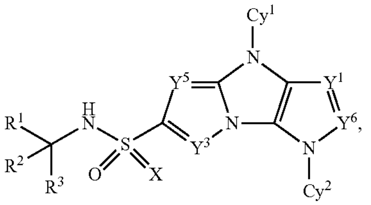

(Iq)

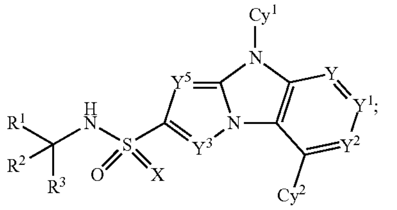

or a pharmaceutically acceptable salt, stereoisomer, solvate, N-oxide, tautomeric, isotopic variants, prodrugs or deuterated compound thereof;

wherein, $R^1$, $R^2$, $R^3$, X, $X^3$, $X^4$, Y, $Y^1$, $Y^2$, $Y^3$, $Y^5$, $Y^6$, $Cy^1$, and $Cy^2$ are defined with respect to Formula (I).

In some embodiments, $Y^3$ is N, $Y^4$ is $CR^4$, and $Y^5$ is $CR^4$.

In some embodiments, $Y^3$ is N, $Y^4$ is N, and $Y^5$ is $CR^4$.

In some embodiments, $Y^3$ is N, $Y^4$ is N, and $Y^5$ is N.

In some embodiments, $Y^3$ is N, $Y^4$ is $CR^4$, and $Y^5$ is N.

In some embodiments, $Y^3$ is $CR^4$, $Y^4$ is $CR^4$, and $Y^5$ is $CR^4$.

In some embodiments, $Y^3$ is $CR^4$, $Y^4$ is N, and $Y^5$ is $CR^4$.

In some embodiments, $Y^3$ is $CR^4$, $Y^4$ is N, and $Y^5$ is N.

In some embodiments, $Y^3$ is $CR^4$, $Y^4$ is $CR^4$, and $Y^5$ is N.

In some embodiments, $Y^5$ is N, and $Y^7$ is S.

In some embodiments, $Y^5$ is N, and $Y^7$ is O.

In some embodiments, $Y^5$ is N, and $Y^7$ is $NR^{16}$.

In some embodiments, $Y^5$ is $CR^4$, and $Y^7$ is S.

In some embodiments, $Y^5$ is $CR^4$, and $Y^7$ is O.

In some embodiments, $Y^5$ is $CR^4$, and $Y^7$ is $NR^{16}$.

In some embodiments, $Y^3$ is N, and $Y^5$ is N.

In some embodiments, $Y^3$ is N, and $Y^5$ is $CR^4$.

In some embodiments, $Y^3$ is $CR^8$, and $Y^5$ is N.

In some embodiments, $Y^3$ is $CR^8$, and $Y^5$ is $CR^4$.

In some embodiments, $Y^1$ is N, and $Y^6$ is S.

In some embodiments, $Y^1$ is N, and $Y^6$ is O.

In some embodiments, $Y^1$ is N, and $Y^6$ is $NR^{14}$.

In some embodiments, $Y^1$ is $CR^6$, and $Y^6$ is S.

In some embodiments, $Y^1$ is $CR^6$, and $Y^6$ is O.

In some embodiments, $Y^1$ is $CR^6$, and $Y^6$ is $NR^{14}$.

In some embodiments, $Y^1$ is N, and $Y^2$ is N.

In some embodiments, $Y^1$ is N, and $Y^2$ is $CR^7$.

In some embodiments, $Y^1$ is $CR^6$, and $Y^2$ is N.

In some embodiments, $Y^1$ is $CR^6$, and $Y^2$ is $CR^7$.

In some embodiments, Y is N, $Y^1$ is $CR^6$, and $Y^2$ is $CR^7$.

In some embodiments, Y is N, $Y^1$ is $CR^6$, and $Y^2$ is N.

In some embodiments, Y is N, $Y^1$ is N, and $Y^2$ is $CR^7$.

In some embodiments, Y is N, $Y^1$ is N, and $Y^2$ is N.

In some embodiments, Y is $CR^{15}$, $Y^1$ is $CR^6$, and $Y^2$ is $CR^7$.

In some embodiments, Y is $CR^{15}$, $Y^1$ is $CR^6$, and $Y^2$ is N.

In some embodiments, Y is $CR^{15}$, $Y^1$ is N, and $Y^2$ is $CR^7$.

In some embodiments, Y is $CR^{15}$, $Y^1$ is N, and $Y^2$ is N.

In some embodiments, Y is N, $Y^1$ is N or $CR^6$, $Y^2$ is N or $CR^7$, and at most one of $Y^1$ or $Y^2$ is N.

In some embodiments, the compounds of Formula (I) are represented by compounds of Formula (II):

(II)

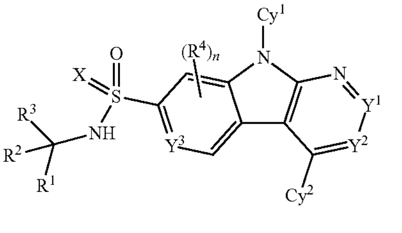

or a pharmaceutically acceptable salt, stereoisomer, solvate, N-oxide, tautomeric, isotopic variants, prodrugs or deuterated compound thereof, wherein:

X is O or $NR^5$;

$Y^1$ is N or $CR^6$;

$Y^2$ is N or $CR^7$, and at most one of $Y^1$ or $Y^2$ is N;

$Y^3$ is N or $CR^8$;

n is 0, 1 or 2;

$Cy^1$ is 5-10 membered heteroaryl optionally substituted by 1, 2, 3, 4, or 5 substituents independently selected from $R^9$;

$Cy^2$ is selected from $C_6$-$C_{10}$ aryl, $C_3$-$C_{10}$ cycloalkyl, 5-10 membered heteroaryl, or 4-14 membered heterocycloalkyl; wherein, the $C_6$-$C_{10}$ aryl, $C_3$-$C_{10}$ cycloalkyl, 5-10 membered heteroaryl, or 4-14 membered heterocycloalkyl is optionally substituted by 1, 2, 3, 4, or 5 substituents independently selected from $R^{10}$;

$R^1$, $R^2$ and $R^3$ are each independently selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein the $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl is optionally substituted by 1-5 substituents independently selected from D, halo, CN, OH, $C_1$-$C_6$ alkyl, $C_1$-$C_6$ haloalkyl, —O—$C_1$-$C_6$ alkyl, —O$C_1$-$C_6$ haloalkyl;

or $R^2$ and $R^3$ together with the carbon atom to which they are attached form $C_3$-$C_7$ cycloalkyl, or 4-7 membered heterocycloalkyl; wherein, the $C_3$-$C_7$ cycloalkyl, 4-7 membered heterocycloalkyl is optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl;

$R^4$ is selected from H, D, halo, OH, CN, $NO_2$, $SF_5$, $C_1$-$C_3$ alkyl, $C_2$-$C_3$ alkenyl, $C_2$-$C_3$ alkynyl, —O—$C_1$-$C_3$ alkyl, or $NR^CR^D$; wherein, the $C_1$-$C_3$ alkyl, $C_2$-$C_3$ alkenyl, $C_2$-$C_3$ alkynyl is optionally substituted with halogen or CN;

$R^5$ is selected from H, D, CN, $OR^B$, or $C_1$-$C_4$ alkyl optionally substituted with at least one of $R^{5A}$; wherein, each $R^{5A}$ is independently selected from D, F, Cl, CN, $NH_2$, OH, —O—$C_1$-$C_6$ alkyl, —O$C_1$-$C_6$ haloalkyl, optionally substituted $C_3$-$C_7$ cycloalkyl, or optionally substituted 4-7 membered heterocycloalkyl; wherein, the optionally substituted substituent is selected from D, halo, CN, OH, $C_1$-$C_4$ alkyl, $C_1$-$C_4$haloalkyl, —O—$C_1$-$C_4$ alkyl, —O$C_1$-$C_4$haloalkyl;

or $R^1$ and $R^5$ together with the atoms to which they are attached form 5-7 membered partially saturated heterocycloalkyl optionally substituted by 1, 2, 3 or 4 substituents independently selected from D, halogen, CN, $CF_3$, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl;

$R^6$ and $R^7$ are each independently selected from H, D, halogen, CN, $NO_2$, $C_1$-$C_6$ alkyl, $C_1$-$C_6$haloalkyl, $C_2$-$C_6$ alkenyl, $C_2$-$C_6$ alkynyl, $OR^A$, $SR^A$, $SF_5$, $NHOR^A$, $C(O)OR^A$, $C(O)R^B$, $C(O)NR^CR^D$, $OC(O)NR^CR^D$, $NR^CR^D$, $NR^CC(O)R^B$, $NR^CC(O)NR^CR^D$, $NR^CC(O)OR^A$, $NR^CS(O)_2R^B$, $B(OR^C)(OR^D)$, $C(=NR^C)NR^CR^D$, $NR^DC(=NR^C)NR^CR^D$, $NR^DC(=NR^C)R^B$, $P(O)R^ER^F$, $P(O)OR^EOR^F$, $OP(O)OR^EOR^F$, $S(O)(=NR^B)R^B$, $S(O)R^B$, $S(O)NR^CR^D$, $S(O)_2R^B$, $S(O)_2NR^CR^D$, $NR^CS(O)_2NR^CR^D$, or $NR^CS(O)(=NR^B)R^B$; wherein, the $C_1$-$C_6$ alkyl, $C_2$-$C_6$ alkenyl, or $C_2$-$C_6$ alkynyl is optionally substituted with 1, 2, or 3 substituents independently selected from $R^{11}$;

$R^8$ is selected from H, D, CN, halo, OH, $NH_2$, $C_1$-$C_3$ alkyl, $C_1$-$C_3$ haloalkyl, —O—$C_1$-$C_3$ alkyl, —O$C_1$-$C_3$ haloalkyl, $C_1$-$C_3$ cyanoalkyl, or $SF_5$;

each $R^9$ is independently selected from H, D, halo, $C_1$-$C_6$ alkyl, $C_2$-$C_6$ alkenyl, $C_2$-$C_6$ alkynyl, $C_1$-$C_6$ haloalkyl, $OC_1$-$C_6$ alkyl, $OC_1$-$C_6$ haloalkyl, $OC_3$-$C_7$ cycloalkyl, $C_3$-$C_7$ cycloalkyl, CN, $NO_2$, $N_3$, or $SF_5$; wherein, the $C_1$-$C_6$ alkyl, $C_2$-$C_6$ alkenyl, $C_2$-$C_6$ alkynyl or $C_3$-$C_7$ cycloalkyl is optionally substituted with 1, 2, or 3 substituents independently selected from $R^{11}$;

each $R^{10}$ is independently selected from H, D, halo, CN, $NO_2$, $N_3$, oxo, $C_1$-$C_6$ alkyl, $C_2$-$C_6$ alkenyl, $C_2$-$C_6$ alkynyl, $OR^A$, $SR^A$, $SF_5$, $NR^COR^A$, $C(O)R^B$, $C(=S)R^B$, $C(O)NR^CR^D$, $C(O)N(R^C)OR^A$, $C(O)OR^A$, $OC(O)R^B$, $OC(O)NR^CR^D$, $NR^CR^D$, $NR^CC(O)R^D$, $NR^CC(O)NR^CR^D$, $NR^CC(O)OR^A$, $B(OR^C)(OR^D)$, $C(=NR^C)NR^CR^D$, $NR^DC(=NR^C)NR^CR^D$, $NR^DC(=NR^C)R^B$, $SiR^GR^HR^I$, $P(O)R^ER^F$, $P(O)OR^EOR^F$, $OP(O)OR^EOR^F$, $S(O)(=NR^B)R^B$, $S(O)R^B$, $S(O)NR^CR^D$, $S(O)_2R^B$, $NR^CS(O)_2R^B$, $S(O)_2NR^CR^D$, $NR^CS(O)_2NR^CR^D$, $NR^CS(O)(=NR^B)R^B$, $Cy^3$, $C_1$-$C_6$ alkyl-$Cy^3$, $OCy^3$, or O—$C_1$-$C_6$ alkyl-$Cy^3$; wherein, the $C_1$-$C_6$ alkyl, $C_2$-$C_6$ alkenyl, $C_2$-$C_6$ alkynyl is optionally substituted with 1, 2, 3, 4 or 5 substituents independently selected from $R^{11}$; or two $R^{10}$ together with the atom(s) to which they are attached form oxo, $C_3$-$C_{10}$ cycloalkyl or 4-10 membered heterocycloalkyl; wherein, the $C_3$-$C_{10}$ cycloalkyl or 4-10 membered heterocycloalkyl optionally substituted by 1, 2, or 3 substituents independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$ cyanoalkyl, CN, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $OP(O)OR^eOR^f$, $P(O)OR^eOR^f$, $S(O)(=NR^b)R^b$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^cS(O)(=NR^b)R^b$, $Cy^4$; wherein, $Cy^4$ is $C_6$-$C_{10}$ aryl, $C_3$-$C_{10}$ cycloalkyl, 5-10 membered heteroaryl, and 4-10 membered heterocycloalkyl; wherein the $C_6$-$C_{10}$ aryl, $C_3$-$C_{10}$ cycloalkyl, 5-10 membered heteroaryl, 4-10 membered heterocycloalkyl is optionally substituted by 1, 2, 3 or 4 substituents independently selected from D, halo, CN, $NO_2$, OH, oxo, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$;

$Cy^3$ is independently selected from $C_6$-$C_{10}$ aryl, $C_3$-$C_{10}$ cycloalkyl, 5-10 membered heteroaryl, or 4-10 membered heterocycloalkyl; wherein the $C_6$-$C_{10}$ aryl, $C_3$-$C_{10}$ cycloalkyl, 5-10 membered heteroaryl, 4-10 membered heterocycloalkyl can be unsubstituted or substituted with 1, 2, 3, 4 or 5 substituents independently selected from $R^{12}$;

each $R^{11}$ is independently selected from H, D, halo, CN, $NO_2$, $N_3$, $C_1$-$C_6$ alkyl, $C_2$-$C_6$ alkenyl, $C_2$-$C_6$ alkynyl, $C_1$-$C_6$ haloalkyl, $OC_1$-$C_6$ alkylOH, $OC_1$-$C_6$ alkyl-O—$C_1$-$C_6$ alkyl, $OR^{a1}$, $SR^{a1}$, $SF_5$, $NHOR^{a1}$, $C(O)R^{b1}$, $C(O)NR^{c1}R^{d1}$, $C(O)OR^{a1}$, $OC(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b1}$, $P(O)OR^{e1}OR^{f1}$, $OP(O)OR^{e1}OR^{f1}$, $S(O)(=NR^{b}1)R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl, wherein, the $C_6$-$C_{10}$ aryl, $C_3$-$C_{10}$ cycloalkyl, 5-10 membered heteroaryl, 4-10 membered heterocycloalkyl can be unsubstituted or substituted by 1, 2, 3, 4 or 5 substituents independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$;

each $R^{12}$ is independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$ alkylOH, $C_1$-$C_6$ alkyl-O—$C_1$-$C_6$ alkyl, CN, $NO_2$, $N_3$, $OR^{a1}$, $SR^{a1}$, $SF_5$, $NHOR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b1}$, $P(O)R^{e1}R^{f1}$, $P(O)OR^{e1}OR^{f1}$, $OP(O)OR^{e1}OR^{f1}$, $S(O)(=NR^{b1})R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl; wherein, the $C_6$-$C_{10}$ aryl, $C_3$-$C_{10}$ cycloalkyl, 5-10 membered heteroaryl, 4-10 membered heterocycloalkyl can be unsubstituted or substituted by 1, 2, 3, 4 or 5 substituents independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$;

$R^A$ is independently selected from H, D, $C_1$-$C_6$ alkyl, $C_2$-$C_4$ alkenyl, $C_2$-$C_4$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein, the $C_1$-$C_6$ alkyl, $C_2$-$C_4$ alkenyl, $C_2$-$C_4$ alkynyl, $C_3$-$C_{10}$ cycloalkyl, 4-10 membered heterocyclalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $NR^cS(O)(=NR^b)R^b$;

$R^B$ is independently selected from H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from $R^{13}$;

each $R^{13}$ is independently selected from H, D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_1$-$C_4$ alkylOH, $OC_1$-$C_4$ alkyl-O—$C_1$-$C_4$ alkyl, $OC_1$-$C_4$ alkyl-O—$C_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, optionally substituted $C_3$-$C_7$ cycloalkyl, or optionally substituted 4-7 membered heterocycloalkyl, $SF_5$, $OR^a$, $SR^a$, $C(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$; wherein, the optionally substituted substituent is selected from D, halo, CN, OH, $C_1$-$C_4$ alkyl, $C_1$-$C_4$haloalkyl, —O—$C_1$-$C_4$ alkyl, —$OC_1$-$C_4$haloalkyl;

$R^C$ and $R^D$ are each independently selected from H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl is optionally substituted with 1, 2, 3, 4 or 5 substituents independently selected from D, OH, CN, halo, oxo, $C_1$-$C_4$ alkyl, $C_1$-$C_4$haloalkyl, $C_1$-$C_4$ cyanoalkyl, $OC_1$-$C_4$ alkyl, $OC_1$-$C_4$haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, $C_1$-$C_4$ alkyl-O—$C_1$-$C_4$ alkyl, $C_1$-$C_4$alkyl-O—$C_1$-$C_4$haloalkyl, $SF_5$, $OC(O)NR^cR^d$, $NR^cR^d$, $NR^cC(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$;

or $R^C$ and $R^D$ together with the N atom to which they are attached form a 4-7 membered heterocycloalkyl optionally substituted with 1, 2, 3, 4 or 5 substituents independently selected from D, OH, oxo, CN, —$NH_2$, —NH($C_1$-$C_4$ alkyl), —N($C_1$-$C_4$ alkyl)$_2$, halo, or $C_1$-$C_4$ alkyl, $C_1$-$C_4$ haloalkyl, $C_1$-$C_4$ cyanoalkyl, O$C_1$-$C_4$ alkyl, or O$C_1$-$C_4$haloalkyl, O$C_2$-$C_4$ alkylOH, O$C_2$-$C_4$ alkyl-O—$C_1$-$C_4$ alkyl, O$C_2$-$C_4$ alkyl-O—$C_1$-$C_4$haloalkyl;

$R^a$ and $R^{a1}$ are each independently selected from H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, or $C_1$-$C_4$haloalkoxy;

$R^b$ and $R^{b1}$ are each independently selected from H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, arylalkyl, heteroarylalkyl, cycloalkylalkyl, or heterocycloalkylalkyl; wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, arylalkyl, heteroarylalkyl, cycloalkylalkyl, or heterocycloalkylalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, $C_1$-$C_4$haloalkoxy, $C_6$-$C_{10}$ aryl, $C_3$-$C_{10}$ cycloalkyl, 5-10 membered heteroaryl, or 4-10 membered heterocycloalkyl;

$R^c$ and $R^d$ are each independently selected from H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl; wherein the $C_{1-4}$ alkyl, $C_{2-4}$ alkenyl, $C_{2-4}$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, C(O)O$R^{a1}$, C(O)$R^{b1}$, S(O)$_2R^{b1}$, $C_1$-$C_4$ alkyl-O—$C_1$-$C_4$ alkyl, and $C_1$-$C_4$ alkyl-O—$C_1$-$C_4$ alkyl-O—;

or $R^c$ and $R^d$ together with the N atom to which they are attached form a 4-7 membered heterocycloalkyl optionally substituted with 1, 2, or 3 substituents independently selected from D, OH, CN, —$NH_2$, —NH ($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, C(O)O$R^{a1}$, C(O)$R^{b1}$, S(O)$_2$ $R^{b1}$, $C_1$-$C_4$ alkoxy-$C_1$-$C_4$ alkyl, and $C_1$-$C_4$ alkoxy-$C_1$-$C_4$ alkoxy;

$R^{c1}$ and $R^{d1}$ are each independently selected from H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl or heterocycloalkylalkyl; wherein the $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl or heterocycloalkylalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, or $C_1$-$C_4$haloalkoxy;

or $R^{c1}$ and $R^{d1}$ together with the N atom to which they are attached form a 4-7 membered heterocycloalkyl optionally substituted with 1, 2, or 3 substituents independently selected from D, OH, CN, —$NH_2$, —NH ($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, and $C_{1-4}$haloalkoxy;

$R^E$, $R^e$ and $R^{e1}$ are each independently selected from H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 3-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl;

$R^F$, $R^f$ and $R^{f1}$ are each independently selected from H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl;

$R^G$, $R^H$ and $R^I$ are each independently selected from $C_1$-$C_4$ alkyl or phenyl.

In some embodiments, X is O or $NR^5$. In some embodiments, X is O. In other embodiments, X is $NR^5$.

In the compounds of Formula I, $R^5$ is H, D, CN, $OR^B$, $C_1$-$C_4$alkyl optionally substituted with at least one of $R^{5A}$; wherein, each $R^{5A}$ is independently selected from D, F, Cl, CN, $NH_2$, OH, —O—$C_1$-$C_6$ alkyl, —O$C_1$-$C_6$ haloalkyl, optionally substituted $C_3$-$C_7$ cycloalkyl, or optionally substituted 4-7 membered heterocycloalkyl; wherein, the optionally substituted substituent is selected from D, halo, CN, OH, $C_1$-$C_4$ alkyl, $C_1$-$C_4$haloalkyl, —O—$C_1$-$C_4$ alkyl, —O$C_1$-$C_4$haloalkyl.

In some embodiments, $R^5$ is H. In some embodiments, $R^5$ is D. In some embodiments, $R^5$ is CN. In some embodiments, $R^5$ is $OR^B$.

In some embodiments, $R^5$ is $C_1$-$C_4$ alkyl optionally substituted with at least one of $R^{5A}$; wherein, each $R^{5A}$ is independently selected from D, F, Cl, CN, $NH_2$, OH, —O—$C_1$-$C_6$ alkyl, —O$C_1$-$C_6$ haloalkyl, optionally substituted $C_3$-$C_7$ cycloalkyl, or optionally substituted 4-7 membered heterocycloalkyl; wherein, the optionally substituted substituent is selected from D, halo, CN, OH, $C_1$-$C_4$ alkyl, $C_1$-$C_4$haloalkyl, —O—$C_1$-$C_4$ alkyl, —O$C_1$-$C_4$haloalkyl.

In some embodiments, Y is N or $CR^{15}$.

In some embodiments, $Y^1$ is N or $CR^6$. In some embodiments, $Y^1$ is N. In other embodiments, $Y^1$ is $CR^6$.

In some embodiments, $Y^2$ is N or $CR^7$. In some embodiments, $Y^2$ is N. In other embodiments, $Y^2$ is $CR^7$.

In some embodiments, only one of $Y^1$ and $Y^2$ is N. In some embodiments, $Y^1$ is N, and $Y^2$ is $CR^7$. In other embodiments, $Y^1$ is $CR^6$, and $Y^2$ is N. In yet other embodiments, $Y^1$ is $CR^6$, and $Y^2$ is $CR^7$.

In the compounds of Formula I, $R^6$ and $R^7$ are independently selected from H, D, halogen, CN, $NO_2$, $C_1$-$C_6$ alkyl, $C_1$-$C_6$ haloalkyl, $C_2$-$C_6$ alkenyl, $C_2$-$C_6$ alkynyl, $OR^A$, $SR^A$, $SF_5$, $NHOR^A$, $C(O)OR^A$, $C(O)R^B$, $C(O)NR^CR^D$, $OC(O)NR^CR^D$, $NR^CR^D$, $NR^CC(O)R^B$, $NR^CC(O)NR^CR^D$, $NR^CC(O)OR^A$, $NR^CS(O)_2R^B$, $B(OR^C)(OR^D)$, $C({=}NR^C)NR^CR^D$, $NR^DC({=}NR^C)NR^CR^D$, $NR^DC({=}NR^C)R^B$, $P(O)R^ER^F$, $P(O)OR^EOR^F$, $OP(O)OR^EOR^F$, $S(O)({=}NR^B)R^B$, $S(O)R^B$, $S(O)NR^CR^D$, $S(O)_2R^B$, $S(O)_2NR^CR^D$, $NR^CS(O)_2NR^CR^D$, or $NR^CS(O)({=}NR^B)R^B$; wherein, the $C_1$-$C_6$alkyl, $C_2$-$C_6$ alkenyl, or $C_2$-$C_6$ alkynyl is optionally substituted with 1, 2, or 3 substituents independently selected from $R^{11}$.

In some embodiments, each $R^6$ is independently H, D, halogen, CN, $NO_2$, $OR^A$, $SR^A$, $SF_5$, $C_1$-$C_6$ alkyl or $C_1$-$C_6$ haloalkyl. In some embodiments, $R^6$ is H. In some embodiments, $R^6$ is D.

In some embodiments, $R^6$ is halogen. In some embodiments, $R^6$ is F. In some embodiments, $R^6$ is $C_1$. In some embodiments, $R^6$ is Br. In some embodiments, $R^6$ is I. In some embodiments, $R^6$ is CN. In some embodiments, $R^6$ is $NO_2$. In some embodiments, $R^6$ is $SF_5$. In some embodiments, $R^6$ is $OR^A$, for example, but not limited to, —OH, —OMe, —$OCF_3$. In some embodiments, $R^6$ is $SR^A$, for example, but not limited to, —SMe.

In some embodiments, $R^6$ is $C_1$-$C_6$ alkyl (such as $C_1$-$C_5$ alkyl, $C_1$-$C_4$ alkyl, $C_1$-$C_3$ alkyl, $C_1$-$C_2$ alkyl) optionally substituted with 1, 2, or 3 substituents independently selected from $R^{11}$, for example, but not limited to, —$CH_3$, —$CH_2CH_3$. In some embodiments, $R^6$ is $C_1$-$C_6$ haloalkyl, for example, —$CF_3$, —$CHF_2$, —$CH_2F$.

In some embodiments, $R^6$ is $C_2$-$C_6$ alkenyl optionally substituted with 1, 2, or 3 substituents independently selected from $R^{11}$. In some embodiments, $R^6$ is $C_2$-$C_6$ alkynyl optionally substituted with 1, 2, or 3 substituents independently selected from $R^{11}$.

In some embodiments, $R^6$ is $B(OR^C)(OR^D)$, for example, $B(OH)_2$. In some embodiments, $R^6$ is $NHOR^A$, for example, NHOH. In some embodiments, $R^6$ is $NR^CR^D$, for example, —$NH_2$, —$NCH_3$, —$N(CH_3)_2$.

In some embodiments, each $R^7$ is independently H, D, halogen, $OR^A$, CN, $NO_2$, or $SF_5$. In some embodiments, each $R^7$ is independently H, D, F, Cl, OH, CN, $NO_2$, or $SF_5$. In some embodiments, $R^7$ is H. In some embodiments, $R^7$ is D. In some embodiments, $R^7$ is halogen. In some embodiments, $R^7$ is F. In some embodiments, $R^7$ is Cl. In some embodiments, $R^7$ is Br. In some embodiments, $R^7$ is I. In some embodiments, $R^7$ is $OR^A$, for example, but not limited to, —OH, —OMe. In some embodiments, $R^7$ is CN. In some embodiments, $R^7$ is $NO_2$. In some embodiments, $R^7$ is $SF_5$.

In some embodiments, $R^7$ is $SR^A$. In some embodiments, $R^7$ is $B(OR^C)(OR^D)$, for example, $B(OH)_2$. In some embodiments, $R^7$ is $NHOR^A$. In some embodiments, $R^7$ is $NR^CR^D$.

In some embodiments, $R^7$ is $C_1$-$C_6$ alkyl (such as $C_1$-$C_5$ alkyl, $C_1$-$C_4$ alkyl, $C_1$-$C_3$ alkyl, $C_1$-$C_2$ alkyl) optionally substituted with 1, 2, or 3 substituents independently selected from $R^{11}$, for example, but not limited to, —$CH_3$. In some embodiments, $R^7$ is $C_1$-$C_6$ haloalkyl, for example, but not limited to, —$CF_3$.

In some embodiments, $R^7$ is $C_2$-$C_6$ alkenyl optionally substituted with 1, 2, or 3 substituents independently selected from $R^{11}$. In some embodiments, $R^7$ is $C_2$-$C_6$ alkynyl optionally substituted with 1, 2, or 3 substituents independently selected from $R^{1D}$.

In some embodiments, each $R^{15}$ is independently H, D, halogen, CN, $NO_2$, $OR^A$, $SR^A$, $SF_5$, $C_1$-$C_6$ alkyl or $C_1$-$C_6$ haloalkyl. In some embodiments, $R^{15}$ is H. In some embodiments, $R^{15}$ is D.

In some embodiments, $R^{15}$ is halogen. In some embodiments, $R^{15}$ is F. In some embodiments, $R^{15}$ is Cl. In some embodiments, $R^{15}$ is Br. In some embodiments, $R^{15}$ is I. In some embodiments, $R^{15}$ is CN. In some embodiments, $R^{15}$ is $NO_2$. In some embodiments, $R^{15}$ is $SF_5$. In some embodiments, $R^{15}$ is $OR^A$, for example, but not limited to, —OH, —OMe, —$OCF_3$. In some embodiments, $R^{15}$ is $SR^A$, for example, but not limited to, —SMe.

In some embodiments, $R^{15}$ is $C_1$-$C_6$ alkyl (such as $C_1$-$C_5$ alkyl, $C_1$-$C_4$ alkyl, $C_1$-$C_3$ alkyl, $C_1$-$C_2$ alkyl) optionally substituted with 1, 2, or 3 substituents independently selected from $R^{11}$, for example, but not limited to, —$CH_3$, —$CH_2CH_3$. In some embodiments, $R^{15}$ is $C_1$-$C_6$ haloalkyl, for example, —$CF_3$, —$CHF_2$, —$CH_2F$.

In some embodiments, $R^{15}$ is $C_2$-$C_6$ alkenyl optionally substituted with 1, 2, or 3 substituents independently selected from $R^{11}$. In some embodiments, $R^{15}$ is $C_2$-$C_6$ alkynyl optionally substituted with 1, 2, or 3 substituents independently selected from $R^{11}$.

In some embodiments, $R^{15}$ is $B(OR^C)(OR^D)$, for example, $B(OH)_2$. In some embodiments, $R^{15}$ is $NHOR^A$, for example, NHOH. In some embodiments, $R^{15}$ is $NR^CR^D$, for example, —$NH_2$, —$NCH_3$, —$N(CH_3)_2$.

In some embodiments, $Y^3$ is N or $CR^8$. In some embodiments, $Y^3$ is N. In other embodiments, $Y^3$ is $CR^8$.

In the compounds of Formula I, each $R^1$ is selected from H, D, CN, halo, OH, $NH_2$, $C_1$-$C_3$ alkyl (such as, but not limited to, $CH_3$, $CH_2CH_3$, $CH_2CH_2CH_3$, $CH(CH_3)_2$), $C_1$-$C_3$ haloalkyl (such as $C_1$ haloalkyl, $C_2$ haloalkyl, $C_3$ haloalkyl; for example, but not limited to $CF_3$, $CHF_2$, $CH_2F$), —O—$C_1$-$C_3$ alkyl (such as, but not limited to, $OCH_3$, $OCH_2CH_3$, $OCH_2CH_2CH_3$, $OCH(CH_3)_2$), —$OC_1$-$C_3$ haloalkyl (such as —$OC_1$-$C_3$ haloalkyl, —$OC_1$-$C_2$haloalkyl), $C_1$-$C_3$ cyanoalkyl (such as $C_1$-$C_3$ cyanoalkyl, $C_1$-$C_2$ cyanoalkyl), or $SF_5$.

In other embodiments, $R^8$ is selected from H, D, F, Cl, OH, $NH_2$, CN, $CH_3$, $CF_3$, OMe, $OCF_3$, or $SF_5$.

In some embodiments, $R^8$ is H. In some embodiments, $R^8$ is D. In some embodiments, $R^8$ is F. In some embodiments, $R^8$ is Cl. In some embodiments, $R^8$ is OH. In some embodiments, $R^8$ is CN.

In some embodiments, $R^8$ is $C_1$-$C_3$ alkyl, for example, but not limited to, $CH_3$. In some embodiments, $R^8$ is $C_1$-$C_3$ haloalkyl, for example, but not limited to, $CF_3$. In some embodiments, $R^8$ is —O—$C_1$-$C_3$ alkyl, for example, but not limited to, OMe. In some embodiments, $R^8$ is —$OC_1$-$C_3$ haloalkyl, for example, but not limited to, $OCF_3$. In some embodiments, $R^8$ is $SF_5$.

In the compounds of Formula I, n is 0, 1, or 2. In some embodiments, n is 0. In some embodiments, n is 1. In some embodiments, n is 2.

In some embodiments, $R^1$, $R^2$ and $R^3$ are each independently selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, 4-7 membered heterocycloalkyl is optionally substituted by 1-5 substituents (such as 1, 2, 3, 4, or 5 substituents) independently selected from D, halo, CN, OH, $C_1$-$C_6$ alkyl, $C_1$-$C_6$ haloalkyl, —O—$C_1$-$C_6$alkyl, —$OC_1$-$C_6$ haloalkyl.

In some embodiments, $R^1$ is selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, 4-7 membered heterocycloalkyl is optionally substituted by 1-5 substituents (such as 1, 2, 3, 4, or 5 substituents) independently selected from D, halo, CN, OH, $C_1$-$C_6$ alkyl, $C_1$-$C_6$ haloalkyl, —O—$C_1$-$C_6$ alkyl, —$OC_1$-$C_6$ haloalkyl.

In some embodiments, $R^1$ is independently selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl is optionally substituted by 1-5 substituents (such as 1, 2, 3, 4, or 5 substituents) independently selected from D, halo (such as F, Cl, Br or I), CN, OH, Me, $CF_3$, OMe, $OCF_3$, OEt.

In some embodiments, $R^1$ is independently selected from H, D, CN, $CH_3$, $CD_3$, $CH_2CH_3$, $CF_3$, $CHF_2$, $CH_2F$, $CH_2CH_2F$, $CH_2OH$, $CH_2OCH_3$ or $CH_2CN$, etc.

In some embodiments, $R^1$ is independently selected from CN, $CH_3$, $CH_2CH_3$, $CF_3$, $CHF_2$, $CH_2F$ or $CH_2CH_2F$. In some embodiments, $R^1$ is $CF_3$. In some embodiments, $R^1$ is $CHF_2$. In some embodiments, $R^1$ is $CH_2F$. In some embodiments, $R^1$ is $CH_3$. In some embodiments, $R^1$ is CN.

In some embodiments, $R^1$ and $R^5$ together with the atoms to which they are attached form 5- to 7-membered partially saturated heterocycloalkyl (such as 5-membered partially saturated heterocycloalkyl, 6-membered partially saturated heterocycloalkyl, 7-membered partially saturated heterocycloalkyl) optionally substituted by 1, 2, 3 or 4 substituents independently selected from D, halogen, CN, $CF_3$, $NO_2$, oxo, OH, $C_1$-$C_3$ alkyl, $C_1$-$C_3$ haloalkyl, —O—$C_1$-$C_3$ alkyl, —O$C_1$-$C_3$ haloalkyl.

In some embodiments, $R^1$ and $R^5$ together with the atoms to which they are attached form 5- to 7-membered partially saturated heterocycloalkyl optionally substituted by 1, 2, 3 or 4 substituents independently selected from D, halogen, CN, $CF_3$, $NO_2$, oxo, OH, Me, $CF_3$, OMe, $OCF_3$, OEt.

In some embodiments, $R^2$ is selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, 4-7 membered heterocycloalkyl is optionally substituted by 1-5 substituents (such as 1, 2, 3, 4, or 5 substituents) independently selected from D, halo, CN, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^2$ is independently selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl is optionally substituted by 1-5 substituents (such as 1, 2, 3, 4, or 5 substituents) independently selected from D, halo, CN, OH, Me, $CF_3$, OMe, $OCF_3$, OEt.

In some embodiments, $R^2$ is selected from $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, 4-7 membered heterocycloalkyl is optionally substituted by 1-5 substituents (such as 1, 2, 3, 4, or 5 substituents) independently selected from D, halo, CN, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^3$ is selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, 4-7 membered heterocycloalkyl is optionally substituted by 1-5 substituents (such as 1, 2, 3, 4, or 5 substituents) independently selected from D, halo, CN, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^3$ is independently selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl is optionally substituted by 1-5 substituents (such as 1, 2, 3, 4, or 5 substituents) independently selected from D, halo, CN, OH, Me, $CF_3$, OMe, $OCF_3$, OEt.

In some embodiments, $R^3$ is independently selected from $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl, wherein the $C_1$-$C_3$ alkyl, $C_2$-$C_3$ alkenyl, $C_2$-$C_3$ alkynyl, $C_3$-$C_7$ cycloalkyl, 4-7 membered heterocycloalkyl is optionally substituted by 1-5 substituents independently selected from D, halo, CN, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^2$ and $R^3$ together with the carbon atom to which they are attached form $C_3$-$C_7$ cycloalkyl, or 4-7 membered heterocycloalkyl; wherein, the $C_3$-$C_7$ cycloalkyl, 4-7 membered heterocycloalkyl is optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^2$ and $R^3$ together with the carbon atom to which they are attached form 4-7 membered heterocycloalkyl (such as 4-membered heterocycloalkyl, 5-membered heterocycloalkyl, 6-membered heterocycloalkyl, 7-membered heterocycloalkyl) optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^2$ and $R^3$ together with the carbon atom to which they are attached form $C_3$-$C_7$ cycloalkyl (such as $C_3$ cycloalkyl, $C_4$ cycloalkyl, $C_5$ cycloalkyl, $C_6$ cycloalkyl, $C_7$ cycloalkyl) optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^2$ and $R^3$ together with the carbon atom to which they are attached form cyclobutyl optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl. In some embodiments, $R^2$ and $R^3$ together with the carbon atom to which they are attached form cyclopropyl optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl.

In some embodiments, $R^2$ and $R^3$ together with the carbon atom to which they are attached form cyclobutyl. In some embodiments, $R^2$ and $R^3$ together with the carbon atom to which they are attached form cyclopropyl.

In the compounds of Formula I, each $R^4$ is independently selected from H, D, halo, OH, CN, $NO_2$, $SF_5$, $C_1$-$C_3$ alkyl, $C_2$-$C_3$ alkenyl, $C_2$-$C_3$ alkynyl, —O$C_1$-$C_3$ alkyl, or $NR^CR^D$; wherein, the $C_1$-$C_3$ alkyl, $C_2$-$C_3$ alkenyl, $C_2$-$C_3$ alkynyl is optionally substituted with halogen or CN.

In some embodiments, each $R^4$ is independently selected from H, D, OH, CN, $NO_2$, $SF_5$, halo, $C_1$-$C_3$ alkyl optionally substituted with halogen or CN.

In some embodiments, each $R^4$ is independently selected from H, D, halo (such as F, Cl, Br or I), $C_1$-$C_3$ alkyl.

In some embodiments, each $R^4$ is independently selected from H, D, F, Cl or $CH_3$.

In some embodiments, $Cy^1$ is 5-10 membered heteroaryl (such as 5-membered heteroaryl, 6-membered heteroaryl, 7-membered heteroaryl, 8-membered heteroaryl, 9-membered heteroaryl, 10-membered heteroaryl) optionally substituted by 1, 2, 3, 4, or 5 substituents independently selected from $R^9$.

In some embodiments, $Cy^1$ is 6 membered heteroaryl optionally substituted by 1, 2, 3, or 4 substituents independently selected from $R^9$.

In some embodiments, $Cy^1$ is 5 membered heteroaryl optionally substituted by 1, 2, or 3 substituents independently selected from $R^9$.

In some embodiments, $Cy^1$ is

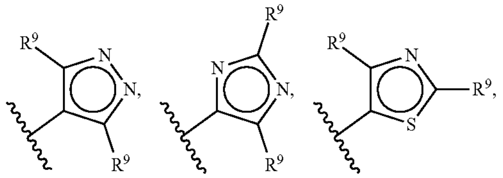

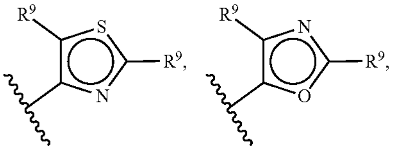

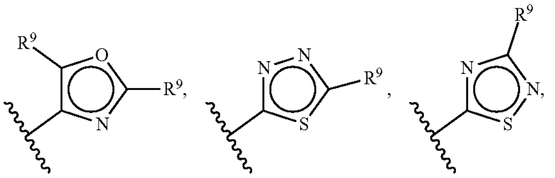

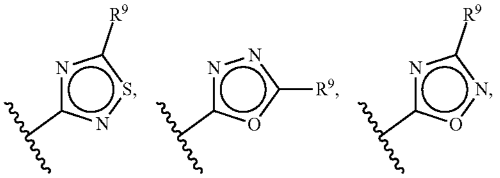

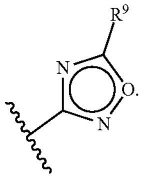

In some embodiments, $Cy^1$ is

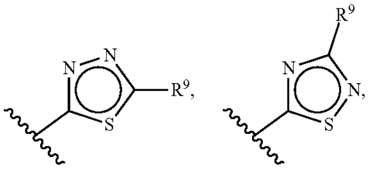

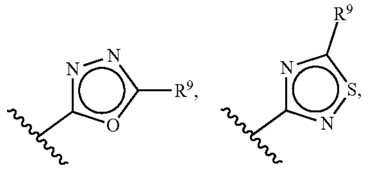

or

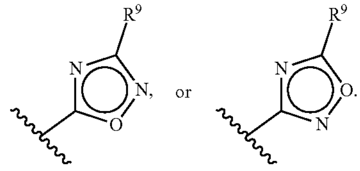

In some embodiments, $Cy^1$ is

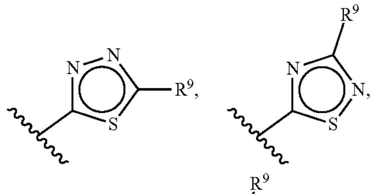

or

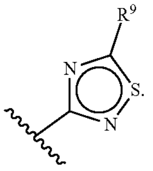

In some embodiments, $Cy^1$ is

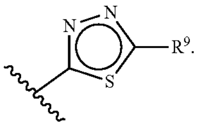

In some embodiments, each $R^9$ in Formula I is independently selected from H, D, halo, $C_1$-$C_6$ alkyl, $C_2$-$C_6$ alkenyl, $C_2$-$C_6$ alkynyl, $C_1$-$C_6$ haloalkyl, $OC_1$-$C_6$ alkyl, $C_1$-$C_6$ haloalkyl, $OC_3$-$C_7$ cycloalkyl, $C_3$-$C_7$ cycloalkyl, CN, $NO_2$, $N_3$, or SF; wherein the $C_1$-$C_6$ alkyl, $C_2$-$C_6$ alkenyl, $C_2$-$C_6$ alkynyl or $C_3$-$C_7$ cycloalkyl is optionally substituted with 1, 2, or 3 substituents independently selected from $R^{11}$.

In some embodiments, each $R^9$ is independently H. In some embodiments, each $R^9$ is independently D. In some embodiments, each $R^9$ is independently halo. In some embodiments, each $R^9$ is independently F, Cl, Br, I. In some embodiments, each $R^9$ is independently CN. In some embodiments, each $R^9$ is independently $NO_2$. In some embodiments, each $R^9$ is independently $N_3$. In some embodiments, each $R^9$ is independently $SF_5$.

In yet other embodiments, each $R^9$ is independently selected from $C_1$-$C_6$, alkyl, $C_2$-$C_6$ alkenyl, $C_2$-$C_6$ alkynyl, $C_1$-$C_6$ haloalkyl; wherein the $C_1$-$C_6$ alkyl, $C_2$-$C_6$ alkenyl, or $C_2$-$C_3$ alkynyl is optionally substituted with 1, 2, or 3 substituents independently selected from $R^{1D}$.

In yet other embodiments, each $R^9$ is independently $C_1$-$C_6$ alkyl, $C_2$-$C_6$ alkenyl, $C_2$-$C_6$ alkynyl, $C_1$-$C_6$ haloalkyl. In some embodiments, each $R^9$ is $C_1$-$C_6$ alkyl. In some embodiments, each $R^9$ is methyl. In some embodiments, each $R^9$ is ethyl. In some embodiments, each $R^9$ is isopropyl. In some embodiments, each $R^9$ is t-butyl.

In other embodiments, each $R^9$ is $C_2$-$C_6$ alkenyl. In yet other embodiments, each $R^9$ is independently $C_2$-$C_6$ alkynyl. In yet other embodiments, each $R^9$ is independently $C_1$-$C_6$ haloalkyl. In some embodiments, each $R^9$ is $CF_3$. In some embodiments, each $R^9$ is $CHF_2$. In some embodiments, each $R^9$ is $CH_2F$. In some embodiments, each $R^9$ is $CDF_2$.

In yet other embodiments, each $R^9$ is independently selected from $C_3$-$C_7$ cycloalkyl optionally substituted with 1, 2, or 3 substituents independently selected from $R^{11}$. In yet other embodiments, each $R^9$ is independently $C_3$-$C_7$ cycloalkyl. In yet other embodiments, $R^9$ is cyclobutyl. In yet other embodiments, $R^9$ is cyclopropyl.

In yet other embodiments, each $R^9$ is independently selected from $OC_1$-$C_6$ alkyl, $OC_1$-$C_6$ haloalkyl, $OC_3$-$C_7$ cycloalkyl; wherein, the $C_1$-$C_6$ alkyl or $C_3$-$C_7$ cycloalkyl is optionally substituted with 1, 2, or 3 substituents independently selected from $R^{10}$. In some embodiments, each $R^9$ is independently optionally substituted $OC_1$-$C_6$ alkyl. In some embodiments, each $R^9$ is independently optionally substituted $OC_1$-$C_6$ haloalkyl. In some embodiments, each $R^9$ is independently optionally substituted $OC_3$-$C_7$ cycloalkyl.

In some embodiments, $Cy^2$ is independently selected from $C_6$-$C_{10}$ aryl, $C_3$-$C_{10}$ cycloalkyl, 5-10 membered heteroaryl, or 4-14 membered heterocycloalkyl; wherein, the $C_6$-$C_{10}$ aryl, $C_3$-$C_{10}$ cycloalkyl, 5-10 membered heteroaryl, or 4-14 membered heterocycloalkyl optionally substituted by 1, 2, 3, 4 or 5 substituents independently selected from $R^{10}$.

In some embodiments, $Cy^2$ is independently selected from $C_6$-$C_{10}$ aryl, $C_3$-$C_{10}$ cycloalkyl, 5-10 membered heteroaryl, or 4-10 membered heterocycloalkyl; wherein, the $C_6$-$C_{10}$ aryl, $C_3$-$C_{10}$ cycloalkyl, 5-10 membered heteroaryl, or 4-10 membered heterocycloalkyl optionally substituted by 1, 2, 3, 4 or 5 substituents independently selected from $R^{10}$.

In some embodiments, $Cy^2$ is $C_6$-$C_{10}$ aryl optionally substituted by 1, 2, 3, 4 or 5 substituents independently selected from $R^{10}$. In some embodiments, $Cy^2$ is phenyl optionally substituted by 1, 2, 3, 4 or 5 $R^{10}$.

In some embodiments, $Cy^2$ is 5-10 membered heteroaryl (such as 5-membered heteroaryl, 6-membered heteroaryl, 7-membered heteroaryl, 8-membered heteroaryl, 9-membered heteroaryl, 10-membered heteroaryl) optionally substituted by 1, 2, 3, 4 or 5 substituents independently selected from $R^{10}$. In some embodiments, for example, but not limited to, $Cy^2$ is

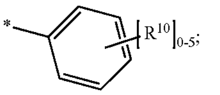

wherein, $[R^{10}]_{0-5}$ means each ring can be unsubstituted or substituted by 1, 2, 3, 4, or 5 $R^{10}$.

In some embodiments, for example, but not limited to, $Cy^2$ is pyrrolyl, furanyl, thiophenyl, imidazolyl, oxazolyl, thiazolyl, pyrazolyl, triazolyl, thiadiazolyl, oxadiazolyl, pyridinyl, pyrimidinyl, pyrazinyl, pyridazinyl, indolyl, indazolyl, benzo[d]imidazolyl, quinolinyl, quinoxalinyl, pyrrolo[3,2-b]pyridinyl, indolizinyl, each ring optionally substituted by 1, 2, 3, 4 or 5 substituents independently selected from $R^{10}$. In some embodiments, for example, but not limited to, $Cy^2$ is

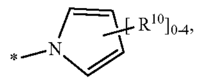
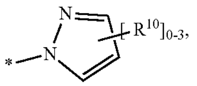
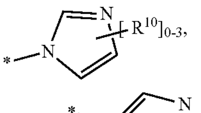
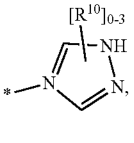
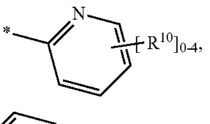
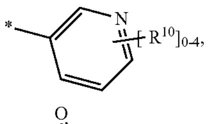
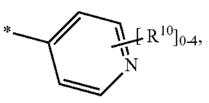
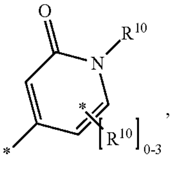
,
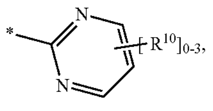

-continued

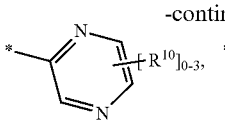
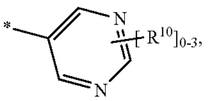
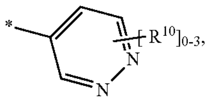
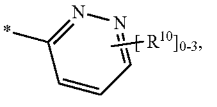
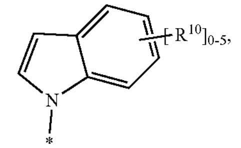
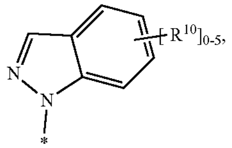
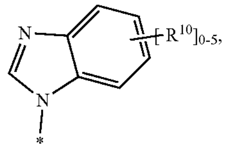
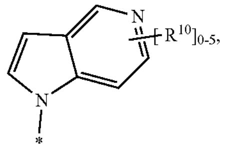
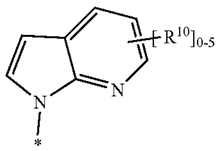
or
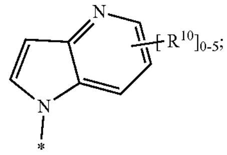

wherein, $[R^{10}]_{0-3}$ means each ring can be unsubstituted or substituted by 1, 2, or 3 $R^{10}$, $[R^{10}]_{0-4}$ means each ring can be unsubstituted or substituted by 1, 2, 3, or 4 $R^{10}$, $[R^{10}]_{0-5}$ means each ring can be unsubstituted or substituted by 1, 2, 3, 4, or 5 $R^{10}$.

In some embodiments, $Cy^2$ is $C_3$-$C_{10}$ cycloalkyl (such as $C_3$ cycloalkyl, $C_4$ cycloalkyl, $C_5$ cycloalkyl, $C_6$ cycloalkyl, $C_7$ cycloalkyl, $C_8$ cycloalkyl, $C_9$ cycloalkyl, $C_{10}$ cycloalkyl) optionally substituted by 1, 2, 3, 4 or 5 substituents independently selected from $R^{10}$.

In some embodiments, $Cy^2$ is saturated $C_3$-$C_{10}$ cycloalkyl optionally substituted by 1, 2, 3, 4 or 5 substituents independently selected from $R^{10}$.

In some embodiments, $Cy^2$ is saturated $C_3$-$C_{10}$ monocycloalkyl optionally substituted by 1, 2, 3, 4 or 5 substituents independently selected from $R^{10}$. In some embodiments, $Cy^2$ is cyclopropyl, cyclobutyl, cyclopentyl, cyclohexyl, or cycloheptyl, each ring optionally substituted by 1, 2, 3, 4 or 5 substituents independently selected from $R^{10}$. In some embodiments, for example, but not limited to, $Cy^2$ is

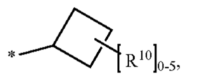
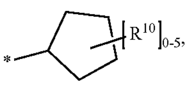
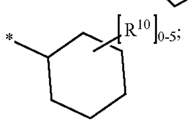

wherein, $[R^{10}]_{0-5}$ means each ring can be unsubstituted or substituted by 1, 2, 3, 4, or 5 $R^{10}$.

In some embodiments, $Cy^2$ is saturated $C_4$-$C_{10}$ bicycloalkyl optionally substituted by 1, 2, 3, 4 or 5 substituents independently selected from $R^{10}$. In some embodiments, $Cy^2$ is saturated $C_6$-$C_{10}$ bicycloalkyl optionally substituted by 1, 2, 3, 4 or 5 substituents independently selected from $R^{10}$.

In some embodiments, $Cy^2$ is saturated $C_5$-$C_{10}$ spirocycloalkyl optionally substituted by 1, 2, 3, 4 or 5 substituents independently selected from $R^{10}$.

In some embodiments, $Cy^2$ is saturated $C_4$-$C_{10}$ bridged cycloalkyl optionally substituted by 1, 2, 3, 4 or 5 $R^{10}$. In some embodiments, $Cy^2$ is saturated $C_5$-$C_{10}$ bridged cycloalkyl optionally substituted by 1, 2, 3, 4 or 5 substituents independently selected from $R^{10}$.

In some embodiments, $Cy^2$ is $C_7$-$C_{10}$ fused cycloalkyl optionally substituted by 1, 2, 3, 4 or $R^{10}$. In some embodiments, $Cy^2$ is saturated $C_8$-$C_{10}$ fused cycloalkyl optionally substituted by 1, 2, 3, 4 or 5 substituents independently selected from $R^{10}$.

In some embodiments, $Cy^2$ is partially unsaturated $C_3$-$C_{10}$ cycloalkyl optionally substituted by 1, 2, 3, 4 or 5 substituents independently selected from $R^{10}$.

In some embodiments, $Cy^2$ is partially unsaturated $C_3$-$C_{10}$ mono-cycloalkyl optionally substituted by 1, 2, 3, 4 or 5 substituents independently selected from $R^{10}$. In some embodiments, $Cy^2$ is cyclopropenyl, cyclobutenyl, cyclopentenyl, cyclopentadienyl, and cyclohexenyl, each ring optionally substituted by 1, 2, 3, 4 or 5 substituents independently selected from $R^{10}$. In some embodiments, for example, but not limited to, $Cy^2$ is

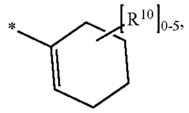 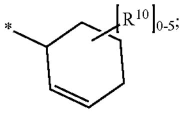

wherein, $[R^{10}]_{0-5}$ means each ring can be unsubstituted or substituted by 1, 2, 3, 4, or 5 $R^{10}$.

In some embodiments, $Cy^2$ is partially unsaturated $C_4$-$C_{10}$ bicycloalkyl optionally substituted by 1, 2, 3, 4 or 5 substituents independently selected from $R^{10}$. In some embodiments, $Cy^2$ is partially unsaturated $C_6$-$C_{10}$ bicycloalkyl optionally substituted by 1, 2, 3, 4 or 5 substituents independently selected from $R^{10}$.

In some embodiments, $Cy^2$ is partially unsaturated $C_5$-$C_{10}$ spirocycloalkyl optionally substituted by 1, 2, 3, 4 or 5 substituents independently selected from $R^{10}$. In some embodiments, $Cy^2$ is partially unsaturated $C_7$-$C_{10}$ spirocycloalkyl optionally substituted by 1, 2, 3, 4 or 5 substituents independently selected from $R^{10}$.

In some embodiments, $Cy^2$ is partially unsaturated $C_4$-$C_{10}$ bridged cycloalkyl optionally substituted by 1, 2, 3, 4 or 5 substituents independently selected from $R^{10}$. In some embodiments, $Cy^2$ is partially unsaturated $C_7$-$C_{10}$ bridged cycloalkyl optionally substituted by 1, 2, 3, 4 or 5 substituents independently selected from $R^{10}$.

In some embodiments, $Cy^2$ is partially unsaturated $C_7$-$C_{10}$ fused cycloalkyl optionally substituted by 1, 2, 3, 4 or 5 substituents independently selected from $R^{10}$. In some embodiments, $Cy^2$ is partially unsaturated $C_8$-$C_{10}$ fused cycloalkyl optionally substituted by 1, 2, 3, 4 or 5 substituents independently selected from $R^{10}$.

In some embodiments, $Cy^2$ is saturated 4-14 membered heterocycloalkyl optionally substituted by 1, 2, 3, 4 or 5 substituents independently selected from $R^{10}$. In some embodiments, $Cy^2$ is saturated 4-14 membered heterocycloalkyl having 1, 2, 3, 4 heteroatoms independently selected from N, O, S, P, Si and heteroatoms can be optionally substituted by one or more oxo or sulfido (e.g., S(O), $S(O)_2$, or P(O)), wherein, the 4-14 membered heterocycloalkyl is optionally substituted by 1, 2, 3, 4 or 5 substituents independently selected from $R^{10}$.

In some embodiments, $Cy^2$ is saturated 4-10 membered heterocycloalkyl optionally substituted by 1, 2, 3, 4 or 5 substituents independently selected from $R^{10}$. In some embodiments, $Cy^2$ is saturated 4-10 membered heterocycloalkyl having 1, 2, 3, 4 heteroatoms independently selected from N, O, S, P, Si and heteroatoms can be optionally substituted by one or more oxo or sulfido (e.g., S(O), $S(O)_2$, or P(O)), wherein, the 4-14 membered heterocycloalkyl is optionally substituted by 1, 2, 3, 4 or 5 substituents independently selected from $R^{10}$.

In some embodiments, $Cy^2$ is saturated 4-14 membered mono-heterocycloalkyl (such as saturated 4-membered mono-heterocycloalkyl, saturated 5-membered mono-heterocycloalkyl, saturated 6-membered mono-heterocycloalkyl, saturated 7-membered mono-heterocycloalkyl, saturated 8-membered mono-heterocycloalkyl, saturated 9-membered mono-heterocycloalkyl, saturated 10-membered mono-heterocycloalkyl, saturated 11-membered mono-heterocycloalkyl, saturated 12-membered mono-heterocycloalkyl, saturated 13-membered mono-heterocycloalkyl, saturated 14-membered mono-heterocycloalkyl) optionally substituted by 1, 2, 3, 4 or 5 $R^{10}$.

In some embodiments, for example, $Cy^2$ is azetidinyl, oxetanyl, thietanyl, pyrrolidinyl, tetrahydrofuranyl, tetrahydrothiophenyl, piperidinyl, dioxanyl tetrahydropyranyl, tetrahydrothiopyranyl, piperazinyl, morpholinyl, azepanyl, diazocanyl, diazepanyl, oxazepanyl, azepanyl, thiomorpholine 1,1-dioxidyl, piperazinonyl, tetrahydro-2H-thiopyran 1,1-dioxidyl; each ring optionally substituted by 1, 2, 3, 4 or 5 substituents independently selected from $R^{10}$.

In some embodiments, for example, but not limited to, $Cy^2$ is

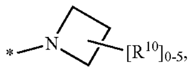 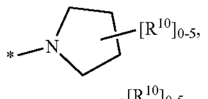

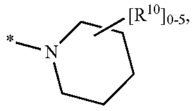 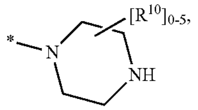

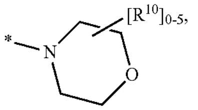 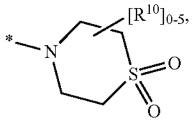

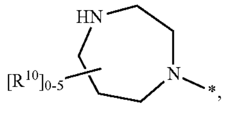 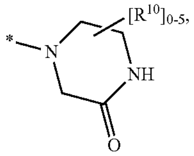

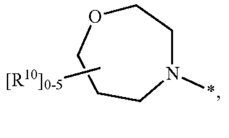 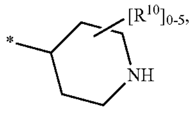

-continued

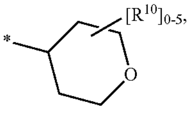
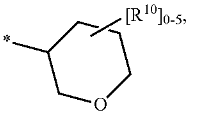
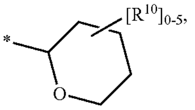
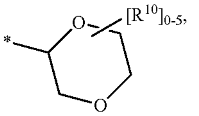
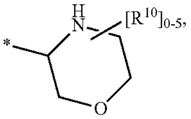
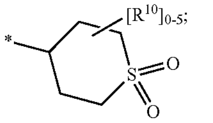

wherein $[R^{10}]_{0-5}$ means each ring can be unsubstituted or substituted by 1, 2, 3, 4, or 5 $R^{10}$.

In some embodiments, $Cy^2$ is saturated 4-14 membered bicyclic heterocycloalkyl (such as saturated 4-membered bicyclic heterocycloalkyl, saturated 5-membered bicyclic heterocycloalkyl, saturated 6-membered bicyclic heterocycloalkyl, saturated 7-membered bicyclic heterocycloalkyl, saturated 8-membered bicyclic heterocycloalkyl, saturated 9-membered bicyclic heterocycloalkyl, saturated 10-membered bicyclic heterocycloalkyl, saturated 11-membered bicyclic heterocycloalkyl, saturated 12-membered bicyclic heterocycloalkyl, saturated 13-membered bicyclic heterocycloalkyl, saturated 14-membered bicyclic heterocycloalkyl) optionally substituted by 1, 2, 3, 4 or 5 substituents independently selected from $R^{10}$.

In some embodiments, for example, $Cy^2$ is octahydropyrrolo[3,4-c]pyrrolyl, hexahydrofuro[3,4-c]pyrrolyl, hexahydrothieno[3,4-c]pyrrolyl, octahydrocyclopenta[b]pyrrolyl, octahydropyrrolo[3,2-b]pyrrolyl, hexahydrofuro[3,2-b]pyrrolyl, octahydropyrano[3,2-b]pyrrolyl, octahydropyrrolo[3,2-b]pyridinyl, hexahydropyrrolo[1,2-a]imidazolyl, octahydropyrrolo[2,3-c]pyridinyl, octahydropyrrolo[3,2-c]pyridinyl, octahydroimidazo[1,2-a]pyridinyl, octahydropyrrolo[3,4-c]pyridinyl, decahydroquinolinyl, octahydrochromenyl, decahydroquinoxalinyl, octahydropyrido[1,2-a]pyrazinyl, octahydropyrazino[2,1-c][1,4]oxazinyl, octahydropyrido[2,1-c][1,4]oxazinyl, octahydropyrano[3,2-c]pyridinyl, decahydro-2,6-naphthyridinyl, octahydropyrano[3,4-c]pyridinyl, octahydropyrrolo[1,2-a]pyrazinyl, hexahydrooxazolo[3,4-a]pyrazinyl, hexahydro-5H-cyclopenta[b][1,4]dioxinyl, hexahydroimidazo[1,5-a]pyrazin-3(2H)-only, hexahydro [1,4]dioxino[2,3-c]pyrrol, hexahydro-oxazolo[3,4-a]pyrazin-3-onyl, octahydro-2H-pyrazino[1,2-a]pyrazinyl, hexahydropyrazino[2,1-c][1,4]oxazin-3(4H)-onyl, hexahydropyrazino[2,1-c][1,4]oxazin-4(3H)-onyl; each ring optionally substituted by 1, 2, 3, 4 or 5 substituents independently selected from $R^{10}$.

In some embodiments, for example, but not limited to, $Cy^2$ is

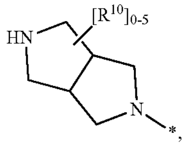
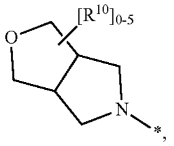
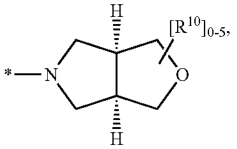
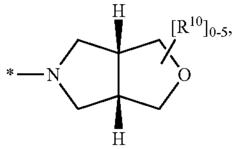

-continued

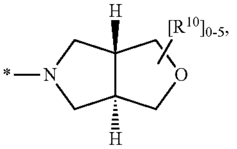
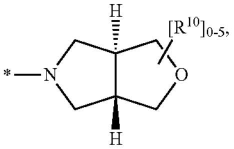
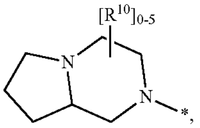
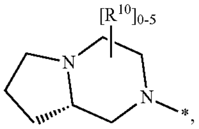
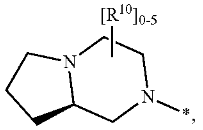
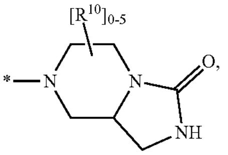
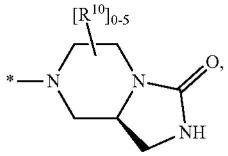
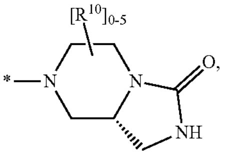
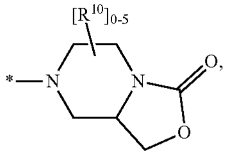
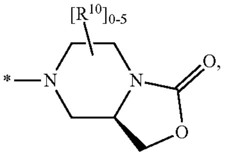
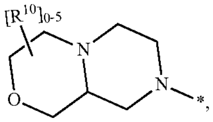
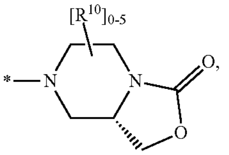
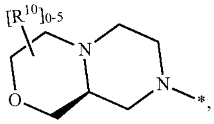
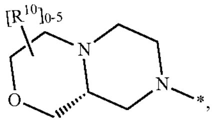
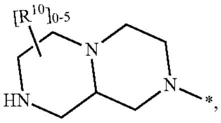
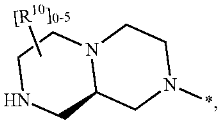
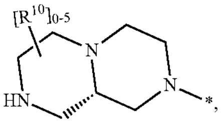
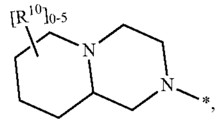
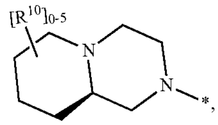
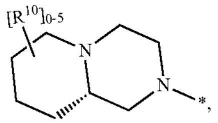

-continued

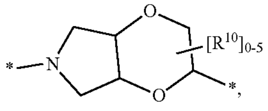

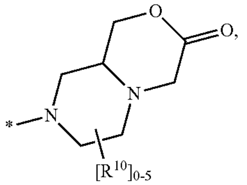

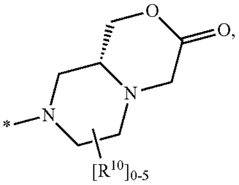

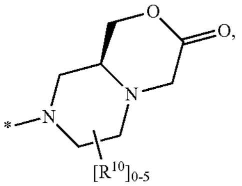

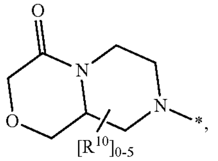

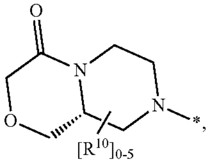

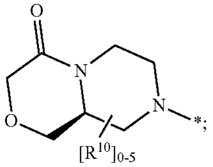

wherein, $[R^{10}]_{0\text{-}5}$ means each ring can be unsubstituted or substituted by 1, 2, 3, 4, or 5 $R^{10}$.

In some embodiments, $Cy^2$ is saturated 5-14 membered spiro-heterocycloalkyl (such as saturated 5-membered spiro-heterocycloalkyl, saturated 6-membered spiro-heterocycloalkyl, saturated 7-membered spiro-heterocycloalkyl, saturated 8-membered spiro-heterocycloalkyl, saturated 9-membered spiro-heterocycloalkyl, saturated 10-membered spiro-heterocycloalkyl, saturated 11-membered spiro-heterocycloalkyl, saturated 12-membered spiro-heterocycloalkyl, saturated 13-membered spiro-heterocycloalkyl, saturated 14-membered spiro-heterocycloalkyl) optionally substituted by 1, 2, 3, 4 or 5 substituents independently selected from $R^{10}$.

In some embodiments, for example, $Cy^2$ is 2,6-diazaspiro[3.3]heptanyl, 2-oxa-6-azaspiro[3.3]heptanyl, 2,6-diazaspiro[3.4]octanyl, 2,7-diazaspiro[3.5]nonanyl, 2,7-diazaspiro[4.4]nonanyl, 3,9-diazaspiro[5.5]undecanyl, 2-oxa-7-azaspiro[3.5]nonanyl, 2-oxa-6-azaspiro[3.4]octanyl, 7-oxa-2-azaspiro[3.5]nonanyl, 6-oxa-2-azaspiro[3.4]octanyl, 1-oxa-8-azaspiro[4.5]decanyl, 2-oxa-8-azaspiro[4.5]decanyl, 2-oxaspiro[3.5]nonanyl, 4,7-diazaspiro[2.5]octanyl, 1-oxa-7-azaspiro[3.5]nonanyl, 5,8-diazaspiro[3.5]nonanyl, 7-oxa-4-azaspiro[2.5]octanyl, 4-oxa-7-azaspiro[2.5]octanyl, 8-oxa-5-azaspiro[3.5]nonanyl, 5-oxa-8-azaspiro[3.5]nonanyl; each ring optionally substituted by 1, 2, 3, 4 or 5 substituents independently selected from $R^{10}$.

In some embodiments, for example, but not limited to, $Cy^2$ is

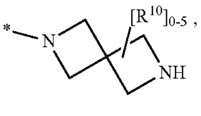

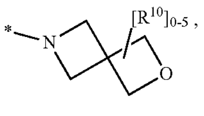

-continued

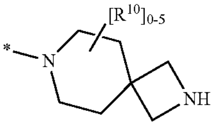

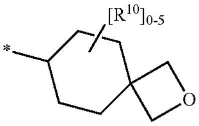

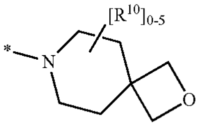

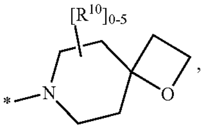

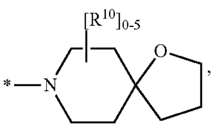

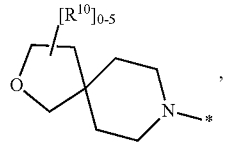

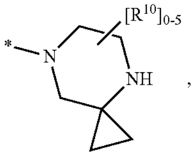

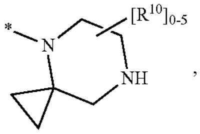

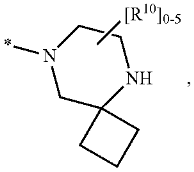

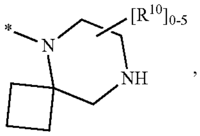

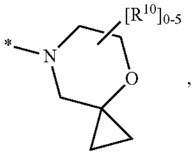

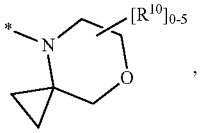

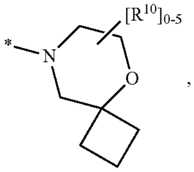

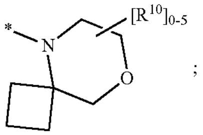

wherein, $[R^{10}]_{0\text{-}5}$ means each ring can be unsubstituted or substituted by 1, 2, 3, 4, or 5 $R^{10}$.

In some embodiments, $Cy^2$ is saturated 4-14 membered bridged heterocycloalkyl (such as saturated 4-membered bridged heterocycloalkyl, saturated 5-membered bridged heterocycloalkyl, saturated 6-membered bridged heterocycloalkyl, saturated 7-membered bridged heterocycloalkyl, saturated 8-membered bridged heterocycloalkyl, saturated 9-membered bridged heterocycloalkyl, saturated 10-membered bridged heterocycloalkyl, saturated 11-membered bridged heterocycloalkyl, saturated 12-membered bridged heterocycloalkyl, saturated 13-membered bridged heterocycloalkyl, saturated 14-membered bridged heterocycloalkyl) optionally substituted by 1, 2, 3, 4 or 5 substituents independently selected from $R^{10}$.

In some embodiments, for example, $Cy^2$ is 2-azabicyclo[1.1.1]pentanyl, 5-azabicyclo[2.1.1]hexanyl, 2-azabicyclo[2.2.1]heptanyl, 2-azabicyclo[2.2.2]octanyl, 6-azabicyclo[3.1.1]heptanyl, 3-azabicyclo[3.2.1]octanyl, 3-azabicyclo[3.3.1]nonanyl, 3-azabicyclo[3.3.2]decanyl, 3-azabicyclo[3.3.3]undecanyl, 3,6-diazabicyclo[3.1.1]heptanyl, 3,8-diazabicyclo[3.2.1]octanyl, 2,5-diazabicyclo[2.2.2]octanyl, 3,6-diazabicyclo[3.1.1]heptanyl, 6-oxa-3-azabicyclo[3.1.1]heptanyl, 3-oxa-6-azabicyclo[3.1.1]heptanyl, 2,5-diazabicyclo[2.2.1]heptanyl, 2-oxa-5-azabicyclo[2.2.1]heptanyl, 2-oxa-5-azabicyclo[2.2.2]octanyl, 3,8-diazabicyclo[3.2.1]octanyl, 8-oxa-3-azabicyclo[3.2.1]octanyl, 3-oxa-8-azabicyclo[3.2.1]octanyl; each ring optionally substituted by 1, 2, 3, 4 or 5 substituents independently selected from $R^{10}$.

In some embodiments, for example, but not limited to, $Cy^2$ is

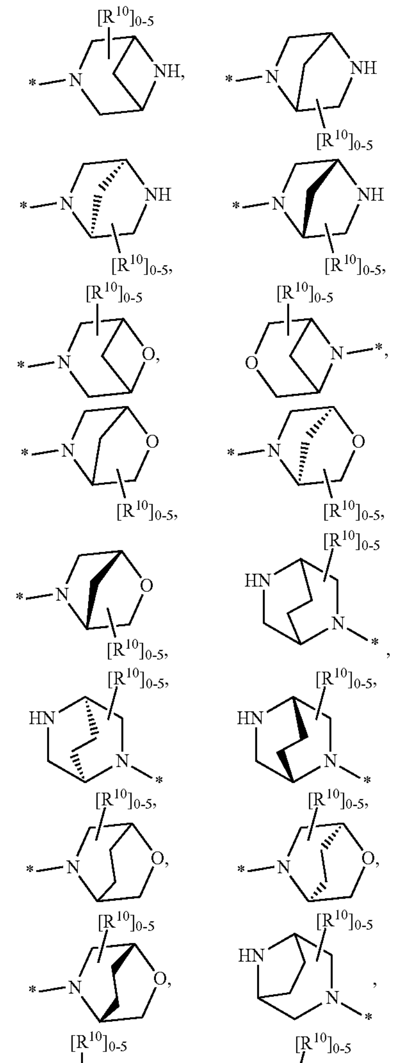

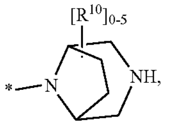

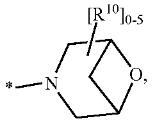

or

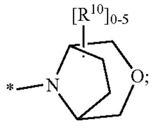

wherein, $[R^{10}]_{0-5}$ means each ring can be unsubstituted or substituted by 1, 2, 3, 4, or 5 $R^{10}$.

In some embodiments, $Cy^2$ is 7-14 membered fused heterocycloalkyl (such as 7-membered fused heterocycloalkyl, 8-membered fused heterocycloalkyl, 9-membered fused heterocycloalkyl, 10-membered fused heterocycloalkyl, 11-membered fused heterocycloalkyl, 12-membered fused heterocycloalkyl, 13-membered fused heterocycloalkyl, 14-membered fused heterocycloalkyl) optionally substituted by 1, 2, 3, 4 or 5 substituents independently selected from $R^{10}$.

In some embodiments, for example, $Cy^2$ is 5,6,7,8-tetrahydroimidazo[1,5-a]pyrazinyl, 5,6,7,8-tetrahydroimidazo[1,2-a]pyrazinyl, 5,6,7,8-tetrahydro-[1,2,4]triazolo[4,3-a]pyrazinyl, 4,5,6,7-tetrahydro-1H-pyrazolo[3,4-c]pyridinyl, 6,7,8,8a-tetrahydro-5H-[1,2,4]oxadiazolo[4,5-a]pyrazinyl, 4,5,6,7-tetrahydroisoxazolo[5,4-c]pyridinyl, 5,6,7,8-tetrahydro-1,7-naphthyridinyl, 5,6,7,8-tetrahydro-1,6-naphthyridinyl, 1,2,3,4-tetrahydro-2,7-naphthyridinyl, 1,2,3,4-tetrahydroisoquinolinyl, 4,5,6,7-tetrahydropyrazolo[1,5-a]pyrazinyl, 5,6,7,8-tetrahydropyrido[3,4-d]pyrimidinyl; each ring optionally substituted by 1, 2, 3, 4 or 5 substituents independently selected from $R^{10}$.

In some embodiments, for example, but not limited to, $Cy^2$ is

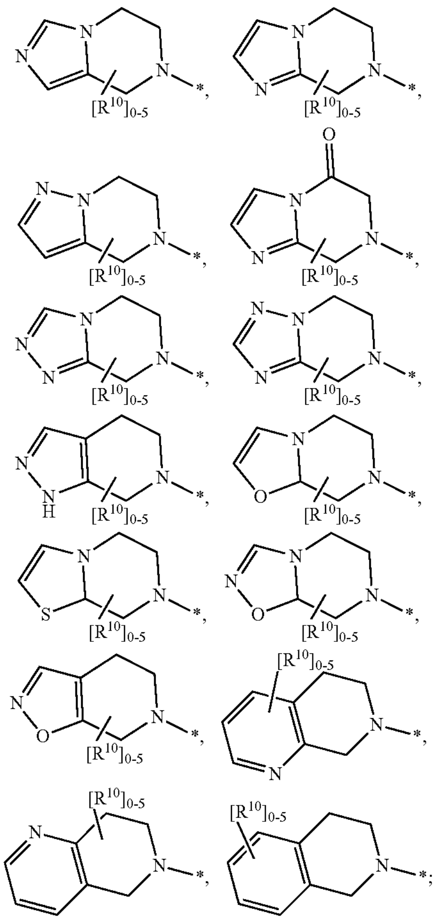

wherein, $[R^{10}]_{0-5}$ means each ring can be unsubstituted or substituted by 1, 2, 3, 4, or 5 $R^{10}$.

In some embodiments, $Cy^2$ is partially unsaturated 4-14 membered heterocycloalkyl (such as partially unsaturated 4-membered heterocycloalkyl, partially unsaturated 5-membered heterocycloalkyl, partially unsaturated 6-membered heterocycloalkyl, partially unsaturated 7-membered heterocycloalkyl, partially unsaturated 8-membered heterocycloalkyl, partially unsaturated 9-membered heterocycloalkyl, partially unsaturated 10-membered heterocycloalkyl, partially unsaturated 11-membered heterocycloalkyl, partially unsaturated 12-membered heterocycloalkyl, partially unsaturated 13-membered heterocycloalkyl, partially unsaturated 14-membered heterocycloalkyl) optionally substituted by 1, 2, 3, 4 or 5 $R^{10}$.

In some embodiments, $Cy^2$ is partially unsaturated 4-14 membered mono-heterocycloalkyl optionally substituted by 1, 2, 3, 4 or 5 $R^{10}$.

In some embodiments, for example, $Cy^2$ is 1,2,3,6-tetrahydropyridinyl, 3,6-dihydro-2H-pyranyl, 1,2,3,4-tetrahydropyridinyl, 3,4-dihydro-2H-pyranyl, 2,3-dihydro-1H-pyrrolyl, 2,5-dihydro-1H-pyrrolyl, 2,3-dihydrofuranyl, 2,5-dihydrofuranyl; each ring optionally substituted by 1, 2, 3, 4 or 5 $R^{10}$.

In some embodiments, for example, but not limited to, $Cy^2$ is

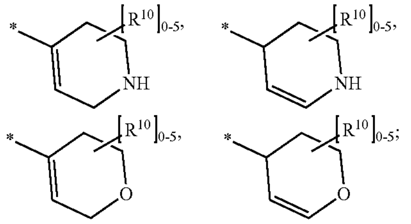

wherein, $[R^{10}]_{0-5}$ means each ring can be unsubstituted or substituted by 1, 2, 3, 4, or 5 $R^{10}$.

In some embodiments, $Cy^2$ is partially unsaturated 4-14 membered bicyclic heterocycloalkyl (such as partially unsaturated 6-membered bicyclic heterocycloalkyl, partially unsaturated 7-membered bicyclic heterocycloalkyl, partially unsaturated 8-membered bicyclic heterocycloalkyl, partially unsaturated 9-membered bicyclic heterocycloalkyl, partially unsaturated 10-membered bicyclic heterocycloalkyl, partially unsaturated 11-membered bicyclic heterocycloalkyl, partially unsaturated 12-membered bicyclic heterocycloalkyl, partially unsaturated 13-membered bicyclic heterocycloalkyl, partially unsaturated 14-membered bicyclic heterocycloalkyl) optionally substituted by 1, 2, 3, 4 or 5 $R^{10}$.

In some embodiments, $Cy^2$ is partially unsaturated 4-14 membered spiro-heterocycloalkyl (such as partially unsaturated 7-membered spiro-heterocycloalkyl, partially unsaturated 8-membered spiro-heterocycloalkyl, partially unsaturated 9-membered spiro-heterocycloalkyl, partially unsaturated 10-membered spiro-heterocycloalkyl, partially unsaturated 11-membered spiro-heterocycloalkyl, partially unsaturated 12-membered spiro-heterocycloalkyl, partially unsaturated 13-membered spiro-heterocycloalkyl, partially unsaturated 14-membered spiro-heterocycloalkyl) optionally substituted by 1, 2, 3, 4 or 5 $R^{10}$.

In some embodiments, $Cy^2$ is partially unsaturated 4-14 membered bridged heterocycloalkyl (such as partially unsaturated 7-membered bridged heterocycloalkyl, partially unsaturated 8-membered bridged heterocycloalkyl, partially unsaturated 9-membered bridged heterocycloalkyl, partially unsaturated 10-membered bridged heterocycloalkyl, partially unsaturated 11-membered bridged heterocycloalkyl, partially unsaturated 12-membered bridged heterocycloalkyl, partially unsaturated 13-membered bridged heterocycloalkyl, partially unsaturated 14-membered bridged heterocycloalkyl) optionally substituted by 1, 2, 3, 4 or 5 $R^{10}$.

In some embodiments, $Cy^2$ is partially unsaturated 4-14 membered fused heterocycloalkyl (such as partially unsaturated 8-membered fused heterocycloalkyl, partially unsaturated 9-membered fused heterocycloalkyl, partially unsaturated 10-membered fused heterocycloalkyl, partially unsaturated 11-membered fused heterocycloalkyl, partially unsaturated 12-membered fused heterocycloalkyl, partially unsaturated 13-membered fused heterocycloalkyl, partially unsaturated 14-membered fused heterocycloalkyl) optionally substituted by 1, 2, 3, 4 or 5 $R^{10}$.

In some embodiments, each $R^{10}$ in Formula I is independently selected from H, D, halo, CN, $NO_2$, $N_3$, oxo, $C_1$-$C_6$ alkyl, $C_2$-$C_6$ alkenyl, $C_2$-$C_6$ alkynyl, $OR^A$, $SR^A$, $SF_5$, $NR^COR^A$, $C(O)R^B$, $C({=}S)R^B$, $C(O)NR^CR^D$, $C(O)NR^COR^A$, $C(O)OR^A$, $C({=}NR^C)NR^CR^D$, $OC(O)R^B$, $OC(O)NR^CR^D$, $NR^CR^D$, $NR^CC(O)R^D$, $NR^CC(O)NR^CR^D$, $NR^CC(O)OR^A$, $B(OR^C)(OR^D)$, $NR^DC({=}NR^C)NR^CR^D$, $NR^DC({=}NR^C)R^B$, $SiR^GR^HR^I$, $P(O)R^ER^F$, $P(O)OR^EOR^F$, $OP(O)OR^EOR^F$, $S(O)({=}NR^B)R^B$, $S(O)R^B$, $S(O)NR^CR^D$, $S(O)_2R^B$, $NR^CS(O)_2R^B$, $S(O)_2NR^CR^D$, $NR^CS(O)_2NR^CR^D$, $NR^CS(O)({=}NR^B)R^B$, $Cy^3$, $C_1$-$C_6$ alkyl-$Cy^3$, $OCy^3$, O—$C_1$-$C_6$ alkyl-$Cy^3$; wherein, the $C_1$-$C_6$ alkyl, $C_2$-$C_6$ alkenyl, $C_2$-$C_6$ alkynyl is optionally substituted 1, 2, 3, 4 or 5 $R^D$.

In some embodiments, each $R^{10}$ is independently selected H, D, halo, CN, $NO_2$, $N_3$, $C_1$-$C_6$ alkyl, $C_2$-$C_6$ alkenyl, $C_2$-$C_6$ alkynyl, $C_1$-$C_6$ haloalkyl, $C_1$-$C_6$ cyanoalkyl, $OR^A$, $SR^A$, $SF_5$, $NHOR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $NR^CC(O)OR^A$, $B(OR^C)(OR^D)$, $C({=}NR^C)NR^CR^D$, $NR^DC({=}NR^C)NR^CR^D$, $NR^DC({=}NR^C)R^B$, $P(O)R^ER^F$, $P(O)OR^E$-$OR^F$, $OP(O)OR^EOR^F$, $S(O)({=}NR^B)R^B$, $S(O)R^B$, $S(O)NR^CR^D$, $S(O)_2R^B$, $NR^CS(O)_2R^B$, $S(O)_2NR^CR^D$, $NR^CS(O)_2NR^CR^D$, $NR^CS(O)({=}NR^B)R^B$, $Cy^3$, $C_1$-$C_6$ alkyl-$Cy^3$, $OCy^3$, or O—$C_1$-$C_6$ alkyl-$Cy^3$.

In some embodiments, each $R^{10}$ is independently selected from H, D, halo, CN, $NO_2$, $N_3$, oxo, $SF_5$. In some embodiments, each $R^{10}$ is independently selected from H. In some embodiments, each $R^{10}$ is independently selected from D. In some embodiments, each $R^{10}$ is independently selected from halo (such as F, Cl, Br, I). In some embodiments, each $R^{10}$ is independently selected from CN. In some embodiments, each $R^{10}$ is independently selected from $NO_2$. In some embodiments, each $R^{10}$ is independently selected from $N_3$. In some embodiments, each $R^{10}$ is independently selected from oxo, such as carbon atoms and heteroatoms can be optionally substituted by one or more oxo or sulfido (e.g., C(O), S(O), C(S), or $S(O)_2$, or P(O), etc.). In some embodiments, each $R^{10}$ is independently selected from $SF_5$.

In some embodiments, each $R^{10}$ is independently selected from $OR^A$. In some embodiments, for example, each $R^{10}$ is independently selected from OH, $OCH_3$, $OCH_2CH_3$, $OCF_3$, $OCH_2CF_3$.

In some embodiments, each $R^{10}$ is independently selected from $SR^A$. In some embodiments, each $R^{10}$ is independently selected from $NHOR^A$, such as NHOH.

In some embodiments, each $R^{10}$ is independently selected from $C(O)R^B$.

In some embodiments, each $R^{10}$ is independently selected from $C(O)R^B$, and $R^B$ is selected from H, D. In some embodiments, each $R^{10}$ is selected from CHO.

In some embodiments, each $R^{10}$ is independently selected from $C(O)R^B$, and $R^B$ is selected from $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; each is optionally substituted with 1, 2, 3, 4 or 5 substituents independently selected from $R^{13}$.

In some embodiments, each $R^{10}$ is independently selected from $C(O)R^B$, and $R^B$ is selected from $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; each is optionally substituted with 1, 2, 3, 4 or 5 substituents independently selected from $R^{13}$.

In some embodiments, for example, but not limited to, each $R^{10}$ is independently selected from $C(O)CH_3$, $C(O)CH_2CH_3$, $C(O)CH_2CH_2CH_3$, $C(O)CH(CH_3)_2$, $C(O)CH_2CH(CH_3)_2$, $C(O)C(CH_3)_3$, $C(O)CF_3$, $C(O)CH_2CF_3$, $C(O)CH_2OH$, $C(O)CH_2OCH_3$,

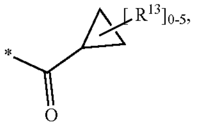
,
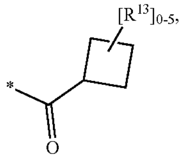
,
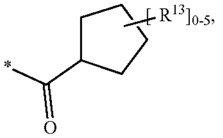
,
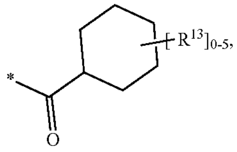
,
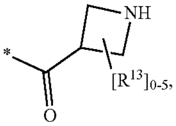
,
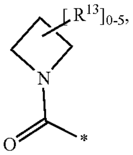
,
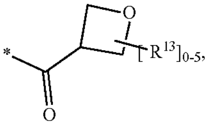
,
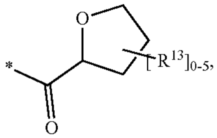
,
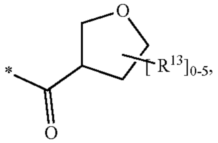
,
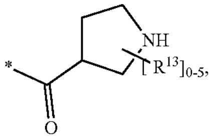
,
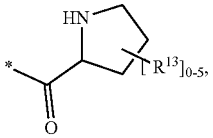
,
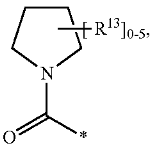
,
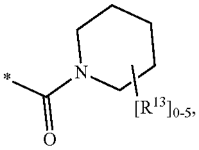
,
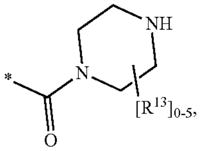
,
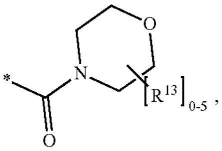
,
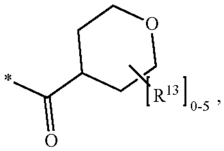
,
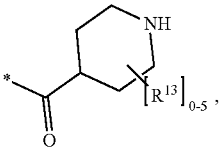
,
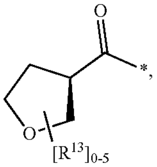
,
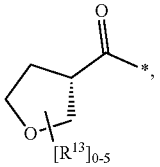
, -continued

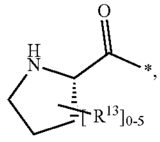
,
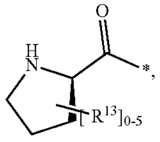
,
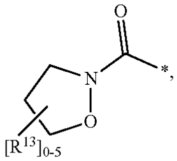
,
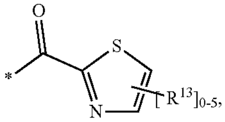
,
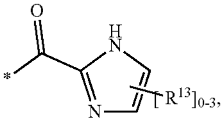
,
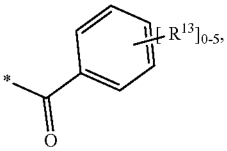
,
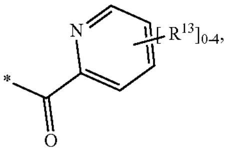
,
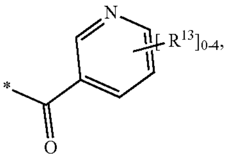
,
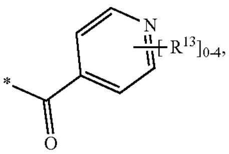
,
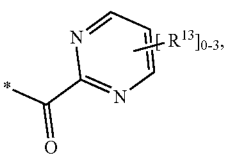
,
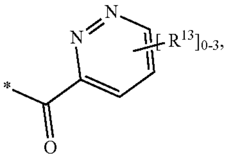
,
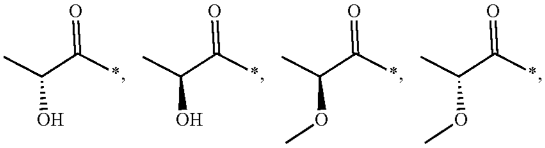
,
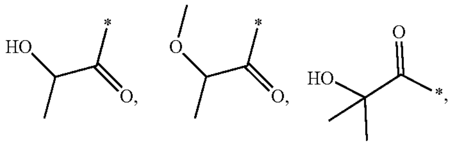
,
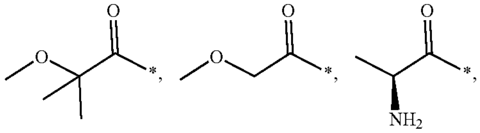
,
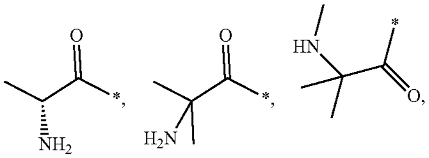
,
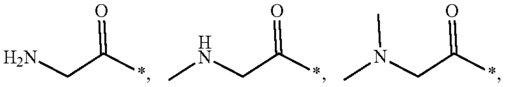
,
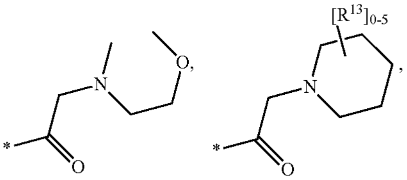
, -continued

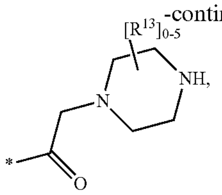
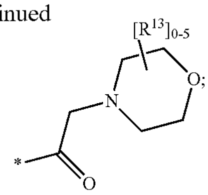

wherein, $[R^{13}]_{0-5}$ means each ring can be unsubstituted or substituted by 1, 2, 3, 4, or 5 $R^{13}$.

In some embodiments, each $R^{10}$ is independently selected from $C(=S)R^B$. In some embodiments, each $R^{10}$ is independently selected from $C(=S)CH_3$, $C(=S)CH_2CH_3$, $C(=S)CH_2CH_2CH_3$, $C(=S)CH(CH_3)_2$, $C(=S)C(CH_3)_3$.

In some embodiments, each $R^{10}$ is independently selected from $C(O)NR^CR^D$. In some embodiments, each $R^{10}$ is independently selected from $C(O)NH_2$, $C(O)NHCH_3$, $C(O)N(CH_3)_2$, $C(O)N(CH_3)CH_2CH_3$, $C(O)N(CH_3)CH_2CF_3$, $C(O)N(CH_3)CH_2CH_2OH$, $C(O)N(CH_3)CH_2CH_2OCH_3$, $C(O)N(CH_3)OCH_3$, $C(O)N(CH_3)CH_2CH(CH_3)OH$.

In some embodiments, each $R^{10}$ is independently selected from $C(O)NR^COR^A$, such as

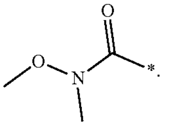

In some embodiments, each $R^{10}$ is independently selected from $C(O)OR^A$. In some embodiments, each $R^{10}$ is independently selected from $C(O)OH$, $C(O)OCH_3$, $C(O)OCH_2CH_3$, $C(O)OCH_2CH_2CH_3$, $C(O)OCH(CH_3)_2$, $C(O)OC(CH_3)_3$.

In some embodiments, each $R^{10}$ is independently selected from $C(=NR^C)NR^CR^D$. In other embodiments, each $R^{10}$ is independently selected from $OC(O)R^B$. In other embodiments, each $R^{10}$ is independently selected from $OC(O)NR^CR^D$.

In other embodiments, each $R^{10}$ is independently selected from $NR^CR^D$. In other embodiments, each $R^{10}$ is independently selected from $NH_2$, $NHCH_3$, $N(CH_3)_2$, $N(CH_3)CH_2CH_3$, $N(CH_3)CH_2CF_3$.

In other embodiments, each $R^{10}$ is independently $NR^CC(O)R^D$. In other embodiments, each $R^{10}$ is independently $NR^CC(O)NR^CR^D$. In other embodiments, each $R^{10}$ is independently $NR^CC(O)OR^A$. In other embodiments, each $R^{10}$ is independently $NR^DC(=NR^C)NR^CR^D$. In other embodiments, each $R^{10}$ is independently $NR^DC(=NR^C)R^B$.

In other embodiments, each $R^{10}$ is independently $B(OR^C)(OR^D)$. In other embodiments, each $R^{10}$ is independently $SiR^GR^HR^I$, for example, each $R^{10}$ is independently $Si(CH_3)_3$. In other embodiments, each $R^{10}$ is independently $P(O)R^ER^F$, for example, each $R^{10}$ is independently $P(O)(CH_3)_2$. In other embodiments, each $R^{10}$ is independently $P(O)OR^EOR^F$. In other embodiments, each $R^{10}$ is independently $OP(O)OR^EOR^F$. In other embodiments, each $R^{10}$ is independently $S(O)(=NR^B)R^B$.

In other embodiments, each $R^{10}$ is independently $S(O)R^B$, for example, each $R^{10}$ is independently $S(O)CH_3$, $S(O)CH_2CH_3$, $S(O)CH(CH_3)_2$, $S(O)C(CH_3)_3$.

In other embodiments, each $R^{10}$ is independently $S(O)NR^CR^D$.

In other embodiments, each $R^{10}$ is independently $S(O)_2R^B$, for example, each $R^{10}$ is independently $S(O)_2CH_3$, $S(O)_2CH_2CH_3$, $S(O)_2CH(CH_3)_2$, $S(O)_2C(CH_3)_3$.

In other embodiments, each $R^{10}$ is independently $NR^CS(O)_2R^B$. In other embodiments, each $R^{10}$ is independently $S(O)_2NR^CR^D$. In other embodiments, each $R^{10}$ is independently $NR^CS(O)_2NR^CR^D$. In other embodiments, each $R^{10}$ is independently $NR^CS(O)(=NR^B)R^B$.

In other embodiments, each $R^{10}$ is independently $Cy^3$, for example, but not limited to, each $R^{10}$ is independently phenyl, naphthalenyl, pyrrolyl, furanyl, thiophenyl, imidazolyl, oxazolyl, thiazolyl, tetrazolyl, pyrazolyl, triazolyl, thiadiazolyl, oxadiazolyl, pyridinyl, pyrimidinyl, pyrazinyl, pyridazinyl, indolyl, isoindolyl, indolizinyl, benzofuranyl, isobenzofuranyl, benzo[b]thiophenyl, benzo[c]thiophenyl, indazolyl, benzo[d]imidazolyl, pyrrolo[3,2-b]pyridinyl, pyrrolo[3,2-c]pyridinyl, pyrrolo[2,3-c]pyridinyl, pyrrolo[2,3-b]pyridinyl, pyrrolo[3,4-b]pyridinyl, pyrrolo[3,4-c]pyridinyl, benzo[d]isoxazolyl, benzo[d]oxazolyl, furo[3,2-b]pyridinyl, furo[3,2-c]pyridinyl, furo[2,3-c]pyridinyl, furo[2,3-b]pyridinyl, benzo[c]isoxazolyl, furo[3,4-b]pyridinyl, furo[3,4-c]pyridinyl, benzo[d]isothiazolyl, benzo[d]thiazolyl, thieno[3,2-b]pyridinyl, thieno[3,4-c]pyridinyl, benzo[d][1,2,3]triazolyl, pyrazolo[4,3-b]pyridinyl, pyrazolo[4,3-c]pyridinyl, pyrazolo[3,4-c]pyridinyl, pyrazolo[3,4-b]pyridinyl, imidazo[4,5-b]pyridinyl, imidazo[4,5-c]pyridinyl, imidazo[4,5-c]pyridinyl, imidazo[4,5-b]pyridinyl, pyrrolo[3,2-c]pyridazinyl, pyrrolo[3,2-d]pyrimidinyl, pyrrolo[2,3-b]pyrazinyl, pyrrolo[2,3-d]pyridazinyl, pyrrolo[2,3-d]pyrimidinyl, pyrrolo[2,3-c]pyridazinyl, pyrrolo[3,4-c]pyridazinyl, pyrrolo[3,4-d]pyrimidinyl, pyrrolo[3,4-b]pyrazinyl, pyrrolo[3,4-d]pyridazinyl, pyrrolo[3,4-d]pyrimidinyl, 6H-pyrrolo[3,4-c]pyridazinyl, azetidinyl, oxetanyl, thietanyl, pyrrolidinyl, tetrahydrofuranyl, tetrahydrothiophenyl, piperidinyl, dioxanyl tetrahydropyranyl, tetrahydrothiopyranyl, piperazinyl, morpholinyl, azepanyl, diazocanyl, diazepanyl, azepanyl, cyclopropyl, cyclobutyl, cyclopentyl, cyclohexyl, cycloheptyl, each ring is optionally substituted with 1, 2, 3, 4 or 5 $R^{12}$.

In other embodiments, for example, but not limited to, each $R^{10}$ is

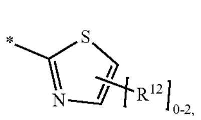
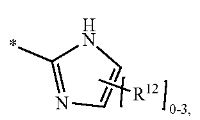
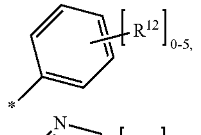
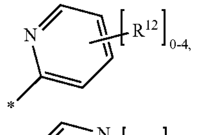
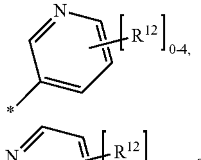
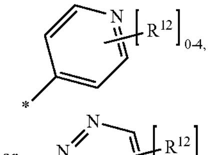
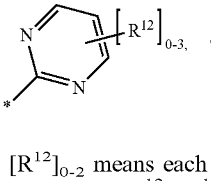
or
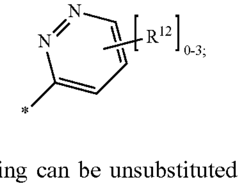

wherein, $[R^{12}]_{0-2}$ means each ring can be unsubstituted or substituted by 1 or 2 $R^{12}$, $[R^{12}]_{0-3}$ means each ring can be unsubstituted or substituted by 1, 2, or 3 $R^{12}$, $[R^{12}]_{0-4}$ means each ring can be unsubstituted or substituted by 1, 2, 3, or 4 $R^{12}$, $[R^{12}]_{0-5}$ means each ring can be unsubstituted or substituted by 1, 2, 3, 4, or 5 $R^{12}$.

In other embodiments, each $R^{10}$ is independently $C_1$-$C_6$ alkyl-$Cy^3$. In other embodiments, each $R^{10}$ is independently $C_1$ alkyl-$Cy^3$, for example, but not limited to, each $R^{10}$ is independently

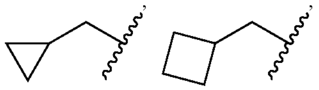

etc. In other embodiments, each $R^{10}$ is independently $C_2$ alkyl-$Cy^3$. In other embodiments, each $R^{10}$ is independently $C_3$ alkyl-$Cy^3$. In other embodiments, each $R^{10}$ is independently $C_4$ alkyl-$Cy^3$. In other embodiments, each $R^{10}$ is independently $C_5$ alkyl-$Cy^3$. In other embodiments, each $R^{10}$ is independently $C_6$ alkyl-$Cy^3$.

In other embodiments, each $R^{10}$ is independently $OCy^3$. In other embodiments, each $R^{10}$ is independently $OC_6$-$C_{10}$ aryl. In other embodiments, each $R^{10}$ is independently $OC_3$-$C_{10}$ cycloalkyl. In other embodiments, each $R^{10}$ is independently O-5-10 membered heteroaryl. In other embodiments, each $R^{10}$ is independently O-4-10 membered heterocycloalkyl.

In other embodiments, each $R^{10}$ is independently O—$C_1$-$C_6$ alkyl-$Cy^3$. In other embodiments, each $R^{10}$ is independently O—$C_1$ alkyl-$Cy^3$. In other embodiments, each $R^{10}$ is independently O—$C_2$ alkyl-$Cy^3$. In other embodiments, each $R^{10}$ is independently O—$C_3$ alkyl-$Cy^3$. In other embodiments, each $R^{10}$ is independently O—$C_4$ alkyl-$Cy^3$. In other embodiments, each $R^{10}$ is independently O—$C_5$ alkyl-$Cy^3$. In other embodiments, each $R^{10}$ is independently O—$C_6$ alkyl-$Cy^3$.

In some embodiments, each $R^{10}$ is independently selected from $C_1$-$C_6$ alkyl optionally substituted 1, 2, 3, 4 or 5 $R^{D1}$. In some embodiments, each $R^{10}$ is independently selected from methyl, ethyl, n-propyl, i-propyl, n-butyl, i-butyl, t-butyl, pentyl, hexyl, $CH_2F$, $CHF_2$, $CF_3$, $CH_2CH_2F$, $CH_2CHF_2$, $CH_2CF_3$, $CH_2OH$, $CH_2OCH_3$, $CH_2CH_2OCH_3$, $CH_2SCH_3$, $CH_2CH_2NCH_3$, $CH_2CN$,

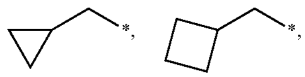

etc.

In some embodiments, each $R^{10}$ is independently selected from $C_2$-$C_6$ alkenyl optionally substituted 1, 2, 3, 4 or 5 $R^D$.

In some embodiments, each $R^{10}$ is independently selected from $C_2$-$C_6$ alkynyl optionally substituted 1, 2, 3, 4 or 5 $R^D$.

In some embodiments, two $R^{10}$, together with the atom(s) to which they are attached form oxo.

In some embodiments, two adjacent $R^{10}$ together with the atoms to which they are attached form $C_3$-$C_{10}$ membered cycloalkyl or 4-10 membered heterocycloalkyl, wherein, the $C_3$-$C_{10}$ membered cycloalkyl or 4-10 membered heterocycloalkyl optionally substituted by 1, 2, or 3 substituents independently selected from D, halo, $C_1$-$C_6$ alkyl, $C_2$-$C_6$ alkenyl, $C_2$-$C_6$ alkynyl, $C_1$-$C_6$haloalkyl, $C_1$-$C_6$-cyanoalkyl, CN, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^e)(OR^d)$, $C(=NR^c)NR^cR^d$, $NR^dC(=NR^c)NR^cR^d$, $NR^dC(=NR^c)R^b$, $OP(O)OR^eOR^f$, $P(O)OR^eOR^f$, $S(O)(=NR^b)R^b$, $S(O)R^b$, $S(O)NR^cR^d$, $S(O)_2R^b$, $NR^cS(O)_2R^b$, $S(O)_2NR^cR^d$, $NR^eS(O)_2$ $NR^cR^d$, $NR^eS(O)(=NR^b)R^b$, $C_6$-$C_{10}$ aryl, $C_3$-$C_{10}$ cycloalkyl, 5-10 membered heteroaryl, and 4-10 membered heterocycloalkyl, wherein the $C_6$-$C_{10}$ aryl, $C_3$-$C_{10}$ cycloalkyl, 5-10 membered heteroaryl, 4-10 membered heterocycloalkyl is optionally substituted by 1, 2, 3 or 4 substituents independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$.

In some embodiments, two adjacent $R^{10}$ together with the atoms to which they are attached form $C_3$-$C_{10}$ membered cycloalkyl optionally substituted by 1, 2, or 3 substituents independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$-cyanoalkyl, CN, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^e)(OR^d)$, $C(=NR^c)NR^cR^d$, $NR^dC(=NR^c)NR^cR^d$, $NR^dC(=NR^c)R^b$, $OP(O)OR^eOR^f$, $P(O)OR^eOR^f$, $S(O)(=NR^b)R^b$, $S(O)R^b$, $S(O)NR^cR^d$, $S(O)_2R^b$, $NR'S(O)_2R^b$, $S(O)_2NR^cR^d$, $NR^cS(O)_2$ $NR^cR^d$, $NR^cS(O)(=NR^b)R^b$, $Cy^4$; wherein, $Cy^4$ is $C_6$-$C_{10}$ aryl, $C_3$-$C_{10}$ cycloalkyl, 5-10 membered heteroaryl, and 4-10 membered heterocycloalkyl; wherein, the $C_6$-$C_{10}$ aryl, $C_3$-$C_{10}$ cycloalkyl, 5-10 membered heteroaryl, 4-10 membered heterocycloalkyl is optionally substituted by 1, 2, 3 or 4 substituents independently selected from D, halo, CN, $NO_2$, OH, oxo, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$.

In some embodiments, two adjacent $R^{10}$ together with the atoms to which they are attached form 4-10 membered heterocycloalkyl optionally substituted by 1, 2, or 3 substituents independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$-cyanoalkyl, CN, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^eC(O)OR^a$, $B(OR^e)(OR^d)$, $C(=NR^c)NR^cR^d$, $NR^dC(=NR^c)NR^cR^d$, $NR^dC(=NR^c)R^b$, $OP(O)OR^eOR^f$, $P(O)OR^eOR^f$, $S(O)(=NR^b)R^b$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^eS(O)(=NR^b)R^b$, $Cy^4$; wherein, $Cy^4$ is $C_6$-$C_{10}$ aryl, $C_3$-$C_{10}$ cycloalkyl, 5-10 membered heteroaryl, and 4-10 membered heterocycloalkyl; wherein, the $C_6$-$C_{10}$ aryl, $C_3$-$C_{10}$ cycloalkyl, 5-10 membered heteroaryl, 4-10 membered heterocycloalkyl is optionally substituted by 1, 2, 3 or 4 substituents independently selected from D, halo, CN, $NO_2$, OH, oxo, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$.

In some embodiments, each $Cy^3$ is independently selected from optionally substituted $C_6$-$C_{10}$ aryl, $C_3$-$C_{10}$ cycloalkyl, 5-10 membered heteroaryl, or 4-10 membered heterocycloalkyl; each ring can be unsubstituted or substituted with 1, 2, 3, 4 or 5 substituents independently selected from $R^{12}$.

In some embodiments, $Cy^3$ is $C_6$-$C_{10}$ aryl optionally substituted with 1, 2, 3, 4 or 5 substituents independently selected from $R^{12}$. In some embodiments, $Cy^3$ is phenyl, naphthalenyl optionally substituted with 1, 2, 3, 4 or 5 substituents independently selected from $R^{12}$. In some embodiments, $Cy^3$ is phenyl optionally substituted with 1, 2, 3, 4 or 5 substituents independently selected from $R^{12}$.

In some embodiments, $Cy^3$ is 5-10 membered heteroaryl optionally substituted with 1, 2, 3, 4 or 5 substituents independently selected from $R^{12}$.

In some embodiments, $Cy^3$ is pyrrolyl, furanyl, thiophenyl, imidazolyl, oxazolyl, thiazolyl, tetrazolyl, pyrazolyl, triazolyl, thiadiazolyl, oxadiazolyl, pyridinyl, pyrimidinyl, pyrazinyl, pyridazinyl, indolyl, isoindolyl, indolizinyl, benzofuranyl, isobenzofuranyl, benzo[b]thiophenyl, benzo[c] thiophenyl, indazolyl, benzo[d]imidazolyl, pyrrolo[3,2-b] pyridinyl, pyrrolo[3,2-c]pyridinyl, pyrrolo[2,3-c]pyridinyl, pyrrolo[2,3-b]pyridinyl, pyrrolo[3,4-b]pyridinyl, pyrrolo[3,4-c]pyridinyl, benzo[d]isoxazolyl, benzo[d]oxazolyl, furo [3,2-b]pyridinyl, furo[3,2-c]pyridinyl, furo[2,3-c]pyridinyl, furo[2,3-b]pyridinyl, benzo[c]isoxazolyl, furo[3,4-b]pyridinyl, furo[3,4-c]pyridinyl, benzo[d]isothiazolyl, benzo[d]thiazolyl, thieno[3,2-b]pyridinyl, thieno[3,4-c]pyridinyl, benzo [d][1,2,3]triazolyl, pyrazolo[4,3-b]pyridinyl, pyrazolo[4,3-c]pyridinyl, pyrazolo[3,4-c]pyridinyl, pyrazolo[3,4-b] pyridinyl, imidazo[4,5-b]pyridinyl, imidazo[4,5-c] pyridinyl, imidazo[4,5-c]pyridinyl, imidazo[4,5-b] pyridinyl, pyrrolo[3,2-c]pyridazinyl, pyrrolo[3,2-d] pyrimidinyl, pyrrolo[2,3-b]pyrazinyl, pyrrolo[2,3-d] pyridazinyl, pyrrolo[2,3-d]pyrimidinyl, pyrrolo[2,3-c] pyridazinyl, pyrrolo[3,4-c]pyridazinyl, pyrrolo[3,4-d] pyrimidinyl, pyrrolo[3,4-b]pyrazinyl, pyrrolo[3,4-d] pyridazinyl, pyrrolo[3,4-d]pyrimidinyl, 6H-pyrrolo[3,4-c] pyridazinyl; each ring is optionally substituted with 1, 2, 3, 4 or 5 substituents independently selected from $R^{12}$.

In some embodiments, $Cy^3$ is pyrimidinyl optionally substituted with 1, 2, 3, 4 or 5 substituents independently selected from $R^{12}$. In some embodiments, $Cy^3$ is pyridazinyl optionally substituted with 1, 2, 3, 4 or 5 substituents independently selected from $R^{12}$. In some embodiments, $Cy^3$ is pyrazinyl optionally substituted with 1, 2, 3, 4 or 5 substituents independently selected from $R^{12}$. In other embodiments, $Cy^3$ is pyrazolyl optionally substituted with 1, 2, 3, 4 or 5 substituents independently selected from $R^{12}$.

In other embodiments, $Cy^3$ is $C_3$-$C_{10}$ cycloalkyl optionally substituted with 1, 2, 3, 4 or 5 substituents independently selected from $R^{12}$.

In other embodiments, $Cy^3$ is cycloheptyl optionally substituted with 1, 2, 3, 4 or 5 substituents independently selected from $R^{12}$. In other embodiments, $Cy^3$ is cyclohexanyl optionally substituted with 1, 2, 3, 4 or 5 substituents independently selected from $R^{12}$. In other embodiments, $Cy^3$ is cyclopentyl optionally substituted with 1, 2, 3, 4 or 5 substituents independently selected from $R^{12}$. In other embodiments, $Cy^3$ is cyclobutyl optionally substituted with 1, 2, 3, 4 or 5 substituents independently selected from $R^{12}$. In other embodiments, $Cy^3$ is cyclopropyl optionally substituted with 1, 2, 3, 4 or 5 substituents independently selected from $R^{12}$.

In other embodiments, $Cy^3$ is 4-10 membered heterocycloalkyl optionally substituted with 1, 2, 3, 4 or 5 substituents independently selected from $R^{12}$.

In some embodiments, $Cy^3$ is azetidinyl, oxetanyl, thietanyl, pyrrolidinyl, tetrahydrofuranyl, tetrahydrothiophenyl, piperidinyl, dioxanyl tetrahydropyranyl, tetrahydrothiopyranyl, piperazinyl, morpholinyl, azepanyl, diazocanyl, diazepanyl, azepanyl; each ring is optionally substituted with 1, 2, 3, 4 or 5 $R^{12}$.

In some embodiments, $Cy^3$ is 4-methylpiperazin-1-yl.

In other embodiments, each $R^{11}$ is independently selected from H, D, halo, CN, $NO_2$, $N_3$, $C_1$-$C_6$ alkyl, $C_2$-$C_6$ alkenyl, $C_2$-$C_6$ alkynyl, $C_1$-$C_6$ haloalkyl, $C_1$-$C_6$ alkylOH, $C_1$-$C_6$ alkyl-O—$C_1$-$C_6$ alkyl, $OR^{a1}$, $SR^{a1}$, $SF_5$, $NHOR^{a1}$, $C(O)R^{b1}$, $C(O)NR^{c1}R^{d1}$, $C(O)OR^{a1}$, $OC(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b}1$, $P(O)OR^{e1}OR^{f1}$, $OP(O)OR^{e1}OR^{f1}$, $S(O)(=NR^{b}1)R^{b}1$, $S(O)R^{b1}$, $S(O)NR^{c1}R^{d1}$, $S(O)_2R^{b1}$, $NR^{c1}S(O)_2R^{b}1$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl.

In some embodiments, each $R^{11}$ is independently selected from H, D, halo, CN, $NO_2$, $N_3$, $SF_5$, $C_1$-$C_6$ alkyl, $C_2$-$C_6$ alkenyl, $C_2$-$C_6$ alkynyl, $C_1$-$C_6$ haloalkyl, $OC_1$-$C_6$ alkylOH, $OC_1$-$C_6$ alkyl-0-$C_1$-$C_6$ alkyl, $OR^{a1}$, $SR^{a1}$, $C(O)R^{b1}$, $C(O)NR^{c1}R^{d1}$, $S(O)_2R^{b1}$, $C_6$-$C_{10}$ aryl, $C_3$-$C_{10}$ cycloalkyl, 5-10 membered heteroaryl, and 4-10 membered heterocycloalkyl; wherein, the $C_6$-$C_{10}$ aryl, $C_3$-$C_{10}$ cycloalkyl, 5-10 membered heteroaryl, 4-10 membered heterocycloalkyl can be unsubstituted or substituted independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$.

In some embodiments, each $R^{11}$ is independently selected from H, D, halo, CN, $NO_2$, $N_3$, $SF_5$. In some embodiments, each $R^{11}$ is independently selected from H. In some embodiments, each $R^{11}$ is independently selected from D. In some embodiments, each $R^{11}$ is independently selected from halo (such as F, Cl, Br, I). In some embodiments, each $R^{11}$ is independently selected from CN. In some embodiments, each $R^{11}$ is independently selected from $NO_2$. In some embodiments, each $R^{11}$ is independently selected from $N_3$. In some embodiments, each $R^{11}$ is independently selected from $SF_5$.

In some embodiments, each $R^{11}$ is independently selected from $C_1$-$C_6$ alkyl, $C_2$-$C_6$ alkenyl, $C_2$-$C_6$ alkynyl, $C_1$-$C_6$ haloalkyl, $OC_1$-$C_6$ alkylOH, $OC_1$-$C_6$ alkyl-O—$C_1$-$C_6$ alkyl. In some embodiments, for example, each $R^{11}$ is independently selected from $CH_3$, $CH_2CH_3$, $CH_2CH_2CH_3$, $CH(CH_3)_2$, $C(CH_3)_3$, $CH_2F$, $CHF_2$, $CF_3$, $OCH_2CH_2OH$, $OCH_2CH_2OCH_3$.

In some embodiments, each $R^{11}$ is independently selected from $OR^{a1}$. In some embodiments, for example, each $R^{11}$ is independently selected from OH, $OCH_3$, $OCH_2CH_3$, $OCH_2CH_2CH_3$, $OCH(CH_3)_2$, $OCH_2F$, $OCHF_2$, $OCF_3$.

In some embodiments, each $R^{11}$ is independently selected from $SR^{a1}$. In some embodiments, each $R^{11}$ is independently selected from $SCH_3$, etc.

In some embodiments, each $R^{11}$ is independently selected from $NHOR^{a1}$. In some embodiments, each $R^{11}$ is independently selected from $C(O)R^{b1}$. In some embodiments, each $R^{11}$ is independently selected from $C(O)NR^{c1}R^{d1}$. In some embodiments, each $R^{11}$ is independently selected from $C(O)OR^{a1}$. In some embodiments, each $R^{11}$ is independently selected from $OC(O)OR^{a1}$. In some embodiments, each $R^{11}$ is independently selected from $OC(O)R^{b1}$. In some embodiments, each $R^{11}$ is independently selected from $OC(O)NR^{c1}R^{d1}$.

In some embodiments, each $R^{11}$ is independently selected from $NR^{c1}R^{d1}$. In some embodiments, each $R^{11}$ is independently selected from $NR^{c1}C(O)R^{b1}$. In some embodiments, each $R^{11}$ is independently selected from $NR^{c1}C(O)NR^{c1}R^{d1}$. In some embodiments, each $R^{11}$ is independently selected from $NR^{c1}C(O)OR^{a1}$ In some embodiments, each $R^{11}$ is independently selected from $B(OR^{c1})(OR^{d1})$. In some embodiments, each $R^{11}$ is independently selected from $C(=NR^{c1})NR^{c1}R^{d1}$. In some embodiments, each $R^{11}$ is independently selected from $NR^{d1}C(=NR^{c1})NR^{c1}R^{d1}$. In some embodiments, each $R^{11}$ is independently selected from $NR^{d1}C(=NR^{c1})R^{b1}$.

In some embodiments, each $R^{11}$ is independently selected from $P(O)OR^{e1}OR^{f1}$. In some embodiments, each $R^{11}$ is independently selected from $OP(O)OR^{e1}OR^{f1}$.

In some embodiments, each $R^{11}$ is independently selected from $S(O)(=NR^{b1})R^{b1}$. In some embodiments, each $R^{11}$ is independently selected from $S(O)R^{b1}$. In some embodiments, each $R^{11}$ is independently selected from $S(O)NR^{c1}R^{d1}$.

In some embodiments, each $R^{11}$ is independently selected from $S(O)_2R^{b1}$. In some embodiments, each $R^{11}$ is independently selected from $NR^{c1}S(O)_2R^{b1}$. In some embodiments, each $R^{11}$ is independently selected from $S(O)_2NR^{c1}R^{d1}$. In some embodiments, each $R^{11}$ is independently selected from $NR^{c1}S(O)_2NR^{c1}R^{d1}$. In some embodiments, each $R^{11}$ is independently selected from $NR^{e1}S(O)(=NR^{b1})R^{b1}$.

In some embodiments, each $R^{11}$ is independently selected from $C_6$-$C_{10}$ aryl, $C_3$-$C_{10}$ cycloalkyl, 5-10 membered heteroaryl, and 4-10 membered heterocycloalkyl; wherein, the $C_6$-$C_{10}$ aryl, $C_3$-$C_{10}$ cycloalkyl, 5-10 membered heteroaryl, 4-10 membered heterocycloalkyl can be unsubstituted or substituted by 1, 2, 3, 4 or 5 substituents independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$.

In some embodiments, each $R^{12}$ is independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$ alkylOH, $C_1$-$C_6$ alkyl-O—$C_1$-$C_6$ alkyl, CN, $NO_2$, $N_3$, $OR^{a1}$, $SR^{a1}$, $SF_5$, $NHOR^{a1}$, $C(O)R^{b}1$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b1}$, $P(O)R^{e1}R^{f1}$, $P(O)OR^{e1}OR^{f1}$, $OP(O)OR^{e1}OR^{f1}$, $S(O)(=NR^{b1})R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl, wherein the $C_6$-$C_{10}$ aryl, $C_3$-$C_{10}$ cycloalkyl, 5-10 membered heteroaryl, 4-10 membered heterocycloalkyl can be unsubstituted or substituted independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$.

In some embodiments, each $R^{12}$ is independently selected from D, halo, CN, $NO_2$, $N_3$, $OR^{a1}$, $SR^{a1}$, $SF_5$, or $NHOR^{a1}$. In some embodiments, each $R^{12}$ is independently selected from D.

In some embodiments, each $R^{12}$ is independently selected from halo (such as F, Cl, Br, I). In some embodiments, each $R^{12}$ is independently selected from CN. In some embodiments, each $R^{12}$ is independently selected from $NO_2$. In some embodiments, each $R^{12}$ is independently selected from $N_3$. In some embodiments, each $R^{12}$ is independently selected from $OR^{a1}$ (such as OH, $OCH_3$, $OCH_2CH_3$, $OCH_2F$, $OCHF_2$, $OCF_3$). In some embodiments, each $R^{12}$ is independently selected from $SR^{a1}$ (such as $SCH_3$). In some embodiments, each $R^{12}$ is independently selected from $SF_5$. In some embodiments, each $R^{12}$ is independently selected from $NHOR^{a1}$.

In some embodiments, each $R^{12}$ is independently selected from $C(O)R^{b1}$. In some embodiments, each $R^{12}$ is independently selected from $C(O)NR^{c1}R^{d1}$. In some embodiments, each $R^{12}$ is independently selected from $C(O)OR^{a1}$.

In some embodiments, each $R^{12}$ is independently selected from $OC(O)R^{b1}$. In some embodiments, each $R^{12}$ is independently selected from $OC(O)NR^{c1}R^{d1}$.

In some embodiments, each $R^{12}$ is independently selected from $NR^{c1}R^{d1}$ (such as $NH_2$, $NHCH_3$, $N(CH_3)_2$). In some embodiments, each $R^{12}$ is independently selected from $NR^{c1}C(O)R^{b1}$. In some embodiments, each $R^{12}$ is independently selected from $NR^{c1}C(O)NR^{c1}R^{d1}$. In some embodiments, each $R^{12}$ is independently selected from $NR^{c1}C(O)OR^{a1}$.

In some embodiments, each $R^{12}$ is independently selected from $B(OR^{c1})(OR^{d1})$. In some embodiments, each $R^{12}$ is independently selected from $C(=NR^{c1})NR^{c1}R^{d1}$. In some embodiments, each $R^{12}$ is independently selected from $NR^{d1}C(=NR^{c1})NR^{c1}R^{d1}$. In some embodiments, each $R^{12}$ is independently selected from $NR^{d1}C(=NR^{c1})R^{b1}$.

In some embodiments, each $R^{12}$ is independently selected from $P(O)R^{e1}R^{f1}$. In some embodiments, each $R^{12}$ is independently selected from $P(O)OR^{e1}OR^{f1}$. In some embodiments, each $R^{12}$ is independently selected from $OP(O)OR^{e1}OR^{f1}$.

In some embodiments, each $R^{12}$ is independently selected from $S(O)(=NR^{b1})R^{b1}$. In some embodiments, each $R^{12}$ is independently selected from $S(O)R^{b1}$. In some embodiments, each $R^{12}$ is independently selected from $S(O)NR^{c1}R^{d1}$.

In some embodiments, each $R^{12}$ is independently selected from $S(O)_2R^{b1}$. In some embodiments, each $R^{12}$ is independently selected from $NR^{c1}S(O)_2R^{b1}$. In some embodiments, each $R^{12}$ is independently selected from $S(O)_2NR^{c1}R^{d1}$. In some embodiments, each $R^{12}$ is independently selected from $NR^{c1}S(O)_2NR^{c1}R^{d1}$. In some embodiments, each $R^{12}$ is independently selected from $NR^{c1}S(O)(=NR^{b1})R^{b1}$.

In other embodiments, each $R^{12}$ is independently selected from $C_1$-$C_6$ alkyl, $C_2$-$C_6$ alkenyl, $C_2$-$C_6$ alkynyl, $C_1$-$C_6$ haloalkyl, $C_1$-$C_6$ alkylOH, $C_1$-$C_6$ alkyl-O—$C_1$-$C_6$ alkyl. In other embodiments, for example, each $R^{12}$ is independently selected from $CH_3$, $CH_2CH_3$, $CH_2CH_2CH_3$, $CH(CH_3)_2$, $C(CH_3)_3$, $CH_2F$, $CHF_2$, $CF_3$, $CH_2CF_3$, $CH_2OH$, $CH_2CH_2OH$, $CH(OH)CH_3$, $CH_2OCH_3$.

In other embodiments, each $R^{12}$ is independently selected from $C_6$-$C_{10}$ aryl, $C_3$-$C_{10}$ cycloalkyl, 5-10 membered heteroaryl, and 4-10 membered heterocycloalkyl; wherein, the $C_6$-$C_{10}$ aryl, $C_3$-$C_{10}$ cycloalkyl, 5-10 membered heteroaryl, 4-10 membered heterocycloalkyl can be unsubstituted or substituted by 1, 2, 3, 4 or 5 substituents independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, or $SF_5$.

In other embodiments, each $R^{13}$ is independently selected from H, D, OH, CN, halo, oxo, $C_1$-$C_4$ alkyl, $C_1$-$C_4$haloalkyl, $C_1$-$C_4$ cyanoalkyl, $OC_1$-$C_4$ alkyl, $OC_1$-$C_4$haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, $C_1$-$C_4$ alkyl-O—$C_1$-$C_4$ alkyl, $C_1$-$C_4$ alkyl-O—$C_1$-$C_4$haloalkyl, optionally substituted $C_3$-$C_7$ cycloalkyl, or optionally substituted 4-7 membered heterocycloalkyl, $SF_5$, $OR^a$, $SR^a$, $C(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$; wherein, the optionally substituted substituent is selected from D, halo, CN, OH, $C_1$-$C_4$ alkyl, $C_1$-$C_4$haloalkyl, —O—$C_1$-$C_4$ alkyl, —$OC_1$-$C_4$ haloalkyl.

In other embodiments, each $R^{13}$ is independently selected from H, D, OH, CN, halo, oxo, $SF_5$. In some embodiments, each $R^{13}$ is independently selected from H. In some embodiments, each $R^{13}$ is independently selected from D. In some embodiments, each $R^{13}$ is independently selected from OH. In some embodiments, each $R^{13}$ is independently selected from CN. In some embodiments, each $R^{13}$ is independently selected from halo (such as F, Cl, Br). In some embodiments, each $R^{13}$ is independently selected from oxo. In some embodiments, each $R^{13}$ is independently selected from $SF_5$.

In other embodiments, each $R^{13}$ is independently selected from $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl. In some embodiments, for example, each $R^{13}$ is independently selected from $CH_3$, $CH_2CH_3$, $CH_2CH_2CH_3$, $CH(CH_3)_2$, $C(CH_3)_3$, $CH_2F$, $CHF_2$, $CF_3$, $CH_2CF_3$, $OCH_3$, $OCH_2CH_3$, $OCF_3$, $OCH_2CH_2OH$, $OCH_2CH_2OCH_3$, $OCH_2CH_2OCF_3$.

In other embodiments, each $R^{13}$ is independently selected from optionally substituted $C_3$-$C_7$ cycloalkyl, or optionally substituted 4-7 membered heterocycloalkyl; wherein, the optionally substituted substituent is selected from D, halo, CN, OH, $C_1$-$C_4$ alkyl, $C_1$-$C_4$haloalkyl, —O—$C_1$-$C_4$ alkyl, —$OC_1$-$C_4$haloalkyl.

In some embodiments, each $R^{13}$ is independently selected from $C_3$-$C_7$ cycloalkyl optionally substituted with D, halo, CN, OH, $C_1$-$C_4$ alkyl, $C_1$-$C_4$haloalkyl, —O—$C_1$-$C_4$ alkyl, —$OC_1$-$C_4$ haloalkyl.

In some embodiments, each $R^{13}$ is independently selected from 4-7 membered heterocycloalkyl optionally substituted with D, halo, CN, OH, $C_1$-$C_4$ alkyl, $C_1$-$C_4$haloalkyl, —O—$C_1$-$C_4$ alkyl, —$OC_1$-$C_4$haloalkyl.

In other embodiments, each $R^{13}$ is independently selected from $OR^a$, $SR^a$, $C(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$.

In some embodiments, each $R^{13}$ is independently selected from $OR^a$. In some embodiments, each $R^{13}$ is independently selected from $SR^a$.

In some embodiments, each $R^{13}$ is independently selected from $C(O)R^b$. In some embodiments, each $R^{13}$ is independently selected from $OC(O)NR^cR^d$.

In some embodiments, each $R^{13}$ is independently selected from $NR^cR^d$. In some embodiments, each $R^{13}$ is independently selected from $NR^cC(O)R^b$. In some embodiments, each $R^{13}$ is independently selected from $NR^cC(O)NR^cR^d$. In some embodiments, each $R^{13}$ is independently selected from $NR^cC(O)OR^a$.

In some embodiments, each $R^{13}$ is independently selected from $S(O)R^b$. In some embodiments, each $R^{13}$ is independently selected from $S(O)NR^cR^d$.

In some embodiments, each $R^{13}$ is independently selected from $S(O)_2R^b$. In some embodiments, each $R^{13}$ is independently selected from $NR^cS(O)_2R^b$. In some embodiments, each $R^{13}$ is independently selected from $S(O)_2NR^cR^d$.

In some embodiments, each $R^{13}$ is independently selected from NR $S(O)_2NR^cR^d$. In some embodiments, each $R^{13}$ is independently selected from $B(OR^c)(OR^d)$.

In some embodiments, $R^{14}$ and $R^{16}$ are each selected from H, D, $C_1$-$C_6$ alkyl, $C_1$-$C_6$ haloalkyl, $C_2$-$C_6$ alkenyl, $C_2$-$C_6$ alkynyl, $C_1$-$C_6$ alkyl-OH, $C_1$-$C_6$ alkyl-CN, $C_1$-$C_6$ alkyl-O—$C_1$-$C_6$ alkyl.

In some embodiments, $R^{14}$ is H. In some embodiments, $R^{14}$ is D. In some embodiments, $R^{14}$ is $C_1$-$C_6$ alkyl. In some embodiments, $R^{14}$ is $C_1$-$C_6$ haloalkyl. In some embodiments, $R^{14}$ is $C_2$-$C_6$ alkenyl. In some embodiments, $R^{14}$ is $C_2$-$C_6$ alkynyl. In some embodiments, $R^{14}$ is $C_1$-$C_6$ alkyl-OH. In some embodiments, $R^{14}$ is $C_1$-$C_6$ alkyl-CN. In some embodiments, $R^{14}$ is $C_1$-$C_6$ alkyl-O—$C_1$-$C_6$ alkyl.

In some embodiments, $R^{16}$ is H. In some embodiments, $R^{16}$ is D. In some embodiments, $R^{16}$ is $C_1$-$C_6$ alkyl. In some embodiments, $R^{16}$ is $C_1$-$C_6$ haloalkyl. In some embodiments, $R^{16}$ is $C_2$-$C_6$ alkenyl. In some embodiments, $R^{16}$ is $C_2$-$C_6$ alkynyl. In some embodiments, $R^{16}$ is $C_1$-$C_6$ alkyl-OH. In some embodiments, $R^{16}$ is $C_1$-$C_6$ alkyl-CN. In some embodiments, $R^{16}$ is $C_1$-$C_6$ alkyl-O—$C_1$-$C_6$ alkyl.

In compounds of Formula I, $R^A$ is independently selected from H, D, $C_1$-$C_6$ alkyl, $C_2$-$C_4$ alkenyl, $C_2$-$C_4$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_4$ alkenyl, $C_2$-$C_4$ alkynyl, $C_3$-$C_{10}$cycloalkyl, 4-10 membered heterocyclalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^eS(O)(=NR^b)R^b$.

In some embodiments, $R^A$ is independently selected from H, D, $C_1$-$C_6$ alkyl, $C_2$-$C_4$ alkenyl or $C_2$-$C_4$ alkynyl, wherein, the $C_1$-$C_6$ alkyl, $C_2$-$C_4$ alkenyl or $C_2$-$C_4$ alkynyl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^eS(O)(=NR^b)R^b$.

In other embodiments, $R^A$ is independently selected from $C_3$-$C_{10}$ cycloalkyl, 4-10 membered heterocycloalkyl, $C_6$-$C_{10}$ aryl, 5-10 membered heteroaryl; wherein; the $C_3$-$C_{10}$ cycloalkyl, 4-10 membered heterocyclalkyl, $C_6$-$C_{10}$ aryl, 5-10 membered heteroaryl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^eS(O)(=NR^b)R^b$.

In some embodiments, $R^A$ is independently selected from arylalkyl, heteroarylalkyl, cycloalkylalkyl, or heterocycloalkyl-alkyl; wherein; the arylalkyl, heteroarylalkyl, cycloalkylalkyl, or heterocycloalkylalkyl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^cS(O)(=NR^b)R^b$.

In other embodiments, $R^A$ is independently selected from $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein; the $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^cS(O)(=NR^b)R^b$.

In compounds of Formula I, $R^B$ is independently selected from H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_{10}$cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from $R^{13}$.

In some embodiments, $R^B$ is independently selected from H, D, $C_1$-$C_6$ alkyl, $C_2$-$C_6$ alkenyl or $C_2$-$C_6$ alkynyl, wherein, the $C_1$-$C_6$ alkyl, $C_2$-$C_6$ alkenyl, or $C_2$-$C_6$ alkynyl is optionally substituted with 1, 2, 3, 4 or 5 substituents independently selected from $R^{13}$.

In some embodiments, $R^B$ is $C_2$-$C_6$ alkynyl optionally substituted with 1, 2, 3, 4 or 5 substituents independently selected from $R^{13}$.

In some embodiments, $R^B$ is $C_2$-$C_6$ alkenyl optionally substituted with 1, 2, 3, 4 or 5 substituents independently selected from $R^{13}$.

In some embodiments, $R^B$ is $C_1$-$C_6$ alkyl optionally substituted with 1, 2, 3, 4 or 5 substituents independently selected from $R^{13}$.

In some embodiments, $R^B$ is $C_1$-$C_6$ alkyl. In some embodiments, $R^B$ is methyl. In some embodiments, $R^B$ is ethyl. In some embodiments, $R^B$ is n-propyl. In some embodiments, $R^B$ is isopropyl. In some embodiments, $R^B$ is isobutyl. In some embodiments, $R^B$ is tert-butyl.

In some embodiments, $R^B$ is $C_3$-$C_{10}$ cycloalkyl optionally substituted with 1, 2, 3, 4 or 5 substituents independently selected from $R^{13}$. In some embodiments, $R^B$ is cyclopropyl optionally substituted with 1, 2, 3, 4 or 5 substituents independently selected from $R^{13}$. In some embodiments, $R^B$ is cyclobutyl optionally substituted with 1, 2, 3, 4 or 5 substituents independently selected from $R^{13}$. In some embodiments, $R^B$ is cycylopentyl optionally substituted with 1, 2, 3, 4 or 5 substituents independently selected from $R^{13}$. In some embodiments, $R^B$ is cycylohexanyl optionally substituted with 1, 2, 3, 4 or 5 substituents independently selected from $R^{13}$.

In other embodiments, $R^B$ is 4-10 membered heterocycloalkyl optionally substituted with 1, 2, 3, 4 or 5 substituents independently selected from $R^{13}$. In some embodiments, $R^B$ is azetidinyl, oxetanyl, thietanyl, pyrrolidinyl, tetrahydrofuranyl, tetrahydrothiophenyl, piperidinyl, dioxanyl tetrahydropyranyl, tetrahydrothiopyranyl, piperazinyl, morpholinyl, azepanyl, diazocanyl, diazepanyl, azepanyl; each ring is optionally substituted with 1, 2, 3, 4 or 5 substituents independently selected from $R^{13}$.

In other embodiments, $R^B$ is $C_6$-$C_{10}$ aryl optionally substituted with 1, 2, 3, 4 or 5 substituents independently selected from $R^{13}$. In other embodiments, $R^B$ is phenyl, naphthalenyl; each ring is optionally substituted with 1, 2, 3, 4 or 5 substituents independently selected from $R^{13}$.

In other embodiments, $R^B$ is 5-10 membered heteroaryl optionally substituted with 1, 2, 3, 4 or 5 substituents independently selected from $R^{13}$.

In other embodiments, $R^B$ is pyrrolyl, furanyl, thiophenyl, imidazolyl, oxazolyl, thiazolyl, tetrazolyl, pyrazolyl, triazolyl, thiadiazolyl, oxadiazolyl, pyridinyl, pyrimidinyl, pyrazinyl, pyridazinyl, indolyl, isoindolyl, indolizinyl, benzofuranyl, isobenzofuranyl, benzo[b]thiophenyl, benzo[c]thiophenyl, indazolyl, benzo[d]imidazolyl, pyrrolo[3,2-b]pyridinyl, pyrrolo[3,2-c]pyridinyl, pyrrolo[2,3-c]pyridinyl, pyrrolo[2,3-b]pyridinyl, pyrrolo[3,4-b]pyridinyl, pyrrolo[3,4-c]pyridinyl, benzo[d]isoxazolyl, benzo[d]oxazolyl, furo[3,2-b]pyridinyl, furo[3,2-c]pyridinyl, furo[2,3-c]pyridinyl, furo[2,3-b]pyridinyl, benzo[c]isoxazolyl, furo[3,4-b]pyridinyl, furo[3,4-c]pyridinyl, benzo[d]isothiazolyl, benzo[d]thiazolyl, thieno[3,2-b]pyridinyl, thieno[3,4-c]pyridinyl, benzo[d][1,2,3]triazolyl, pyrazolo[4,3-b]pyridinyl, pyrazolo[4,3-c]pyridinyl, pyrazolo[3,4-c]pyridinyl, pyrazolo[3,4-b]pyridinyl, imidazo[4,5-b]pyridinyl, imidazo[4,5-c]pyridinyl, imidazo[4,5-c]pyridinyl, imidazo[4,5-b]pyridinyl, pyrrolo[3,2-c]pyridazinyl, pyrrolo[3,2-d]pyrimidinyl, pyrrolo[2,3-b]pyrazinyl, pyrrolo[2,3-d]pyridazinyl, pyrrolo[2,3-d]pyrimidinyl, pyrrolo[2,3-c]pyridazinyl, pyrrolo[3,4-c]pyridazinyl, pyrrolo[3,4-d]pyrimidinyl, pyrrolo[3,4-b]pyrazinyl, pyrrolo[3,4-d]pyridazinyl, pyrrolo[3,4-d]pyrimidinyl, 6H-pyrrolo[3,4-c]pyridazinyl; each ring is optionally substituted with 1, 2, 3, 4 or 5 substituents independently selected from $R^{13}$.

In other embodiments, $R^B$ is arylalkyl, heteroarylalkyl, cycloalkylalkyl, or heterocycloalkylalkyl; wherein, the arylalkyl, heteroarylalkyl, cycloalkylalkyl, or heterocycloalkylalkyl is optionally substituted with 1, 2, 3, 4 or 5 substituents independently selected from $R^{13}$.

In some embodiments, $R^B$ is $C_6$-$C_{11}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein; the $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, 3, 4 or 5 substituents independently selected from $R^{13}$.

In some embodiments, $R^C$ and $R^D$ are each independently selected from H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein the $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, 3, 4 or 5 substituents independently selected from D, OH, CN, halo, oxo, $C_1$-$C_4$ alkyl, $C_1$-$C_4$haloalkyl, $C_1$-$C_4$ cyanoalkyl, $OC_1$-$C_4$ alkyl, $OC_1$-$C_4$haloalkyl, $C_1$-$C_4$ alkyl-O—$C_1$-$C_4$ alkyl, $C_1$-$C_4$ alkyl-O—$C_1$-$C_4$ haloalkyl, $OC_2$-$C_4$ alkylOH, $OC_2$-$C_4$ alkyl-O—$C_1$-$C_4$ alkyl, $OC_2$-$C_4$alkyl-O—$C_1$-$C_4$haloalkyl, $SF_5$, $OC(O)NR^cR^d$, $NR^cR^d$, $NR^cC(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$.

In some embodiments, $R^C$ is independently selected from H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein the $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, 3, 4 or 5 substituents independently selected from D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$haloalkyl, $SF_5$, OC(O)$NR^cR^d$, $NR^cR^d$, $NR^c$C(O)$R^b$, S(O)$NR^cR^d$, $S(O)_2R^b$, NR $S(O)_2R^b$, $S(O)_2NR^cR^d$, $NR^cS(O)_2NR^cR^d$, or B($OR^c$)($OR^d$).

In some embodiments, $R^D$ is independently selected from H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein the $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, 3, 4 or 5 substituents independently selected from D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$haloalkyl, $SF_5$, OC(O)$NR^cR^d$, $NR^cR^d$, $NR^c$C(O)$R^b$, S(O)$NR^cR^d$, $S(O)_2R^b$, $NR^cS(O)_2R^b$, $S(O)_2NR^cR^d$, $NR^cS(O)_2NR^cR^d$, or B($OR^c$)($OR^d$).

In other embodiments, $R^C$ and $R^D$ together with the N atom to which they are attached form 4-7 membered heterocycloalkyl optionally substituted with 1, 2, 3, 4 or 5 substituents independently selected from D, OH, oxo, CN, —$NH_2$, —NH($C_1$-$C_4$ alkyl), —N($C_1$-$C_4$ alkyl)$_2$, halo, $C_1$-$C_4$ alkyl, $C_1$-$C_4$haloalkyl, $C_1$-$C_4$ cyanoalkyl, $OC_1$-$C_4$ alkyl, $OC_1$-$C_4$haloalkyl, $OC_2$-$C_4$ alkylOH, $OC_2$-$C_4$ alkyl-O—$C_1$-$C_4$ alkyl, or $OC_2$-$C_4$ alkyl-O—$C_1$-$C_4$haloalkyl.

In some embodiments, each $R^E$ is independently selected from H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl.

In some embodiments, each $R^F$ is independently selected from H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl.

In some embodiments, each $R^a$ is independently selected from H, D.

In some embodiments, each $R^a$ is independently selected from $C_1$-$C_4$ alkyl, $C_2$-$C_4$ alkenyl, $C_2$-$C_4$ alkynyl; wherein, the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, or $C_1$-$C_4$haloalkoxy.

In some embodiments, each $R^a$ is independently selected from phenyl, $C_3$-$C_7$ cycloalkyl, 5-6 membered heteroaryl, or 4-7 membered heterocycloalkyl; wherein, the phenyl, $C_3$-$C_7$ cycloalkyl, 5-6 membered heteroaryl, or 4-7 membered heterocycloalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, or $C_1$-$C_4$ haloalkoxy.

In some embodiments, each $R^b$ is independently selected from H, D.

In some embodiments, each $R^b$ is independently selected from $C_1$-$C_4$ alkyl, $C_2$-$C_4$ alkenyl, $C_2$-$C_4$ alkynyl; wherein, the $C_1$-$C_4$ alkyl, $C_2$-$C_4$ alkenyl, $C_2$-$C_4$ alkynyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, $C_1$-$C_4$haloalkoxy, $C_6$-$C_{10}$ aryl, $C_3$-$C_{10}$ cycloalkyl, 5-10 membered heteroaryl, or 4-10 membered heterocycloalkyl.

In some embodiments, each $R^b$ is independently selected from phenyl, $C_3$-$C_7$ cycloalkyl, 5-6 membered heteroaryl, or 4-7 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein, the phenyl, $C_3$-$C_7$ cycloalkyl, 5-6 membered heteroaryl, or 4-7 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, $C_1$-$C_4$ haloalkoxy, $C_6$-$C_{10}$ aryl, $C_3$-$C_{10}$ cycloalkyl, 5-10 membered heteroaryl, or 4-10 membered heterocycloalkyl.

In some embodiments, $R^c$ and $R^d$ are each independently selected from H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, 4-10 membered heterocycloalkyl-$C_1$-$C_6$ alkyl, $C_6$-$C_{10}$ aryl-$C_3$-$C_{10}$ cycloalkyl, $C_{10}$ aryl-4-10 membered heterocycloalkyl, $C_6$-$C_{10}$ aryl-5-10 membered heteroaryl, bi($C_6$-$C_{10}$ aryl), 5-10 membered heteroaryl-$C_3$-$C_{10}$ cycloalkyl, 5-10 membered heteroaryl-4-10 membered heterocycloalkyl, 5-10 membered heteroaryl-$C_6$-$C_{10}$ aryl, or bi(5-10 membered heteroaryl); wherein the $C_{1-4}$ alkyl, $C_{2-4}$ alkenyl, $C_{2-4}$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, 4-10 membered heterocycloalkyl-$C_1$-$C_6$ alkyl, $C_6$-$C_{10}$ aryl-$C_3$-$C_{10}$ cycloalkyl, $C_6$-$C_{10}$ aryl-4-10 membered heterocycloalkyl, $C_6$-$C_{10}$ aryl-5-10 membered heteroaryl, bi($C_6$-$C_{10}$ aryl), 5-10 membered heteroaryl-$C_3$-$C_{10}$ cycloalkyl, 5-10 membered heteroaryl-4-10 membered heterocycloalkyl, 5-10 membered heteroaryl-$C_6$-$C_{10}$ aryl, or bi(5-10 membered heteroaryl) is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, C(O)$OR^{a1}$, C(O)$R^{b1}$, $S(O)_2R^{b1}$, $C_1$-$C_4$ alkyl-O—$C_1$-$C_4$ alkyl, and $C_1$-$C_4$ alkyl-O—$C_1$-$C_4$ alkyl-O—.

In some embodiments, $R^c$ and $R^d$ together with the N atom to which they are attached form 4-7 membered heterocycloalkyl (such as 4-membered heterocycloalkyl, 5-membered heterocycloalkyl, 6-membered heterocycloalkyl, 7-membered heterocycloalkyl) optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, C(O)$OR^{a1}$, C(O)$R^{b1}$, $S(O)_2R^{b1}$, $C_1$-$C_4$ alkoxy-$C_1$-$C_4$ alkyl, and $C_1$-$C_4$ alkoxy-$C_1$-$C_4$ alkoxy.

In some embodiments, each $R^e$ is each independently selected from H. In some embodiments, each $R^e$ is each independently selected from D.

In some embodiments, each $R^e$ is each independently selected from $C_1$-$C_4$ alkyl. In some embodiments, each $R^e$ is each independently selected from $C_1$-$C_4$ haloalkyl, In some embodiments, each $R^e$ is each independently selected from $C_2$-$C_4$ alkenyl.

In some embodiments, each $R^e$ is each independently selected from ($C_1$-$C_4$ alkoxy)-$C_1$-$C_4$ alkyl. In some embodiments, each $R^e$ is each independently selected from $C_2$-$C_4$ alkynyl.

In some embodiments, each $R^e$ is each independently selected from $C_6$-$C_{10}$ aryl. In some embodiments, each $R^e$ is each independently selected from 5-10 membered heteroaryl. In some embodiments, each $R^e$ is each independently selected from $C_3$-$C_{10}$ cycloalkyl. In some embodiments, each $R^e$ is each independently selected from 3-10 membered heterocycloalkyl.

In some embodiments, each $R^e$ is each independently selected from $C_6$-$C_{10}$ aryl-$C_1$-$C_4$ alkyl. In some embodiments, each $R^e$ is each independently selected from $C_3$-$C_{10}$ cycloalkyl-$C_1$-$C_4$ alkyl. In some embodiments, each $R^e$ is each independently selected from 5-10 membered heteroaryl-$C_1$-$C_4$ alkyl. In some embodiments, each $R^e$ is each independently selected from 4-10 membered heterocycloalkyl-$C_1$-$C_4$ alkyl.

In some embodiments, each $R^f$ is independently selected from H, D.

In some embodiments, each $R^f$ is independently selected from $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl.

In some embodiments, each $R^{a1}$ is independently selected from H, D.

In some embodiments, each $R^{a1}$ is independently selected from $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl; wherein, the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, or $C_1$-$C_4$ haloalkoxy.

In some embodiments, each $R^{b1}$ is independently selected from H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein, the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$haloalkoxy, $C_6$-$C_{10}$ aryl, $C_3$-$C_{10}$ cycloalkyl, 5-10 membered heteroaryl, or 4-10 membered heterocycloalkyl.

In some embodiments, $R^{c1}$ and $R^{d1}$ are each independently selected from H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl; wherein the $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_6$ alkyl, 5-10 membered heteroaryl-$C_1$-$C_6$ alkyl, $C_3$-$C_{10}$ cycloalkyl-$C_1$-$C_6$ alkyl, or 4-10 membered heterocycloalkyl-$C_1$-$C_6$ alkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, or $C_1$-$C_4$haloalkoxy.

In some embodiments, $R^{c1}$ and $R^{d1}$ together with the N atom to which they are attached form a 4-7 membered heterocycloalkyl (such as 4-membered heterocycloalkyl, 5-membered heterocycloalkyl, 6-membered heterocycloalkyl, 7-membered heterocycloalkyl) optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, and $C_1$-$C_4$ haloalkoxy.

In some embodiments, each $R^{e1}$ is each independently selected from H, D.

In some embodiments, each $R^{e1}$ is each independently selected from $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 3-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl.

In some embodiments, each $R^{f1}$ is independently selected from H, D.

In some embodiments, each $R^{f1}$ is independently selected from $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 3-10 membered heterocycloalkyl.

In some embodiments, $R^G$, $R^H$ and $R^I$ are each independently selected from $C_1$-$C_4$ alkyl or phenyl.

In some embodiments, $R^G$ is selected from $C_1$-$C_4$ alkyl or phenyl. In some embodiments, $R^G$ is selected from methyl, ethyl, n-propyl, i-propyl, n-butyl, i-butyl, t-butyl, or phenyl.

In some embodiments, $R^H$ is selected from $C_1$-$C_4$ alkyl or phenyl. In some embodiments, $R^G$ is selected from methyl, ethyl, n-propyl, i-propyl, n-butyl, i-butyl, t-butyl, or phenyl.

In some embodiments, $R^8$ is selected from $C_1$-$C_4$ alkyl or phenyl. In some embodiments, $R^G$ is selected from methyl, ethyl, n-propyl, i-propyl, n-butyl, i-butyl, t-butyl, or phenyl.

In some embodiments, the compounds of Formula (I) are the pharmaceutically acceptable salts. In some embodiments, the compounds of Formula (I) are stereoisomers. In some embodiments, the compounds of Formula (I) are solvates. In some embodiments, the compounds of Formula (I) are N-oxides of the compounds of Formula (I).

In some embodiments, the compounds of Formula (I) are represented by compounds of Formula (IIA):

(IIA)

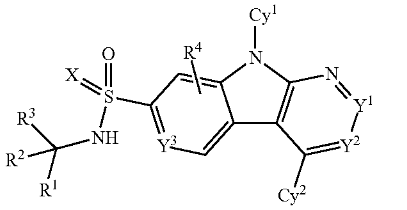

or pharmaceutically acceptable salt, stereoisomer, solvate, N-oxide, tautomeric, isotopic variants, prodrugs or deuterated compound thereof; wherein, each $R^1$, $R^2$, $R^3$, $R^4$, $Cy^1$, $Cy^2$, X, $Y^1$, $Y^2$ and $Y^3$ are defined with respect to Formula (I).

In some embodiments, the compounds of Formula (I) are represented by compounds of Formula (IIa) and (IIb):

(IIa)

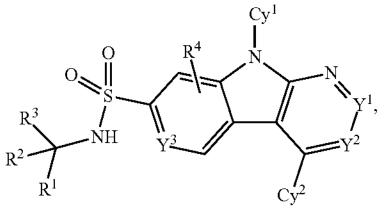

(IIb)

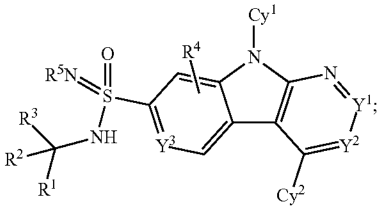

or pharmaceutically acceptable salt, stereoisomer, solvate, N-oxide, tautomeric, isotopic variants, prodrugs or deuterated compound thereof; wherein, each $R^1$, $R^2$, $R^3$, $R^4$, $R^5$, $Cy^1$, $Cy^2$, $Y^1$, $Y^2$ and $Y^3$ are defined with respect to Formula (I).

In some embodiments, the compounds of Formula (I) are represented by compounds of Formula (IIIa) and (IIIb):

(IIIa)

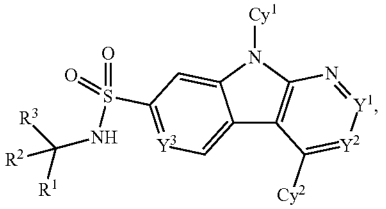

(IIIb)

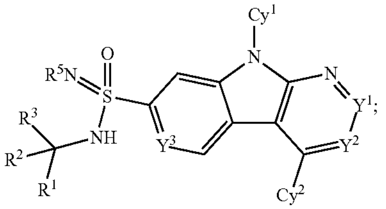

or pharmaceutically acceptable salt, stereoisomer, solvate, N-oxide, tautomeric, isotopic variants, prodrugs or deuterated compound thereof; wherein, each $R^1$, $R^2$, $R^3$, $R^5$, $Cy^1$, $Cy^2$, $Y^1$, $Y^2$ and $Y^3$ are defined with respect to Formula (I).

In some embodiments, the compounds of Formula (I) are represented by compounds of Formula (IV)

(IV)

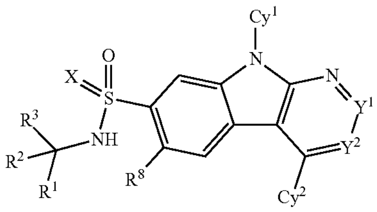

or pharmaceutically acceptable salt, stereoisomer, solvate, N-oxide, tautomeric, isotopic variants, prodrugs or deuterated compound thereof; wherein each $R^1$, $R^2$, $R^3$, $R^8$, X, $Cy^1$, $Cy^2$, X, $Y^1$, and $Y^2$ are defined with respect to Formula (I).

In some embodiments, X in Formula (IV) is independently $NR^5$. In some embodiments, X in Formula (IV) is independently O.

In the compounds of Formula (IV), each $R^8$ is selected from H, D, F, Cl, OH, CN, $CF_3$, OMe, $OCF_3$, or $SF_5$. In some embodiments, $R^8$ is H. In some embodiments, $R^8$ is D. In some embodiments, $R^8$ is F. In some embodiments, $R^8$ is Cl. In some embodiments, $R^8$ is OH. In some embodiments, $R^8$ is CN. In some embodiments, $R^8$ is $CF_3$. In some embodiments, $R^8$ is OMe. In some embodiments, $R^8$ is $OCF_3$. In some embodiments, $R^8$ is $SF_5$.

In some embodiments, the compounds of Formula (I) are represented by compounds of Formula (IVa) or (IVb):

(IVa)

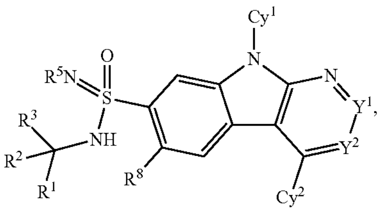

(IVb)

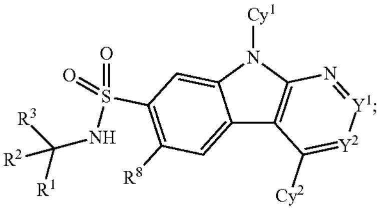

or pharmaceutically acceptable salt, stereoisomer, solvate, N-oxide, tautomeric, isotopic variants, prodrugs or deuterated compound thereof; wherein each $R^1$, $R^2$, $R^3$, $R^5$, $R^8$, $Cy^1$, $Cy^2$, $Y^1$, and $Y^2$ are defined with respect to Formula (I).

In some embodiments, $Cy^1$ in Formula (IVa) is 5-6 membered heteroaryl optionally substituted by 1, 2, 3, or 4 $R^9$. In some embodiments, $Cy^1$ is 6 membered heteroaryl optionally substituted by 1, 2, 3, or 4 $R^9$. In some embodiments, $Cy^1$ is 5 membered heteroaryl optionally substituted by 1, 2, or 3 $R^9$.

In some embodiments, $Cy^1$ in Formula (IVb) is 5-6 membered heteroaryl optionally substituted by 1, 2, 3, or 4 $R^9$. In some embodiments, $Cy^1$ is 6 membered heteroaryl optionally substituted by 1, 2, 3, or 4 $R^9$. In some embodiments, $Cy^1$ is 5 membered heteroaryl optionally substituted by 1, 2, or 3 $R^9$.

In some embodiments, the compounds of Formula (I) are represented by compounds of Formula (Va), (Vb), or (Vc):

(Va)

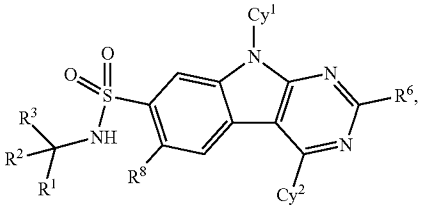

(Vb)

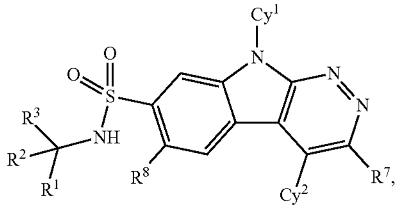

(Vc)

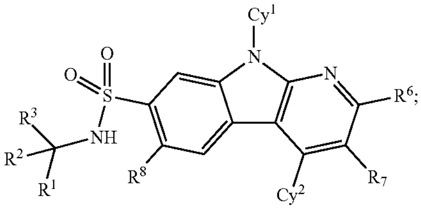

or pharmaceutically acceptable salt, stereoisomer, solvate, N-oxide, tautomeric, isotopic variants, prodrugs or deuterated compound thereof; wherein each $R^1$, $R^2$, $R^3$, $R^6$, $R^7$, $R^1$, $Cy^1$, and $Cy^2$ are defined with respect to Formula (I).

In some embodiments, $Cy^1$ in Formula (Va), (Vb), or (Vc) is 5-6 membered heteroaryl optionally substituted by 1, 2, 3, or 4 $R^9$. In some embodiments, $Cy^1$ is 6 membered heteroaryl optionally substituted by 1, 2, 3, or 4 $R^9$. In some embodiments, $Cy^1$ is 5 membered heteroaryl optionally substituted by 1, 2, or 3 $R^9$.

In some embodiments, $Cy^1$ is

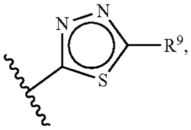, 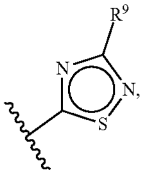, 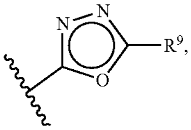, 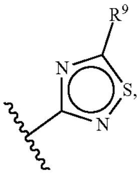, 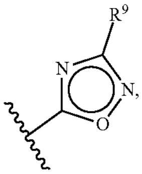, or 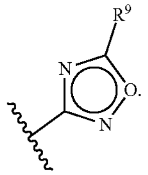.

In some embodiments, $Cy^1$ is

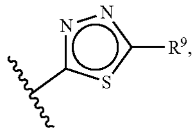, 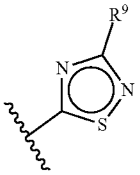 or 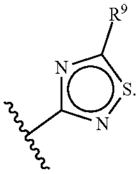.

In some embodiments, $Cy^1$ is

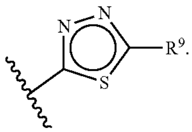.

In some embodiments, the compounds of Formula (I) are represented by compounds of Formula (VI):

(VI)

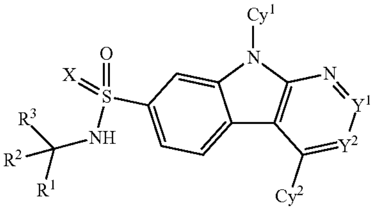

or pharmaceutically acceptable salt, stereoisomer, solvate, N-oxide, tautomeric, isotopic variants, prodrugs or deuterated compound thereof;

wherein, $Cy^1$ is 5 membered heteroaryl having 1, 2, 3 or 4 heteroatoms independently selected from N, O and S, wherein, the 5 membered heteroaryl optionally substituted by 1, 2, 3, or 4 $R^9$;

each $R^1$, $R^2$, $R^3$, $R^9$, $Cy^2$, X, $Y^1$, and $Y^2$ are defined with respect to Formula (I).

In some embodiments, the compounds of Formula (I) are represented by compounds of Formula (VIa) or (VIb):

(VIa)

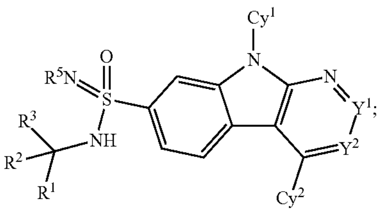

-continued (VIb)

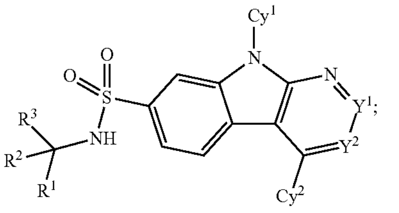

or pharmaceutically acceptable salt, stereoisomer, solvate, N-oxide, tautomeric, isotopic variants, prodrugs or deuterated compound thereof; wherein, $Cy^1$ is 5 membered heteroaryl having 1, 2, 3 or 4 heteroatoms independently selected from N, O and S, wherein, the 5 membered heteroaryl optionally substituted by 1, 2, 3, or 4 $R^9$;

each $R^1$, $R^2$, $R^3$, $R^5$, $R^9$, $Cy^2$, $Y^1$, and $Y^2$ are defined with respect to Formula (I).

In some embodiments, the compounds of Formula (I) are represented by compounds of Formula (VII):

(VII)

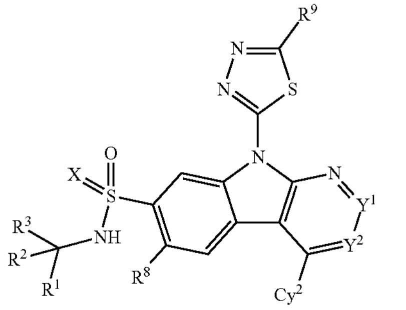

or pharmaceutically acceptable salt, stereoisomer, solvate, N-oxide, tautomeric, isotopic variants, prodrugs or deuterated compound thereof; wherein each $R^1$, $R^2$, $R^3$, $R^1$, $R^9$, $Cy^2$, X, $Y^1$, and $Y^2$ are defined with respect to Formula (I).

In some embodiments of Formula (VII), X is $NR^5$. In some embodiments of Formula (VII), X is O.

In some embodiments, the compounds of Formula (I) are represented by compounds of Formula (VIIa) or (VIIb):

(VIIa)

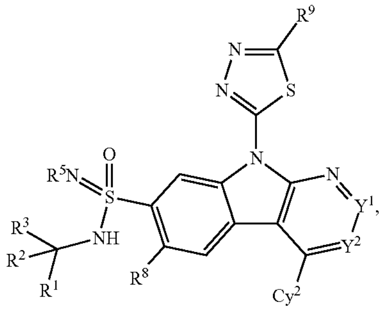

-continued (VIIb)

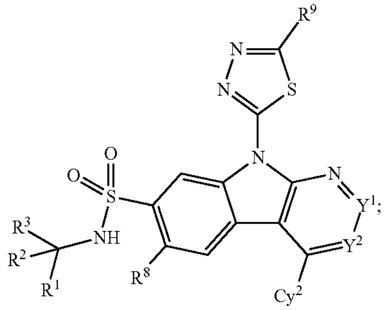

or pharmaceutically acceptable salt, stereoisomer, solvate, N-oxide, tautomeric, isotopic variants, prodrugs or deuterated compound thereof; wherein each $R^1$, $R^2$, $R^3$, $R^5$, $R^1$, $R^9$, $Cy^2$, $Y^1$, and $Y^2$ are defined with respect to Formula (I).

In some embodiments, the compounds of Formula (I) are represented by compounds of Formula (VIIIa), (VIIIb), or (VIIIc):

(VIIIa)

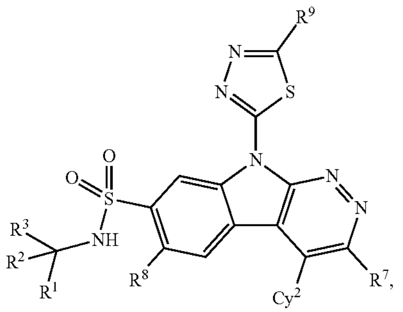

(VIIIb)

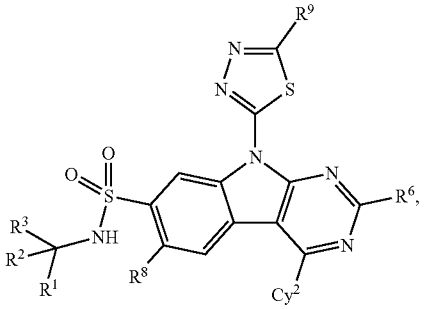

(VIIIc)

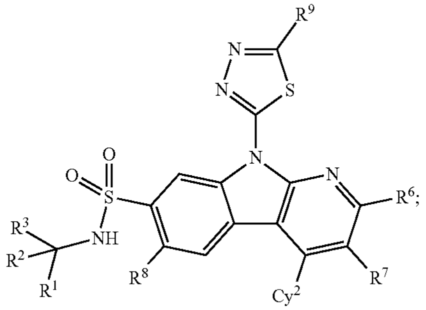

or pharmaceutically acceptable salt, stereoisomer, solvate, N-oxide, tautomeric, isotopic variants, prodrugs or deuterated compound thereof; wherein each $R^1$, $R^2$, $R^3$, $R^6$, $R^7$, $R^8$, $R^9$, and $Cy^2$ are defined with respect to Formula (I).

In some embodiments, the compounds of Formula (I) are represented by compounds of Formula (IXa), (IXb), or (IXc):

(IXa)

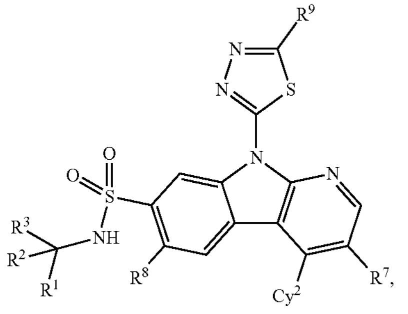

(IXb)

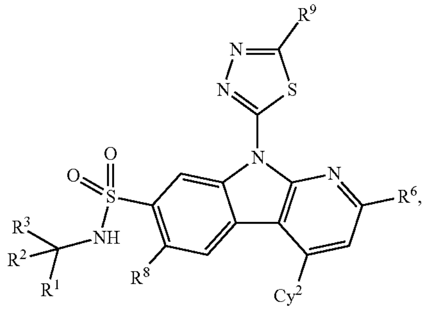

(IXc)

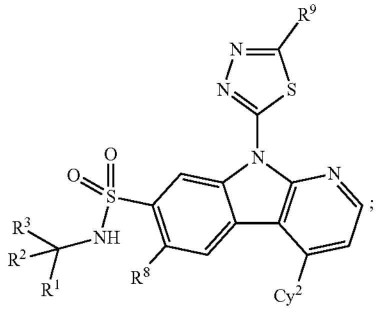

or pharmaceutically acceptable salt, stereoisomer, solvate, N-oxide, tautomeric, isotopic variants, prodrugs or deuterated compound thereof; wherein each $R^1$, $R^2$, $R^3$, $R^6$, $R^7$, $R^1$, $R^9$, and $Cy^2$ are defined with respect to Formula (I).

In some embodiments, the compounds of Formula (I) are represented by compounds of Formula (Xa), or (Xb):

(Xa)

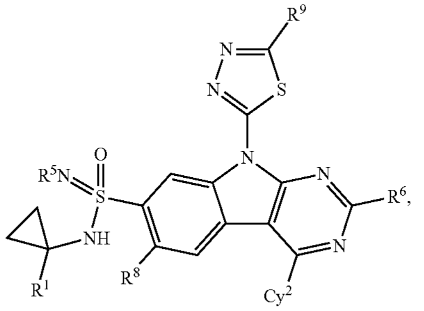

(Xb)

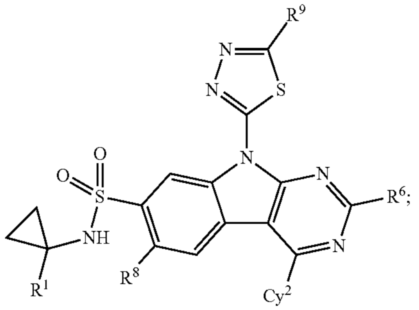

or pharmaceutically acceptable salt, stereoisomer, solvate, N-oxide, tautomeric, isotopic variants, prodrugs or deuterated compound thereof; wherein each $R^1$, $R^5$, $R^6$, $R^1$, $R^9$, and $Cy^2$ are defined with respect to Formula (I).

In some embodiments, the compounds of Formula (Xa) and (Xb), $R^1$ is independently selected from CN, $CH_3$, $CD_3$, $CF_3$, $CHF_2$, or $CH_2F$. In some embodiments, $R^1$ is $CF_3$. In some embodiments, $R^1$ is $CHF_2$. In some embodiments, $R^1$ is $CH_2F$. In some embodiments, $R^1$ is $CH_3$. In some embodiments, $R^1$ is $CD_3$. In some embodiments, $R^1$ is CN.

In some embodiments, the compounds of Formula (Xa) and (Xb), $R^6$ is independently H, D, OH, $C_1$-$C_6$ alkyl, $C_1$-$C_6$ haloalkyl, $C_2$-$C_6$ alkenyl, $C_2$-$C_6$ alkynyl, $OR^A$, $NR^CR^D$. In some embodiments, $R^6$ is H. In some embodiments, $R^6$ is D. In some embodiments, $R^6$ is $C_1$-$C_6$ alkyl, for example, $-CH_3$. In some embodiments, $R^6$ is $C_1$-$C_6$ haloalkyl, for example, $-CF_3$. In some embodiments, $R^6$ is $C_2$-$C_6$ alkenyl. In some embodiments, $R^6$ is $C_2$-$C_6$ alkynyl. In some embodiments, $R^6$ is $OR^A$, for example, $-OCH_3$, or $-OCF_3$. In some embodiments, $R^6$ is $NR^CR^D$.

In other embodiments, the compounds of Formula (Xa) and (Xb), $R^8$ is selected from H, D, F, Cl, OH, CN, $CH_3$, $CF_3$, OMe, $OCF_3$, or $SF_5$. In some embodiments, $R^8$ is H. In some embodiments, $R^8$ is D. In some embodiments, $R^8$ is F. In some embodiments, $R^8$ is $C_1$. In some embodiments, $R^8$ is OH. In some embodiments, $R^8$ is CN. In some embodiments, $R^8$ is $CH_3$. In some embodiments, $R^8$ is $CF_3$. In some embodiments, $R^8$ is OMe. In some embodiments, $R^8$ is $OCF_3$. In some embodiments, $R^N$ is $SF_5$.

Stereoisomers of the compounds of Formula I, and the pharmaceutical salts and solvates thereof, are also contemplated, described, and encompassed herein. Methods of using compounds of Formula I are described, as well as pharmaceutical compositions including the compounds of Formula I.

In some embodiments, the compound of Formula (I) is:
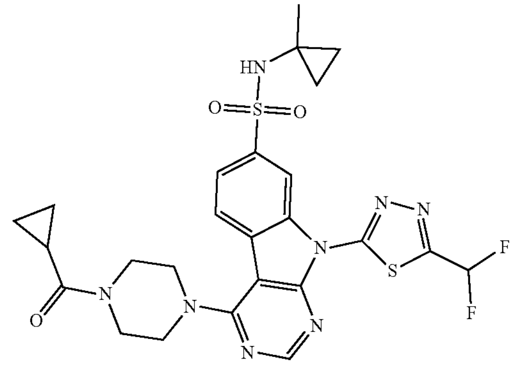 [SMILES: CC1(NS(=O)(=O)c2ccc3c4c(N5CCN(C(=O)C6CC6)CC5)ncnc4n(-c4nnc(C(F)F)s4)c3c2)CC1]
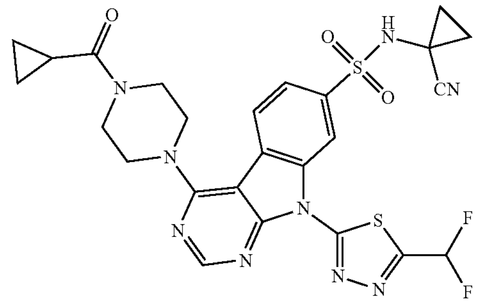 [SMILES: N#CC1(NS(=O)(=O)c2ccc3c4c(N5CCN(C(=O)C6CC6)CC5)ncnc4n(-c4nnc(C(F)F)s4)c3c2)CC1]
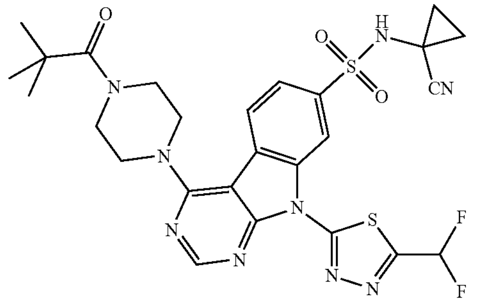 [SMILES: CC(C)(C)C(=O)N1CCN(c2ncnc3c2c2ccc(S(=O)(=O)NC4(C#N)CC4)cc2n3-c2nnc(C(F)F)s2)CC1]
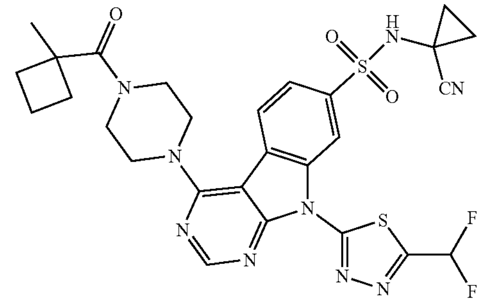 [SMILES: CC1(C(=O)N2CCN(c3ncnc4c3c3ccc(S(=O)(=O)NC5(C#N)CC5)cc3n4-c3nnc(C(F)F)s3)CC2)CCC1]
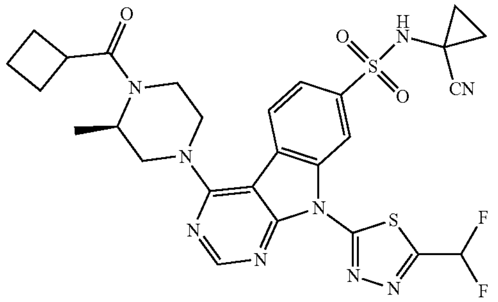 [SMILES: C[C@@H]1CN(c2ncnc3c2c2ccc(S(=O)(=O)NC4(C#N)CC4)cc2n3-c2nnc(C(F)F)s2)CCN1C(=O)C1CCC1]
-continued
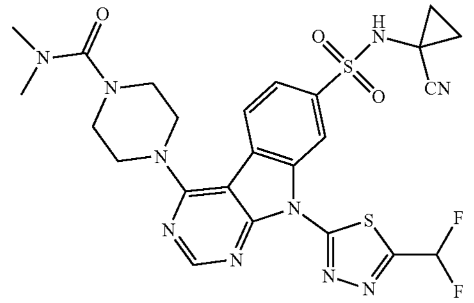
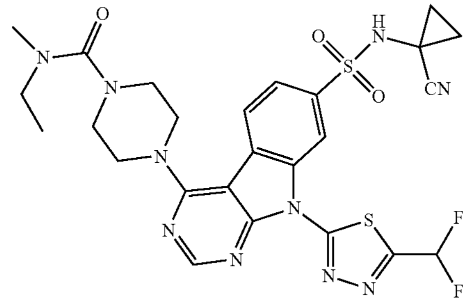 [SMILES: CCN(C)C(=O)N1CCN(c2ncnc3c2c2ccc(S(=O)(=O)NC4(C#N)CC4)cc2n3-c2nnc(C(F)F)s2)CC1]
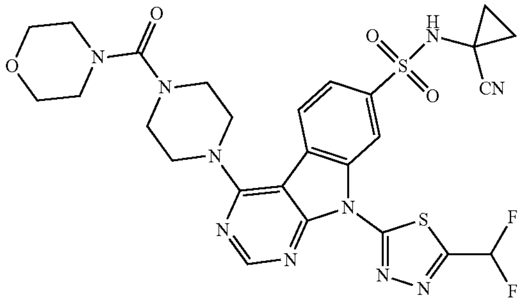 [SMILES: N#CC1(NS(=O)(=O)c2ccc3c4c(N5CCN(C(=O)N6CCOCC6)CC5)ncnc4n(-c4nnc(C(F)F)s4)c3c2)CC1]
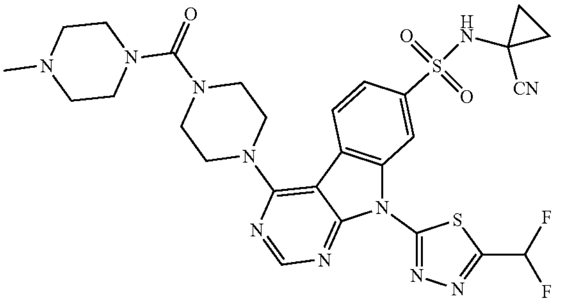 [SMILES: CN1CCN(C(=O)N2CCN(c3ncnc4c3c3ccc(S(=O)(=O)NC5(C#N)CC5)cc3n4-c3nnc(C(F)F)s3)CC2)CC1]
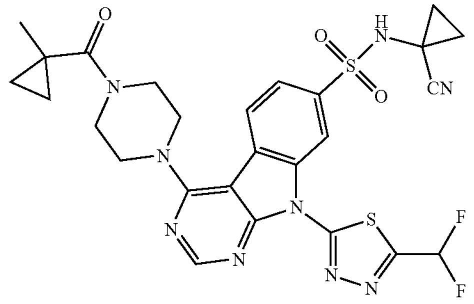 [SMILES: CC1(C(=O)N2CCN(c3ncnc4c3c3ccc(S(=O)(=O)NC5(C#N)CC5)cc3n4-c3nnc(C(F)F)s3)CC2)CC1]

-continued
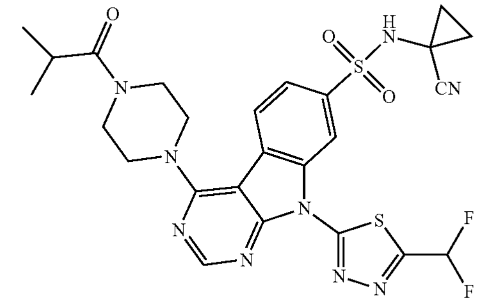 [SMILES: CC(C)C(=O)N1CCN(c2ncnc3c2c2ccc(S(=O)(=O)NC4(C#N)CC4)cc2n3-c2nnc(C(F)F)s2)CC1]
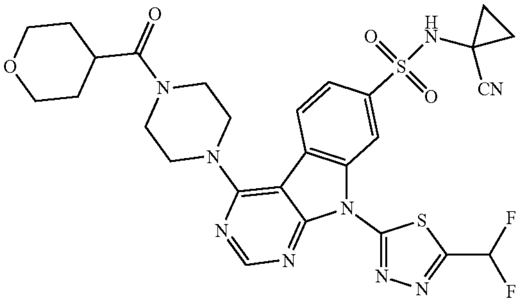
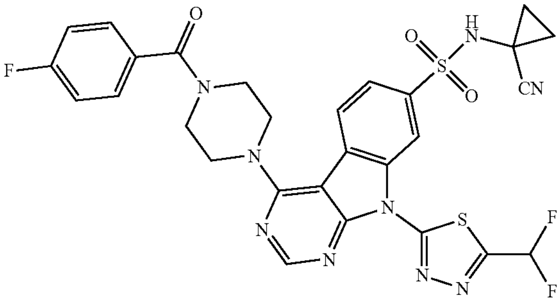 [SMILES: N#CC1(NS(=O)(=O)c2ccc3c4c(N5CCN(C(=O)c6ccc(F)cc6)CC5)ncnc4n(-c4nnc(C(F)F)s4)c3c2)CC1]
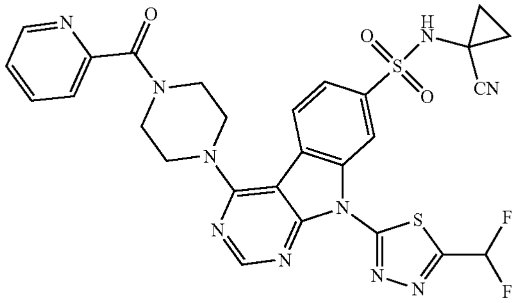 [SMILES: N#CC1(NS(=O)(=O)c2ccc3c4c(N5CCN(C(=O)c6ccccn6)CC5)ncnc4n(-c4nnc(C(F)F)s4)c3c2)CC1]
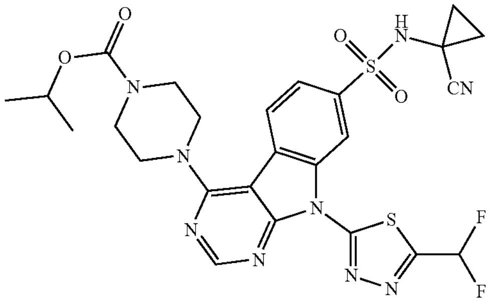 [SMILES: CC(C)OC(=O)N1CCN(c2ncnc3c2c2ccc(S(=O)(=O)NC4(C#N)CC4)cc2n3-c2nnc(C(F)F)s2)CC1]
-continued
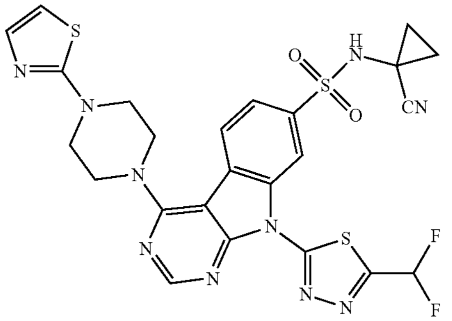 [SMILES: N#CC1(NS(=O)(=O)c2ccc3c4c(N5CCN(c6nccs6)CC5)ncnc4n(-c4nnc(C(F)F)s4)c3c2)CC1]
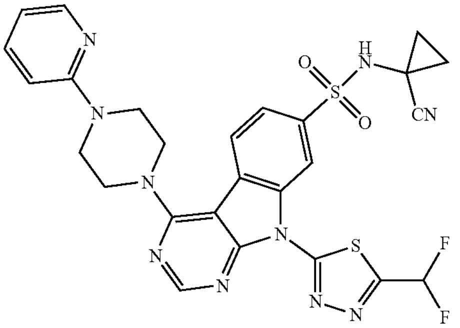 [SMILES: N#CC1(NS(=O)(=O)c2ccc3c4c(N5CCN(c6ccccn6)CC5)ncnc4n(-c4nnc(C(F)F)s4)c3c2)CC1]
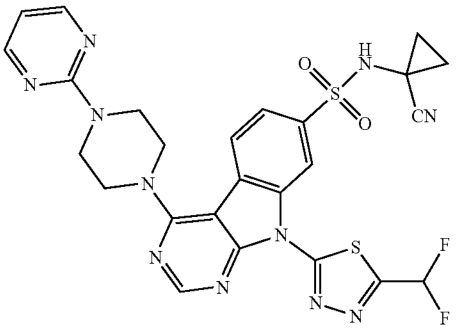 [SMILES: N#CC1(NS(=O)(=O)c2ccc3c4c(N5CCN(c6ncccn6)CC5)ncnc4n(-c4nnc(C(F)F)s4)c3c2)CC1]
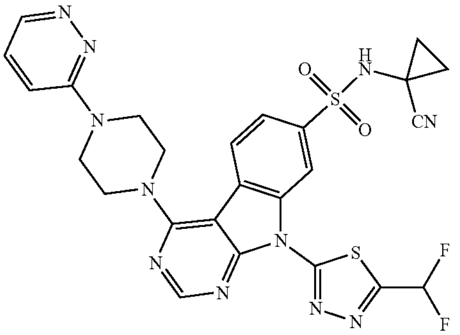 [SMILES: N#CC1(NS(=O)(=O)c2ccc3c4c(N5CCN(c6cccnn6)CC5)ncnc4n(-c4nnc(C(F)F)s4)c3c2)CC1]
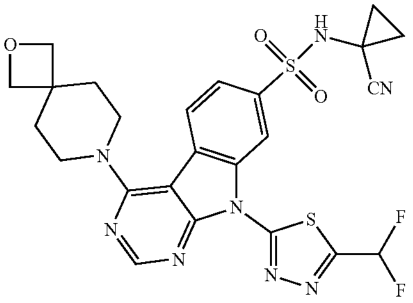 [SMILES: N#CC1(NS(=O)(=O)c2ccc3c4c(N5CCC6(CC5)COC6)ncnc4n(-c4nnc(C(F)F)s4)c3c2)CC1]

-continued
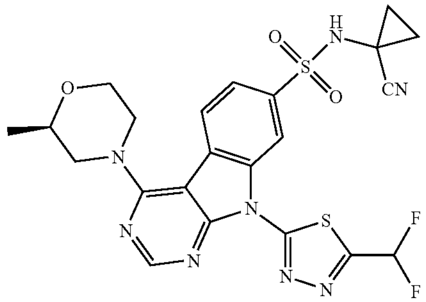 [SMILES: C[C@@H]1CN(c2ncnc3c2c2ccc(S(=O)(=O)NC4(C#N)CC4)cc2n3-c2nnc(C(F)F)s2)CCO1]
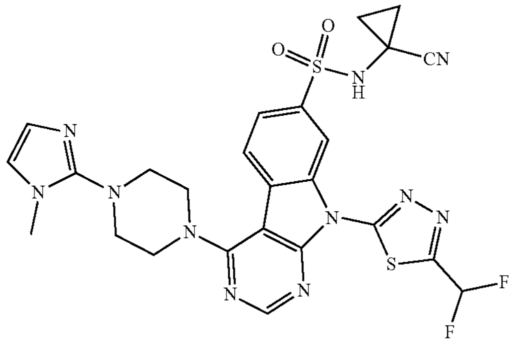 [SMILES: Cn1ccnc1N1CCN(c2ncnc3c2c2ccc(S(=O)(=O)NC4(C#N)CC4)cc2n3-c2nnc(C(F)F)s2)CC1]
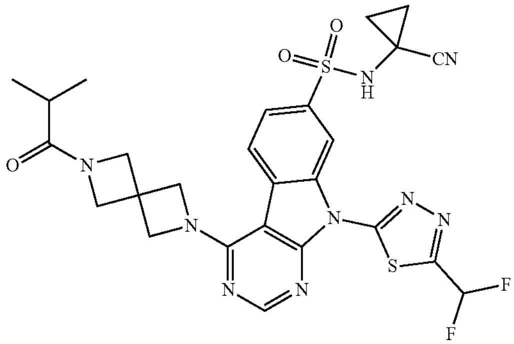 [SMILES: CC(C)C(=O)N1CC2(C1)CN(c1ncnc3c1c1ccc(S(=O)(=O)NC4(C#N)CC4)cc1n3-c1nnc(C(F)F)s1)C2]
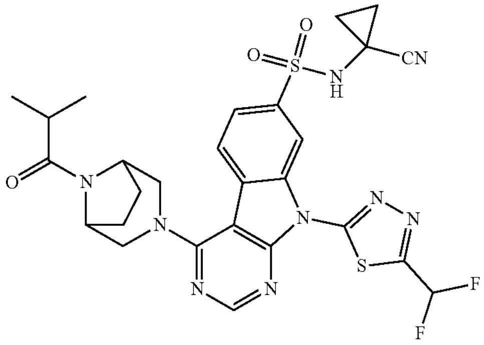 [SMILES: CC(C)C(=O)N1C2CCC1CN(c1ncnc3c1c1ccc(S(=O)(=O)NC4(C#N)CC4)cc1n3-c1nnc(C(F)F)s1)C2]
-continued
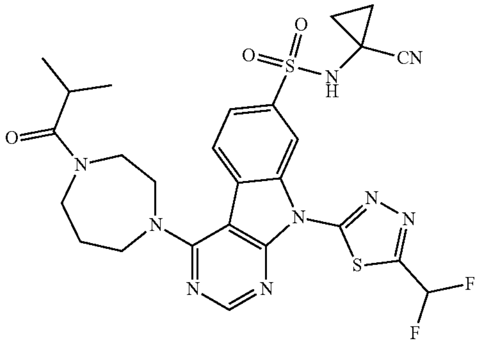 [SMILES: CC(C)C(=O)N1CCCN(c2ncnc3c2c2ccc(S(=O)(=O)NC4(C#N)CC4)cc2n3-c2nnc(C(F)F)s2)CC1]
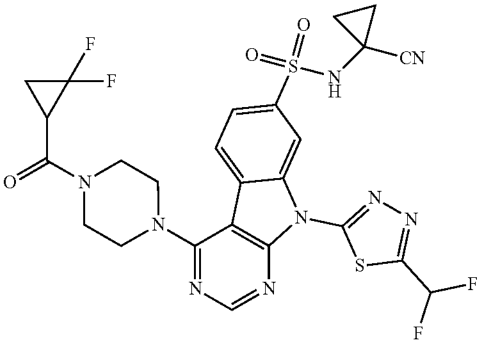 [SMILES: N#CC1(NS(=O)(=O)c2ccc3c4c(N5CCN(C(=O)C6CC6(F)F)CC5)ncnc4n(-c4nnc(C(F)F)s4)c3c2)CC1]
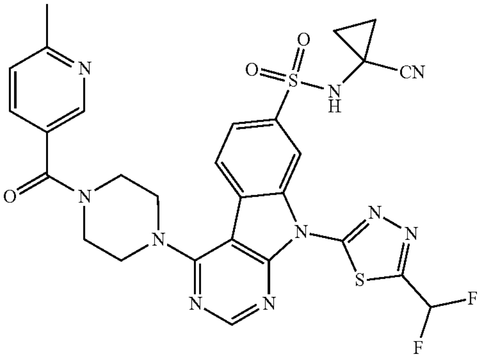 [SMILES: Cc1ccc(C(=O)N2CCN(c3ncnc4c3c3ccc(S(=O)(=O)NC5(C#N)CC5)cc3n4-c3nnc(C(F)F)s3)CC2)cn1]
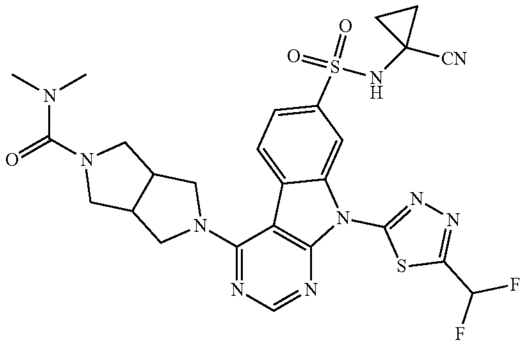 [SMILES: CN(C)C(=O)N1CC2CN(c3ncnc4c3c3ccc(S(=O)(=O)NC5(C#N)CC5)cc3n4-c3nnc(C(F)F)s3)CC2C1]

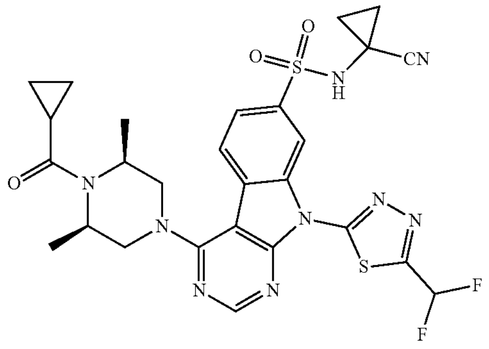 [SMILES: C[C@@H]1CN(c2ncnc3c2c2ccc(S(=O)(=O)NC4(C#N)CC4)cc2n3-c2nnc(C(F)F)s2)C[C@H](C)N1C(=O)C1CC1]
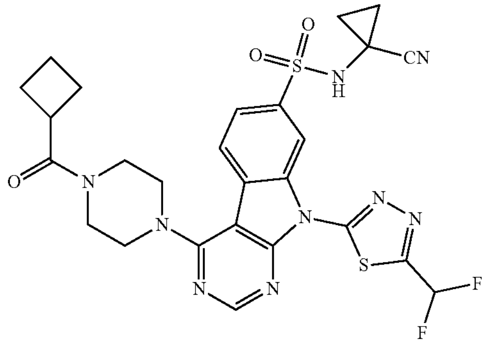 [SMILES: N#CC1(NS(=O)(=O)c2ccc3c4c(N5CCN(C(=O)C6CCC6)CC5)ncnc4n(-c4nnc(C(F)F)s4)c3c2)CC1]
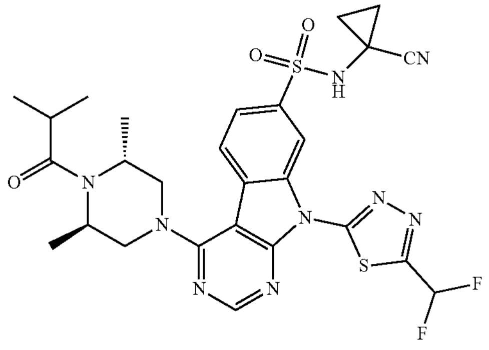 [SMILES: CC(C)C(=O)N1[C@H](C)CN(c2ncnc3c2c2ccc(S(=O)(=O)NC4(C#N)CC4)cc2n3-c2nnc(C(F)F)s2)C[C@H]1C]
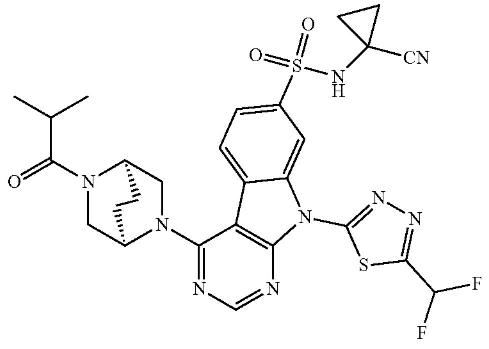
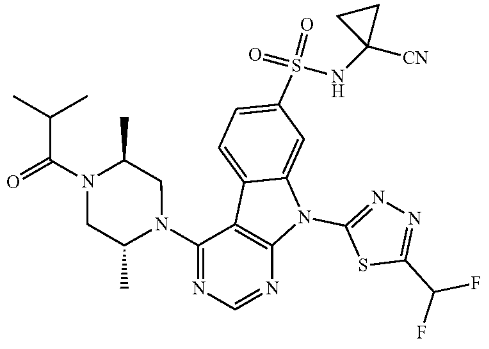 [SMILES: CC(C)C(=O)N1C[C@@H](C)N(c2ncnc3c2c2ccc(S(=O)(=O)NC4(C#N)CC4)cc2n3-c2nnc(C(F)F)s2)C[C@@H]1C]
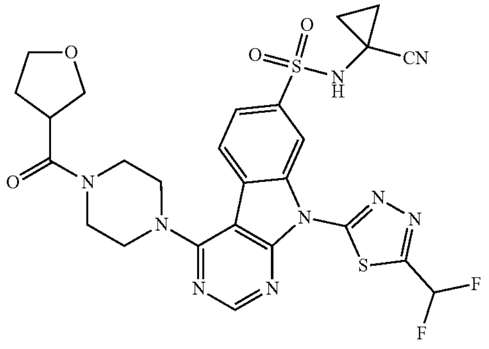 [SMILES: N#CC1(NS(=O)(=O)c2ccc3c4c(N5CCN(C(=O)C6CCOC6)CC5)ncnc4n(-c4nnc(C(F)F)s4)c3c2)CC1]
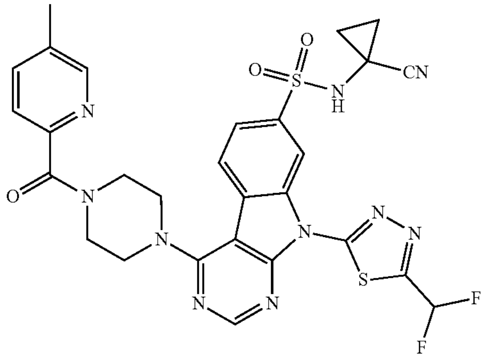 [SMILES: Cc1ccc(C(=O)N2CCN(c3ncnc4c3c3ccc(S(=O)(=O)NC5(C#N)CC5)cc3n4-c3nnc(C(F)F)s3)CC2)nc1]
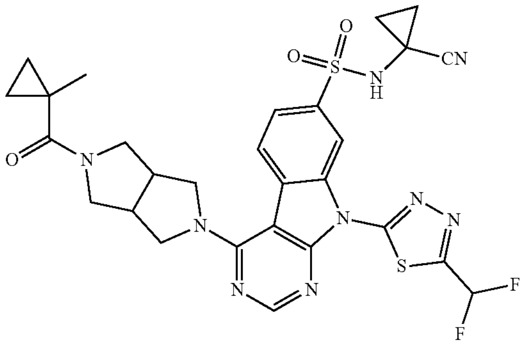 [SMILES: CC1(C(=O)N2CC3CN(c4ncnc5c4c4ccc(S(=O)(=O)NC6(C#N)CC6)cc4n5-c4nnc(C(F)F)s4)CC3C2)CC1]

-continued
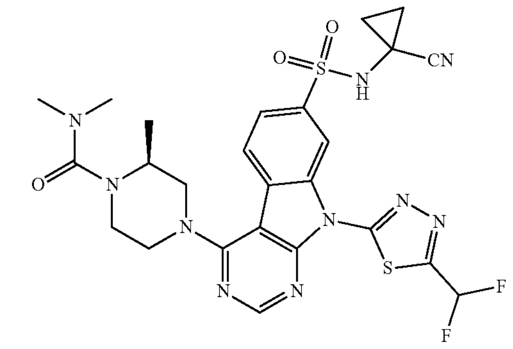
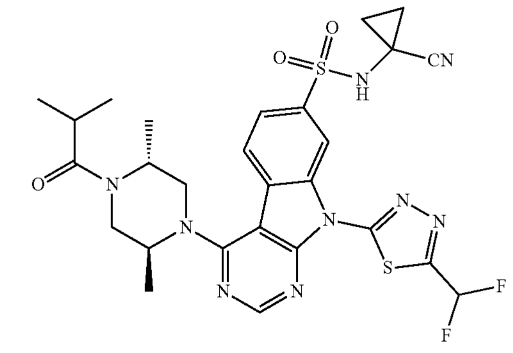 [SMILES: CC(C)C(=O)N1C[C@H](C)N(c2ncnc3c2c2ccc(S(=O)(=O)NC4(C#N)CC4)cc2n3-c2nnc(C(F)F)s2)C[C@H]1C]
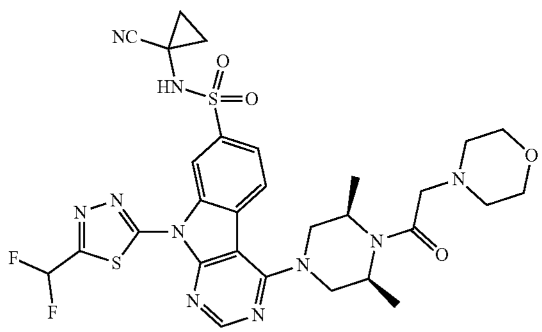 [SMILES: C[C@@H]1CN(c2ncnc3c2c2ccc(S(=O)(=O)NC4(C#N)CC4)cc2n3-c2nnc(C(F)F)s2)C[C@H](C)N1C(=O)CN1CCOCC1]
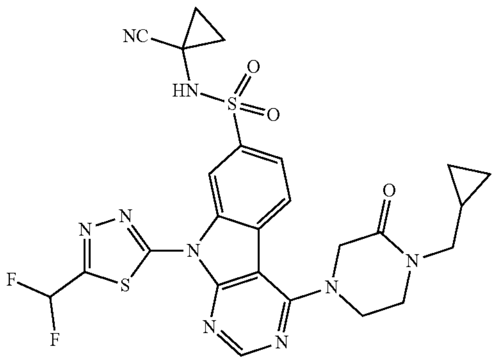 [SMILES: N#CC1(NS(=O)(=O)c2ccc3c4c(N5CCN(CC6CC6)C(=O)C5)ncnc4n(-c4nnc(C(F)F)s4)c3c2)CC1]
-continued
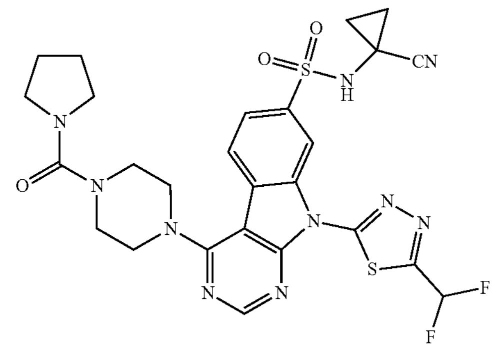
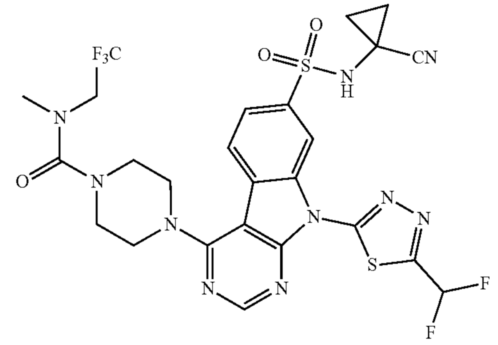 [SMILES: CN(CC(F)(F)F)C(=O)N1CCN(c2ncnc3c2c2ccc(S(=O)(=O)NC4(C#N)CC4)cc2n3-c2nnc(C(F)F)s2)CC1]
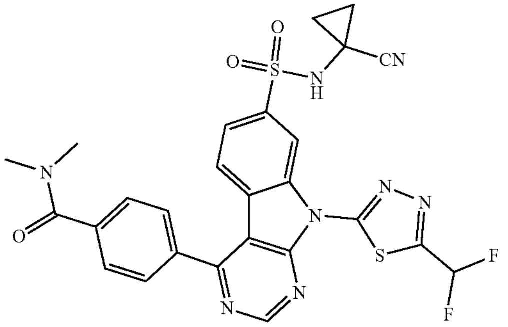 [SMILES: CN(C)C(=O)c1ccc(-c2ncnc3c2c2ccc(S(=O)(=O)NC4(C#N)CC4)cc2n3-c2nnc(C(F)F)s2)cc1]
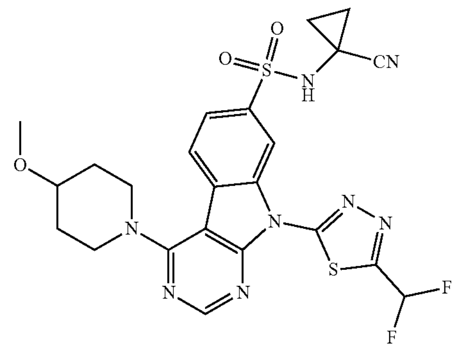

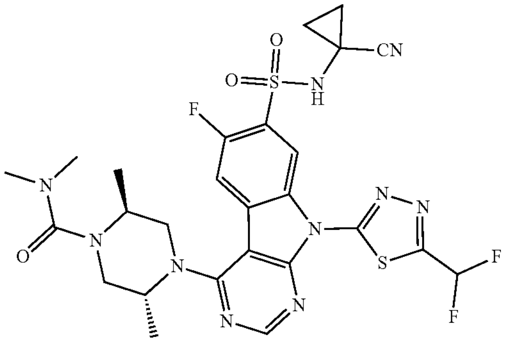 [SMILES: C[C@@H]1CN(C(=O)N(C)C)[C@@H](C)CN1c1ncnc2c1c1cc(F)c(S(=O)(=O)NC3(C#N)CC3)cc1n2-c1nnc(C(F)F)s1]
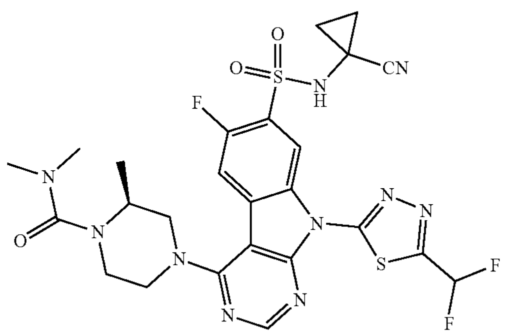 [SMILES: C[C@H]1CN(c2ncnc3c2c2cc(F)c(S(=O)(=O)NC4(C#N)CC4)cc2n3-c2nnc(C(F)F)s2)CCN1C(=O)N(C)C]
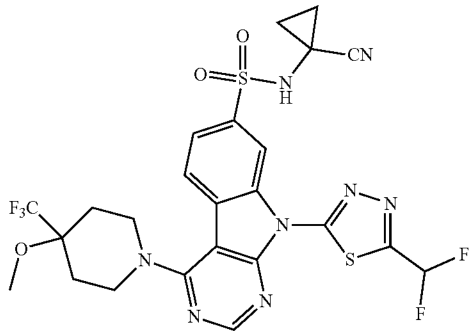 [SMILES: COC1(C(F)(F)F)CCN(c2ncnc3c2c2ccc(S(=O)(=O)NC4(C#N)CC4)cc2n3-c2nnc(C(F)F)s2)CC1]
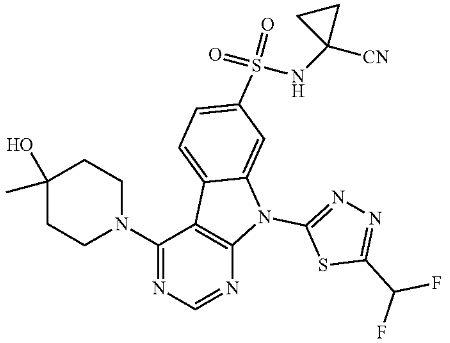 [SMILES: CC1(O)CCN(c2ncnc3c2c2ccc(S(=O)(=O)NC4(C#N)CC4)cc2n3-c2nnc(C(F)F)s2)CC1]
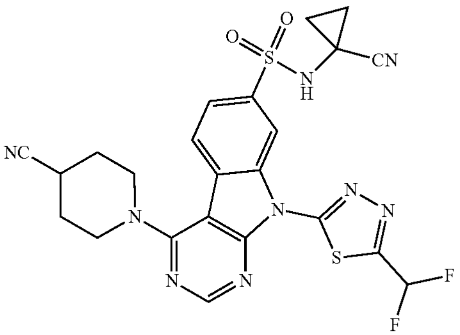 [SMILES: N#CC1CCN(c2ncnc3c2c2ccc(S(=O)(=O)NC4(C#N)CC4)cc2n3-c2nnc(C(F)F)s2)CC1]
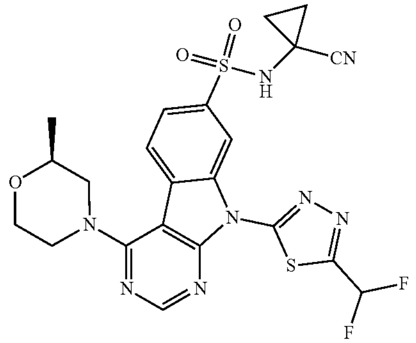 [SMILES: C[C@H]1CN(c2ncnc3c2c2ccc(S(=O)(=O)NC4(C#N)CC4)cc2n3-c2nnc(C(F)F)s2)CCO1]
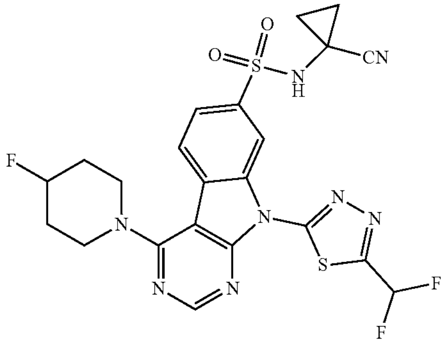 [SMILES: N#CC1(NS(=O)(=O)c2ccc3c4c(N5CCC(F)CC5)ncnc4n(-c4nnc(C(F)F)s4)c3c2)CC1]
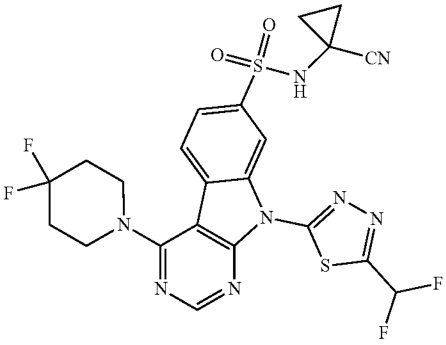 [SMILES: N#CC1(NS(=O)(=O)c2ccc3c4c(N5CCC(F)(F)CC5)ncnc4n(-c4nnc(C(F)F)s4)c3c2)CC1]

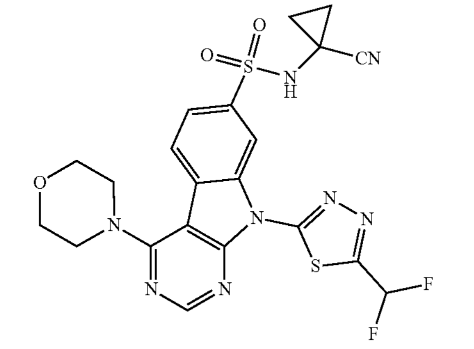 [SMILES: N#CC1(NS(=O)(=O)c2ccc3c4c(N5CCOCC5)ncnc4n(-c4nnc(C(F)F)s4)c3c2)CC1]
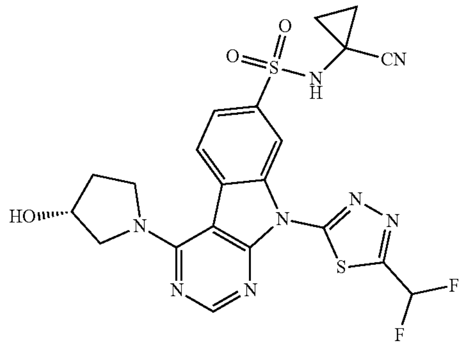 [SMILES: N#CC1(NS(=O)(=O)c2ccc3c4c(N5CC[C@@H](O)C5)ncnc4n(-c4nnc(C(F)F)s4)c3c2)CC1]
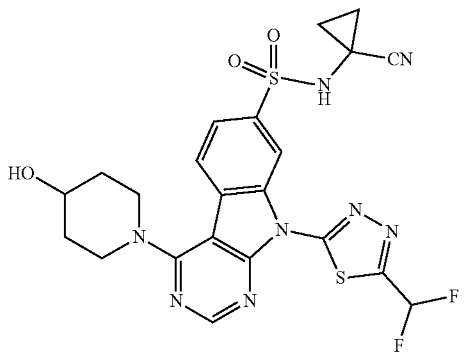 [SMILES: N#CC1(NS(=O)(=O)c2ccc3c4c(N5CCC(O)CC5)ncnc4n(-c4nnc(C(F)F)s4)c3c2)CC1]
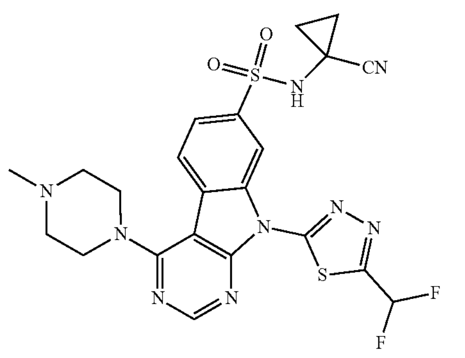 [SMILES: CN1CCN(c2ncnc3c2c2ccc(S(=O)(=O)NC4(C#N)CC4)cc2n3-c2nnc(C(F)F)s2)CC1]
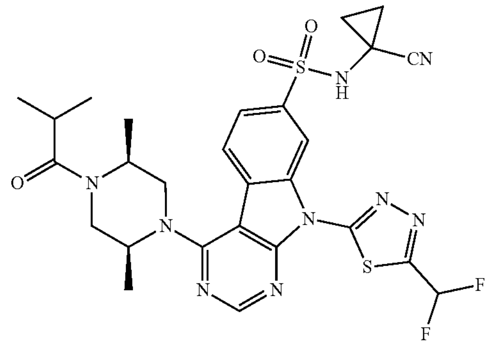 [SMILES: CC(C)C(=O)N1C[C@H](C)N(c2ncnc3c2c2ccc(S(=O)(=O)NC4(C#N)CC4)cc2n3-c2nnc(C(F)F)s2)C[C@@H]1C]
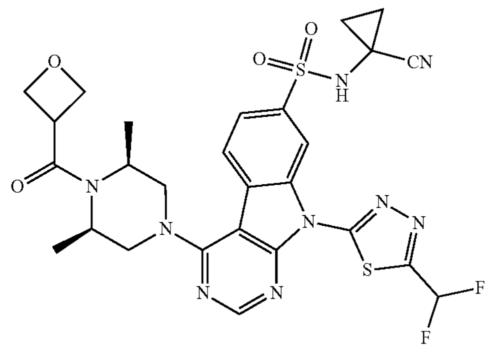 [SMILES: C[C@@H]1CN(c2ncnc3c2c2ccc(S(=O)(=O)NC4(C#N)CC4)cc2n3-c2nnc(C(F)F)s2)C[C@H](C)N1C(=O)C1COC1]
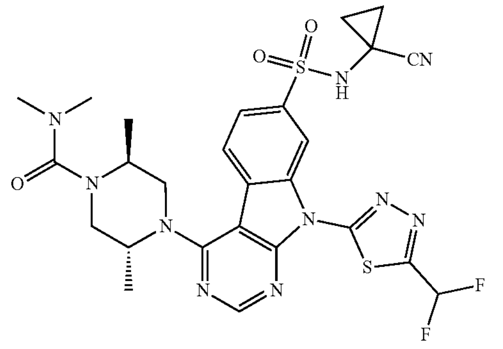
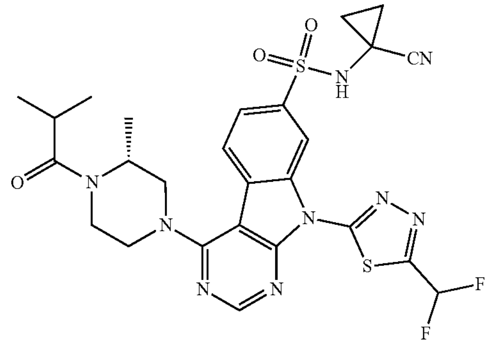 [SMILES: CC(C)C(=O)N1CCN(c2ncnc3c2c2ccc(S(=O)(=O)NC4(C#N)CC4)cc2n3-c2nnc(C(F)F)s2)C[C@H]1C]

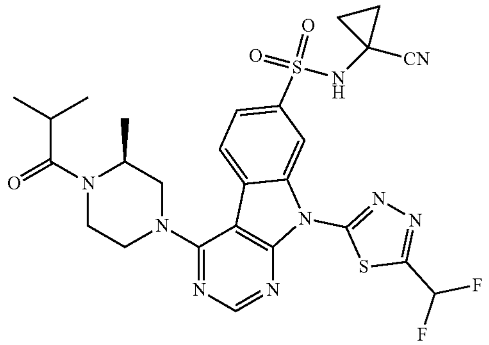 [SMILES: CC(C)C(=O)N1CCN(c2ncnc3c2c2ccc(S(=O)(=O)NC4(C#N)CC4)cc2n3-c2nnc(C(F)F)s2)C[C@@H]1C]
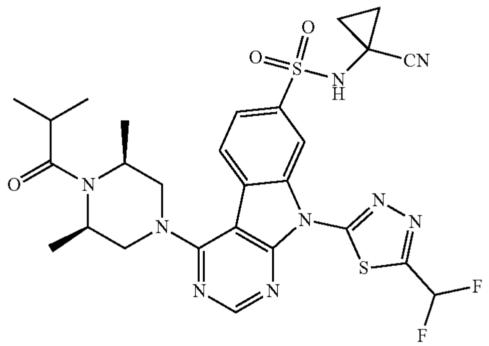 [SMILES: CC(C)C(=O)N1[C@H](C)CN(c2ncnc3c2c2ccc(S(=O)(=O)NC4(C#N)CC4)cc2n3-c2nnc(C(F)F)s2)C[C@@H]1C]
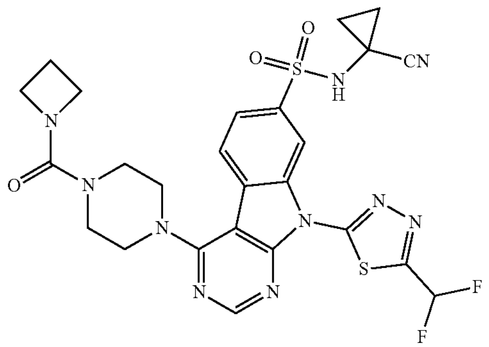
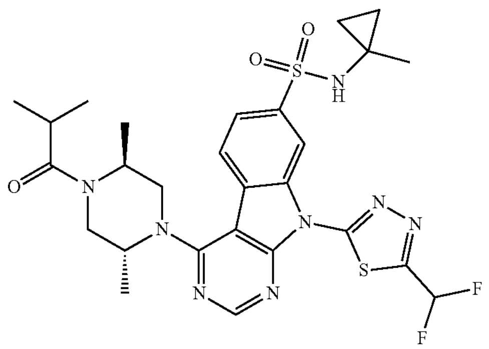 [SMILES: CC(C)C(=O)N1C[C@@H](C)N(c2ncnc3c2c2ccc(S(=O)(=O)NC4(C)CC4)cc2n3-c2nnc(C(F)F)s2)C[C@@H]1C]
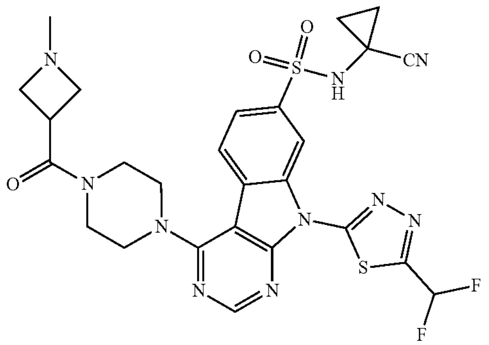 [SMILES: CN1CC(C(=O)N2CCN(c3ncnc4c3c3ccc(S(=O)(=O)NC5(C#N)CC5)cc3n4-c3nnc(C(F)F)s3)CC2)C1]
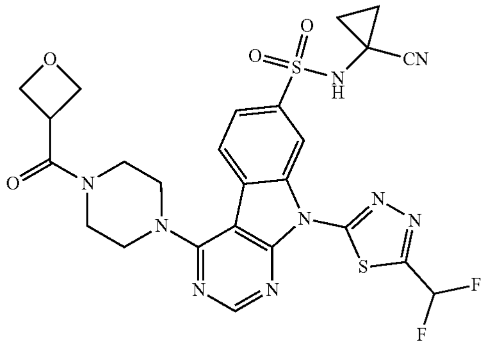
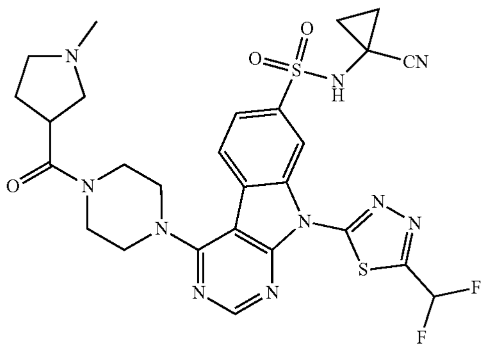 [SMILES: CN1CCC(C(=O)N2CCN(c3ncnc4c3c3ccc(S(=O)(=O)NC5(C#N)CC5)cc3n4-c3nnc(C(F)F)s3)CC2)C1]
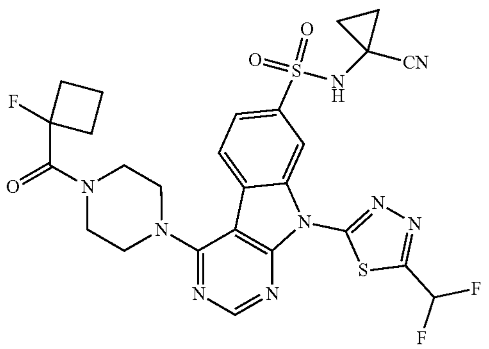 [SMILES: N#CC1(NS(=O)(=O)c2ccc3c4c(N5CCN(C(=O)C6(F)CCC6)CC5)ncnc4n(-c4nnc(C(F)F)s4)c3c2)CC1]

-continued
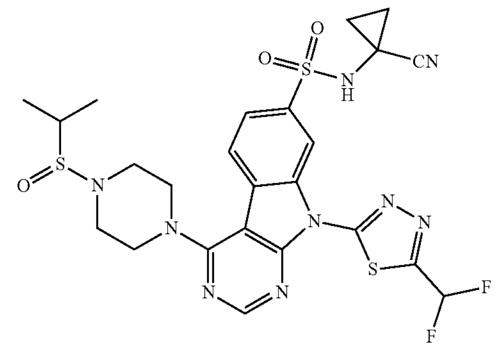 [SMILES: CC(C)S(=O)N1CCN(c2ncnc3c2c2ccc(S(=O)(=O)NC4(C#N)CC4)cc2n3-c2nnc(C(F)F)s2)CC1]
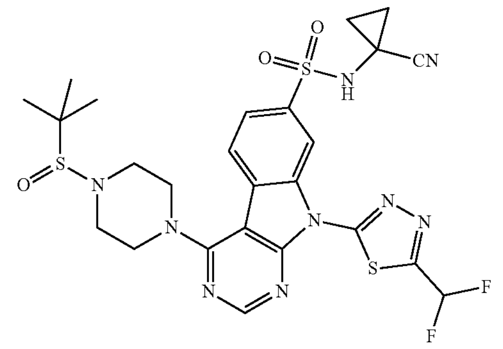 [SMILES: CC(C)(C)S(=O)N1CCN(c2ncnc3c2c2ccc(S(=O)(=O)NC4(C#N)CC4)cc2n3-c2nnc(C(F)F)s2)CC1]
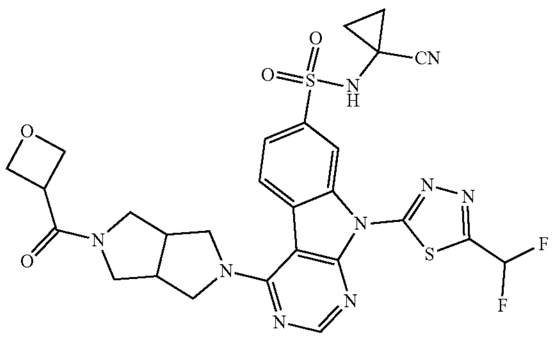 [SMILES: N#CC1(NS(=O)(=O)c2ccc3c4c(N5CC6CN(C(=O)C7COC7)CC6C5)ncnc4n(-c4nnc(C(F)F)s4)c3c2)CC1]
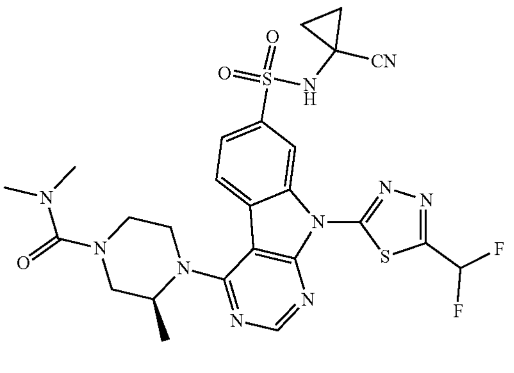 [SMILES: C[C@H]1CN(C(=O)N(C)C)CCN1c1ncnc2c1c1ccc(S(=O)(=O)NC3(C#N)CC3)cc1n2-c1nnc(C(F)F)s1]
-continued
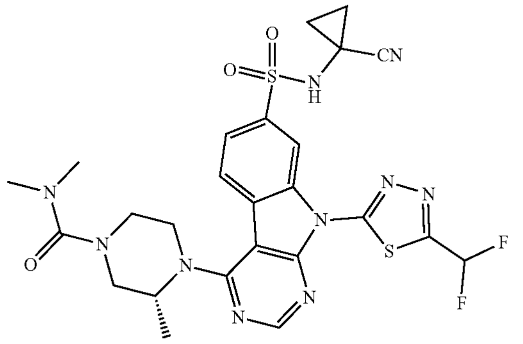 [SMILES: C[C@@H]1CN(C(=O)N(C)C)CCN1c1ncnc2c1c1ccc(S(=O)(=O)NC3(C#N)CC3)cc1n2-c1nnc(C(F)F)s1]
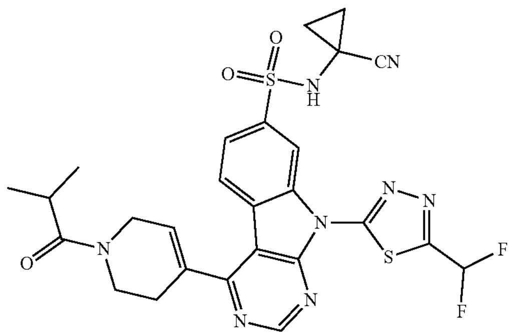 [SMILES: CC(C)C(=O)N1CC=C(c2ncnc3c2c2ccc(S(=O)(=O)NC4(C#N)CC4)cc2n3-c2nnc(C(F)F)s2)CC1]
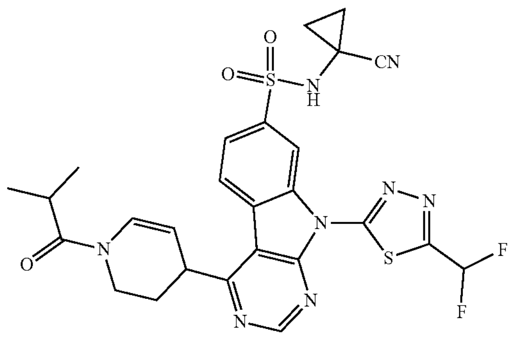 [SMILES: CC(C)C(=O)N1C=CC(c2ncnc3c2c2ccc(S(=O)(=O)NC4(C#N)CC4)cc2n3-c2nnc(C(F)F)s2)CC1]
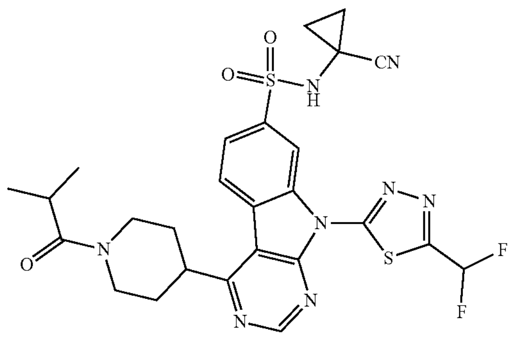 [SMILES: CC(C)C(=O)N1CCC(c2ncnc3c2c2ccc(S(=O)(=O)NC4(C#N)CC4)cc2n3-c2nnc(C(F)F)s2)CC1]

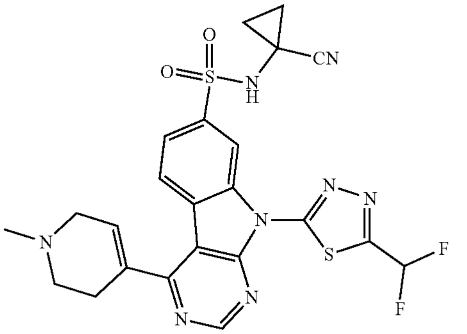 [SMILES: CN1CC=C(c2ncnc3c2c2ccc(S(=O)(=O)NC4(C#N)CC4)cc2n3-c2nnc(C(F)F)s2)CC1]
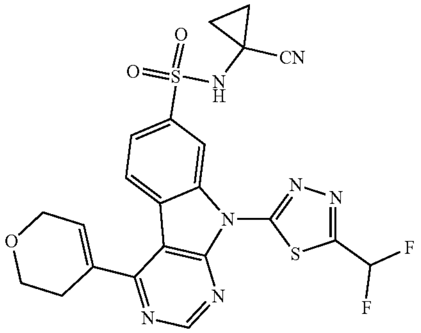 [SMILES: N#CC1(NS(=O)(=O)c2ccc3c4c(C5=CCOCC5)ncnc4n(-c4nnc(C(F)F)s4)c3c2)CC1]
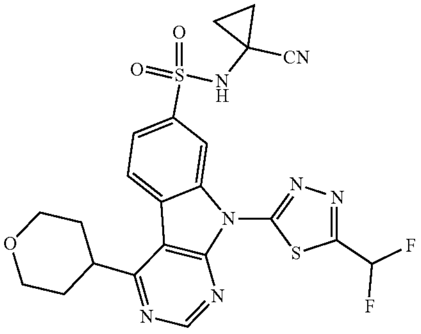 [SMILES: N#CC1(NS(=O)(=O)c2ccc3c4c(C5CCOCC5)ncnc4n(-c4nnc(C(F)F)s4)c3c2)CC1]
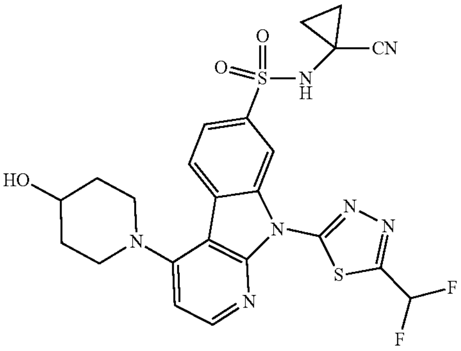 [SMILES: N#CC1(NS(=O)(=O)c2ccc3c4c(N5CCC(O)CC5)ccnc4n(-c4nnc(C(F)F)s4)c3c2)CC1]
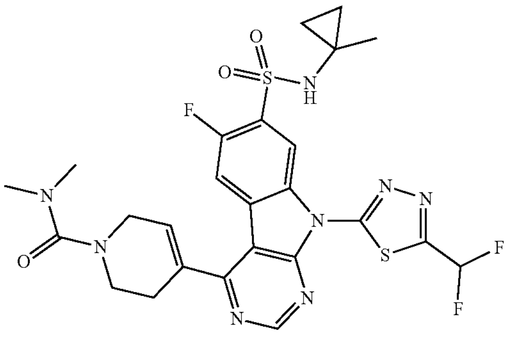 [SMILES: CN(C)C(=O)N1CC=C(c2ncnc3c2c2cc(F)c(S(=O)(=O)NC4(C)CC4)cc2n3-c2nnc(C(F)F)s2)CC1]
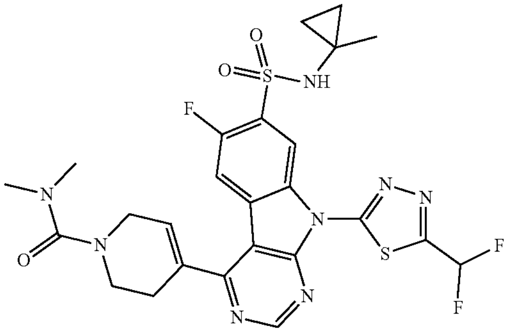 [SMILES: CN(C)C(=O)N1CC=C(c2ncnc3c2c2cc(F)c(S(=O)(=O)NC4(C)CC4)cc2n3-c2nnc(C(F)F)s2)CC1]
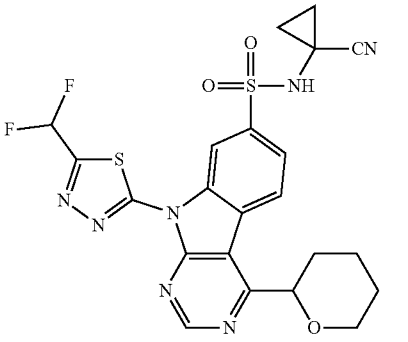 [SMILES: N#CC1(NS(=O)(=O)c2ccc3c4c(C5CCCCO5)ncnc4n(-c4nnc(C(F)F)s4)c3c2)CC1]
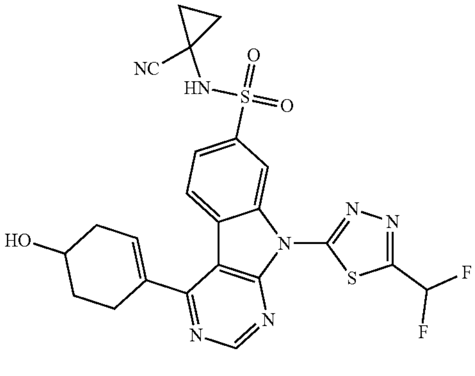 [SMILES: N#CC1(NS(=O)(=O)c2ccc3c4c(C5=CCC(O)CC5)ncnc4n(-c4nnc(C(F)F)s4)c3c2)CC1]

-continued
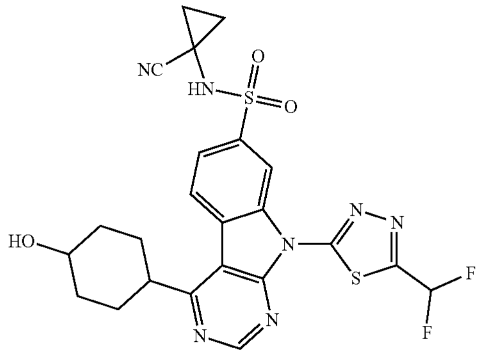 [SMILES: N#CC1(NS(=O)(=O)c2ccc3c4c(C5CCC(O)CC5)ncnc4n(-c4nnc(C(F)F)s4)c3c2)CC1]
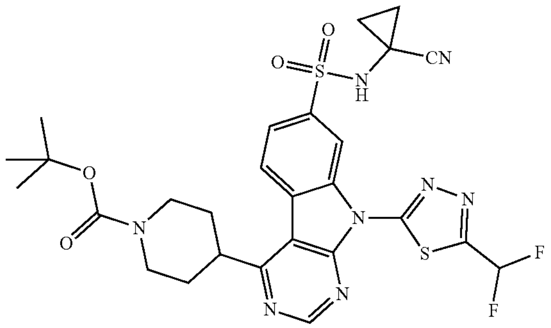 [SMILES: CC(C)(C)OC(=O)N1CCC(c2ncnc3c2c2ccc(S(=O)(=O)NC4(C#N)CC4)cc2n3-c2nnc(C(F)F)s2)CC1]
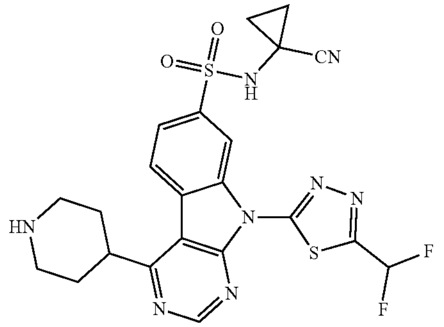 [SMILES: N#CC1(NS(=O)(=O)c2ccc3c4c(C5CCNCC5)ncnc4n(-c4nnc(C(F)F)s4)c3c2)CC1]
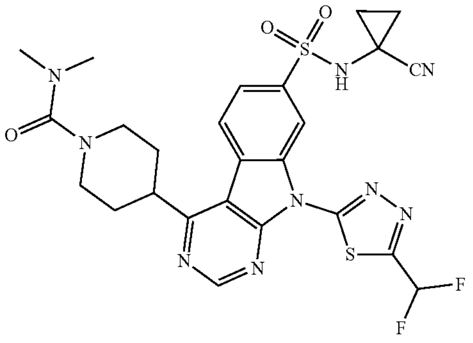 [SMILES: CN(C)C(=O)N1CCC(c2ncnc3c2c2ccc(S(=O)(=O)NC4(C#N)CC4)cc2n3-c2nnc(C(F)F)s2)CC1]
-continued
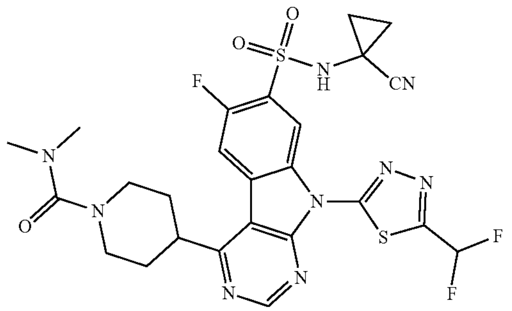 [SMILES: CN(C)C(=O)N1CCC(c2ncnc3c2c2cc(F)c(S(=O)(=O)NC4(C#N)CC4)cc2n3-c2nnc(C(F)F)s2)CC1]
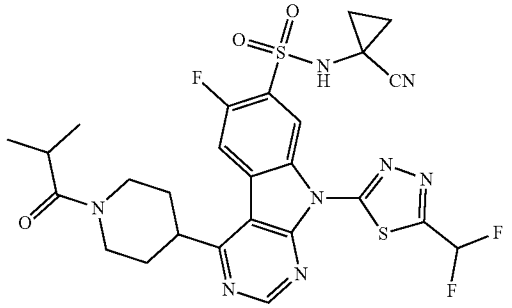
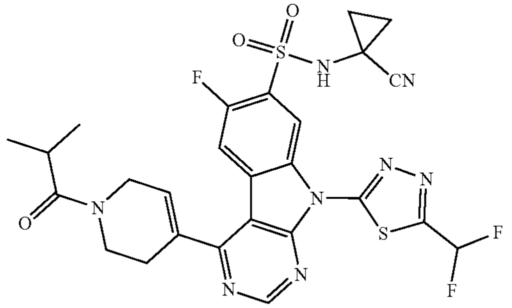 [SMILES: CC(C)C(=O)N1CC=C(c2ncnc3c2c2cc(F)c(S(=O)(=O)NC4(C#N)CC4)cc2n3-c2nnc(C(F)F)s2)CC1]
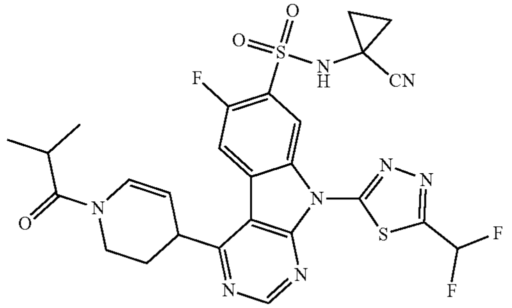 [SMILES: CC(C)C(=O)N1C=CC(c2ncnc3c2c2cc(F)c(S(=O)(=O)NC4(C#N)CC4)cc2n3-c2nnc(C(F)F)s2)CC1]
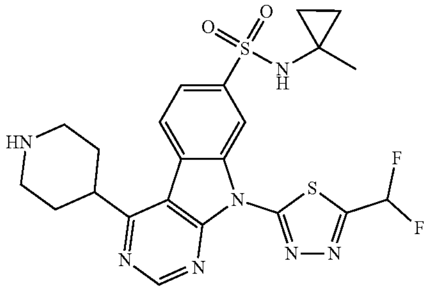 [SMILES: CC1(NS(=O)(=O)c2ccc3c4c(C5CCNCC5)ncnc4n(-c4nnc(C(F)F)s4)c3c2)CC1]

-continued
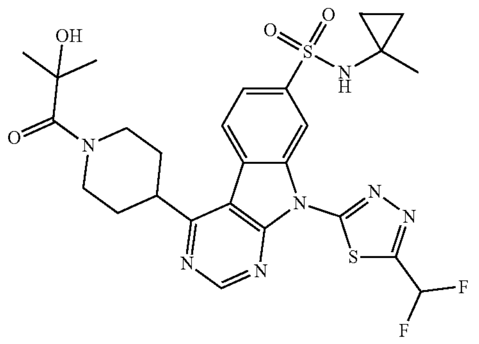 [SMILES: CC1(NS(=O)(=O)c2ccc3c4c(C5CCN(C(=O)C(C)(C)O)CC5)ncnc4n(-c4nnc(C(F)F)s4)c3c2)CC1]
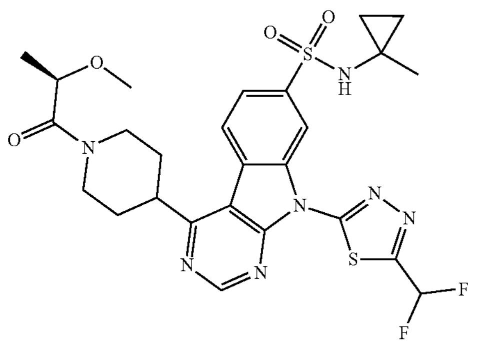 [SMILES: CO[C@H](C)C(=O)N1CCC(c2ncnc3c2c2ccc(S(=O)(=O)NC4(C)CC4)cc2n3-c2nnc(C(F)F)s2)CC1]
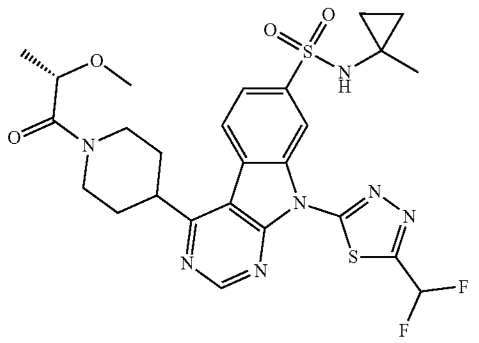 [SMILES: CO[C@@H](C)C(=O)N1CCC(c2ncnc3c2c2ccc(S(=O)(=O)NC4(C)CC4)cc2n3-c2nnc(C(F)F)s2)CC1]
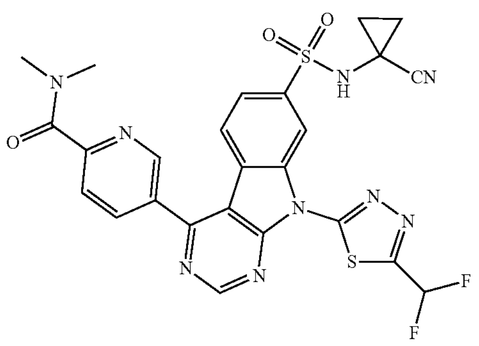 [SMILES: CN(C)C(=O)c1ccc(-c2ncnc3c2c2ccc(S(=O)(=O)NC4(C#N)CC4)cc2n3-c2nnc(C(F)F)s2)cn1]
-continued
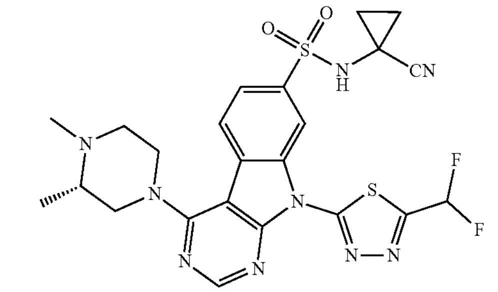 [SMILES: C[C@H]1CN(c2ncnc3c2c2ccc(S(=O)(=O)NC4(C#N)CC4)cc2n3-c2nnc(C(F)F)s2)CCN1C]
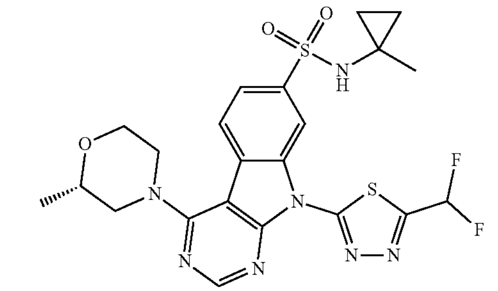 [SMILES: C[C@H]1CN(c2ncnc3c2c2ccc(S(=O)(=O)NC4(C)CC4)cc2n3-c2nnc(C(F)F)s2)CCO1]
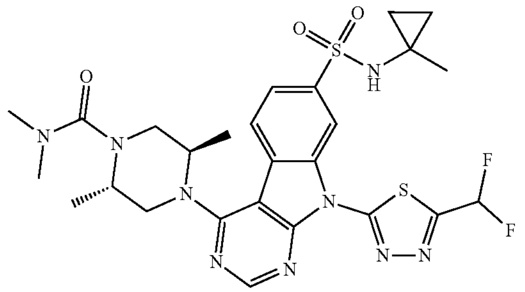 [SMILES: C[C@@H]1CN(C(=O)N(C)C)[C@@H](C)CN1c1ncnc2c1c1ccc(S(=O)(=O)NC3(C)CC3)cc1n2-c1nnc(C(F)F)s1]
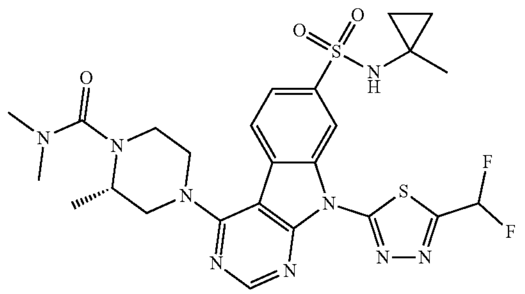 [SMILES: C[C@H]1CN(c2ncnc3c2c2ccc(S(=O)(=O)NC4(C)CC4)cc2n3-c2nnc(C(F)F)s2)CCN1C(=O)N(C)C]
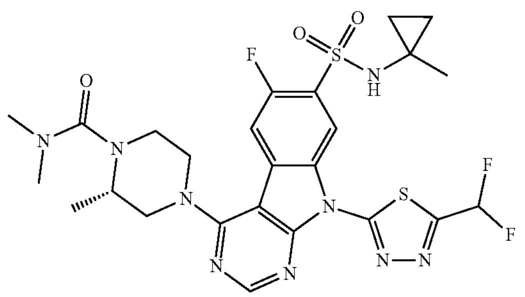 [SMILES: C[C@H]1CN(c2ncnc3c2c2cc(F)c(S(=O)(=O)NC4(C)CC4)cc2n3-c2nnc(C(F)F)s2)CCN1C(=O)N(C)C]

-continued
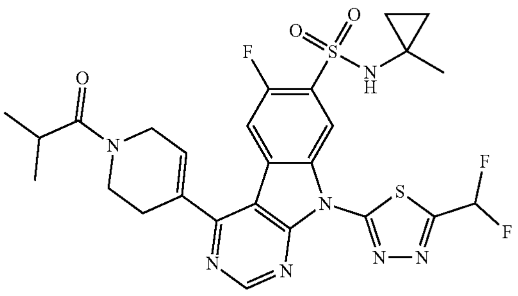 [SMILES: CC(C)C(=O)N1CC=C(c2ncnc3c2c2cc(F)c(S(=O)(=O)NC4(C)CC4)cc2n3-c2nnc(C(F)F)s2)CC1]
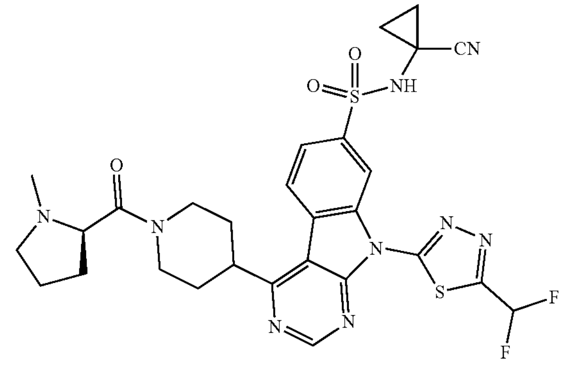 [SMILES: CN1CCC[C@@H]1C(=O)N1CCC(c2ncnc3c2c2ccc(S(=O)(=O)NC4(C#N)CC4)cc2n3-c2nnc(C(F)F)s2)CC1]
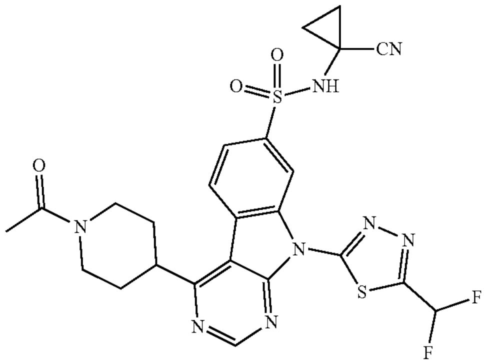 [SMILES: CC(=O)N1CCC(c2ncnc3c2c2ccc(S(=O)(=O)NC4(C#N)CC4)cc2n3-c2nnc(C(F)F)s2)CC1]
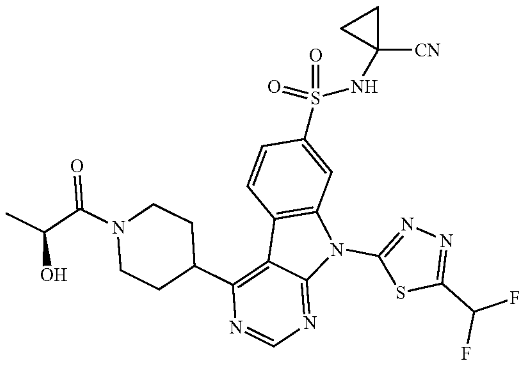 [SMILES: C[C@H](O)C(=O)N1CCC(c2ncnc3c2c2ccc(S(=O)(=O)NC4(C#N)CC4)cc2n3-c2nnc(C(F)F)s2)CC1]
-continued
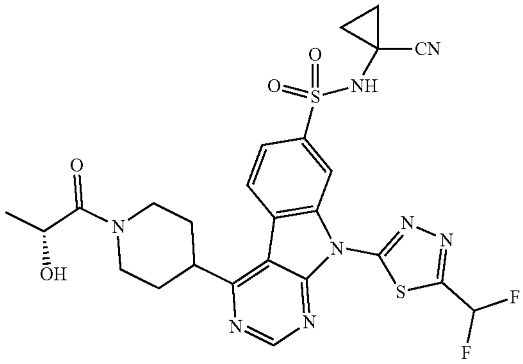 [SMILES: C[C@@H](O)C(=O)N1CCC(c2ncnc3c2c2ccc(S(=O)(=O)NC4(C#N)CC4)cc2n3-c2nnc(C(F)F)s2)CC1]
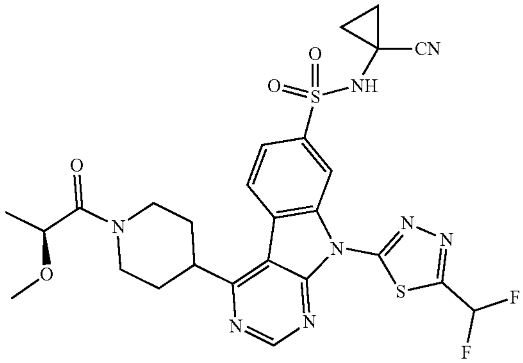 [SMILES: CO[C@@H](C)C(=O)N1CCC(c2ncnc3c2c2ccc(S(=O)(=O)NC4(C#N)CC4)cc2n3-c2nnc(C(F)F)s2)CC1]
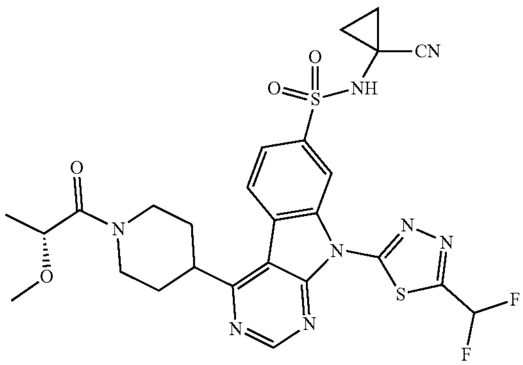 [SMILES: CO[C@H](C)C(=O)N1CCC(c2ncnc3c2c2ccc(S(=O)(=O)NC4(C#N)CC4)cc2n3-c2nnc(C(F)F)s2)CC1]
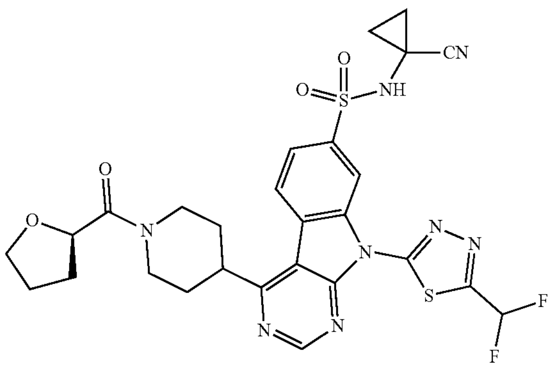 [SMILES: N#CC1(NS(=O)(=O)c2ccc3c4c(C5CCN(C(=O)[C@H]6CCCO6)CC5)ncnc4n(-c4nnc(C(F)F)s4)c3c2)CC1]

-continued
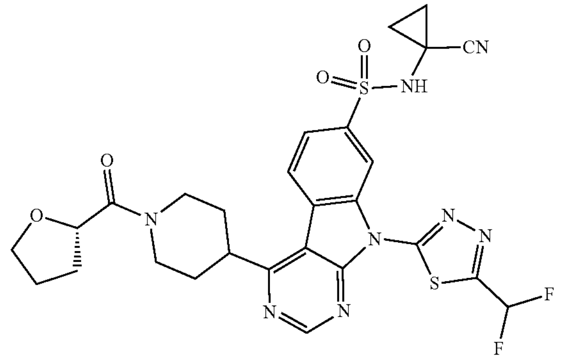 [SMILES: N#CC1(NS(=O)(=O)c2ccc3c4c(C5CCN(C(=O)[C@@H]6CCCO6)CC5)ncnc4n(-c4nnc(C(F)F)s4)c3c2)CC1]
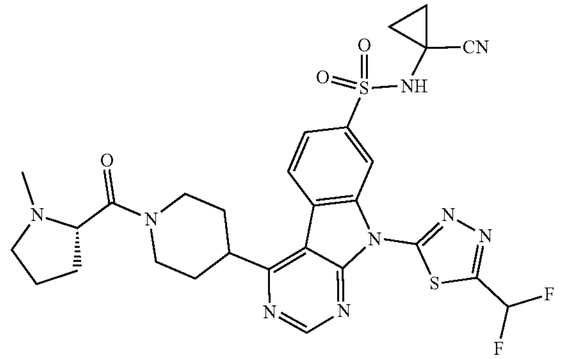 [SMILES: CN1CCC[C@H]1C(=O)N1CCC(c2ncnc3c2c2ccc(S(=O)(=O)NC4(C#N)CC4)cc2n3-c2nnc(C(F)F)s2)CC1]
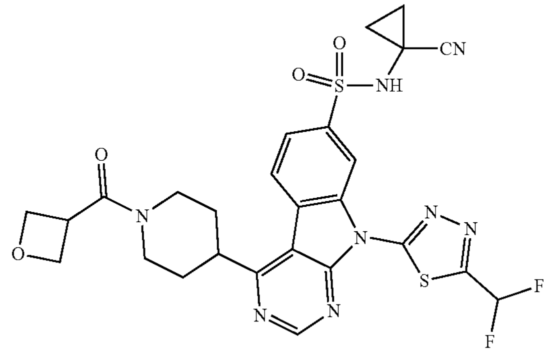 [SMILES: N#CC1(NS(=O)(=O)c2ccc3c4c(C5CCN(C(=O)C6COC6)CC5)ncnc4n(-c4nnc(C(F)F)s4)c3c2)CC1]
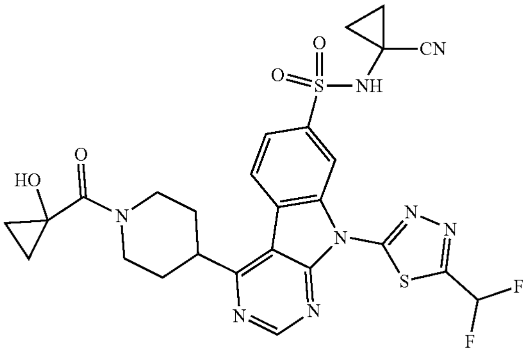 [SMILES: N#CC1(NS(=O)(=O)c2ccc3c4c(C5CCN(C(=O)C6(O)CC6)CC5)ncnc4n(-c4nnc(C(F)F)s4)c3c2)CC1]
-continued
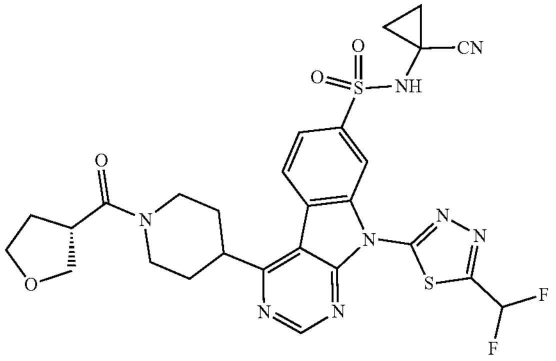 [SMILES: N#CC1(NS(=O)(=O)c2ccc3c4c(C5CCN(C(=O)[C@H]6CCOC6)CC5)ncnc4n(-c4nnc(C(F)F)s4)c3c2)CC1]
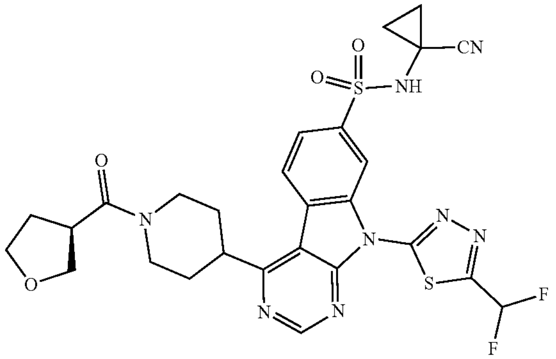 [SMILES: N#CC1(NS(=O)(=O)c2ccc3c4c(C5CCN(C(=O)[C@@H]6CCOC6)CC5)ncnc4n(-c4nnc(C(F)F)s4)c3c2)CC1]
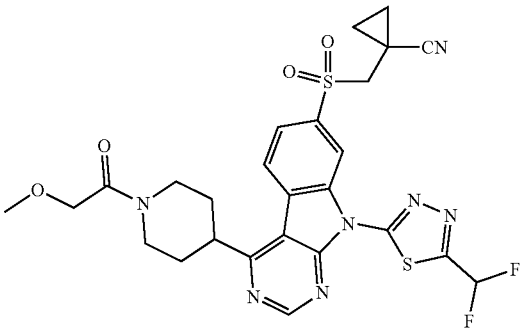 [SMILES: COCC(=O)N1CCC(c2ncnc3c2c2ccc(S(=O)(=O)CC4(C#N)CC4)cc2n3-c2nnc(C(F)F)s2)CC1]
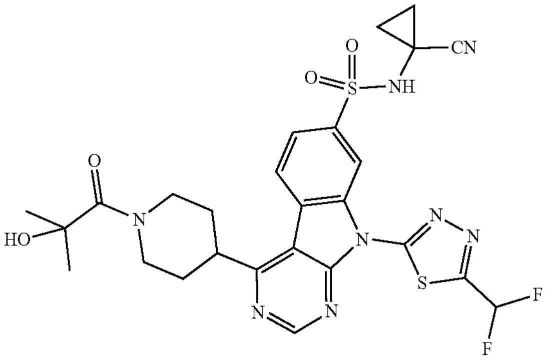 [SMILES: CC(C)(O)C(=O)N1CCC(c2ncnc3c2c2ccc(S(=O)(=O)NC4(C#N)CC4)cc2n3-c2nnc(C(F)F)s2)CC1]

-continued
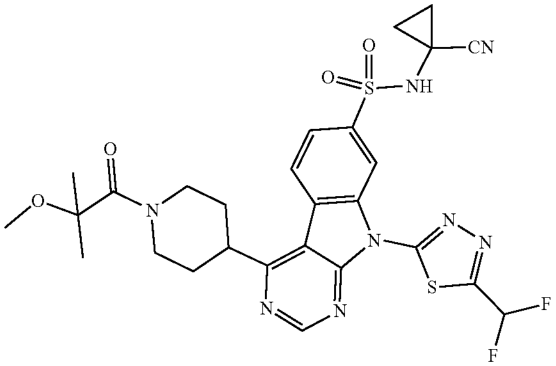 [SMILES: COC(C)(C)C(=O)N1CCC(c2ncnc3c2c2ccc(S(=O)(=O)NC4(C#N)CC4)cc2n3-c2nnc(C(F)F)s2)CC1]
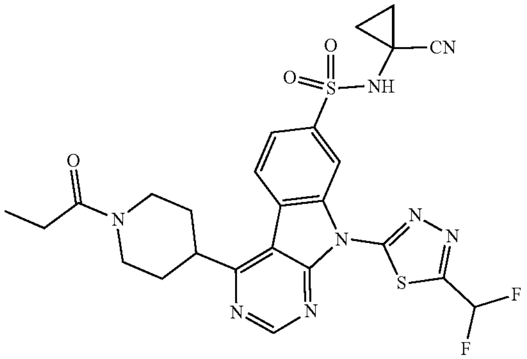 [SMILES: CCC(=O)N1CCC(c2ncnc3c2c2ccc(S(=O)(=O)NC4(C#N)CC4)cc2n3-c2nnc(C(F)F)s2)CC1]
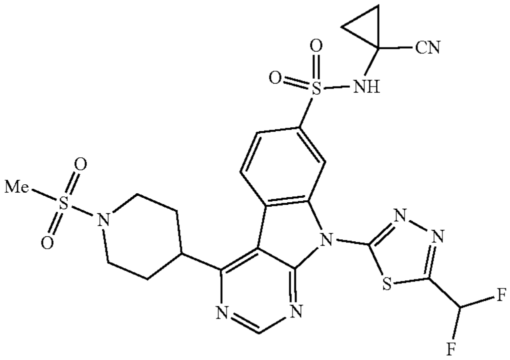 [SMILES: CS(=O)(=O)N1CCC(c2ncnc3c2c2ccc(S(=O)(=O)NC4(C#N)CC4)cc2n3-c2nnc(C(F)F)s2)CC1]
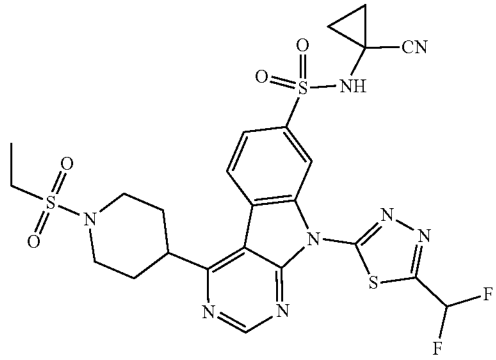 [SMILES: CCS(=O)(=O)N1CCC(c2ncnc3c2c2ccc(S(=O)(=O)NC4(C#N)CC4)cc2n3-c2nnc(C(F)F)s2)CC1]
-continued
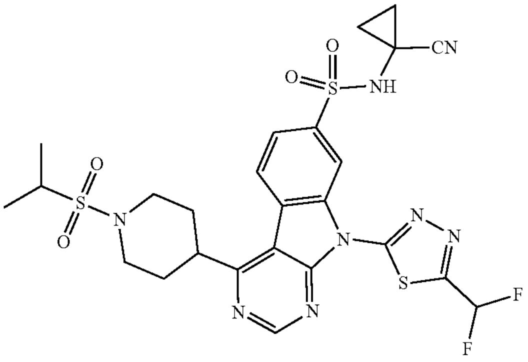 [SMILES: CC(C)S(=O)(=O)N1CCC(c2ncnc3c2c2ccc(S(=O)(=O)NC4(C#N)CC4)cc2n3-c2nnc(C(F)F)s2)CC1]
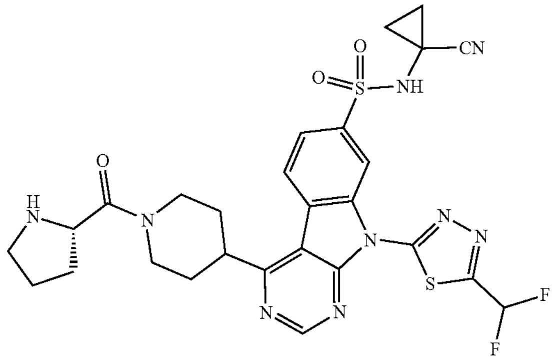 [SMILES: N#CC1(NS(=O)(=O)c2ccc3c4c(C5CCN(C(=O)[C@@H]6CCCN6)CC5)ncnc4n(-c4nnc(C(F)F)s4)c3c2)CC1]
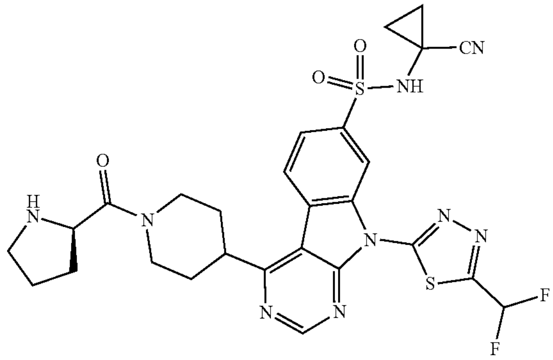 [SMILES: N#CC1(NS(=O)(=O)c2ccc3c4c(C5CCN(C(=O)[C@H]6CCCN6)CC5)ncnc4n(-c4nnc(C(F)F)s4)c3c2)CC1]
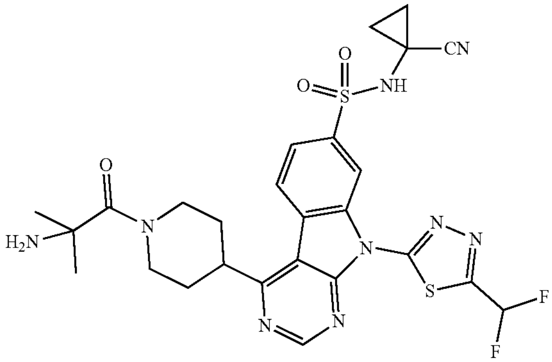 [SMILES: CC(C)(N)C(=O)N1CCC(c2ncnc3c2c2ccc(S(=O)(=O)NC4(C#N)CC4)cc2n3-c2nnc(C(F)F)s2)CC1]

-continued
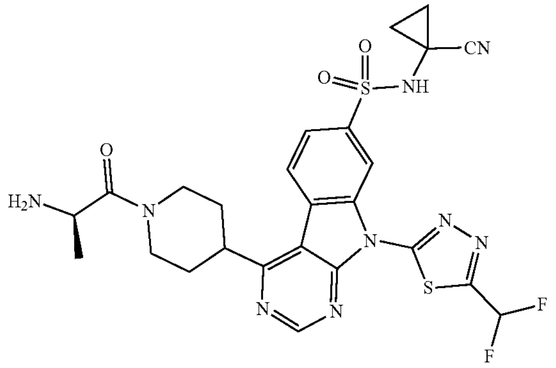 [SMILES: C[C@@H](N)C(=O)N1CCC(c2ncnc3c2c2ccc(S(=O)(=O)NC4(C#N)CC4)cc2n3-c2nnc(C(F)F)s2)CC1]
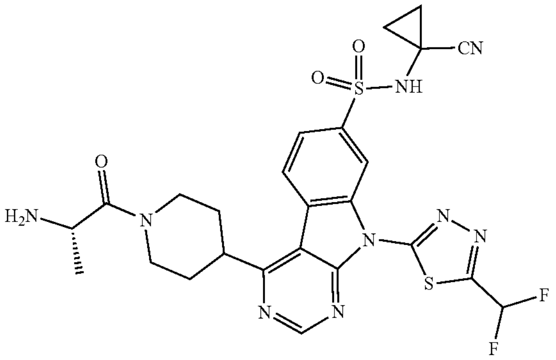 [SMILES: C[C@H](N)C(=O)N1CCC(c2ncnc3c2c2ccc(S(=O)(=O)NC4(C#N)CC4)cc2n3-c2nnc(C(F)F)s2)CC1]
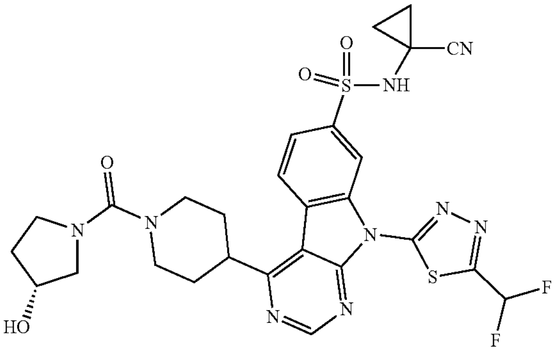 [SMILES: N#CC1(NS(=O)(=O)c2ccc3c4c(C5CCN(C(=O)N6CC[C@@H](O)C6)CC5)ncnc4n(-c4nnc(C(F)F)s4)c3c2)CC1]
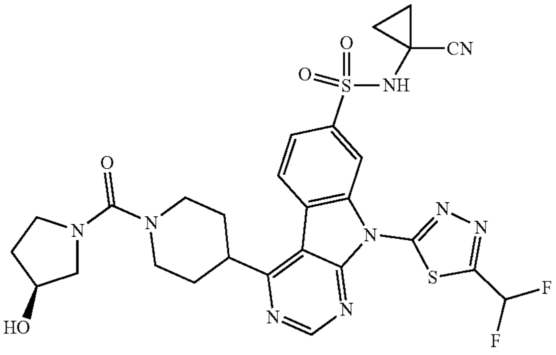 [SMILES: N#CC1(NS(=O)(=O)c2ccc3c4c(C5CCN(C(=O)N6CC[C@H](O)C6)CC5)ncnc4n(-c4nnc(C(F)F)s4)c3c2)CC1]
-continued
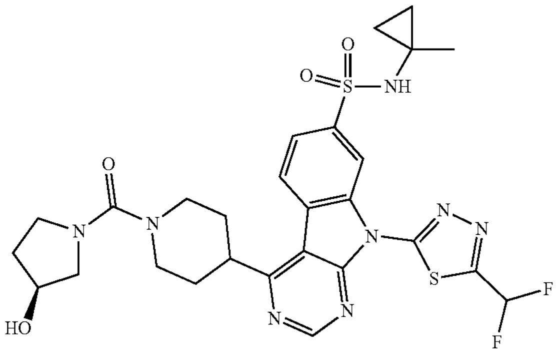 [SMILES: CC1(NS(=O)(=O)c2ccc3c4c(C5CCN(C(=O)N6CC[C@H](O)C6)CC5)ncnc4n(-c4nnc(C(F)F)s4)c3c2)CC1]
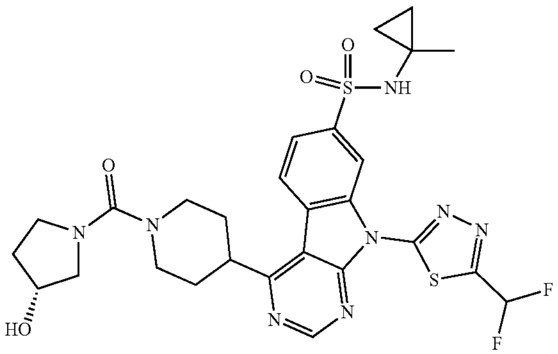
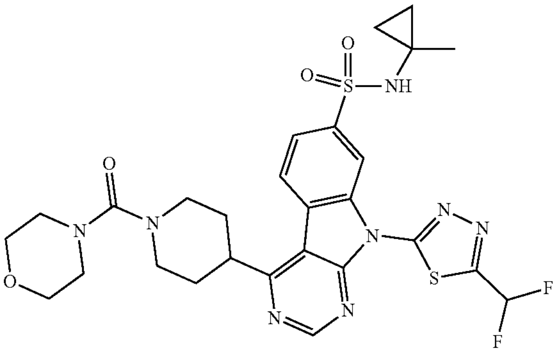 [SMILES: CC1(NS(=O)(=O)c2ccc3c4c(C5CCN(C(=O)N6CCOCC6)CC5)ncnc4n(-c4nnc(C(F)F)s4)c3c2)CC1]
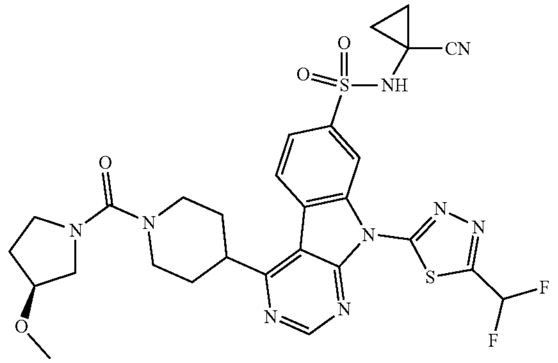 [SMILES: CO[C@H]1CCN(C(=O)N2CCC(c3ncnc4c3c3ccc(S(=O)(=O)NC5(C#N)CC5)cc3n4-c3nnc(C(F)F)s3)CC2)C1]

-continued
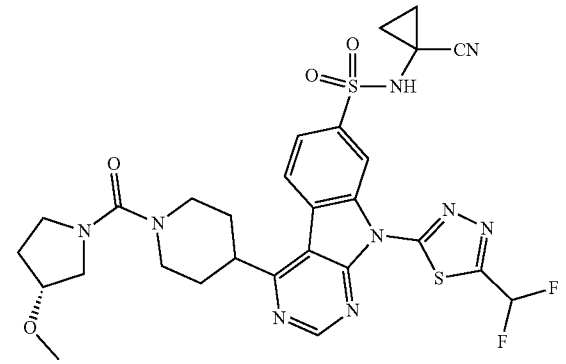 [SMILES: CO[C@@H]1CCN(C(=O)N2CCC(c3ncnc4c3c3ccc(S(=O)(=O)NC5(C#N)CC5)cc3n4-c3nnc(C(F)F)s3)CC2)C1]
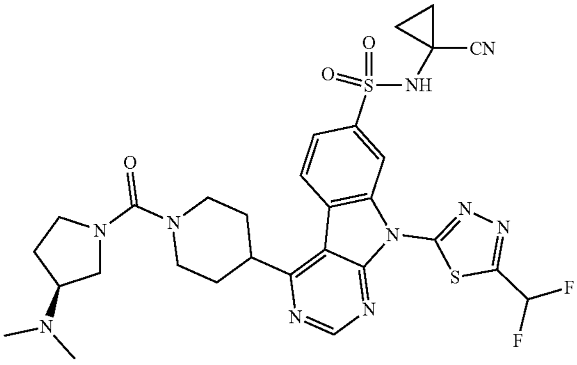 [SMILES: CN(C)[C@H]1CCN(C(=O)N2CCC(c3ncnc4c3c3ccc(S(=O)(=O)NC5(C#N)CC5)cc3n4-c3nnc(C(F)F)s3)CC2)C1]
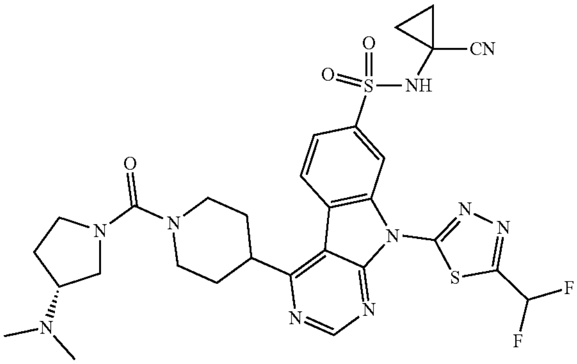
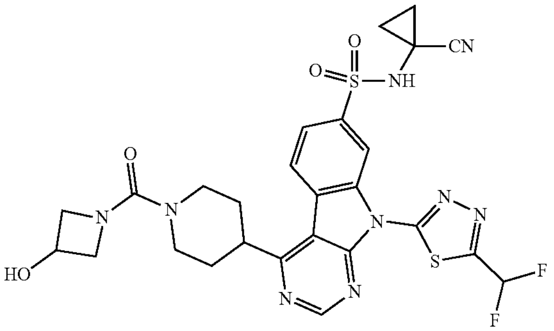 [SMILES: N#CC1(NS(=O)(=O)c2ccc3c4c(C5CCN(C(=O)N6CC(O)C6)CC5)ncnc4n(-c4nnc(C(F)F)s4)c3c2)CC1]
-continued
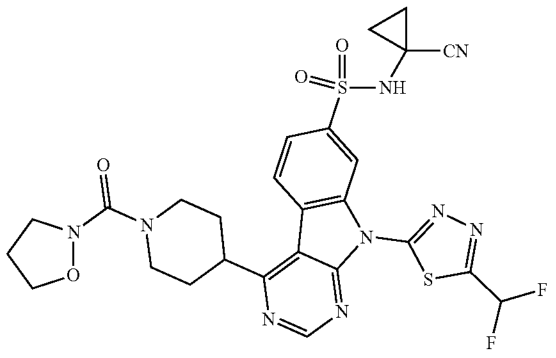 [SMILES: N#CC1(NS(=O)(=O)c2ccc3c4c(C5CCN(C(=O)N6CCCO6)CC5)ncnc4n(-c4nnc(C(F)F)s4)c3c2)CC1]
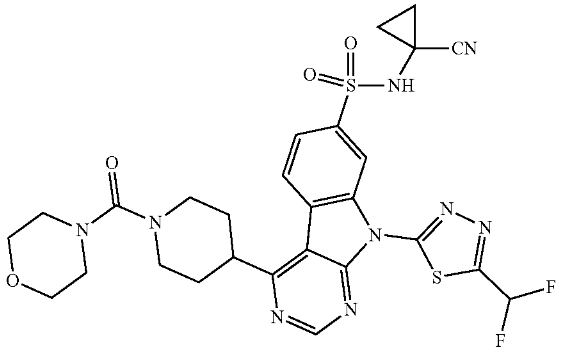 [SMILES: N#CC1(NS(=O)(=O)c2ccc3c4c(C5CCN(C(=O)N6CCOCC6)CC5)ncnc4n(-c4nnc(C(F)F)s4)c3c2)CC1]
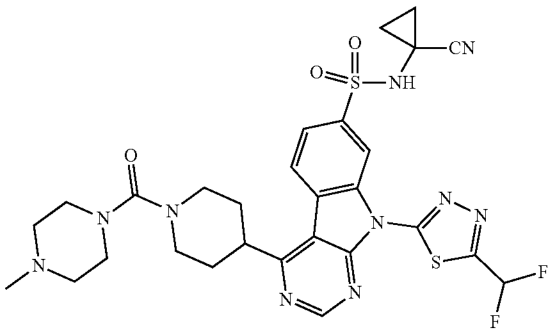 [SMILES: CN1CCN(C(=O)N2CCC(c3ncnc4c3c3ccc(S(=O)(=O)NC5(C#N)CC5)cc3n4-c3nnc(C(F)F)s3)CC2)CC1]
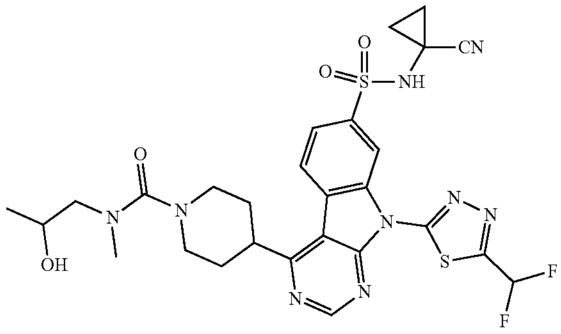 [SMILES: CC(O)CN(C)C(=O)N1CCC(c2ncnc3c2c2ccc(S(=O)(=O)NC4(C#N)CC4)cc2n3-c2nnc(C(F)F)s2)CC1]

-continued
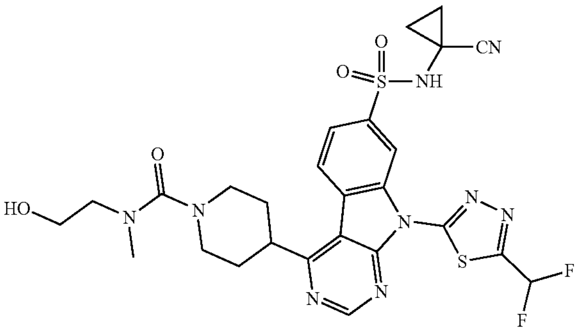 [SMILES: CN(CCO)C(=O)N1CCC(c2ncnc3c2c2ccc(S(=O)(=O)NC4(C#N)CC4)cc2n3-c2nnc(C(F)F)s2)CC1]
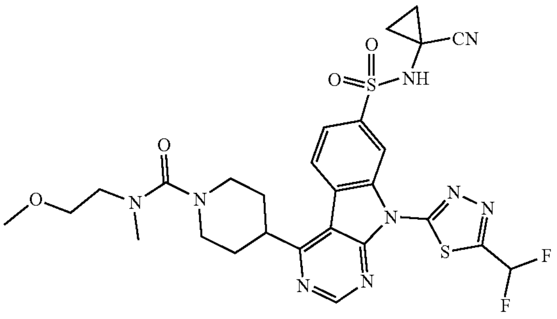 [SMILES: COCCN(C)C(=O)N1CCC(c2ncnc3c2c2ccc(S(=O)(=O)NC4(C#N)CC4)cc2n3-c2nnc(C(F)F)s2)CC1]
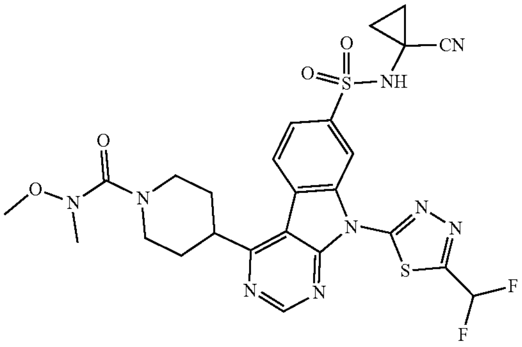 [SMILES: CON(C)C(=O)N1CCC(c2ncnc3c2c2ccc(S(=O)(=O)NC4(C#N)CC4)cc2n3-c2nnc(C(F)F)s2)CC1]
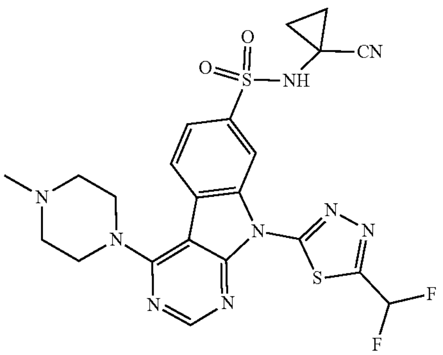 [SMILES: CN1CCN(c2ncnc3c2c2ccc(S(=O)(=O)NC4(C#N)CC4)cc2n3-c2nnc(C(F)F)s2)CC1]
-continued
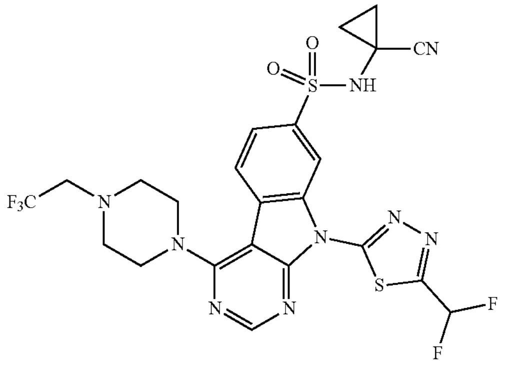 [SMILES: N#CC1(NS(=O)(=O)c2ccc3c4c(N5CCN(CC(F)(F)F)CC5)ncnc4n(-c4nnc(C(F)F)s4)c3c2)CC1]
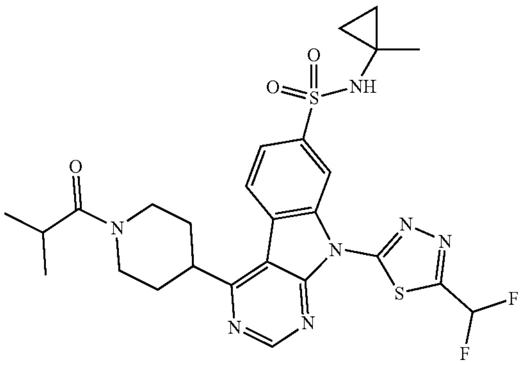 [SMILES: CC(C)C(=O)N1CCC(c2ncnc3c2c2ccc(S(=O)(=O)NC4(C)CC4)cc2n3-c2nnc(C(F)F)s2)CC1]
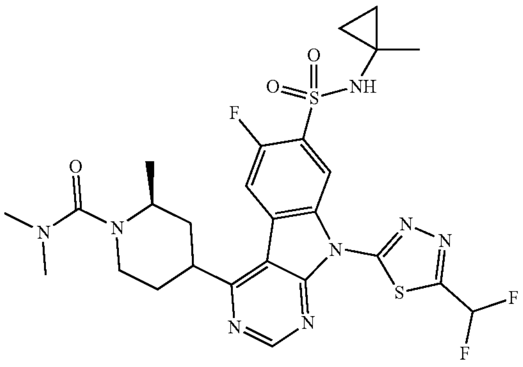 [SMILES: C[C@H]1CC(c2ncnc3c2c2cc(F)c(S(=O)(=O)NC4(C)CC4)cc2n3-c2nnc(C(F)F)s2)CCN1C(=O)N(C)C]
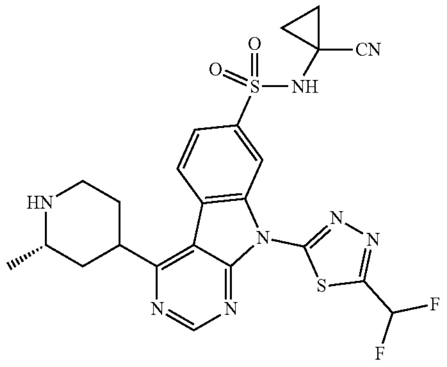 [SMILES: C[C@H]1CC(c2ncnc3c2c2ccc(S(=O)(=O)NC4(C#N)CC4)cc2n3-c2nnc(C(F)F)s2)CCN1]

-continued
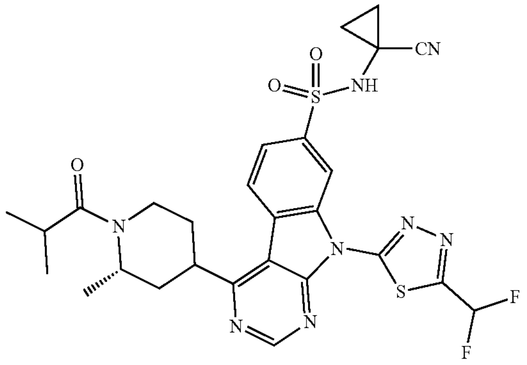 [SMILES: CC(C)C(=O)N1CCC(c2ncnc3c2c2ccc(S(=O)(=O)NC4(C#N)CC4)cc2n3-c2nnc(C(F)F)s2)C[C@@H]1C]
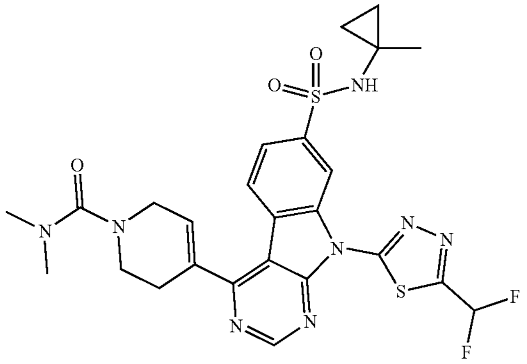 [SMILES: CN(C)C(=O)N1CC=C(c2ncnc3c2c2ccc(S(=O)(=O)NC4(C)CC4)cc2n3-c2nnc(C(F)F)s2)CC1]
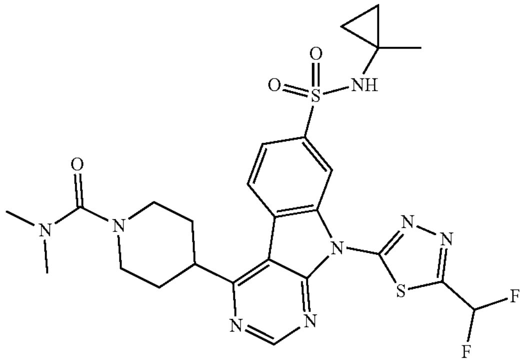
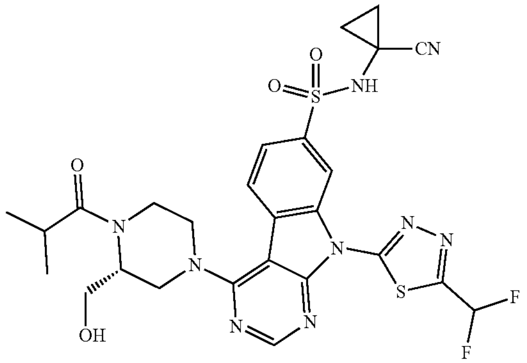 [SMILES: CC(C)C(=O)N1CCN(c2ncnc3c2c2ccc(S(=O)(=O)NC4(C#N)CC4)cc2n3-c2nnc(C(F)F)s2)C[C@@H]1CO]
-continued
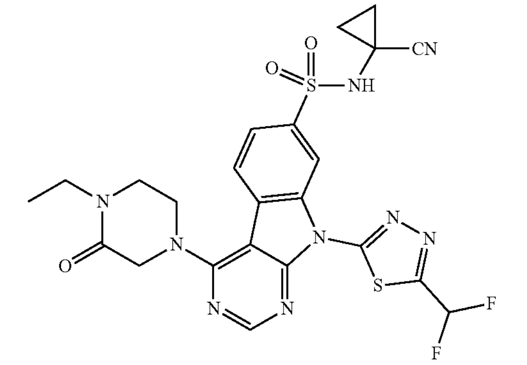 [SMILES: CCN1CCN(c2ncnc3c2c2ccc(S(=O)(=O)NC4(C#N)CC4)cc2n3-c2nnc(C(F)F)s2)CC1=O]
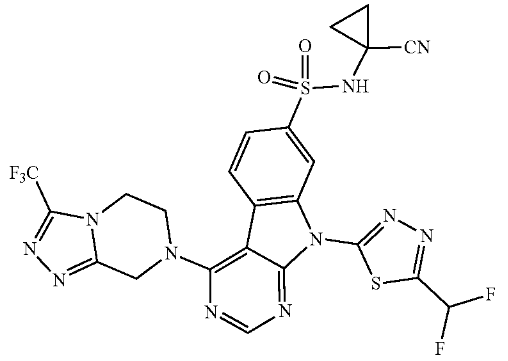 [SMILES: N#CC1(NS(=O)(=O)c2ccc3c4c(N5CCn6c(nnc6C(F)(F)F)C5)ncnc4n(-c4nnc(C(F)F)s4)c3c2)CC1]
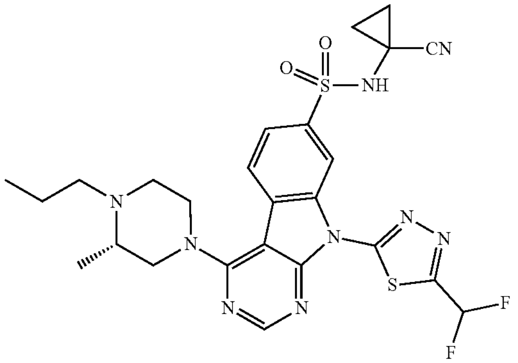 [SMILES: CCCN1CCN(c2ncnc3c2c2ccc(S(=O)(=O)NC4(C#N)CC4)cc2n3-c2nnc(C(F)F)s2)C[C@@H]1C]
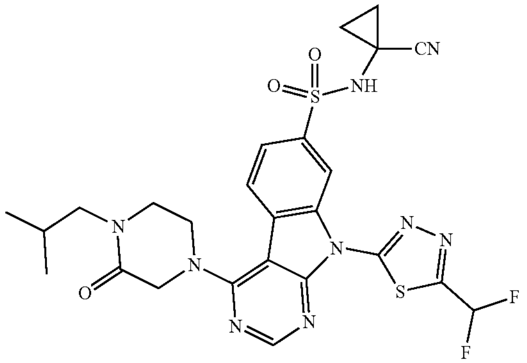 [SMILES: CC(C)CN1CCN(c2ncnc3c2c2ccc(S(=O)(=O)NC4(C#N)CC4)cc2n3-c2nnc(C(F)F)s2)CC1=O]

-continued
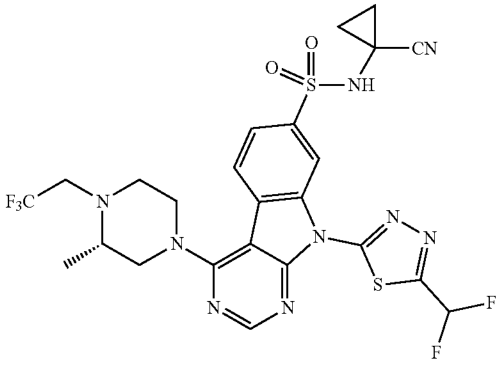 [SMILES: C[C@H]1CN(c2ncnc3c2c2ccc(S(=O)(=O)NC4(C#N)CC4)cc2n3-c2nnc(C(F)F)s2)CCN1CC(F)(F)F]
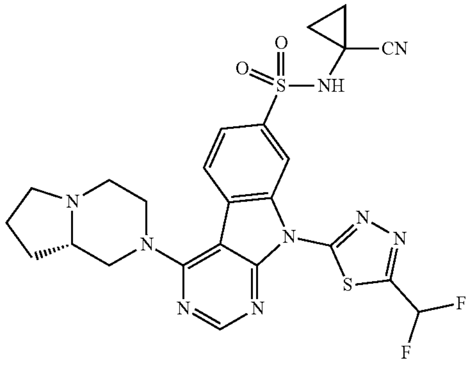
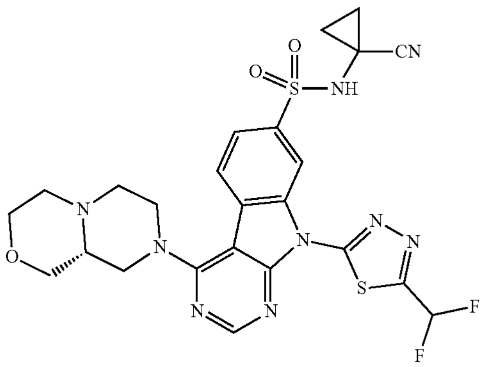 [SMILES: N#CC1(NS(=O)(=O)c2ccc3c4c(N5CCN6CCOC[C@H]6C5)ncnc4n(-c4nnc(C(F)F)s4)c3c2)CC1]
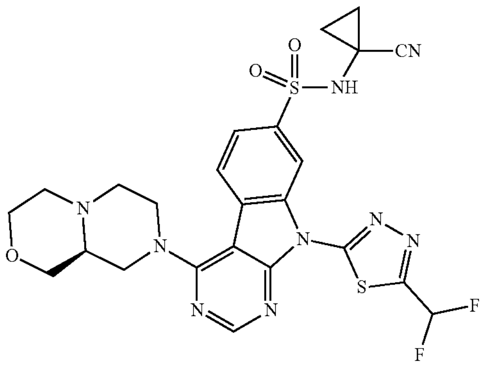 [SMILES: N#CC1(NS(=O)(=O)c2ccc3c4c(N5CCN6CCOC[C@@H]6C5)ncnc4n(-c4nnc(C(F)F)s4)c3c2)CC1]
-continued
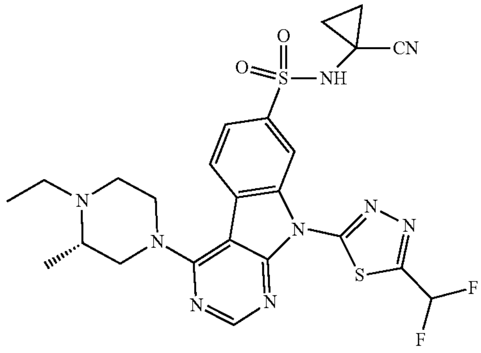 [SMILES: CCN1CCN(c2ncnc3c2c2ccc(S(=O)(=O)NC4(C#N)CC4)cc2n3-c2nnc(C(F)F)s2)C[C@@H]1C]
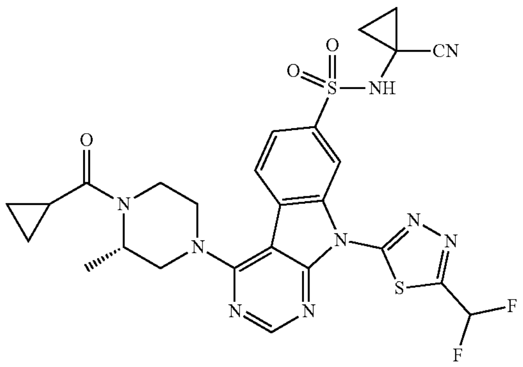 [SMILES: C[C@H]1CN(c2ncnc3c2c2ccc(S(=O)(=O)NC4(C#N)CC4)cc2n3-c2nnc(C(F)F)s2)CCN1C(=O)C1CC1]
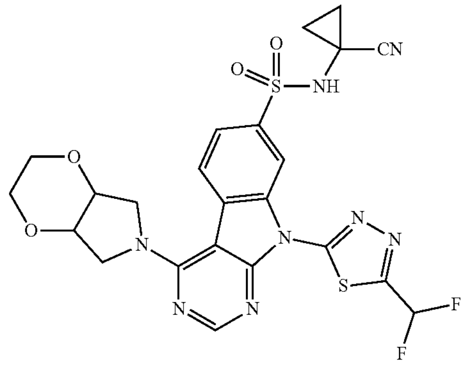 [SMILES: N#CC1(NS(=O)(=O)c2ccc3c4c(N5CC6OCCOC6C5)ncnc4n(-c4nnc(C(F)F)s4)c3c2)CC1]
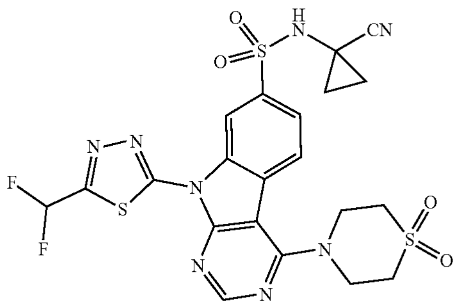 [SMILES: N#CC1(NS(=O)(=O)c2ccc3c4c(N5CCS(=O)(=O)CC5)ncnc4n(-c4nnc(C(F)F)s4)c3c2)CC1]

-continued
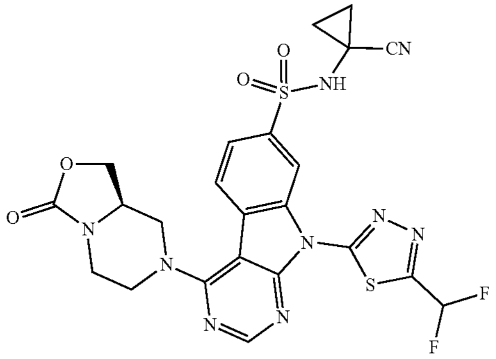 [SMILES: N#CC1(NS(=O)(=O)c2ccc3c4c(N5CCN6C(=O)OC[C@H]6C5)ncnc4n(-c4nnc(C(F)F)s4)c3c2)CC1]
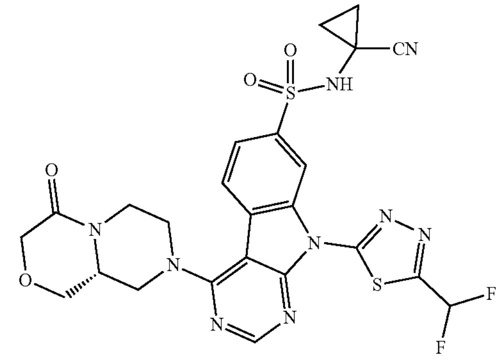 [SMILES: N#CC1(NS(=O)(=O)c2ccc3c4c(N5CCN6C(=O)COC[C@H]6C5)ncnc4n(-c4nnc(C(F)F)s4)c3c2)CC1]
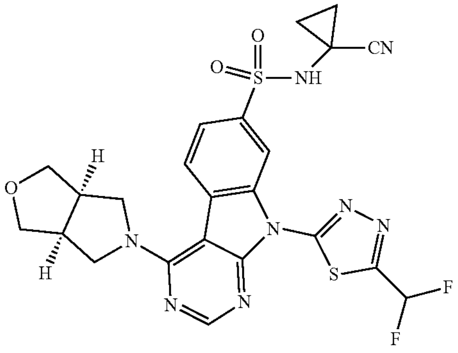 [SMILES: N#CC1(NS(=O)(=O)c2ccc3c4c(N5C[C@H]6COC[C@H]6C5)ncnc4n(-c4nnc(C(F)F)s4)c3c2)CC1]
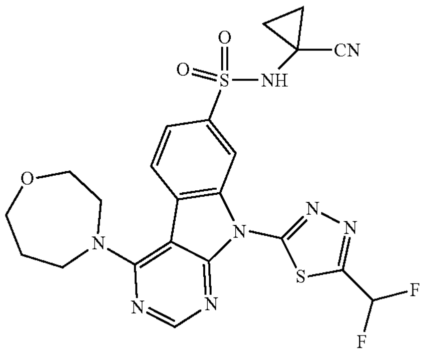 [SMILES: N#CC1(NS(=O)(=O)c2ccc3c4c(N5CCCOCC5)ncnc4n(-c4nnc(C(F)F)s4)c3c2)CC1]
-continued
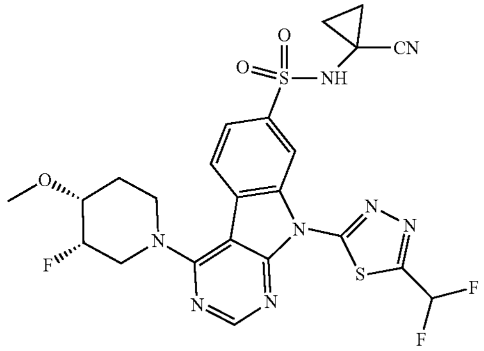
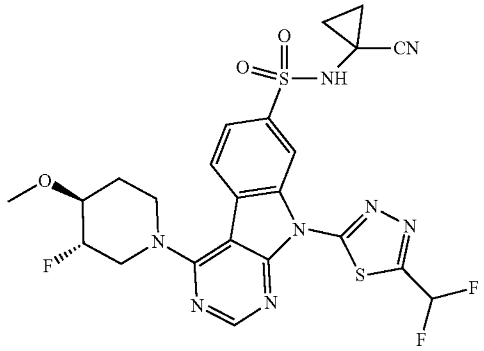 [SMILES: CO[C@H]1CCN(c2ncnc3c2c2ccc(S(=O)(=O)NC4(C#N)CC4)cc2n3-c2nnc(C(F)F)s2)C[C@@H]1F]
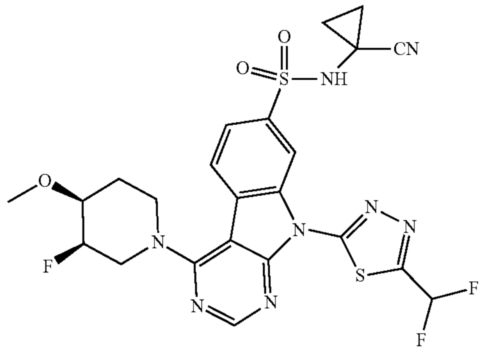 [SMILES: CO[C@H]1CCN(c2ncnc3c2c2ccc(S(=O)(=O)NC4(C#N)CC4)cc2n3-c2nnc(C(F)F)s2)C[C@H]1F]
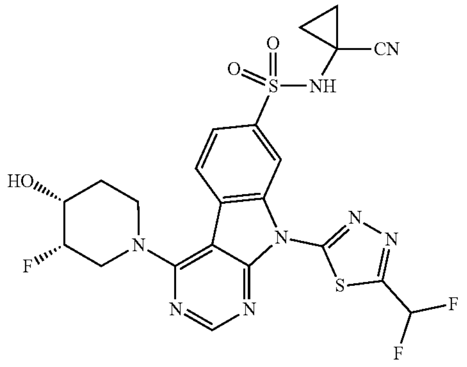 [SMILES: N#CC1(NS(=O)(=O)c2ccc3c4c(N5CC[C@@H](O)[C@@H](F)C5)ncnc4n(-c4nnc(C(F)F)s4)c3c2)CC1]

-continued
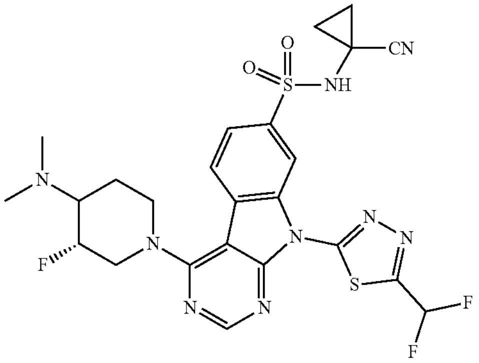 [SMILES: CN(C)C1CCN(c2ncnc3c2c2ccc(S(=O)(=O)NC4(C#N)CC4)cc2n3-c2nnc(C(F)F)s2)C[C@@H]1F]
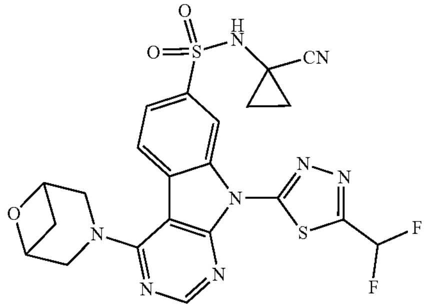 [SMILES: N#CC1(NS(=O)(=O)c2ccc3c4c(N5CC6CC(C5)O6)ncnc4n(-c4nnc(C(F)F)s4)c3c2)CC1]
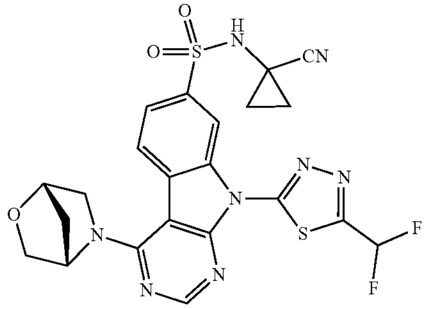 [SMILES: N#CC1(NS(=O)(=O)c2ccc3c4c(N5C[C@@H]6C[C@H]5CO6)ncnc4n(-c4nnc(C(F)F)s4)c3c2)CC1]
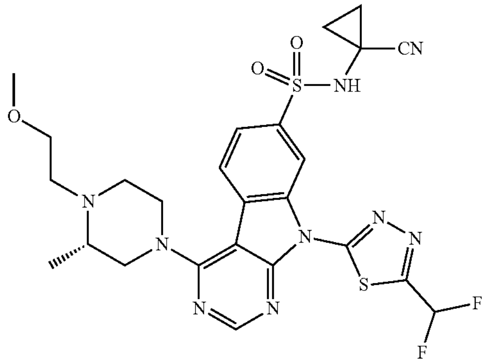 [SMILES: COCCN1CCN(c2ncnc3c2c2ccc(S(=O)(=O)NC4(C#N)CC4)cc2n3-c2nnc(C(F)F)s2)C[C@@H]1C]
-continued
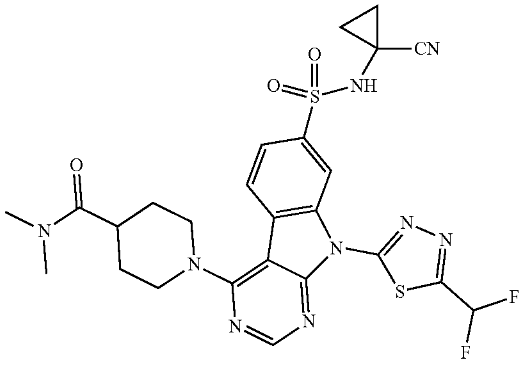 [SMILES: CN(C)C(=O)C1CCN(c2ncnc3c2c2ccc(S(=O)(=O)NC4(C#N)CC4)cc2n3-c2nnc(C(F)F)s2)CC1]
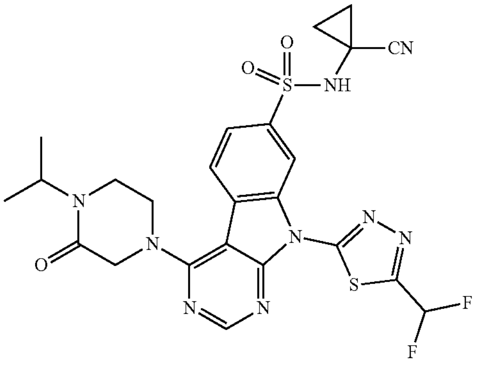 [SMILES: CC(C)N1CCN(c2ncnc3c2c2ccc(S(=O)(=O)NC4(C#N)CC4)cc2n3-c2nnc(C(F)F)s2)CC1=O]
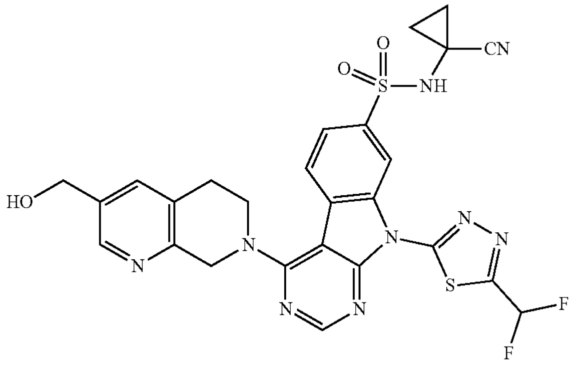 [SMILES: N#CC1(NS(=O)(=O)c2ccc3c4c(N5CCc6cc(CO)cnc6C5)ncnc4n(-c4nnc(C(F)F)s4)c3c2)CC1]
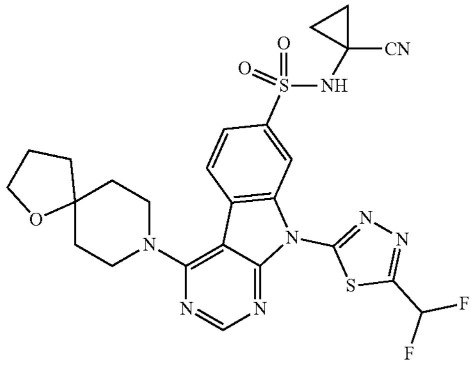 [SMILES: N#CC1(NS(=O)(=O)c2ccc3c4c(N5CCC6(CCCO6)CC5)ncnc4n(-c4nnc(C(F)F)s4)c3c2)CC1]

-continued
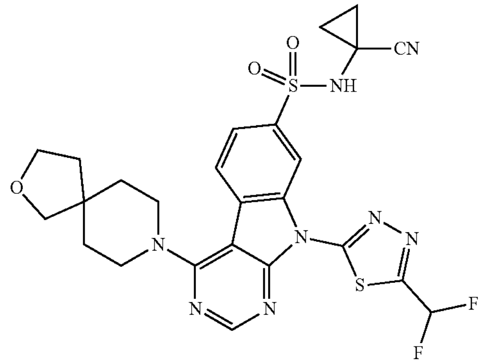 [SMILES: N#CC1(NS(=O)(=O)c2ccc3c4c(N5CCC6(CCOC6)CC5)ncnc4n(-c4nnc(C(F)F)s4)c3c2)CC1]
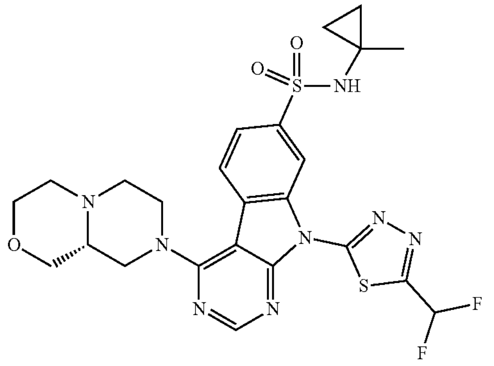 [SMILES: CC1(NS(=O)(=O)c2ccc3c4c(N5CCN6CCOC[C@H]6C5)ncnc4n(-c4nnc(C(F)F)s4)c3c2)CC1]
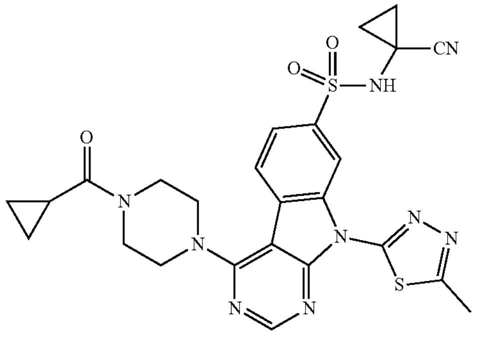 [SMILES: Cc1nnc(-n2c3cc(S(=O)(=O)NC4(C#N)CC4)ccc3c3c(N4CCN(C(=O)C5CC5)CC4)ncnc32)s1]
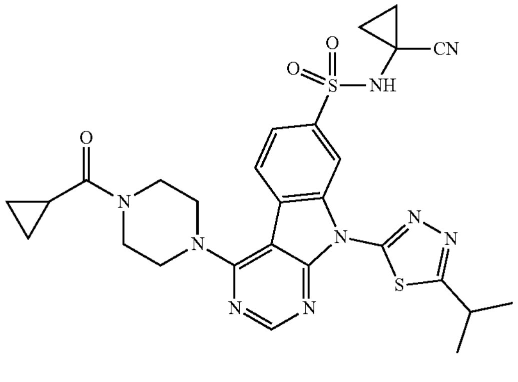 [SMILES: CC(C)c1nnc(-n2c3cc(S(=O)(=O)NC4(C#N)CC4)ccc3c3c(N4CCN(C(=O)C5CC5)CC4)ncnc32)s1]
-continued
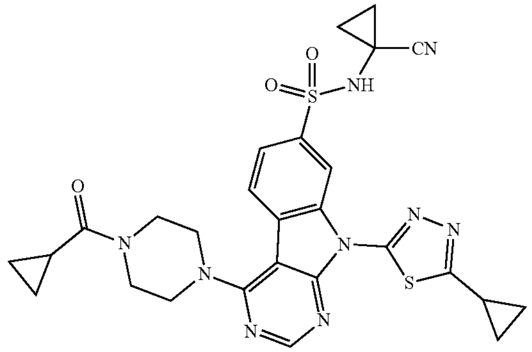 [SMILES: N#CC1(NS(=O)(=O)c2ccc3c4c(N5CCN(C(=O)C6CC6)CC5)ncnc4n(-c4nnc(C5CC5)s4)c3c2)CC1]
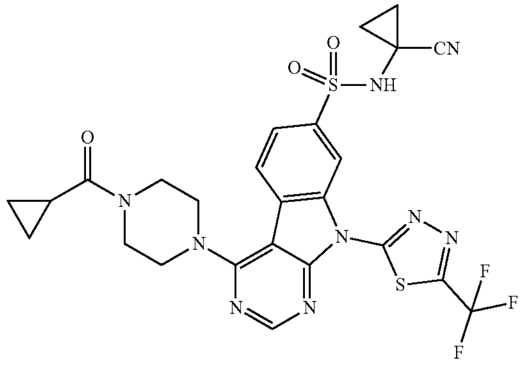 [SMILES: N#CC1(NS(=O)(=O)c2ccc3c4c(N5CCN(C(=O)C6CC6)CC5)ncnc4n(-c4nnc(C(F)(F)F)s4)c3c2)CC1]
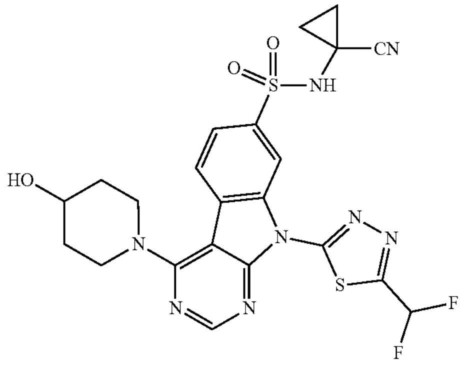 [SMILES: N#CC1(NS(=O)(=O)c2ccc3c4c(N5CCC(O)CC5)ncnc4n(-c4nnc(C(F)F)s4)c3c2)CC1]
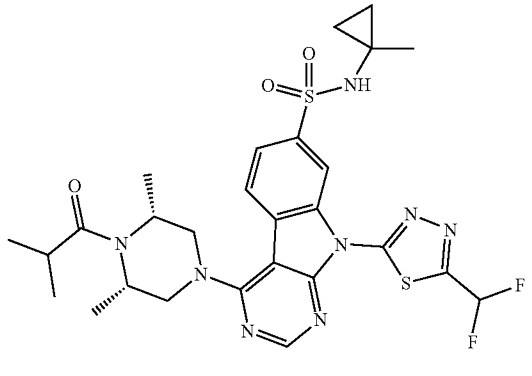 [SMILES: CC(C)C(=O)N1[C@H](C)CN(c2ncnc3c2c2ccc(S(=O)(=O)NC4(C)CC4)cc2n3-c2nnc(C(F)F)s2)C[C@@H]1C]

-continued
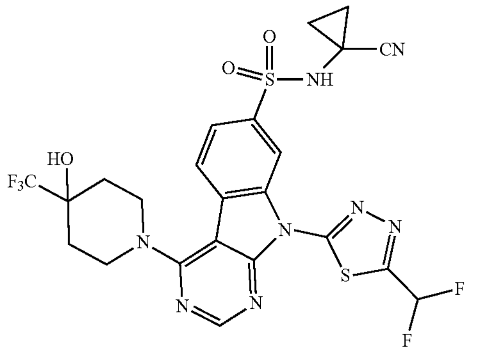 [SMILES: N#CC1(NS(=O)(=O)c2ccc3c4c(N5CCC(O)(C(F)(F)F)CC5)ncnc4n(-c4nnc(C(F)F)s4)c3c2)CC1]
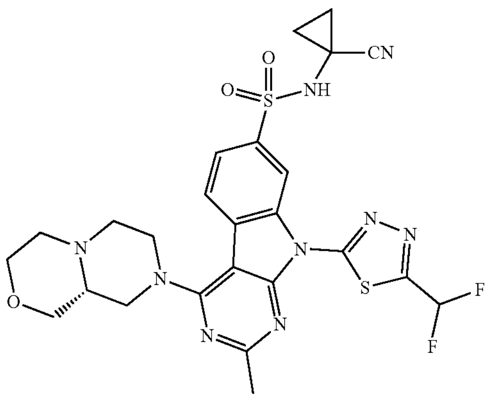 [SMILES: Cc1nc(N2CCN3CCOC[C@H]3C2)c2c3ccc(S(=O)(=O)NC4(C#N)CC4)cc3n(-c3nnc(C(F)F)s3)c2n1]
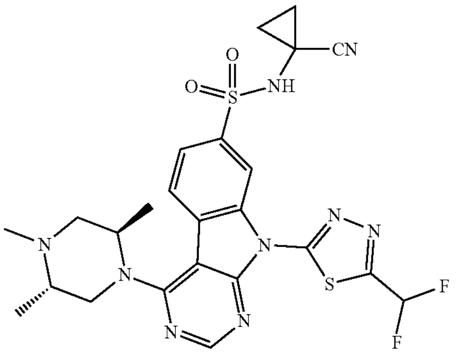 [SMILES: C[C@@H]1CN(C)[C@@H](C)CN1c1ncnc2c1c1ccc(S(=O)(=O)NC3(C#N)CC3)cc1n2-c1nnc(C(F)F)s1]
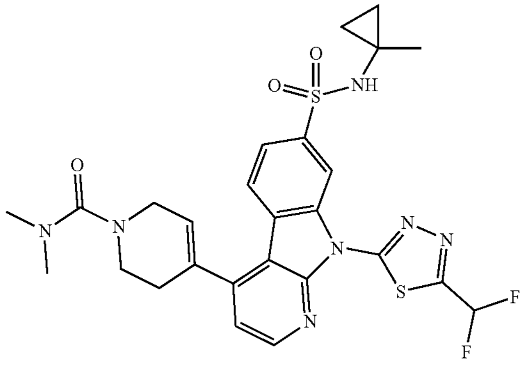
-continued
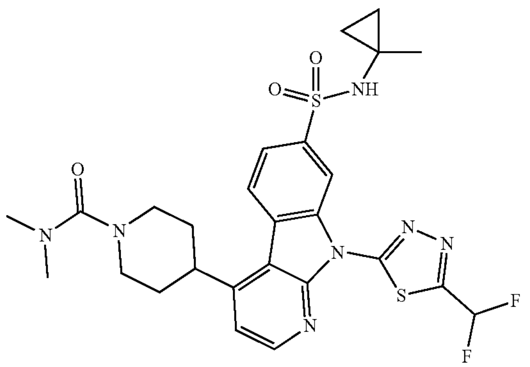 [SMILES: CN(C)C(=O)N1CCC(c2ccnc3c2c2ccc(S(=O)(=O)NC4(C)CC4)cc2n3-c2nnc(C(F)F)s2)CC1]
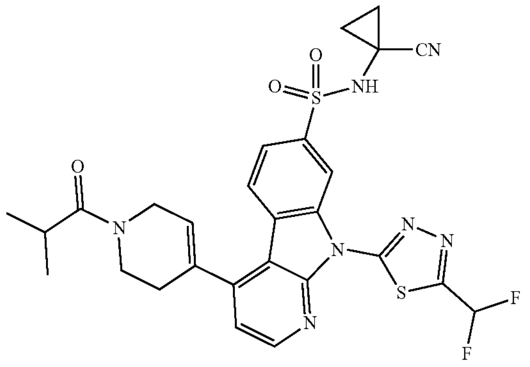 [SMILES: CC(C)C(=O)N1CC=C(c2ccnc3c2c2ccc(S(=O)(=O)NC4(C#N)CC4)cc2n3-c2nnc(C(F)F)s2)CC1]
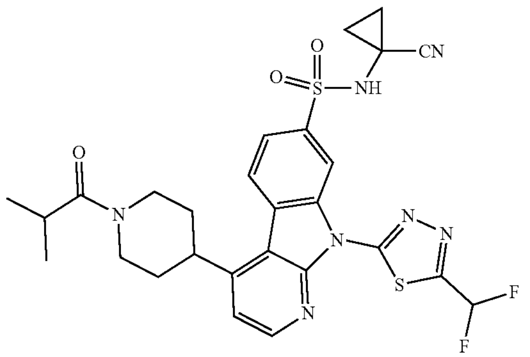 [SMILES: CC(C)C(=O)N1CCC(c2ccnc3c2c2ccc(S(=O)(=O)NC4(C#N)CC4)cc2n3-c2nnc(C(F)F)s2)CC1]
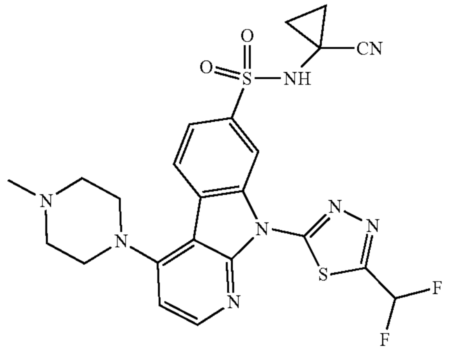 [SMILES: CN1CCN(c2ccnc3c2c2ccc(S(=O)(=O)NC4(C#N)CC4)cc2n3-c2nnc(C(F)F)s2)CC1]

-continued
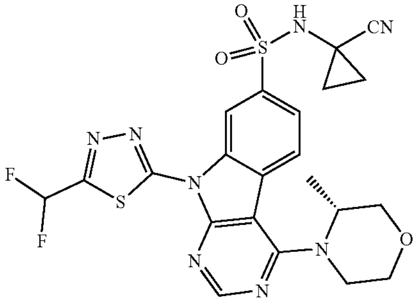 [SMILES: C[C@@H]1COCCN1c1ncnc2c1c1ccc(S(=O)(=O)NC3(C#N)CC3)cc1n2-c1nnc(C(F)F)s1]
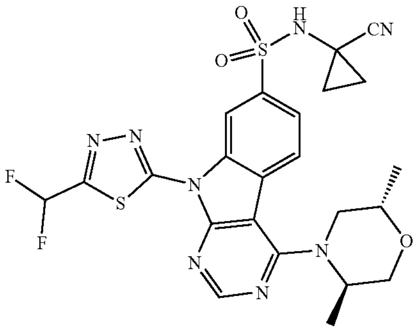 [SMILES: C[C@@H]1CO[C@@H](C)CN1c1ncnc2c1c1ccc(S(=O)(=O)NC3(C#N)CC3)cc1n2-c1nnc(C(F)F)s1]
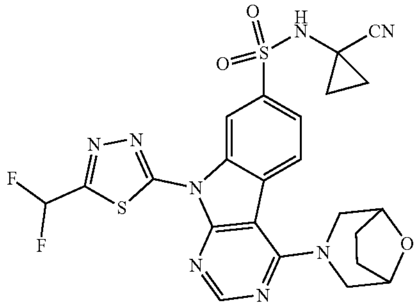 [SMILES: N#CC1(NS(=O)(=O)c2ccc3c4c(N5CC6CCC(C5)O6)ncnc4n(-c4nnc(C(F)F)s4)c3c2)CC1]
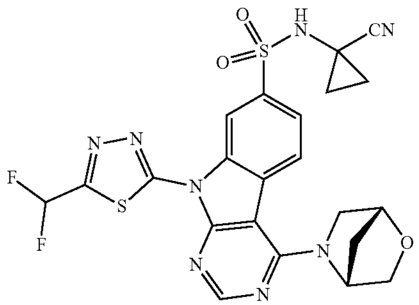 [SMILES: N#CC1(NS(=O)(=O)c2ccc3c4c(N5C[C@H]6C[C@@H]5CO6)ncnc4n(-c4nnc(C(F)F)s4)c3c2)CC1]
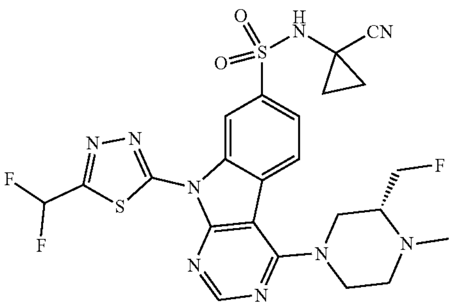 [SMILES: CN1CCN(c2ncnc3c2c2ccc(S(=O)(=O)NC4(C#N)CC4)cc2n3-c2nnc(C(F)F)s2)C[C@@H]1CF]
-continued
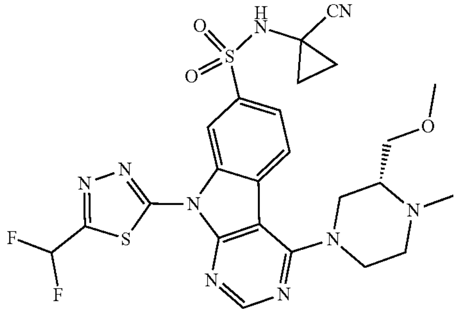
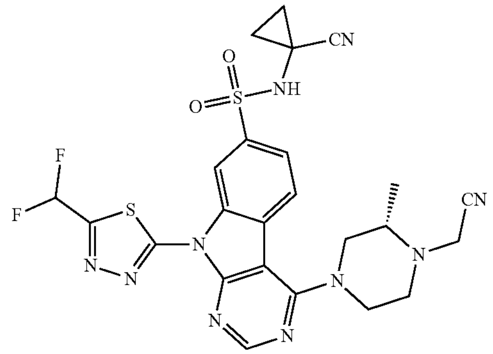
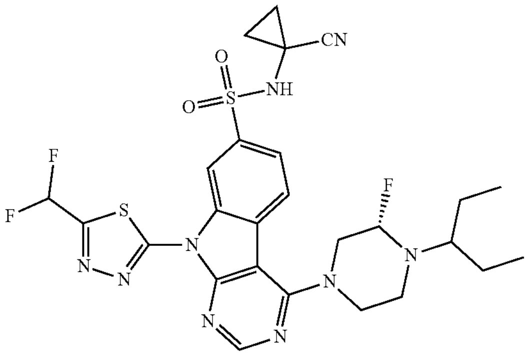 [SMILES: CCC(CC)N1CCN(c2ncnc3c2c2ccc(S(=O)(=O)NC4(C#N)CC4)cc2n3-c2nnc(C(F)F)s2)C[C@@H]1F]
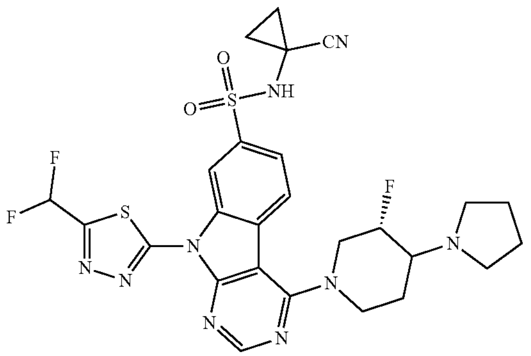

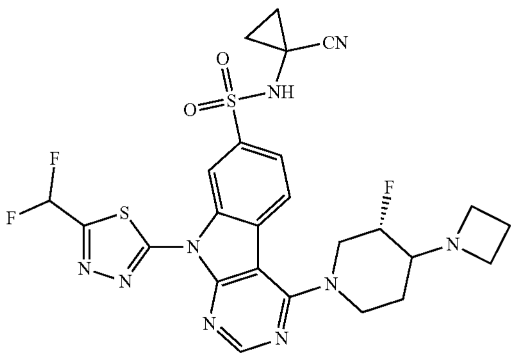
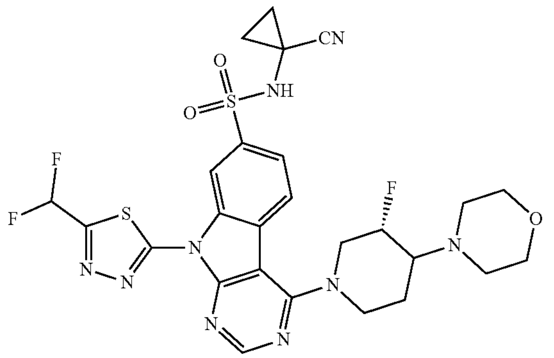 [SMILES: N#CC1(NS(=O)(=O)c2ccc3c4c(N5CCC(N6CCOCC6)[C@@H](F)C5)ncnc4n(-c4nnc(C(F)F)s4)c3c2)CC1]
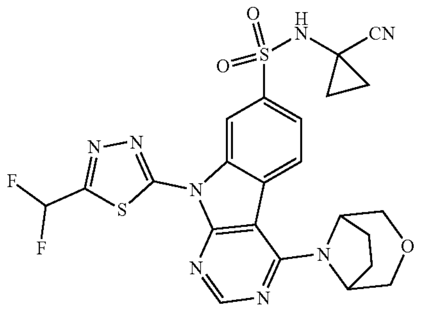 [SMILES: N#CC1(NS(=O)(=O)c2ccc3c4c(N5C6CCC5COC6)ncnc4n(-c4nnc(C(F)F)s4)c3c2)CC1]
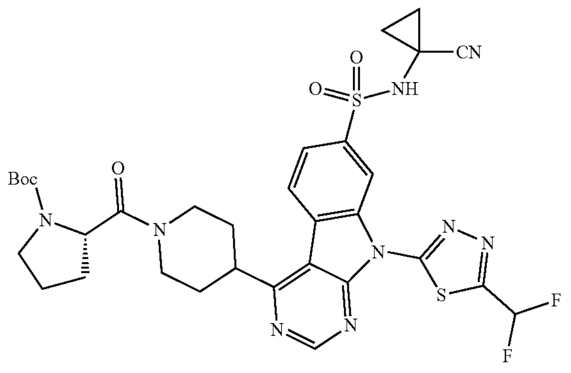
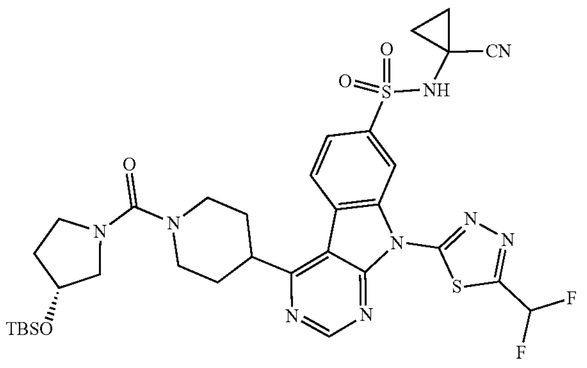 [SMILES: CC(C)(C)[Si](C)(C)O[C@@H]1CCN(C(=O)N2CCC(c3ncnc4c3c3ccc(S(=O)(=O)NC5(C#N)CC5)cc3n4-c3nnc(C(F)F)s3)CC2)C1]
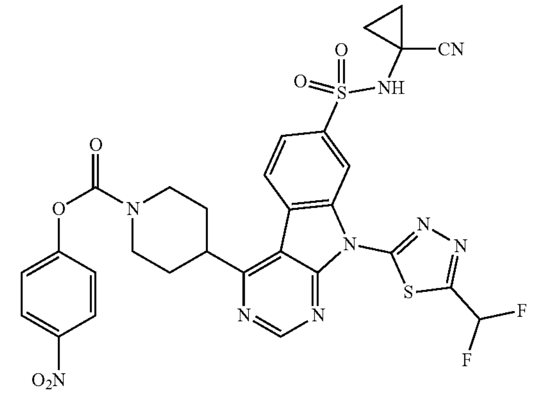 [SMILES: N#CC1(NS(=O)(=O)c2ccc3c4c(C5CCN(C(=O)Oc6ccc([N+](=O)[O-])cc6)CC5)ncnc4n(-c4nnc(C(F)F)s4)c3c2)CC1]
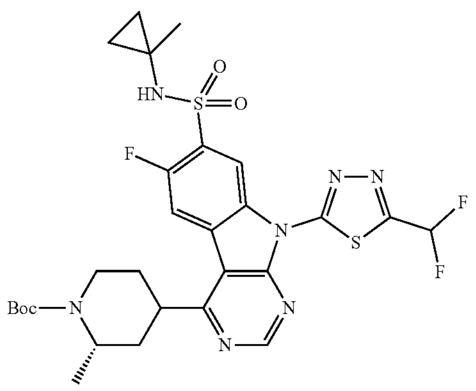 [SMILES: C[C@H]1CC(c2ncnc3c2c2cc(F)c(S(=O)(=O)NC4(C)CC4)cc2n3-c2nnc(C(F)F)s2)CCN1C(=O)OC(C)(C)C]
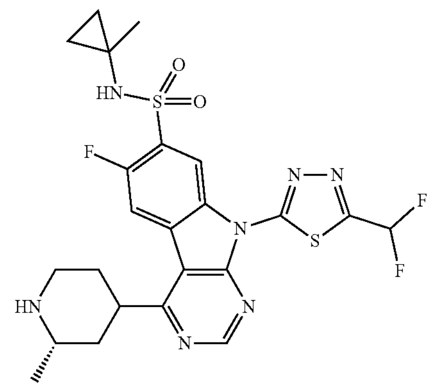 [SMILES: C[C@H]1CC(c2ncnc3c2c2cc(F)c(S(=O)(=O)NC4(C)CC4)cc2n3-c2nnc(C(F)F)s2)CCN1]

-continued
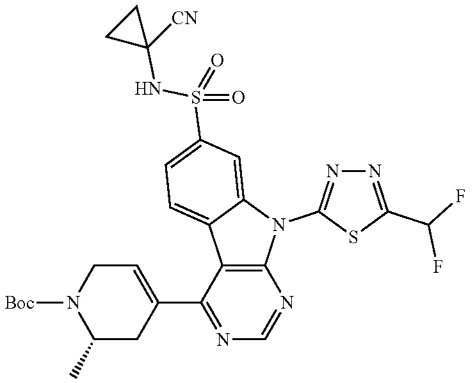 [SMILES: C[C@H]1CC(c2ncnc3c2c2ccc(S(=O)(=O)NC4(C#N)CC4)cc2n3-c2nnc(C(F)F)s2)=CCN1C(=O)OC(C)(C)C]
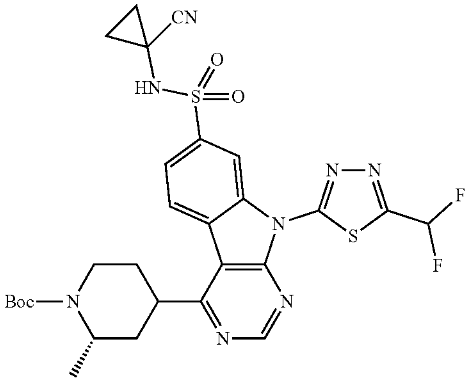 [SMILES: C[C@H]1CC(c2ncnc3c2c2ccc(S(=O)(=O)NC4(C#N)CC4)cc2n3-c2nnc(C(F)F)s2)CCN1C(=O)OC(C)(C)C]
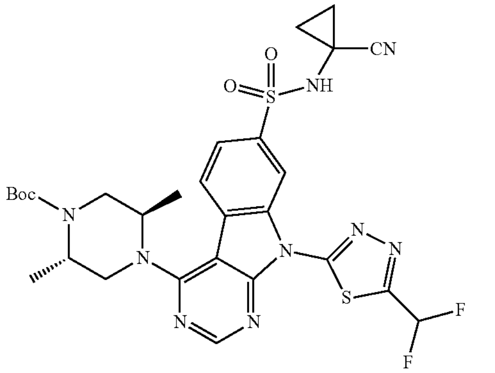 [SMILES: C[C@@H]1CN(C(=O)OC(C)(C)C)[C@@H](C)CN1c1ncnc2c1c1ccc(S(=O)(=O)NC3(C#N)CC3)cc1n2-c1nnc(C(F)F)s1]
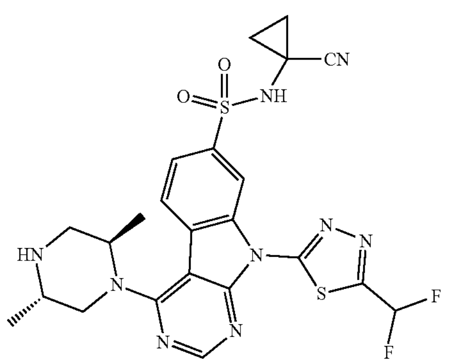 [SMILES: C[C@@H]1CN[C@@H](C)CN1c1ncnc2c1c1ccc(S(=O)(=O)NC3(C#N)CC3)cc1n2-c1nnc(C(F)F)s1]
-continued
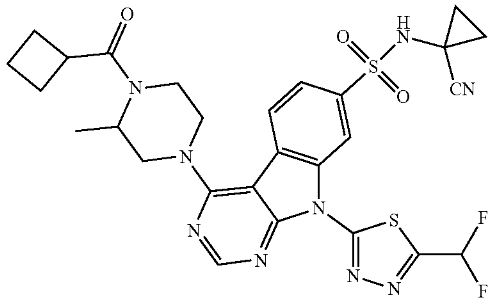 [SMILES: CC1CN(c2ncnc3c2c2ccc(S(=O)(=O)NC4(C#N)CC4)cc2n3-c2nnc(C(F)F)s2)CCN1C(=O)C1CCC1]
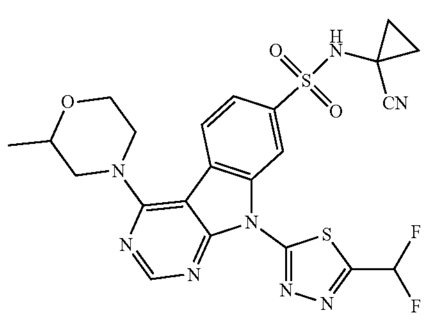 [SMILES: CC1CN(c2ncnc3c2c2ccc(S(=O)(=O)NC4(C#N)CC4)cc2n3-c2nnc(C(F)F)s2)CCO1]
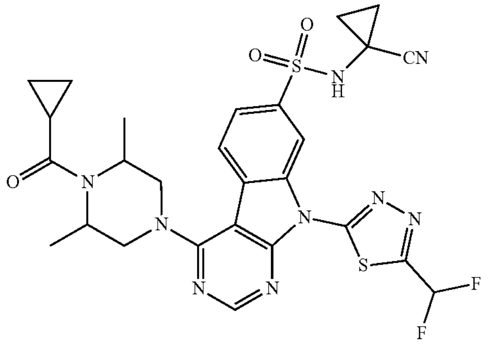 [SMILES: CC1CN(c2ncnc3c2c2ccc(S(=O)(=O)NC4(C#N)CC4)cc2n3-c2nnc(C(F)F)s2)CC(C)N1C(=O)C1CC1]
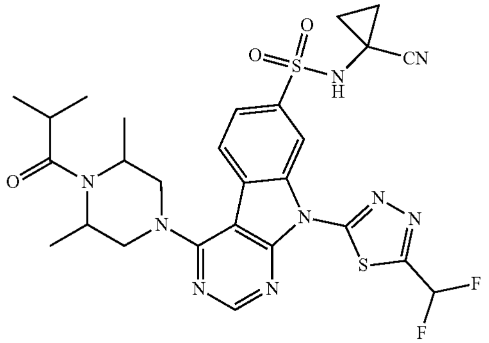 [SMILES: CC(C)C(=O)N1C(C)CN(c2ncnc3c2c2ccc(S(=O)(=O)NC4(C#N)CC4)cc2n3-c2nnc(C(F)F)s2)CC1C]

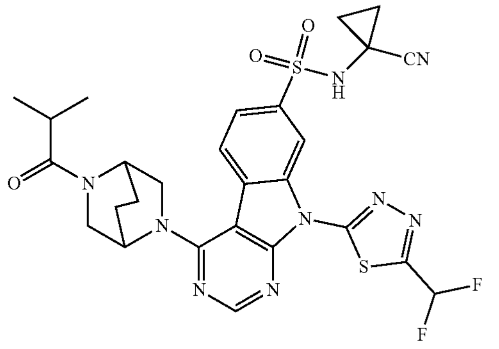
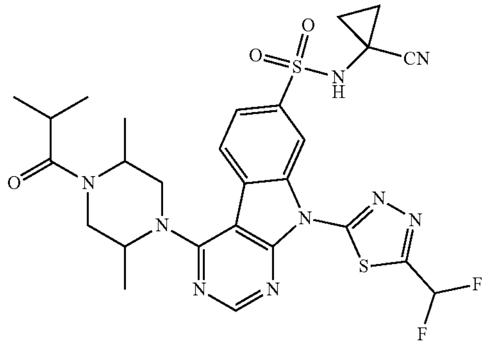
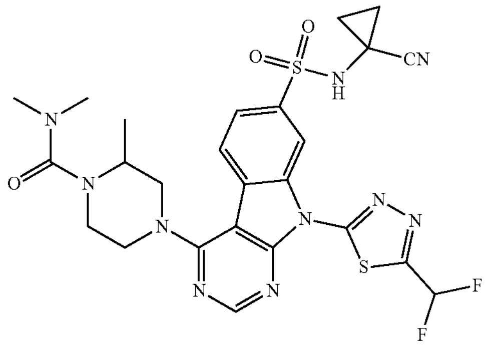
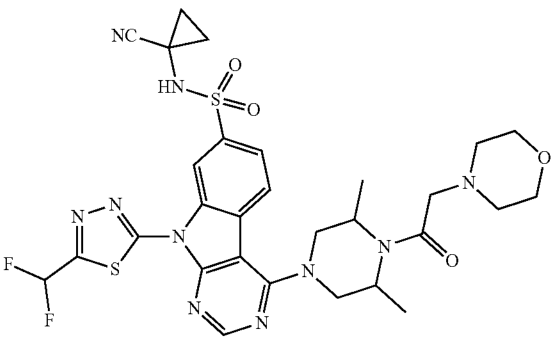 [SMILES: CC1CN(c2ncnc3c2c2ccc(S(=O)(=O)NC4(C#N)CC4)cc2n3-c2nnc(C(F)F)s2)CC(C)N1C(=O)CN1CCOCC1]
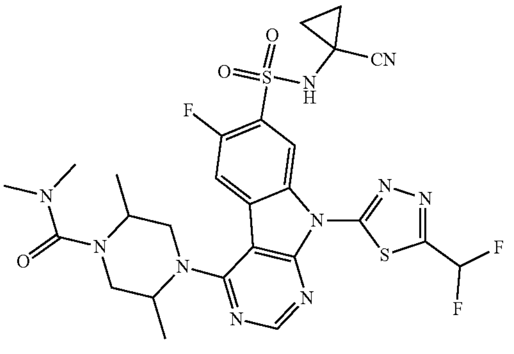 [SMILES: CC1CN(c2ncnc3c2c2cc(F)c(S(=O)(=O)NC4(C#N)CC4)cc2n3-c2nnc(C(F)F)s2)C(C)CN1C(=O)N(C)C]
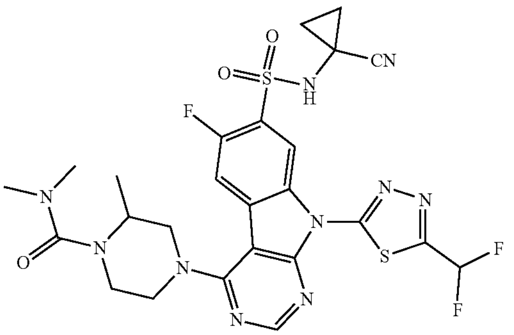 [SMILES: CC1CN(c2ncnc3c2c2cc(F)c(S(=O)(=O)NC4(C#N)CC4)cc2n3-c2nnc(C(F)F)s2)CCN1C(=O)N(C)C]
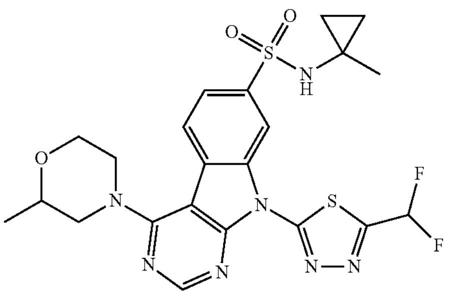 [SMILES: CC1CN(c2ncnc3c2c2ccc(S(=O)(=O)NC4(C)CC4)cc2n3-c2nnc(C(F)F)s2)CCO1]
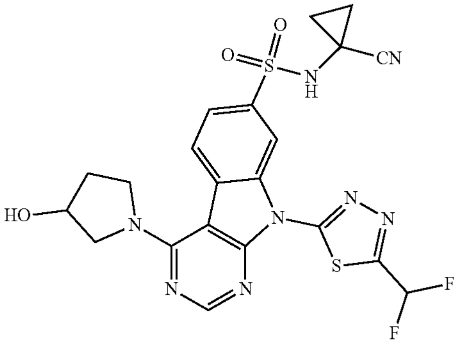

-continued
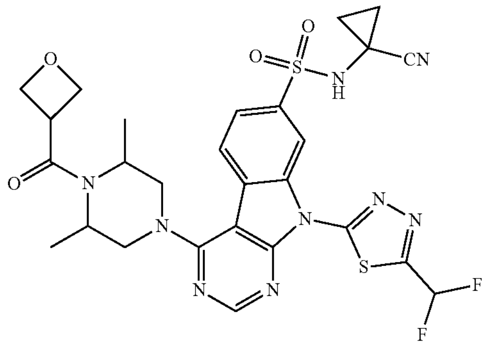 [SMILES: CC1CN(c2ncnc3c2c2ccc(S(=O)(=O)NC4(C#N)CC4)cc2n3-c2nnc(C(F)F)s2)CC(C)N1C(=O)C1COC1]
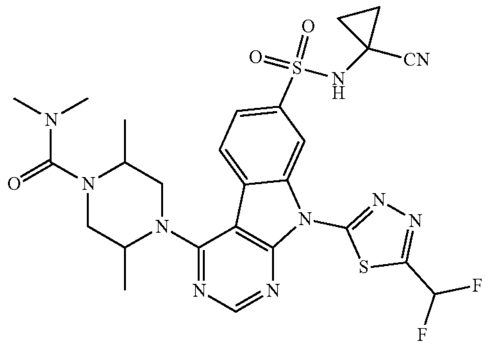 [SMILES: CC1CN(c2ncnc3c2c2ccc(S(=O)(=O)NC4(C#N)CC4)cc2n3-c2nnc(C(F)F)s2)C(C)CN1C(=O)N(C)C]
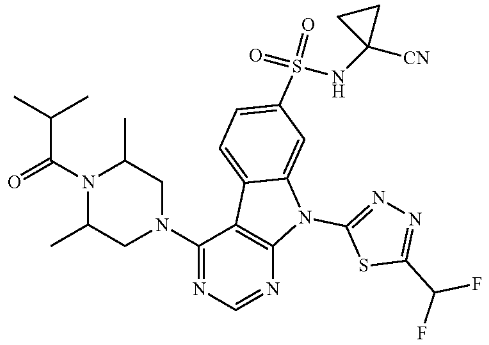 [SMILES: CC(C)C(=O)N1C(C)CN(c2ncnc3c2c2ccc(S(=O)(=O)NC4(C#N)CC4)cc2n3-c2nnc(C(F)F)s2)CC1C]
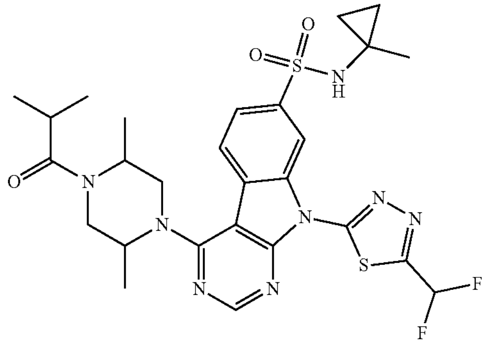 [SMILES: CC(C)C(=O)N1CC(C)N(c2ncnc3c2c2ccc(S(=O)(=O)NC4(C)CC4)cc2n3-c2nnc(C(F)F)s2)CC1C]
-continued
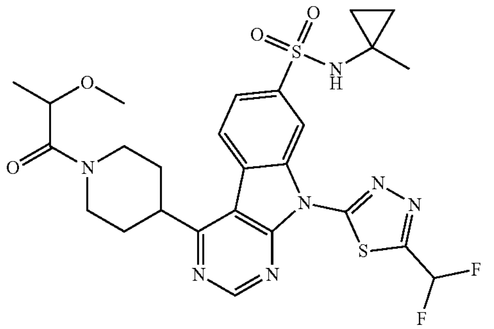 [SMILES: COC(C)C(=O)N1CCC(c2ncnc3c2c2ccc(S(=O)(=O)NC4(C)CC4)cc2n3-c2nnc(C(F)F)s2)CC1]
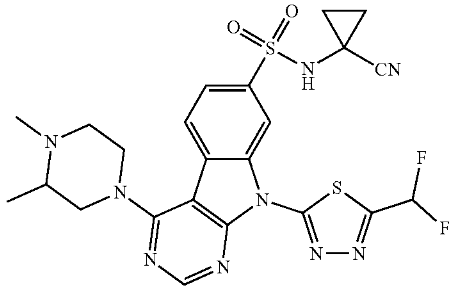 [SMILES: CC1CN(c2ncnc3c2c2ccc(S(=O)(=O)NC4(C#N)CC4)cc2n3-c2nnc(C(F)F)s2)CCN1C]
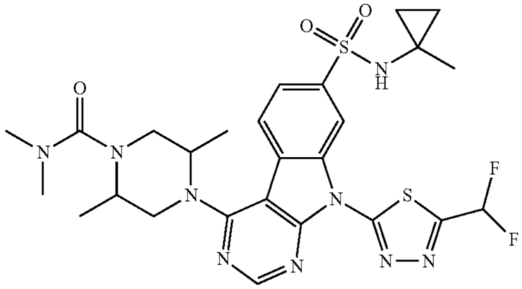 [SMILES: CC1CN(c2ncnc3c2c2ccc(S(=O)(=O)NC4(C)CC4)cc2n3-c2nnc(C(F)F)s2)C(C)CN1C(=O)N(C)C]
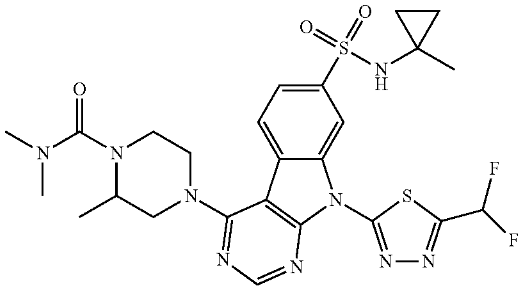 [SMILES: CC1CN(c2ncnc3c2c2ccc(S(=O)(=O)NC4(C)CC4)cc2n3-c2nnc(C(F)F)s2)CCN1C(=O)N(C)C]
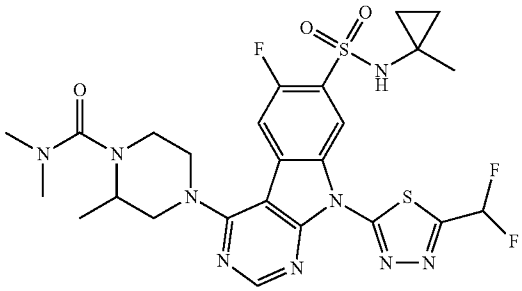

-continued
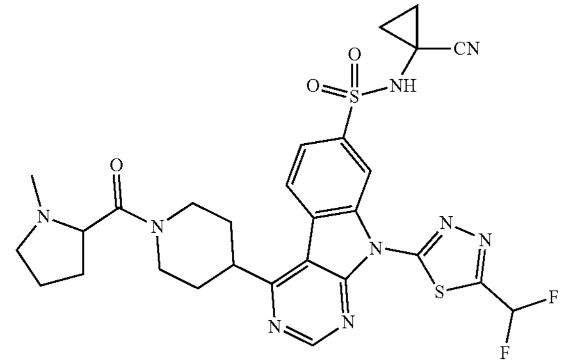 [SMILES: CN1CCCC1C(=O)N1CCC(c2ncnc3c2c2ccc(S(=O)(=O)NC4(C#N)CC4)cc2n3-c2nnc(C(F)F)s2)CC1]
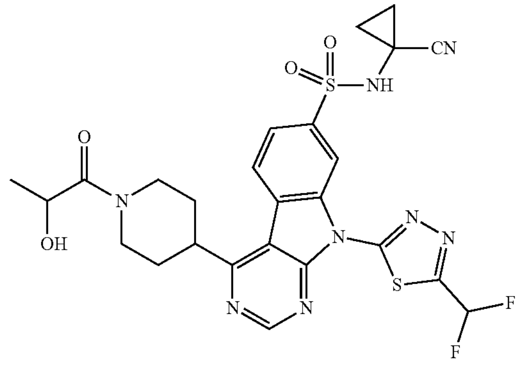 [SMILES: CC(O)C(=O)N1CCC(c2ncnc3c2c2ccc(S(=O)(=O)NC4(C#N)CC4)cc2n3-c2nnc(C(F)F)s2)CC1]
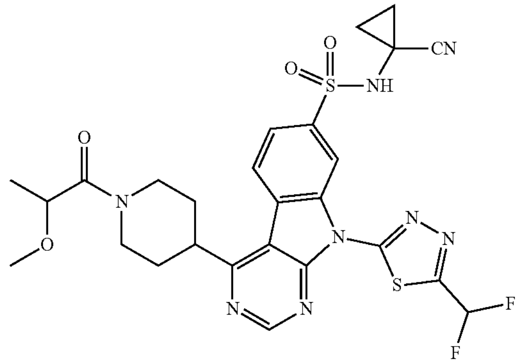
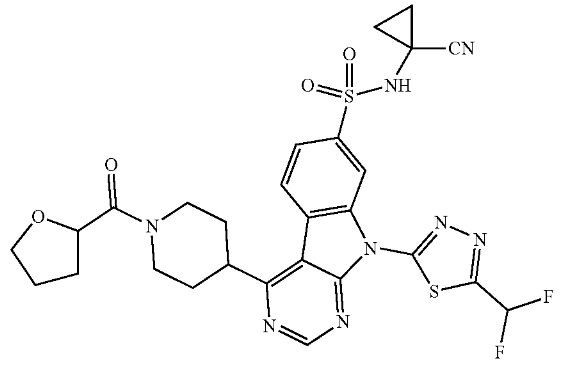 [SMILES: N#CC1(NS(=O)(=O)c2ccc3c4c(C5CCN(C(=O)C6CCCO6)CC5)ncnc4n(-c4nnc(C(F)F)s4)c3c2)CC1]
-continued
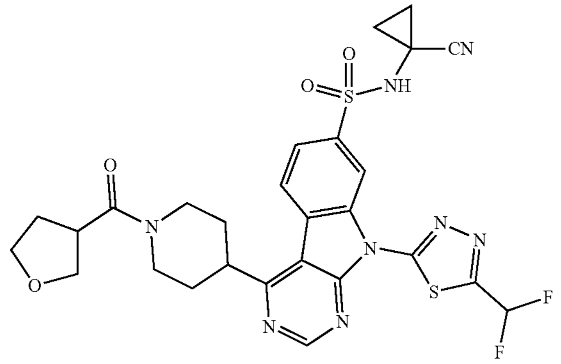 [SMILES: N#CC1(NS(=O)(=O)c2ccc3c4c(C5CCN(C(=O)C6CCOC6)CC5)ncnc4n(-c4nnc(C(F)F)s4)c3c2)CC1]
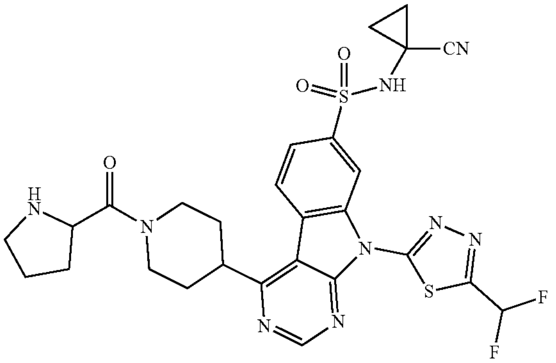 [SMILES: N#CC1(NS(=O)(=O)c2ccc3c4c(C5CCN(C(=O)C6CCCN6)CC5)ncnc4n(-c4nnc(C(F)F)s4)c3c2)CC1]
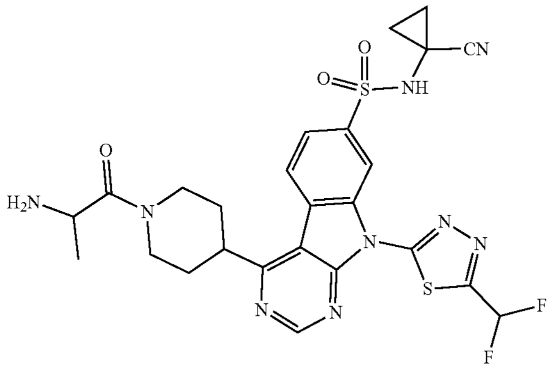 [SMILES: CC(N)C(=O)N1CCC(c2ncnc3c2c2ccc(S(=O)(=O)NC4(C#N)CC4)cc2n3-c2nnc(C(F)F)s2)CC1]
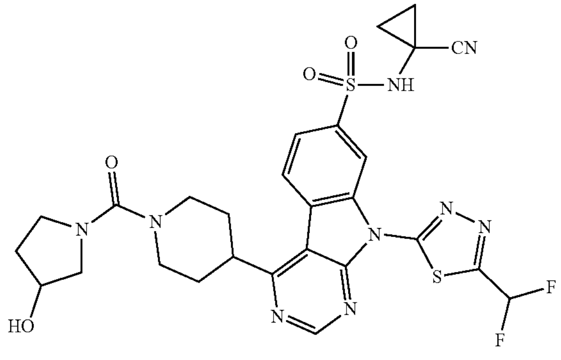 [SMILES: N#CC1(NS(=O)(=O)c2ccc3c4c(C5CCN(C(=O)N6CCC(O)C6)CC5)ncnc4n(-c4nnc(C(F)F)s4)c3c2)CC1]

-continued
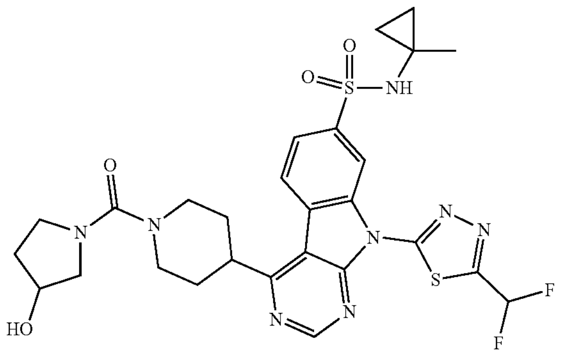 [SMILES: CC1(NS(=O)(=O)c2ccc3c4c(C5CCN(C(=O)N6CCC(O)C6)CC5)ncnc4n(-c4nnc(C(F)F)s4)c3c2)CC1]
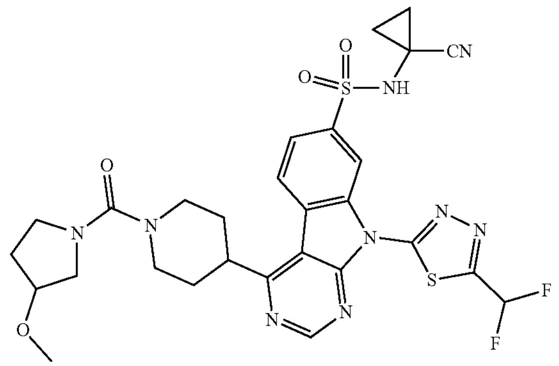
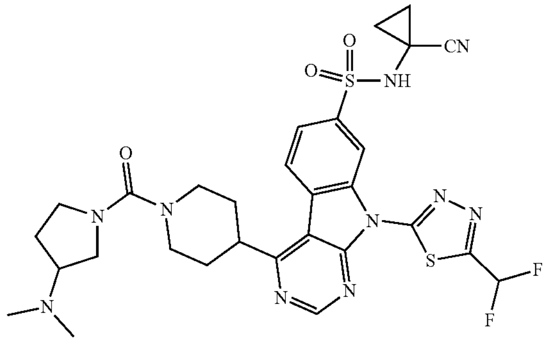 [SMILES: CN(C)C1CCN(C(=O)N2CCC(c3ncnc4c3c3ccc(S(=O)(=O)NC5(C#N)CC5)cc3n4-c3nnc(C(F)F)s3)CC2)C1]
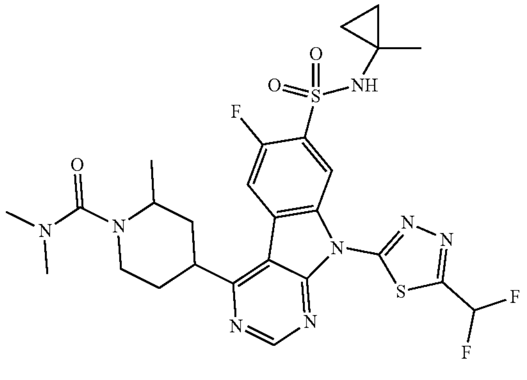 [SMILES: CC1CC(c2ncnc3c2c2cc(F)c(S(=O)(=O)NC4(C)CC4)cc2n3-c2nnc(C(F)F)s2)CCN1C(=O)N(C)C]
-continued
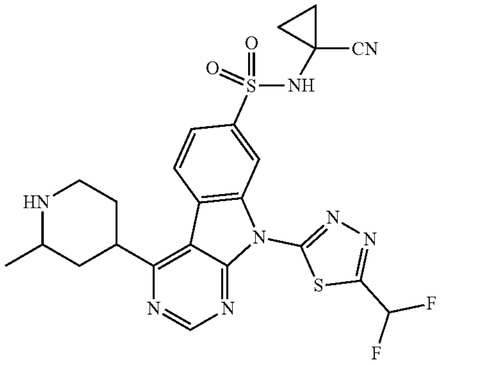
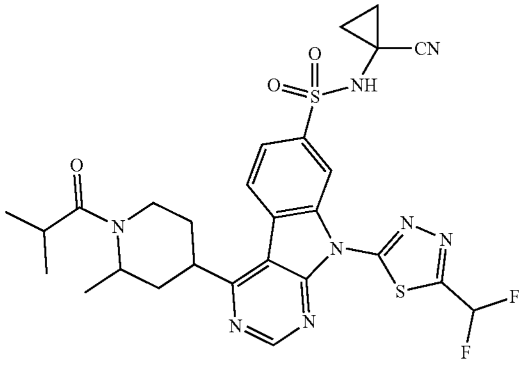 [SMILES: CC(C)C(=O)N1CCC(c2ncnc3c2c2ccc(S(=O)(=O)NC4(C#N)CC4)cc2n3-c2nnc(C(F)F)s2)CC1C]
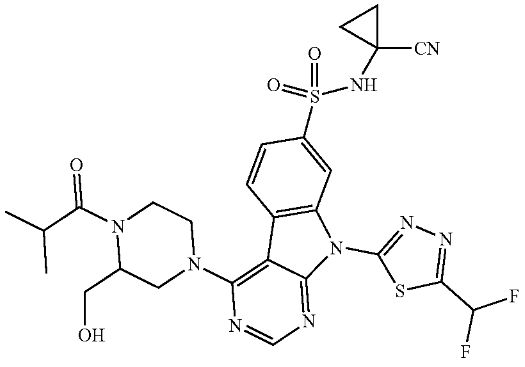 [SMILES: CC(C)C(=O)N1CCN(c2ncnc3c2c2ccc(S(=O)(=O)NC4(C#N)CC4)cc2n3-c2nnc(C(F)F)s2)CC1CO]
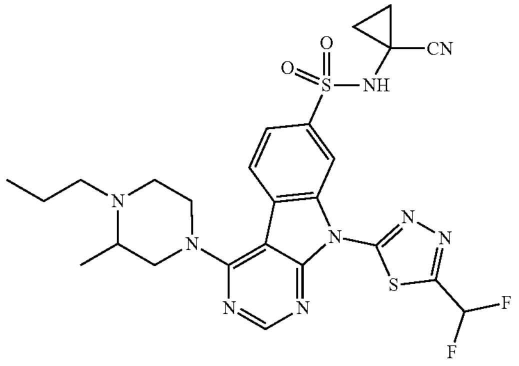 [SMILES: CCCN1CCN(c2ncnc3c2c2ccc(S(=O)(=O)NC4(C#N)CC4)cc2n3-c2nnc(C(F)F)s2)CC1C]

-continued
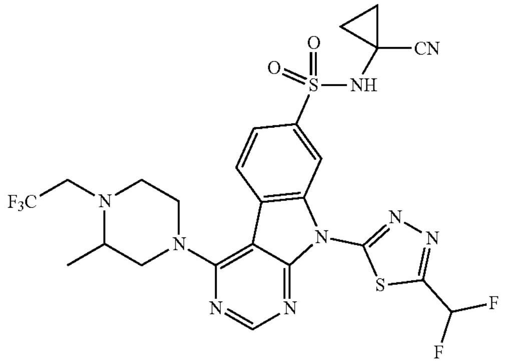 [SMILES: CC1CN(c2ncnc3c2c2ccc(S(=O)(=O)NC4(C#N)CC4)cc2n3-c2nnc(C(F)F)s2)CCN1CC(F)(F)F]
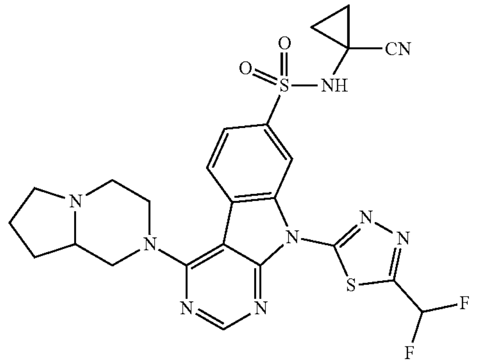 [SMILES: N#CC1(NS(=O)(=O)c2ccc3c4c(N5CCN6CCCC6C5)ncnc4n(-c4nnc(C(F)F)s4)c3c2)CC1]
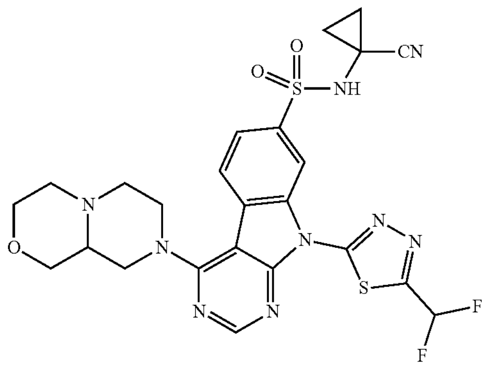 [SMILES: N#CC1(NS(=O)(=O)c2ccc3c4c(N5CCN6CCOCC6C5)ncnc4n(-c4nnc(C(F)F)s4)c3c2)CC1]
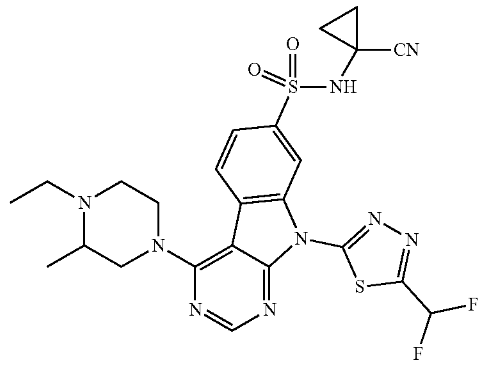 [SMILES: CCN1CCN(c2ncnc3c2c2ccc(S(=O)(=O)NC4(C#N)CC4)cc2n3-c2nnc(C(F)F)s2)CC1C]
-continued
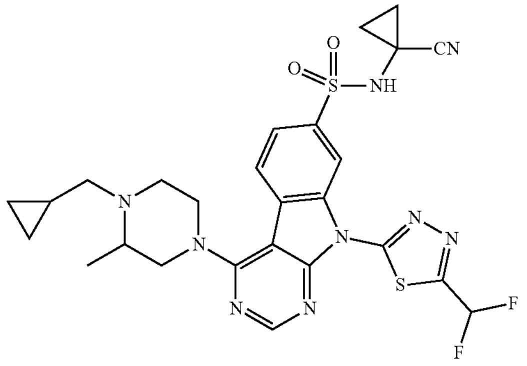
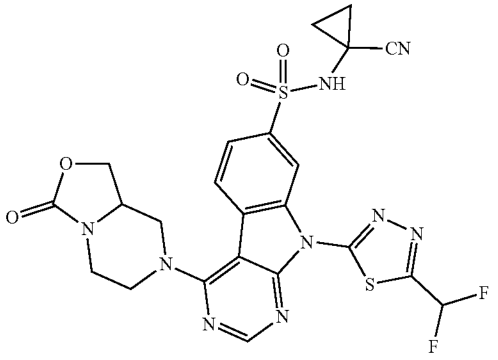 [SMILES: N#CC1(NS(=O)(=O)c2ccc3c4c(N5CCN6C(=O)OCC6C5)ncnc4n(-c4nnc(C(F)F)s4)c3c2)CC1]
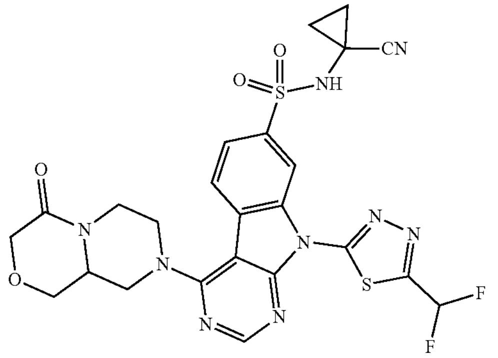 [SMILES: N#CC1(NS(=O)(=O)c2ccc3c4c(N5CCN6C(=O)COCC6C5)ncnc4n(-c4nnc(C(F)F)s4)c3c2)CC1]
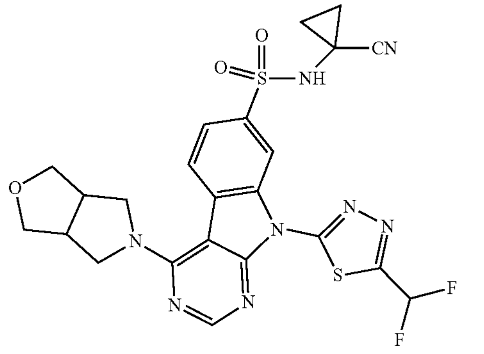 [SMILES: N#CC1(NS(=O)(=O)c2ccc3c4c(N5CC6COCC6C5)ncnc4n(-c4nnc(C(F)F)s4)c3c2)CC1]

-continued
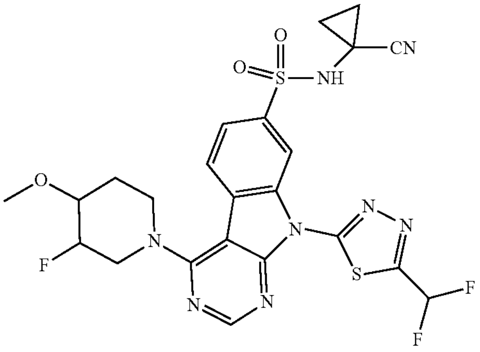 [SMILES: COC1CCN(c2ncnc3c2c2ccc(S(=O)(=O)NC4(C#N)CC4)cc2n3-c2nnc(C(F)F)s2)CC1F]
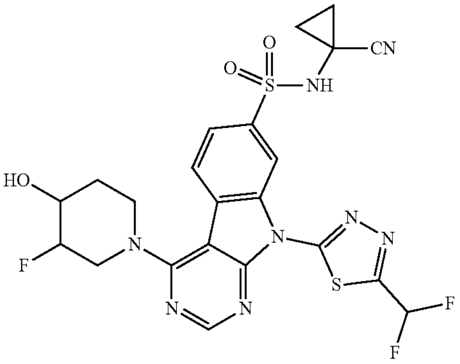
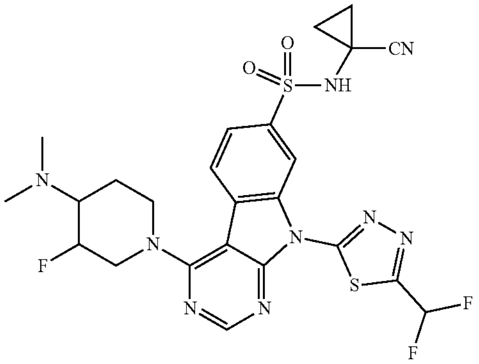
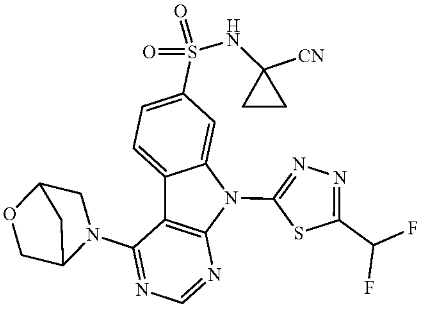 [SMILES: N#CC1(NS(=O)(=O)c2ccc3c4c(N5CC6CC5CO6)ncnc4n(-c4nnc(C(F)F)s4)c3c2)CC1]
-continued
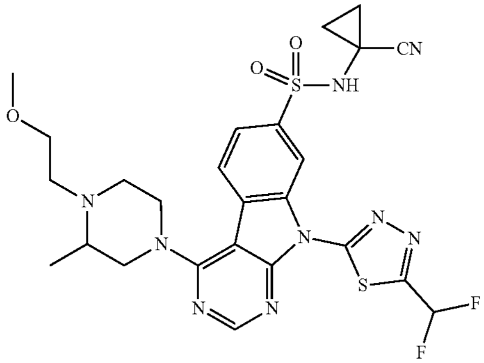
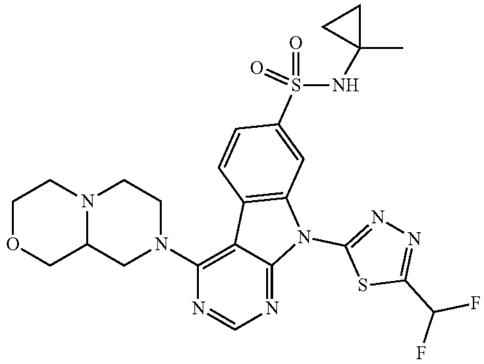
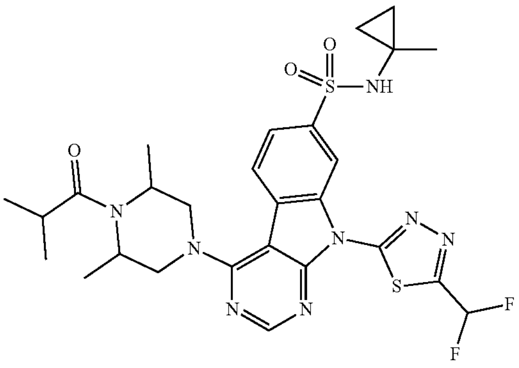 [SMILES: CC(C)C(=O)N1C(C)CN(c2ncnc3c2c2ccc(S(=O)(=O)NC4(C)CC4)cc2n3-c2nnc(C(F)F)s2)CC1C]
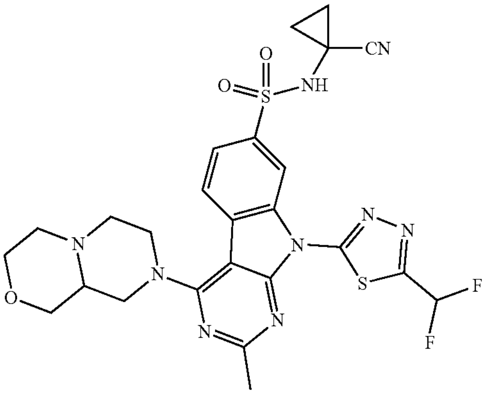 [SMILES: Cc1nc(N2CCN3CCOCC3C2)c2c3ccc(S(=O)(=O)NC4(C#N)CC4)cc3n(-c3nnc(C(F)F)s3)c2n1]

-continued
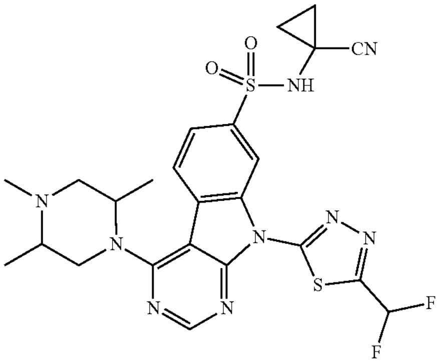 [SMILES: CC1CN(c2ncnc3c2c2ccc(S(=O)(=O)NC4(C#N)CC4)cc2n3-c2nnc(C(F)F)s2)C(C)CN1C]
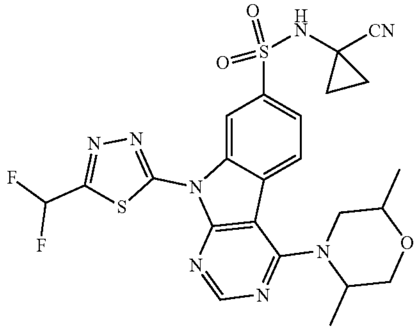 [SMILES: CC1CN(c2ncnc3c2c2ccc(S(=O)(=O)NC4(C#N)CC4)cc2n3-c2nnc(C(F)F)s2)C(C)CO1]
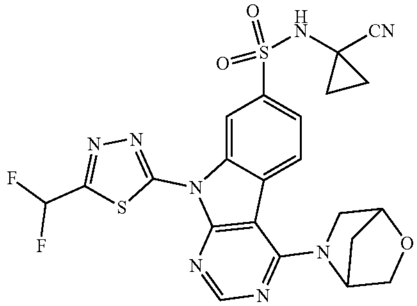 [SMILES: N#CC1(NS(=O)(=O)c2ccc3c4c(N5CC6CC5CO6)ncnc4n(-c4nnc(C(F)F)s4)c3c2)CC1]
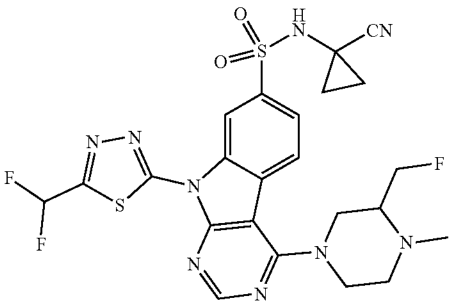 [SMILES: CN1CCN(c2ncnc3c2c2ccc(S(=O)(=O)NC4(C#N)CC4)cc2n3-c2nnc(C(F)F)s2)CC1CF]
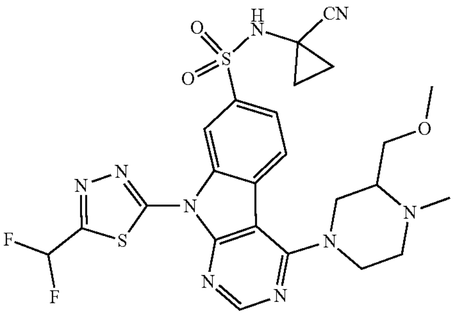 [SMILES: COCC1CN(c2ncnc3c2c2ccc(S(=O)(=O)NC4(C#N)CC4)cc2n3-c2nnc(C(F)F)s2)CCN1C]
-continued
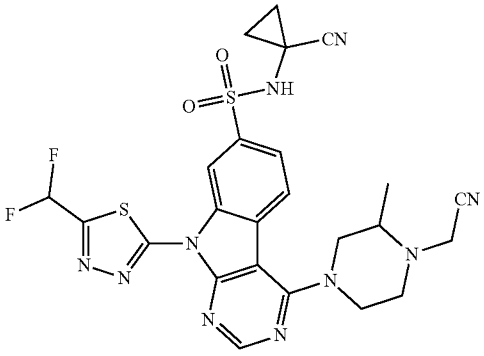 [SMILES: CC1CN(c2ncnc3c2c2ccc(S(=O)(=O)NC4(C#N)CC4)cc2n3-c2nnc(C(F)F)s2)CCN1CC#N]
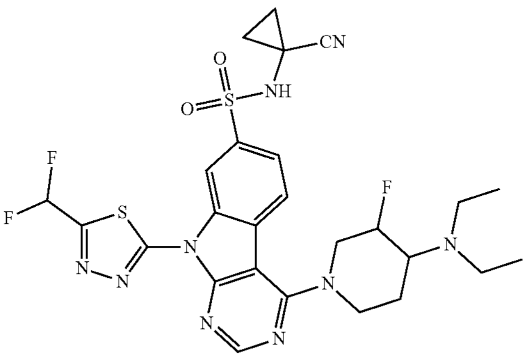 [SMILES: CCN(CC)C1CCN(c2ncnc3c2c2ccc(S(=O)(=O)NC4(C#N)CC4)cc2n3-c2nnc(C(F)F)s2)CC1F]
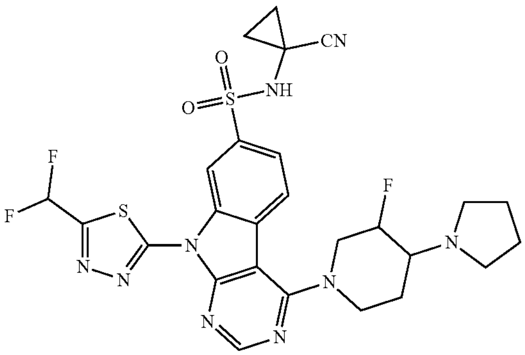 [SMILES: N#CC1(NS(=O)(=O)c2ccc3c4c(N5CCC(N6CCCC6)C(F)C5)ncnc4n(-c4nnc(C(F)F)s4)c3c2)CC1]
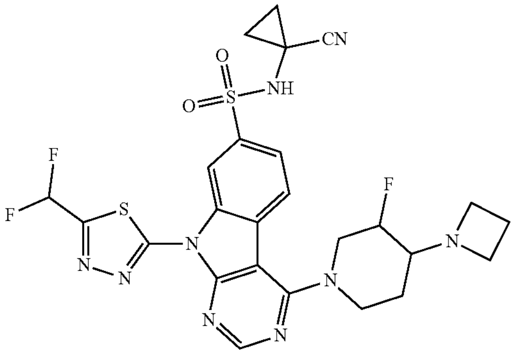 [SMILES: N#CC1(NS(=O)(=O)c2ccc3c4c(N5CCC(N6CCC6)C(F)C5)ncnc4n(-c4nnc(C(F)F)s4)c3c2)CC1]

-continued
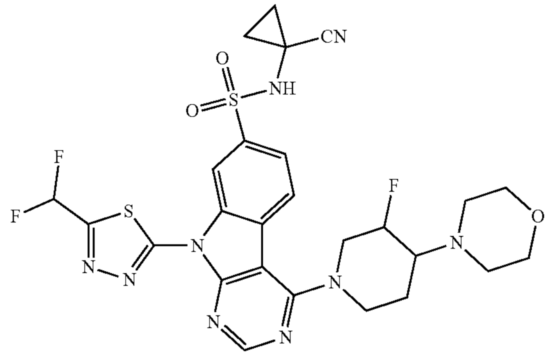
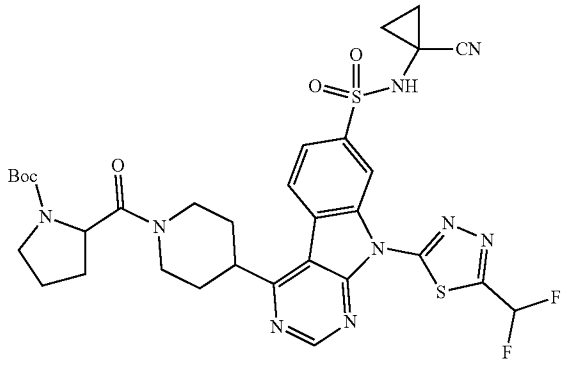 [SMILES: CC(C)(C)OC(=O)N1CCCC1C(=O)N1CCC(c2ncnc3c2c2ccc(S(=O)(=O)NC4(C#N)CC4)cc2n3-c2nnc(C(F)F)s2)CC1]
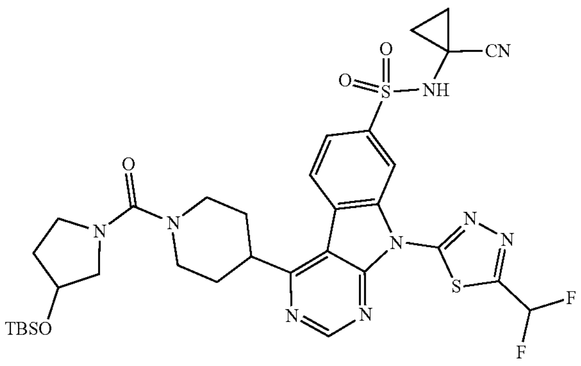 [SMILES: CC(C)(C)[Si](C)(C)OC1CCN(C(=O)N2CCC(c3ncnc4c3c3ccc(S(=O)(=O)NC5(C#N)CC5)cc3n4-c3nnc(C(F)F)s3)CC2)C1]
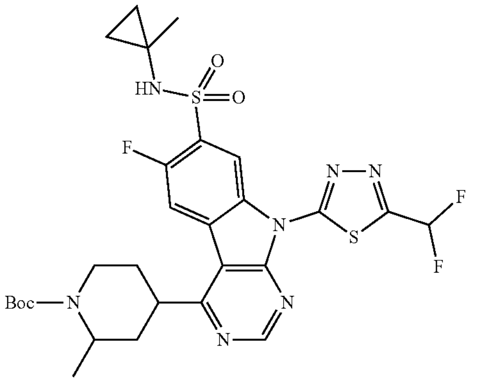 [SMILES: CC1CC(c2ncnc3c2c2cc(F)c(S(=O)(=O)NC4(C)CC4)cc2n3-c2nnc(C(F)F)s2)CCN1C(=O)OC(C)(C)C]
-continued
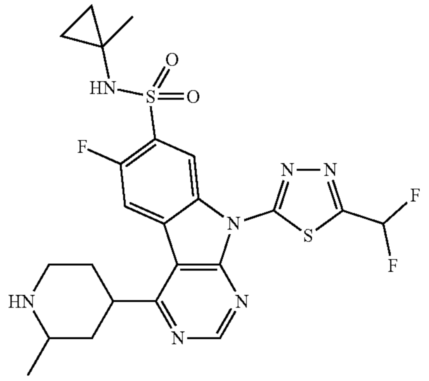 [SMILES: CC1CC(c2ncnc3c2c2cc(F)c(S(=O)(=O)NC4(C)CC4)cc2n3-c2nnc(C(F)F)s2)CCN1]
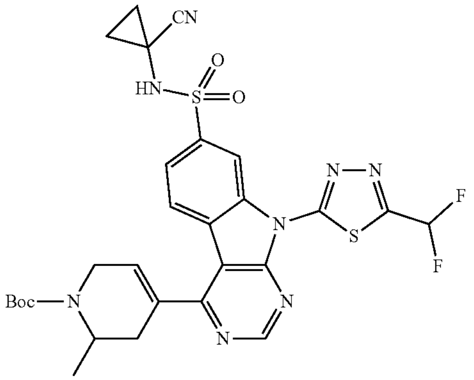 [SMILES: CC1CC(c2ncnc3c2c2ccc(S(=O)(=O)NC4(C#N)CC4)cc2n3-c2nnc(C(F)F)s2)=CCN1C(=O)OC(C)(C)C]
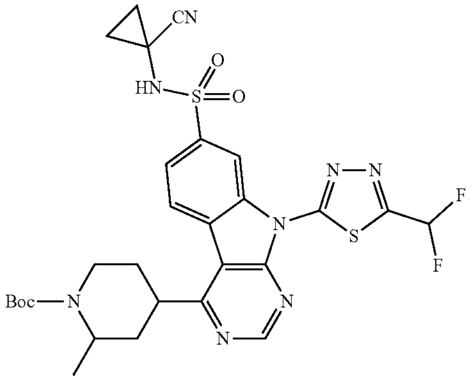 [SMILES: CC1CC(c2ncnc3c2c2ccc(S(=O)(=O)NC4(C#N)CC4)cc2n3-c2nnc(C(F)F)s2)CCN1C(=O)OC(C)(C)C]
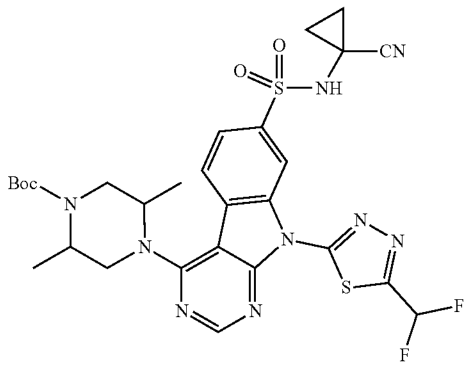 [SMILES: CC1CN(c2ncnc3c2c2ccc(S(=O)(=O)NC4(C#N)CC4)cc2n3-c2nnc(C(F)F)s2)C(C)CN1C(=O)OC(C)(C)C]

-continued

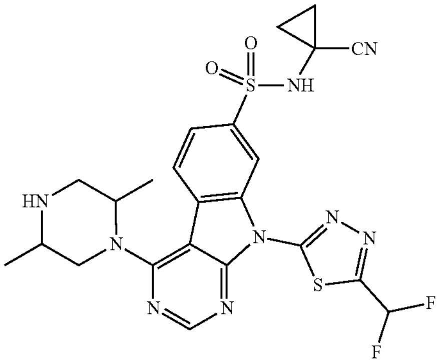 [SMILES: CC1CN(c2ncnc3c2c2ccc(S(=O)(=O)NC4(C#N)CC4)cc2n3-c2nnc(C(F)F)s2)C(C)CN1]

or a pharmaceutically acceptable salt thereof.

It will be apparent that the compounds of Formula I, including all subgenera described herein, may have multiple stereogenic centers. As a result, there exist multiple stereoisomers (enantiomers and diastereomers) of the compounds of Formula I (and subgenera described herein). The present disclosure contemplates and encompasses each stereoisomer of any compound of Formula I (and subgenera described herein), as well as mixtures of said stereoisomers.

Pharmaceutically acceptable salts and solvates of the compounds of Formula I (including all subgenera described herein) are also within the scope of the disclosure.

Isotopic variants of the compounds of Formula I (including all subgenera described herein) are also contemplated by the present disclosure.

The present disclosure further provides compounds described herein, or a pharmaceutically acceptable salt thereof, for use in any of the methods described herein. The present disclosure further provides uses of a compound described herein, or a pharmaceutically acceptable salt thereof, for the preparation of a medicament for use in any of the methods described herein.

The present disclosure further provides pharmaceutical compositions comprising a compound described herein, or a pharmaceutically acceptable salt thereof, and a pharmaceutically acceptable carrier.

The PARG inhibitors of the present disclosure may be useful in the treatment of various types of cancer, including but not limited to breast, ovarian, gastric, prostate, pancreatic, uterine, cervical, endometrial, lung, brain, bile duct and hematological cancers.

Routs of administration for the compounds in the present disclosure include, but not limited to oral, injection, topical and inhalation.

The compounds of the present disclosure may be used as single agent or combined with other treatments. Such treatment may include one or more of the following categories of cancer therapies: such as surgery, chemotherapies, radiation therapies, targeted therapy (for example kinase inhibitors, growth factor inhibitors, cyclin dependent kinase inhibitors and so on), other DDR modulators (for example DNA-PK inhibitor, ATM inhibitor, ATR inhibitor, CHK1 inhibitor, WEE1 inhibitor, CDK1 inhibitor, LIG4 inhibitor, HIF-1 inhibitor, HDAC inhibitor, RAD51 inhibitor, Polθ inhibitor, WRN inhibitor, PRMT5 inhibitor, MAT2A inhibitor and PKMYT1 inhibitor and so on), immunotherapies, and gene and cell therapy approaches.

An intermediate compound of formula (A), wherein:

(A)

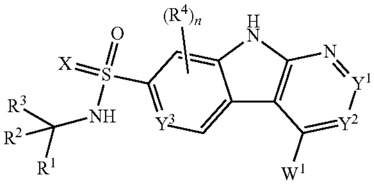

$W^1$ is a leaving group (such as halogen (e.g., Cl, Br, or I), pseudohalogen (e.g., OTf, OTs or OMs), etc.);

X is O or $NR^5$;

Y is N or $CR^6$;

$Y^2$ is N or $CR^7$, and at most one of $Y^1$ or $Y^2$ is N;

$Y^3$ is N or $CR^8$;

n is 0, 1 or 2;

$R^1$, $R^2$ and $R^3$ are each independently selected from H, D, CN, $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl; wherein, the $C_1$-$C_3$ alkyl, $C_2$-$C_3$ alkenyl, $C_2$-$C_3$ alkynyl, $C_3$-$C_7$ cycloalkyl, or 4-7 membered heterocycloalkyl is optionally substituted by 1-5 substituents independently selected from D, halo, CN, OH, $C_1$-$C_6$ alkyl, $C_1$-$C_6$ haloalkyl, —O—$C_1$-$C_6$ alkyl, —O$C_1$-$C_6$ haloalkyl;

or $R^2$ and $R^3$ together with the carbon atom to which they are attached form $C_3$-$C_7$ cycloalkyl, or 4-7 membered heterocycloalkyl; wherein, the $C_3$-$C_7$ cycloalkyl, 4-7 membered heterocycloalkyl is optionally substituted by 1, 2, 3 or 4 substituents independently selected from D, halo, CN, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl;

$R^4$ is selected from H, D, halo, OH, CN, $NO_2$, $SF_5$, $C_1$-$C_3$ alkyl, $C_2$-$C_3$ alkenyl, $C_2$-$C_3$ alkynyl, —O—$C_1$-$C_3$ alkyl, or $NR^CR^D$; wherein, the $C_1$-$C_3$ alkyl, $C_2$-$C_3$ alkenyl, $C_2$-$C_3$ alkynyl is optionally substituted with halogen or CN;

$R^5$ is selected from H, D, CN, $OR^B$, or $C_1$-$C_4$ alkyl optionally substituted with at least one of $R^{5A}$; wherein, each $R^{5A}$ is independently selected from D, F, Cl, CN, $NH_2$, OH, —O—$C_1$-$C_6$ alkyl, —O$C_1$-$C_6$ haloalkyl, optionally substituted $C_3$-$C_7$ cycloalkyl, or optionally substituted 4-7 membered heterocycloalkyl; wherein, the optionally substituted substituent is selected from D, halo, CN, OH, $C_1$-$C_4$ alkyl, $C_1$-$C_4$haloalkyl, —O—$C_1$-$C_4$ alkyl, —O$C_1$-$C_4$haloalkyl;

or $R^1$ and $R^5$ together with the atoms to which they are attached form 5-7 membered partially saturated heterocycloalkyl optionally substituted by 1, 2, 3 or 4 substituents independently selected from D, halogen, CN, $CF_3$, $NO_2$, oxo, OH, $C_1$-$C_6$ alkyl, $C_1$-$C_6$ haloalkyl, —O—$C_1$-$C_6$ alkyl, —O$C_1$-$C_6$ haloalkyl;

$R^6$ and $R^7$ are each independently selected from H, D, halogen, CN, $NO_2$, $C_1$-$C_6$ alkyl, $C_1$-$C_6$haloalkyl, $C_2$-$C_6$ alkenyl, $C_2$-$C_6$ alkynyl, $OR^A$, $SR^A$, $SF_5$, $NHOR^A$, C(O)$OR^A$, C(O)$R^B$, C(O)$NR^CR^D$, OC(O)$NR^CR^D$, $NR^CR^D$, $NR^C$C(O)$R^B$, $NR^C$C(O)$NR^CR^D$, $NR^C$C(O)$OR^A$, $NR^C$S(O)$_2R^B$, B($OR^C$)($OR^D$), C(=$NR^C$)$NR^CR^D$, $NR^D$C(=$NR^C$)$NR^CR^D$, $NR^D$C(=$NR^C$)$R^B$, P(O)$R^ER^F$, P(O)$OR^EOR^F$, OP(O)$OR^EOR^F$, S(O)(=$NR^B$)$R^B$, S(O)$R^B$, S(O)$NR^CR^D$, S(O)$_2R^B$, S(O)$_2NR^CR^D$, $NR^C$S(O)$_2NR^CR^D$, or $NR^C$S(O)(=$NR^B$)$R^B$; wherein, the $C_1$-$C_6$ alkyl, $C_2$-$C_6$ alkenyl, or $C_2$-$C_6$ alkynyl is optionally substituted with 1, 2, or 3 substituents independently selected from $R^{11}$;

$R^8$ is selected from H, D, CN, halo, OH, $NH_2$, $C_1$-$C_3$ alkyl, $C_1$-$C_3$ haloalkyl, —O—$C_1$-$C_3$ alkyl, —$OC_1$-$C_3$ haloalkyl, $C_1$-$C_3$ cyanoalkyl, or $SF_5$;

$R^A$ is independently selected from H, D, $C_1$-$C_6$ alkyl, $C_2$-$C_4$ alkenyl, $C_2$-$C_4$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein, the $C_1$-$C_6$ alkyl, $C_2$-$C_4$ alkenyl, $C_2$-$C_4$ alkynyl, $C_3$-$C_{10}$ cycloalkyl, 4-10 membered heterocyclalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^dC(=NR^c)NR^cR^d$, $NR^dC(=NR^c)R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $NR^cS(O)(=NR^b)R^b$;

$R^B$ is independently selected from H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl is optionally substituted with 1, 2, 3, 4 or 5 substituents independently selected from $R^{13}$;

each $R^{13}$ is independently selected from H, D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_1$-$C_4$ alkylOH, $OC_1$-$C_4$ alkyl-O—$C_1$-$C_4$ alkyl, $OC_1$-$C_4$ alkyl-O—$C_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, optionally substituted $C_3$-$C_7$ cycloalkyl, or optionally substituted 4-7 membered heterocycloalkyl, $SF_5$, $OR^a$, $SR^a$, $C(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$; wherein, the optionally substituted substituent is selected from D, halo, CN, OH, $C_1$-$C_4$ alkyl, $C_1$-$C_4$haloalkyl, —O—$C_1$-$C_4$ alkyl, —$OC_1$-$C_4$haloalkyl;

$R^C$ and $R^D$ are each independently selected from H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl is optionally substituted with 1, 2, 3, 4 or 5 substituents independently selected from D, OH, CN, halo, oxo, $C_1$-$C_4$ alkyl, $C_1$-$C_4$haloalkyl, $C_1$-$C_4$ cyanoalkyl, $OC_1$-$C_4$ alkyl, $OC_1$-$C_4$haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, $C_1$-$C_4$ alkyl-O—$C_1$-$C_4$ alkyl, $C_1$-$C_4$alkyl-O—$C_1$-$C_4$haloalkyl, $SF_5$, $OC(O)NR^cR^d$, $NR^cR^d$, $NR^cC(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)(OR^d)$;

or $R^C$ and $R^D$ together with the N atom to which they are attached form a 4-7 membered heterocycloalkyl optionally substituted with 1, 2, 3, 4 or 5 substituents independently selected from D, OH, oxo, CN, —$NH_2$, —NH($C_1$-$C_4$ alkyl), —N($C_1$-$C_4$ alkyl)$_2$, halo, or $C_1$-$C_4$ alkyl, $C_1$-$C_4$ haloalkyl, $C_1$-$C_4$ cyanoalkyl, $OC_1$-$C_4$ alkyl, or $OC_1$-$C_4$haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl;

$R^a$ and $R^{a1}$ are each independently selected from H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, or $C_1$-$C_4$haloalkoxy;

$R^b$ and $R^{b1}$ are each independently selected from H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, arylalkyl, heteroarylalkyl, cycloalkylalkyl, or heterocycloalkylalkyl; wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, arylalkyl, heteroarylalkyl, cycloalkylalkyl, or heterocycloalkylalkyl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$haloalkyl, $C_1$-$C_4$haloalkoxy, $C_6$-$C_{10}$ aryl, $C_3$-$C_{10}$ cycloalkyl, 5-10 membered heteroaryl, or 4-10 membered heterocycloalkyl;

$R^c$ and $R^d$ are each independently selected from H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl; wherein the $C_{1-4}$ alkyl, $C_{2-4}$ alkenyl, $C_{2-4}$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl is optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkyl-O—$C_1$-$C_4$ alkyl, and $C_1$-$C_4$ alkyl-O—$C_1$-$C_4$ alkyl-O—;

or $R^c$ and $R^d$ together with the N atom to which they are attached form a 4-7 membered heterocycloalkyl optionally substituted with 1, 2, or 3 substituents independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkoxy-$C_1$-$C_4$ alkyl, and $C_1$-$C_4$ alkoxy-$C_1$-$C_4$ alkoxy;

$R^E$ and $R^e$ are each independently selected from H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 3-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl;

$R^F$ and $R^f$ are each independently selected from H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl.

In some embodiments, the intermediate compounds of Formula (A) are represented by compounds of Formula (Aa), or (Ab):

(Aa)

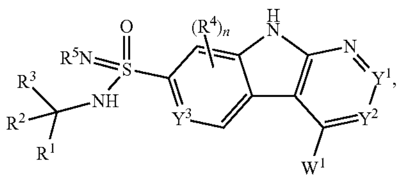

(Ab)

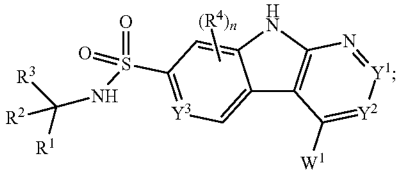

wherein, $R^1$, $R^2$, $R^3$, $R^4$, $R^5$, $Y^1$, $Y^2$ and $W^1$ are defined with respect to Formula (A).

In some embodiments, the intermediate compounds are:

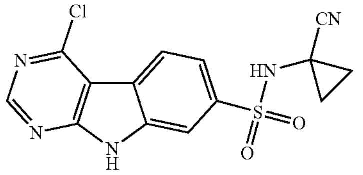

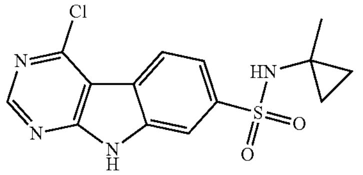 [SMILES: CC1(NS(=O)(=O)c2ccc3c(c2)[nH]c2ncnc(Cl)c23)CC1]

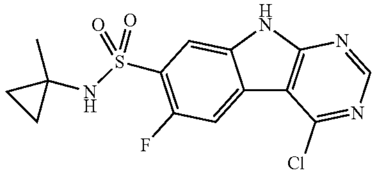 [SMILES: CC1(NS(=O)(=O)c2cc3[nH]c4ncnc(Cl)c4c3cc2F)CC1]

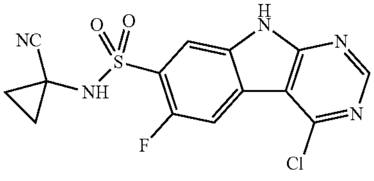 [SMILES: N#CC1(NS(=O)(=O)c2cc3[nH]c4ncnc(Cl)c4c3cc2F)CC1]

-continued

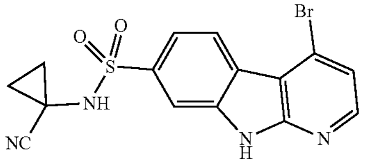 [SMILES: N#CC1(NS(=O)(=O)c2ccc3c(c2)[nH]c2nccc(Br)c23)CC1]

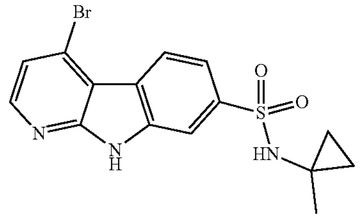 [SMILES: CC1(NS(=O)(=O)c2ccc3c(c2)[nH]c2nccc(Br)c23)CC1]

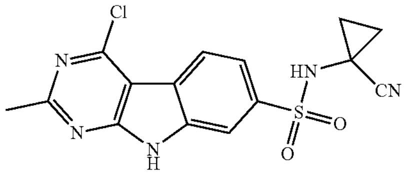 [SMILES: Cc1nc(Cl)c2c(n1)[nH]c1cc(S(=O)(=O)NC3(C#N)CC3)ccc12]

or salts thereof.

Definitions

Unless other indicated, the following terms are intended to have the meaning set forth below. Other terms are defined elsewhere throughout the specification.

As used herein, the singular forms "a", "an", and "the" include plural referents unless the context clearly dictates otherwise. It is further noted that the claims may be drafted to exclude any optional element. As such, this statement is intended to serve as antecedent basis for use of such exclusive terminology such as "solely", "only" and the like in connection with the recitation of claim elements, or use of a "negative" limitation.

At various places in the present specification, variables defining divalent linking groups are described. It is specifically intended that each linking substituent include both the forward and backward forms of the linking substituent. For example, —NR(CR'R")— includes both —NR(CR'R")— and —(CR'R")NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "Cn-Cm" indicates a range which includes the endpoints, wherein n and m are integers and indicate the number of carbons. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. "$C_0$ alkyl" refers to a covalent bond.

It is further intended that the compounds of the disclosure are stable. As used herein "stable" refers to a compound that is sufficiently robust to survive isolation to a useful degree of purity from a reaction mixture, and preferably capable of formulation into an efficacious therapeutic agent.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable sub-combination.

As used herein, unless otherwise indicated, the term "alkyl", by itself or as part of another substituent, is meant to refer to a saturated hydrocarbon group which is straight-chained or branched. An alkyl group can contain from 1 to about 20, from 2 to about 20, from 1 to about 10, from 1 to about 8, from 1 to about 6, from 1 to about 4, or from 1 to about 3 carbon atoms. Similarly, $C_{1-8}$, as in $C_{1-8}$ alkyl is defined to identify the group as having 1, 2, 3, 4, 5, 6, 7 or 8 carbon atoms in a linear or branched arrangement. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

As used herein, unless otherwise indicated, "alkenyl" refers to an alkyl group having one or more double carbon-carbon bonds. Example alkenyl groups include, but are not limited to, ethenyl, propenyl, and the like.

As used herein, unless otherwise indicated, "alkynyl" refers to an alkyl group having one or more triple carbon-carbon bonds. Example alkynyl groups include, but are not limited to, ethynyl, propynyl, and the like.

As used herein, unless otherwise indicated, "haloalkyl" refers to an alkyl group having one or more halogen substituents. Example haloalkyl groups include, but are not limited to, $CF_3$, $C_2F_5$, $CHF_2$, $CH_2F$, $CCl_3$, $CHCl_2$, $C_2Cl_5$, and the like.

As used herein, unless otherwise indicated, "aryl" refers to an unsubstituted or substituted monocyclic or polycyclic (e.g., having 2, 3 or 4 fused rings) aromatic hydrocarbons. In some embodiments, aryl groups have from 6 to about 20 carbon atoms. In some embodiments, aryl groups have from 6 to about 14 carbon atoms. In some embodiments, aryl groups have from 6 to about 10 carbon atoms. Example aryl groups include, but are not limited to, phenyl, naphthyl, anthracenyl, phenanthrenyl, indanyl, indenyl, and the like.

As used herein, unless otherwise indicated, "cycloalkyl" refers to an unsubstituted or substituted non-aromatic carbocycles (saturated or partially unsaturated ring) including cyclized alkyl, alkenyl, and alkynyl groups. Cycloalkyl groups can include mono- or polycyclic (e.g., having 2, 3 or 4 fused rings) ring systems, including fused rings, spirocyclic rings, and bridged rings (e.g., a bridged bicycloalkyl group). In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Cycloalkyl groups can be optionally substituted by oxo or sulfido (e.g., —C(O)— or —C(S)—). Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. In some embodiments, the cycloalkyl is a $C_3$-$C_7$ monocyclic cycloalkyl. In some embodiments, the cycloalkyl is a $C_4$-$C_{10}$ spirocycle or bridged cycloalkyl.

Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl. In some embodiments, cycloalkyl are cyclic-containing, non-aromatic hydrocarbon groups having from 3 to 12 carbon atoms ("$C_3$-$C_{12}$"), preferably from 3 to 6 carbon atoms ("$C_3$. $C_6$"). Examples of cycloalkyl groups include, for example, cyclopropyl ($C_3$; 3-membered), cyclobutyl ($C_4$; 4-membered), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like.

The term "spirocycloalkyl" when used alone or as part of a substituent group refers to a non-aromatic hydrocarbon group containing two cycloalkyl rings, and wherein the two cycloalyl rings share a single carbon atom in common.

As used herein, unless otherwise indicated, a "heteroaryl" group refers to an unsubstituted or substituted aromatic heterocycle having at least one heteroatom ring member such as boron, sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, unless otherwise indicated, "heterocycloalkyl" refers to an unsubstituted or substituted monocyclic (saturated or partially unsaturated ring) or polycyclic heterocycles having at least one non-aromatic ring (saturated or partially unsaturated ring), wherein one or more of the ring-forming carbon atoms of the heterocycloalkyl is replaced by a heteroatom selected from N, O, S, Si, P and B, and wherein the ring-forming carbon atoms and heteroatoms of the heterocycloalkyl group can be optionally substituted by one or more oxo or sulfido (e.g., C(O), S(O), C(S), $S(O)_2$, or P(O), etc.). Heterocycloalkyl groups include monocyclic and polycyclic (e.g., having 2 fused rings) systems. Included in heterocycloalkyl are monocyclic and polycyclic 3-10, 4-10, 3-7, 4-7, and 5-6 membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S, Si, P and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include, but are not limited to, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, diazabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, oxa-azaspiro[3.5]nonanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl, octahydropyrrolo[3,4-c]pyrrolyl and the like.

In some embodiments, heterocycloalkyl refers to any three to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, and the like.

In some embodiments, the term "spiroheterocycloalkyl" when used alone or as part of a substituent group refers to a non-aromatic group containing two rings, at least one of which is a heterocycloalkyl ring, and wherein the two rings share a single carbon atom in common.

As used herein, unless otherwise indicated, "arylcycloalkyl" refers to cycloalkyl group substituted by an aryl group.

As used herein, unless otherwise indicated, "arylheterocycloalkyl" refers to a heterocycloalkyl group substituted by an aryl group.

As used herein, unless otherwise indicated, "arylheteroaryl" refers to a heteroaryl group substituted by an aryl group.

As used herein, unless otherwise indicated, "biaryl" refers to an aryl group substituted by another aryl group.

As used herein, unless otherwise indicated, "heteroarylcycloalkyl" refers to a cycloalkyl group substituted by a heteroaryl group.

As used herein, unless otherwise indicated, "heteroarylheterocycloalkyl" refers to a heterocycloalkyl group substituted by a heteroaryl group.

As used herein, unless otherwise indicated, "heteroarylaryl" refers to an aryl group substituted by a heteroaryl group.

As used herein, unless otherwise indicated, "biheteroaryl" refers to a heteroaryl group substituted by another heteroaryl group.

As used herein, "halo" or "halogen" includes fluoro, chloro, bromo, and iodo.

As used herein, unless otherwise indicated, "alkoxy" refers to an —O-alkyl group. Example alkoxy groups include methoxy, ethoxy, propoxy (e.g., n-propoxy and isopropoxy), t-butoxy, and the like.

As used herein, unless otherwise indicated, "hydroxylalkyl" refers to an alkyl group substituted by OH.

As used herein, unless otherwise indicated, "cyanoalkyl" refers to an alkyl group substituted by CN.

As used herein, unless otherwise indicated, "alkoxyalkyl" refers to an alkyl group substituted by an alkoxy group.

As used herein, unless otherwise indicated, "alkoxyalkoxy" refers to an alkoxy group substituted by alkoxy.

As used herein, unless otherwise indicated, "haloalkoxy" refers to an —O-(haloalkyl) group.

As used herein, unless otherwise indicated, "arylalkyl" refers to alkyl substituted by aryl and "cycloalkylalkyl" refers to alkyl substituted by cycloalkyl. An example arylalkyl group is benzyl.

As used herein, unless otherwise indicated, "heteroarylalkyl" refers to alkyl substituted by heteroaryl and "heterocycloalkylalkyl" refers to alkyl substituted by heterocycloalkyl.

As used herein, unless otherwise indicated, "oxo" refers to an oxygen substituent that is connected by a double bond (i.e., =O).

As used herein, unless otherwise indicated, the phrase "optionally substituted" means unsubstituted or substituted.

As used herein, unless otherwise indicated, the term "substituted" refers to a group in which one or more hydrogen atoms are each independently replaced with the same or different substituent(s). Typical substituents include, but are not limited to, D, halo, oxo, $C_1$-$C_6$ alkyl, $C_2$-$C_6$alkenyl, $C_2$-$C_6$ alkynyl, $C_1$-$C_6$ haloalkyl, $C_1$-$C_6$ alkyl-$NR^{c1}R^{d1}$, —$(CH_2CH_2O)_oC_1$-$C_6$alkyl wherein o is 1-10; $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, CN, $NO_2$, $N_3$, $OR^{a1}$, $SR^{a1}$, $C(O)R^{b1}$, $C(O)NR^{c1}R^{d1}$, —$CH_2C(O)NR^{c1}R^{d1}$, $C(O)OR^{a1}$, $OC(O)R^{b1}$, $OC(O)NR^{c1}R^{d1}$, —$NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, —$SO(=NR^{b1})$; $S(O)NR^{c1}R^{d1}$, $S(O)_2R^{b1}$, $NR^{c1}S(O)_2R^{b1}$, $S(O)_2NR^{c1}R^{d1}$; aryl, heteroaryl, spirocycloalkyl, spiroheterocycloalkyl, cycloalkyl, or heterocycloalkyl, wherein the aryl, heteroaryl, spirocycloalkyl, spiroheterocycloalkyl, cycloalkyl, or heterocycloalkyl are optionally substituted with D, halo, oxo, $C_1$-$C_6$ alkyl, $C_2$-$C_6$ alkenyl, $C_2$-$C_6$ alkynyl, $C_1$-$C_6$ haloalkyl, $C_1$-$C_6$ alkyl-$NR^{c1}R^{d1}$, $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, CN, $NO_2$, $N_3$, $OR^{a1}$, $SR^{a1}$, $C(O)R^{b1}$, $C(O)NR^{c1}R^{d1}$, $—CH_2C(O)NR^{c1}R^{d1}$, $C(O)OR^{a1}$, $OC(O)R^{b1}$, $OC(O)NR^{c1}R^{d1}$, $—NR^{c1}R^{d1}$, $NR^{c1}C(O)R^{b1}$, $NR^{c1}C(O)NR^{c1}R^{d1}$, $NR^{c1}C(O)OR^{a1}$, $C({=}NR^{g1})NR^{c1}R^{d1}$, $NR^{c1}C({=}NR^{g1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole; certain hydroxy substituted compounds may exist as tautomers as shown below:

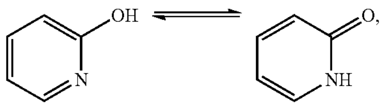 [SMILES: Oc1ccccn1 ; O=c1cccc[nH]1]

etc. Tautomeric forms can be in equilibrium or sterically locked into one form by appropriate substitution.

In some cases, the compounds of the present disclosure may exist as rotational isomers. Descriptions of a compound of the disclosure that do not indicate a particular rotational isomer are intended to encompass any individual rotational isomers, as well as mixtures of rotational isomers in any proportion. Depiction of a particular rotational isomer is meant to refer to the depicted rotational isomer, substantially free of other rotational isomers.

Compounds of the disclosure can also include all isotopes of atoms occurring in the intermediates or final compounds. Isotopes include those atoms having the same atomic number but different mass numbers. For example, isotopes of hydrogen include tritium and deuterium.

In some embodiments, the compounds of the disclosure, and salts thereof, are substantially isolated. By "substantially isolated" is meant that the compound is at least partially or substantially separated from the environment in which was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

A "leaving group" refers to an atom or a group of atoms that is displaced in a chemical reaction as stable species taking with it the bonding electrons, e.g., typically forming an anion. Preferably, a leaving group is selected from the group comprising: halogen, in particular a chloro, bromo or iodo, (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitrophenyl)sulfonyl]oxy-, [(4- isopropylphenyl)sulfonyl]oxy-, [(2,4,6-triisopropylphenyl) sulfonyl]oxy-, [(2,4,6-trimethylphenyl)sulfonyl]oxy-, [(4-tert-butylphenyl)sulfonyl]oxy-, (phenylsulfonyl)oxy-, and a [(4-methoxyphenyl)sulfonyl]oxy group.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I as described herein, as well as its subgenera, which expression includes the stereoisomers (e.g., entaniomers, diastereomers) and constitutional isomers (e.g., tautomers) of compounds of Formula I as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

Pharmaceutical Compositions

Also provided are pharmaceutical compositions comprising compounds of Formula I, or a pharmaceutically acceptable salt, stereoisomer, solvate, N-oxide, tautomeric, isotopic variants, prodrugs or deuterated compound thereof, and a pharmaceutically acceptable carrier.

The compositions may be in a form suitable for oral use (for example as tablets, lozenges, hard or soft capsules, aqueous or oily suspensions, emulsions, dispersible powders or granules, syrups or elixirs), for injection use (for example as aqueous or oil suspensions, or emulsions, with sesame oil, corn oil, cottonseed oil, or peanut oil, as well as elixirs, mannitol, dextrose, or a sterile aqueous solution, and similar pharmaceutical vehicles), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions may be obtained by conventional procedures using conventional pharmaceutical excipients, well known in the art. Thus, compositions intended for oral use may contain, for example, one or more coloring, sweetening, flavoring and/or preservative agents.

An effective amount of a compound of Formula (I) or a pharmaceutically salt thereof for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.1 mg to 1000 mg of Formula (I) or a pharmaceutically salt thereof with an appropriate and convenient amount of excipients which may vary from about 5 to about 98 percent by weight of the total composition.

The size of the dose for therapeutic or prophylactic purposes of a compound of the Formula (I) will naturally vary according to the nature and severity of the conditions, the age and sex of the animal or patient and the route of administration, according to well-known principles of medicine.

Described below are non-limiting exemplary pharmaceutical compositions and methods for preparing the same.

Methods of Administration

The compounds of Formula (I) or a pharmaceutically salt thereof or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrastemal; by implant of a depot or reservoir, for example, subcutaneously or intramuscularly.

Methods of Use

The method typically comprises administering to a subject a therapeutically effective amount of a compound of the disclosure. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or $IC_{50}$).

In some embodiments, the subject methods (PARG enzymatic activity assay) utilize a PARG inhibitor with an $IC_{50}$ value of about or less than a predetermined value, as ascertained in an in vitro assay. In some embodiments, the PARG inhibitor inhibits PARG with an $IC_{50}$ value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 μM or less, 1.1 μM or less, 1.2 μM or less, 1.3 μM or less, 1.4 μM or less, 1.5 μM or less, 1.6 μM or less, 1.7 μM or less, 1.8 μM or less, 1.9 μM or less, 2 μM or less, 5 μM or less, 10 μM or less, 15 μM or less, 20 μM or less, 25 μM or less, 30 μM or less, 40 μM or less, 50 μM, 60 μM, 70 μM, 80 μM, 90 μM, 100 μM, 200 μM, 300 μM, 400 μM, or 500 μM, or less, (or a number in the range defined by and including any two numbers above).

The subject methods are useful for treating a disease condition associated with PARG. Any disease condition that results directly or indirectly from an abnormal activity or expression level of PARG can be an intended disease condition.

Different disease conditions associated with PARG have been reported. PARG has been implicated, for example, auto-immune diseases, neurodegeneration (such as Parkinson's disease), cardiovascular disease (such as ischaemia stroke and myocardial infarction), inflammatory diseases (such as septic shock), diabetes, and cancer such as, for example, breast, ovarian, gastric, prostate, pancreatic, uterine, cervical, endometrial, lung, brain, bile duct and hematological cancer.

Non-limiting examples of such conditions include but are not limited to breast cancer, Invasive ductal carcinoma, Invasive lobular carcinoma, Paget's disease of the breast, Hereditary breast-ovarian cancer syndrome, Medullary breast cancer, Mucinous breast cancer, Inflammatory breast cancer, Ovarian Cancer, Ovarian Epithelial Cancer, Ovarian Germ Cell Tumor, Ovarian Low Malignant Potential Tumor, Gastric Cancer, Gastric lymphoma, Gastrointestinal cancer, Gastrointestinal Carcinoid Tumor, Gastrointestinal Stromal Tumor, Gastrointestinal stromal tumor, Prostate cancer, Acinar adenocarcinoma of prostate, Prostatic ductal adenocarcinoma, Prostate sarcoma, Small cell prostate cancer, Squamous cell prostate cancer, Pancreatic Cancer, Exocrine pancreatic cancer, Neuroendocrine pancreatic cancer, Uterine cancer, Uterine sarcoma, Uterine corpus sarcoma, Cervical Cancer, Squamous cell cervical cancer, Cervical adenocarcinoma, Cervical adenosquamous carcinoma, Small cell cervical cancer, Cervical mucinous tumor, Clear cell cervical cancer, Cervical lymphoma, Cervical sarcoma, Endometrial cancer, Endometrial Uterine Cancer, Endometrioid tumor, Lung cancer, Non-Small Cell Lung Cancer, Small Cell Lung Cancer, Brain Stem Glioma, Brain cancer, Cerebellar Astrocytoma, Cerebral Astrocytoma, Head and Neck Cancer, Glioblastoma multiforme, Glioma, Gliomatosis cerebri, Ganglioglioma, Ganglioneuroma, Paraganglioma, Primitive neuroectodermal tumor, Supratentorial Primitive Neuroectodermal Tumor, Visual Pathway Glioma, Neurinoma, Neuroblastoma, Neuroblastoma, Neurofibroma, Neuroma, Esthesioneuroblastoma, Extrahepatic Bile Duct Cancer, Bellini duct carcinoma, Cholangiocarcinoma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adult T-cell leukemia, Aggressive NK-cell leukemia, Chronic Lymphocytic Leukemia, Chronic monocytic leukemia, Chronic myelogenous leukemia, Chronic Myeloproliferative Disorder, Chronic neutrophilic leukemia, Erythroleukemia, Hairy Cell Leukemia, Leukemia, Lymphoid leukemia, Lymphoma, Macroglobulinemia, Mast cell leukemia, Monocytic leukemia, Myeloid leukemia, T-cell acute lymphoblastic leukemia, T-cell large granular lymphocyte leukemia, T-cell leukemia, T-cell prolymphocytic leukemia, AIDS-related lymphoma, Angioimmunoblastic T-cell lymphoma, B-cell leukemia, B-cell lymphoma, Cutaneous T-cell lymphoma, Diffuse large B cell lymphoma, Enteropathy-associated T-cell lymphoma, Follicular lymphoma, Hepatosplenic T-cell lymphoma, Hodgkin Lymphoma, Hodgkin's lymphoma, Lymphangioma, Lymphangiosarcoma, Lymphoepithelioma, MALT lymphoma, Mantle cell lymphoma, Non-Hodgkin Lymphoma, Non-Hodgkin lymphoma, Precursor T-lymphoblastic lymphoma, Primary central nervous system lymphoma, Primary effusion lymphoma, Small cell lymphoma, T-cell lymphoma, Terminal lymphatic cancer.

In some embodiments, said method is for treating a disease selected from the group consisting of tumor angiogenesis, auto-immune diseases, neurodegeneration (such as Parkinson's disease), cardiovascular disease (such as ischaemia stroke and myocardial infarction), inflammatory diseases (such as septic shock), diabetes, and cancer such as, for example, breast, ovarian, gastric, prostate, pancreatic, uterine, cervical, endometrial, lung, brain, bile duct and hematological cancer.

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, chronic myelogenous leukemia (CML), mastocytosis, chronic lymphocytic leukemia (CLL), multiple myeloma (MM), myelodysplastic syndrome (MDS) or epidermoid cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

Combination Therapies

The compounds of the present disclosure may be used as a single agent or combined with other treatments. Such treatment may include one or more of the following categories of cancer therapies: such as surgery, chemotherapies, radiation therapies, targeted therapy (for example growth factor inhibitors, kinase inhibitors, cyclin dependent kinase inhibitors and so on), other DDR modulators (for example DNA-PK inhibitor, ATM inhibitor, ATR inhibitor, CHK1 inhibitor, WEE1 inhibitor, CDK1 inhibitor, LIG4 inhibitor, HIF-1 inhibitor, HDAC inhibitor, RAD51 inhibitor, Polθ inhibitor, WRN inhibitor, PRMT5 inhibitor, MAT2A inhibitor and PKMYT1 inhibitor and so on), immunotherapies, and gene and cell therapy approaches.

For treating cancers and other proliferative diseases, the compounds of the disclosure can be used in combination with a medical therapy such as surgery, radiotherapy or chemotherapy. Examples of radiotherapies include gamma-radiation, neutron beam radiotherapy, electron beam radiotherapy, proton therapy, brachytherapy, and systemic radioactive isotopes. Examples of suitable chemotherapeutic agents include one or more of the following categories of anti-tumor agents: other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like bleomycin, doxorubicin, daunomycin, epimbicin, idarubicin, mitomycin-C, dactinomycin and mithramycin); antimitotic agents (for example vinca alkaloids like vincristine, vinblastine, vindesine and vinorelbine and antineoplastic drugs like taxol and taxotere and polokinase inhibitors); and topoisomerase inhibitors (for example epipodophyllotoxins like etoposide and teniposide, amsacrine, topotecan and camptothecin); cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase (for example finasteride); anti-invasion agents such as c-Src kinase family inhibitors (for example AZD0530, dasatinib and bosutinib), and metalloproteinase inhibitors (for example marimastat, inhibitors of urokinase plasminogen activator receptor function or antibodies to heparanase).

For treating cancer and other proliferative diseases, the compounds of the disclosure can be used in combination with targeted therapies, including inhibitors of growth factor function (for example the anti-erbB2 antibody trastuzumab, the anti-EGFR antibody panitumumab, the anti-erbB antibody cetuximab and any growth factor or growth factor receptor antibodies disclosed by Stem et al. (Critical reviews in oncology/haematology, 2005, Vol. 54, ppl 1-29); such inhibitors also include tyrosine kinase inhibitors (for example inhibitors of the EGFR family tyrosine kinase inhibitors such as gefitinib, erlotinib and Cl 1033), erbB2 tyrosine kinase inhibitors such as lapatinib; inhibitors of the hepatocyte growth factor family; inhibitors of the insulin growth factor family; inhibitors of the platelet-derived growth factor family such as imatinib and/or nilotinib; inhibitors of serine/threonine kinases (for example Ras/Raf inhibitors such as sorafenib, tipifamib and lonafamib); inhibitors of cell proliferation through MEK and/or AKT kinases; c-kit inhibitors; ab1 kinase inhibitors; PI3 kinase inhibitors; Flt3 kinase inhibitors, CSF-IR kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4/6 inhibitors; antiangiogenic agents such as those which inhibit the effects of vascular endothelial growth factor (for example the anti-vascular endothelial cell growth factor antibody bevacizumab and for example, a VEGF receptor tyrosine kinase inhibitor such as vandetanib, vatalanib, sunitinib, axitinib, pazopanib, AZD2171 compounds such as those disclosed in International Patent Applications WO97/22596, WO 97/30035, WO97/32856 and WO98/13354 and compounds that work by other mechanisms (for example linomide, inhibitors of integrin $\alpha v\beta 3$ function and angiostatin)); vascular damaging agents such as combretastatin A4 and compounds disclosed in International Patent Applications WO99/02166, WO00/40529, WO00/41669, WO01/92224, WO02/04434 and WO02/08213; an endothelin receptor antagonist, for example zibotentan or atrasentan; DNA damage repair modulator such as DNA-PK inhibitor (for example LY294002, NU7026, NU7441, IC86621, IC87102, IC87361, OK-1035, SU11752, vanillin, NK314, IC486241, BVAN08, M3814, AZD7648, VX-984, Doxycycline), ATM inhibitor (for example caffeine, wortmannin, CP-466722, KU-55933, KU-60019, and KU-559403), ATR inhibitor (for example schisandrin B, NU6027, NVP-BEZ235, VE-821, VE-822, AZ20, Elimusertib, RP-3500 and AZD6738), CHK1 inhibitor (for example LY2606368, PF-00477736, SRA737, SCH900776, MK8776, CCT244747 and AZD6738), WEE1 inhibitor (for example AZD1775, ZN-c3 and PD0166285), CDK1 (for example AZD5438, RO-3306, JNJ-7706621 and MER162), DNA LIG4 inhibitor (for example SCR7), HIF-1 inhibitor (for example LW6 and PX-478), HDAC inhibitor (for example short-chain fatty acids, benzamides, hydroxamic acids, and cyclic tetrapeptides, suberoylanilide hydroxamic acid (SAHA), trichostatin A), RAD51 inhibitor (for example CYT-0851, SCR-6992, SAT-93/101, CAM833, JKYN-1 (IBR120-series, B02-iso)), Polθ inhibitor (for example ART558, ART4215, and compounds disclosed in International Patent Application WO2020/243459, WO2020/160213, WO2021/028644, WO2020/160134, WO2022/026565, WO2022259204A1, WO2020243459A1, WO2022118210A1, CN115353512A, CN115960079A, WO2019079297A1), WRN (for example NCGC00029283, US20230046859A1, WO2022249060A1), PKMYT1 (for example RP6306); antisense therapies, for example those which are directed to the targets listed above, such as ISIS 2503, an anti-ras antisense; gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

Synthesis

Compounds of the disclosure, including salts thereof, can be prepared using known organic synthesis techniques and can be synthesized according to any of numerous possible synthetic routes, such as those in the Schemes below.

The reactions for preparing compounds of the disclosure can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith el ah, *March's Advanced Organic Chemistry: Reactions, Mechanisms, and Structure*, 6th Ed. (Wiley, 2007); Petursson et al, "Protecting Groups in Carbohydrate Chemistry," *J Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t." as used herein, are understood in the art, and refer generally to a temperature, e.g. a reaction temperature, that is about the temperature of the room in which the reaction is carried out, for example, a temperature from about 20° C. to about 30° C.

Compounds of the disclosure can be prepared according to numerous preparatory routes known in the literature. The Schemes below provide general guidance in connection with preparing the compounds of the disclosure. One skilled in the art would understand that the preparations shown in the Schemes can be modified or optimized using general knowledge of organic chemistry to prepare various compounds of the disclosure. Example synthetic methods for preparing compounds of the disclosure are provided in the Schemes below.

The following Examples are provided to illustrate some of the concepts described within this disclosure. While the Examples are considered to provide an embodiment, it should not be considered to limit the more general embodiments described herein.

| | |
|---|---|
| t-$Bu_3P$ | Tri-tert-butylphosphine |
| MTBE | Methyl tert-butyl ether |
| DIPEA | N,N-diisopropylethylamine |
| DIEA | N,N-diisopropylethylamine |
| DMAc | Dimethylacetamide |
| m-CPBA | m-Chloroperbenzoic Acid |
| TBTU | O-(Benzotriazol-1-yl)-N,N,N',N'-tetramethyluronium tetrafluoroborate |
| CDI | N,N'-Carbonyldiimidazole |
| BOP | (Benzotriazol-1-yloxy)tris(dimethylamino)phosphonium hexafluorophosphate |
| PyBOP | (Benzotriazol-1-yloxy)tripyrrolidinophosphonium hexafluorophosphate |
| HATU | 2-(7-Azabenzotriazol-1-yl)-N,N,N',N'-tetramethyluronium hexafluorophosphate |
| HBTU | O-(Benzotriazol-1-yl)-N,N,N',N'-tetramethyluronium hexafluorophosphate |
| EDCI | N-(3-Dimethylaminopropyl)-N'-ethylcarbodiimide hydrochloride |
| DMAP | 4-Dimethylaminopyridine |
| DAST | Diethylaminosulfur trifluoride |
| BrettPhos Pd G3 | [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate |

-continued

| | |
|---|---|
| t-BuXphos Pd G3 | [(2-Di-tert-butylphosphino-2',4',6'-triisopropyl-1,1'-biphenyl)-2-(2'-amino-1,1'-biphenyl)] palladium(II) methanesulfonate |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate |
| XantPhos Pd G3 | [(4,5-Bis(diphenylphosphino)-9,9-dimethylxanthene)-2-(2'-amino-1,1'-biphenyl)]palladium(II) methanesulfonate |
| SPhos Pd G3 | (2-Dicyclohexylphosphino-2',6'-dimethoxybiphenyl) [2-(2'-amino-1,T-bi-phenyl)]palladium(ll) methanesulfonate |
| $Pd(OAc)_2$ | Palladium (II) Acetate |
| $Pd(dppf)Cl_2$ | [1,1'-Bis(diphenylphosphino)ferrocene]dichloropalladium(II) |
| $Pd_2(dba)_3$ | Bis(dibenzylideneacetone)palladium(0) |
| $Pd(PPh_3)_4$ | Tetrakis(triphenylphosphine)palladium(0) |
| DBU | 1,8-Diazabicyclo[5.4.0]undec-7-ene |
| TEA | Triethylamine |
| LDA | Lithium diisopropylamide |
| DEAD | Diethyl azodicarboxylate |
| DIAD | Diisopropyl Azodicarboxylate |
| TFA | Trifluoroacetic acid |
| NaHMDS | Sodium bis(trimethylsilyl)amide |
| EtOAc/EA | Ethyl acetate |
| DMF | N,N-dimethylformamide |
| PE | Petroleum ether |
| $CS_2$ | Carbon disulfide |
| THF | Tetrahydrofuran |
| DMSO | Dimethylsulfoxide |
| DCM | Dichloromethane |
| MeCN/ACN | Acetonitrile |
| LCMS | Liquid chromatography-mass spectrometry |
| $^1H$ NMR | Hydrogen-1 nuclear magnetic resonance spectroscopy |
| EDTA | Ethylene diamine tetra-acetic acid |
| EGTA | Ethylenebis(oxyethylenenitrilo)tetra-acetic acid |
| DTT | DL-Dithiothreitol |
| BSA | Bovine albumin |
| FBS | Fetal Bovine Serum |
| brine | Saturated solution of sodium chloride |
| r.t. | Room temperature |
| aq | Aqueous |

1M or 1N = 1 mol/L, 2M or 2N = 2 mol/L etc.

General Synthetic Procedures

A series of tricyclic derivatives of formula 1-7 to 1-13 can be prepared by the methods outlined in Scheme 1. Compounds 1-3 where t and s are an integer (e.g., 2, 3, or 4) can be prepared by reactions of compounds 1-1 where $W^1$ is halogen (e.g., Cl, Br, or I) or pseudohalogen (e.g., OTf or OMs) with a suitable amine derivative 1-2 in the presence of a base such as Hunig's base. Buchwald coupling of compounds 1-3 with a suitable 5-6 membered heteroaryl derivatives $Cy^1W$ 1-4 where W is halogen (e.g., Cl, Br, or I) or pseudohalogen (e.g., OTf or OMs) under standard Buchwald coupling conditions (e.g., in the presence of a palladium catalyst, such as BrettPhos Pd G3, t-BuXphos Pd G3, RuPhos Pd G3 or XantPhos Pd G3 and a base, such as t-BuOK, t-BuONa, $Cs_2CO_3$, or $K_2CO_3$) or under Ullmann coupling conditions (e.g., CuI, CsF and $N_1N_2$-dimethylcyclohexane-1,2-diamine) can provide compounds 1-5. Removal of the Boc group in compounds 1-5 to compounds 1-6 can be achieved by the treatment with acid such as TFA in DCM, HCl in dioxane or other acidic media. In the presence of a base (e.g., hunig's base or $K_2CO_3$), reactions of compounds 1-6 with acyl chloride $R^bCOCl$ can afford the corresponding compounds 1-7, with suitable chloroformate $R^bOCOCl$ the corresponding compounds 1-8, with isocyanate $R^cN{=}C{=}O$ compounds 1-9, with carbamic chloride $R^cR^dNCOCl$ compounds 1-10, with sulfinic chloride $R^bSOCl$ compounds 1-11, with sulfonyl chloride $R^bSO_2Cl$ compounds 1-12, and with sulfamoyl chloride $R^cR^dNSO_2Cl$ compounds 1-13.

Scheme 1
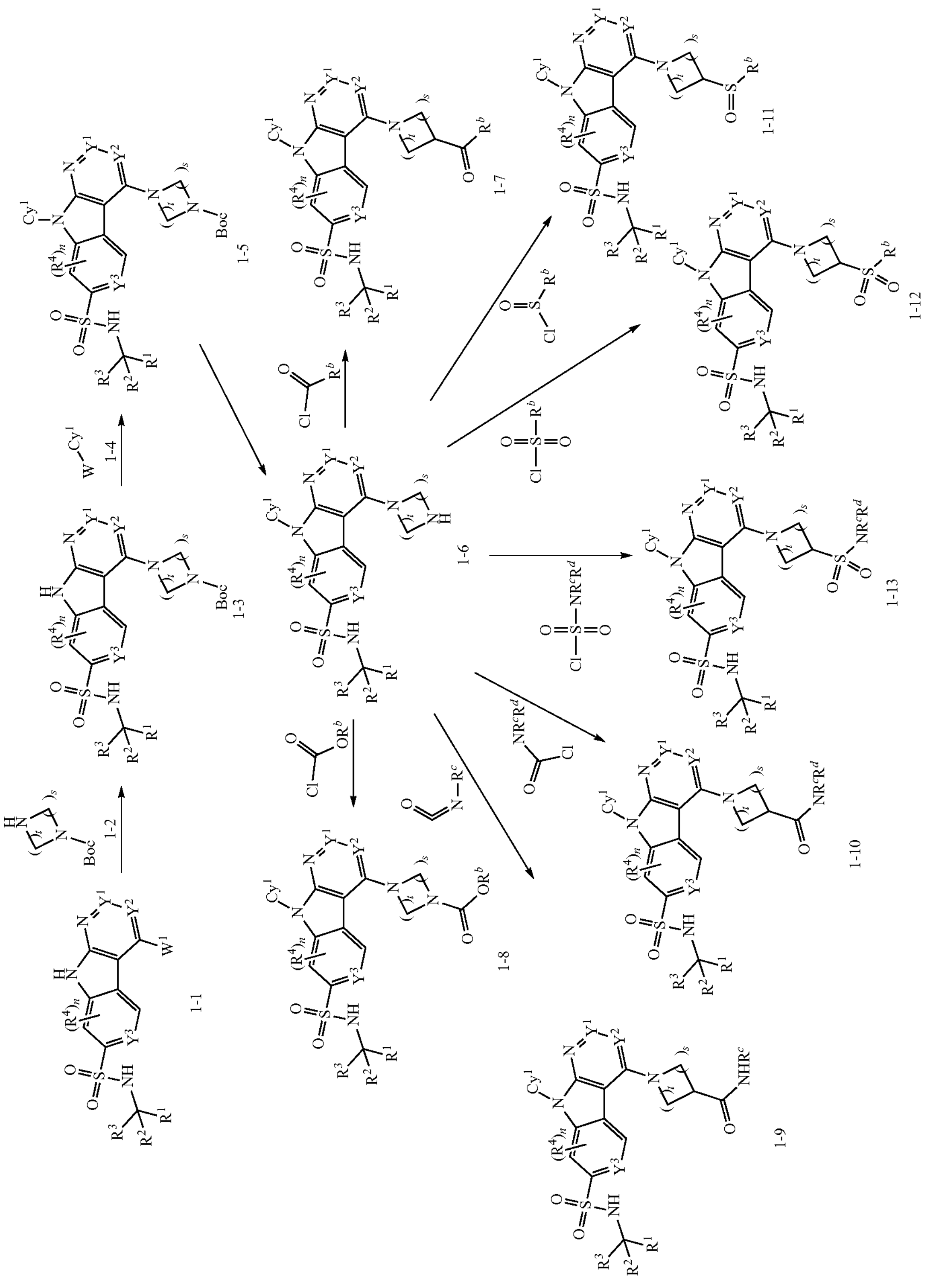

A series of tricyclic derivatives of formula 2-2 to 2-4 can be prepared by the methods outlined in Scheme 2. Tricyclic derivatives 2-2 can be prepared by N-alkylation with a suitable reagent $R^{10}$—W where W is halogen (e.g., Cl, Br, or I) or pseudohalogen (e.g., OTf or OMs) under alkylation conditions (e.g., in the presence of a base, such as Hunig's base, NaH, t-BuOK, t-BuONa, $CS_2CO_3$, or $K_2CO_3$). Alternatively, tricyclic derivatives 2-3 can be obtained by reductive amination with an aldehyde, ketone or cyclic ketone $R^{10a}C(O)R^{10b}$, where $R^{10a}$ and $R^{10b}$ are selected from H or alkyl or $R^{10a}$ and $R^{10b}$ together with the carbon atom to which they are attached is a $C_3$-$C_{10}$ cycloalkyl, or 4-10 membered heterocycloalkyl, under standard reductive amination's conditions (e.g., in the presence of a reductive reagent, such as $NaBH(OAc)_3$, or $NaBH_3CN$). Treatment of compounds 2-1 with a suitable aryl or heteroaryl reagent $Cy^3$-W under standard Buchwald-Hartwig amination conditions (e.g., in the presence of a palladium catalyst, such as XPhos Pd G3, and a base, such as $Cs_2CO_3$ or $K_3PO_4$) can provide compounds 2-4.

Scheme 2

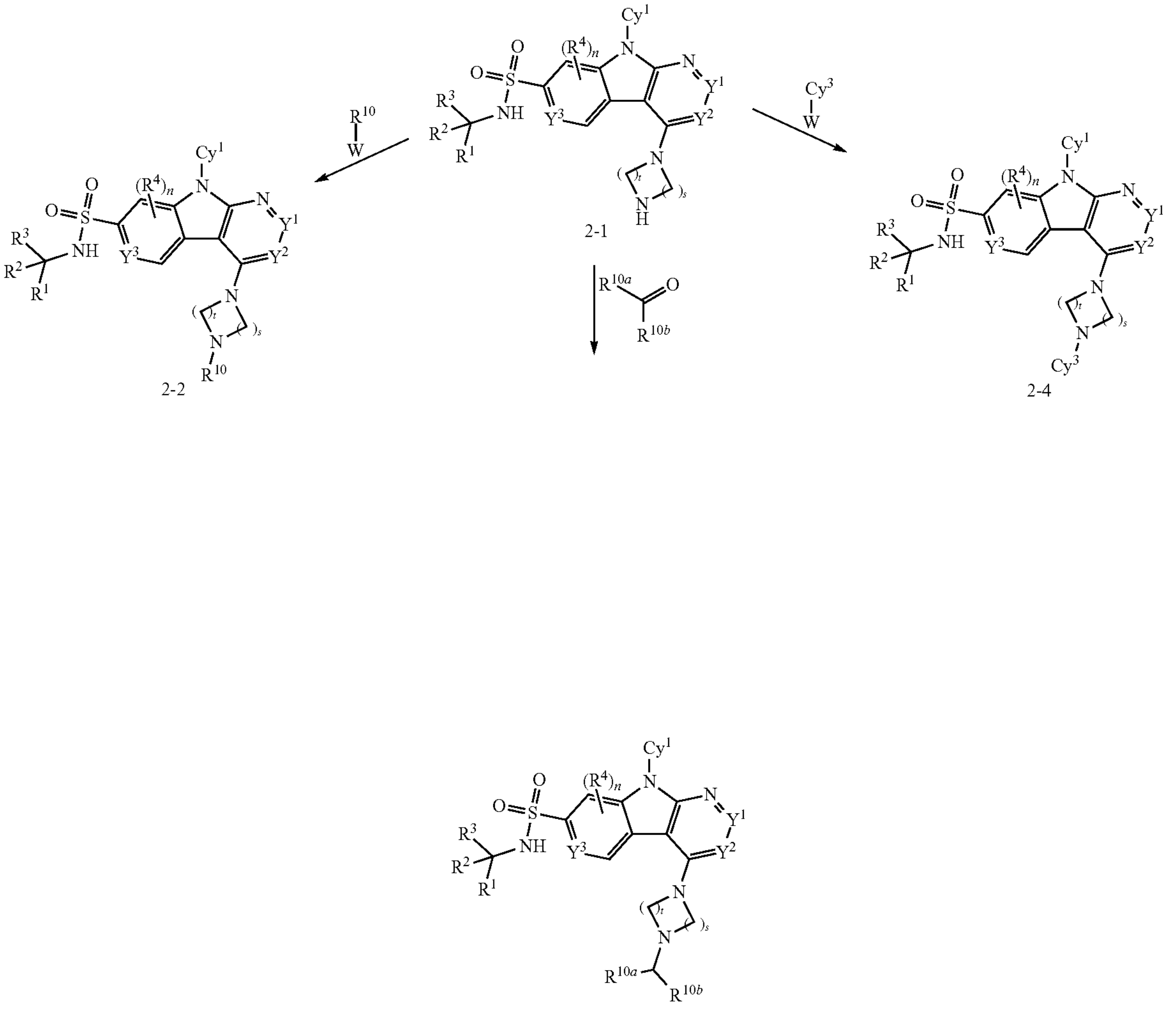

2-1

2-2

2-4

2-3

A series of tricyclic derivatives of formula 3-5 to 3-9 can be prepared by the methods outlined in Scheme 3. Suzuki coupling of compounds 3-1 where $W^1$ is halogen (e.g., Cl, Br, or I) or pseudohalogen (e.g., OTf or OMs) with vinyl boronic acid or boronate ester 3-2 where $R^{10a}$ and $R^{10b}$ are selected from H or alkyl, or $R^{10a}$ and $R^{10b}$ together with the carbon atom to which they are attached is a $C_3$-$C_{10}$ cycloalkyl, or 4-10 membered heterocycloalkyl can afford compounds 3-5 under standard Suzuki conditions (e.g., in the presence of a palladium catalyst, such as [1,1'-bis(diphenylphosphino)ferrocene]dichloropalladium(II) and a base, such as $K_3PO_4$). Hydrogenation of compounds 3-5 can produce the corresponding compounds 3-6 in the presence of a palladium catalyst such as Pd/C or $Pd(OH)_2$/C.

Similarly, compounds 3-1 can be coupled with $R^{10}$—Ar-M (e.g., Ar is aryl or heteroaryl; M is $B(OH)_2$, Bpin, $BF_3K$, $Sn(Me)_3$, $Sn(Bu)_3$, or $ZnCl_2$) under standard Suzuki conditions (e.g., in the presence of a palladium catalyst, such as Xanphos Pd, or [1,1'-bis(diphenylphosphino)ferrocene] dichloropalladium(II) and a base, such as $K_3PO_4$), or standard Negishi conditions (e.g., in the presence of a palladium catalyst, such as tetrakis(triphenylphosphine)palladium(0) or [1,1'-bis(diphenylphosphino)-ferrocene]dichloropalladium(II)), or standard Stille conditions (e.g., in the presence of a palladium(0) catalyst, such as tetrakis(triphenyl-phosphine)palladium(0)) to afford compounds 3-7. When $R^{10}$ group in compounds 3-7 is a carbonate ester group, it can be saponified to acid 3-8 under basic conditions in the presence of a base such as LiOH, NaOH or KOH. Coupling of compounds 3-8 with amines $R^cR^dNH$ 3-4 under standard amide coupling conditions (e.g., in the presence of a coupling reagent, such as BOP, PyBOP, HATU or HBTU, and a base, such as $Et_3N$ or Hunig's base) can provide compounds 3-9.

Scheme 3
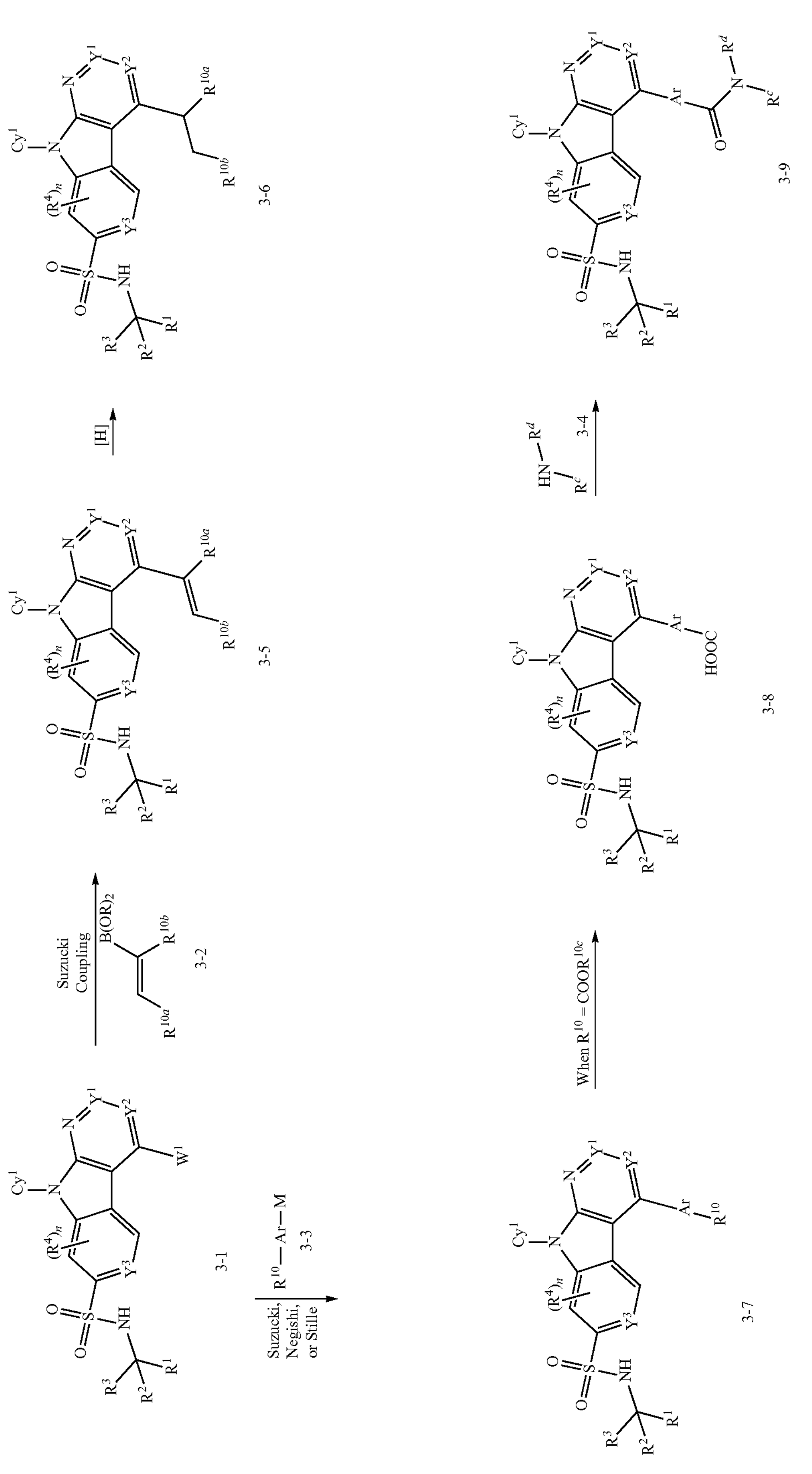
3-1
3-5
3-6
3-7
3-8
3-9

A series of tricyclic intermediates of formula 4-7 can be prepared by the methods outlined in Scheme 4. Sulfonamides 4-3 can be prepared by reaction of the sulfonyl chloride 4-1 with an amine 4-2 in the presence of a base such as Hunig's base. Coupling of the sulfonamides 4-3 with 2-cyanoacetamide in the presence of a base, such as NaH, t-BuONa, or t-BuOK can afford compounds 4-4 which can be transformed into indole derivatives 4-5 by the nitro group with a reductive reagent such as $Zn/FeCl_3$ in acid media or $Fe/NH_4C_1$ followed the ring closure under the reaction conditions. Treatment of the indole derivatives 4-5 with trialkyl orthoformate 4-6 in the presence of an acid such as p-TsOH, or HCl can form the desired product indole-pyrimidone 4-7 which can be transformed into the intermediates 4-8 where $W^1$ is halogen (e.g., $C_1$, or Br) or pseudohalogen (e.g., OTf or OMs) either by reaction with a halogenation reagent such as $SOCl_2$, $POCl_3$ or $POBr_3$ with or without the catalytic of DMF (where $W^1$ is $C_1$ or Br) or reaction with TfCl or MsCl (where $W^1$ is OTf or OMs) in the presence of a base such as Hunig's base.

Scheme 4

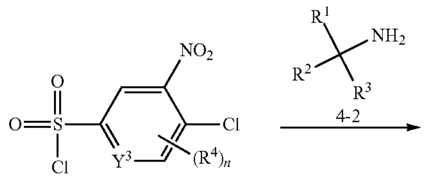

4-2

4-1

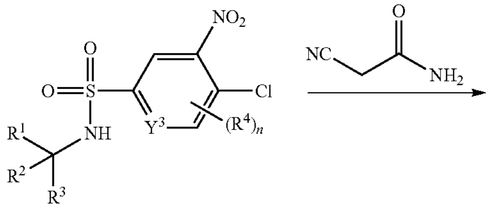

4-3

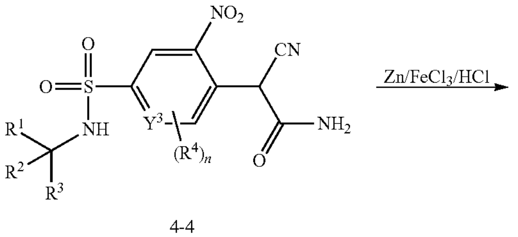

4-4

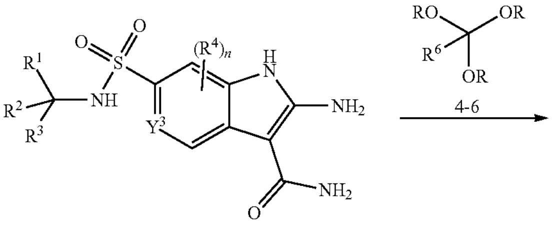

4-6

4-5

-continued

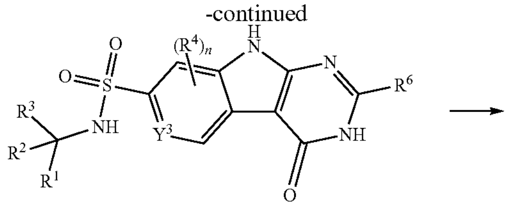

4-7

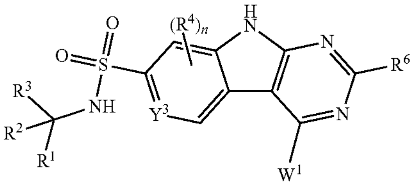

4-8

A series of tricyclic intermediates of formula 5-8 can be prepared by the methods outlined in Scheme 5. Coupling of compounds 5-1 where $W^2$ is halogen (e.g., Cl, Br, or I) or pseudohalogen (e.g., OTf or OMs), and $W^3$ is halogen (e.g., Br, or I) or pseudohalogen (e.g., OTf) with compounds 5-2 under Buchwald coupling conditions (e.g., in the presence of a palladium catalyst, such as BrettPhos Pd G3, t-BuXphos Pd G3, RuPhos Pd G3 or XantPhos Pd G3 and a base, such as t-BuOK, t-BuONa, $Cs_2CO_3$, or $K_2CO_3$), followed by ring closure by intra-molecular Heck reaction under the standard Heck reaction conditions (e.g., in the presence of a palladium catalyst, such as dichlorobis(triphenylphosphine)palladium, palladium diacetate, or tetrakis(triphenylphosphine) palladium and a base, such as $Na_2CO_3$, $K_2CO_3$, or NaOAc) can afford tricyclic compounds 5-3, which can be transformed into the corresponding sulfonyl chloride 5-4 by oxidation reagents, such as N-chlorosuccinimide, sodium hypochlorite or treatment with a suitable reagent such as 1,3-dichloro-5,5-dimethylimidazolidine-2,4-dione.

Reaction of the sulfonyl chlorides 5-4 with an amine 5-5 in the presence of a base such as Hunig's base can produce the sulfonamides 5-6 which can be transformed into 5-7 by oxidative reagents such as hydrogen peroxide, oxone, and m-chloroperbenzoic acid. The compound 5-7 can be converted into the intermediates 5-8 where $W^1$ is halogen (e.g., $C_1$, or Br) or pseudohalogen (e.g., OTf or OMs) by reaction with a halogenation reagent such as $SOCl_2$, $POCl_3$ or $POBr_3$ or reaction with TfCl or MsCl in the presence of a base such as Hunig's base.

Scheme 5

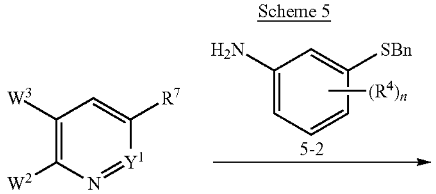

5-2

5-1

-continued

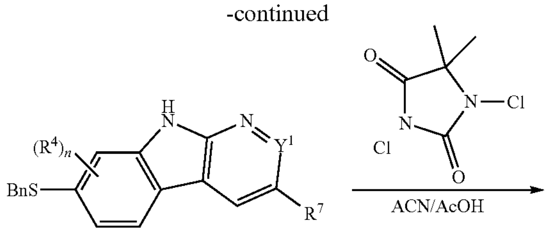

5-3

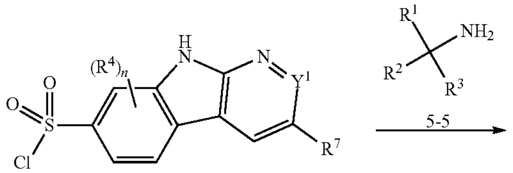

5-4

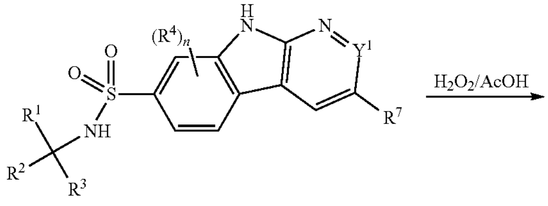

5-6

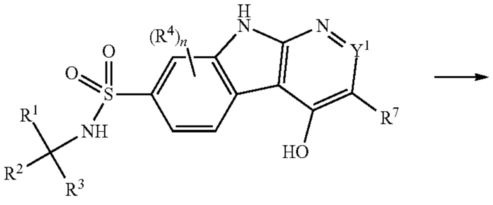

5-7

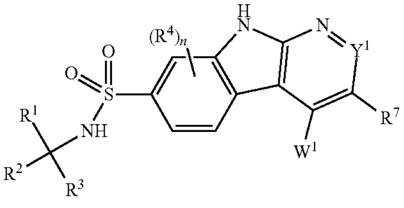

5-8

Alternatively, a series of tricyclic intermediates of formula 6-10 can be prepared by the methods outlined in Scheme 6. Tricyclic compounds 6-3 can be obtained in the similar way as describes in scheme 5 for the tricyclic compounds 5-3 by reaction with a suitable aniline 6-2. The removal of benzyl group in compounds 6-3 to the corresponding OH compounds 6-4 can be achieved by hydrogenation in the presence of a catalyst, such as Pd/C or $Pd(OH)_2/C$. Treatment the compounds 6-4 with trifluoromethanesulfonic anhydride afford the compounds 6-5 which can be transformed into 6-6 by reaction with phenylmethanethiol or sodium phenylmethanethiolate in the presence of a base such as Hunig's base, $Cs_2CO_3$, t-BuOK, t-BuONa. The oxidation of compounds 6-6 with oxidation reagents, such as N-chlorosuccinimide, sodium hypochlorite can form the sulfonyl chloride 6-7 which then can be transformed into the desired intermediates 6-10 by reaction with a suitable amine 6-8 in the presence of a base, such as Hunig's base, $Na_2CO_3$, or $K_2CO_3$, followed by removal of the protecting group Tf in the products 6-9 under basic conditions such as NaOH, or KOH.

Scheme 6

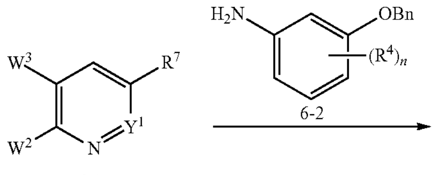

6-1

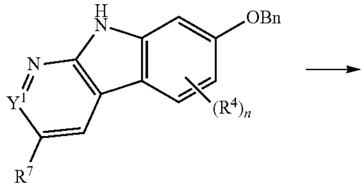

6-3

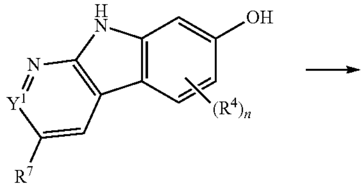

6-4

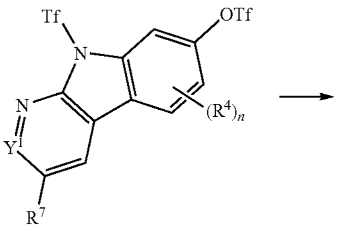

6-5

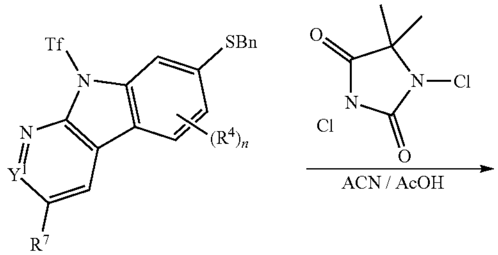

6-6

-continued

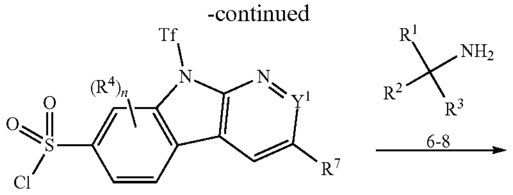

6-7

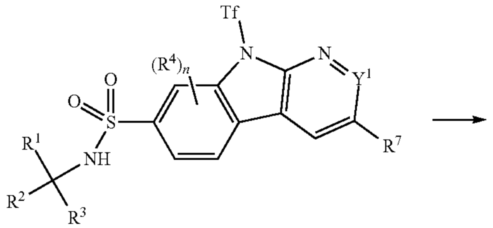

6-9

-continued

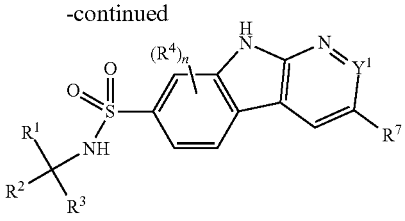

6-10

Alternatively, a series of tricyclic intermediates of formula 7-3 and 7-5 can be prepared by the methods outlined in the scheme 7. The compounds 7-3 and 7-5 can be prepared by Buchwald coupling compounds 7-1 where $W^2$ is halogen (e.g., Cl, Br, or I) or pseudohalogen (e.g., OTf or OMs), with compounds 7-2 and 7-4, respectively under standard conditions (e.g., in the presence of a palladium catalyst, such as BrettPhos Pd G3, t-BuXphos Pd G3, RuPhos Pd G3 or XantPhos Pd G3 and a base, such as t-BuOK, t-BuONa, $Cs_2CO_3$, or $K_2CO_3$), followed by intramolecular ring closure in the presence of a Lewis acid, such as $AlCl_3$, $ZnCl_2$ or other acidic media such as polyphosphoric acid, $POCl_3$.

Scheme 7

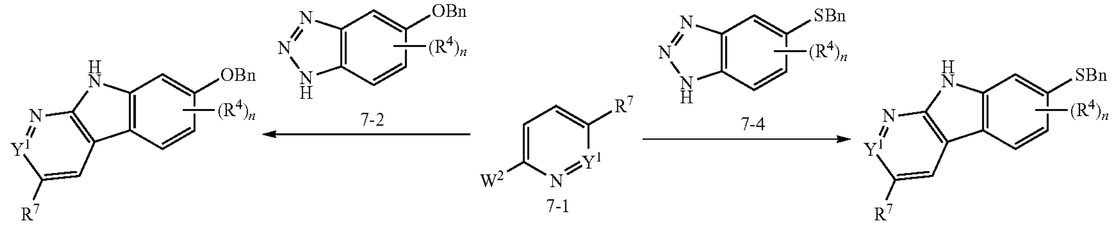

7-1

7-3

7-5

In a similar manner, a series of tricyclic intermediates of formula 8-3 and 8-5 can be prepared by the methods outlined in the scheme 8. The compounds 8-3 and 8-5 can be prepared by Buchwald coupling compounds 8-1 where $W^3$ is halogen (e.g., Cl, Br, or I) or pseudohalogen (e.g., OTf or OMs), with compounds 8-2 and 8-5, respectively under standard conditions (e.g., in the presence of a palladium catalyst, such as BrettPhos Pd G3, t-BuXphos Pd G3, RuPhos Pd G3 or XantPhos Pd G3 and a base, such as t-BuOK, t-BuONa, $Cs_2CO_3$, or $K_2CO_3$), followed by ring closure by intramolecular Heck reaction under the standard reaction condition (e.g., in the presence of a palladium catalyst, such as dichlorobis(triphenylphosphine)palladium, palladium diacetate, tetrakis(triphenylphosphine)palladium and a base, such as $Na_2CO_3$, $K_2CO_3$, or NaOAc).

Scheme 8

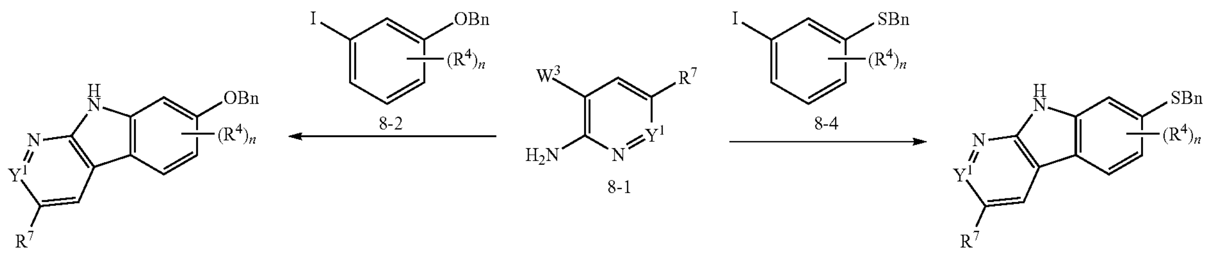

8-3

8-1

8-5

A series of tricyclic intermediates of formula 9-7 where A is O or S can be prepared by the methods outlined in the scheme 9. The compounds 9-3 can be prepared by nucleophile alkylation of compound 9-1 where $W^2$ is halogen (e.g., F, Cl, Br, or I) or pseudohalogen (e.g., OTf or OMs), with 2-cyanoacetate 9-2 where R is alkyl (e.g., Me, Et or t-Bu) in the presence of a strong base, such as t-BuOK, t-BuONa, NaH). Reduction of the nitro group in 9-3 can be achieved by treatment with a reductive reagent such as Zn dust, or Fe powder in acidic conditions (such as acetic acid or HCl), followed by intramolecular ring closure to produce compounds 9-4. Heating the mixture of compounds 9-4 with an acetal 9-5 bearing alfa-H in the presence of a base such as NaOMe or NaOEt can yield tricyclic compounds 9-6. Halogenation of compounds 9-6 can provide the desired intermediates 9-7 (where $W^1$ is $C_1$ or Br) with a halogenation reagent such as $SOCl_2$, $POCl_3$ or $POBr_3$ or 9-7 (where $W^1$ is OTf or OMs) with TfCl or MsCl in the presence of a base such as Hunig's base.

Scheme 9

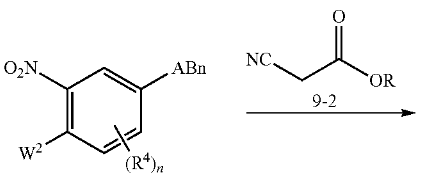

9-1

-continued

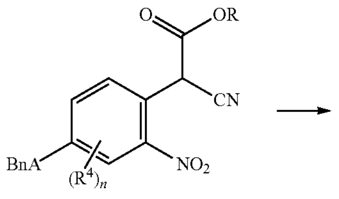

9-3

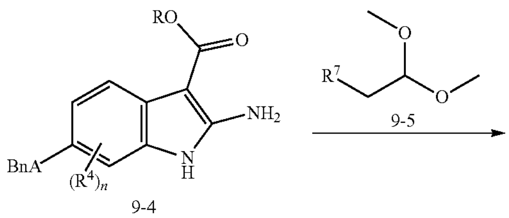

9-4

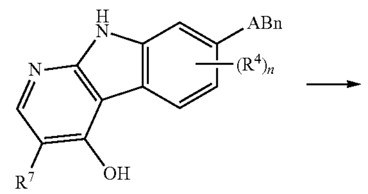

9-6

-continued

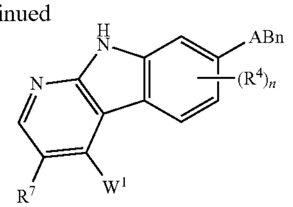

9-7

EXAMPLES

Example 1: 4-(4-(Cyclopropanecarbonyl)piperazin-1-yl)-9-(5-(difluoromethyl)-1,3,4-thiadiazol-2-yl)-N-(1-methylcyclopropyl)-9H-pyrimido[4,5-b]indole-7-sulfonamide

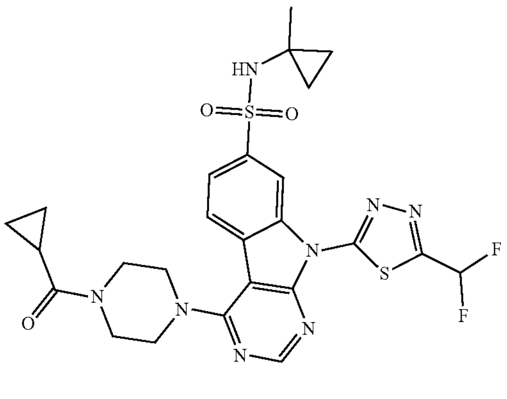 [SMILES: CC1(NS(=O)(=O)c2ccc3c4c(N5CCN(C(=O)C6CC6)CC5)ncnc4n(-c4nnc(C(F)F)s4)c3c2)CC1]

Step 1: 4-(4-(cyclopropanecarbonyl)piperazin-1-yl)-N-(1-methylcyclopropyl)-9H-pyrimido[4,5-b]indole-7-sulfonamide

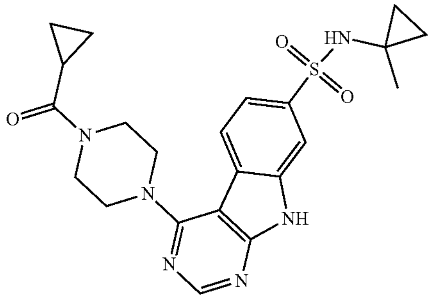 [SMILES: CC1(NS(=O)(=O)c2ccc3c(c2)[nH]c2ncnc(N4CCN(C(=O)C5CC5)CC4)c23)CC1]

To a solution of 4-chloro-N-(1-methylcyclopropyl)-9H-pyrimido[4,5-b]indole-7-sulfonamide (111 mg, 0.330 mmol, Intermediate 2) and cyclopropyl(piperazin-1-yl)methanone (189 mg, 0.992 mmol) in MeCN (15 mL) was added $NaHCO_3$ (1.11 g, 13.2 mmol). The mixture was stirred under reflux overnight. The reaction mixture was diluted with $H_2O$ (10 mL) and extracted with EtOAc (10 mL×3). The combined organic layers were washed with brine (20 mL×2), dried over $Na_2SO_4$, filtered and concentrated under reduced pressure. The residue was purified by flash chromatography on a silica gel column eluting with EtOAc/PE (0-5%) to afford 4-(4-(cyclopropanecarbonyl)piperazin-1-yl)-N-(1-methylcyclopropyl)-9H-pyrimido[4,5-b]indole-7-sulfonamide (100 mg, 66.5% yield) as a white solid. $^1$H NMR: (400 MHz, DMSO-$d_6$) δ 12.6 (s, 1H), 8.55 (s, 1H), 8.11 (s, 1H), 7.93-7.95 (m, 2H), 7.69-7.72 (m, 1H), 3.72-3.94 (m, 8H), 2.02-2.07 (m, 1H), 1.11 (s, 3H), 0.73-0.81 (m, 4H), 0.59-0.61 (m, 2H), 0.35-0.38 (m, 2H). LCMS calc. for $C_{22}H_{25}N_6O_3S$ $[M-H]^-$: m/z=453.2; Found: 453.1.

Step 2: 4-(4-(cyclopropanecarbonyl)piperazin-1-yl)-9-(5-(difluoromethyl)-1,3,4-thiadiazol-2-yl)-N-(1-methylcyclopropyl)-9H-pyrimido[4,5-b]indole-7-sulfonamide A mixture of 4-(4-(cyclopropanecarbonyl)piperazin-1-yl)-N-(1-methylcyclopropyl)-9H-pyrimido[4,5-b]indole-7-sulfonamide (20 mg, 0.044 mmol), 2-bromo-5-(difluoromethyl)-1,3,4-thiadiazole (75.7 mg, 0.352 mmol), t-BusP (125 mg, 0.616 mmol), $Pd_2(dba)_3$ (60.4 mg, 0.066.0 mmol) and t-BuONa (123 mg, 1.28 mmol) in xylene (3 mL) was degassed and recharged with $N_2$ for three cycles. The mixture was stirred at 110° C. overnight under $N_2$ atmosphere. After cooling, the mixture was filtered. The filtrate was concentrated under reduced pressure. The residue was purified by prep-HPLC on a C18 column with ACN/water (30%-60% with ($NH_3 \cdot H_2O+NH_4HCO_3$)) to afford 4-(4-(cyclopropanecarbonyl)piperazin-1-yl)-9-(5-(difluoromethyl)-1,3,4-thiadiazol-2-yl)-N-(1-methylcyclopropyl)-9H-pyrimido[4,5-b]indole-7-sulfonamide (1.8 mg, 3.47% yield) as a white solid. $^1$H NMR: (400 MHz, DMSO-$d_6$) δ 9.46 (s, 1H), 8.82 (s, 1H), 8.36 (s, 1H), 8.09 (d, J=8.0 Hz, 1H), 7.99 (d, J=8.0 Hz, 1H), 7.68 (t, J=25.6 Hz, 1H), 3.73-4.04 (m, 8H), 1.44 (d, J=13.2 Hz, 1H), 1.12 (s, 3H), 0.76-0.80 (m, 4H), 0.64-0.66 (m, 2H), 0.39-0.42 (m, 2H). LCMS calc. for $C_{25}H_{25}F_2N_8O_3S_2$ $[M-H]^-$: m/z=587.2; Found: 587.2.

The compounds listed in Table 1 below were prepared by using an Intermediate 1 (Int A, sulfonamide derivative) and an appropriate Intermediate 10-55 (Int B, amine derivative) or commercially available material (CAM, amine derivative) as the methods substantially analogous to those described for preparing Example 1.

TABLE 1

| Preparations of Examples (Ex) | | | | |
|---|---|---|---|---|
| Ex # | Int A/ Int B | Structure | Name | LCMS Cacl./ Found |
| 2 | Int 1/ Int 11 | 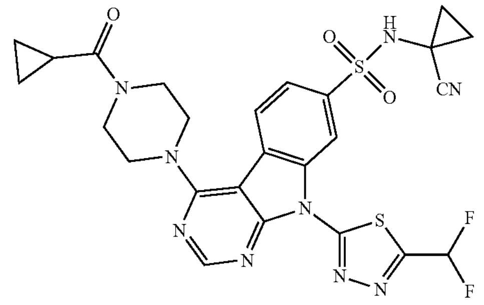 [SMILES: N#CC1(NS(=O)(=O)c2ccc3c4c(N5CCN(C(=O)C6CC6)CC5)ncnc4n(-c4nnc(C(F)F)s4)c3c2)CC1] | N-(1-Cyanocyclopropyl)-4-(4-(cyclopropanecarbonyl)piperazin-1-yl)-9-(5-(difluoromethyl)-1,3,4-thiadiazol-2-yl)-9H-pyrimido[4,5-b]indole-7-sulfonamide | [M − H]$^-$ 598.1/ 598.2 |
| 3 | Int 1/ Int 13 | 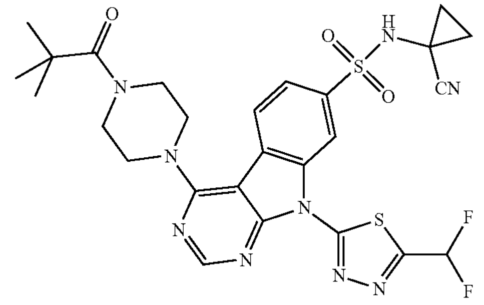 [SMILES: CC(C)(C)C(=O)N1CCN(c2ncnc3c2c2ccc(S(=O)(=O)NC4(C#N)CC4)cc2n3-c2nnc(C(F)F)s2)CC1] | N-(1-Cyanocyclopropyl)-9-(5-(difluoromethyl)-1,3,4-thiadiazol-2-yl)-4-(4-pivaloylpiperazin-1-yl)-9H-pyrimido[4,5-b]indole-7-sulfonamide | [M − H]$^-$ 614.2/ 614.2 |
| 4 | Int 1/ Int 10 | 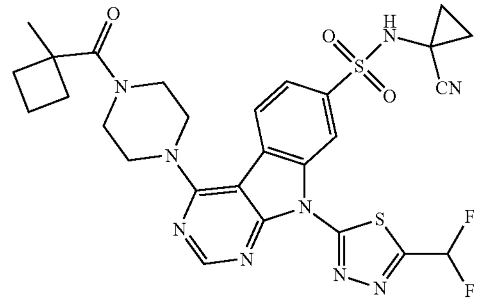 [SMILES: CC1(C(=O)N2CCN(c3ncnc4c3c3ccc(S(=O)(=O)NC5(C#N)CC5)cc3n4-c3nnc(C(F)F)s3)CC2)CCC1] | N-(1-Cyanocyclopropyl)-9-(5-(difluoromethyl)-1,3,4-thiadiazol-2-yl)-4-(4-(1-methylcyclobutane-1-carbonyl)piperazin-1-yl)-9H-pyrimido[4,5-b]indole-7-sulfonamide | [M + H]$^+$ 628.2/ 628.1 |
| 5 | Int 1/ Int 19 | 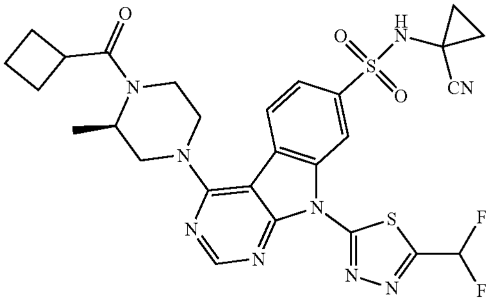 [SMILES: C[C@@H]1CN(c2ncnc3c2c2ccc(S(=O)(=O)NC4(C#N)CC4)cc2n3-c2nnc(C(F)F)s2)CCN1C(=O)C1CCC1] | (R)-N-(1-Cyanocyclopropyl)-4-(4-(cyclobutanecarbonyl)-3-methylpiperazin-1-yl)-9-(5-(difluoromethyl)-1,3,4-thiadiazol-2-yl)-9H-pyrimido[4,5-b]indole-7-sulfonamide | [M − H]$^-$ 626.2/ 626.2 |

TABLE 1-continued

| Preparations of Examples (Ex) | | | | |
|---|---|---|---|---|
| Ex # | Int A/ Int B | Structure | Name | LCMS Cacl./ Found |
| 6 | Int 1/ Int 32 | 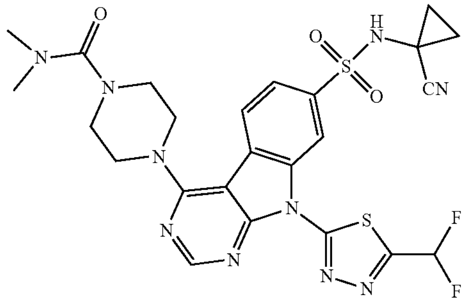 [SMILES: CN(C)C(=O)N1CCN(c2ncnc3c2c2ccc(S(=O)(=O)NC4(C#N)CC4)cc2n3-c2nnc(C(F)F)s2)CC1] | 4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N-dimethylpiperazine-1-carboxamide | $[M - H]^-$ 601.1/ 601.2 |
| 7 | Int 1/ Int 31 | 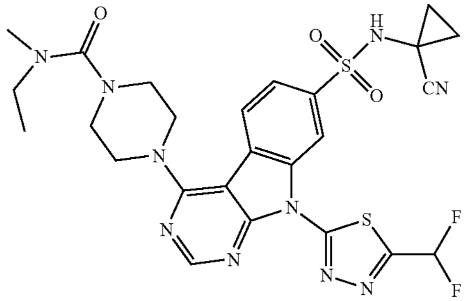 [SMILES: CCN(C)C(=O)N1CCN(c2ncnc3c2c2ccc(S(=O)(=O)NC4(C#N)CC4)cc2n3-c2nnc(C(F)F)s2)CC1] | 4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N-ethyl-N-methylpiperazine-1-carboxamide | $[M - H]^-$ 615.2/ 615.2 |
| 8 | Int 1/ Int 33 | 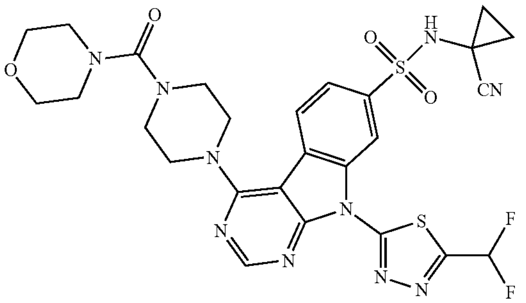 [SMILES: N#CC1(NS(=O)(=O)c2ccc3c4c(N5CCN(C(=O)N6CCOCC6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(morpholine-4-carbonyl)piperazin-1-yl)-9H-pyrimido[4,5-b]indole-7-sulfonamide | $[M + H]^+$ 645.2/ 645.2 |
| 9 | Int 1/ Int 34 | 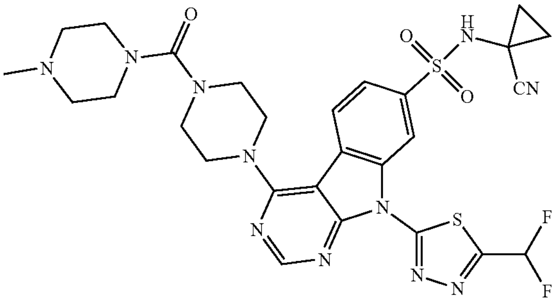 [SMILES: CN1CCN(C(=O)N2CCN(c3ncnc4c3c3ccc(S(=O)(=O)NC5(C#N)CC5)cc3n4-c3nnc(C(F)F)s3)CC2)CC1] | N-(1-Cyanocyclopropyl)-9-(5-(difluoromethyl)-1,3,4-thiadiazol-2-yl)-4-(4-(4-methylpiperazine-1-carbonyl)piperazin-1-yl)-9H-pyrimido[4,5-b]indole-7-sulfonamide | $[M - H]^-$ 656.2/ 656.2 |

TABLE 1-continued

Preparations of Examples (Ex)

| Ex # | Int A/ Int B | Structure | Name | LCMS Cacl./ Found |
|---|---|---|---|---|
| 10 | Int 1/ Int 14 | 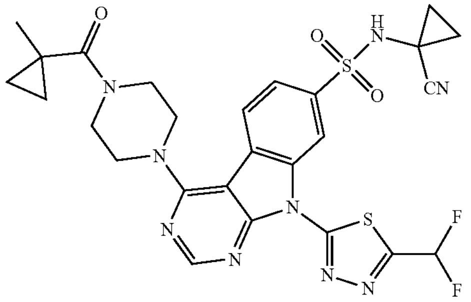 [SMILES: CC1(C(=O)N2CCN(c3ncnc4c3c3ccc(S(=O)(=O)NC5(C#N)CC5)cc3n4-c3nnc(C(F)F)s3)CC2)CC1] | N-(1-Cyanocyclopropyl)-9-(5-(difluoromethyl)-1,3,4-thiadiazol-2-yl)-4-(4-(1-methylcyclopropane-1-carbonyl)piperazin-1-yl)-9H-pyrimido[4,5-b]indole-7-sulfonamide | $[M + H]^+$ 614.1/ 614.1 |
| 11 | Int 1/ Int 15 | 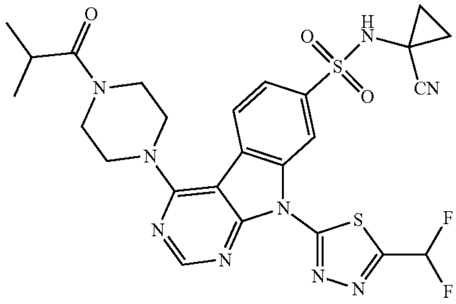 [SMILES: CC(C)C(=O)N1CCN(c2ncnc3c2c2ccc(S(=O)(=O)NC4(C#N)CC4)cc2n3-c2nnc(C(F)F)s2)CC1] | N-(1-Cyanocyclopropyl)-9-(5-(difluoromethyl)-1,3,4-thiadiazol-2-yl)-4-(4-isobutyrylpiperazin-1-yl)-9H-pyrimido[4,5-b]indole-7-sulfonamide | $[M + H]^+$ 602.2/ 602.1 |
| 12 | Int 1/ Int 16 | 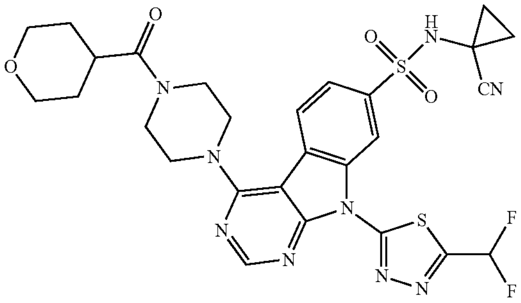 | N-(1-Cyanocyclopropyl)-9-(5-(difluoromethyl)-1,3,4-thiadiazol-2-yl)-4-(4-(tetrahydro-2H-pyran-4-carbonyl)piperazin-1-yl)-9H-pyrimido[4,5-b]indole-7-sulfonamide | $[M + H]^+$ 644.2/ 644.1 |
| 13 | Int 1/ Int 17 | 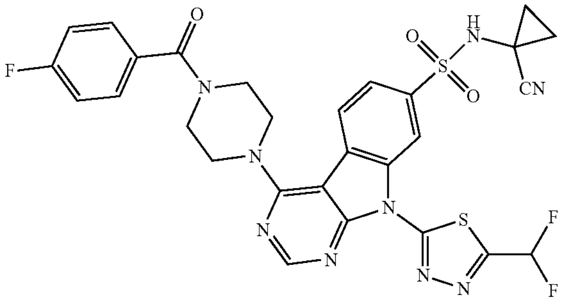 [SMILES: N#CC1(NS(=O)(=O)c2ccc3c4c(N5CCN(C(=O)c6ccc(F)cc6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(4-fluorobenzoyl)piperazin-1-yl)-9H-pyrimido[4,5-b]indole-7-sulfonamide | $[M + H]^+$ 654.1/ 654.1 |

TABLE 1-continued

| Ex # | Int A/ Int B | Structure | Name | LCMS Cacl./ Found |
|---|---|---|---|---|
| Preparations of Examples (Ex) | | | | |
| 14 | Int 1/ Int 18 | 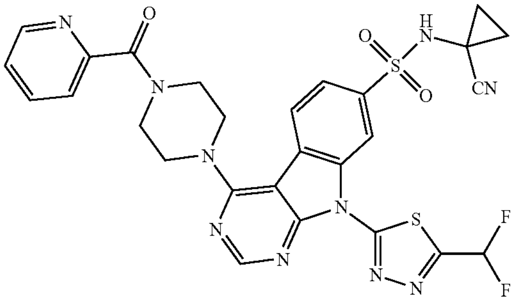 [SMILES: N#CC1(NS(=O)(=O)c2ccc3c4c(N5CCN(C(=O)c6ccccn6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-picolinoylpiperazin-1-yl)-9H-pyrimido[4,5-b]indole-7-sulfonamide | [M − H]⁻ 635.1/ 635.2 |
| 15 | Int 1/ Int 35 | 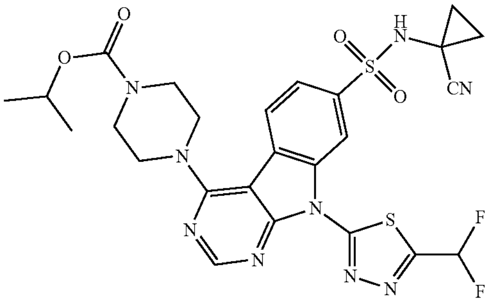 [SMILES: CC(C)OC(=O)N1CCN(c2ncnc3c2c2ccc(S(=O)(=O)NC4(C#N)CC4)cc2n3-c2nnc(C(F)F)s2)CC1] | Isopropyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperazine-1-carboxylate | [M + H]⁺ 616.1/ 616.2 |
| 16 | Int 1/ Int 55 | 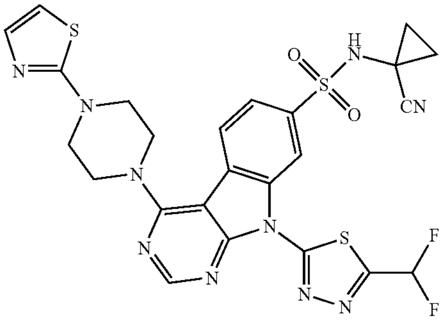 [SMILES: N#CC1(NS(=O)(=O)c2ccc3c4c(N5CCN(c6nccs6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(thiazol-2-yl)piperazin-1-yl)-9H-pyrimido[4,5-b]indole-7-sulfonamide | [M − H]⁻ 613.1/ 613.2 |
| 17 | Int 1/ CAM | 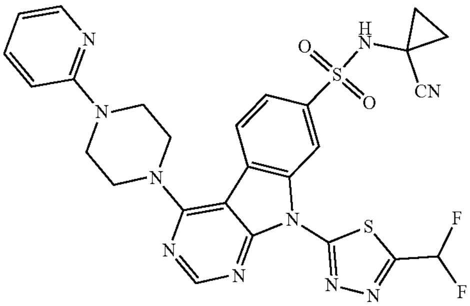 [SMILES: N#CC1(NS(=O)(=O)c2ccc3c4c(N5CCN(c6ccccn6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(pyridin-2-yl)piperazin-1-yl)-9H-pyrimido[4,5-b]indole-7-sulfonamide | [M − H]⁻ 607.1/ 607.2 |

TABLE 1-continued

| Preparations of Examples (Ex) | | | | |
|---|---|---|---|---|
| Ex # | Int A/ Int B | Structure | Name | LCMS Cacl./ Found |
| 18 | Int 1/ Int 53 | 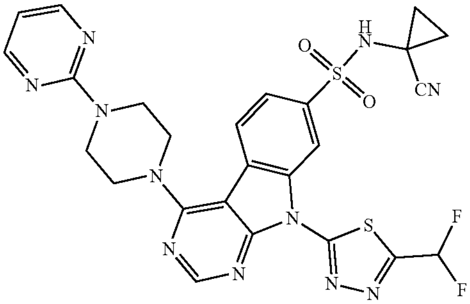 [SMILES: N#CC1(NS(=O)(=O)c2ccc3c4c(N5CCN(c6ncccn6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(pyrimidin-2-yl)piperazin-1-yl)-9H-pyrimido[4,5-b]indole-7-sulfonamide | $[M-H]^-$ 608.1/ 608.0 |
| 19 | Int 1/ Int 54 | 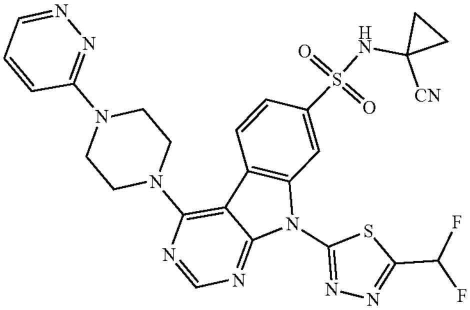 [SMILES: N#CC1(NS(=O)(=O)c2ccc3c4c(N5CCN(c6cccnn6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(pyridazin-3-yl)piperazin-1-yl)-9H-pyrimido[4,5-b]indole-7-sulfonamide | $[M-H]^-$ 608.1/ 608.2 |
| 20 | Int 1/ CAM | 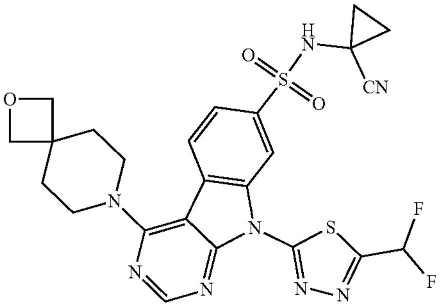 [SMILES: N#CC1(NS(=O)(=O)c2ccc3c4c(N5CCC6(CC5)COC6)ncnc4n(-c4nnc(C(F)F)s4)c3c2)CC1] | N-(1-Cyanocyclopropyl)-9-(5-(difluoromethyl)-1,3,4-thiadiazol-2-yl)-4-(2-oxa-7-azaspiro[3.5]nonan-7-yl)-9H-pyrimido[4,5-b]indole-7-sulfonamide | $[M+H]^+$ 573.1/ 573.1 |
| 21 | Int 1/ CAM | 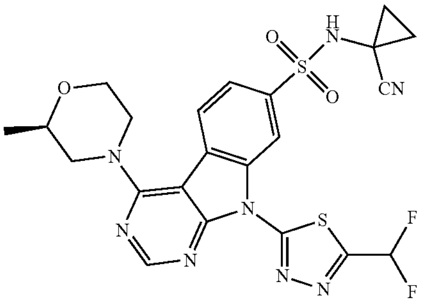 [SMILES: C[C@@H]1CN(c2ncnc3c2c2ccc(S(=O)(=O)NC4(C#N)CC4)cc2n3-c2nnc(C(F)F)s2)CCO1] | (R)-N-(1-cyanocyclopropyl)-9-(5-(difluoromethyl)-1,3,4-thiadiazol-2-yl)-4-(2-methylmorpholino)-9H-pyrimido[4,5-b]indole-7-sulfonamide | $[M+H]^+$ 547.1/ 547.1 |

Example 22: N-(1-Cyanocyclopropyl)-9-(5-(difluoromethyl)-1,3,4-thiadiazol-2-yl)-4-(4-(1-methyl-JH-imidazol-2-yl)piperazin-1-yl)-9H-pyrimido[4,5-b]indole-7-sulfonamide

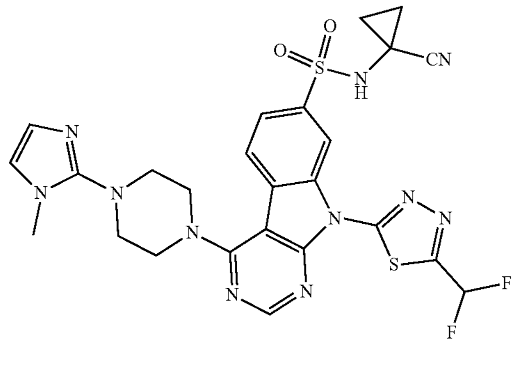 [SMILES: Cn1ccnc1N1CCN(c2ncnc3c2c2ccc(S(=O)(=O)NC4(C#N)CC4)cc2n3-c2nnc(C(F)F)s2)CC1]

Step 1: N-(1-cyanocyclopropyl)-4-(4-(1-methyl-1H-imidazol-2-yl)piperazin-1-yl)-9H-pyrimido[4,5-b]indole-7-sulfonamide

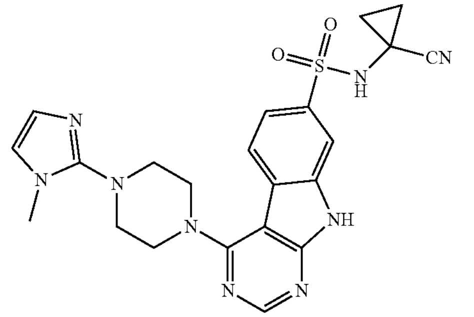 [SMILES: Cn1ccnc1N1CCN(c2ncnc3[nH]c4cc(S(=O)(=O)NC5(C#N)CC5)ccc4c23)CC1]

This compound was prepared using procedures analogous to those described for Example 1 Step 1 using 4-chloro-N-(1-cyanocyclopropyl)-9H-pyrimido[4,5-b]indole-7-sulfonamide (Intermediate 1) and 1-(1-methyl-1H-imidazol-2-yl)piperazine. LCMS calc. for $C_{22}H_{24}N_9O_2S$ $[M+H]^+$: m/z=478.2; Found: 478.1.

Step 2: N-(1-cyanocyclopropyl)-9-(5-(difluoromethyl)-1,3,4-thiadiazol-2-yl)-4-(4-(1-methyl-1H-imidazol-2-yl)piperazin-1-yl)-9H-pyrimido[4,5-b]indole-7-sulfonamide To a mixture of N-(1-cyanocyclopropyl)-4-(4-(1-methyl-1H-imidazol-2-yl)piperazin-1-yl)-9H-pyrimido[4,5-b]indole-7-sulfonamide (75 mg, 0.16 mmol), 2-bromo-5-(difluoromethyl)-1,3,4-thiadiazole (169 mg, 0.78 mmol) in dioxane (10 mL) and DMF (0.5 mL) was added t-BuONa (90.6 mg, 0.94 mmol) under $N_2$, followed by addition of BrettPhos Pd G3 (85.4 mg, 0.094 mmol) under $N_2$. The reaction mixture was degassed and recharged with $N_2$ for three cycles, stirred at 110° C. for 12 h. The reaction mixture was cooled to r.t. and concentrated under reduced pressure. The residue was purified by prep-HPLC on a C18 column eluting with MeOH/water (40%-65%, with 1% HCl) to afford the title compound (14.18 mg, 14.1% yield) as off-white solid. $^1$H NMR: (400 MHz, DMSO-$d_6$) δ 5 9.53 (s, 1H), 9.47 (s, 1H), 8.90 (s, 1H), 8.15 (d, J=8.4 Hz, 1H), 8.05-8.06 (d, J=8.4 Hz, 1H), 7.71 (t, J=53.6 Hz, 1H), 7.37-7.39 (m, 2H), 4.06 (s, 4H), 3.70 (s, 3H), 3.54 (s, 3H), 1.43-1.47 (m, 2H), 1.29-1.32 (in, 2H). LCMS calc. for $C_{25}H_{24}F_2N_{11}O_2S_2$ $[M+H]^+$: m/z=612.1; Found: 612.1.

The compounds listed in Table 2 below were prepared by using an Intermediate 1 (Int A, sulfonamide derivative) and an appropriate Intermediate 10-55 (Int B, amine derivative) as the methods substantially analogous to those described for preparing Example 22.

TABLE 2

Preparations of Examples (Ex)

| Ex # | Int B | Structure | Name | LCMS Cacl./ Found |
|---|---|---|---|---|
| 23 | Int 20 | 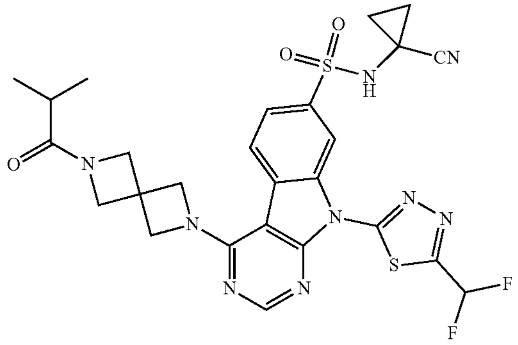 [SMILES: CC(C)C(=O)N1CC2(C1)CN(c1ncnc3c1c1ccc(S(=O)(=O)NC4(C#N)CC4)cc1n3-c1nnc(C(F)F)s1)C2] | N-(1-Cyanocyclopropyl)-9-[5-(difluoromethyl)-1,3,4-thiadiazol-2-yl]-4-[2-(2-methylpropanoyl)-2,6-diazaspiro[3.3]heptan-6-yl]pyrimido[4,5-b]indole-7-sulfonamide | $[M + H]^+$ 614.2/ 614.2 |

TABLE 2-continued

Preparations of Examples (Ex)

| Ex # | Int B | Structure | Name | LCMS Cacl./ Found |
|---|---|---|---|---|
| 24 | Int 21 | 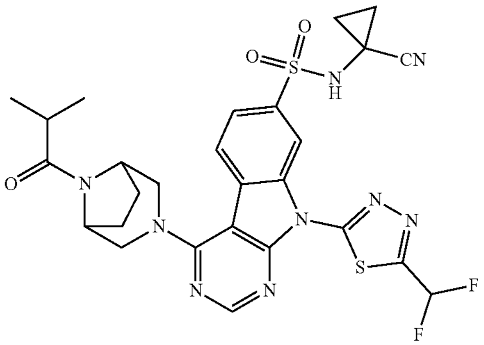 [SMILES: CC(C)C(=O)N1C2CCC1CN(c1ncnc3c1c1ccc(S(=O)(=O)NC4(C#N)CC4)cc1n3-c1nnc(C(F)F)s1)C2] | N-(1-Cyanocyclopropyl)-9-[5-(difluoromethyl)-1,3,4-thiadiazol-2-yl]-4-[8-(2-methylpropanoyl)-3,8-diazabicyclo[3.2.1]octan-3-yl]pyrimido[4,5-b]indole-7-sulfonamide | $[M + H]^+$ 628.2/ 628.2 |
| 25 | Int 22 | 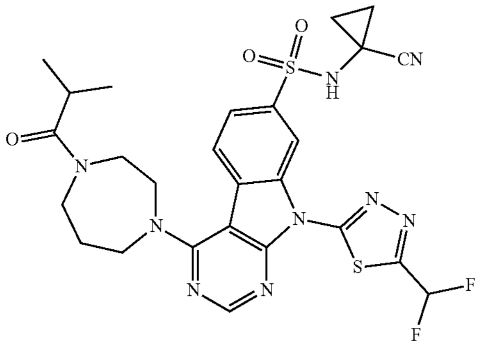 [SMILES: CC(C)C(=O)N1CCCN(c2ncnc3c2c2ccc(S(=O)(=O)NC4(C#N)CC4)cc2n3-c2nnc(C(F)F)s2)CC1] | N-(1-Cyanocyclopropyl)-9-(5-(difluoromethyl)-1,3,4-thiadiazol-2-yl)-4-(4-isobutyryl-1,4-diazepan-1-yl)-9H-pyrimido[4,5-b]indole-7-sulfonamide | $[M + H]^+$ 616.2/ 616.2 |
| 26 | Int 23 | 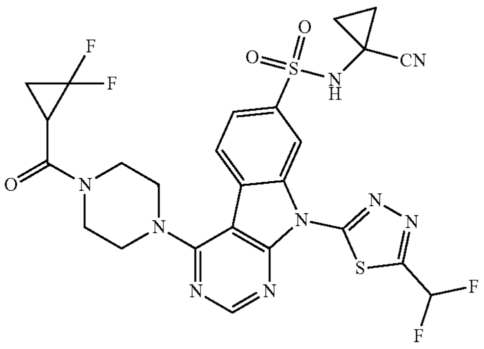 [SMILES: N#CC1(NS(=O)(=O)c2ccc3c4c(N5CCN(C(=O)C6CC6(F)F)CC5)ncnc4n(-c4nnc(C(F)F)s4)c3c2)CC1] | N-(1-Cyanocyclopropyl)-4-(4-(2,2-difluorocyclopropane-1-carbonyl)piperazin-1-yl)-9-(5-(difluoromethyl)-1,3,4-thiadiazol-2-yl)-9H-pyrimido[4,5-b]indole-7-sulfonamide | $[M + H]^+$ 636.1/ 635.9 |
| 27 | Int 24 | 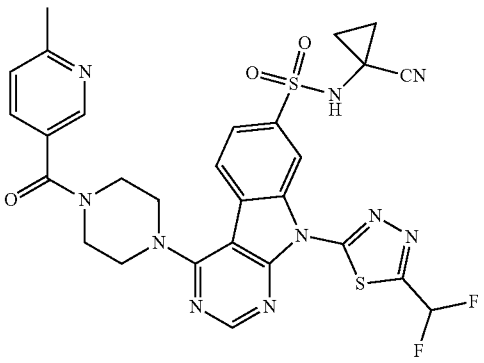 [SMILES: Cc1ccc(C(=O)N2CCN(c3ncnc4c3c3ccc(S(=O)(=O)NC5(C#N)CC5)cc3n4-c3nnc(C(F)F)s3)CC2)cn1] | N-(1-Cyanocyclopropyl)-9-(5-(difluoromethyl)-1,3,4-thiadiazol-2-yl)-4-(4-(6-methylnicotinoyl)piperazin-1-yl)-9H-pyrimido[4,5-b]indole-7-sulfonamide | $[M + H]^+$ 651.1/ 651.2 |

TABLE 2-continued

| Preparations of Examples (Ex) | | | | |
|---|---|---|---|---|
| Ex # | Int B | Structure | Name | LCMS Cacl./ Found |
| 28 | Int 36 | 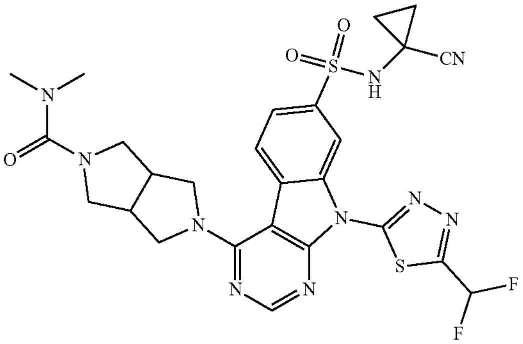 [SMILES: CN(C)C(=O)N1CC2CN(c3ncnc4c3c3ccc(S(=O)(=O)NC5(C#N)CC5)cc3n4-c3nnc(C(F)F)s3)CC2C1] | 5-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N-dimethylhexahydropyrrolo[3,4-c]pyrrole-2(1H)-carboxamide | [M + H]+ 629.2/ 629.2 |
| 29 | Int 37 | 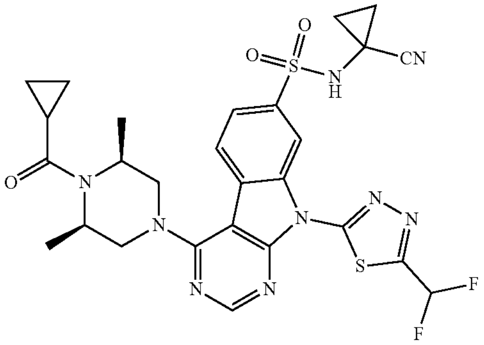 [SMILES: C[C@@H]1CN(c2ncnc3c2c2ccc(S(=O)(=O)NC4(C#N)CC4)cc2n3-c2nnc(C(F)F)s2)C[C@H](C)N1C(=O)C1CC1] | N-(1-Cyanocyclopropyl)-4-((3S,5R)-4-(cyclopropanecarbonyl)-3,5-dimethylpiperazin-1-yl)-9-(5-(difluoromethyl)-1,3,4-thiadiazol-2-yl)-9H-pyrimido[4,5-b]indole-7-sulfonamide | [M + H]+ 628.2/ 628.2 |
| 30 | Int 12 | 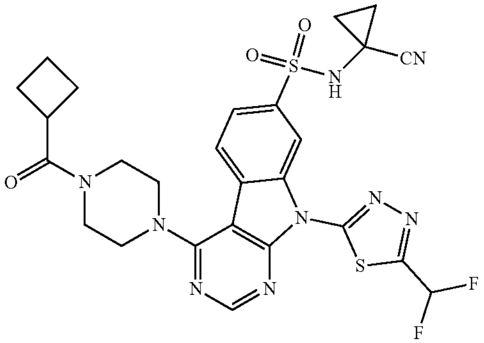 | N-(1-Cyanocyclopropyl)-4-(4-(cyclobutanecarbonyl)piperazin-1-yl)-9-(5-(difluoromethyl)-1,3,4-thiadiazol-2-yl)-9H-pyrimido[4,5-b]indole-7-sulfonamide | [M + H]+ 614.2/ 614.2 |
| 31 | Int 38 | 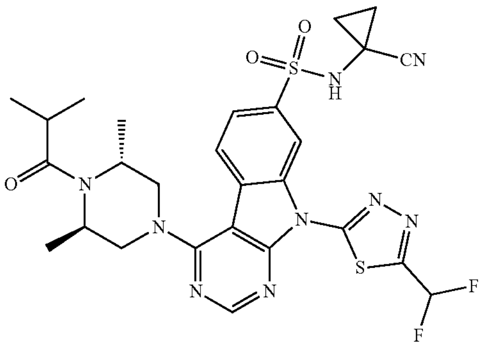 [SMILES: CC(C)C(=O)N1[C@H](C)CN(c2ncnc3c2c2ccc(S(=O)(=O)NC4(C#N)CC4)cc2n3-c2nnc(C(F)F)s2)C[C@H]1C] | N-(1-Cyanocyclopropyl)-9-(5-(difluoromethyl)-1,3,4-thiadiazol-2-yl)-4-((3R,5R)-4-isobutyryl-3,5-dimethylpiperazin-1-yl)-9H-pyrimido[4,5-b]indole-7-sulfonamide | [M + H]+ 630.2/ 630.2 |

TABLE 2-continued

| Preparations of Examples (Ex) | | | | |
|---|---|---|---|---|
| Ex # | Int B | Structure | Name | LCMS Cacl./ Found |
| 32 | Int 25 | 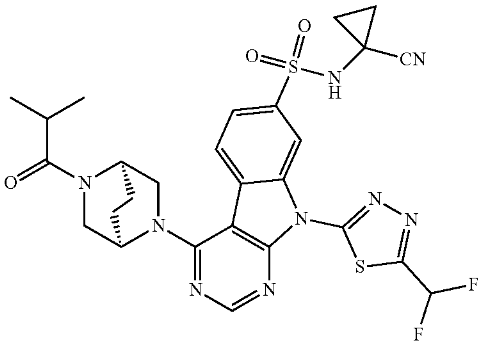 | N-(1-Cyanocyclopropyl)-9-(5-(difluoromethyl)-1,3,4-thiadiazol-2-yl)-4-((1R,4R)-5-isobutyryl-2,5-diazabicyclo[2.2.2]octan-2-yl)-9H-pyrimido[4,5-b]indole-7-sulfonamide | $[M + H]^+$ 628.2/ 628.2 |
| 33 | Int 39 | 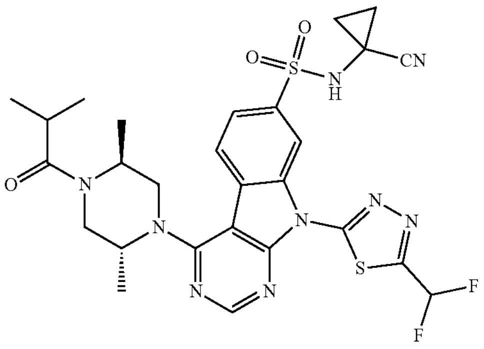 [SMILES: CC(C)C(=O)N1C[C@@H](C)N(c2ncnc3c2c2ccc(S(=O)(=O)NC4(C#N)CC4)cc2n3-c2nnc(C(F)F)s2)C[C@@H]1C] | N-(1-Cyanocyclopropyl)-9-(5-(difluoromethyl)-1,3,4-thiadiazol-2-yl)-4-((2R,5S)-4-isobutyryl-2,5-dimethylpiperazin-1-yl)-9H-pyrimido[4,5-b]indole-7-sulfonamide | $[M + H]^+$ 630.2/ 630.2 |
| 34 | Int 26 | 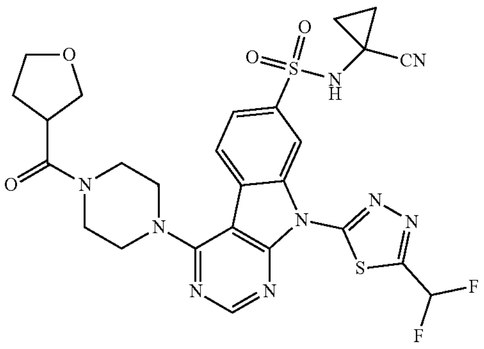 [SMILES: N#CC1(NS(=O)(=O)c2ccc3c4c(N5CCN(C(=O)C6CCOC6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(tetrahydrofuran-3-carbonyl)piperazin-1-yl)-9H-pyrimido[4,5-b]indole-7-sulfonamide | $[M + H]^+$ 630.1/ 630.2 |
| 35 | Int 27 | 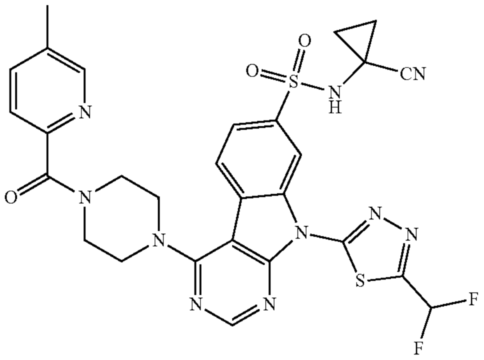 [SMILES: Cc1ccc(C(=O)N2CCN(c3ncnc4c3c3ccc(S(=O)(=O)NC5(C#N)CC5)cc3n4-c3nnc(C(F)F)s3)CC2)nc1] | N-(1-Cyanocyclopropyl)-9-(5-(difluoromethyl)-1,3,4-thiadiazol-2-yl)-4-(4-(5-methylpicolinoyl)piperazin-1-yl)-9H-pyrimido[4,5-b]indole-7-sulfonamide | $[M + H]^+$ 651.1/ 651.2 |

TABLE 2-continued

| Preparations of Examples (Ex) | | | | |
|---|---|---|---|---|
| Ex # | Int B | Structure | Name | LCMS Cacl./ Found |
| 36 | Int 30 | 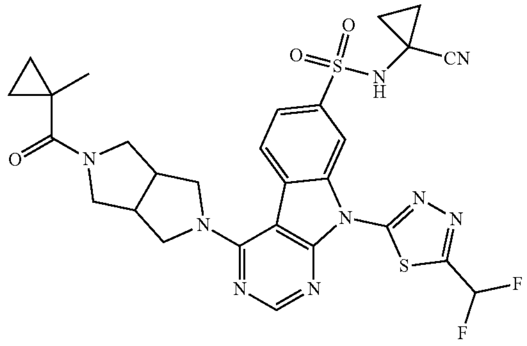 [SMILES: CC1(C(=O)N2CC3CN(c4ncnc5c4c4ccc(S(=O)(=O)NC6(C#N)CC6)cc4n5-c4nnc(C(F)F)s4)CC3C2)CC1] | N-(1-Cyanocyclopropyl)-9-(5-(difluoromethyl)-1,3,4-thiadiazol-2-yl)-4-(5-(1-methylcyclopropane-1-carbonyl)hexahydropyrrolo[3,4-c]pyrrol-2(1H)-yl)-9H-pyrimido[4,5-b]indole-7-sulfonamide | $[M + H]^+$ 640.2/ 640.1 |
| 37 | Int 47 | 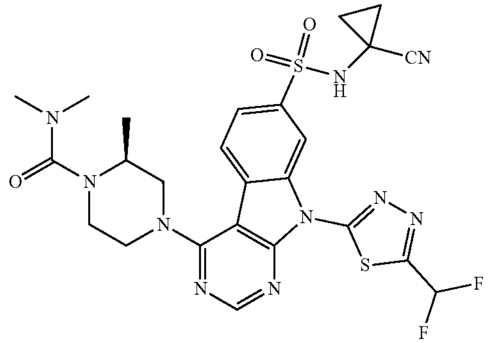 [SMILES: C[C@H]1CN(c2ncnc3c2c2ccc(S(=O)(=O)NC4(C#N)CC4)cc2n3-c2nnc(C(F)F)s2)CCN1C(=O)N(C)C] | (S)-4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N,2-trimethylpiperazine-1-carboxamide | $[M + H]^+$ 617.2/ 617.2 |
| 38 | Int 41 | 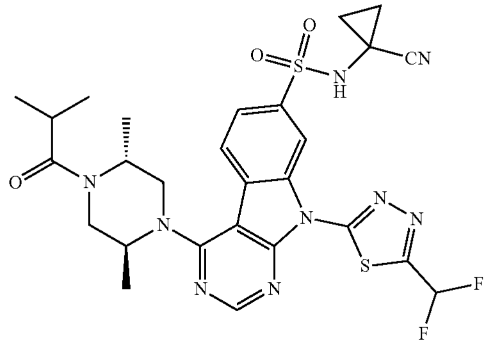 [SMILES: CC(C)C(=O)N1C[C@H](C)N(c2ncnc3c2c2ccc(S(=O)(=O)NC4(C#N)CC4)cc2n3-c2nnc(C(F)F)s2)C[C@H]1C] | N-(1-Cyanocyclopropyl)-9-(5-(difluoromethyl)-1,3,4-thiadiazol-2-yl)-4-((2S,5R)-4-isobutyryl-2,5-dimethylpiperazin-1-yl)-9H-pyrimido[4,5-b]indole-7-sulfonamide | $[M + H]^+$ 630.2/ 630.2 |
| 39 | Int 29 | 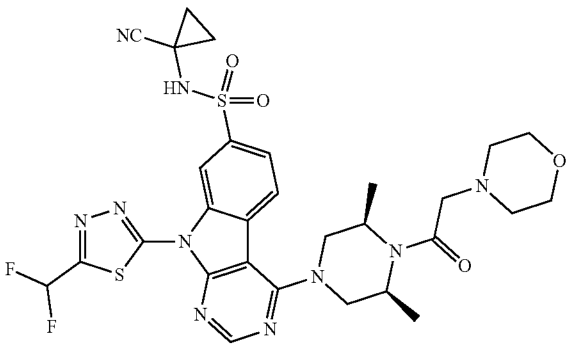 [SMILES: C[C@@H]1CN(c2ncnc3c2c2ccc(S(=O)(=O)NC4(C#N)CC4)cc2n3-c2nnc(C(F)F)s2)C[C@H](C)N1C(=O)CN1CCOCC1] | N-(1-Cyanocyclopropyl)-9-(5-(difluoromethyl)-1,3,4-thiadiazol-2-yl)-4-((3R,5S)-3,5-dimethyl-4-(2-morpholinoacetyl)piperazin-1-yl)-9H-pyrimido[4,5-b]indole-7-sulfonamide | $[M + H]^+$ 687.2/ 687.3 |

TABLE 2-continued

| Preparations of Examples (Ex) | | | | |
|---|---|---|---|---|
| Ex # | Int B | Structure | Name | LCMS Cacl./ Found |
| 40 | Int 48 | 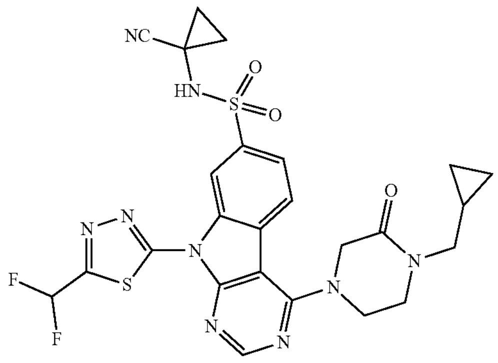 [SMILES: N#CC1(NS(=O)(=O)c2ccc3c4c(N5CCN(CC6CC6)C(=O)C5)ncnc4n(-c4nnc(C(F)F)s4)c3c2)CC1] | N-(1-Cyanocyclopropyl)-4-(4-(cyclopropylmethyl)-3-oxopiperazin-1-yl)-9-(5-(difluoromethyl)-1,3,4-thiadiazol-2-yl)-9H-pyrimido[4,5-b]indole-7-sulfonamide | $[M + H]^+$ 600.1/ 600.2 |
| 41 | Int 49 | 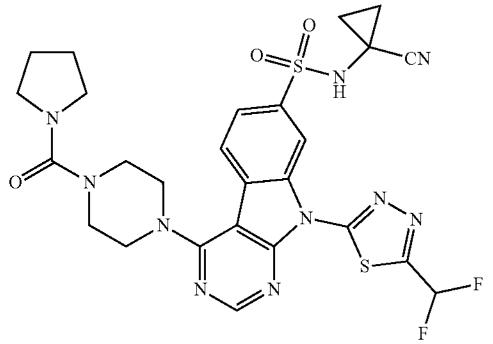 | N-(1-Cyanocyclopropyl)-9-(5-(difluoromethyl)-1,3,4-thiadiazol-2-yl)-4-(4-(pyrrolidine-1-carbonyl)piperazin-1-yl)-9H-pyrimido[4,5-b]indole-7-sulfonamide | $[M - H]^-$ 627.2/ 627.3 |
| 42 | Int 51 | 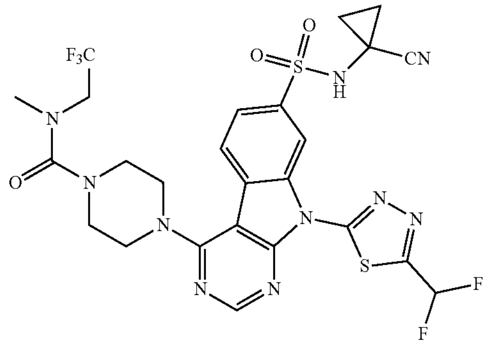 [SMILES: CN(CC(F)(F)F)C(=O)N1CCN(c2ncnc3c2c2ccc(S(=O)(=O)NC4(C#N)CC4)cc2n3-c2nnc(C(F)F)s2)CC1] | 4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N-methyl-N-(2,2,2-trifluoroethyl)piperazine-1-carboxamide | $[M + H]^+$ 671.1/ 671.1 |

Example 43: 4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N-dimethylbenzamide

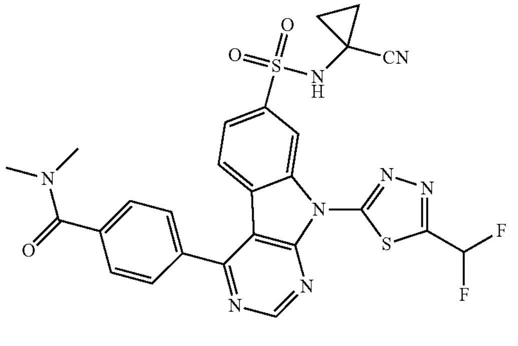 [SMILES: CN(C)C(=O)c1ccc(-c2ncnc3c2c2ccc(S(=O)(=O)NC4(C#N)CC4)cc2n3-c2nnc(C(F)F)s2)cc1]

Step 1: 4-(7-(N-(1-cyanocyclopropyl)sulfamoyl)-9H-pyrimido[4,5-b]indol-4-yl)-N,N-dimethylbenzamide

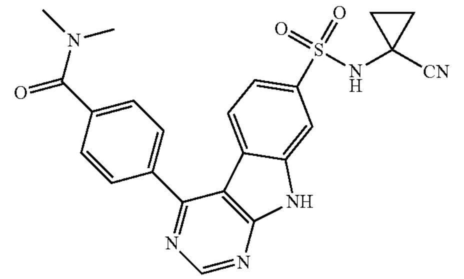 [SMILES: CN(C)C(=O)c1ccc(-c2ncnc3[nH]c4cc(S(=O)(=O)NC5(C#N)CC5)ccc4c23)cc1]

A mixture of 4-chloro-N-(1-cyanocyclopropyl)-9H-pyrimido[4,5-b]indole-7-sulfonamide (300 mg, 0.86 mmol), [4-(dimethylcarbamoyl)phenyl]boronic acid (183 mg, 0.95 mmol), $K_3PO_4$ (549 mg, 2.59 mmol), Pd(dppf)$Cl_2$·$CH_2Cl_2$ (70.4 mg, 0.086 mmol) in dioxane (3 mL) and $H_2O$ (0.5 mL) was degassed and recharged with $N_2$ for three cycles, stirred at 100° C. for 12 h under $N_2$ atmosphere. The reaction mixture was concentrated under reduced pressure. The residue was purified by flash chromatography on a silica gel column eluting with EtOAc/PE (1-10%) to afford the title compound (300 mg, 75.5% yield) as a yellow solid. LCMS calc. for $C_{23}H_{21}N_6O_3S$ $[M+H]^+$: m/z=461.1; found: 461.0.

Step 2: 4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N-dimethylbenzamide To a mixture of 4-(7-(N-(1-cyanocyclopropyl)sulfamoyl)-9H-pyrimido[4,5-b]indol-4-yl)-N,N-dimethylbenzamide (85 mg, 0.18 mmol), 2-bromo-5-(difluoromethyl)-1,3,4-thiadiazole (198 mg, 0.92 mmol) in dioxane (10 mL) and DMF (0.5 mL) was added tBuXPhos Pd G3 (14.6 mg, 0.018 mmol) and t-BuONa (106 mg, 1.11 mmol) under $N_2$. The reaction mixture was degassed and recharged with $N_2$ for three cycles, and stirred at 130° C. overnight. After cooled to r.t., the reaction mixture was concentrated under reduced pressure. The residue was purified by prep-HPLC on a C18 column eluting with MeCN/water (35%-65%, with 0.5% TFA) to afford the title compound (11.7 mg, 10.6% yield) as off-white solid. $^1$H NMR: (400 MHz, DMSO-$d_6$) δ 9.57 (d, J=1.6 Hz, 1H), 9.49 (s, 1H), 9.45 (s, 1H), 8.18 (d, J=8.4 Hz, 1H), 8.04 (d, J=8.0 Hz, 2H), 7.98-8.00 (m, 1H), 7.60-7.76 (m, 3H), 3.05 (d, J=10.8 Hz, 6H), 1.42-1.45 (m, 2H), 1.24-1.27 (m, 2H). LCMS calc. for $C_{26}H_{21}F_2N_8O_3S_2$ $[M+H]^+$: m/z=595.1; Found: 595.1.

Example 44: N-(1-Cyanocyclopropyl)-9-(5-(difluoromethyl)-1,3,4-thiadiazol-2-yl)-4-(4-methoxypiperidin-1-yl)-9H-pyrimido[4,5-b]indole-7-sulfonamide

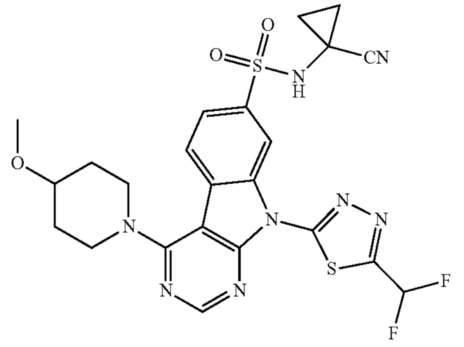 [SMILES: COC1CCN(c2ncnc3c2c2ccc(S(=O)(=O)NC4(C#N)CC4)cc2n3-c2nnc(C(F)F)s2)CC1]

Step 1: N-(1-cyanocyclopropyl)-4-(4-methoxypiperidin-1-yl)-9H-pyrimido[4,5-b]indole-7-sulfonamide

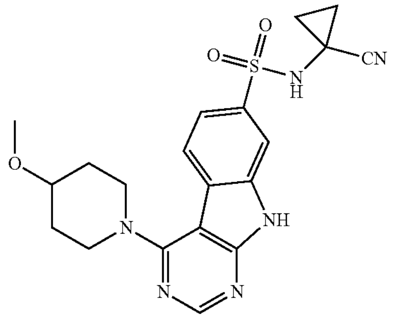 [SMILES: COC1CCN(c2ncnc3[nH]c4cc(S(=O)(=O)NC5(C#N)CC5)ccc4c23)CC1]

This compound was prepared using procedures analogous to those described for Example 1 Step 1 using 4-chloro-N-(1-cyanocyclopropyl)-9H-pyrimido[4,5-b]indole-7-sulfonamide (Intermediate 1) and 4-methoxypiperidine. $^1$H NMR: (400 MHz, DMSO-$d_6$) δ 8.51 (s, 1H), 7.89-7.96 (m, 2H), 7.72-7.75 (m, 1H), 5.76 (s, 1H), 3.98-4.03 (m, 2H), 3.43-3.60 (m, 2H), 2.03-2.06 (m, 2H), 1.63-1.67 (m, 2H), 1.35 (s, 2H), 1.18-1.26 (m, 2H).

Step 2: N-(1-cyanocyclopropyl)-9-(5-(difluoromethyl)-1,3,4-thiadiazol-2-yl)-4-(4-methoxypiperidin-1-yl)-9H-pyrimido[4,5-b]indole-7-sulfonamide To a mixture of N-(1-cyanocyclopropyl)-4-(4-methoxypiperidin-1-yl)-9H-pyrimido[4,5-b]indole-7-sulfonamide (50.0 mg, 0.12 mmol), 2-bromo-5-(difluoromethyl)-1,3,4-thiadiazole (30.2 mg, 0.14 mmol) in dioxane (2 mL) was added $Cs_2CO_3$ (76.4 mg, 0.234 mmol), XPhos Pd G3 (4.96 mg, 0.006 mmol) under $N_2$. The reaction mixture was degassed and recharged with $N_2$ for three cycles, stirred at 100° C. for 12 h. After cooled to r.t., the mixture was concentrated under reduced pressure. The residue was purified by prep-HPLC on a C18 column eluting with MeCN/water (45%-75%, with 0.5% TFA) to afford the title compound (2.41 mg, 3.67% yield) as light-yellow solid. $^1$H NMR: (400 MHz, DMSO-$d_6$) δ 9.49 (s, 1H), 9.39 (s, 1H), 8.79 (s, 1H), 8.03-8.10 (m, 2H), 7.68 (t, J=53.2 Hz, 1H), 4.04-4.08 (m, 2H), 3.56-3.65 (m, 3H), 2.03-2.06 (m, 2H), 1.65-1.70 (m, 2H), 1.41-1.45 (m, 2H), 1.26-1.29 (m, 2H). LCMS calc. for $C_{23}H_{23}F_2N_8O_3S_2$ [M+H]$^+$: m/z=561.1; Found: 561.1.

The compounds listed in Table 3 below were prepared by using an Intermediate 1-3 (Int A, sulfonamide derivative) and an appropriate Intermediate 10-55 (Int B, amine derivative) or commercially available material (CAM, amine derivative) as the methods substantially analogous to those described for preparing Example 44.

TABLE 3

Preparations of Examples (Ex)

| Ex # | Int A/ Int B | Structure | Name | LCMS Cacl./ Found |
|---|---|---|---|---|
| 45 | Int 3/ Int 42 | 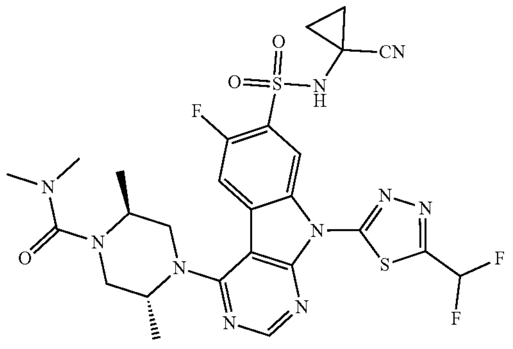 [SMILES: C[C@@H]1CN(C(=O)N(C)C)[C@@H](C)CN1c1ncnc2c1c1cc(F)c(S(=O)(=O)NC3(C#N)CC3)cc1n2-c1nnc(C(F)F)s1] | (2S,5R)-4-(7-(N-(1-Cyanocyclopropyl)sulfamoyl)-9-(5-(difluoromethyl)-1,3,4-thiadiazol-2-yl)-6-fluoro-9H-pyrimido[4,5-b]indol-4-yl)-N,N,2,5-tetramethylpiperazine-1-carboxamide | [M + H]$^+$ 649.2/ 649.1 |
| 46 | Int 3/ Int 47 | 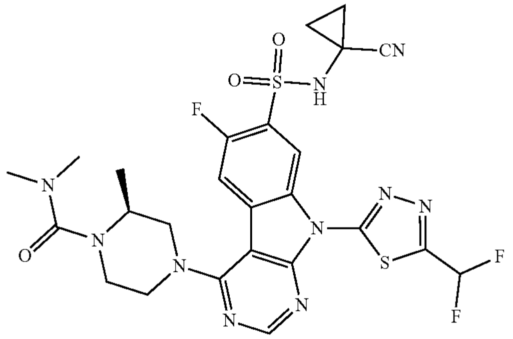 [SMILES: C[C@H]1CN(c2ncnc3c2c2cc(F)c(S(=O)(=O)NC4(C#N)CC4)cc2n3-c2nnc(C(F)F)s2)CCN1C(=O)N(C)C] | (S)-4-(7-(N-(1-Cyanocyclopropyl)sulfamoyl)-9-(5-(difluoromethyl)-1,3,4-thiadiazol-2-yl)-6-fluoro-9H-pyrimido[4,5-b]indol-4-yl)-N,N,2-trimethylpiperazine-1-carboxamide | [M + H]$^+$ 635.2/ 635.2 |
| 47 | Int 1/ Int 52 | 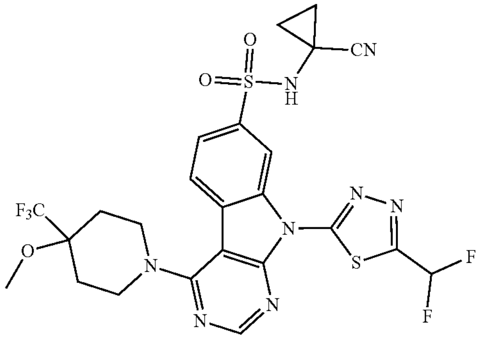 [SMILES: COC1(C(F)(F)F)CCN(c2ncnc3c2c2ccc(S(=O)(=O)NC4(C#N)CC4)cc2n3-c2nnc(C(F)F)s2)CC1] | N-(1-Cyanocyclopropyl)-9-(5-(difluoromethyl)-1,3,4-thiadiazol-2-yl)-4-(4-methoxy-4-(trifluoromethyl)piperidin-1-yl)-9H-pyrimido[4,5-b]indole-7-sulfonamide | [M + H]$^+$ 629.1/ 629.0 |

TABLE 3-continued

Preparations of Examples (Ex)

| Ex # | Int A/ Int B | Structure | Name | LCMS Cacl./ Found |
|---|---|---|---|---|
| 48 | Int 1/ CAM | 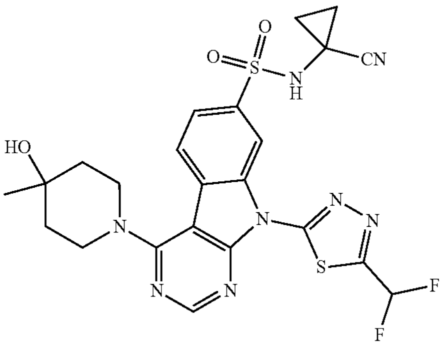 [SMILES: CC1(O)CCN(c2ncnc3c2c2ccc(S(=O)(=O)NC4(C#N)CC4)cc2n3-c2nnc(C(F)F)s2)CC1] | N-(1-Cyanocyclopropyl)-9-(5-(difluoromethyl)-1,3,4-thiadiazol-2-yl)-4-(4-hydroxy-4-methylpiperidin-1-yl)-9H-pyrimido[4,5-b]indole-7-sulfonamide | $[M + H]^+$ 561.1/ 561.1 |
| 49 | Int 1/ CAM | 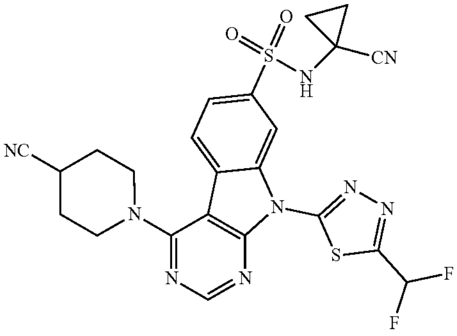 [SMILES: N#CC1CCN(c2ncnc3c2c2ccc(S(=O)(=O)NC4(C#N)CC4)cc2n3-c2nnc(C(F)F)s2)CC1] | N-(1-Cyanocyclopropyl)-4-(4-cyanopiperidin-1-yl)-9-(5-(difluoromethyl)-1,3,4-thiadiazol-2-yl)-9H-pyrimido[4,5-b]indole-7-sulfonamide | $[M + H]^+$ 556.1/ 556.1 |
| 50 | Int 1/ CAM | 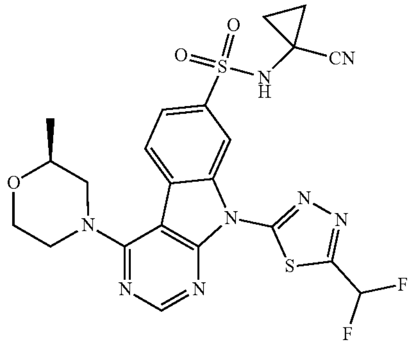 [SMILES: C[C@H]1CN(c2ncnc3c2c2ccc(S(=O)(=O)NC4(C#N)CC4)cc2n3-c2nnc(C(F)F)s2)CCO1] | (S)-N-(1-Cyanocyclopropyl)-9-(5-(difluoromethyl)-1,3,4-thiadiazol-2-yl)-4-(2-methylmorpholino)-9H-pyrimido[4,5-b]indole-7-sulfonamide | $[M + H]^+$ 547.1/ 547.1 |
| 51 | Int 1/ CAM | 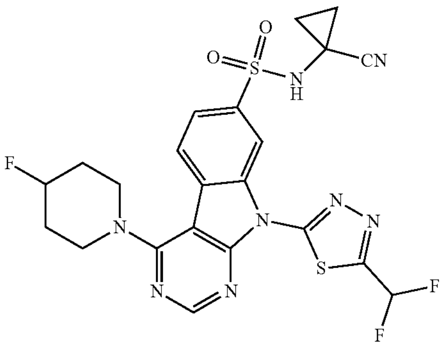 [SMILES: N#CC1(NS(=O)(=O)c2ccc3c4c(N5CCC(F)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-fluoropiperidin-1-yl)-9H-pyrimido[4,5-b]indole-7-sulfonamide | $[M + H]^+$ 549.1/ 549.2 |

TABLE 3-continued

Preparations of Examples (Ex)

| Ex # | Int A/ Int B | Structure | Name | LCMS Cacl./ Found |
|---|---|---|---|---|
| 52 | Int 1/ CAM | 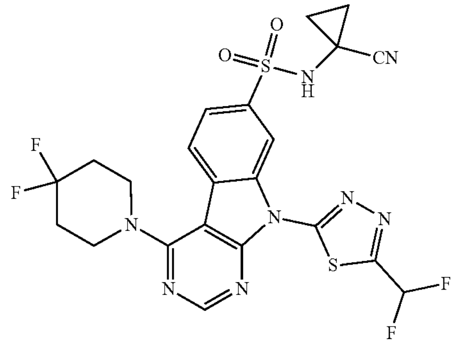 [SMILES: N#CC1(NS(=O)(=O)c2ccc3c4c(N5CCC(F)(F)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4,4-difluoropiperidin-1-yl)-9H-pyrimido[4,5-b]indole-7-sulfonamide | $[M + H]^+$ 567.1/ 567.1 |
| 53 | Int 1/ CAM | 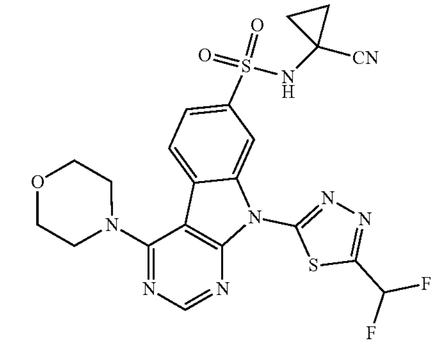 [SMILES: N#CC1(NS(=O)(=O)c2ccc3c4c(N5CCOCC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(piperazin-1-yl)-9H-pyrimido[4,5-b]indole-7-sulfonamide | $[M + H]^+$ 533.1/ 533.0 |
| 54 | Int 1/ CAM | 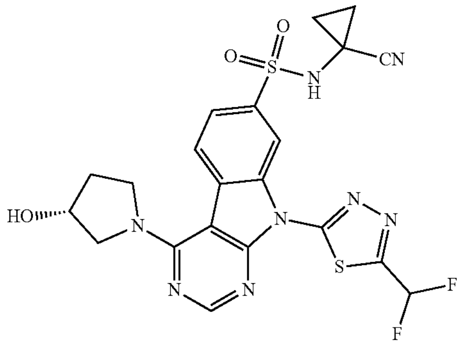 | (R)-N-(1-Cyanocyclopropyl)-9-(5-(difluoromethyl)-1,3,4-thiadiazol-2-yl)-4-(3-hydroxypyrrolidin-1-yl)-9H-pyrimido[4,5-b]indole-7-sulfonamide | $[M + H]^+$ 533.1/ 533.1 |
| 55 | Int 3/ CAM | 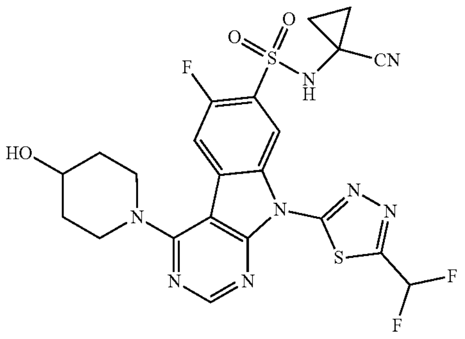 [SMILES: N#CC1(NS(=O)(=O)c2cc3c(cc2F)c2c(N4CCC(O)CC4)ncnc2n3-c2nnc(C(F)F)s2)CC1] | N-(1-Cyanocyclopropyl)-9-(5-(difluoromethyl)-1,3,4-thiadiazol-2-yl)-6-fluoro-4-(4-hydroxypiperidin-1-yl)-9H-pyrimido[4,5-b]indole-7-sulfonamide | $[M + H]^+$ 565.1/ 565.0 |

TABLE 3-continued

| Ex # | Int A/ Int B | Structure | Name | LCMS Cacl./ Found |
|---|---|---|---|---|
| Preparations of Examples (Ex) | | | | |
| 56 | Int 1/ CAM | 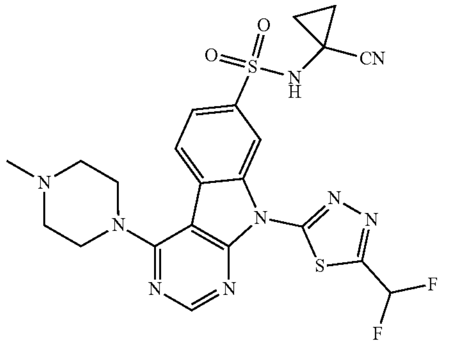 [SMILES: CN1CCN(c2ncnc3c2c2ccc(S(=O)(=O)NC4(C#N)CC4)cc2n3-c2nnc(C(F)F)s2)CC1] | N-(1-Cyanocyclopropyl)-9-(5-(difluoromethyl)-1,3,4-thiadiazol-2-yl)-4-(4-methylpiperazin-1-yl)-9H-pyrimido[4,5-b]indole-7-sulfonamide | $[M + H]^+$ 546.1/ 546.1 |
| 57 | Int 1/ Int 40 | 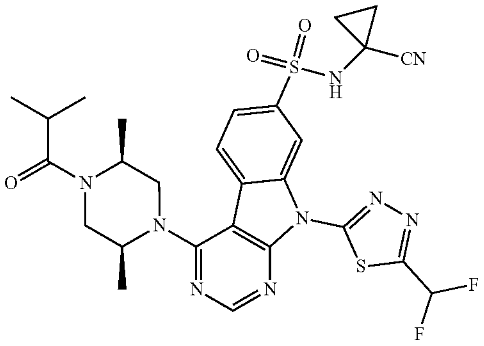 [SMILES: CC(C)C(=O)N1C[C@H](C)N(c2ncnc3c2c2ccc(S(=O)(=O)NC4(C#N)CC4)cc2n3-c2nnc(C(F)F)s2)C[C@@H]1C] | N-(1-cyanocyclopropyl)-9-(5-(difluoromethyl)-1,3,4-thiadiazol-2-yl)-4-((2S,5S)-4-isobutyryl-2,5-dimethylpiperazin-1-yl)-9H-pyrimido[4,5-b]indole-7-sulfonamide | $[M + H]^+$ 630.2/ 630.3 |
| 58 | Int 1/ Int 28 | 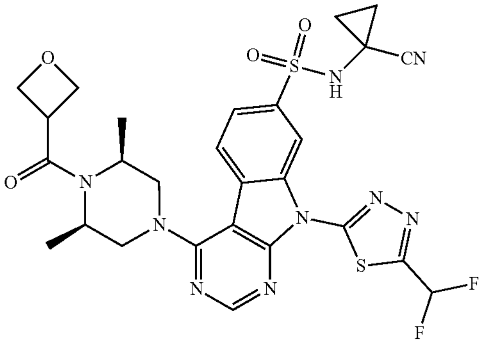 [SMILES: C[C@@H]1CN(c2ncnc3c2c2ccc(S(=O)(=O)NC4(C#N)CC4)cc2n3-c2nnc(C(F)F)s2)C[C@H](C)N1C(=O)C1COC1] | N-(1-Cyanocyclopropyl)-9-(5-(difluoromethyl)-1,3,4-thiadiazol-2-yl)-4-((3S,5R)-3,5-dimethyl-4-(oxetane-3-carbonyl)piperazin-1-yl)-9H-pyrimido[4,5-b]indole-7-sulfonamide | $[M + H]^+$ 644.2/ 644.1 |
| 59 | Int 1/ Int 42 | 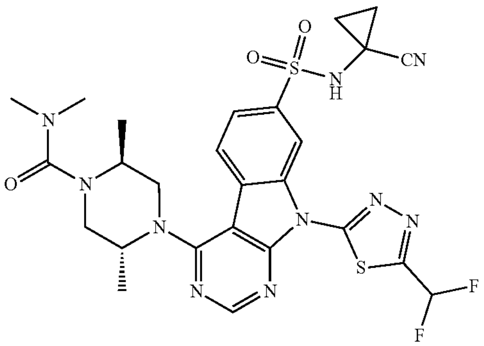 | (2S,5R)-4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N,2,5-tetramethylpiperazine-1-carboxamide | $[M + H]^+$ 631.2/ 631.2 |

TABLE 3-continued

| Preparations of Examples (Ex) | | | | |
|---|---|---|---|---|
| Ex # | Int A/ Int B | Structure | Name | LCMS Cacl./ Found |
| 60 | Int 1/ Int 43 | 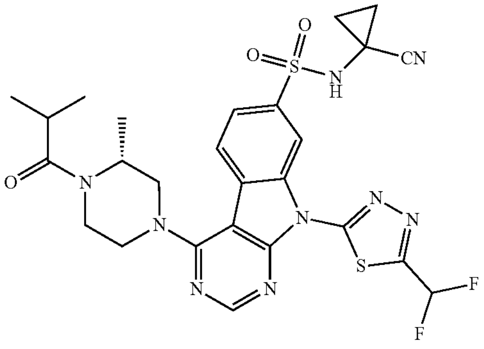 [SMILES: CC(C)C(=O)N1CCN(c2ncnc3c2c2ccc(S(=O)(=O)NC4(C#N)CC4)cc2n3-c2nnc(C(F)F)s2)C[C@H]1C] | (R)-N-(1-cyanocyclopropyl)-9-(5-(difluoromethyl)-1,3,4-thiadiazol-2-yl)-4-(4-isobutyryl-3-methylpiperazin-1-yl)-9H-pyrimido[4,5-b]indole-7-sulfonamide | $[M + H]^+$ 616.2/ 616.2 |
| 61 | Int 1/ Int 44 | 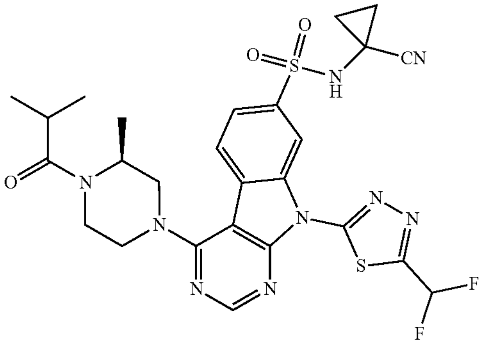 | (S)-N-(1-cyanocyclopropyl)-9-(5-(difluoromethyl)-1,3,4-thiadiazol-2-yl)-4-(4-isobutyryl-3-methylpiperazin-1-yl)-9H-pyrimido[4,5-b]indole-7-sulfonamide | $[M + H]^+$ 616.2/ 616.3 |
| 62 | Int 1/ Int 45 | 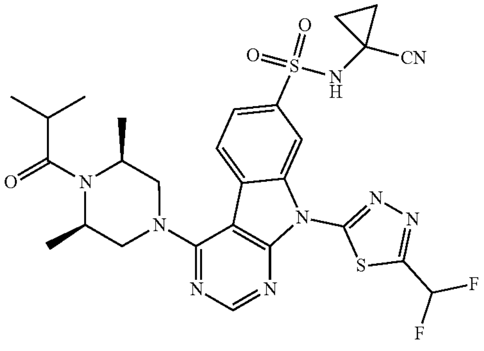 [SMILES: CC(C)C(=O)N1[C@H](C)CN(c2ncnc3c2c2ccc(S(=O)(=O)NC4(C#N)CC4)cc2n3-c2nnc(C(F)F)s2)C[C@@H]1C] | N-(1-Cyanocyclopropyl)-9-(5-(difluoromethyl)-1,3,4-thiadiazol-2-yl)-4-((3S,5R)-4-isobutyryl-3,5-dimethylpiperazin-1-yl)-9H-pyrimido[4,5-b]indole-7-sulfonamide | $[M + H]^+$ 630.2/ 630.2 |

TABLE 3-continued

| Ex # | Int A/ Int B | Structure | Name | LCMS Cacl./ Found |
|---|---|---|---|---|
| Preparations of Examples (Ex) | | | | |
| 63 | Int 1/ Int 50 | 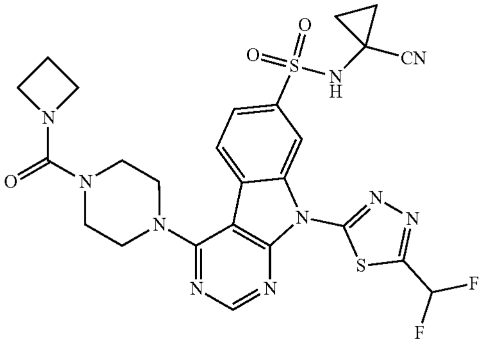 | 4-(4-(Azetidine-1-carbonyl)piperazin-1-yl)-N-(1-cyanocyclopropyl)-9-(5-(difluoromethyl)-1,3,4-thiadiazol-2-yl)-9H-pyrimido[4,5-b]indole-7-sulfonamide | $[M + H]^+$ 615.1/ 615.2 |
| 64 | Int 2/ Int 39 | 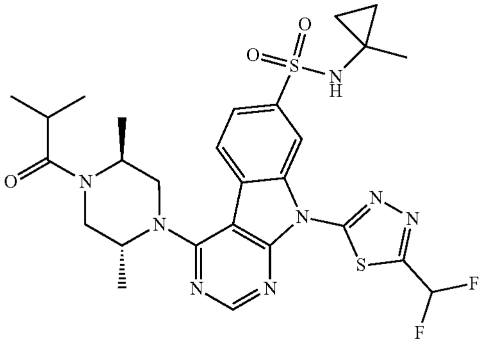 [SMILES: CC(C)C(=O)N1C[C@@H](C)N(c2ncnc3c2c2ccc(S(=O)(=O)NC4(C)CC4)cc2n3-c2nnc(C(F)F)s2)C[C@@H]1C] | 9-(5-(Difluoromethyl)-1,3,4-thiadiazol-2-yl)-4-((2R,5S)-4-isobutyryl-2,5-dimethylpiperazin-1-yl)-N-(1-methylcyclopropyl)-9H-pyrimido[4,5-b]indole-7-sulfonamide | $[M + H]^+$ 619.2/ 619.2 |

Example 65: N-(1-Cyanocyclopropyl)-9-(5-(difluoromethyl)-1,3,4-thiadiazol-2-yl)-4-(4-(1-methylazetidine-3-carbonyl)piperazin-1-yl)-9H-pyrimido[4,5-b]indole-7-sulfonamide

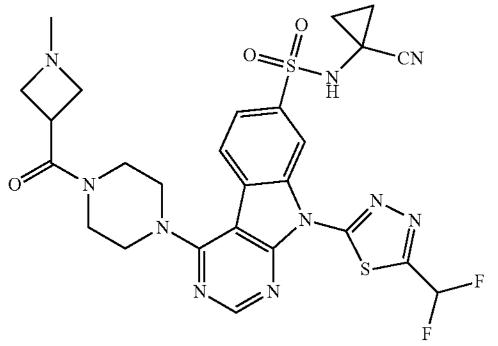 [SMILES: CN1CC(C(=O)N2CCN(c3ncnc4c3c3ccc(S(=O)(=O)NC5(C#N)CC5)cc3n4-c3nnc(C(F)F)s3)CC2)C1]

Step 1: tert-butyl 4-(7-(N-(1-cyanocyclopropyl)sulfamoyl)-9H-pyrimido[4,5-b]indol-4-yl)piperazine-1-carboxylate

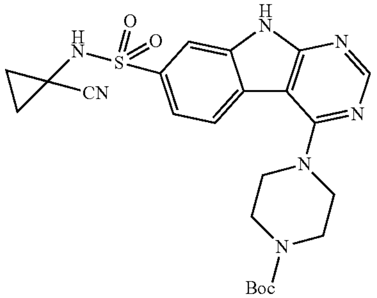 [SMILES: CC(C)(C)OC(=O)N1CCN(c2ncnc3[nH]c4cc(S(=O)(=O)NC5(C#N)CC5)ccc4c23)CC1]

To a solution of 4-chloro-N-(1-cyanocyclopropyl)-9H-pyrimido[4,5-b]indole-7-sulfonamide (0.30 g, 0.86 mmol, Intermediate 1) and tert-butyl piperazine-1-carboxylate (482 mg, 2.59 mmol) in MeCN (5 mL) was added $NaHCO_3$ (2.90 g, 34.5 mmol). The reaction mixture was stirred under reflux for 12 h. The solid was removed by filtration and the filtrate was concentrated under reduced pressure. The residue was purified by flash chromatography on a silica gel column eluting with EtOAc/PE (10-100%) to afford the title compound (236 mg, 55% yield) as an off-white solid. LCMS calculated for $C_{23}H_{28}N_7O_4S$ $[M+H]^+$: m/z=498.2; Found: 498.1.

Step 2: tert-butyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperazine-1-carboxylate

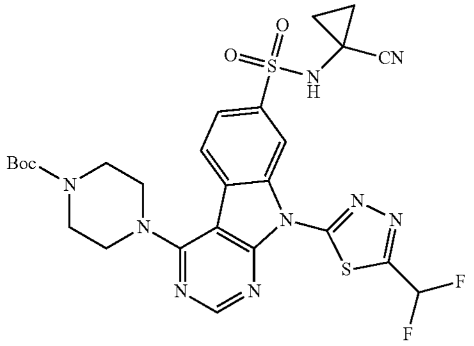 [SMILES: CC(C)(C)OC(=O)N1CCN(c2ncnc3c2c2ccc(S(=O)(=O)NC4(C#N)CC4)cc2n3-c2nnc(C(F)F)s2)CC1]

A mixture of tert-butyl 4-(7-(N-(1-cyanocyclopropyl)sulfamoyl)-9H-pyrimido[4,5-b]indol-4-yl)piperazine-1-carboxylate (0.03 g, 0.06 mmol), 2-bromo-5-(difluoromethyl)-1,3,4-thiadiazole (64.8 mg, 0.3 mmol), BrettPhos Pd G3 (27.3 mg, 0.03 mmol), t-BuONa (34.8 mg, 0.36 mol) in dioxane (4 mL) was degassed and recharged with $N_2$ for three cycles, stirred at 95° C. for 12 h. under $N_2$ atmosphere. After cooled to r.t., the solid was removed by filtration and the filtrate was concentrated under reduced pressure, the residue was purified by prep-HPLC on a C18 column eluting with MeCN/water (50%-86% with 1% $NH_4HCO_3$) to afford the title compound (5 mg) as a brown solid. $^1$H NMR: (400 MHz, DMSO-d6) δ 12.6 (s, 1H), 9.14 (s, 1H), 8.55 (s, 1H), 7.95-7.97 (m, 2H), 7.75 (d, J=7.2 Hz, 1H), 3.70-3.71 (m, 7H), 3.58-3.59 (m, 4H), 1.45 (s, 9H), 1.40-1.41 (m, 2H), 1.23-1.25 (m, 2H). LCMS calculated for $C_{26}H_{26}F_2N_9O_4S_2$ $[M-H]^-$: m/z=630.2; Found: 630.2.

Step 3: N-(1-cyanocyclopropyl)-9-(5-(difluoromethyl)-1,3,4-thiadiazol-2-yl)-4-(piperazin-1-yl)-9H-pyrimido[4,5-b]indole-7-sulfonamide

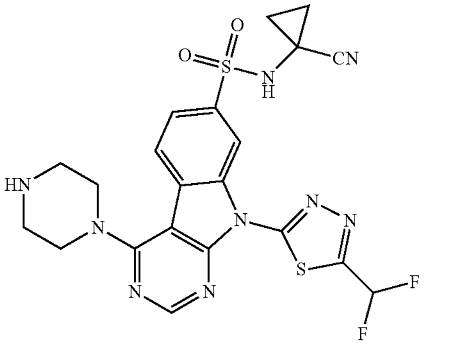 [SMILES: N#CC1(NS(=O)(=O)c2ccc3c4c(N5CCNCC5)ncnc4n(-c4nnc(C(F)F)s4)c3c2)CC1]

A solution of tert-butyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperazine-1-carboxylate (0.08 g, 0.13 mmol) in HCl/MeOH (4 M, 32.0 mL) was stirred at 15° C. for 2 h. The reaction mixture was concentrated under reduced pressure to give the title compound as HCl salt (0.08 g) as brown oil. LCMS calc. for $C_{21}H_{20}F_2N_9O_2S_2[M+H]^+$: m/z=532.1; Found: 532.0.

Step 4: N-(1-Cyanocyclopropyl)-9-(5-(difluoromethyl)-1,3,4-thiadiazol-2-yl)-4-(4-(1-methylazetidine-3-carbonyl)piperazin-1-yl)-9H-pyrimido[4,5-b]indole-7-sulfonamide To a mixture of N-(1-cyanocyclopropyl)-9-(5-(difluoromethyl)-1,3,4-thiadiazol-2-yl)-4-(piperazin-1-yl)-9H-pyrimido[4,5-b]indole-7-sulfonamide (0.02 g, 0.035 mmol) in DMF (1.00 mL) was added 1-methylazetidine-3-carboxylic acid (4.05 mg, 0.035 mmol) and DIEA (13.6 mg, 0.11 mmol). The reaction mixture was stirred at 25° C. for 30 min. before cooling to 10° C., followed by addition of TBTU (13.6 mg, 0.042 mmol). The reaction mixture was stirred for 1 h., and concentrated directly under reduced pressure. The residue was purified by prep-HPLC on a C18 column eluting with MeCN/water (30%-60% with 1% $NH_4HCO_3$) to afford the title compound (2 mg, 8.68% yield) as an off-white solid. $^1H$ NMR: (400 MHz, DMSO-d6) δ 9.49 (s, 1H), 8.83 (s, 1H), 8.10 (d, J=8.4 Hz, 1H), 8.02 (dd, J=8.4 Hz, 1.6 Hz, 1H), 7.68 (t, J=53.2 Hz, 1H), 3.82-3.83 (m, 4H), 3.69 (br.s, 2H), 3.51-3.52 (m, 2H), 3.44-3.47 (m, 3H), 3.12-3.15 (m, 2H), 2.18 (s, 3H), 1.40-1.43 (m, 2H), 1.23-1.27 (m, 2H). LCMS calc. for $C_{26}H_{25}F_2N_{10}O_3S_2[M-H]^-$: m/z=627.2; Found: 627.2.

The compounds listed in Table 4 below were prepared as the methods substantially analogous to those described for preparing Example 65 by using an appropriate acid to replace 1-methylazetidine-3-carboxylic acid in Step 4.

TABLE 4

Preparations of Examples (Ex)

| Ex # | acid | Structure | Name | LCMS Cacl./ Found |
|---|---|---|---|---|
| 66 | 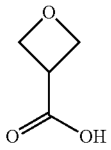 | 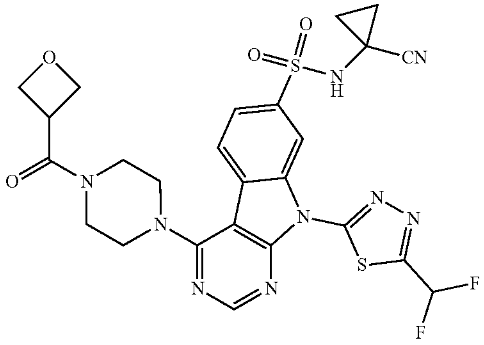 | N-(1-Cyanocyclopropyl)-9-(5-(difluoromethyl)-1,3,4-thiadiazol-2-yl)-4-(4-(oxetane-3-carbonyl)piperazin-1-yl)-9H-pyrimido[4,5-b]indole-7-sulfonamide | $[M-H]^-$ 614.1/ 614.1 |
| 67 | 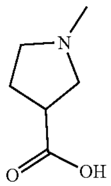 | 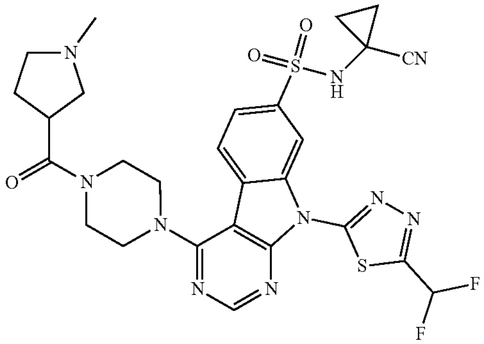 [SMILES: CN1CCC(C(=O)N2CCN(c3ncnc4c3c3ccc(S(=O)(=O)NC5(C#N)CC5)cc3n4-c3nnc(C(F)F)s3)CC2)C1] | N-(1-Cyanocyclopropyl)-9-(5-(difluoromethyl)-1,3,4-thiadiazol-2-yl)-4-(4-(1-methylpyrrolidine-3-carbonyl)piperazin-1-yl)-9H-pyrimido[4,5-b]indole-7-sulfonamide | $[M-H]^-$ 641.2/ 641.2 |
| 68 | 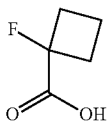 | 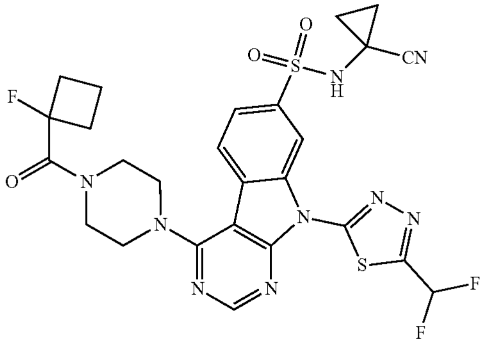 [SMILES: N#CC1(NS(=O)(=O)c2ccc3c4c(N5CCN(C(=O)C6(F)CCC6)CC5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(4-(1-fluorocyclobutane-1-carbonyl)piperazin-1-yl)-9H-pyrimido[4,5-b]indole-7-sulfonamide | $[M-H]^-$ 630.1/ 630.0 |

TABLE 5

| Ex # | $^1$H NMR: (MHz, Solvent) δ |
|---|---|
| | $^1$H NMR data of Examples (Ex) |
| 2 | $^1$H NMR: (400 MHz, DMSO-$d_6$) δ 9.50 (d, J = 1.6 Hz, 1H), 9.41 (s, 1H), 8.84 (s, 1H), 8.14 (d, J = 8.4 Hz, 1H), 8.03 (t, J = 6.8 Hz, 1H), 7.68 (t, J = 53.2 Hz, 1H), 3.72-3.94 (m, 8H), 2.04-2.08 (m, 1H), 1.43-1.45 (t, J = 5.6 Hz, 2H), 1.28 (t, J = 5.2 Hz, 2H), 0.76-0.80 (m, 4H). |
| 3 | $^1$H NMR: (400 MHz, DMSO-$d_6$) δ 9.50 (s, 1H), 9.41 (s, 1H), 8.84 (s, 1H), 8.14 (d, J = 8.8 Hz, 1H), 8.05 (d, J = 8.4 Hz, 1H), 7.69 (t, J = 53.6 Hz, 1H), 3.86 (s, 4H), 3.82 (s, 4H), 1.43 (s, 2H), 1.26 (s, 11H). |
| 4 | $^1$H NMR: (400 MHz, DMSO-$d_6$) δ 9.51 (s, 1H), 9.42 (s, 1H), 8.84 (s, 1H), 8.13 (d, J = 8.4 Hz, 1H), 8.06 (d, J = 1.6 Hz, 1H), 7.69 (t, J = 53.6 Hz, IH), 3.86 (s, 4H), 3.54-3.69 (m, 4H), 1.83-1.96 (m, 4H), 1.46-1.65 (m, 2H), 1.43-1.45 (m, 2H), 1.30 (s, 3H), 1.26-1.28 (m, 2H). |
| 5 | $^1$H NMR: (400 MHz, DMSO-$d_6$) δ 9.50 (s, 1H), 9.41 (s, 1H), 8.81 (s, 1H), 8.16 (d, J = 8.4 Hz, 1H), 8.03 (d, J = 8.4 Hz, 1H), 7.69 (t, J = 52.8 Hz, 1H), 4.72 (s, 1H), 4.36 (s, 2H), 4.20-4.22 (m, 2H), 3.67-3.75 (m, 2H), 2.12-2.19 (m, 3H), 1.79 (s, 1H), 1.76 (s, 1H), 1.42-1.46 (m, 2H), 1.28 (s, 3H), 1.26-1.28 (m, 2H), 1.01-1.02 (m, 2H). |
| 6 | $^1$H NMR: (400 MHz, DMSO-$d_6$) δ 9.49 (d, J = 1.6 Hz, 1H), 9.41 (s, 1H), 8.82 (s, 1H), 8.11 (t, J = 8.8 Hz, 1H), 8.03 (t, J = 6.8 Hz, 1H), 7.68 (t, J = 53.2 Hz, 1H), 3.88 (s, 4H), 3.41 (s, 4H), 2.81 (s, 6H), 1.42-1.45 (m, 2H), 1.25-1.28 (m, 2H). |
| 7 | $^1$H NMR: (400 MHz, DMSO-$d_6$) δ 9.50 (s, 1H), 9.40 (s, 1H), 8.82 (s, 1H), 8.12 (d, J = 8.4 Hz, 1H), 8.04 (dd, J = 8.4, 1.6 Hz, 1H), 7.68 (t, J = 53.2 Hz, 1H), 3.88 (s, 4H), 3.48 (s, 4H), 3.16-3.21 (m, 2H), 2.81 (s, 3H), 1.42-1.44 (m, 2H), 1.25-1.29 (m, 2H), 1.10 (t, J = 7.2 Hz, 3H). |
| 8 | $^1$H NMR: (400 MHz, DMSO-$d_6$) δ 9.50 (d, J = 1.6 Hz, 1H), 9.41 (s, 1H), 8.83 (s, 1H), 8.11 (d, J = 8.4 Hz, 1H), 8.03 (dd, J = 8.4, 1.6 Hz, 1H), 7.69 (t, J = 53.2 Hz, 1H), 3.88 (s, 4H), 3.61 (t, 4 Hz, 4H), 3.44 (s, 4H), 3.22 (t, J= 4.4 Hz, 4H), 1.43-1.50 (m, 2H), 1.28 (d, J= 2.8 Hz, 2H). |
| 9 | $^1$H NMR: (400 MHz, DMSO-$d_6$) δ 9.50 (d, J = 1.6 Hz, 1H), 9.41 (s, 1H), 8.83 (s, 1H), 8.12 (d, J = 8.8 Hz, 1H), 8.05 (dd, J = 8.4, 1.6 Hz, 1H), 7.69 (t, J = 53.2 Hz, 1H), 3.88 (s, 4H), 3.41 (m, 6H), 3.25 (d, J = 8 Hz, 4H), 2.34 (s, 3H), 2.21 (s, 2H), 1.43-1.52 (m, 2H), 1.24-1.29 (m, 2H). |
| 10 | $^1$H NMR: (400 MHz, DMSO-$d_6$) δ 9.50 (d, J = 1.6 Hz, 1H), 9.41 (s, 1H), 8.84 (s, 1H), 8.13 (d, J = 8.4 Hz, 1H), 8.05 (dd, J = 8.4, 1.6 Hz, 1H), 7.69 (t, J = 53.2 Hz, IH), 3.75-3.94 (m, 8H), 1.42-1.46 (m, 2H), 1.29 (s, 3H), 1.25-1.28 (m, 2H), 0.86 (t, J = 6.0 Hz, 2H), 0.59 (t, J = 6.0 Hz, 2H). |
| 11 | $^1$H NMR: (400 MHz, DMSO-$d_6$) δ 9.51 (d, J = 1.6 Hz, 1H), 9.42 (s, 1H), 8.84 (s, 1H), 8.15 (d, J = 8.0 Hz, 1H), 8.05 (dd, J = 8.4, 1.6 Hz, 1H), 7.69 (t, J = 53.2 Hz, 1H), 3.72-3.90 (m, 8H), 2.92-3.00 (m, 1H), 1.43-1.46 (m, 2H), 1.26-1.30 (m, 2H), 1.06 (d, J = 6.8 Hz, 6H). |
| 12 | $^1$H NMR: (400 MHz, DMSO-$d_6$) δ 9.50 (d, J = 1.6 Hz, 1H), 9.41 (s, 1H), 8.84 (s, 1H), 8.13 (d, J = 8.4 Hz, 1H), 8.04 (dd, J = 8.4, 2.0 Hz, 1H), 7.69 (t, J = 53.2 Hz, 1H), 3.71-3.90 (m, 10H), 3.38-3.43 (m, 2H), 2.97 (t, J = 5.6 Hz, 1H), 1.61-1.63 (m, 4H), 1.42-1.45 (m, 2H), 1.28 (t, J = 5.2 Hz, 2H). |
| 13 | $^1$H NMR: (400 MHz, DMSO-$d_6$) δ 9.49 (s, 1H), 9.36 (br s, 1H), 8.84 (s, 1H), 8.10 (d, J = 8.4 Hz, 1H), 8.02 (d, J = 10.4 Hz, 1H), 7.69 (t, J = 53.2 Hz, 1H), 7.57 (dd, J = 8.8 Hz, J = 1.6 Hz, 2H), 7.32 (t, J = 8.8 Hz, 2H), 3.65-3.92 (m, 8H), 1.40-1.43 (m, 2H), 1.23-1.26 (m, 2H). |
| 14 | $^1$H NMR: (400 MHz, DMSO-$d_6$) δ 9.49 (s, 1H), 9.40 (s, 1H), 8.85 (s, 1H), 8.64 (d, J = 4.4 Hz, 1H), 8.14 (d, J = 8.4 Hz, 1H), 7.97-8.04 (m, 2H), 7.52-7.68 (m, 3H), 3.89-3.98 (m, 6H), 3.72 (s, 2H), 1.41-1.45 (m, 2H), 1.24-1.28 (m, 2H). |
| 15 | $^1$H NMR: (400 MHz, DMSO-$d_6$) δ 9.50 (d, J= 1.6 Hz, 1H), 9.42 (s, 1H), 8.84 (s, 1H), 8.13 (d, J = 8.4 Hz, 1H), 8.05 (dd, J = 8.4 Hz, J = 1.6 Hz, 1H), 7.69 (t, J = 53.6 Hz, 1H), 4.85 (t, J = 6.0 Hz, 1H), 3.86 (s, 4H), 3.63 (s, 4H), 1.42-1.46 (m, 2H), 1.24-1.29 (m, 8H). |
| 16 | $^1$H NMR: (400 MHz, DMSO-$d_6$) δ 9.51 (s, 1H), 9.42 (s, 1H), 8.87 (s, 1H), 8.17 (d, J = 8.8 Hz, IH), 8.04 (dd, J = 8.4, 1.6 Hz, 1H), 7.70 (t, J = 53.6 Hz, 1H), 7.24 (d, J = 3.6 Hz, 1H), 6.94 (d, J = 3.6 Hz, 1H), 3.98 (s, 4H), 3.70 (s, 4H), 1.43-1.44 (m, 2H), 1.27-1.29 (m, 2H). |
| 17 | $^1$H NMR: (400 MHz, DMSO-$d_6$) δ 9.52 (d, J = 2.0 Hz, 1H), 9.42 (s, 1H), 8.85 (s, 1H), 8.19 (d, J = 3.2 Hz, 2H), 8.06 (dd, J = 8.4, 1.6 Hz, 1H), 7.70 (t, J = 53.6 Hz, 1H), 7.56-7.61 (m, 1H), 6.95 (d, J = 8.8 Hz, 1H), 6.70-6.73 (m, 1H), 3.97-3.98 (m, 4H), 3.79-3.80 (m, 4H), 1.43-1.46 (m, 2H), 1.27-1.30 (m, 2H). |
| 18 | $^1$H NMR: (400 MHz, DMSO-$d_6$) δ 9.50 (d, J = 1.6 Hz, 1H), 9.41 (s, 1H), 8.84 (s, 1H), 8.44 (d, J = 4.8 Hz, 2H), 8.16 (d, J = 8.4 Hz, 1H), 8.05 (dd, J = 8.4, 1.8 Hz, 1H), 7.69 (t, J = 53.2 Hz, 1H), 6.71 (t, J = 4.8 Hz, 1H), 3.95-4.01 (m, 8H), 1.41-1.46 (m, 2H), 1.25-1.29 (m, 2H). |
| 19 | $^1$H NMR: (400 MHz, DMSO-$d_6$) δ 9.52 (d, J = 1.6 Hz, 1H), 9.42 (s, 1H), 8.86 (s, 1H), 8.67 (d, J = 4.4 Hz, 1H), 8.18 (d, J = 8.4 Hz, 1H), 8.05 (dd, J = 8.4, 1.6 Hz, 1H), 7.69 (t, J = 54.0 Hz, 1H), 7.53-7.60 (m, 2H), 4.00-4.04 (m, 4H), 3.90-3.94 (m, 4H), 1.42-1.46 (m, 2H), 1.27-1.30 (m, 2H). |
| 20 | $^1$H NMR: (400 MHz, DMSO-$d_6$) δ 9.49 (s, 1 H), 9.39 (s, 1 H), 8.79 (s, 1 H), 8.06 (dd, J = 12.8 Hz, J = 8 Hz, 2 H), 7.68 (t, J = 53.6 Hz, 1 H), 4.43 (s, 4 H), 3.77 (s, 4 H), 2.02 (s, 4 H), 1.41-1.46 (m, 2 H), 1.23-1.30 (m, 2 H). |
| 21 | $^1$H NMR: (400 MHz, DMSO-$d_6$) δ 9.49 (s, 1H), 9.39 (s, 1H), 8.82 (s, 1H), 8.07 (dd, J = 16.6 Hz, J = 8.4 Hz, 2H), 7.68 (t, J = 53.2 Hz, 1H), 4.27 (d, J = 13.2 Hz, 1H), 4.19 (d, J = 13.2 Hz, 1H), 3.98 (d, J = 12.0 Hz, 1H), 3.46-3.53 (m, 2H), 3.10-3.16 (m, 2H), 1.42-1.45 (m, 2H), 1.26-1.30 (m, 2H), 1.17 (d, J = 6.0 Hz, 3H). |
| 23 | $^1$H NMR: (400 MHz, DMSO-$d_6$) δ 9.48 (s, 1H), 9.38 (s, 1H), 8.70 (s, 1H), 8.36 (d, J = 8.0 Hz, 1H), 7.93 (d, J = 8.0 Hz, 1H), 7.70 (t, J = 53.2 Hz, 1H), 4.79 (s, 4H), 4.43 (s, 2H), 4.12 (s, 2H), 2.33-2.46 (m, 1H), 1.42-1.45 (m, 2H), 1.27-1.29 (m, 2H), 0.99 (d, J = 6.8 Hz, 6H). |
| 24 | $^1$H NMR: (400 MHz, DMSO-$d_6$) δ 9.48 (s, 1H), 9.38 (s, 1H), 8.75 (s, 1H), 8.19 (d, J = 8.0 Hz, 1H), 7.98 (t, J = 8.4 Hz, 1H), 7.68 (t, J = 52.0 Hz, 1H), 4.50-4.83 (m, 4H), 3.68-3.71 (m, 2H), 2.90-2.92 (m, 1H), 1.68-1.76 (m, 4H), 1.43 (d, J = 2.8 Hz, 2H), 1.26 (t, J = 3.2 Hz, 2H), 1.03 (d, J = 6.4 Hz, 6H). |
| 25 | $^1$H NMR: (400 MHz, DMSO-$d_6$) δ 9.43-9.45 (m, 1H), 9.30 (s, 1H), 8.63, (s, 1H), 8.16 (t, J = 8.4 Hz, 1H), 7.91 (t, J = 7.2 Hz, 1H), 7.60 (t, J = 53.2 Hz, 1H), 3.96-4.08 (m, 4H), 3.69-3.76 (m, 2H), 3.45-3.56 (m, 2H), 2.69-2.72 (m, 1H), 2.01-2.09 (m, 1H), 1.84 (s, 1H), 1.35-1.39 (m, 2H), 1.20-1.22 (m, 2H), 0.74 (d, J = 6.4 Hz, 6H). |
| 26 | $^1$H NMR: (400 MHz, DMSO-$d_6$) δ 9.51 (s, 1H), 9.42 (s, 1H), 8.86 (s, 1H), 8.16 (d, J = 8.4 Hz, 1H), 8.04-8.07 (m, 1H), 7.70 (d, J = 53.2 Hz, 1H), 3.81-3.97 (m, 8H), 3.25-3.30 (m, 1H), 1.91-2.01 (m, 2 H), 1.43-1.46 (m, 2H), 1.27-1.30 (m, 2 H). |

TABLE 5-continued

| $^{1}$H NMR data of Examples (Ex) | |
|---|---|
| Ex # | $^{1}$H NMR: (MHz, Solvent) δ |
| 27 | $^{1}$H NMR: (400 MHz, DMSO-$d_6$) δ 9.49 (s, 1H), 9.41 (s, 1H), 8.86 (m, 1H), 8.65 (d, J = 1.6 Hz, 1H), 8.10-8.12 (m, 1H), 8.03 (dd, J = 8.4, 2.0 Hz, 1H), 7.93 (dd, J = 8.0, 1.6 Hz, 1H), 7.69 (t, J = 53.2 Hz, 1H), 7.48 (d, J = 8.0 Hz, 1H), 3.92 (s, 7H), 3.65 (s, 1H), 2.57 (s, 3H), 1.41-1.44 (m, 2H), 1.24-1.28 (m, 2H). |
| 28 | $^{1}$H NMR: (400 MHz, DMSO-$d_6$) δ 9.51 (d, J = 2.0 Hz, 1H), 9.36 (s, 1H), 8.66 (s, 1H), 8.48 (d, J = 8.8 Hz, 1H), 7.93 (d, J = 8.0 Hz, 1H), 7.67 (t, J = 53.6 Hz, 1H), 4.21-4.26 (m, 2H), 3.88-3.91 (m, 2H), 3.55-3.57 (m, 2H), 3.02 (s, 2H), 2.73 (s, 6H), 1.42-1.45 (m, 2H), 1.24-1.29 (m, 4H). |
| 29 | $^{1}$H NMR: (400 MHz, DMSO-$d_6$) δ 9.50 (s, 1H), 8.78 (s, 1H), 8.22 (d, J = 8.0 Hz, 1H), 8.01 (d, J = 8.0 Hz, 1H), 7.68 (t, J = 52.0 Hz, 1H), 4.66-4.69 (m, 2H), 4.38 (d, J = 12.0 Hz, 2H), 3.78-3.83 (m, 2H), 1.93-1.98 (m, 1H), 1.25-1.43 (m, 4H), 1.19 (d, J = 8.0 Hz, 6H), 0.73-0.78 (m, 4H). |
| 30 | $^{1}$H NMR: (400 MHz, DMSO-$d_6$) δ 9.49 (s, 1 H), 9.41 (s, 1H), 8.82 (s, 1H), 8.12 (d, J = 8.4 Hz, 1H), 8.04 (d, J = 8.4 Hz, 1H), 7.68 (t, J = 53.2 Hz, 1H), 3.77-3.86 (m, 8H), 3.58-3.65 (m, 1H), 1.76-1.94 (m, 4H), 1.40-1.44 (m, 2H), 1.20-1.30 (m, 4H). |
| 31 | $^{1}$H NMR: (400 MHz, DMSO-$d_6$) δ 9.50 (d, J = 0.8 Hz, 1 H), 9.39 (s, 1H), 8.77 (s, 1H), 8.42 (d, J = 8 Hz, 1H), 7.93 (d, J = 8 Hz, 1H), 7.68 (t, J = 54 Hz, 1H), 4.39-4.44 (m, 4H), 3.59-3.86 (m, 2H), 2.49-2.65 (m, 1H), 1.41-1.42 (m, 3H), 1.24-1.27 (m, 4H), 1.04-1.07 (m, 9H). |
| 32 | $^{1}$H NMR: (400 MHz, DMSO-$d_6$) δ 9.52 (s, 1 H), 9.38 (s, 1H), 8.74 (s, 1H), 8.29 (d, J = 16 Hz, 1H), 7.98 (d, J = 8 Hz, 1H), 7.68 (t, J = 62 Hz, 1H), 4.09-4.26 (m, 1H), 4.04-4.06 (m, 3H), 3.69-3.86 (m, 1H), 3.64-3.69 (m, 1H), 2.50-2.68 (m, 1H), 2.11-2.22 (m, 1H), 1.93-1.95 (m, 3H), 1.42-1.44 (m, 2H), 1.27-1.28 (m, 2H), 1.00-1.05 (m, 6H). |
| 33 | $^{1}$H NMR: (400 MHz, DMSO-$d_6$) δ 9.50 (s, 1 H), 9.41 (s, 1H), 8.84 (s, 1H), 8.12 (d, J = 8.4 Hz, 1H), 8.03 (t, J = 8.4 Hz, 1H), 7.69 (t, J = 53.2 Hz, 1H), 4.69-4.88 (m, 2H), 4.20-4.40 (m, 1H), 4.02-4.10 (m, 1H), 3.81-3.92 (m, 2H), 2.87-2.96 (m, 1H), 1.42-1.45 (m, 2H), 1.20-1.31 (m, 5H), 0.92-1.15 (m, 9H). |
| 34 | $^{1}$H NMR: (400 MHz, DMSO-$d_6$) δ 9.51 (s, 1H), 9.42 (s, 1H), 8.85 (s, 1H), 8.13 (t, J = 8.4 Hz, 1H), 8.05 (d, J = 7.2 Hz, 1H), 7.69 (t, J = 53.2 Hz, 1H), 3.90-3.93 (m, 4H), 3.72-3.79 (m, 7H), 3.43-3.45 (m, 1H), 2.05-2.10 (m, 2H), 1.43-1.46 (m, 2H), 1.26-1.30 (m, 2H). |
| 35 | $^{1}$H NMR: (400 MHz, DMSO-$d_6$) δ 9.50 (d, J = 1.60 Hz, 1H), 9.41 (s, 1H), 8.85 (s, 1H), 8.48 (s, 1 H), 8.14 (d, J = 8.8 Hz, 1H), 8.04 (d, J = 6.8 Hz, 1H), 7.56-7.81 (m, 3H), 3.99 (s, 2H), 3.89-3.91 (m, 4H), 3.76 (s, 2H), 2.37 (s, 3H), 1.43-1.45 (m, 2H), 1.25-1.29 (m, 2H). |
| 36 | $^{1}$H NMR: (400 MHz, DMSO-$d_6$) δ 9.49 (s, 1 H), 9.35 (s, 1H), 8.64 (s, 1H), 8.50 (d, J = 8.8 Hz, 1H), 7.91 (d, J = 9.2 Hz, 1H), 7.65 (t, J = 53.2 Hz, 1H), 4.22-4.27 (m, 3H), 3.87-3.91 (m, 3H), 3.06 (s, 2H), 1.39-1.43 (m, 2H), 1.25-1.27 (m, 2H), 1.22 (s, 5H), 0.80-0.82 (m, 2H), 0.48 (d, J = 4.4 Hz, 2H). |
| 37 | $^{1}$H NMR: (400 MHz, DMSO-$d_6$) δ 9.49 (d, J = 1.2 Hz, 1H), 9.39 (s, 1H), 8.79 (s, 1H), 8.15 (d, J = 8.4 Hz, 1H), 8.04 (t, J = 1.6 Hz, 1H), 7.68 (t, J = 53.6 Hz, 1H), 4.22 (d, J = 12.8 Hz, 1H), 4.07 (d, J = 11.2 Hz, 1H), 3.93-3.94 (m, 1H), 3.75-3.79 (m, 1H), 3.56-3.63 (m, 1H), 3.39-3.43 (m, 2H), 2.80 (s, 6H), 1.42-1.45 (m, 2H), 1.25-1.29 (m, 2H), 1.07 (d, J = 6.8 Hz, 3H). |
| 38 | $^{1}$H NMR: (400 MHz, DMSO-$d_6$) δ 9.51 (s, 1H), 9.42 (s, 1H), 8.85 (s, 1H), 8.13 (d, J = 8.4 Hz, 1H), 8.04 (d, J = 8.4 Hz, 1H), 7.69 (t, J = 53.6 Hz, 1H), 4.88 (s, 1H), 4.69 (s, 1H), 4.40 (s, 1H), 4.18-4.27 (m, 1H), 4.01-4.08 (m, 1H), 3.83-3.90 (m, 2H), 1.25-1.31 (m, 4H), 1.21-1.24 (m, 3H), 1.14 (d, J = 6.8 Hz, 2H), 1.00-1.08 (m, 6H), 0.93 (d, J = 6.4 Hz, 2H). |
| 39 | $^{1}$H NMR (400 MHz, DMSO-$d_6$) δ 9.52 (d, J = 1.6 Hz, 1H), 9.42 (s, 1H), 8.81 (s, 1H), 8.22 (d, J = 8.4 Hz, 1H), 8.03 (t, J = 6.8 Hz, 1H), 7.70 (t, J = 53.2 Hz, 1H), 4.71 (s, 2H), 4.34-4.41 (m, 3H), 4.13 (s, 2H), 3.76-3.94 (m, 9H), 1.42-1.46 (m, 3H), 1.28-1.31 (m, 5H), 1.18-1.20 (m, 2H). |
| 40 | $^{1}$H NMR (400 MHz, DMSO-$d_6$) δ 9.50 (d, J = 1.6 Hz, 1H), 8.84 (s, 1H), 8.20 (d, J = 8.4 Hz, 1H), 8.04-8.06 (t, J = 8.4 Hz, 1H), 7.55-7.82 (t, J = 53.6 Hz, 1H), 7.29-7.40 (m, 1H), 4.49 (s, 2H), 4.17 (t, J = 5.2 Hz, 2H), 3.66 (t, J = 4.8 Hz, 2H), 3.25 (d, J = 7.2 Hz, 2H), 1.39-1.42 (m, 2H), 1.23-1.27 (m, 2H), 0.95-1.00 (m, 1H), 0.43-0.48 (m, 2H), 0.22-0.25 (m, 2H). |
| 41 | $^{1}$H NMR: (400 MHz, DMSO-$d_6$) δ 9.47 (s, 1 H), 9.40 (s, 1H), 8.79 (s, 1H), 8.10 (d, J = 8.4 Hz, IH), 8.02 (d, J = 8.4 Hz, 1H), 7.67 (t, J = 53.2 Hz, 1H), 3.85-3.89 (m, 4H), 3.40-3.45 (m, 4H), 3.31-3.36 (m, 4H), 2.75 (d, J = 5.2 Hz, 1H), 1.76-1.81 (m, 4H), 1.40-1.45 (m, 2H), 1.23-1.29 (m, 2H). |
| 42 | $^{1}$H NMR: (400 MHz, DMSO-$d_6$) δ 9.50 (d, J = 1.6 Hz, IH), 9.42 (s, 1H), 8.84 (s, 1H), 8.14 (d, J = 8.8 Hz, 1H), 8.06 (t, J = 1.6 Hz, 1H), 7.69 (t, J = 54 Hz, 1H), 4.09-4.14 (m, 2H), 3.89 (s, 4H), 3.45 (s, 4H), 3.05 (s, 3H), 1.43-1.46 (m, 2H), 1.24-1.29 (m, 2H). |
| 45 | $^{1}$H NMR: (400 MHz, DMSO-$d_6$) δ 9.67 (s, 1H), 9.48 (d, J = 6.4 Hz, 1H), 8.79 (s, 1H), 7.86 (d, J = 10.8 Hz, 1H), 7.68 (d, J = 53.2 Hz, 1H), 4.95 (br s, 1H), 4.19 (m, 1H), 4.04 (br s, 1H), 3.77-3.81 (m, 1H), 3.54-3.59 (m, 1H), 3.35 (s, 1H), 2.79 (s, 6H), 1.20-1.53 (m, 8H), 0.91 (d, J = 6.8 Hz, 2H). |
| 46 | $^{1}$H NMR: (400 MHz, DMSO) δ 9.65 (s, 1H), 9.48 (d, J = 6.4 Hz, IH), 8.78 (s, 1H), 7.92 (d, J = 10.8 Hz, 1 H), 7.68 (t, J = 53.2 Hz, 1H), 4.23 (d, J = 12.4 Hz, 1H), 3.88-4.11 (m, 2H), 3.60-3.85 (m, 2H), 3.36-3.43 (m, 1H), 3.26 (d, J = 2.4 Hz, 1H), 2.80 (s, 6H), 1.43-1.48 (m, 2H), 1.26-1.31 (m, 2H), 1.03 (d, J = 6.4 Hz, 3H). |
| 47 | $^{1}$H NMR: (400 MHz, DMSO-$d_6$) δ 9.50 (d, J = 1.6 Hz, 1H), 9.41 (s, 1H), 8.84 (s, 1H), 8.16 (d, J = 8 Hz, 1H), 8.05 (dd, J = 8.4 Hz, J = 1.6 Hz, 1H), 7.69 (t, J = 53.2 Hz, 1H), 4.31 (d, J = 8 Hz, 2H), 3.71 (s, 5H), 2.14 (d, J = 8 Hz, 2H), 1.93-2.00 (m, 2H), 1.43-1.46 (m, 2H), 1.28 (t, J = 5.6 Hz, 2H). |
| 48 | $^{1}$H NMR: (400 MHz, DMSO-$d_6$) δ 9.48 (d, J = 1.6 Hz, IH), 9.38 (s, 1H), 8.76 (s, 1H), 8.09 (d, J = 8.4 Hz, 1H), 8.03 (t, J = 1.6 Hz, 1H), 7.68 (t, J = 53.2 Hz, 1H), 4.57 (br.s, 1H), 4.05-4.08 (m, 2H), 3.67-3.73 (m, 2H), 1.68 (br. s, 4H), 1.41-1.45 (m, 2H), 1.26-1.30 (m, 2H), 1.22 (s, 3H). |
| 49 | $^{1}$H NMR: (400 MHz, DMSO-$d_6$) δ 9.49 (s, 1H), 9.40 (s, 1H), 8.83 (s, 1H), 8.10 (d, J = 8.4 Hz, 1H), 8.04 (t, J = 1.6 Hz, 1H), 7.68 (t, J = 53.2 Hz, 1H), 4.01-4.05 (m, 2H), 3.66-3.71 (m, 2H), 3.27-3.32 (m, 1H), 2.11-2.14 (m, 2H), 1.95-1.99 (m, 2H), 1.42-1.44 (m, 2H), 1.26-1.29 (m, 2H). |
| 50 | $^{1}$H NMR: (400 MHz, DMSO) δ 9.49 (s, 1H), 9.39 (s, 1H), 8.82 (s, 1H), 8.03-8.10 (m, 1H), 7.68 (t, J = 53.6 Hz, 1H), 4.23 (dd, J = 13.2 Hz, J = 32 Hz, 2H), 3.96-4.00 (m, 1H), 3.72-3.96 (m, 1H), 3.49-3.52 (m, 2H), 3.13 (t, J = 10.4 Hz, 1H), 1.42-1.45 (m, 2H), 1.28 (t, J = 3.2 Hz, 2H), 1.17 (d, J = 6 Hz, 3H). |
| 51 | $^{1}$H NMR: (400 MHz, DMSO-$d_6$) δ 9.49 (d, J = 1.6 Hz, 1H), 9.39 (s, 1H), 8.82 (s, 1H), 8.11 (d, J = 8.4 Hz, 1H), 8.06 (t, J = 1.6 Hz, 1H), 7.68 (t, J = 53.2 Hz, 1H), 5.05 (d, J = 48.8 Hz, 1H), 3.93-3.98 (m, 2H), 3.81-3.85 (m, 2H), 2.07-2.17 (m, 2H), 1.93-1.96 (m, 2H), 1.41-1.43 (m, 2H), 1.23-1.29 (m, 2H). |

TABLE 5-continued

| $^1$H NMR data of Examples (Ex) | |
|---|---|
| Ex # | $^1$H NMR: (MHz, Solvent) δ |
| 52 | $^1$H NMR: (400 MHz, DMSO-$d_6$) δ 9.50 (d, J = 1.6 Hz, 1H), 9.41 (s, 1H), 8.86 (s, 1H), 8.17 (d, J = 8.4 Hz, 1H), 8.04 (d, J = 6.4 Hz, 1H), 7.69 (t, J = 53.2 Hz, 1H), 3.95 (br.s, 4H), 2.23 (br.s, 4H), 1.37-1.44 (m, 2H), 1.25-1.28 (m, 2H). |
| 53 | $^1$H NMR: (400 MHz, DMSO-$d_6$) δ 9.49 (d, J = 1.2 Hz, 1H), 9.40 (s, 1H), 8.82 (s, 1H), 8.04-8.08 (m, 2H), 7.68 (t, J = 52.0 Hz, 1H), 3.82-3.87 (m, 8H), 1.41-1.43 (m, 2H), 1.27-1.29 (m, 2H). |
| 54 | $^1$H NMR (400 MHz, DMSO-$d_6$) δ 9.51 (d, J = 2.0 Hz, 1H), 9.35 (s, 1H), 8.66 (s, 1H), 8.46 (d, J = 8.8 Hz, 1H), 7.95 (t, J = 1.6 Hz, 1H), 7.567 (t, J = 53.2 Hz, 1H), 4.48 (br.s, 1H), 4.15-4.19 (m, 2H), 3.91-3.95 (m, 1H), 3.74 (d, J = 11.6 Hz, 1H), 2.01-2.09 (m, 3H), 1.41-1.45 (m, 2H), 1.26-1.29 (m, 2H). |
| 55 | $^1$H NMR (DMSO-$d_6$, 400 MHz): δ 9.64 (s, 1H), 9.47 (d, J = 6.4 Hz, 1H), 8.77 (s, 1H), 7.83 (s, 1H), 7.68 (t, J = 52.8 Hz, 1H), 4.88 (br s, 1H), 4.11-4.15 (m, 2H), 3.87 (br s, 1H), 3.58-3.63 (m, 2H), 1.92-1.95 (m, 2H), 1.53-1.55 (m, 2H), 1.45-1.48 (m, 2H), 1.31-1.33 (m, 2H). |
| 56 | $^1$H NMR: (400 MHz, DMSO-$d_6$) δ 10.06-10.09 (m, 1 H), 9.52 (s, 1H), 9.47 (s, 1H), 8.93 (s, 1H), 8.17 (d, J = 8.4 Hz, 1H), 8.07 (dd, J = 8.4 Hz, 1.6 Hz, 1H), 7.71 (t, J = 53.2 Hz, 1H), 4.41-4.45 (m, 2H), 3.64-3.67 (m, 4H), 3.27-3.29 (m, 2H), 2.88 (br.s, 3H), 1.43-1.47 (m, 2H), 1.27-1.31 (m, 2H). |
| 57 | $^1$H NMR: (400 MHz, DMSO) δ 9.51 (d, J = 1.2 Hz, 1H), 9.39 (s, 1H), 8.76 (s, 1H), 8.15 (d, J = 8.4 Hz, 1H), 8.05 (d, J = 8.4 Hz, 1H), 7.68 (t, J = 53.6 Hz, 1H), 4.92 (br.s, 1H), 4.08-4.10 (m, 3H), 3.85 (br.s, 1H), 2.97 (br.s, 1H), 1.44 (s, 2H), 1.31 (t, J = 6.4 Hz, 6H), 1.10 (br.s, 4H), 0.99 (d, J = 6.4 Hz, 4H). |
| 58 | $^1$H NMR: (400 MHz, DMSO-$d_6$) δ 9.50 (d, J = 1.6 Hz, 1H), 9.39 (s, 1H), 8.78 (s, 1H), 8.19 (d, J = 8.0 Hz, 1H), 8.02 (t, J = 1.6 Hz, 1H), 7.68 (t, J = 53.2 Hz, 1H), 4.67-4.75 (m, 5H), 4.32 (br.s, 2H), 4.14-4.18 (m, 1H), 3.75-3.78 (m, 3H), 1.42-1.44 (m, 2H), 1.26-1.30 (m, 2H), 1.15 (d, J = 4.0 Hz, 6H). |
| 59 | $^1$H NMR: (400 MHz, DMSO) δ 9.50 (d, J = 2.0 Hz, 1H), 9.41 (s, 1H), 8.82 (s, 1H), 8.11 (d, J = 8.4 Hz, 1H), 8.05 (t, J = 1.6 Hz, 1H), 7.68 (t, J = 53.2 Hz, 1H), 4.88-4.90 (m, 1H), 4.05-4.10 (m, 2H), 3.82 (d, J = 11.2 Hz, 1H), 3.64-3.68 (m, 1H), 3.39 (s, 1H), 2.80 (s, 6H), 1.42-1.45 (m, 2H), 1.25-1.31 (m, 5H), 0.98 (d, J = 6.8 Hz, 3H). |
| 60 | $^1$H NMR (400 MHz, DMSO-$d_6$) δ 9.51 (d, J = 1.6 Hz, 1H), 9.40 (s, 1H), 8.82 (s, 1H), 8.18 (d, J = 8.4 Hz, 1H), 8.03 (t, J = 6.8 Hz, 1H), 7.69 (t, J = 53.2 Hz, 1H), 4.77 (br.s, 1H), 4.37 (d, J = 12.0 Hz, 1H), 4.23 (d, J = 12.8 Hz, 1H), 4.00 (br.s, 1H), 3.68 (br.s, 3H), 2.88-2.93 (m, 1H), 1.43-1.46 (m, 2H), 1.26-1.29 (m, 2H), 1.05 (d, J = 5.6 Hz, 9H). |
| 61 | $^1$H NMR (400 MHz, DMSO-$d_6$) δ 9.51 (d, J = 1.6 Hz, 1H), 9.40 (s, 1H), 8.82 (s, 1H), 8.18 (d, J = 8.4 Hz, 1H), 8.03 (dd, J = 8.6 Hz, J = 2.0 Hz, 1H), 7.69 (t, J = 53.2 Hz, 1H), 4.76 (br.s, 1H), 4.37 (d, J = 12.0 Hz, 1H), 4.23 (d, J = 12.8 Hz, 1H), 4.02 (br.s, 1H), 3.70 (br.s, 2H), 3.47 (br.s, 1H), 2.88-2.94 (m, 1H), 1.43-1.46 (m, 2H), 1.26-1.29 (m, 2H), 1.05 (d, J = 5.6 Hz, 9H). |
| 62 | $^1$H NMR: (400 MHz, DMSO-$d_6$) δ 9.50 (d, J = 1.6 Hz, 1H), 9.37 (s, 1H), 8.78 (s, 1H), 8.22 (d, J = 8.0 Hz, 1H), 8.01 (dd, J = 8.4 Hz, J = 1.6 Hz, 1H), 7.68 (t, J = 53.6 Hz, 1H), 4.34-4.70 (m, 4H), 3.74-3.82 (m, 2H), 2.81-2.88 (m, 1H), 1.41-1.45 (m, 2H), 1.28-1.30 (m, 2H), 1.17 (s, 6H), 1.05 (d, J = 6.0 Hz, 6H). |
| 63 | $^1$H NMR: (400 MHz, DMSO) δ 9.52 (d, J = 1.2 Hz, 1H), δ 9.48 (s, 1H), δ 9.45 (s, 1H), 8.88 (s, 1H), 8.15 (d, J = 8.8 Hz, 1H), 8.06 (dd, J = 8.4, 1.6 Hz, 1H), 7.69 (t, J = 53.2 Hz, 1H), 4.60 (t, J = 4.8 Hz, 2H), 4.00 (br.s, 4H), 3.74 (br.s, 4H), 2.08-2.12 (m, 2H), 1.43-1.46 (m, 2H), 1.28-1.31 (m, 2H), 1.24 (s, 2H). |
| 64 | $^1$H NMR: (400 MHz, DMSO-$d_6$) δ 9.46 (d, J = 1.6 Hz, 1H), 8.82 (s, 1H), 8.37 (s, 1H), 8.07 (d, J = 8.4 Hz, 1H), 7.99 (dd, J = 8.4 Hz, 1.6 Hz, 1H), 7.68 (t, J = 53.2 Hz, 1H), 4.83-4.87 (m, 1H), 4.35-4.74 (m, 1H), 4.01-4.21 (m, 2H), 3.80-3.91 (m, 2H), 2.88-2.96 (m, 1H), 1.29 (d, J = 6.4 Hz, 3H), 1.13 (s, 3H), 1.00-1.10 (m, 7H), 0.95 (d, J = 6.8 Hz, 2H), 0.63-0.67 (m, 2H), 0.41 (t, J = 5.2 Hz, 2H). |
| 66 | $^1$H NMR: (400 MHz, DMSO-d6) δ 9.49 (d, J = 1.6 Hz, 1H), 8.83 (s, 1H), 8.10 (d, J = 8.4 Hz, 1H), 8.04 (dd, J = 8.4 Hz, 1.6 Hz, 1H), 7.68 (t, J = 53.2 Hz, 1H), 4.70-4.76 (m, 4H), 4.19-4.23 (m, 1H), 3.70-3.88 (m, 8H), 1.42 (d, J = 7.6 Hz, 2H), 1.25 (t, J = 4.8 Hz, 2H). |
| 67 | $^1$H NMR: (400 MHz, DMSO-d6) δ 9.49 (d, J = 1.6 Hz, 1H), 8.83 (s, 1H), 8.12 (d, J = 8.4 Hz, 1H), 8.04 (dd, J = 8.4 Hz, 1.6 Hz, 1H), 7.68 (t, J = 53.2 Hz, 1H), 3.84-3.86 (m, 4H), 3.72 (br s, 2H), 2.78-2.80 (m, 1H), 2.53-2.58 (m, 3H), 2.35-2.37 (m, 1H), 2.25 (s, 3H), 1.98-2.02 (m, 2H), 1.41 (t, J = 2.8 Hz, 2H), 1.26 (t, J = 2.8 Hz, 2H). |
| 68 | $^1$H NMR: (400 MHz, DMSO-d6) δ 9.49 (s, 1H), 9.40 (br s, 1H), 8.45 (s, 1H), 8.13 (d, J = 8.4 Hz, 1H), 8.04 (dd, J = 8.4 Hz, 1.6 Hz, 1H), 7.68 (t, J = 53.2 Hz, 1H), 3.89-3.90 (m, 4H), 3.69-3.77 (m, 4H), 2.70-2.76 (m, 2H), 2.39-2.44 (m, 2H), 1.88-1.89 (m, 1H), 1.52-1.55 (m, 1H), 1.40-1.42 (m, 2H), 1.23-1.27 (m, 2H). |

Example 69: N-(1-Cyanocyclopropyl)-9-(5-(difluoromethyl)-1,3,4-thiadiazol-2-yl)-4-(4-(isopropylsulfinyl)piperazin-1-yl)-9H-pyrimido[4,5-b]indole-7-sulfonamide

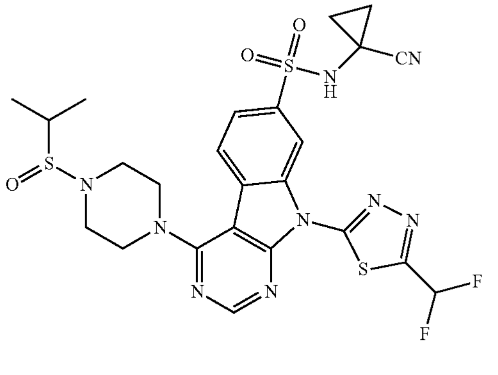 [SMILES: CC(C)S(=O)N1CCN(c2ncnc3c2c2ccc(S(=O)(=O)NC4(C#N)CC4)cc2n3-c2nnc(C(F)F)s2)CC1]

Step 1: S-isopropyl propane-2-sulfinothioate

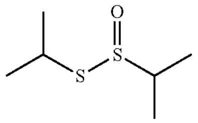

To a solution of 1,2-diisopropyldisulfane (5.00 g, 33.3 mmol) in MeCN (25.0 mL) was added dropwise $H_2O_2$ (5.66 g, 49.9 mmol, 30%) at 0° C. The reaction mixture was stirred at 15° C. for 12 h., and then quenched with $H_2O$ (50 mL) at 0° C. The mixture was extracted with DCM (50 mL×3). The combined organic layers were washed with $NaHSO_3$ (30 mL×2), $NaHCO_3$ (30 mL×5) and brine (30 mL×2), dried over $Na_2SO_4$, filtered and concentrated under reduced pressure to afford the title compound (2.50 g, 45.2% yield) as light-yellow oil. $^1$H NMR: (400 MHz, $CDCl_3$) δ 3.61-3.65 (m, 1H), 3.19-3.23 (m, 1H), 1.47-1.49 (m, 6H), 1.37-1.40 (m, 6H).

Step 2: propane-2-sulfinic chloride

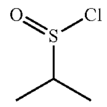

To a solution of S-isopropyl propane-2-sulfinothioate (0.05 g, 0.30 mmol) in DCM (1 mL) was added dropwise sulfuryl chloride (40.6 mg, 0.30 mmol) at 0° C. The reaction mixture was stirred at 0° C. for 2 h. The mixture was used directly in next step without purification.

Step 3: N-(1-cyanocyclopropyl)-9-(5-(difluoromethyl)-1,3,4-thiadiazol-2-yl)-4-(4-(isopropylsulfinyl)piperazin-1-yl)-9H-pyrimido[4,5-b]indole-7-sulfonamide To a mixture of N-(1-cyanocyclopropyl)-9-(5-(difluoromethyl)-1,3,4-thiadiazol-2-yl)-4-(piperazin-1-yl)-9H-pyrimido[4,5-b]indole-7-sulfonamide (Example 65 Step 3) (0.02 g, 0.035 mmol), TEA (21.4 mg, 0.021 mmol) and DMAP (0.086 mg, 0.0007 mmol) in DCM (1.0 mL) was added dropwise a solution of propane-2-sulfinyl chloride (step 2 at 0° C. The reaction mixture was degassed and recharged with $N_2$ for three cycles, stirred at 0° C. for 2 h. under $N_2$.

The reaction was concentrated directly under reduced pressure. The residue was purified by prep-HPLC on a C18 column eluting with MeCN/water (50%-70% with 1% $NH_4HCO_3$) to afford the title compound (1.80 mg, 8.22% yield) as an off-white solid. $^1$H NMR: (400 MHz, DMSO-d6) δ 9.47 (s, 1H), 8.84 (s, 1H), 8.10 (d, J=8.0 Hz, 1H), 8.03 (d, J=8.0 Hz, 1H), 7.68 (t, J=53.2 Hz, 1H), 3.93-3.95 (m, 4H), 3.23-3.27 (m, 2H), 3.08-3.11 (m, 1H), 1.34-1.36 (m, 2H), 1.21-1.23 (m, 5H), 1.15 (d, J=6.8 Hz, 3H). LCMS calc. for $C_{24}H_{24}F_2N_9O_3S_3$ $[M-H]^-$: m/z=620.1; Found: 620.2.

Example 70: 4-(4-(Tert-butylsulfinyl)piperazin-1-yl)-N-(1-cyanocyclopropyl)-9-(5-(difluoromethyl)-1,3,4-thiadiazol-2-yl)-9H-pyrimido[4,5-b]indole-7-sulfonamide

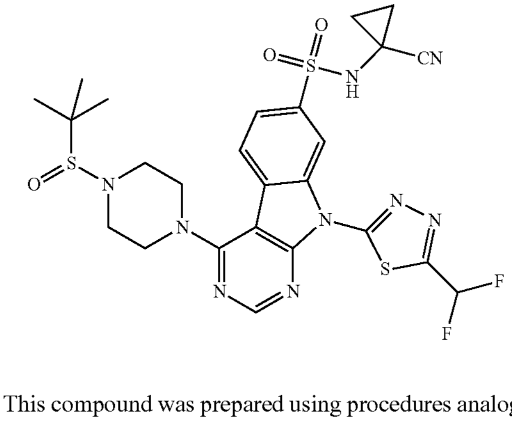

This compound was prepared using procedures analogous to those described for Example 69 Step 3 using N-(1-cyanocyclopropyl)-9-(5-(difluoromethyl)-1,3,4-thiadiazol-2-yl)-4-(piperazin-1-yl)-9H-pyrimido[4,5-b]indole-7-sulfonamide (Example 65 Step 3) and 2-methylpropane-2-sulfinyl chloride. $^1$H NMR: (400 MHz, DMSO-d6) δ 9.49 (d, J=1.2 Hz, 1H), 8.83 (s, 1H), 8.11 (d, J=8.4 Hz, 1H), 8.03 (dd, J=8.4 Hz, 1.6 Hz, 1H), 7.68 (t, J=53.2 Hz, 1H), 3.88-3.91 (m, 4H), 3.22-3.27 (m, 4H), 1.40-1.41 (m, 2H), 1.24-1.25 (m, 2H), 1.16 (s, 9H). LCMS calc. for $C_{25}H_{26}F_2N_9O_3S_3$ $[M-H]^-$: m/z=634.1; Found: 633.9.

Example 71: N-(1-Cyanocyclopropyl)-9-(5-(difluoromethyl)-1,3,4-thiadiazol-2-yl)-4-(5-(oxetane-3-carbonyl)hexahydropyrrolo[3,4-c]pyrrol-2(1H)-yl)-9H-pyrimido[4,5-b]indole-7-sulfonamide

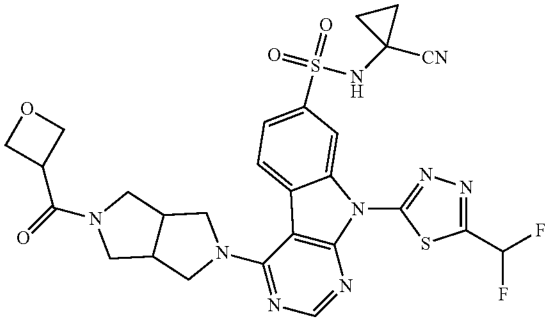 [SMILES: N#CC1(NS(=O)(=O)c2ccc3c4c(N5CC6CN(C(=O)C7COC7)CC6C5)ncnc4n(-c4nnc(C(F)F)s4)c3c2)CC1]

Step 1: N-(1-cyanocyclopropyl)-9-(5-(difluoromethyl)-1,3,4-thiadiazol-2-yl)-4-(hexahydropyrrolo[3,4-c]pyrrol-2(1H)-yl)-9H-pyrimido[4,5-b]indole-7-sulfonamide

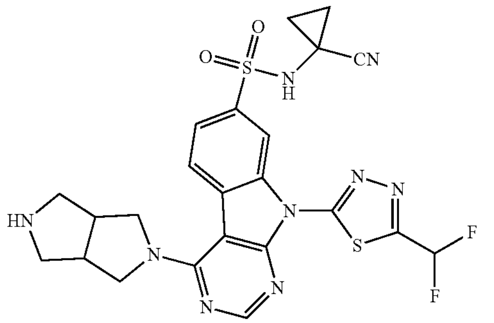 [SMILES: N#CC1(NS(=O)(=O)c2ccc3c4c(N5CC6CNCC6C5)ncnc4n(-c4nnc(C(F)F)s4)c3c2)CC1]

This compound was prepared using procedures analogous to those described for Example 65 Step 1-3 using 4-chloro-N-(1-cyanocyclopropyl)-9H-pyrimido[4,5-b]indole-7-sulfonamide (Intermediate 1) and tert-butyl hexahydropyrrolo[3,4-c]pyrrole-2(1H)-carboxylate as the starting material in step 1. LCMS calc. for $C_{23}H_{22}F_2N_9O_2S_2$ $[M+H]^+$: m/z=558.1; Found: 558.1.

Step 2: N-(1-cyanocyclopropyl)-9-(5-(difluoromethyl)-1,3,4-thiadiazol-2-yl)-4-(5-(oxetane-3-carbonyl)hexahydropyrrolo[3,4-c]pyrrol-2(1H)-yl)-9H-pyrimido[4,5-b]indole-7-sulfonamide This compound was prepared using procedures analogous to those described for Example 65 Step 4 using N-(1-cyanocyclopropyl)-9-(5-(difluoromethyl)-1,3,4-thiadiazol-2-yl)-4-(hexahydropyrrolo[3,4-c]pyrrol-2(1H)-yl)-9H-pyrimido[4,5-b]indole-7-sulfonamide and oxetane-3-carboxylic acid. $^1H$ NMR: (400 MHz, DMSO-$d_6$) δ 9.51 (d, J=2.0 Hz, 1H), 9.37 (s, 1H), 8.67 (s, 1H), 8.50 (d, J=8.8 Hz, 1H), 7.94 (dd, J=6.8 Hz, 2.0 Hz, 1H), 7.68 (t, J=53.2 Hz, 1H), 4.66-4.71 (m, 2H), 4.20-4.29 (m, 2H), 4.03-4.07 (s, 1H), 3.86-3.95 (m, 2H), 3.62-3.67 (m, 2H), 3.52-3.56 (m, 2H), 3.28-3.32 (m, 2H), 3.04-3.12 (m, 2H), 1.42-1.45 (m, 2H), 1.26-1.30 (m, 2H). LCMS calc. for $C_{27}H_{26}F_2N_9O_4S_2$ $[M+H]^+$: m/z=642.1; Found: 642.1.

Example 72: (S)-4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N,3-trimethylpiperazine-1-carboxamide

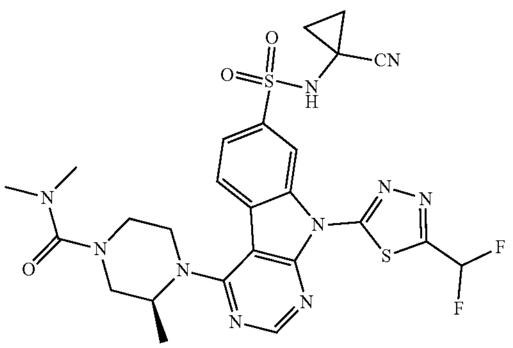 [SMILES: C[C@H]1CN(C(=O)N(C)C)CCN1c1ncnc2c1c1ccc(S(=O)(=O)NC3(C#N)CC3)cc1n2-c1nnc(C(F)F)s1]

Step 1: (S)—N-(1-cyanocyclopropyl)-9-(5-(difluoromethyl)-1,3,4-thiadiazol-2-yl)-4-(2-methylpiperazin-1-yl)-9H-pyrimido[4,5-b]indole-7-sulfonamide

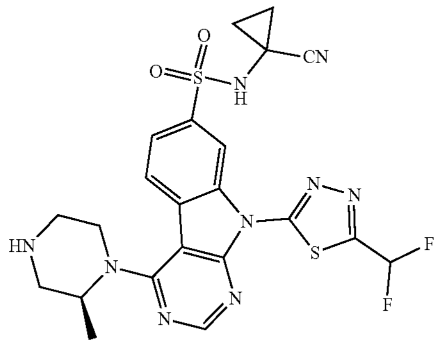 [SMILES: C[C@H]1CNCCN1c1ncnc2c1c1ccc(S(=O)(=O)NC3(C#N)CC3)cc1n2-c1nnc(C(F)F)s1]

This compound was prepared using procedures analogous to those described for Example 65 Step 1-3 using 4-chloro-N-(1-cyanocyclopropyl)-9H-pyrimido[4,5-b]indole-7-sulfonamide (Intermediate 1) and tert-butyl (3S)-3-methylpiperazine-1-carboxylate as the starting material in step 1. LCMS calc. for $C_{22}H_{22}F_2N_9O_2S_2$ $[M+H]^+$: m/z=546.1; Found: 546.0.

Step 2: (S)-4-(7-(N-(1-cyanocyclopropyl)sulfamoyl)-9-(5-(difluoromethyl)-1,3,4-thiadiazol-2-yl)-9H-pyrimido[4,5-b]indol-4-yl)-N,N,3-trimethylpiperazine-1-carboxamide To a solution of (S)—N-(1-cyanocyclopropyl)-9-(5-(difluoromethyl)-1,3,4-thiadiazol-2-yl)-4-(2-methylpiperazin-1-yl)-9H-pyrimido[4,5-b]indole-7-sulfonamide (10 mg, 0.017 mmol) in DCM (2.5 mL) was added TEA (10.4 mg, 0.1 mmol) and DMAP (0.042 mg), followed by slowly addition of dimethylcarbamyl chloride (1.83 mg, 0.017 mmol) at 0° C. The reaction mixture was stirred at 20° C. for 6 h., and concentrated under reduced pressure. The residue was purified by prep-HPLC on a C18 column eluting with MeCN/water (45%-75% with 0.5% TFA) to afford the title compound (1.42 mg, 12.5% yield) as off-white solid. $^1H$ NMR (400 MHz, DMSO-$d_6$) δ 9.54 (s, 1H), 9.50 (s, 1H), 8.82 (s, 1H), 8.06 (s, 2H), 7.68 (t, J=53.2 Hz, 1H), 4.79-4.81 (m, 1H), 3.97-4.00 (m, 1H), 3.80-3.83 (m, 1H), 3.67-3.77 (m, 1H), 3.54-3.57 (m, 1H), 3.01-3.04 (m, 1H), 2.82 (s, 6H), 1.42-1.45 (m, 2H), 1.36 (d, J=6.8 Hz, 3H), 1.27-1.29 (m, 3H). LCMS calc. for $C_{25}H_{27}F_2N_{10}O_3S_2[M+H]^+$: m/z=617.2; Found: 617.3.

Example 73: (R)-4-(7-(N-(1-Cyanocyclopropyl) sulfamoyl)-9-(5-(difluoromethyl)-1,3,4-thiadiazol-2-yl)-9H-pyrimido[4,5-b]indol-4-yl)-N,N,3-trimethylpiperazine-1-carboxamide

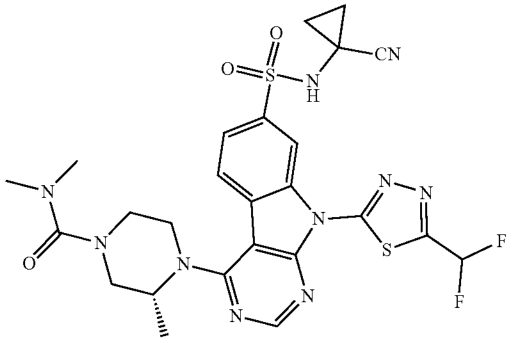 [SMILES: C[C@@H]1CN(C(=O)N(C)C)CCN1c1ncnc2c1c1ccc(S(=O)(=O)NC3(C#N)CC3)cc1n2-c1nnc(C(F)F)s1]

Step 1: (R)—N-(1-cyanocyclopropyl)-9-(5-(difluoromethyl)-1,3,4-thiadiazol-2-yl)-4-(2-methylpiperazin-1-yl)-9H-pyrimido[4,5-b]indole-7-sulfonamide

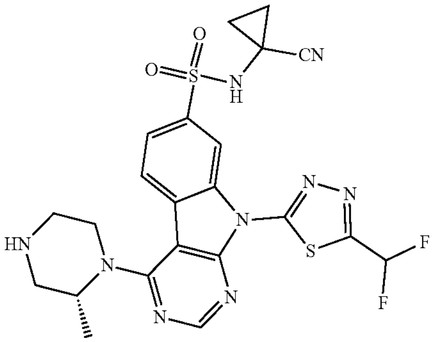 [SMILES: C[C@@H]1CNCCN1c1ncnc2c1c1ccc(S(=O)(=O)NC3(C#N)CC3)cc1n2-c1nnc(C(F)F)s1]

This compound was prepared using procedures analogous to those described for Example 65 Step 1-3 using 4-chloro-N-(1-cyanocyclopropyl)-9H-pyrimido[4,5-b]indole-7-sulfonamide (Intermediate 1) and tert-butyl (3R)-3-methylpiperazine-1-carboxylate as the starting material in step 1. LCMS calc. for $C_{22}H_{22}F_2N_9O_2S_2$ $[M+H]^+$: m/z=546.1; Found: 546.0.

Step 2: (R)-4-(7-(N-(1-cyanocyclopropyl)sulfamoyl)-9-(5-(difluoromethyl)-1,3,4-thiadiazol-2-yl)-9H-pyrimido[4,5-b]indol-4-yl)-N,N,3-trimethylpiperazine-1-carboxamide To a solution of (R)—N-(1-cyanocyclopropyl)-9-(5-(difluoromethyl)-1,3,4-thiadiazol-2-yl)-4-(2-methylpiperazin-1-yl)-9H-pyrimido[4,5-b]indole-7-sulfonamide (10 mg, 0.017 mmol, HCl salt) in DCM (1 mL) was added TEA (10.4 mg, 0.1 mmol) and DMAP (0.042 mg, 0.344 umol), followed by slow addition of N,N-dimethylcarbamoyl chloride (2.77 mg, 0.026 mmol) at 0° C. The reaction mixture was stirred at 20° C. for 6 h. The mixture was concentrated under reduced pressure. The residue was purified by prep-HPLC on a C18 column eluting with MeCN/water (45%-75%, TFA) to afford the title compound (2.11 mg, 8.91% yield) as off-white solid. $^1H$ NMR: (400 MHz, DMSO) δ 9.50 (s, 1H), 9.41 (s, 1H), 8.82 (s, 1H), 8.05 (s, 2H), 7.68 (t, J=53.2 Hz, 1H), 4.79-4.85 (m, 1H), 3.98 (d, J=13.2 Hz, 2H), 3.80 (t, J=11.6 Hz, 1H), 3.69 (t, J=12.8 Hz, 1H), 3.25 (d, J=3.2 Hz, 1H), 3.02 (t, J=2.0 Hz, 1H), 2.82 (s, 6H), 1.45-1.41 (m, 2H), 1.36 (d, J=36.4 Hz, 3H), 1.27 (t, J=5.2 Hz, 3H). LCMS calc. for $C_{25}H_{27}N_{10}S_2O_3F_2$ $[M+H]^+$: m/z=617.2; Found: 617.2.

Example 74: N-(1-Cyanocyclopropyl)-9-(5-(difluoromethyl)-1,3,4-thiadiazol-2-yl)-4-(1-isobutyryl-1,2,3,6-tetrahydropyridin-4-yl)-9H-pyrimido[4,5-b]indole-7-sulfonamide

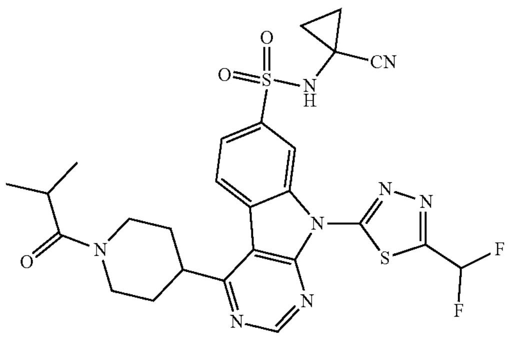 [SMILES: CC(C)C(=O)N1CCC(c2ncnc3c2c2ccc(S(=O)(=O)NC4(C#N)CC4)cc2n3-c2nnc(C(F)F)s2)CC1]

Step 1: tert-butyl 4-(7-(N-(1-cyanocyclopropyl)sulfamoyl)-9H-pyrimido[4,5-b]indol-4-yl)-3,6-dihydropyridine-1(2H)-carboxylate

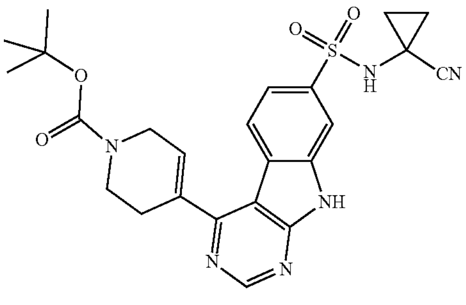 [SMILES: CC(C)(C)OC(=O)N1CC=C(c2ncnc3[nH]c4cc(S(=O)(=O)NC5(C#N)CC5)ccc4c23)CC1]

To a mixture of 4-chloro-N-(1-cyanocyclopropyl)-9H-pyrimido[4,5-b]indole-7-sulfonamide (5.0 g, 14.4 mmol) in dioxane (50 mL) and $H_2O$ (5 mL) was added tert-butyl 4-(4,4,5,5-tetramethyl-1,3,2-dioxaborolan-2-yl)-3,6-dihydropyridine-1(2H)-carboxylate (5.8 g, 18.7 mmol), Pd(dppf)$Cl_2$ (505 mg, 0.72 mmol), $Na_2CO_3$ (4.6 g, 43.2 mmol). The reaction mixture was degassed and recharged with $N_2$ for three cycles, and stirred at 100° C. for 6 h. Then the mixture was cooled to 25° C., diluted with $H_2O$ (30 mL), extracted with DCM (30 mL×3). The combined organic layers were washed with brine (30 mL), dried over $Na_2SO_4$, filtered and concentrated under reduced pressure. The crude product was purified by flash chromatography on a silica gel column eluting with EtOAc/PE (0-70%) to afford the title compound (4.3 g, 60.5% yield). LCMS calc. for $C_{24}H_{27}N_6O_4S$ $[M+H]^+$: m/z=495.2; Found: 495.2.

Step 2: tert-butyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)-3,6-dihydropyridine-1(2H)-carboxylate

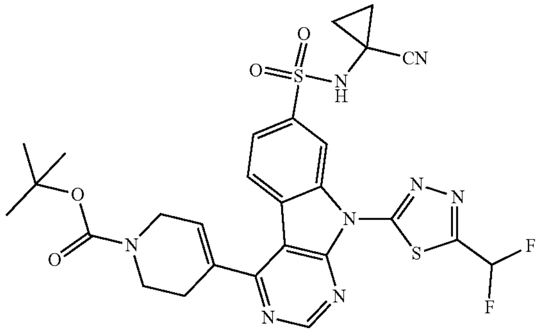 [SMILES: CC(C)(C)OC(=O)N1CC=C(c2ncnc3c2c2ccc(S(=O)(=O)NC4(C#N)CC4)cc2n3-c2nnc(C(F)F)s2)CC1]

To a mixture of tert-butyl 4-(7-(N-(1-cyanocyclopropyl) sulfamoyl)-9H-pyrimido[4,5-b]indol-4-yl)-3,6-dihydropyridine-1(2H)-carboxylate (4.3 g, 8.7 mmol) in dioxane (85 mL) was added CsF (3.9 g, 25.7 mmol), CuI (0.98 g, 5.15 mmol) and (1R,2R)—$N^1$,$N^2$-dimethylcyclohexane-1,2-diamine (1.46 g, 10.3 mmol) and 2-bromo-5-(difluoromethyl)-1,3,4-thiadiazole (5.5 g, 25.7 mmol). The reaction mixture was degassed and recharged with $N_2$ for three cycles, and stirred at 105° C. for 3 h. Then the mixture was cooled to 25° C., diluted with $H_2O$ (250 mL), extracted with DCM (300 mL×3). The combined organic layers were washed with brine (400 mL×2), dried over $Na_2SO_4$, filtered and concentrated under reduced pressure.

The crude product was purified by flash chromatography on a silica gel column eluting with EtOAc/PE (0-70%) to afford the title compound (2.15 g, 39.8% yield). LCMS calc. for $C_{23}H_{19}F_2N_8O_4S_2$ $[M-56+H]^+$: m/z=573.2; Found: 573.1.

Step 3: N-(1-cyanocyclopropyl)-9-(5-(difluoromethyl)-1,3,4-thiadiazol-2-yl)-4-(1,2,3,6-tetrahydropyridin-4-yl)-9H-pyrimido[4,5-b]indole-7-sulfonamide

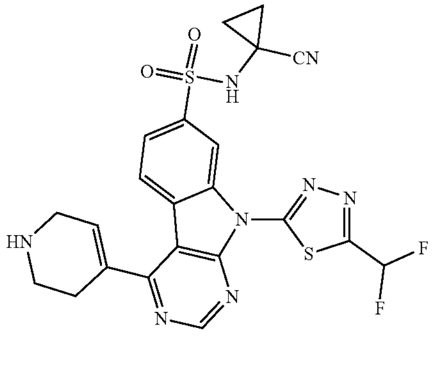 [SMILES: N#CC1(NS(=O)(=O)c2ccc3c4c(C5=CCNCC5)ncnc4n(-c4nnc(C(F)F)s4)c3c2)CC1]

To a solution of tert-butyl 4-(7-(N-(1-cyanocyclopropyl) sulfamoyl)-9-(5-(difluoromethyl)-1,3,4-thiadiazol-2-yl)-9H-pyrimido[4,5-b]indol-4-yl)-3,6-dihydropyridine-1(2H)-carboxylate (1.0 g, 1.59 mmol) in DCM (20 mL) was added TFA (7.0 mL). The reaction mixture was stirred at r.t. for 2 h. The mixture was evaporated under reduced pressure. The residue was slurry with MTBE (30 mL), the solid was collected by filtration, dried in vacuum to afford the title compound (0.99 g, 97.1% yield). LCMS calc. for $C_{22}H_{19}F_2N_8O_2S_2$ $[M+H]^+$: m/z=529.1; Found: 529.2.

Step 4: N-(1-cyanocyclopropyl)-9-(5-(difluoromethyl)-1,3,4-thiadiazol-2-yl)-4-(1-isobutyryl-1,2,3,6-tetrahydropyridin-4-yl)-9H-pyrimido[4,5-b]indole-7-sulfonamide To a solution of N-(1-cyanocyclopropyl)-9-(5-(difluoromethyl)-1,3,4-thiadiazol-2-yl)-4-(1,2,3,6-tetrahydropyridin-4-yl)-9H-pyrimido[4,5-b]indole-7-sulfonamide (0.99 g, 1.75 mmol) in THF (30 mL) and $H_2O$ (2 mL) was added sodium bicarbonate (2.0 g, 23.8 mmol). To the mixture was dropwise added isobutyryl chloride (0.265 g 2.49 mmol) at 0-10° C., stirred at 0-10° C. for 2 h. The reaction mixture was poured into water (80 mL), stirred at r.t. for 30 min.

The mixture was concentrated under reduced pressure. The residue was purified by prep-HPLC on a C18 column eluting with MeCN/water (30%-50%) to afford the title compound (0.42 g 44.6% yield) as white solid. $^1H$ NMR: (400 MHz, DMSO-$d_6$) δ 9.48 (d, J=1.6 Hz, 1H), 9.43 (s, 1H), 9.24 (s, 1H), 8.49-8.54 (m, 1H), 7.97 (d, J=8.0 Hz, 1H), 7.65 (t, J=53.2 Hz, 1H), 6.60 (d, J=15.2 Hz, 1H), 4.45 (br s, 1H), 4.31 (br s, 1H), 3.81 (br s, 2H), 2.94-3.01 (m, 1H), 2.79 (br.s, 1H), 2.67 (br.s, 1H), 1.36-1.39 (m, 2H), 1.18-1.22 (m, 2H), 1.03 (d, J=6.8 Hz, 6H). LCMS calc. for $C_{26}H_{25}F_2N_8O_3S_2$ $[M+H]^+$: m/z=599.1; Found: 599.2. LCMS calc. for $C_{26}H_{25}F_2N_8O_3S_2$ $[M+H]^+$: m/z=599.1; Found: 599.2.

Example 75: N-(1-Cyanocyclopropyl)-9-(5-(difluoromethyl)-1,3,4-thiadiazol-2-yl)-4-(1-isobutyryl-1,2,3,4-tetrahydropyridin-4-yl)-9H-pyrimido[4,5-b]indole-7-sulfonamide

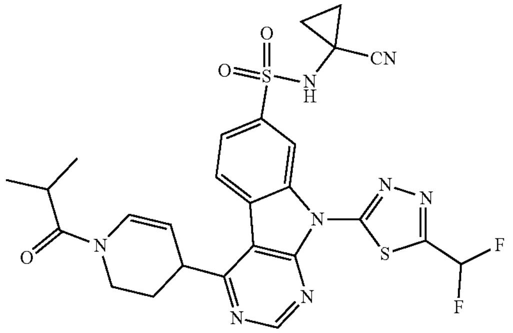 [SMILES: CC(C)C(=O)N1C=CC(c2ncnc3c2c2ccc(S(=O)(=O)NC4(C#N)CC4)cc2n3-c2nnc(C(F)F)s2)CC1]

To a solution of N-(1-cyanocyclopropyl)-9-(5-(difluoromethyl)-1,3,4-thiadiazol-2-yl)-4-(1-isobutyryl-1,2,3,6-tetrahydropyridin-4-yl)-9H-pyrimido[4,5-b]indole-7-sulfonamide (0.8 g, 1.34 mmol) in dioxane (16 mL) was added cesium carbonate (870.8 mg, 2.67 mmol). The reaction mixture was stirred at 100° C. for 1 h. After cooled to r.t., the mixture was concentrated under reduced pressure. The crude residue was purified by flash chromatography on a silica gel column eluting with PE/EtOAc (0-100%) to afford the crude compound. The residue was further purified by prep-HPLC eluting with MeCN/$H_2O$ (10% to 80% with 0.05% $NH_4HCO_3$) to afford the title product (520 mg, 66% yield) as white solid. $^1H$ NMR: (400 MHz, DMSO-$d_6$) δ 9.54 (d, J=1.2 Hz, 1H), 9.29 (s, 1H), 8.65 (t, J=8.4 Hz, 1H), 8.10 (d, J=9.6 Hz, 1H), 7.70 (t, J=53.2 Hz, 1H), 7.18-7.36 (m, 1H), 5.21-5.24 (m, 1H), 4.69 (brs, 1H), 4.02-4.06 (m, 1H), 3.71 (t, J=2.8 Hz, 1H), 3.07-3.12 (m, 2H), 2.32-2.33 (t, 2H), 2.10-2.25 (m, 1H), 1.42-1.46 (m, 2H), 1.25-1.29 (m, 2H), 1.08 (d, J=6.4 Hz, 6H). LCMS calc. for $C_{26}H_{25}F_2N_8O_3S_2$ $[M+H]^+$: m/z=599.1; Found: 599.2.

Example 76: N-(1-Cyanocyclopropyl)-9-(5-(difluoromethyl)-1,3,4-thiadiazol-2-yl)-4-(1-isobutyrylpiperidin-4-yl)-9H-pyrimido[4,5-b]indole-7-sulfonamide

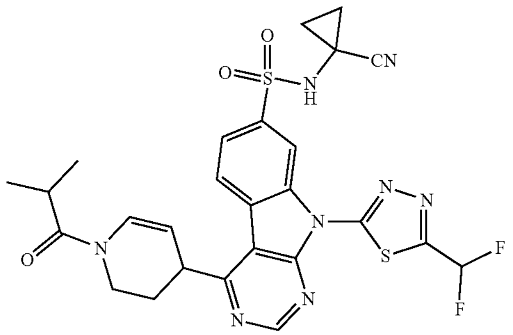 [SMILES: CC(C)C(=O)N1C=CC(c2ncnc3c2c2ccc(S(=O)(=O)NC4(C#N)CC4)cc2n3-c2nnc(C(F)F)s2)CC1]

To a mixture of N-(1-cyanocyclopropyl)-9-(5-(difluoromethyl)-1,3,4-thiadiazol-2-yl)-4-(1-isobutyryl-1,2,3,6-tetrahydropyridin-4-yl)-9H-pyrimido[4,5-b]indole-7-sulfonamide (20 mg, 0.034 mmol, Example 74) in THF (1 mL) was added Pd/C (36 mg, 10% wet). The reaction mixture was degassed and recharged with $H_2$ for three cycles, and stirred at 20° C. for 4 h. at $H_2$ (15 psi). The reaction mixture was filtered and concentrated under reduced pressure. The residue was purified by prep-HPLC on a C18 column eluting with MeCN/water (35%-55% with 1% $NH_4HCO_3$) to afford the title compound (3.59 mg, 3.59% yield) as off-white solid. $^1H$ NMR: (400 MHz, DMSO-$d_6$) δ 9.53 (s, 1H), 9.30 (s, 1H), 8.68 (d, J=8.4 Hz, 1H), 8.08 (dd, J=8.4 Hz, 1.6 Hz, 1H), 7.72 (t, J=53.6 Hz, 1H), 4.60-4.64 (m, 1H), 4.15-4.18 (m, 1H), 4.01-4.07 (m, 1H), 3.88 (br.s, 1H), 2.94-3.06 (m, 2H), 1.94-2.04 (m, 3H), 1.78-1.81 (m, 1H), 1.37 (br.s, 2H), 1.22 (t, J=4.8 Hz, 2H), 1.10 (d, J=6.8 Hz, 2H), 1.06 (s, 4H). LCMS calc. for $C_{26}H_{27}F_2N_8O_3S_2$ $[M+H]^+$: m/z=601.2; Found: 601.2.

Example 77: N-(1-Cyanocyclopropyl)-9-(5-(difluoromethyl)-1,3,4-thiadiazol-2-yl)-4-(1-methyl-1,2,3,6-tetrahydropyridin-4-yl)-9H-pyrimido[4,5-b]indole-7-sulfonamide

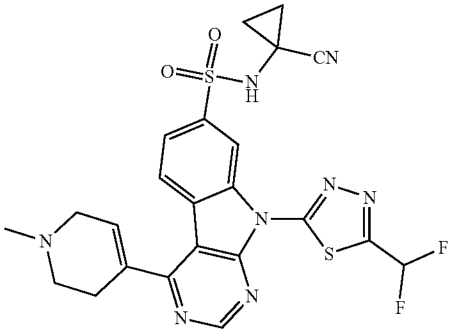 [SMILES: CN1CC=C(c2ncnc3c2c2ccc(S(=O)(=O)NC4(C#N)CC4)cc2n3-c2nnc(C(F)F)s2)CC1]

This compound was prepared using procedures analogous to those described for Example 74 Step 1-2 using 4-chloro-N-(1-cyanocyclopropyl)-9H-pyrimido[4,5-b]indole-7-sulfonamide (Intermediate 1) and 1-methyl-4-(4,4,5,5-tetramethyl-1,3,2-dioxaborolan-2-yl)-1,2,3,6-tetrahydropyridine as the starting material in Step 1. $^1H$ NMR (400 MHz, DMSO-$d_6$) δ 9.55 (d, J=1.6 Hz, 1H), 9.29 (s, 1H), 8.54 (d, J=8.4 Hz, 1H), 8.04 (dd, J=8.4 Hz, 1.6 Hz, 1H), 7.72 (t, J=53.6 Hz, 1H), 6.61 (s, 1H), 3.30 (s, 2H), 2.75-2.78 (m, 4H), 2.42 (s, 3H), 1.44-1.47 (m, 2H), 1.26-1.29 (m, 2H). LCMS calc. for $C_{23}H_{21}F_2N_8O_2S_2$ $[M+H]^+$: m/z=543.1; Found: 543.1.

Example 78: N-(1-Cyanocyclopropyl)-9-(5-(difluoromethyl)-1,3,4-thiadiazol-2-yl)-4-(3,6-dihydro-2H-pyran-4-yl)-9H-pyrimido[4,5-b]indole-7-sulfonamide

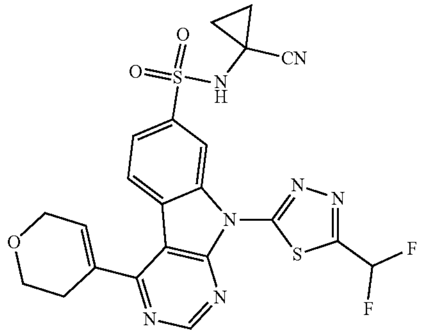 [SMILES: N#CC1(NS(=O)(=O)c2ccc3c4c(C5=CCOCC5)ncnc4n(-c4nnc(C(F)F)s4)c3c2)CC1]

Step 1: N-(1-cyanocyclopropyl)-4-(3,6-dihydro-2H-pyran-4-yl)-9H-pyrimido[4,5-b]indole-7-sulfonamide

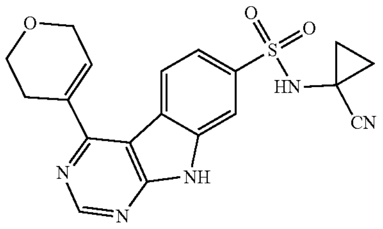

This compound was prepared using procedures analogous to those described for Example 74 Step 1 using 4-chloro-N-(1-cyanocyclopropyl)-9H-pyrimido[4,5-b]indole-7-sulfonamide (Intermediate 1) and 4-(4,4,5,5-tetramethyl-1,3,2-dioxaborolan-2-yl)-1,2,3,6-tetrahydropyridine. LCMS calc. for $C_{19}H_{18}N_5O_3S$ $[M+H]^-$: m/z=396.1; Found: 396.1.

Step 2: N-(1-Cyanocyclopropyl)-9-(5-(difluoromethyl)-1,3,4-thiadiazol-2-yl)-4-(3,6-dihydro-2H-pyran-4-yl)-9H-pyrimido[4,5-b]indole-7-sulfonamide This compound was prepared using procedures analogous to those described for Example 44 Step 2 using N-(1-cyanocyclopropyl)-4-(3,6-dihydro-2H-pyran-4-yl)-9H-pyrimido[4,5-b]indole-7-sulfonamide and 2-bromo-5-(difluoromethyl)-1,3,4-thiadiazole. $^1H$ NMR (400 MHz, DMSO-$d_6$) δ 9.54 (d, J=1.6 Hz, 1H), 9.50 (s, 1H), 9.31 (s, 1H), 8.60 (d, J=8.4 Hz, 1H), 8.035 (dd, J=8.4 Hz, 1.6 Hz, 1H), 7.71 (t, J=53.2 Hz, 1H), 6.72 (s, 1H), 4.48 (d, J=2.4 Hz, 2H), 3.99 (t, J=5.2 Hz, 2H), 2.76 (s, 2H), 1.43-1.47 (m, 2H), 1.25-1.29 (m, 2H). LCMS calc. for $C_{22}H_{18}F_2N_7O_3S_2$ $[M+H]^+$: m/z=530.1; Found: 530.2.

Example 79: N-(1-Cyanocyclopropyl)-9-(5-(difluoromethyl)-1,3,4-thiadiazol-2-yl)-4-(tetrahydro-2H-pyran-4-yl)-9H-pyrimido[4,5-b]indole-7-sulfonamide

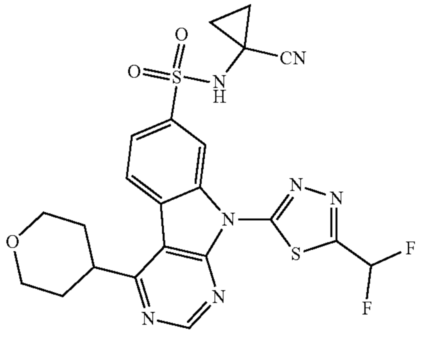 [SMILES: N#CC1(NS(=O)(=O)c2ccc3c4c(C5CCOCC5)ncnc4n(-c4nnc(C(F)F)s4)c3c2)CC1]

Step 1: N-(1-cyanocyclopropyl)-4-(3,6-dihydro-2H-pyran-4-yl)-9H-pyrimido[4,5-b]indole-7-sulfonamide

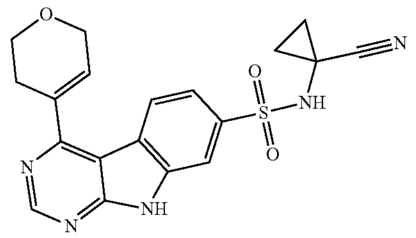 [SMILES: N#CC1(NS(=O)(=O)c2ccc3c(c2)[nH]c2ncnc(C4=CCOCC4)c23)CC1]

This compound was prepared using procedures analogous to those described for Example 74 Step 1 using 2-(3,6-dihydro-2H-pyran-4-yl)-4,4,5,5-tetramethyl-1,3,2-dioxaborolane to replace tert-butyl 4-(4,4,5,5-tetramethyl-1,3,2-dioxaborolan-2-yl)-3,6-dihydropyridine-1(2H)-carboxylate. LCMS calc. for $C_{19}H_{18}N_5O_3S$ $[M+H]^-$: m/z=396.1; found: 396.1.

Step 2: N-(1-cyanocyclopropyl)-4-(tetrahydro-2H-pyran-4-yl)-9H-pyrimido[4,5-b]indole-7-sulfonamide

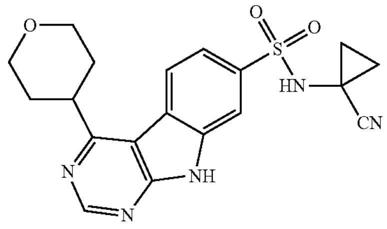

This compound was prepared using procedures analogous to those described for Example 76 using N-(1-cyanocyclopropyl)-4-(3,6-dihydro-2H-pyran-4-yl)-9H-pyrimido[4,5-b]indole-7-sulfonamide. LCMS calc. for $C_{19}H_{18}N_5O_3S$ $[M-H]^-$: m/z=396.1; Found: 396.1.

Step 3: N-(1-cyanocyclopropyl)-9-(5-(difluoromethyl)-1,3,4-thiadiazol-2-yl)-4-(tetrahydro-2H-pyran-4-yl)-9H-pyrimido[4,5-b]indole-7-sulfonamide This compound was prepared using procedures analogous to those described for Example 44 Step 2 using N-(1-cyanocyclopropyl)-4-(tetrahydro-2H-pyran-4-yl)-9H-pyrimido[4,5-b]indole-7-sulfonamide and 2-bromo-5-(difluoromethyl)-1,3,4-thiadiazole. $^1H$ NMR (400 MHz, DMSO-d6) δ 9.55 (d, J=1.2 Hz, 1H), 9.52 (s, 1H), 9.33 (s, 1H), 8.67 (d, J=8.4 Hz, 1H), 8.10 (dd, J=8.4 Hz, 1.6 Hz, 1H), 7.71 (t, J=53.2 Hz, 1H), 4.00-4.06 (m, 3H), 3.73-3.99 (m, 2H), 2.05-2.09 (m, 2H), 1.90 (d, J=11.6 Hz, 2H), 1.45 (t, J=2.8 Hz, 2H), 1.29 (t, J=5.2 Hz, 2H). LCMS calc. for $C_{22}H_{20}F_2N_7O_3S_2[M+H]^+$: m/z=532.1; Found: 532.1.

Example 80: N-(1-Cyanocyclopropyl)-9-(5-(difluoromethyl)-1,3,4-thiadiazol-2-yl)-4-(4-hydroxypiperidin-1-yl)-9H-pyrido[2,3-b]indole-7-sulfonamide

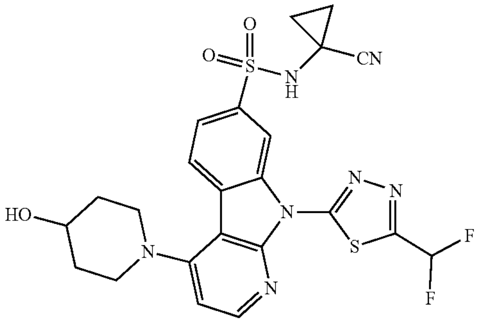 [SMILES: N#CC1(NS(=O)(=O)c2ccc3c4c(N5CCC(O)CC5)ccnc4n(-c4nnc(C(F)F)s4)c3c2)CC1]

Step 1: N-(1-cyanocyclopropyl)-4-(4-hydroxypiperidin-1-yl)-9H-pyrido[2,3-b]indole-7-sulfonamide

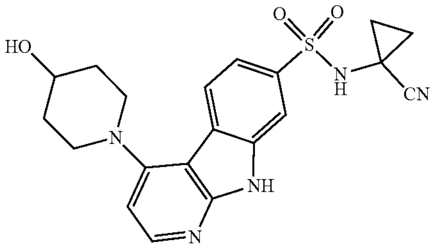 [SMILES: N#CC1(NS(=O)(=O)c2ccc3c(c2)[nH]c2nccc(N4CCC(O)CC4)c23)CC1]

To a mixture of 4-bromo-N-(1-cyanocyclopropyl)-9H-pyrido[2,3-b]indole-7-sulfonamide (2.80 g, 7.16 mmol, Intermediate 5) and piperidin-4-ol (1.45 g, 14.3 mmol) in dioxane (45 mL) was added $Cs_2CO_3$ (4.66 g, 14.3 mmol) and t-BuXPhos Pd G3 (569 mg, 0.72 mmol) at 20° C. under $N_2$. The reaction mixture was degassed and recharged with $N_2$ for three cycles, and stirred at 100° C. overnight. After cooled to r.t., the mixture was diluted with DMF (10 mL), filtered through a pad of diatomite. The filtrate was concentrated under reduced pressure. The residue was purified by prep-HPLC on a C18 column eluting with MeCN/water (5-40% with 0.5% TFA) to afford the title compound (840 mg, 22.3% yield) as a white solid. $^1$H NMR: (400 MHz, DMSO-$d_6$) δ 12.6 (s, 1H), 9.16 (s, 1H), 8.32 (d, J=4.0 Hz, 1H), 7.99-8.06 (m, 2H), 7.78 (d, J=8.0 Hz, 1H), 6.98 (d, J=4.0 Hz, 1H), 3.28-3.86 (m, 5H), 1.99-2.02 (m, 2H), 1.66-1.77 (m, 2H), 1.39-1.42 (m, 2H), 1.23-1.28 (m, 2H). LCMS calc. for $C_{20}H_{22}N_5O_3S$ [M+H]$^-$: m/z=412.1; Found: 412.1.

Step 2: N-(1-cyanocyclopropyl)-9-(5-(difluoromethyl)-1,3,4-thiadiazol-2-yl)-4-(4-hydroxypiperidin-1-yl)-9H-pyrido[2,3-b]indole-7-sulfonamide This compound was prepared using procedures analogous to those described for Example 44 Step 2 using N-(1-cyanocyclopropyl)-4-(4-hydroxypiperidin-1-yl)-9H-pyrido[2,3-b]indole-7-sulfonamide and 2-bromo-5-(difluoromethyl)-1,3,4-thiadiazole. $^1$H NMR: (400 MHz, DMSO-$d_6$) δ 9.53 (d, J=1.2 Hz, 1H), δ 9.36 (s, 1H), 8.54 (d, J=6.0 Hz, 1H), 8.07-8.14 (m, 2H), 7.67 (t, J=53.2 Hz, 1H), 7.20 (d, J=6.0 Hz, 1H), 4.90 (d, J=3.6 Hz, 1H), 3.84 (t, J=3.6 Hz, 1H), 3.59 (t, J=8.4 Hz, 2H), 3.15-3.20 (m, 2H), 2.02-2.04 (m, 2H), 1.75-1.77 (m, 2H), 1.41-1.44 (m, 2H), 1.29 (t, J=4.8 Hz, 2H). LCMS calc. for $C_{23}H_{22}F_2N_7O_3S_2$ [M+H]$^+$: m/z=546.1; Found: 546.1.

Example 81: 4-(9-(5-(Difluoromethyl)-1,3,4-thiadiazol-2-yl)-6-fluoro-7-(N-(1-methyl cyclopropyl) sulfamoyl)-9H-pyrimido[4,5-b]indol-4-yl)-N,N-dimethyl-3,6-dihydropyridine-1(2H)-carboxamide

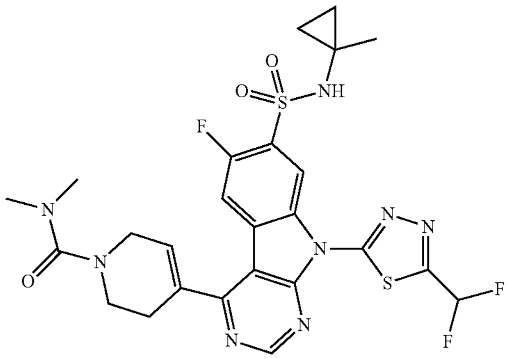 [SMILES: CN(C)C(=O)N1CC=C(c2ncnc3c2c2cc(F)c(S(=O)(=O)NC4(C)CC4)cc2n3-c2nnc(C(F)F)s2)CC1]

Step 1: N, N-dimethyl-4-oxopiperidine-1-carboxamide

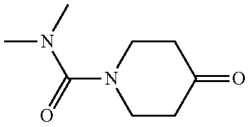

To a solution of piperidin-4-one hydrochloride (2 g, 14.8 mmol) and triethylamine (10.45 g, 103.2 mmol) in dichloromethane (30 mL) was added dropwise dimethylcarbamic chloride (3.17 g, 29.5 mmol) at 0° C. The mixture was warmed to room temperature and stirred for 16 hours. The resulting mixture was poured into water (20 mL), and extracted with EtOAc (20 mL×3). The combined organic layers were dried over anhydrous $Na_2SO_4$, filtered and concentrated under reduced pressure, which was purified by flash chromatography on a silica gel column eluting with EtOAc/Hexanes (0-50%) to afford the title compound (2.56 g, 94% yield). $^1$H NMR (400 MHz, $CDCl_3$) δ 3.48 (t, J=6.0 Hz, 4H), 2.85 (s, 6H), 2.44 (t, J=6.0 Hz, 4H).

Step 2: 1-(dimethylcarbamoyl)-1, 2, 3, 6-tetrahydropyridin-4-yl trifluoromethanesulfonate

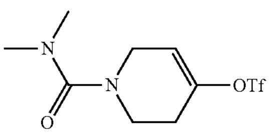

A solution of N, N-dimethyl-4-oxopiperidine-1-carboxamide (2 g, 11.8 mmol) in tetrahydrofuran (15 mL) was cooled to −78° C. and lithium hexamethyldisilazide (17.6 mL, 1 M solution in tetrahydrofuran) was added dropwise under nitrogen atmosphere. After the resulting reaction was stirred for 0.5 h., a solution of 1,1,1-trifluoro-N-phenyl-N-((trifluoromethyl) sulfonyl) methanesulfonamide (6.3 g, 17.6 mmol) was added to the reaction mixture. The resulting solution was warmed slowly to room temperature and stirred for 16 h. The resulting mixture was poured into ice water (20 mL), and extracted with EtOAc (20 mL×3). The combined organic layers were dried over anhydrous sodium sulphate, filtered and concentrated under reduced pressure. The residue was purified by flash chromatography on a silica gel column eluting with EtOAc/Hexanes (0-50%) to afford the title compound (2.06 g, 58% yield). $^1$H NMR (400 MHz, $CDCl_3$) δ 5.91-5.62 (m, 1H), 3.88 (q, J=2.8 Hz, 2H), 3.43 (t, J=5.6 Hz, 2H), 2.86 (s, 6H), 2.52 (q, J=2.8 Hz, 2H).

Step 3: N, N-dimethyl-4-(4,4,5,5-tetramethyl-1,3,2-dioxaborolan-2-yl)-3,6-dihydropyridine-1(2H)-carboxamide

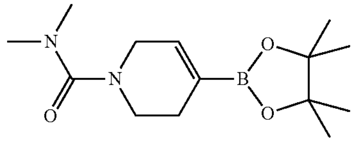

A mixture of 1-(dimethylcarbamoyl)-1,2,3,6-tetrahydropyridin-4-yl trifluoromethanesulfonate (2 g, 6.6 mmol), 4,4,4',4',5,5,5',5'-octamethyl-2,2'-bi(1,3,2-dioxaborolane) (2.52 g, 9.9 mmol), $Pd(dppf)_2Cl_2$ (960 mg, 1.3 mmol) and potassium acetate (1.95 g, 19.8 mmol) in dioxane (40 mL) was degassed and recharged with nitrogen for three cycles, and then stirred at 90° C. for 2 h. The reaction was filtered and the filtrate was diluted with water (20 mL), extracted with EtOAc (20 mL×3). The combined organic layers were dried over anhydrous sodium sulphate, filtered and concentrated under reduced pressure. The residue was purified by flash chromatography on a silica gel column eluting with EtOAc/Hexanes (0-30%) to afford the title compound (1.6 g, 86% yield). $^1$H NMR (400 MHz, $CDCl_3$) δ 6.50 (s, 1H), 3.82 (s, 2H), 3.27 (t, J=4.8 Hz, 2H), 2.83 (s, 6H), 2.30 (s, 2H), 1.26 (s, 12H).

Step 4: 4-(6-fluoro-7-(N-(1-methylcyclopropyl)sulfamoyl)-9H-pyrimido[4,5-b]indol-4-yl)-N,N-dimethyl-3,6-dihydropyridine-1(2H)-carboxamide

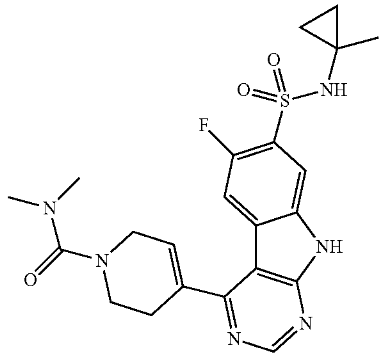

This compound was prepared using procedures analogous to those described for Example 74 Step 1 using 4-chloro-6-fluoro-N-(1-methylcyclopropyl)-9H-pyrimido[4,5-b]indole-7-sulfonamide (Intermediate 3) and N,N-dimethyl-4-(4,4,5,5-tetramethyl-1,3,2-dioxaborolan-2-yl)-3,6-dihydropyridine-1(2H)-carboxamide. LCMS calc. for $C_{22}H_{26}FN_6O_3S$ $[M+H]^+$: m/z=473.2; Found: 473.2.

Step 5: 4-(9-(5-(difluoromethyl)-1,3,4-thiadiazol-2-yl)-6-fluoro-7-(N-(1-methylcyclopropyl) sulfamoyl)-9H-pyrimido[4,5-b]indol-4-yl)-N,N-dimethyl-3,6-dihydropyridine-1(2H)-carboxamide This compound was prepared using procedures analogous to those described for Example 74 Step 2 using 4-(6-fluoro-7-(N-(1-methylcyclopropyl)sulfamoyl)-9H-pyrimido[4,5-b]indol-4-yl)-N,N-dimethyl-3,6-dihydropyridine-1(2H)-carboxamide and 2-bromo-5-(difluoromethyl)-1,3,4-thiadiazole to afford the title compound as white solid. $^1$H NMR (400 MHz, DMSO-$d_6$) δ 9.50 (d, J=6.3 Hz, 1H), 9.29 (s, 1H), 8.70 (s, 1H), 8.21 (d, J=10.2 Hz, 1H), 7.71 (t, J=53.2 Hz, 1H), 6.63 (s, 1H), 4.07 (d, J=2.6 Hz, 2H), 3.53 (t, J=5.5 Hz, 2H), 2.85 (s, 6H), 2.76 (s, 2H), 1.19 (s, 3H), 0.70 (t, J=5.6 Hz, 2H), 0.45 (q, J=5.0 Hz, 2H). LCMS calc. for $C_{25}H_{26}F_3N_8O_3S_2$ $[M+H]^+$: m/z=607.2; Found: 607.2.

Example 82: 4-(9-(5-(Difluoromethyl)-1,3,4-thiadiazol-2-yl)-6-fluoro-7-(N-(1-methyl cyclopropyl) sulfamoyl)-9H-pyrimido[4,5-b]indol-4-yl)-N,N-dimethylpiperidine-1-carboxamide

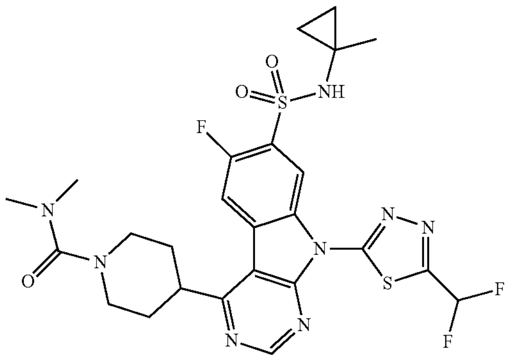 [SMILES: CN(C)C(=O)N1CCC(c2ncnc3c2c2cc(F)c(S(=O)(=O)NC4(C)CC4)cc2n3-c2nnc(C(F)F)s2)CC1]

Step 1: 4-(6-fluoro-7-(N-(1-methylcyclopropyl)sulfamoyl)-9H-pyrimido[4,5-b]indol-4-yl)-N,N-dimethylpiperidine-1-carboxamide

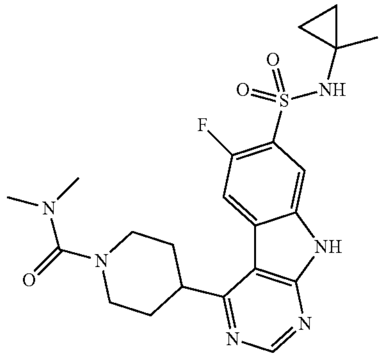

To a solution of 4-(6-fluoro-7-(N-(1-methylcyclopropyl) sulfamoyl)-9H-pyrimido[4,5-b]indol-4-yl)-N,N-dimethyl-3,6-dihydropyridine-1(2H)-carboxamide (100 mg, 0.2 mmol, Example 81 Step 4) in methanol (5 mL) was added Pd/C (35 mg, 10% wet) under $H_2$. The reaction mixture was stirred at r.t. overnight. The mixture was filtered and the filtrate was concentrated under reduced pressure. The residue was purified by flash chromatography on a silica gel column eluting with MeOH/DCM (0-15%) to afford the title compound (100 mg, 100% yield). LCMS calc. for $C_{22}H_{28}FN_6O_3S$ $[M+H]^+$: m/z=475.2; Found: 475.2.

Step 2: 4-(9-(5-(difluoromethyl)-1,3,4-thiadiazol-2-yl)-6-fluoro-7-(N-(1-methylcyclopropyl) sulfamoyl)-9H-pyrimido[4,5-b]indol-4-yl)-N,N-dimethylpiperidine-1-carboxamide This compound was prepared using procedures analogous to those described for Example 74 Step 2 using 4-(6-fluoro-7-(N-(1-methylcyclopropyl)sulfamoyl)-9H-pyrimido[4,5-b]indol-4-yl)-N,N-dimethylpiperidine-1-carboxamide and 2-bromo-5-(difluoromethyl)-1,3,4-thiadiazole to afford the title compound as white solid. $^1H$ NMR (400 MHz, DMSO-$d_6$) δ 9.50 (d, J=6.3 Hz, 1H), 9.30 (s, 1H), 8.71 (s, 1H), 8.53 (d, J=10.1 Hz, 1H), 7.71 (t, J=53.2 Hz, 1H), 3.92 (dd, J=12.1, 7.6 Hz, 1H), 3.71 (d, J=13.0 Hz, 2H), 3.22-3.14 (m, 2H), 2.79 (s, 6H), 1.96 (dd, J=12.9, 9.0 Hz, 4H), 1.18 (s, 3H), 0.71 (t, J=5.5 Hz, 2H), 0.45 (t, J=3.4 Hz, 2H). LCMS calc. for $C_{25}H_{28}F_3N_8O_3S_2$ $[M+H]^+$: m/z=609.2; Found: 609.2.

Example 83: N-(1-cyanocyclopropyl)-9-(5-(difluoromethyl)-1,3,4-thiadiazol-2-yl)-4-(tetrahydro-2H-pyran-2-yl)-9H-pyrimido[4,5-b]indole-7-sulfonamide

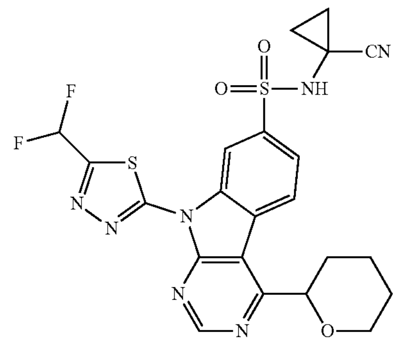 [SMILES: N#CC1(NS(=O)(=O)c2ccc3c4c(C5CCCCO5)ncnc4n(-c4nnc(C(F)F)s4)c3c2)CC1]

Step 1: N-(1-cyanocyclopropyl)-4-(3,4-dihydro-2H-pyran-6-yl)-9H-pyrimido[4,5-b]indole-7

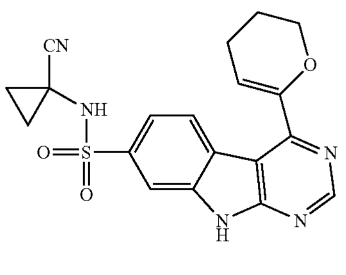 [SMILES: N#CC1(NS(=O)(=O)c2ccc3c(c2)[nH]c2ncnc(C4=CCCCO4)c23)CC1]

To a solution of 4-chloro-N-(1-cyanocyclopropyl)-9H-pyrimido[4,5-b]indole-7-sulfonamide (100 mg, 0.287 mmol, Intermediate 1) in 1,4-dioxane (5 mL) and water (0.1 mL) was added 2-(3,4-dihydro-2H-pyran-6-yl)-4,4,5,5-tetramethyl-1,3,2-dioxaborolane (72.49 mg, 0.345 mmol, 1.2 eq), $NaHCO_3$ (72 mg, 0.861 mmol, 3.0 eq) and Pd(dppf)$Cl_2$ (17 mg, 0.023 mmol, 0.08 eq). The mixture was stirred at 100° C. for 2 h., and concentrated. The residue was purified by flash chromatography on a silica gel eluting with EtOAc/PE (0-50%) to afford the title compound (90 mg, yield: 79.1%) as yellow solid. LCMS for $C_{19}H_{18}N_5O_3S$ $[M+H]^+$: m/z=396.1; Found: 395.8.

Step 2: N-(1-cyanocyclopropyl)-4-(tetrahydro-2H-pyran-2-yl)-9H-pyrimido [4,5-b]indole-7-sulfonamide

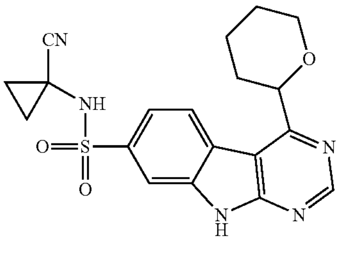 [SMILES: N#CC1(NS(=O)(=O)c2ccc3c(c2)[nH]c2ncnc(C4CCCCO4)c23)CC1]

To a solution of N-(1-cyanocyclopropyl)-4-(3,4-dihydro-2H-pyran-6-yl)-9H-pyrimido [4,5-b]indole-7 sulfonamide (85 mg, 0.215 mmol) in MeOH (20 mL) was Pd/C (34 mg, 0.086 mmol, 10% wet). The mixture was hydrogenated at 40° C. for 16 h. The reaction mixture was filtered. The filtrate was concentrated. The residue was purified by reverse phase chromatography on a C18 column eluting with $H_2O$/MeOH (25-50%) to afford title compound (40 mg, yield: 46.8%) as yellow solid. LCMS for $C_{19}H_{20}N_5O_3S$ $[M+H]^+$: m/z=398.1; Found: 398.3.

Step 3: N-(1-cyanocyclopropyl)-9-(5-(difluoromethyl)-1,3,4-thiadiazol-2-yl)-4-(tetrahydro-2H-pyran-2-yl)-9H-pyrimido[4,5-b]indole-7-sulfonamide To a solution of N-(1-cyanocyclopropyl)-4-(tetrahydro-2H-pyran-2-yl)-9H-pyrimido [4,5-b]indole-7-sulfonamide (40 mg, 0.10 mmol) and (5-(difluoromethyl)-1,3,4-thiadiazol-2-yl)bromonium (32.46 mg, 0.15 mmol) in 1,4-dioxane (4 mL) was added (1R,2S)—N1,N2-dimethylcyclohexane-1,2-diamine (14.21 mg, 0.10 mmol, 1.0 eq), CsF (30.58 mg, 0.20 mmol, 2.0 eq) and CuI (5.75 mg, 0.03 mmol, 0.10 eq). The mixture was stirred at 100° C. for 2 h. The mixture was concentrated under reduced pressure. The residue was purified by prep-HPLC on a C18 column eluting with MeCN/water (45%-60%, with 0.05% FA) to afford the title compound (6.44 mg, yield: 12%) as a yellow solid. $^1H$ NMR (400 MHz, DMSO-$d_6$) δ ppm 9.51 (d, J=1.5 Hz, 1H), 9.30 (s, 1H), 8.70 (d, J=8.4 Hz, 1H), 8.39 (s, 1H), 8.09 (dd, J=8.4, 1.6 Hz, 1H), 7.71 (t, J=53.2 Hz, 1H), 5.13-5.07 (m, 1H), 4.19 (d, J=9.6 Hz, 1H), 3.91-3.83 (m, 1H), 2.01 (d, J=5.4 Hz, 3H), 1.80 (dd, J=29.9, 19.6 Hz, 3H), 1.37 (t, J=6.5 Hz, 2H), 1.21 (dd, J=8.0, 5.3 Hz, 2H). LCMS for $C_{22}H_{20}F_2N_7O_3S_2[M+H]^+$: m/z=532.1; Found: 532.2.

Example 84: N-(1-Cyanocyclopropyl)-9-(5-(difluoromethyl)-1,3,4-thiadiazol-2-yl)-4-(4-hydroxycyclohex-1-en-1-yl)-9H-pyrimido[4,5-b]indole-7-sulfonamide

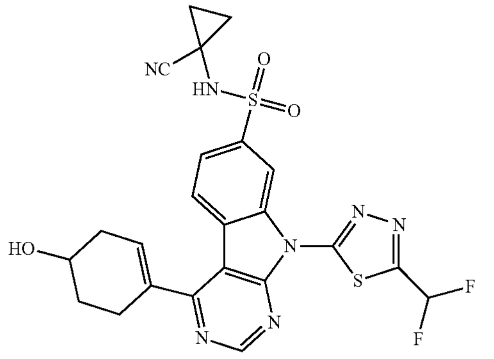 [SMILES: N#CC1(NS(=O)(=O)c2ccc3c4c(C5=CCC(O)CC5)ncnc4n(-c4nnc(C(F)F)s4)c3c2)CC1]

Step 1: N-(1-cyanocyclopropyl)-4-(1,4-dioxaspiro[4.5]dec-7-en-8-yl)-9H-pyrimido[4,5-b]indole-7-sulfonamide

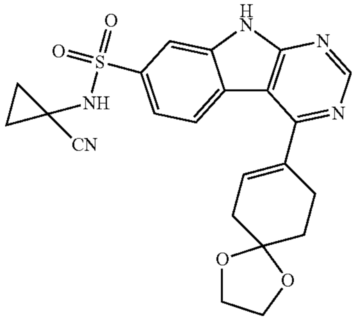 [SMILES: N#CC1(NS(=O)(=O)c2ccc3c(c2)[nH]c2ncnc(C4=CCC5(CC4)OCCO5)c23)CC1]

A mixture of 4-chloro-N-(1-cyanocyclopropyl)-9H-pyrimido[4,5-b]indole-7-sulfonamide (500 mg, 1.44 mmol, Intermediate 1), $K_3PO_4$ (1.53 g, 7.19 mmol), 2-(1,4-dioxaspiro[4.5]dec-7-en-8-yl)-4,4,5,5-tetramethyl-1,3,2-dioxaborolane (459 mg, 1.73 mmol) and Pd(dppf)$Cl_2$—$CH_2Cl_2$ (117 mg, 0.144 mmol) in dioxane (10 mL) and $H_2O$ (2 mL) was degassed and recharged with $N_2$ for 3 cycles. The mixture was stirred at 100° C. overnight. After cooled to r.t., the mixture was concentrated under reduced pressure. The residue was purified by flash chromatography on a silica gel column eluting with MeOH/DCM (0-5%) to afford the title compound (400 mg, 61.6% yield) as a gray solid. $^1$H NMR: (400 MHz, DMSO-$d_6$) δ 12.8 (s, 1H), 9.20 (s, 1H), 8.94 (s, 1H), 8.35 (d, J=8.4 Hz, 1H), 8.03 (d, J=1.2 Hz, 1H), 7.72 (dd, J=8.4, 1.6 Hz, 1H), 6.35 (t, J=2.8 Hz, 1H), 3.98-4.05 (m, 4H), 2.75-2.82 (m, 2H), 2.56-2.62 (m, 2H), 1.94-1.99 (m, 2H), 1.41 (t, J=3.2 Hz, 2H), 1.24-1.27 (m, 2H). LCMS calc. for $C_{22}H_{20}N_5O_4S$ $[M-H]^-$: m/z=450.1; Found: 450.1.

Step 2: N-(1-cyanocyclopropyl)-4-(4-oxocyclohex-1-en-1-yl)-9H-pyrimido[4,5-b]indole-7-sulfonamide

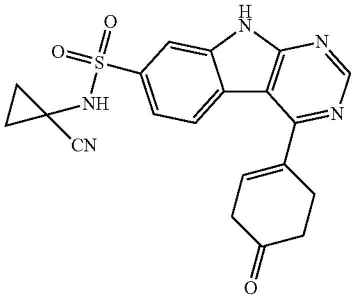 [SMILES: N#CC1(NS(=O)(=O)c2ccc3c(c2)[nH]c2ncnc(C4=CCC(=O)CC4)c23)CC1]

A solution of N-(1-cyanocyclopropyl)-4-(1,4-dioxaspiro[4.5]dec-7-en-8-yl)-9H-pyrimido[4,5-b]indole-7-sulfonamide (200 mg, 0.443 mmol) in DCM (5 mL) was treated with TFA (1.52 g, 13.3 mmol) at 20° C. overnight. The mixture was poured into ice water (30 mL), adjusted to pH 8 with sat. $NaHCO_3$ aq. (50 mL), and extracted with DCM/$CH_3CN$ (v:v=10:1, 50 mL×2). The combined organic layers were dried over $Na_2SO_4$, filtered and concentrated under reduced pressure to afford the title compound (160 mg, 88.6% yield) as a light yellow solid. $^1$H NMR: (400 MHz, DMSO-$d_6$) δ 12.8-13.0 (m, 1H), 9.14-9.31 (m, 1H), 8.99 (d, J=4.8 Hz, 1H), 8.42-8.65 (m, 1H), 7.99-8.13 (m, 1H), 7.67-7.86 (m, 1H), 6.62 (s, 1H), 3.26-3.32 (m, 2H), 3.08 (t, J=6.4 Hz, 2H), 2.70 (t, J=6.8 Hz, 2H), 1.39-1.44 (m, 2H), 1.23-1.28 (m, 2H). LCMS calc. for $C_{20}H_{16}N_5O_3S$ $[M-H]^-$: m/z=406.1; Found: 406.1.

Step 3: N-(1-cyanocyclopropyl)-4-(4-hydroxycyclohex-1-en-1-yl)-9H-pyrimido[4,5-b]indole-7-sulfonamide

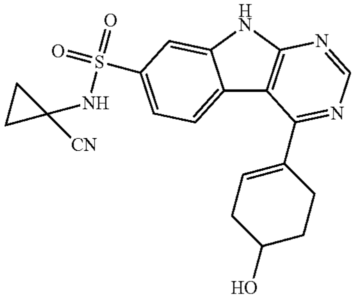 [SMILES: N#CC1(NS(=O)(=O)c2ccc3c(c2)[nH]c2ncnc(C4=CCC(O)CC4)c23)CC1]

To a solution of N-(1-cyanocyclopropyl)-4-(4-oxocyclohex-1-en-1-yl)-9H-pyrimido[4,5-b]indole-7-sulfonamide (300 mg, 0.736 mmol) in THF (15 mL) and EtOH (3 mL) was added $NaBH_4$ (55.7 mg, 1.47 mmol) at 0° C. under $N_2$. The mixture was stirred at 0° C. for 1 h. before quenched with saturated $NH_4Cl$ solution (20 mL) at 0° C. under $N_2$, and extracted with EtOAc (30 mL×2). The combined organic layers were dried over $Na_2SO_4$, filtered and concentrated under reduced pressure. The residue was purified by flash chromatography on a silica gel column eluting with MeOH/DCM (0-5%) to afford the title compound (200 mg, 57.0% yield) as light yellow solid. $^1$H NMR: (400 MHz, DMSO-$d_6$): δ 12.7-12.8 (m, 1H), 9.20-9.26 (m, 1H), 8.93 (s, 1H), 8.31-8.41 (m, 1H), 7.98-8.06 (m, 1H), 7.68-7.85 (m, 1H), 6.37 (s, 1H), 4.88 (s, 1H), 4.00 (br s, 1H), 2.56-2.79 (m, 2H), 2.21-2.39 (m, 1H), 1.72-2.09 (m, 3H), 1.39-1.45 (m, 2H), 1.22-1.29 (m, 2H). LCMS calc. for $C_{20}H_{18}N_5O_3S$ $[M-H]^-$: m/z=408.1; Found: 408.1.

Step 4: N-(1-cyanocyclopropyl)-9-(5-(difluoromethyl)-1,3,4-thiadiazol-2-yl)-4-(4-hydroxycyclohex-1-en-1-yl)-9H-pyrimido[4,5-b]indole-7-sulfonamide A mixture of N-(1-cyanocyclopropyl)-4-(4-hydroxycyclohex-1-en-1-yl)-9H-pyrimido[4,5-b]indole-7-sulfonamide (50 mg, 0.122 mmol), 2-bromo-5-(difluoromethyl)-1,3,4-thiadiazole (31.5 mg, 0.147 mmol), $Cs_2CO_3$ (79.6 mg, 0.244 mmol) and XPhos Pd G3 (5.17 mg, 0.061 mmol) in dioxane (2 mL) was degassed and recharged with $N_2$ for three cycles, and stirred at 100° C. overnight. After cooled to r.t., the solid was removed by filtration through a pad of celite, and washed the cake with THF (20 mL×2). The filtrate was concentrated under reduced pressure. The residue was purified by prep-HPLC on a C18 column eluting with ACN/water (30%-60% with 0.1% TFA) to afford the title compound (19.2 mg, 28.8% yield) as light yellow solid. $^1H$ NMR: (400 MHz, DMSO-$d_6$) δ 9.44-9.59 (m, 2H), 9.23-9.31 (m, 1H), 8.50-8.62 (m, 1H), 7.98-8.14 (m, 1H), 7.71 (t, J=53.2 Hz, 1H), 6.44 (s, 1H), 4.01-4.06 (m, 1H), 2.59-2.83 (m, 2H), 2.18-2.35 (m, 1H), 1.95-2.10 (m, 2H), 1.55-1.90 (m, 2H), 1.41-1.48 (m, 2H), 1.24-1.31 (m, 2H). LCMS calc. for $C_{23}H_{20}F_2N_7O_3S_2[M+H]^+$: m/z=544.1; Found: 544.1.

Example 85: N-(1-Cyanocyclopropyl)-9-(5-(difluoromethyl)-1,3,4-thiadiazol-2-yl)-4-(4-hydroxycyclohexyl)-9H-pyrimido[4,5-b]indole-7-sulfonamide

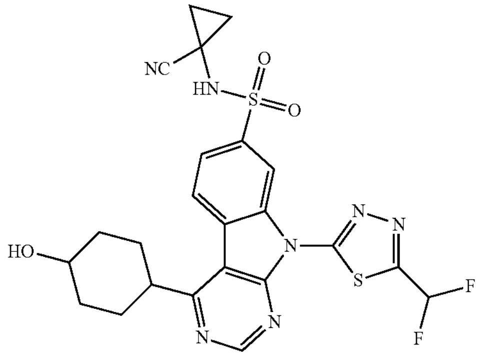 [SMILES: N#CC1(NS(=O)(=O)c2ccc3c4c(C5CCC(O)CC5)ncnc4n(-c4nnc(C(F)F)s4)c3c2)CC1]

Step 1: N-(1-cyanocyclopropyl)-4-(1,4-dioxaspiro[4.5]decan-8-yl)-9H-pyrimido[4,5-b]indole-7-sulfonamide

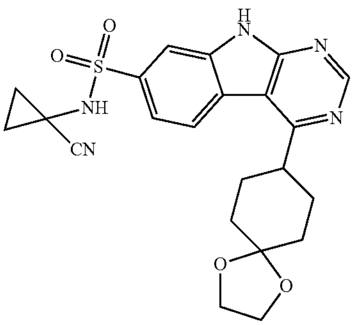 [SMILES: N#CC1(NS(=O)(=O)c2ccc3c(c2)[nH]c2ncnc(C4CCC5(CC4)OCCO5)c23)CC1]

To a solution of N-(1-cyanocyclopropyl)-4-(1,4-dioxaspiro[4.5]dec-7-en-8-yl)-9H-pyrimido[4,5-b]indole-7-sulfonamide (300 mg, 0.664 mmol, Example 84 Step 1) in THF (30 mL) was added Pd/C (150 mg, 5% wet) at 20° C. under Ar. The suspension was degassed and recharged with $H_2$ for three cycles. The mixture was stirred under $H_2$ (40 Psi) at 40° C. overnight. The solid was removed by filtration through a pad of celite, and washed the cake with THF (50 mL×2). The filtrate was concentrated under reduced pressure to afford the title compound (200 mg, 66.4% yield) as a light yellow solid. $^1H$ NMR: (400 MHz, DMSO-$d_6$) δ 12.8 (s, 1H), 9.23 (br.s, 1H), 8.94 (s, 1H), 8.47 (d, J=8.4 Hz, 1H), 8.04 (d, J=1.6 Hz, 1H), 7.79 (dd, J=8.4, 1.6 Hz, 1H), 7.66-7.73 (m, 1H), 3.92 (s, 4H), 2.00-2.11 (m, 2H), 1.87-1.96 (m, 4H), 1.40-1.44 (m, 2H), 1.22-1.30 (m, 5H). LCMS calc. for $C_{22}H_{22}N_5O_4S$ $[M-H]^-$: m/z=452.2; Found: 452.1.

Step 2: N-(1-cyanocyclopropyl)-9-(5-(difluoromethyl)-1,3,4-thiadiazol-2-yl)-4-(4-hydroxycyclohexyl)-9H-pyrimido[4,5-b]indole-7-sulfonamide This compound was prepared using procedures analogous to those described for Example 84 Step 2-4 using N-(1-cyanocyclopropyl)-4-(1,4-dioxaspiro[4.5]decan-8-yl)-9H-pyrimido[4,5-b]indole-7-sulfonamide to afford the title compound (10 mg, 12.4% yield) as light yellow solid. $^1H$ NMR: (400 MHz, DMSO-$d_6$) δ 9.55 (s, 1H), 9.50 (s, 1H), 9.28-9.30 (m, 1H), 8.59 (d, J=8.4 Hz, 1H), 8.09-8.14 (m, 1H), 7.71 (t, J=53.2 Hz, 1H), 3.54-3.68 (m, 2H), 1.85-2.05 (m, 6H), 1.68-1.79 (m, 1H), 1.54-1.65 (m, 2H), 1.43-1.48

(m, 2H), 1.26-1.31 (m, 2H). LCMS calc. for $C_{23}H_{22}F_2N_7O_3S_2$ $[M+H]^+$: m/z=546.1; Found: 546.1.

Example 86: tert-butyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carboxylate

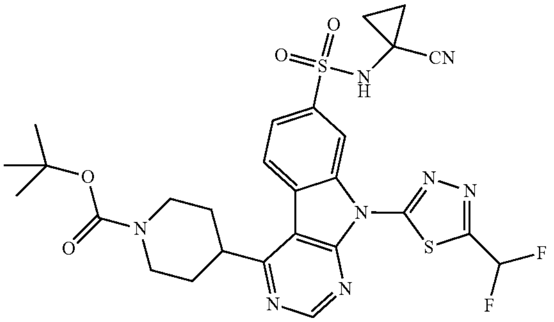 [SMILES: CC(C)(C)OC(=O)N1CCC(c2ncnc3c2c2ccc(S(=O)(=O)NC4(C#N)CC4)cc2n3-c2nnc(C(F)F)s2)CC1]

Step 1: tert-butyl 4-(7-(N-(1-cyanocyclopropyl)sulfamoyl)-9H-pyrimido[4,5-b]indol-4-yl)piperidine-1-carboxylate

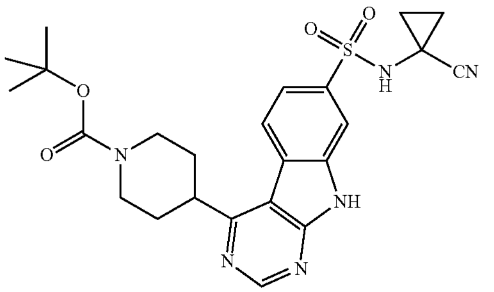 [SMILES: CC(C)(C)OC(=O)N1CCC(c2ncnc3[nH]c4cc(S(=O)(=O)NC5(C#N)CC5)ccc4c23)CC1]

This compound was prepared as light yellow solid using procedures analogous to those described for Example 76 using tert-butyl 4-(7-(N-(1-cyanocyclopropyl)sulfamoyl)-9H-pyrimido[4,5-b]indol-4-yl)-3,4-dihydropyridine-1(2H)-carboxylate (Example 74 Step 1). LCMS calc. for $C_{24}H_{29}N_6O_4S$ $[M+H]^+$: m/z=497.2; Found: 497.2.

Step 2: tert-butyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carboxylate A mixture of tert-butyl 4-(7-(N-(1-cyanocyclopropyl)sulfamoyl)-9H-pyrimido[4,5-b]indol-4-yl)piperidine-1-carboxylate (208 mg, 0.42 mmol), 2-bromo-5-(difluoromethyl)-1,3,4-thiadiazole (108 mg, 0.5 mmol), SPhos Pd G3 (18.1 mg, 0.02 mmol), cesium carbonate (273 mg, 0.84 mol) in dioxane (3 mL) was degassed and recharged with $N_2$ for three cycles, stirred at 120° C. for 12 h under $N_2$ atmosphere. After cooled to r.t., the reaction mixture was concentrated under reduced pressure, the residue was purified by flash chromatography on a silica gel column eluting with EtOAc/PE (5-60%) to afford the title compound (65 mg, 18.9% yield) as light yellow solid. LCMS calc. for $C_{27}H_{29}F_2N_8O_4S_2$ $[M+H]^+$: m/z=631.2; Found: 631.2.

Example 87: N-(1-Cyanocyclopropyl)-9-(5-(difluoromethyl)-1,3,4-thiadiazol-2-yl)-4-(piperidin-4-yl)-9H-pyrimido[4,5-b]indole-7-sulfonamide

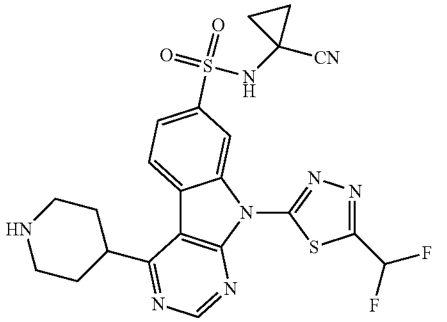 [SMILES: N#CC1(NS(=O)(=O)c2ccc3c4c(C5CCNCC5)ncnc4n(-c4nnc(C(F)F)s4)c3c2)CC1]

To a solution of tert-butyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carboxylate (65 mg, 0.008 mmol, Example 86) in DCM (3 mL) was added TFA (1 mL). The reaction mixture was stirred at r.t. for 2 h. The reaction mixture was evaporated under reduced pressure to afford the title compound (50 mg, 75.8% yield) as off-white solid. LCMS calc. for $C_{22}H_{21}F_2N_8O_3S_2$ $[M+H]^+$: m/z=531.1; Found: 531.2.

Example 88: 4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N,N-dimethylpiperidine-1-carboxamide

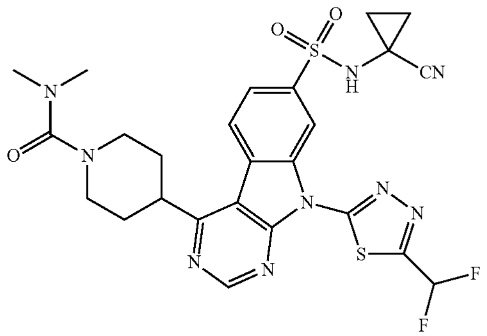 [SMILES: CN(C)C(=O)N1CCC(c2ncnc3c2c2ccc(S(=O)(=O)NC4(C#N)CC4)cc2n3-c2nnc(C(F)F)s2)CC1]

To a solution of N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (50 mg, 0.09 mmol, Example 87) in THF (3 mL) was added sodium bicarbonate (30 mg, 0.36 mmol). To the mixture was dropwise added dimethylcarbamic chloride (19 mg, 0.18 mmol) at 0-10° C., stirred at r.t. for 12 h. The reaction mixture was concentrated under reduced pressure. The residue was purified by prep-HPLC on a C18 column eluting with MeCN/water (0-65%)

to afford the title compound (6.3 mg, 13.7% yield) as white solid. LCMS calc. for $C_{25}H_{26}F_2N_9O_3S_2$ $[M+H]^+$: m/z=602.2; Found: 602.2.

Example 89: 4-(7-(N-(1-Cyanocyclopropyl)sulfamoyl)-9-(5-(difluoromethyl)-1,3,4-thiadiazol-2-yl)-6-fluoro-9H-pyrimido[4,5-b]indol-4-yl)-N,N-dimethylpiperidine-1-carboxamide

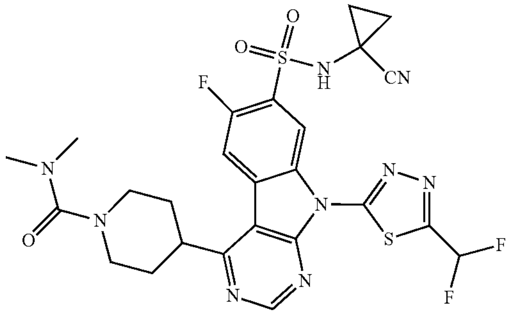 [SMILES: CN(C)C(=O)N1CCC(c2ncnc3c2c2cc(F)c(S(=O)(=O)NC4(C#N)CC4)cc2n3-c2nnc(C(F)F)s2)CC1]

Step 1: tert-butyl 4-(7-(N-(1-cyanocyclopropyl)sulfamoyl)-6-fluoro-9H-pyrimido[4,5-b]indol-4-yl)-3,6-dihydropyridine-1(2H)-carboxylate

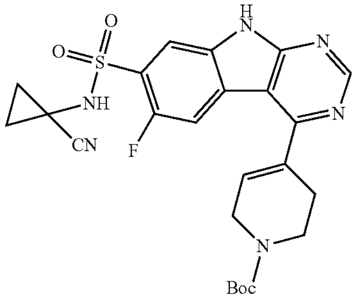 [SMILES: CC(C)(C)OC(=O)N1CC=C(c2ncnc3[nH]c4cc(S(=O)(=O)NC5(C#N)CC5)c(F)cc4c23)CC1]

This compound was prepared as light yellow foam using procedures analogous to those described for Example 74 Step 1 using 4-chloro-N-(1-cyanocyclopropyl)-6-fluoro-9H-pyrimido[4,5-b]indole-7-sulfonamide (Intermediate 4) and tert-butyl 4-(4,4,5,5-tetramethyl-1,3,2-dioxaborolan-2-yl)-3,6-dihydropyridine-1(2H)-carboxylate. $^1$H NMR: (400 MHz, DMSO-$d_6$) δ 12.9 (s, 1H), 9.55 (s, 1H), 8.98 (s, 1H), 8.03 (t, J=5.6 Hz, 2H), 6.55 (s, 1H), 4.21 (s, 2H), 3.66-3.70 (m, 2H), 2.70 (s, 2H), 1.47 (s, 9H), 1.42-1.45 (m, 2H), 1.22-1.27 (m, 2H).

Step 2: tert-butyl 4-(7-(N-(1-cyanocyclopropyl)sulfamoyl)-6-fluoro-9H-pyrimido[4,5-b]indol-4-yl)piperidine-1-carboxylate

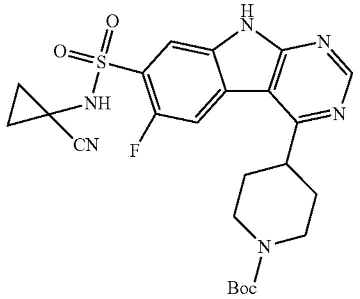 [SMILES: CC(C)(C)OC(=O)N1CCC(c2ncnc3[nH]c4cc(S(=O)(=O)NC5(C#N)CC5)c(F)cc4c23)CC1]

This compound was prepared as light yellow solid using procedures analogous to those described for Example 76 using tert-butyl 4-(7-(N-(1-cyanocyclopropyl)sulfamoyl)-6-fluoro-9H-pyrimido[4,5-b]indol-4-yl)-3,6-dihydropyridine-1(2H)-carboxylate and Pd/C (5% wet) in THF under $H_2$ (50 Psi) at 20° C. for 72 h. $^1$H NMR: (400 MHz, DMSO-$d_6$) δ 12.8 (s, 1H), 9.53 (s, 1H), 8.97 (s, 1H), 8.37 (d, J=10.8 Hz, 1H), 8.02 (d, J=5.6 Hz, 2H), 4.07-4.17 (m, 3H), 3.80-3.84 (m, 1H), 3.04-3.18 (m, 1H), 1.79-1.90 (m, 4H), 1.44 (s, 9H), 1.25-1.28 (m, 2H), 0.85-0.90 (m, 2H). LCMS calc. for $C_{20}H_{20}FN_6O_4S$ $[M-56+H]^+$: m/z=459.1; Found: 459.1.

Step 3: N-(1-cyanocyclopropyl)-6-fluoro-4-(piperidin-4-yl)-9H-pyrimido[4,5-b]indole-7-sulfonamide

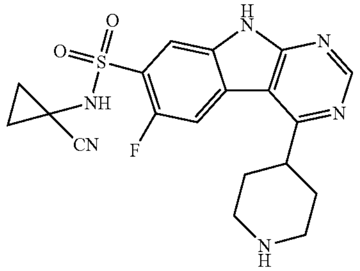 [SMILES: N#CC1(NS(=O)(=O)c2cc3[nH]c4ncnc(C5CCNCC5)c4c3cc2F)CC1]

To a mixture of tert-butyl 4-(7-(N-(1-cyanocyclopropyl)sulfamoyl)-6-fluoro-9H-pyrimido[4,5-b]indol-4-yl)piperidine-1-carboxylate (300 mg, 0.583 mmol) in MeOH (3 mL) was added HCl/MeOH (4 M, 3 mL) at 20° C. The mixture was stirred at 20° C. for 3 h. The mixture was concentrated under reduced pressure to afford the title compound as HCl salt (200 mg, 76.1% yield) as light yellow solid. LCMS calc. for $C_{19}H_{20}FN_6O_2S$ [M+H]$^+$: m/z=415.1; Found: 415.1.

Step 4: 4-(7-(N-(1-cyanocyclopropyl)sulfamoyl)-6-fluoro-9H-pyrimido[4,5-b]indol-4-yl)-N,N-dimethylpiperidine-1-carboxamide

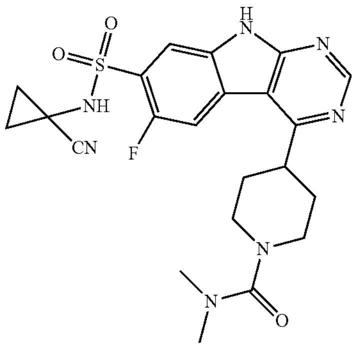 [SMILES: CN(C)C(=O)N1CCC(c2ncnc3[nH]c4cc(S(=O)(=O)NC5(C#N)CC5)c(F)cc4c23)CC1]

To a mixture of N-(1-cyanocyclopropyl)-6-fluoro-4-(piperidin-4-yl)-9H-pyrimido[4,5-b]indole-7-sulfonamide HCl salt (100 mg, 0.22 mmol) in $CH_3CN$ (5 mL) was added TEA (67.3 mg, 0.66 mmol) and N,N-dimethylcarbamoyl chloride (16.7 mg, 0.155 mmol) at 0-5° C. The mixture was stirred at 20° C. for 3 h., and poured into $H_2O$ (20 mL). The mixture was extracted with EtOAc (20 mL×2). The combined organic layers were washed with brine (10 mL), dried over $Na_2SO_4$, filtered, and concentrated under reduced pressure. The residue was purified by flash chromatography on a silica gel column eluting with MeOH/DCM (0-10%) to afford the title compound (70 mg, 65% yield) as light yellow solid. $^1$H NMR: (400 MHz, DMSO-$d_6$) δ 12.8 (s, 1H), 9.53 (s, 1H), 8.97 (s, 1H), 8.35 (d, J=10.8 Hz, 1H), 8.03 (d, J=6.0 Hz, 1H), 3.76-3.82 (m, 1H), 3.69 (d, J=13.0 Hz, 2H), 3.10-3.18 (m, 2H), 2.77 (s, 6H), 1.81-1.99 (m, 4H), 1.42-1.47 (m, 2H), 1.24-1.29 (m, 2H). LCMS calc. for $C_{22}H_{25}FN_7O_3S$ [M+H]$^+$: m/z=486.2; Found: 486.1.

Step 5: 4-(7-(N-(1-cyanocyclopropyl)sulfamoyl)-9-(5-(difluoromethyl)-1,3,4-thiadiazol-2-yl)-6-fluoro-9H-pyrimido[4,5-b]indol-4-yl)-N,N-dimethylpiperidine-1-carboxamide This compound was prepared as light yellow solid using procedures analogous to those described for Example 44 Step 2 using 4-(7-(N-(1-cyanocyclopropyl)sulfamoyl)-6-fluoro-9H-pyrimido[4,5-b]indol-4-yl)-N,N-dimethylpiperidine-1-carboxamide and 2-bromo-5-(difluoromethyl)-1,3,4-thiadiazole. $^1$H NMR: (400 MHz, DMSO-$d_6$) δ 9.76 (br.s, 1H), 9.55 (d, J=6.4 Hz, 1H), 9.32 (s, 1H), 8.60 (d, J=10.4 Hz, 1H), 7.70 (t, J=53.2 Hz, 1H), 3.90-3.99 (m, 1H), 3.71 (d, J=13.0 Hz, 2H), 3.14-3.24 (m, 2H), 2.78 (s, 6H), 1.90-2.02 (m, 4H), 1.44-1.48 (m, 2H), 1.29-1.34 (m, 2H). LCMS calc. for $C_{25}H_{25}F_3N_9O_3S_2$ [M+H]$^+$: m/z=620.1; Found: 620.2.

Example 90: N-(1-Cyanocyclopropyl)-9-(5-(difluoromethyl)-1,3,4-thiadiazol-2-yl)-6-fluoro-4-(1-isobutyrylpiperidin-4-yl)-9H-pyrimido[4,5-b]indole-7-sulfonamide

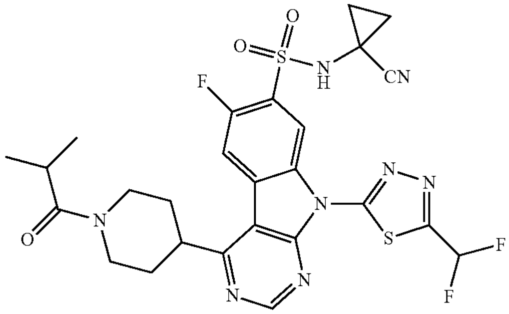 [SMILES: CC(C)C(=O)N1CCC(c2ncnc3c2c2cc(F)c(S(=O)(=O)NC4(C#N)CC4)cc2n3-c2nnc(C(F)F)s2)CC1]

Step 1: N-(1-cyanocyclopropyl)-6-fluoro-4-(1-isobutyrylpiperidin-4-yl)-9H-pyrimido[4,5-b]indole-7-sulfonamide

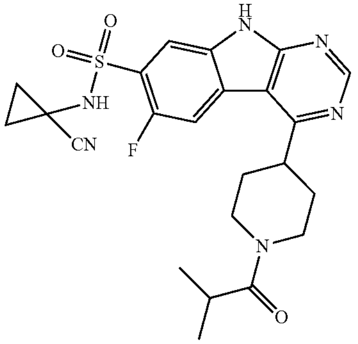 [SMILES: CC(C)C(=O)N1CCC(c2ncnc3[nH]c4cc(S(=O)(=O)NC5(C#N)CC5)c(F)cc4c23)CC1]

To a mixture of N-(1-cyanocyclopropyl)-6-fluoro-4-(piperidin-4-yl)-9H-pyrimido[4,5-b]indole-7-sulfonamide HCl salt (80 mg, 0.177 mmol, Example 89 Step 3) in $CH_3CN$ (4 mL) was added TEA (53.9 mg, 0.532 mmol) and 2-methylpropanoyl chloride (13.2 mg, 0.124 mmol) at 0-5° C. The mixture was stirred at 20° C. for 3 h. The mixture was diluted with water (10 mL), extracted with EtOAc (20 mL×2). The combined organic layer was washed with brine (10 mL), dried over $Na_2SO_4$, filtered and concentrated under reduced pressure. The residue was purified by flash chromatography on a silica gel column eluting with MeOH/DCM (0-10%) to afford the title compound (40 mg, 40.2% yield) as a light yellow solid. $^1$H NMR: (400 MHz, DMSO-$d_6$) δ 12.8 (s, 1H), 9.54 (s, 1H), 8.97 (s, 1H), 8.40 (d, J=10.8 Hz, 1H), 8.03 (d, J=6.0 Hz, 1H), 4.56 (d, J=12.8 Hz, 1H), 4.10 (d, J=12.8 Hz, 1H), 3.89-3.95 (m, 1H), 3.48 (t, J=12.0 Hz, 1H), 2.91-2.97 (m, 2H), 1.90-1.95 (m, 3H), 1.43-1.47 (m, 2H), 1.25-1.29 (m, 2H), 1.04 (s, 7H). LCMS calc. for $C_{23}H_{26}FN_6O_3S$ [M+H]$^+$: m/z=485.2; Found: 485.2.

Step 2: N-(1-cyanocyclopropyl)-9-(5-(difluoromethyl)-1,3,4-thiadiazol-2-yl)-6-fluoro-4-(1-isobutyrylpiperidin-4-yl)-9H-pyrimido[4,5-b]indole-7-sulfonamide This compound was prepared as off-white solid using procedures analogous to those described for Example 44 Step 2 using N-(1-cyanocyclopropyl)-6-fluoro-4-(1-isobutyrylpiperidin-4-yl)-9H-pyrimido[4,5-b]indole-7-sulfonamide and 2-bromo-5-(difluoromethyl)-1,3,4-thiadiazole. $^1$H NMR: (400 MHz, DMSO-$d_6$) δ 9.78 (s, 1H), 9.56 (d, J=6.0 Hz, 1H), 9.30 (s, 1H), 8.65 (d, J=10.0 Hz, 1H), 7.71 (t, J=53.2 Hz, 1H), 4.58 (d, J=12.8 Hz, 1H), 4.04-4.14 (m, 2H), 3.51 (t, J=12.4 Hz, 1H), 2.92-3.05 (m, 2H), 1.95 (t, J=20.0 Hz, 3H), 1.77 (d, J=14.4 Hz, 1H), 1.49 (s, 2H), 1.33 (s, 2H), 1.05 (s, 6H). LCMS calc. for $C_{26}H_{26}F_3N_8O_3S_2$ $[M+H]^+$: m/z=619.1; Found: 619.1.

Example 91: N-(1-Cyanocyclopropyl)-9-(5-(difluoromethyl)-1,3,4-thiadiazol-2-yl)-6-fluoro-4-(1-isobutyryl-1,2,3,6-tetrahydropyridin-4-yl)-9H-pyrimido[4,5-b]indole-7-sulfonamide and Example 92 N-(1-Cyanocyclopropyl)-9-(5-(difluoromethyl)-1,3,4-thiadiazol-2-yl)-6-fluoro-4-(1-isobutyryl-1,2,3,4-tetrahydropyridin-4-yl)-9H-pyrimido[4,5-b]indole-7-sulfonamide Example 91

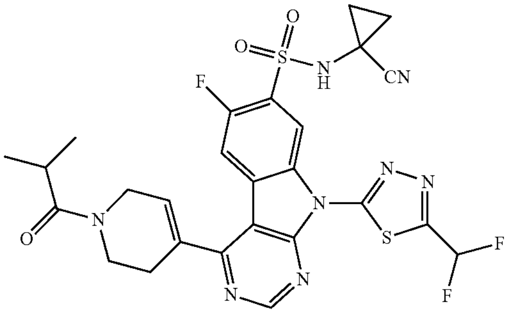

and

Example 92

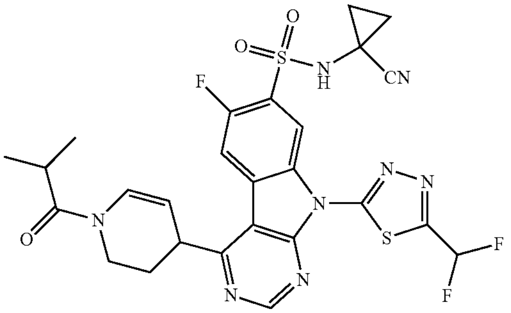

Step 1: 1-isobutyrylpiperidin-4-one

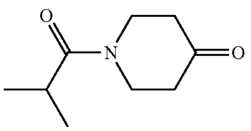

To a solution of piperidin-4-one hydrochloride (10 g, 73.75 mmol) and triethylamine (30.62 g, 302.61 mmol) in dichloromethane (100 mL) was added isobutyryl chloride (16.12 g, 151.3 mmol) dropwise at 0° C. After stirring for 16 h., the resulting mixture was poured into water (60 mL), and extracted with ethyl acetate (60 mL×3). The combined organic layers were dried over anhydrous sodium sulphate, filtered and concentrated under reduced pressure. The residue was purified by flash chromatography on a silica gel column eluting with ethyl acetate/hexanes (0-50%) to afford the title compound (8.15 g, 65.3% yield). $^1$H NMR: (400 MHz, $CDCl_3$) δ 3.83 (s, 4H), 2.87 (dt, J=13.5, 6.8 Hz, 1H), 2.47 (t, J=6.2 Hz, 4H), 1.16 (d, J=6.8 Hz, 6H).

Step 2: 1-isobutyryl-1,2,3,6-tetrahydropyridin-4-yl trifluoromethanesulfonate

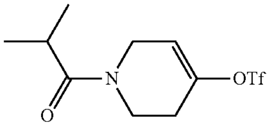 [SMILES: CC(C)C(=O)N1CC=C(OS(=O)(=O)C(F)(F)F)CC1]

To a solution of 1-isobutyrylpiperidin-4-one (6 g, 35.46 mmol) in tetrahydrofuran (45 mL) was cooled to −78° C. and lithium hexamethyldisilazide (46.1 mL, 1 M solution in tetrahydrofuran) was added dropwise under nitrogen atmosphere. Then the resulting reaction was stirred for 0.5 h followed by adding a solution of 1,1,1-trifluoro-N-phenyl-N-((trifluoromethyl) sulfonyl) methanesulfonamide (16.5 g, 46.1 mmol). The mixture was warmed slowly to r.t. and stirred for 16 h. under $N_2$ atmosphere. The resulting mixture was poured into ice water (40 mL), and extracted with ethyl acetate (40 mL×3). The combined organic layers were dried over anhydrous sodium sulphate, filtered and concentrated under reduced pressure.

The residue was purified by flash chromatography on a silica gel column eluting with ethyl acetate/hexanes (0-50%) to afford the title compound (2.66 g, 24.9% yield). $^1$H NMR: (400 MHz, $CDCl_3$) δ 5.83 (s, 1H), 4.19 (d, J=26.0 Hz, 2H), 3.77 (d, J=45.8 Hz, 2H), 2.85-2.72 (m, 1H), 2.49 (d, J=29.6 Hz, 2H), 1.15 (d, J=5.8 Hz, 6H).

Step 3: 2-methyl-1-(4-(4,4,5,5-tetramethyl-1,3,2-dioxaborolan-2-yl)-3,6-dihydropyridin-1(2H)-yl)propan-1-one

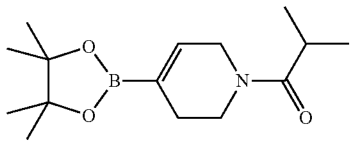 [SMILES: CC(C)C(=O)N1CC=C(B2OC(C)(C)C(C)(C)O2)CC1]

A mixture of 1-isobutyryl-1,2,3,6-tetrahydropyridin-4-yl trifluoromethanesulfonate (2.66 g, 8.83 mmol), 4,4,4',4',5,5,5',5'-octamethyl-2,2'-bi(1,3,2-dioxaborolane) (3.36 g, 13.24 mmol), $Pd(dppf)_2Cl_2$ (641 mg, 0.883 mmol) and potassium acetate (1.73 g, 17.66 mmol) in dioxane (40 mL) was degassed and purged with nitrogen for three cycles, and then stirred at 90° C. for 2 h.

The mixture was cooled to r.t. and filtered, the filtrate was diluted with water (20 mL) and extracted with ethyl acetate (20 mL×3). The combined organic layers were dried over anhydrous sodium sulphate, filtered and concentrated under reduced pressure. The residue was purified by flash chromatography on a silica gel column eluting with ethyl acetate/Hexanes (0-30%) to afford the title compound (1.72 g, 69.9% yield). $^1$H NMR: (400 MHz, $CDCl_3$) δ 6.49 (s, 1H), 4.15-4.08 (m, 2H), 3.57 (s, 2H), 2.86-2.73 (m, 1H), 2.27 (d, J=2.0 Hz, 2H), 1.27 (s, 12H), 1.13 (d, J=6.8 Hz, 6H). LCMS calc. for $C_{15}H_{27}BNO_3$ $[M+H]^+$: m/z=280.2; Found: 280.0.

Step 4: N-(1-cyanocyclopropyl)-6-fluoro-4-(1-isobutyryl-1,2,3,6-tetrahydropyridin-4-yl)-9H-pyrimido[4,5-b]indole-7-sulfonamide

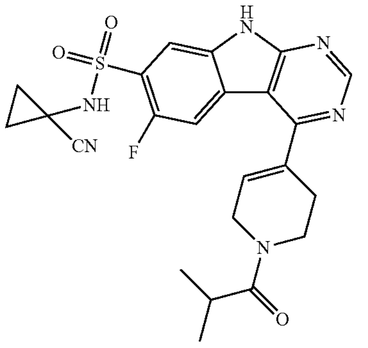 [SMILES: CC(C)C(=O)N1CC=C(c2ncnc3[nH]c4cc(S(=O)(=O)NC5(C#N)CC5)c(F)cc4c23)CC1]

A mixture of 4-chloro-N-(1-cyanocyclopropyl)-6-fluoro-9H-pyrimido[4,5-b]indole-7-sulfonamide (600 mg, 1.64 mmol, Intermediate 4), 2-methyl-1-[4-(4,4,5,5-tetramethyl-1,3,2-dioxaborolan-2-yl)-3,6-dihydro-2H-pyridin-1-yl]propan-1-one (550 mg, 1.97 mmol), Pd(dppf)$Cl_2$—$CH_2Cl_2$ (134 mg, 0.164 mmol) and $K_3PO_4$ (1.74 g, 8.20 mmol) in dioxane (25 mL) and $H_2O$ (5 mL) was degassed and purged with $N_2$ for 3 cycles, then stirred at 100° C. overnight.

The mixture was concentrated under reduced pressure. The residue was purified by flash chromatography on a silica gel column eluting with MeOH/DCM (0-10%) to afford the title compound (300 mg, 37.9% yield) as light yellow solid. $^1$H NMR: (400 MHz, DMSO-$d_6$) δ 12.8 (s, 1H), 9.54 (s, 1H), 8.98 (s, 1H), 8.02-8.10 (m, 2H), 6.51-6.63 (m, 1H), 4.39 (d, J=54.4 Hz, 2H), 3.83 (t, J=4.8 Hz, 2H), 2.99-3.03 (m, 1H), 2.73 (d, J=46.8 Hz, 1H), 1.44 (t, J=2.8 Hz, 2H), 1.35 (s, 1H), 1.23-1.26 (m, 2H), 1.08 (d, J=6.4 Hz, 6H). LCMS calc. for $C_{23}H_{24}FN_6O_3S$ $[M+H]^+$: m/z=483.2; Found: 483.2.

Step 5: N-(1-cyanocyclopropyl)-9-(5-(difluoromethyl)-1,3,4-thiadiazol-2-yl)-6-fluoro-4-(1-isobutyryl-1,2,3,6-tetrahydropyridin-4-yl)-9H-pyrimido[4,5-b]indole-7-sulfonamide (Example 91) and N-(1-Cyanocyclopropyl)-9-(5-(difluoromethyl)-1,3,4-thiadiazol-2-yl)-6-fluoro-4-(1-isobutyryl-1,2,3,4-tetrahydropyridin-4-yl)-9H-pyrimido[4,5-b]indole-7-sulfonamide (Example 92)

A mixture of N-(1-cyanocyclopropyl)-6-fluoro-4-(1-isobutyryl-1,2,3,6-tetrahydropyridin-4-yl)-9H-pyrimido[4,5-b]indole-7-sulfonamide (100 mg, 0.207 mmol), 2-bromo-5-(difluoromethyl)-1,3,4-thiadiazole (53.5 mg, 0.249 mmol), XPhos Pd G3 (8.77 mg, 0.010 mmol) and $Cs_2CO_3$ (135 mg, 0.414 mmol) in dioxane (3 mL) was degassed and recharged with $N_2$ for 3 cycles. The mixture was stirred in a sealed tube at 100° C. overnight. After cooled to r.t., the solid was removed by filtration on celite, washed the cake with THF (20 mL×2). The combined filtrate was concentrated under reduced pressure. The residue was purified by prep-HPLC on a C18 column eluting with water/ACN (45%-80% with (0.05% $NH_3$—$H_2O$+$NH_4HCO_3$)) to afford P1 as a light yellow solid (6.13 mg, the earlier eluted product. Retention time=2.724 min in analytic HPLC) and P2 as a light yellow solid (23.2 mg, the latter eluted product, Retention time=2.791 min in analytic HPLC). Analytic HPLC conditions: Instrument: Agilent 1260; Column: Luna C18 (2.0*50 mm, 5 uM); Column temperature: 40° C.; Detector: 6125B single quadrupole MSD; Mobile A: 0.04% TFA in $H_2O$, Mobile B: 0.02% TFA in ACN; B:A=5-95% from 0.40 to 3.00 min.; Flow rate 1 mL/min.

The P1 was assigned to Example 91. $^1$H NMR: (400 MHz, DMSO-$d_6$) δ 9.79 (s, 1H), 9.56 (d, J=6.4 Hz, 1H), 9.33 (s, 1H), 8.27 (t, J=14.0 Hz, 1H), 7.72 (t, J=53.2 Hz, 1H), 6.66 (d, J=20.0 Hz, 2H), 4.50 (s, 1H), 4.36 (s, 1H), 3.84-3.90 (m, 2H), 3.01-3.06 (m, 1H), 2.84 (s, 1H), 1.47-1.51 (m, 2H), 1.29-1.33 (m, 2H), 1.10 (d, J=6.8 Hz, 6H). LCMS calc. for $C_{26}H_{24}F_3N_8O_3S_2$ $[M+H]^+$: m/z=617.1; Found: 617.1.

The P2 was assigned to Example 92. $^1$H NMR: (400 MHz, DMSO-$d_6$) δ 9.77 (s, 1H), 9.56 (d, J=6.0 Hz, 1H), 9.32 (s, 1H), 8.61 (t, J=10.0 Hz, 1H), 7.71 (t, J=53.2 Hz, 1H), 7.27 (dd, J=62.4, 8.0 Hz, 1H), 5.14 (dd, J=44.4, 8.4 Hz, 1H), 4.71 (s, 1H), 4.01-4.06 (m, 1H), 3.68-3.92 (m, 1H), 3.03-3.14 (m, 1H), 2.09-2.22 (m, 2H), 1.47-1.51 (m, 2H), 1.31-1.35 (m, 2H), 1.08 (d, J=6.4 Hz, 6H). LCMS calc. for $C_{26}H_{24}F_3N_8O_3S_2$ $[M+H]^+$: m/z=617.1; Found: 617.1.

Example 93: 9-(5-(Difluoromethyl)-1,3,4-thiadiazol-2-yl)-N-(1-methylcyclopropyl)-4-(piperidin-4-yl)-9H-pyrimido[4,5-b]indole-7-sulfonamide

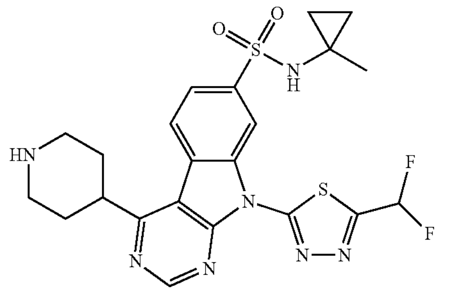 [SMILES: CC1(NS(=O)(=O)c2ccc3c4c(C5CCNCC5)ncnc4n(-c4nnc(C(F)F)s4)c3c2)CC1]

Step 1: tert-butyl 4-(7-(N-(1-methylcyclopropyl)sulfamoyl)-9H-pyrimido[4,5-b]indol-4-yl)-3,6-dihydropyridine-1(2H)-carboxylate

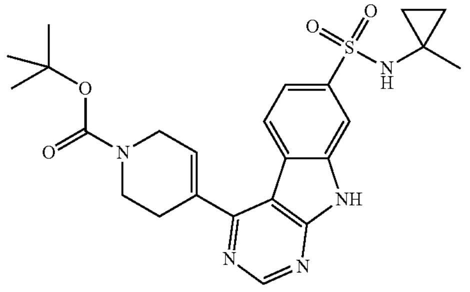 [SMILES: CC1(NS(=O)(=O)c2ccc3c(c2)[nH]c2ncnc(C4=CCN(C(=O)OC(C)(C)C)CC4)c23)CC1]

This compound was prepared using procedures analogous to those described for Example 74 Step 1 using 4-chloro-N-(1-methylcyclopropyl)-9H-pyrimido[4,5-b]indole-7-sulfonamide (intermediate 2) and tert-butyl 4-(4,4,5,5-tetramethyl-1,3,2-dioxaborolan-2-yl)-3,6-dihydropyridine-1(2H)-carboxylate. LCMS calc. for $C_{24}H_{30}N_5O_4S$ $[M+H]^+$: m/z=484.2; Found: 484.2.

Step 2: tert-butyl 4-(7-(N-(1-methylcyclopropyl)sulfamoyl)-9H-pyrimido[4,5-b]indol-4-yl)piperidine-1-carboxylate

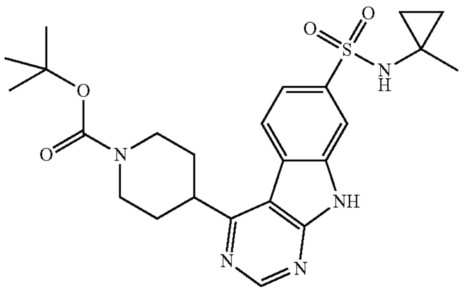 [SMILES: CC1(NS(=O)(=O)c2ccc3c(c2)[nH]c2ncnc(C4CCN(C(=O)OC(C)(C)C)CC4)c23)CC1]

This compound was prepared as light yellow solid using procedures analogous to those described for Example 76 using tert-butyl 4-(7-(N-(1-methylcyclopropyl)sulfamoyl)-9H-pyrimido[4,5-b]indol-4-yl)-3,6-dihydropyridine-1(2H)-carboxylate. LCMS calc. for $C_{24}H_{32}N_5O_4S$ $[M+H]^+$: m/z=486.2; Found: 486.2.

Step 3: tert-butyl 4-(9-(5-(difluoromethyl)-1,3,4-thiadiazol-2-yl)-7-(N-(1-methylcyclopropyl)sulfamoyl)-9H-pyrimido[4,5-b]indol-4-yl)piperidine-1-carboxylate

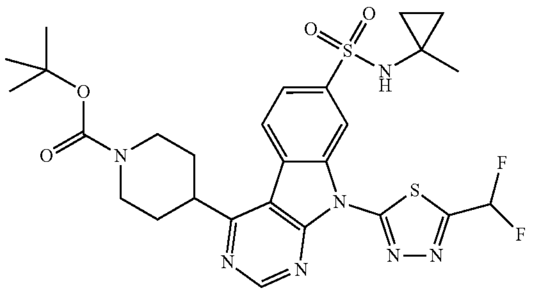 [SMILES: CC1(NS(=O)(=O)c2ccc3c4c(C5CCN(C(=O)OC(C)(C)C)CC5)ncnc4n(-c4nnc(C(F)F)s4)c3c2)CC1]

This compound was prepared as yellow solid using procedures analogous to those described for Example 86 Step 2 using tert-butyl 4-(7-(N-(1-methylcyclopropyl)sulfamoyl)-9H-pyrimido[4,5-b]indol-4-yl)piperidine-1-carboxylate and 2-bromo-5-(difluoromethyl)-1,3,4-thiadiazole. LCMS calc. for $C_{27}H_{32}F_2N_7O_4S_2$ $[M+H]^+$: m/z=620.2; Found: 620.2.

Step 4: 9-(5-(difluoromethyl)-1,3,4-thiadiazol-2-yl)-N-(1-methylcyclopropyl)-4-(piperidin-4-yl)-9H-pyrimido[4,5-b]indole-7-sulfonamide This compound was prepared as yellow solid using procedures analogous to those described for Example 87 using tert-butyl 4-(9-(5-(difluoromethyl)-1,3,4-thiadiazol-2-yl)-7-(N-(1-methylcyclopropyl)sulfamoyl)-9H-pyrimido[4,5-b]indol-4-yl)piperidine-1-carboxylate as starting material. LCMS calc. for $C_{22}H_{24}F_2N_7O_2S_2$ $[M+H]^+$: m/z=520.1; Found: 520.1.

Example 94: 9-(5-(Difluoromethyl)-1,3,4-thiadiazol-2-yl)-4-(1-(2-hydroxy-2-methylpropanoyl)piperidin-4-yl)-N-(1-methylcyclopropyl)-9H-pyrimido[4,5-b]indole-7-sulfonamide

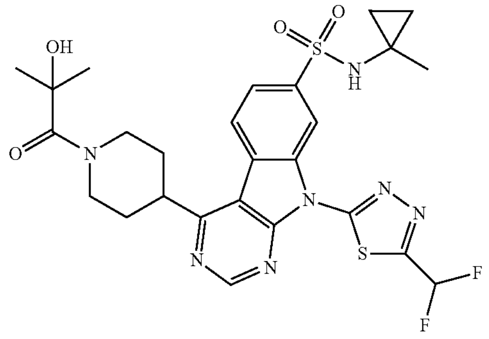 [SMILES: CC1(NS(=O)(=O)c2ccc3c4c(C5CCN(C(=O)C(C)(C)O)CC5)ncnc4n(-c4nnc(C(F)F)s4)c3c2)CC1]

To a mixture of 2-hydroxyisobutyric acid (13 mg, 0.12 mmol), tert-butyl 9-(5-(difluoromethyl)-1,3,4-thiadiazol-2-yl)-N-(1-methylcyclopropyl)-4-(piperidin-4-yl)-9H-pyrimido[4,5-b]indole-7-sulfonamide (52 mg, 0.1 mmol, Example 93), TEA (30 mg, 0.3 mmol) in DMF (2 mL) was added HATU (76 mg, 0.2 mmol). The mixture was stirred at r.t. overnight, and concentrated under reduced pressure. The mixture was purified by prep-HPLC on a C18 column eluting with MeCN/water (0-40%) to afford the title compound (30 mg) as white solid. LCMS calc. for $C_{26}H_{30}F_2N_7O_4S_2[M+H]^+$: m/z=606.2; Found: 606.2.

Example 95: (R)-9-(5-(Difluoromethyl)-1,3,4-thiadiazol-2-yl)-4-(1-(2-methoxypropanoyl)piperidin-4-yl)-N-(1-methylcyclopropyl)-9H-pyrimido[4,5-b]indole-7-sulfonamide

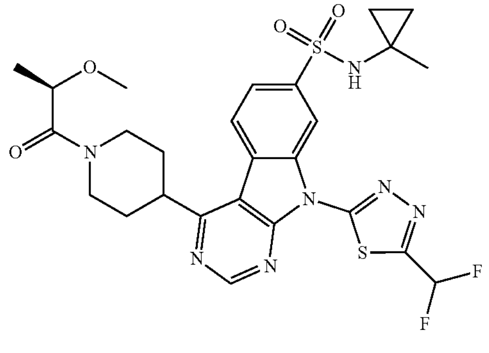 [SMILES: CO[C@H](C)C(=O)N1CCC(c2ncnc3c2c2ccc(S(=O)(=O)NC4(C)CC4)cc2n3-c2nnc(C(F)F)s2)CC1]

This compound was prepared as white solid using procedures analogous to those described for Example 94 using (R)-2-methoxypropanoic acid to replace 2-hydroxyisobutyric acid. LCMS calc. for $C_{26}H_{30}F_2N_7O_4S_2[M+H]^+$: m/z=606.2; Found: 606.2.

Example 96: (S)-9-(5-(Difluoromethyl)-1,3,4-thiadiazol-2-yl)-4-(1-(2-methoxypropanoyl)piperidin-4-yl)-N-(1-methylcyclopropyl)-9H-pyrimido[4,5-b]indole-7-sulfonamide

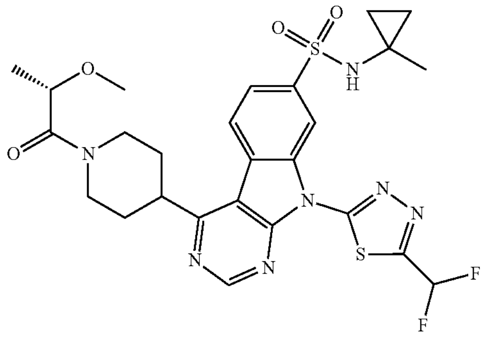 [SMILES: CO[C@@H](C)C(=O)N1CCC(c2ncnc3c2c2ccc(S(=O)(=O)NC4(C)CC4)cc2n3-c2nnc(C(F)F)s2)CC1]

This compound was prepared as white solid using procedures analogous to those described for Example 94 using (S)-2-methoxypropanoic acid to replace 2-hydroxyisobutyric acid. LCMS calc. for $C_{26}H_{30}F_2N_7O_4S_2[M+H]^+$: m/z=606.2; Found: 606.2.

Example 97: 5-(7-(N-(1-cyanocyclopropyl)sulfamoyl)-9-(5-(difluoromethyl)-1,3,4-thiadiazol-2-yl)-9H-pyrimido[4,5-b]indol-4-yl)-N,N-dimethylpicolinamide

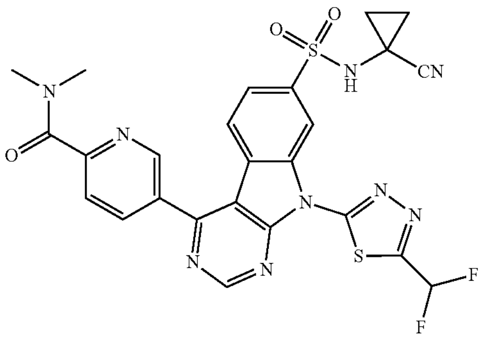 [SMILES: CN(C)C(=O)c1ccc(-c2ncnc3c2c2ccc(S(=O)(=O)NC4(C#N)CC4)cc2n3-c2nnc(C(F)F)s2)cn1]

Step 1: 5-(7-(N-(1-cyanocyclopropyl)sulfamoyl)-9H-pyrimido[4,5-b]indol-4-yl)-N,N-dimethylpicolinamide

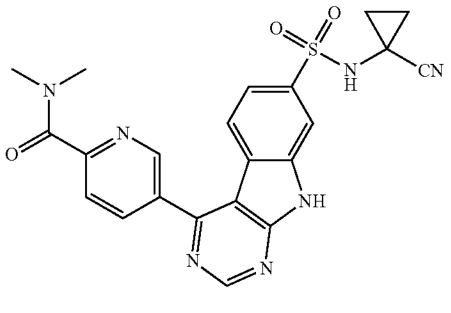 [SMILES: CN(C)C(=O)c1ccc(-c2ncnc3[nH]c4cc(S(=O)(=O)NC5(C#N)CC5)ccc4c23)cn1]

This compound was prepared as brown solid by using procedures analogous to those described for Example 74 Step 1 using 4-chloro-N-(1-cyanocyclopropyl)-9H-pyrimido[4,5-b]indole-7-sulfonamide (Intermediate 1) and N,N-Dimethyl-5-(4,4,5,5-tetramethyl-1,3,2-dioxaborolan-2-yl)picolinamide. LCMS calc. for $C_{22}H_{20}N_7O_3S$ $[M+H]^+$: m/z=462.1; Found: 462.1.

Step 2: 5-(7-(N-(1-cyanocyclopropyl)sulfamoyl)-9-(5-(difluoromethyl)-1,3,4-thiadiazol-2-yl)-9H-pyrimido[4,5-b]indol-4-yl)-N,N-dimethylpicolinamide A mixture of 5-(7-(N-(1-cyanocyclopropyl)sulfamoyl)-9H-pyrimido[4,5-b]indol-4-yl)-N,N-dimethylpicolinamide (568 mg, 1.23 mmol), 2-bromo-5-(difluoromethyl)-1,3,4-thiadiazole (662 mg, 3.08 mmol), SPhos Pd G3 (109 mg, 0.12 mmol), cesium carbonate (1.6 g, 4.9 mmol) in dioxane (3 mL) was degassed and recharged with $N_2$ for three cycles, stirred at 110° C. overnight. After cooled to r.t., the reaction mixture was concentrated under reduced pressure.

The residue was purified by flash chromatography on a silica gel column eluting with MeOH/DCM (0-9%) to give a crude product which was further purified by prep-HPLC on a C18 column eluting with MeCN/water (0-30%) to afford the title compound (3 mg) as white solid as white solid. LCMS calc. for $C_{25}H_{20}F_2N_9O_3S_2[M+H]^+$: m/z=596.1; Found: 596.1.

Example 98: (S)—N-(1-Cyanocyclopropyl)-9-(5-(difluoromethyl)-1,3,4-thiadiazol-2-yl)-4-(3,4-dimethylpiperazin-1-yl)-9H-pyrimido[4,5-b]indole-7-sulfonamide

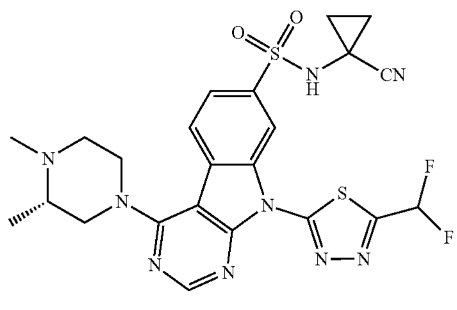 [SMILES: C[C@H]1CN(c2ncnc3c2c2ccc(S(=O)(=O)NC4(C#N)CC4)cc2n3-c2nnc(C(F)F)s2)CCN1C]

Step 1: (S)—N-(1-cyanocyclopropyl)-4-(3,4-dimethylpiperazin-1-yl)-9H-pyrimido[4,5-b]indole-7-sulfonamide

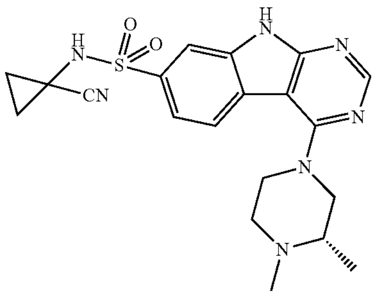 [SMILES: C[C@H]1CN(c2ncnc3[nH]c4cc(S(=O)(=O)NC5(C#N)CC5)ccc4c23)CCN1C]

This compound was prepared by using procedures analogous to those described for Example 1 Step 1 using 4-chloro-N-(1-cyanocyclopropyl)-9H-pyrimido[4,5-b]indole-7-sulfonamide (Intermediate 1) and (2S)-1,2-dimethylpiperazine. LCMS calc. for $C_{20}H_{22}N_7O_2S$ $[M-H]^-$: m/z=424.2; Found: 424.1.

Step 2: (S)—N-(1-cyanocyclopropyl)-9-(5-(difluoromethyl)-1,3,4-thiadiazol-2-yl)-4-(3,4-dimethylpiperazin-1-yl)-9H-pyrimido[4,5-b]indole-7-sulfonamide A mixture of (S)—N-(1-cyanocyclopropyl)-4-(3,4-dimethylpiperazin-1-yl)-9H-pyrimido[4,5-b]indole-7-sulfonamide (200 mg, 0.470 mmol), 2-bromo-5-(difluoromethyl)-1,3,4-thiadiazole (111 mg, 0.517 mmol), (1R,2R)—$N^1$,$N^2$-dimethylcyclohexane-1,2-diamine (107 mg, 0.752 mmol), CuI (71.6 mg, 0.376 mmol) and $Cs_2CO_3$ (306 mg, 0.940 mmol) in dioxane (10 mL) was degassed and purged with $N_2$ for 3 cycles. The mixture was stirred at 120° C. overnight under $N_2$ atmosphere. The reaction mixture was concentrated under reduced pressure. The residue was purified by prep-HPLC on a C18 column with ACN/water (25%-55% with 0.1% TFA) to afford the title compound (33.0 mg, 12.5% yield) as a white solid. $^1H$ NMR: (400 MHz, DMSO-$d_6$) δ 9.46 (s, 1H), 9.40 (s, 1H), 8.93 (s, 1H), 8.17 (d, J=8.0 Hz, 1H), 8.07 (d, J=8.4 Hz, 1H), 7.69 (t, J=56.4 Hz, 1H), 4.41-4.45 (m, 2H), 3.46-3.66 (m, 3H), 3.45 (s, 2H), 2.90 (s, 3H), 1.43-1.44 (m, 2H), 1.35 (s, 3H), 1.29-1.34 (m, 2H). LCMS calc. for $C_{23}H_{24}F_2N_9O_2S_2$ $[M+H]^+$: m/z=560.1; Found: 560.1.

Example 99: (S)-9-(5-(Difluoromethyl)-1,3,4-thiadiazol-2-yl)-N-(1-methylcyclopropyl)-4-(2-methylmorpholino)-9H-pyrimido[4,5-b]indole-7-sulfonamide

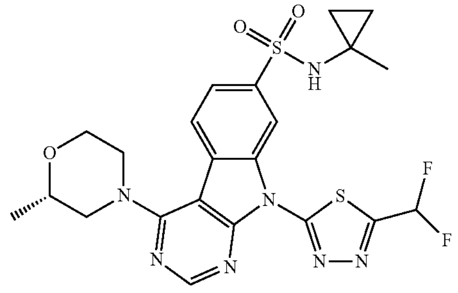 [SMILES: C[C@H]1CN(c2ncnc3c2c2ccc(S(=O)(=O)NC4(C)CC4)cc2n3-c2nnc(C(F)F)s2)CCO1]

Step 1: N-(1-methylcyclopropyl)-4-[(2S)-2-methylmorpholin-4-yl]-9H-pyrimido[4,5-b]indole-7-sulfonamide

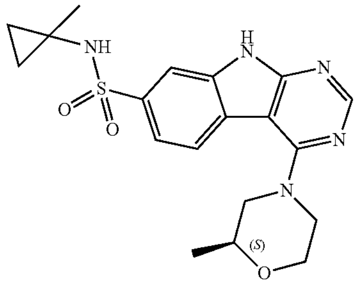

This compound was prepared as a yellow solid by using procedures analogous to those described for Example 1 Step 1 using 4-chloro-N-(1-methylcyclopropyl)-9H-pyrimido[4,5-b]indole-7-sulfonamide (Intermediate 2) and (S)-2-methylmorpholine. LCMS calculated for $C_{19}H_{22}N_5O_3S$ $[M-H]^-$: m/z=400.2; Found: 400.1.

Step 2: 9-[5-(difluoromethyl)-1,3,4-thiadiazol-2-yl]-N-(1-methylcyclopropyl)-4-[(2S)-2-methylmorpholin-4-yl]pyrimido[4,5-b]indole-7-sulfonamide This compound was prepared as a light yellow solid by using procedures analogous to those described for Example 98 Step 2 using (S)—N-(1-methylcyclopropyl)-4-(2-methylmorpholino)-9H-pyrimido[4,5-b]indole-7-sulfonamide (110 mg, 0.274 mmol) and 2-bromo-5-(difluoromethyl)-1,3,4-thiadiazole. $^1H$ NMR: (400 MHz, DMSO-$d_6$) δ 9.45 (s, 1H), 8.80 (s, 1H), 8.35 (s, 1H), 7.98-8.05 (m, 2H), 7.68 (t, J=53.4 Hz, 1H), 4.17-4.30 (m, 2H), 3.98 (d, J=8.0 Hz, 1H), 3.68-3.74 (m, 2H), 3.45-3.52 (m, 1H), 3.08-3.14 (m, 1H), 1.18-1.20 (m, 3H), 1.12 (s, 3H), 0.64-0.67 (m, 2H), 0.39-0.42 (m, 2H). LCMS calculated for $C_{22}H_{24}F_2N_7O_3S_2$ $[M+H]^+$: m/z=536.1; Found: 536.0.

Example 100: (2S,5R)-4-(9-(5-(difluoromethyl)-1,3,4-thiadiazol-2-yl)-7-(N-(1-methylcyclopropyl)sulfamoyl)-9H-pyrimido[4,5-b]indol-4-yl)-N,N,2,5-tetramethylpiperazine-1-carboxamide

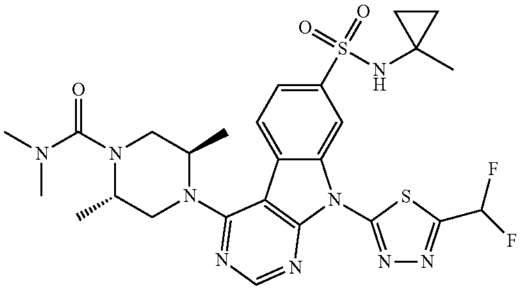 [SMILES: C[C@@H]1CN(C(=O)N(C)C)[C@@H](C)CN1c1ncnc2c1c1ccc(S(=O)(=O)NC3(C)CC3)cc1n2-c1nnc(C(F)F)s1]

Step 1: (2S,5R)—N,N,2,5-tetramethyl-4-(7-(N-(1-methylcyclopropyl)sulfamoyl)-9H-pyrimido[4,5-b]indol-4-yl)piperazine-1-carboxamide

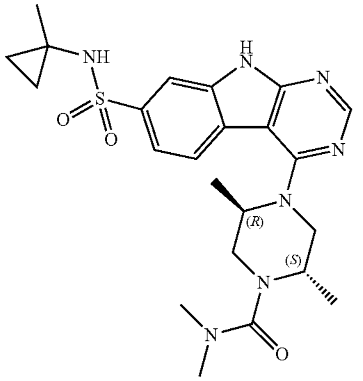

This compound was prepared as a yellow solid by using procedures analogous to those described for Example 1 Step 1 using 4-chloro-N-(1-methylcyclopropyl)-9H-pyrimido[4,5-b]indole-7-sulfonamide (Intermediate 2) and (2S,5R)—N,N,2,5-tetramethylpiperazine-1-carboxamide (Intermediate 42). LCMS calculated for $C_{23}H_{32}N_7O_3S$ $[M+H]^+$: m/z=486.2; Found: 486.2.

Step 2: (2S,5R)-4-(9-(5-(difluoromethyl)-1,3,4-thiadiazol-2-yl)-7-(N-(1-methylcyclopropyl) sulfamoyl)-9H-pyrimido[4,5-b]indol-4-yl)-N,N,2,5-tetramethylpiperazine-1-carboxamide This compound was prepared as a light yellow solid by using procedures analogous to those described for Example 98 Step 2 using (2S,5R)—N,N,2,5-tetramethyl-4-(7-(N-(1-methylcyclopropyl)sulfamoyl)-9H-pyrimido[4,5-b]indol-4-yl)piperazine-1-carboxamide and 2-bromo-5-(difluoromethyl)-1,3,4-thiadiazole. $^1H$ NMR: (400 MHz, DMSO-$d_6$) δ 9.46 (s, 1H), 8.81 (s, 1H), 8.37 (s, 1H), 7.99-8.08 (m, 2H), 7.68 (t, J=53.2 Hz, 1H), 4.87 (s, 1H), 4.07-4.09 (m, 2H), 3.82 (d, J=11.6 Hz, 1H), 3.65-3.69 (m, 1H), 2.81 (s, 6H), 1.29 (d, J=6.8 Hz, 3H), 1.18 (s, 1H), 1.14 (s, 2H), 1.00 (d, J=6.4 Hz, 3H), 0.65-0.67 (m, 2H), 0.40-0.43 (m, 2H). LCMS calculated for $C_{26}H_{32}F_2N_9O_3S_2$ $[M+H]^+$: m/z=620.2; Found: 620.2.

Example 101: (S)-4-(9-(5-(Difluoromethyl)-1,3,4-thiadiazol-2-yl)-7-(N-(1-methylcyclopropyl)sulfamoyl)-9H-pyrimido[4,5-b]indol-4-yl)-N,N,2-trimethylpiperazine-1-carboxamide

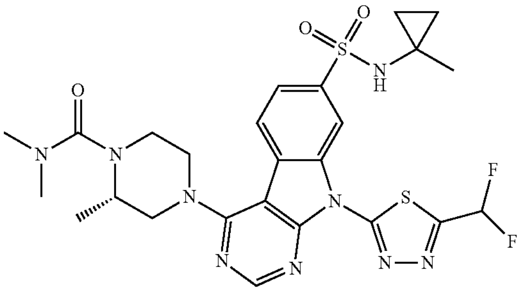 [SMILES: C[C@H]1CN(c2ncnc3c2c2ccc(S(=O)(=O)NC4(C)CC4)cc2n3-c2nnc(C(F)F)s2)CCN1C(=O)N(C)C]

Step 1: (S)—N,N,2-trimethyl-4-(7-(N-(1-methylcyclopropyl)sulfamoyl)-9H-pyrimido[4,5-b]indol-4-yl)piperazine-1-carboxamide

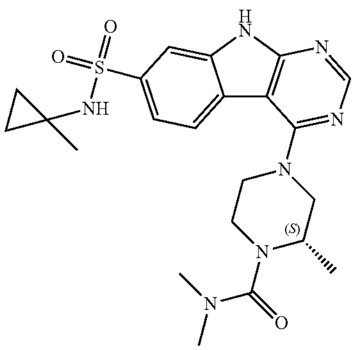

This compound was prepared as a yellow solid by using procedures analogous to those described for Example 1 Step 1 using 4-chloro-N-(1-methylcyclopropyl)-9H-pyrimido[4,5-b]indole-7-sulfonamide (Intermediate 2) and (2S)—N,N,2-trimethylpiperazine-1-carboxamide (Intermediate 47). LCMS calculated for $C_{22}H_{28}N_7O_3S$ $[M-H]^-$: m/z=470.2; Found: 470.2.

Step 2: (S)-4-(9-(5-(difluoromethyl)-1,3,4-thiadiazol-2-yl)-7-(N-(1-methylcyclopropyl)sulfamoyl)-9H-pyrimido[4,5-b]indol-4-yl)-N,N,2-trimethylpiperazine-1-carboxamide A mixture of (S)—N,N,2-trimethyl-4-(7-(N-(1-methylcyclopropyl)sulfamoyl)-9H-pyrimido[4,5-b]indol-4-yl)piperazine-1-carboxamide (120 mg, 0.254 mmol), 2-bromo-5-(difluoromethyl)-1,3,4-thiadiazole (109 mg, 0.509 mmol), CuI (39 mg, 0.204 mmol), CsF (77.3 mg, 0.509 mmol) and (1R,2R)—N1,N2-dimethylcyclohexane-1,2-diamine (57.9 mg, 0.407 mmol) in dioxane (2 mL) was degassed and purged with $N_2$ for 3 cycles. The mixture was stirred at 120° C. overnight. The reaction mixture was concentrated under reduced pressure. The residue was purified by prep-HPLC on a C18 column eluting with water/ACN (40%-70% with 0.1% TFA) to afford the title compound (15.3 mg) as a light yellow solid. $^1H$ NMR: (400 MHz, DMSO-$d_6$) δ 9.45 (s, 1H), 8.79 (s, 1H), 8.35 (s, 1H), 8.11 (d, J=8.4 Hz, 1H), 7.98 (d, J=10 Hz, 1H), 7.68 (t, J=53.2 Hz, 1H), 4.23 (d, J=12.4 Hz, 1H), 4.07 (d, J=13.2 Hz, 1H), 3.94-3.97 (m, 1H), 3.74-3.78 (m, 1H), 3.55-3.60 (m, 1H), 3.37-3.44 (m, 2H), 2.81 (s, 6H), 1.13 (s, 3H), 1.09 (d, J=6.8 Hz, 3H), 0.64-0.67 (m, 2H), 0.40-0.42 (m, 2H). LCMS calculated for $C_{25}H_{30}F_2N_9O_3S_2[M+H]^+$: m/z=606.2; Found: 606.2.

Example 102: (S)-4-(9-(5-(Difluoromethyl)-1,3,4-thiadiazol-2-yl)-6-fluoro-7-(N-(1-methylcyclopropyl)sulfamoyl)-9H-pyrimido[4,5-b]indol-4-yl)-N,N,2-trimethylpiperazine-1-carboxamide

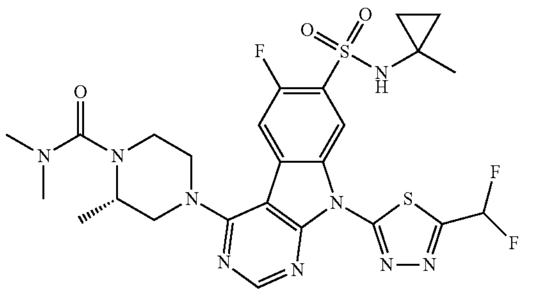

Step 1: (S)-4-(6-fluoro-7-(N-(1-methylcyclopropyl)sulfamoyl)-9H-pyrimido[4,5-b]indol-4-yl)-N,N,2-trimethylpiperazine-1-carboxamide

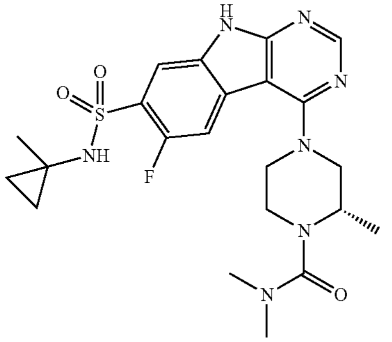 [SMILES: C[C@H]1CN(c2ncnc3[nH]c4cc(S(=O)(=O)NC5(C)CC5)c(F)cc4c23)CCN1C(=O)N(C)C]

To a mixture of 4-chloro-6-fluoro-N-(1-methylcyclopropyl)-9H-pyrimido[4,5-b]indole-7-sulfonamide (60 mg, 0.17 mmol, Intermediate 3) and (S)—N,N,2-trimethylpiperazine-1-carboxamide (58 mg, 0.34 mmol) in tert-butanol (2 mL) was added DIPEA (66 mg, 0.51 mmol). The reaction mixture was stirred at r.t. for 24 h. The mixture was poured into water (20 mL), and extracted with ethyl acetate (30 mL×3). The organic layer was washed with brine (30 mL), dried over $Na_2SO_4$, filtered and concentrated under reduced pressure. The residue was purified by flash chromatography on a silica gel column eluting with MeOH/DCM (0-15%) to afford the title compound (50 mg, 61% yield). LCMS calc. for $C_{22}H_{29}FN_7O_3S$ $[M+H]^+$: m/z=490.2; Found: 490.2.

Step 2: (S)-4-(9-(5-(difluoromethyl)-1,3,4-thiadiazol-2-yl)-6-fluoro-7-(N-(1-methylcyclopropyl)sulfamoyl)-9H-pyrimido[4,5-b]indol-4-yl)-N,N,2-trimethylpiperazine-1-carboxamide This compound was prepared as white solid by procedures analogous to those described for Example 101 Step 2 using (S)-4-(6-fluoro-7-(N-(1-methylcyclopropyl)sulfamoyl)-9H-pyrimido[4,5-b]indol-4-yl)-N,N,2-trimethylpiperazine-1-carboxamide and 2-bromo-5-(difluoromethyl)-1,3,4-thiadiazole. $^1H$ NMR (400 MHz, DMSO-$d_6$) δ 9.43 (d, J=6.5 Hz, 1H), 8.76 (s, 1H), 8.59 (s, 1H), 7.86 (d, J=10.7 Hz, 1H), 7.68 (t, J=53.2 Hz, 1H), 4.24 (d, J=12.9 Hz, 1H), 4.03-4.12 (m, 1H), 3.89-4.00 (m, 1H), 3.75-3.85 (m, 1H), 3.56-3.69 (m, 1H), 3.37-3.45 (m, 1H), 3.25-3.31 (m, 1H), 2.80 (s, 6H), 1.18 (s, 3H), 1.05 (d, J=6.6 Hz, 3H), 0.66-0.75 (m, 2H), 0.41-0.49 (m, 2H). LCMS calc. for $C_{25}H_{29}F_3N_9O_3S_2$ $[M+H]^+$: m/z=624.2; Found: 624.2.

Example 103: 9-(5-(Difluoromethyl)-1,3,4-thiadiazol-2-yl)-6-fluoro-4-(1-isobutyryl-1,2,3,6-tetrahydropyridin-4-yl)-N-(1-methylcyclopropyl)-9H-pyrimido[4,5-b]indole-7-sulfonamide

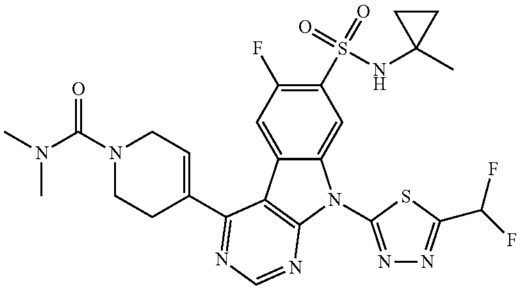 [SMILES: CN(C)C(=O)N1CC=C(c2ncnc3c2c2cc(F)c(S(=O)(=O)NC4(C)CC4)cc2n3-c2nnc(C(F)F)s2)CC1]

Step 1: 6-fluoro-4-(1-isobutyryl-1,2,3,6-tetrahydropyridin-4-yl)-N-(1-methylcyclopropyl)-9H-pyrimido[4,5-b]indole-7-sulfonamide

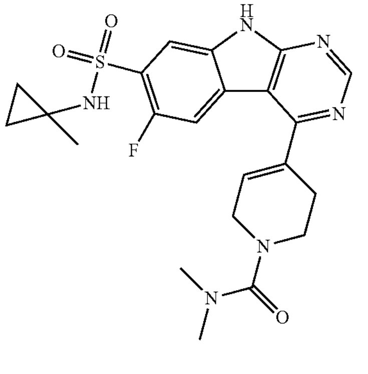 [SMILES: CN(C)C(=O)N1CC=C(c2ncnc3[nH]c4cc(S(=O)(=O)NC5(C)CC5)c(F)cc4c23)CC1]

This compound was prepared by procedures analogous to those described for Example 74 Step 1 using 4-chloro-6-fluoro-N-(1-methylcyclopropyl)-9H-pyrimido[4,5-b]indole-7-sulfonamide (Intermediate 3) and 2-methyl-1-(4-(4,4,5,5-tetramethyl-1,3,2-dioxaborolan-2-yl)-3,6-dihydropyridin-1(2H)-yl)propan-1-one (Example 91 Step 1). LCMS calc. for $C_{23}H_{27}FN_5O_3S$ $[M+H]^+$: m/z=472.1; Found: 472.1.

Step 2: 9-(5-(difluoromethyl)-1,3,4-thiadiazol-2-yl)-6-fluoro-4-(1-isobutyryl-1,2,3,6-tetrahydropyridin-4-yl)-N-(1-methylcyclopropyl)-9H-pyrimido[4,5-b]indole-7-sulfonamide This compound was prepared as white solid by procedures analogous to those described for Example 101 Step 2 using 6-fluoro-4-(1-isobutyryl-1,2,3,6-tetrahydropyridin-4-yl)-N-(1-methylcyclopropyl)-9H-pyrimido[4,5-b]indole-7-sulfonamide and 2-bromo-5-(difluoromethyl)-1,3,4-thiadiazole. $^1H$ NMR (400 MHz, DMSO-$d_6$) δ 9.50 (d, J=6.3 Hz, 1H), 9.30 (s, 1H), 8.71 (s, 1H), 8.20 (t, J=11.4 Hz, 1H), 7.71 (t, J=53.2 Hz, 1H), 6.67 (d, J=20.8 Hz, 1H), 4.42 (d, J=54.5 Hz, 2H), 3.88 (dd, J=10.3, 5.1 Hz, 2H), 3.02 (dd, J=16.0, 7.0 Hz, 1H), 2.77 (d, J=43.6 Hz, 2H), 1.19 (s, 3H), 1.09 (d, J=6.7 Hz, 6H), 0.70 (q, J=5.0 Hz, 2H), 0.45 (q, J=5.0 Hz, 2H). LCMS calc. for $C_{26}H_{27}F_3N_7O_3S_2$ $[M+H]^+$: m/z=606.2; Found: 606.1.

Example 104: N-(1-Cyanocyclopropyl)-9-(5-(difluoromethyl)-1,3,4-thiadiazol-2-yl)-4-(1-(methyl-D-prolyl)piperidin-4-yl)-9H-pyrimido[4,5-b]indole-7-sulfonamide

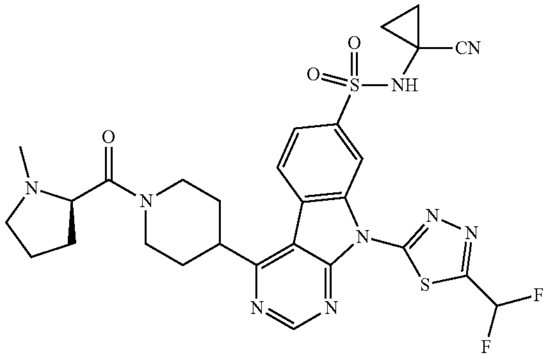 [SMILES: CN1CCC[C@@H]1C(=O)N1CCC(c2ncnc3c2c2ccc(S(=O)(=O)NC4(C#N)CC4)cc2n3-c2nnc(C(F)F)s2)CC1]

To a solution of methyl-D-proline (7.3 mg, 0.06 mmol) and N,N-diisopropylethylamine (14 mg, 0.11 mmol) in DMF (0.5 mL) was added o-(7-azabenzotriazol-1-yl)-N,N,N',N'-tetramethyluronium hexafluorophosphate (HATU) (23.0 mg, 0.11 mmol) and N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (20.0 mg, 0.04 mmol, Example 87). The reaction mixture was stirred at r.t. for 2 h, poured into water (10 mL) and extracted with ethyl acetate (10 mL×3). The combined organic layer was washed with brine (10 mL×3), dried over anhydrous $Na_2SO_4$, filtered and concentrated under reduced pressure. The residue was purified by prep-HPLC eluting with ACN/water (10-95%, with 1% $NH_4HCO_3$) to afford the title compound (4.3 mg, 17.7% yield). $^1H$ NMR (400 MHz, DMSO-$d_6$) δ 9.55 (d, J=1.6 Hz, 1H), 9.31 (s, 1H), 8.73 (d, J=8.2 Hz, 1H), 8.13 (dd, J=8.4, 1.6 Hz, 1H), 7.72 (t, J=53.2 Hz, 1H), 4.65-4.53 (m, 1H), 4.42-4.24 (m, 1H), 4.06 (t, J=11.2 Hz, 1H), 3.58-3.54 (m, 1H), 3.14-2.98 (m, 3H), 2.34 (s, 3H), 2.25-2.20 (m, 1H), 2.09-1.97 (m, 4H), 1.80-1.60 (m, 4H), 1.46-1.43 (m, 2H), 1.31-1.28 (m, 2H). LCMS calc. for $C_{28}H_{30}F_2N_9O_3S_2$$[M+H]^+$: m/z=642.2; Found: 642.6.

The compounds listed in Table 6 below were prepared by using N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (Example 87) and an appropriate acid (Int B) as the methods substantially analogous to those described for preparing Example 104.

TABLE 6

Preparations of Examples (Ex)

| Ex # | Int B | Structure | Name | LCMS Cacl./ Found |
|---|---|---|---|---|
| 105 | 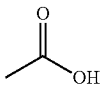 | 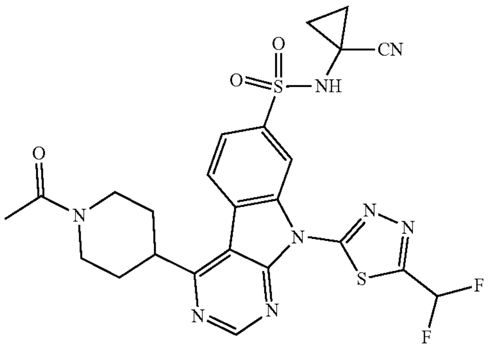 [SMILES: CC(=O)N1CCC(c2ncnc3c2c2ccc(S(=O)(=O)NC4(C#N)CC4)cc2n3-c2nnc(C(F)F)s2)CC1] | 4-(1-acetylpiperidin-4-yl)-N-(1-cyanocyclopropyl)-9-(5-(difluoromethyl)-1,3,4-thiadiazol-2-yl)-9H-pyrimido[4,5-b]indole-7-sulfonamide | $[M + H]^+$ 573.1/ 573.2 |
| 106 | 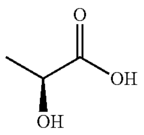 | 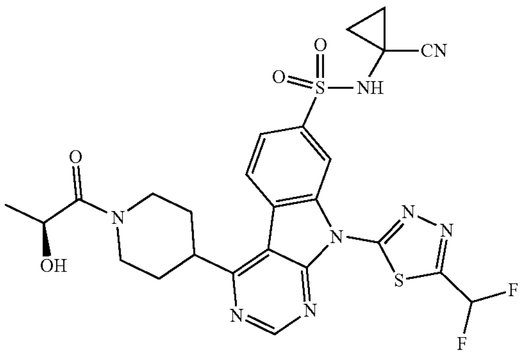 [SMILES: C[C@H](O)C(=O)N1CCC(c2ncnc3c2c2ccc(S(=O)(=O)NC4(C#N)CC4)cc2n3-c2nnc(C(F)F)s2)CC1] | (S)-N-(1-Cyanocyclopropyl)-9-(5-(difluoromethyl)-1,3,4-thiadiazol-2-yl)-4-(1-(2-hydroxypropanoyl) piperidin-4-yl)-9H-pyrimido[4,5-b]indole-7-sulfonamide | $[M + H]^+$ 603.1/ 603.2 |
| 107 | 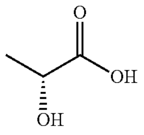 | 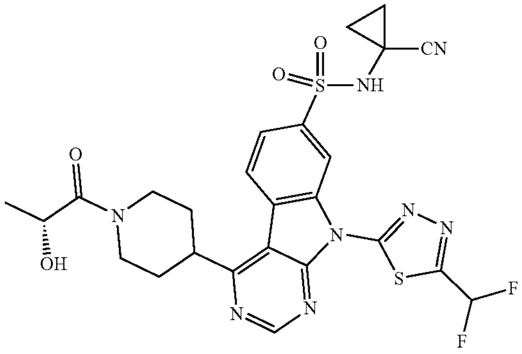 [SMILES: C[C@@H](O)C(=O)N1CCC(c2ncnc3c2c2ccc(S(=O)(=O)NC4(C#N)CC4)cc2n3-c2nnc(C(F)F)s2)CC1] | (R)-N-(1-Cyanocyclopropyl)-9-(5-(difluoromethyl)-1,3,4-thiadiazol-2-yl)-4-(1-(2-hydroxypropanoyl) piperidin-4-yl)-9H-pyrimido[4,5-b]indole-7-sulfonamide | $[M + H]^+$ 603.1/ 603.2 |
| 108 | 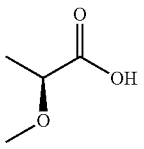 | 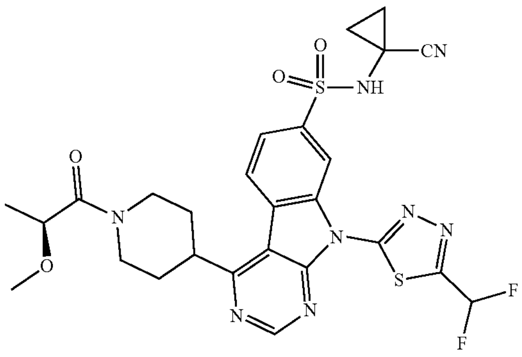 [SMILES: CO[C@@H](C)C(=O)N1CCC(c2ncnc3c2c2ccc(S(=O)(=O)NC4(C#N)CC4)cc2n3-c2nnc(C(F)F)s2)CC1] | (S)-N-(1-Cyanocyclopropyl)-9-(5-(difluoromethyl)-1,3,4-thiadiazol-2-yl)-4-(1-(2-methoxypropanoyl) piperidin-4-yl)-9H-pyrimido[4,5-b]indole-7-sulfonamide | $[M + H]^+$ 617.2/ 617.2 |

TABLE 6-continued

Preparations of Examples (Ex)

| Ex # | Int B | Structure | Name | LCMS Cacl./ Found |
|---|---|---|---|---|
| 109 | 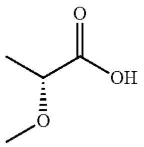 | 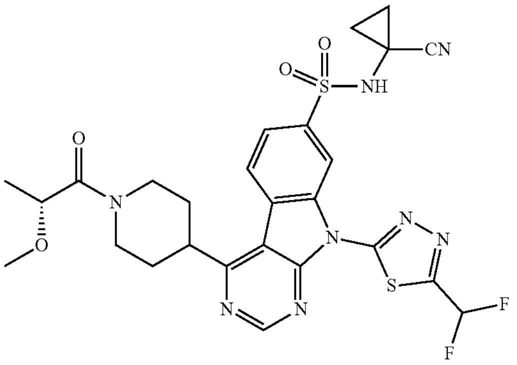 [SMILES: CO[C@H](C)C(=O)N1CCC(c2ncnc3c2c2ccc(S(=O)(=O)NC4(C#N)CC4)cc2n3-c2nnc(C(F)F)s2)CC1] | (R)-N-(1-cyanocyclopropyl)-9-(5-(difluoromethyl)-1,3,4-thiadiazol-2-yl)-4-(1-(2-methoxypropanoyl) piperidin-4-yl)-9H-pyrimido[4,5-b]indole-7-sulfonamide | [M + H]+ 617.2/ 617.2 |
| 110 | 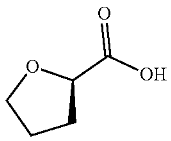 | 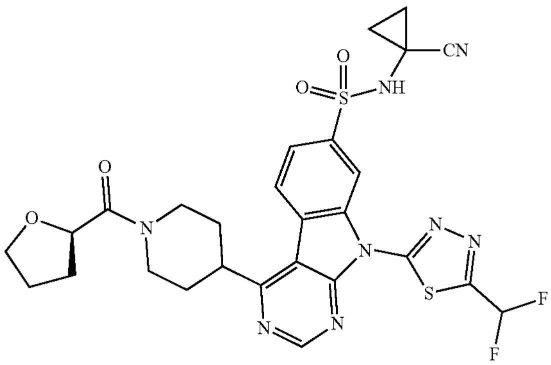 [SMILES: N#CC1(NS(=O)(=O)c2ccc3c4c(C5CCN(C(=O)[C@H]6CCCO6)CC5)ncnc4n(-c4nnc(C(F)F)s4)c3c2)CC1] | (R)-N-(1-cyanocyclopropyl)-9-(5-(difluoromethyl)-1,3,4-thiadiazol-2-yl)-4-(1-(tetrahydrofuran-2-carbonyl) piperidin-4-yl)-9H-pyrimido[4,5-b]indole-7-sulfonamide | [M + H]+ 629.2/ 629.4 |
| 111 | 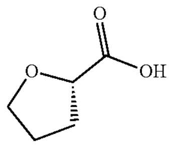 | 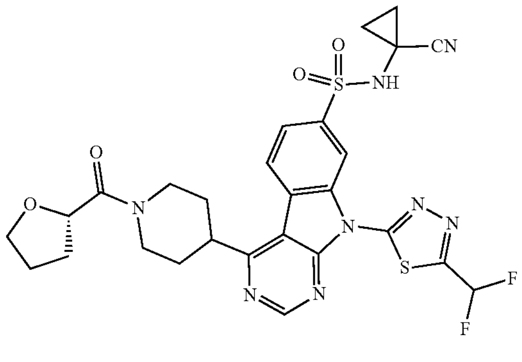 [SMILES: N#CC1(NS(=O)(=O)c2ccc3c4c(C5CCN(C(=O)[C@@H]6CCCO6)CC5)ncnc4n(-c4nnc(C(F)F)s4)c3c2)CC1] | (S)-N-(1-cyanocyclopropyl)-9-(5-(difluoromethyl)-1,3,4-thiadiazol-2-yl)-4-(1-(tetrahydrofuran-2-carbonyl) piperidin-4-yl)-9H-pyrimido[4,5-b]indole-7-sulfonamide | [M + H]+ 629.2/ 629.2 |
| 112 | 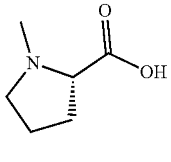 | 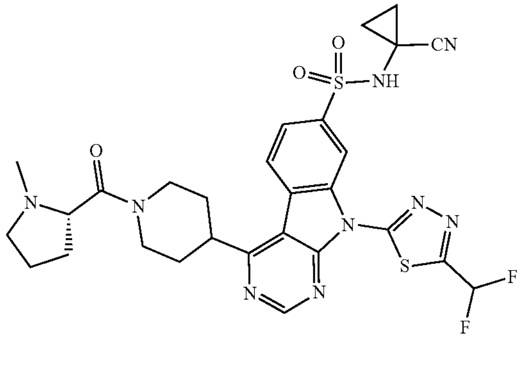 [SMILES: CN1CCC[C@H]1C(=O)N1CCC(c2ncnc3c2c2ccc(S(=O)(=O)NC4(C#N)CC4)cc2n3-c2nnc(C(F)F)s2)CC1] | N-(1-cyanocyclopropyl)-9-(5-(difluoromethyl)-1,3,4-thiadiazol-2-yl)-4-(1-(methyl-L-prolyl) piperidin-4-yl)-9H-pyrimido[4,5-b]indole-7-sulfonamide | [M + H]+ 642.2/ 642.2 |

TABLE 6-continued

| Preparations of Examples (Ex) | | | | |
|---|---|---|---|---|
| Ex # | Int B | Structure | Name | LCMS Cacl./ Found |
| 113 | 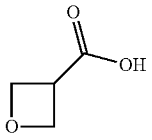 | 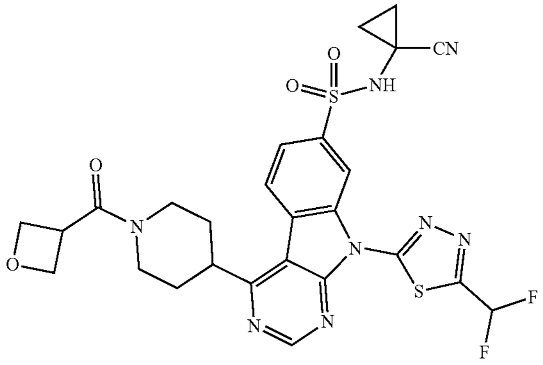 [SMILES: N#CC1(NS(=O)(=O)c2ccc3c4c(C5CCN(C(=O)C6COC6)CC5)ncnc4n(-c4nnc(C(F)F)s4)c3c2)CC1] | N-(1-cyanocyclopropyl)-9-(5-(difluoromethyl)-1,3,4-thiadiazol-2-yl)-4-(1-(oxetane-3-carbonyl) piperidin-4-yl)-9H-pyrimido[4,5-b]indole-7-sulfonamide | [M + H]+ 615.1/ 615.0 |
| 114 | 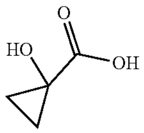 | 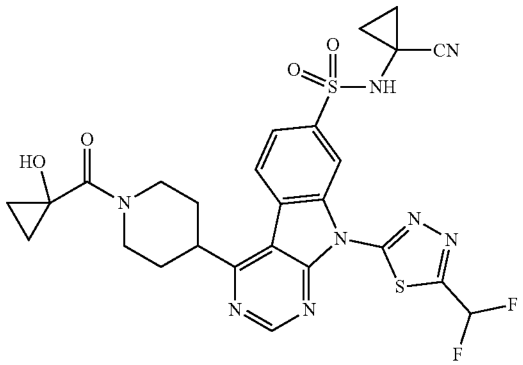 [SMILES: N#CC1(NS(=O)(=O)c2ccc3c4c(C5CCN(C(=O)C6(O)CC6)CC5)ncnc4n(-c4nnc(C(F)F)s4)c3c2)CC1] | N-(1-cyanocyclopropyl)-9-(5-(difluoromethyl)-1,3,4-thiadiazol-2-yl)-4-(1-(1-hydroxycyclopropane-1-carbonyl)piperidin-4-yl)-9H-pyrimido[4,5-b]indole-7-sulfonamide | [M + H]+ 615.1/ 615.1 |
| 115 | 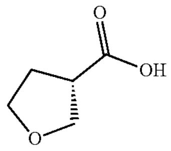 | 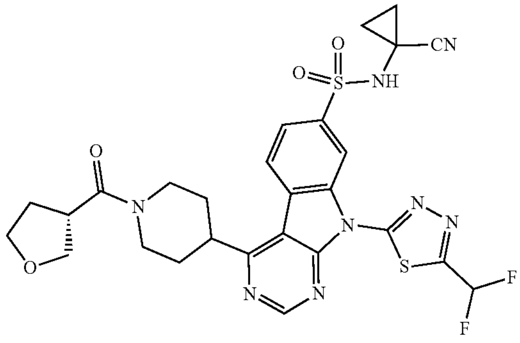 [SMILES: N#CC1(NS(=O)(=O)c2ccc3c4c(C5CCN(C(=O)[C@H]6CCOC6)CC5)ncnc4n(-c4nnc(C(F)F)s4)c3c2)CC1] | (S)-N-(1-cyanocyclopropyl)-9-(5-(difluoromethyl)-1,3,4-thiadiazol-2-yl)-4-(1-(tetrahydrofuran-3-carbonyl) piperidin-4-yl)-9H-pyrimido[4,5-b]indole-7-sulfonamide | [M + H]+ 629.2/ 628.9 |
| 116 | 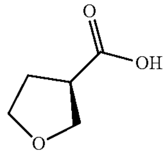 | 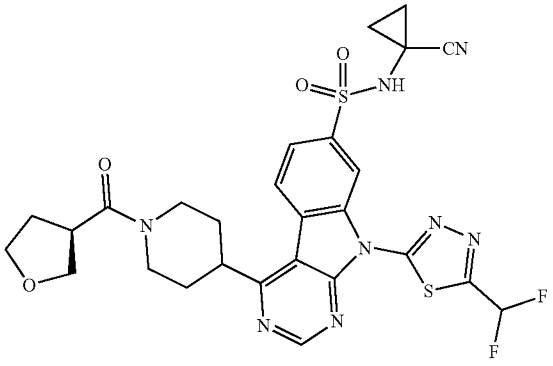 [SMILES: N#CC1(NS(=O)(=O)c2ccc3c4c(C5CCN(C(=O)[C@@H]6CCOC6)CC5)ncnc4n(-c4nnc(C(F)F)s4)c3c2)CC1] | (R)-N-(1-cyanocyclopropyl)-9-(5-(difluoromethyl)-1,3,4-thiadiazol-2-yl)-4-(1-(tetrahydrofuran-3-carbonyl) piperidin-4-yl)-9H-pyrimido[4,5-b]indole-7-sulfonamide | [M + H]+ 629.2/ 628.9 |

TABLE 6-continued

| Preparations of Examples (Ex) | | | | |
|---|---|---|---|---|
| Ex # | Int B | Structure | Name | LCMS Cacl./ Found |
| 117 | 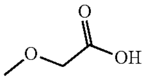 | 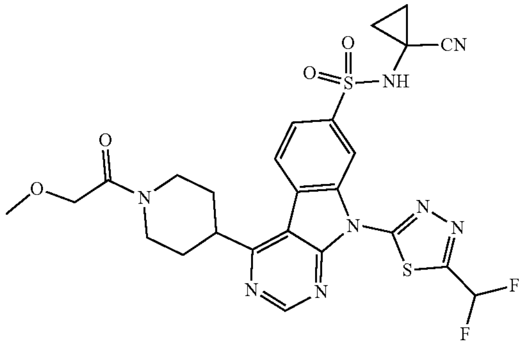 [SMILES: COCC(=O)N1CCC(c2ncnc3c2c2ccc(S(=O)(=O)NC4(C#N)CC4)cc2n3-c2nnc(C(F)F)s2)CC1] | N-(1-cyanocyclopropyl)-9-(5-(difluoromethyl)-1,3,4-thiadiazol-2-yl)-4-(1-(2-methoxyacetyl) piperidin-4-yl)-9H-pyrimido[4,5-b]indole-7-sulfonamide | $[M+H]^+$ 603.1/ 602.9 |
| 118 | 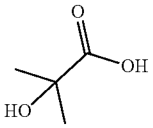 | 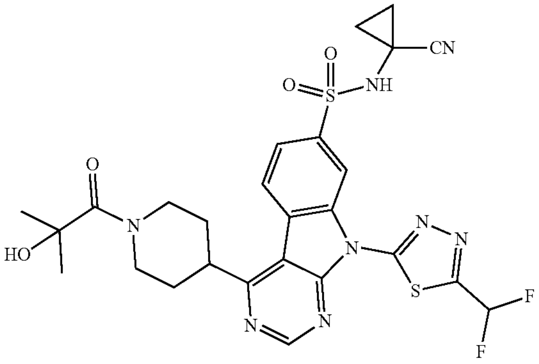 [SMILES: CC(C)(O)C(=O)N1CCC(c2ncnc3c2c2ccc(S(=O)(=O)NC4(C#N)CC4)cc2n3-c2nnc(C(F)F)s2)CC1] | N-(1-cyanocyclopropyl)-9-(5-(difluoromethyl)-1,3,4-thiadiazol-2-yl)-4-(1-(2-hydroxy-2-methylpropanoyl) piperidin-4-yl)-9H-pyrimido[4,5-b]indole-7-sulfonamide | $[M+H]^+$ 617.2/ 617.2 |
| 119 | 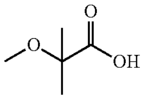 | 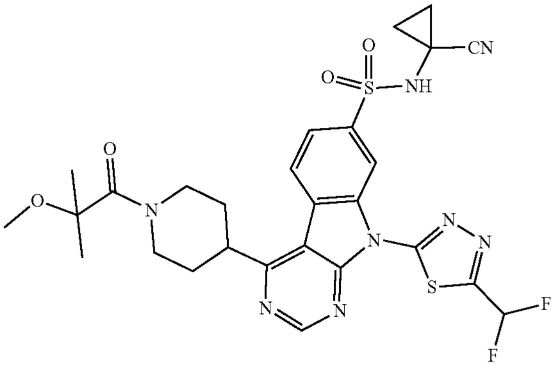 [SMILES: COC(C)(C)C(=O)N1CCC(c2ncnc3c2c2ccc(S(=O)(=O)NC4(C#N)CC4)cc2n3-c2nnc(C(F)F)s2)CC1] | N-(1-cyanocyclopropyl)-9-(5-(difluoromethyl)-1,3,4-thiadiazol-2-yl)-4-(1-(2-methoxy-2-methylpropanoyl) piperidin-4-yl)-9H-pyrimido[4,5-b]indole-7-sulfonamide | $[M+H]^+$ 631.2/ 631.2 |

Example 120: N-(1-cyanocyclopropyl)-9-(5-(difluoromethyl)-1,3,4-thiadiazol-2-yl)-4-(1-propionylpiperidin-4-yl)-9H-pyrimido[4,5-b]indole-7-sulfonamide

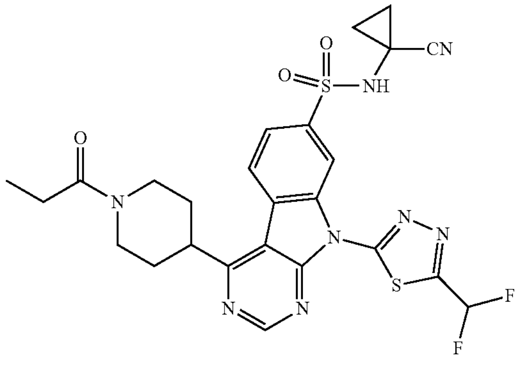 [SMILES: CCC(=O)N1CCC(c2ncnc3c2c2ccc(S(=O)(=O)NC4(C#N)CC4)cc2n3-c2nnc(C(F)F)s2)CC1]

A mixture of N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (100 mg, 0.016 mmol, Example 87) and $NaHCO_3$ (39.6 mg, 0.46 mmol) in THF (1.5 mL) and $H_2O$ (0.3 mL) were added propionic anhydride (30.26 mg, 0.23 mmol) at 0° C. The reaction mixture was stirred at ambient temperature for 1 h. The mixture was concentrated under reduced pressure, then purified by flash chromatography on a C18 column eluting with ACN/$H_2O$ (5%-55%) to afford the title compound (61.69 mg, 55.8% yield) as a white solid. LCMS calculated for $C_{25}H_{25}F_2N_8O_3S_2$ $[M+H]^+$: m/z=587.1; Found: 587.2.

Example 121: N-(1-Cyanocyclopropyl)-9-(5-(difluoromethyl)-1,3,4-thiadiazol-2-yl)-4-(1-(methylsulfonyl)piperidin-4-yl)-9H-pyrimido[4,5-b]indole-7-sulfonamide

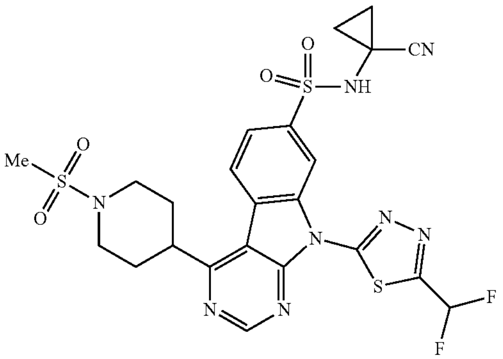 [SMILES: CS(=O)(=O)N1CCC(c2ncnc3c2c2ccc(S(=O)(=O)NC4(C#N)CC4)cc2n3-c2nnc(C(F)F)s2)CC1]

This compound was prepared as white solid by procedures analogous to those described for Example 120 using N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (Example 87) and methanesulfonyl chloride. LCMS calc. for $C_{23}H_{23}F_2N_8O_4S_3$ $[M+H]^+$: m/z=609.1; Found: 609.1.

Example 122: N-(1-Cyanocyclopropyl)-9-(5-(difluoromethyl)-1,3,4-thiadiazol-2-yl)-4-(1-(ethylsulfonyl)piperidin-4-yl)-9H-pyrimido[4,5-b]indole-7-sulfonamide

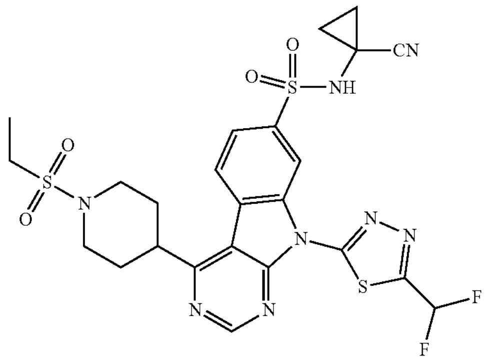 [SMILES: CCS(=O)(=O)N1CCC(c2ncnc3c2c2ccc(S(=O)(=O)NC4(C#N)CC4)cc2n3-c2nnc(C(F)F)s2)CC1]

This compound was prepared as white solid by procedures analogous to those described for Example 120 using N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (Example 87) and ethanesulfonyl chloride. LCMS calc. for $C_{24}H_{25}F_2N_8O_4S_3$ $[M+H]^+$: m/z=623.1; Found: 623.3.

Example 123: N-(1-Cyanocyclopropyl)-9-(5-(difluoromethyl)-1,3,4-thiadiazol-2-yl)-4-(1-(isopropylsulfonyl)piperidin-4-yl)-9H-pyrimido[4,5-b]indole-7-sulfonamide

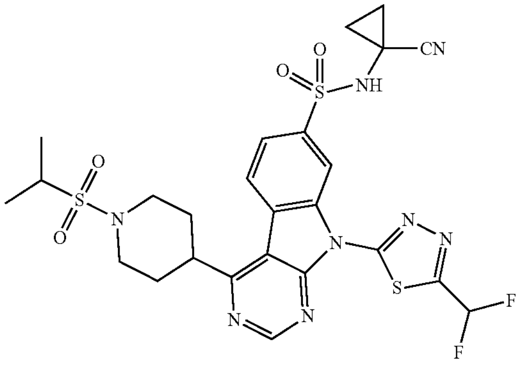 [SMILES: CC(C)S(=O)(=O)N1CCC(c2ncnc3c2c2ccc(S(=O)(=O)NC4(C#N)CC4)cc2n3-c2nnc(C(F)F)s2)CC1]

This compound was prepared as white solid by procedures analogous to those described for Example 120 using N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (Example 87) and isopropylsulfonyl chloride. LCMS calc. for $C_{25}H_{27}F_2N_8O_4S_3$ $[M+H]^+$: m/z=637.1; Found: 637.2.

Example 124: (S)—N-(1-Cyanocyclopropyl)-9-(5-(difluoromethyl)-1,3,4-thiadiazol-2-yl)-4-(1-prolylpiperidin-4-yl)-9H-pyrimido[4,5-b]indole-7-sulfonamide

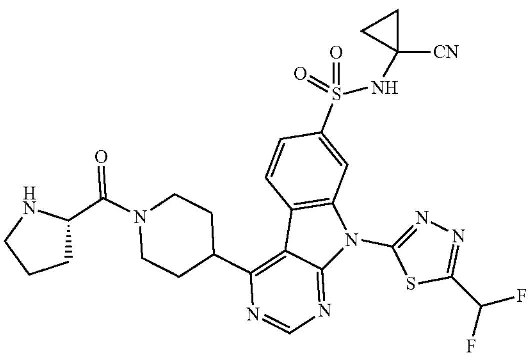 [SMILES: N#CC1(NS(=O)(=O)c2ccc3c4c(C5CCN(C(=O)[C@@H]6CCCN6)CC5)ncnc4n(-c4nnc(C(F)F)s4)c3c2)CC1]

Step 1: tert-butyl (S)-2-(4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carbonyl)pyrrolidine-1-carboxylate

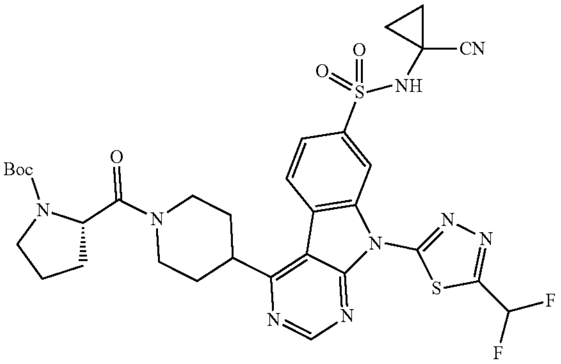 [SMILES: CC(C)(C)OC(=O)N1CCC[C@H]1C(=O)N1CCC(c2ncnc3c2c2ccc(S(=O)(=O)NC4(C#N)CC4)cc2n3-c2nnc(C(F)F)s2)CC1]

To a solution of (tert-butoxycarbonyl)-D-proline (18.3 mg, 0.085 mmol) and N,N-diisopropylethylamine (22.0 mg, 0.17 mmol) in N,N-dimethylformamide (0.5 mL) was added HATU (35.0 mg, 0.11 mmol) and N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (30.0 mg, 0.057 mmol, Example 87). The reaction mixture was stirred at r.t. for 2 h., poured into water (10 mL) and extracted with ethyl acetate (10 mL×3). The combined organic layer was washed with brine (10 mL×3), dried over anhydrous $Na_2SO_4$, filtered and concentrated under reduced pressure. The residue was purified by flash chromatography on a silica gel column eluting with ethyl acetate/petroleum ether (30-100%) to afford the title compound (15.0 mg, 36.5% yield). LCMS calc. for $C_{32}H_{36}F_2N_9O_5S_2$ $[M+H]^+$: m/z=728.2; Found: 728.7.

Step 2: (S)—N-(1-cyanocyclopropyl)-9-(5-(difluoromethyl)-1,3,4-thiadiazol-2-yl)-4-(1-prolylpiperidin-4-yl)-9H-pyrimido[4,5-b]indole-7-sulfonamide To a solution of tert-butyl (S)-2-(4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carbonyl)pyrrolidine-1-carboxylate (15.0 mg, 0.02 mmol) in dichloromethane (0.5 mL) was added trifluoroacetic acid (0.5 mL). The reaction mixture was stirred at r.t. for 1 h. Then the reaction mixture was concentrated under reduced pressure and purified by Prep-HPLC eluting with ACN/water (10-95% with 10 mM $NH_4HCO_3$) to afford the title compound (4.07 mg, 31.5% yield). $^1H$ NMR: (400 MHz, $CD_3OD$) δ 9.48 (s, 1H), 9.09 (d, J=3.8 Hz, 1H), 8.45 (d, J=8.2 Hz, 1H), 8.10-8.03 (m, 1H), 7.34 (t, J=53.6 Hz, 1H), 4.73 (d, J=13.0 Hz, 2H), 4.28-4.20 (m, 2H), 4.06-3.98 (m, 1H), 3.59-3.57 (m, 1H), 3.18 (t, J=12.6 Hz, 1H), 3.04-3.00 (m, 1H), 2.44-2.14 (m, 4H), 2.08-1.83 (m, 4H), 1.45-1.42 (m, 2H), 1.39-1.33 (in, 2H). LCMS calc. for $C_{27}H_{28}F_2N_9O_3S_2$ $[M+H]^+$: m/z=628.2; Found: 628.2.

The compounds listed in Table 7 below were prepared by using N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (Example 87) and an appropriate acid derivative (Int B) as the methods substantially analogous to those described for preparing Example 124.

TABLE 7

| Preparations of Examples (Ex) | | | | |
|---|---|---|---|---|
| Ex # | Int B | Structure | Name | LCMS Cacl./ Found |
| 125 | 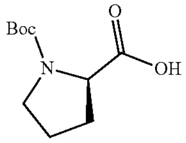 [SMILES: CC(C)(C)OC(=O)N1CCC[C@@H]1C(=O)O] | 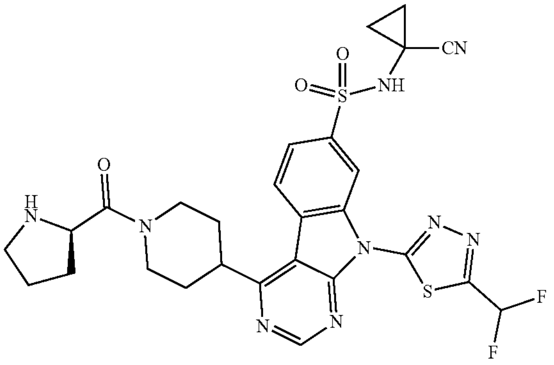 [SMILES: N#CC1(NS(=O)(=O)c2ccc3c4c(C5CCN(C(=O)[C@H]6CCCN6)CC5)ncnc4n(-c4nnc(C(F)F)s4)c3c2)CC1] | (R)-N-(1-cyanocyclopropyl)-9-(5-(difluoromethyl)-1,3,4-thiadiazol-2-yl)-4-(1-prolylpiperidin-4-yl)-9H-pyrimido[4,5-b]indole-7-sulfonamide | $[M + H]^+$ 628.2/ 628.2 |
| 126 | 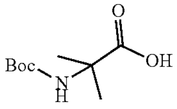 | 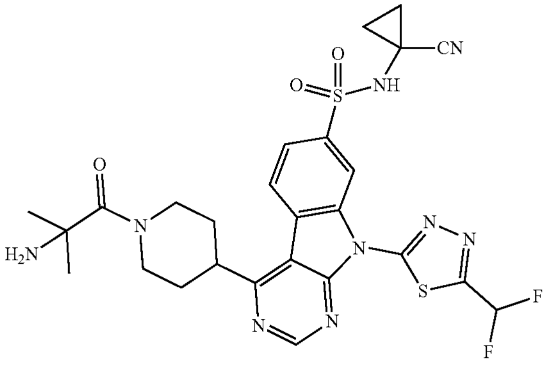 [SMILES: CC(C)(N)C(=O)N1CCC(c2ncnc3c2c2ccc(S(=O)(=O)NC4(C#N)CC4)cc2n3-c2nnc(C(F)F)s2)CC1] | 4-(1-(2-Amino-2-methylpropanoyl) piperidin-4-yl)-N-(1-cyanocyclopropyl)-9-(5-(difluoromethyl)-1,3,4-thiadiazol-2-yl)-9H-pyrimido[4,5-b]indole-7-sulfonamide | $[M + H]^+$ 616.2/ 616.2 |
| 127 | 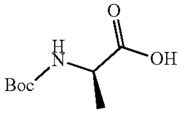 | 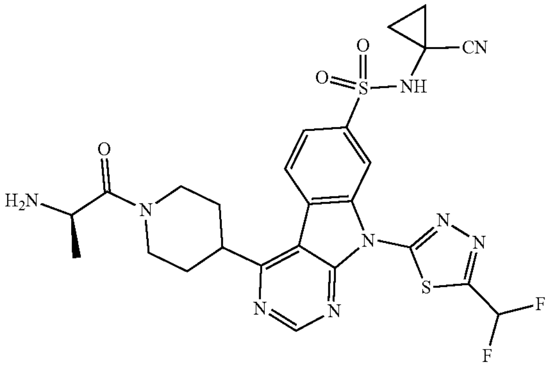 [SMILES: C[C@@H](N)C(=O)N1CCC(c2ncnc3c2c2ccc(S(=O)(=O)NC4(C#N)CC4)cc2n3-c2nnc(C(F)F)s2)CC1] | 4-(1-(D-Alanyl) piperidin-4-yl)-N-(1-cyanocyclopropyl)-9-(5-(difluoromethyl)-1,3,4-thiadiazol-2-yl)-9H-pyrimido[4,5-b]indole-7-sulfonamide | $[M + H]^+$ 602.2/ 602.2 |
| 128 | 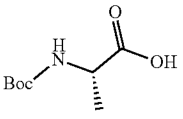 | 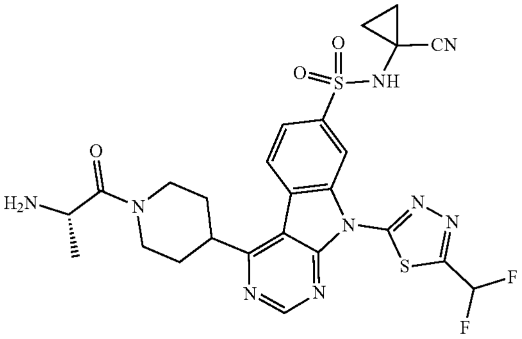 [SMILES: C[C@H](N)C(=O)N1CCC(c2ncnc3c2c2ccc(S(=O)(=O)NC4(C#N)CC4)cc2n3-c2nnc(C(F)F)s2)CC1] | 4-(1-(L-alanyl) piperidin-4-yl)-N-(1-cyanocyclopropyl)-9-(5-(difluoromethyl)-1,3,4-thiadiazol-2-yl)-9H-pyrimido[4,5-b]indole-7-sulfonamide | $[M + H]^+$ 602.2/ 602.2 |

Example 129: (R)—N-(1-Cyanocyclopropyl)-9-(5-(difluoromethyl)-1,3,4-thiadiazol-2-yl)-4-(1-(3-hydroxypyrrolidine-1-carbonyl)piperidin-4-yl)-9H-pyrimido[4,5-b]indole-7-sulfonamide

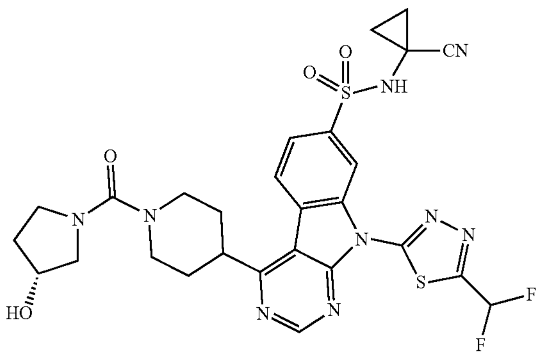 [SMILES: N#CC1(NS(=O)(=O)c2ccc3c4c(C5CCN(C(=O)N6CC[C@@H](O)C6)CC5)ncnc4n(-c4nnc(C(F)F)s4)c3c2)CC1]

Step 1: (R)-4-(1-(3-((tert-butyldimethylsilyl)oxy)pyrrolidine-1-carbonyl)piperidin-4-yl)-N-(1-cyanocyclopropyl)-9-(5-(difluoromethyl)-1,3,4-thiadiazol-2-yl)-9H-pyrimido[4,5-b]indole-7-sulfonamide

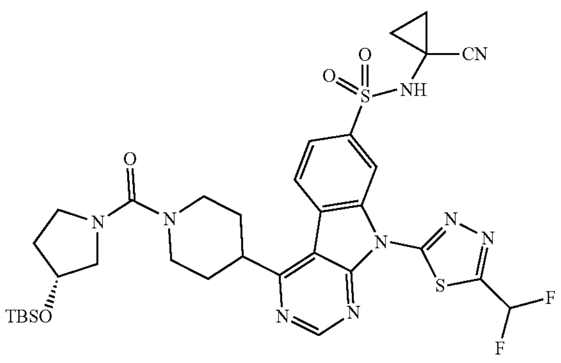 [SMILES: CC(C)(C)[Si](C)(C)O[C@@H]1CCN(C(=O)N2CCC(c3ncnc4c3c3ccc(S(=O)(=O)NC5(C#N)CC5)cc3n4-c3nnc(C(F)F)s3)CC2)C1]

To a solution of N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (100 mg, 0.16 mmol, Example 87) in THF (1 mL) was added DIEA (60 mg, 0.47 mmol), (R)-1-(3-((tert-butyldimethylsilyl)oxy)pyrrolidine-1-carbonyl)-3-methyl-1H-imidazol-3-ium iodide (58 mg, 0.19 mmol, Intermediate 56). The reaction mixture was stirred at 25° C. for 2 h. The mixture was concentrated under reduced pressure to afford the title compound (100 mg, 85.5% yield) as a yellow oil. LCMS calc. for $C_{33}H_{42}F_2N_9O_4S_2Si$ $[M+H]^+$: m/z=758.3; Found: 758.2.

Step 2: (R)—N-(1-cyanocyclopropyl)-9-(5-(difluoromethyl)-1,3,4-thiadiazol-2-yl)-4-(1-(3-hydroxypyrrolidine-1-carbonyl)piperidin-4-yl)-9H-pyrimido[4,5-b]indole-7-sulfonamide To a solution of (R)-4-(1-(3-((tert-butyldimethylsilyl)oxy)pyrrolidine-1-carbonyl)piperidin-4-yl)-N-(1-cyanocyclopropyl)-9-(5-(difluoromethyl)-1,3,4-thiadiazol-2-yl)-9H-pyrimido[4,5-b]indole-7-sulfonamide (100 mg, 0.132 mmol) in THF (5 mL) was added triethylamine trihydrofluoride (1 mL). The reaction mixture was stirred at 25° C. for 12 h. The reaction mixture was concentrated under reduced pressure. The crude product was purified by prep-HPLC on a C18 column eluting with ACN/$H_2O$ (45-50%) to afford the title compound (70 mg, 82.4% yield) as a white solid. LCMS calc. for $C_{27}H_{28}F_2N904S_2$ $[M+H]^+$: m/z=644.2; Found: 644.2.

Example 130: (S)—N-(1-Cyanocyclopropyl)-9-(5-(difluoromethyl)-1,3,4-thiadiazol-2-yl)-4-(1-(3-hydroxypyrrolidine-1-carbonyl)piperidin-4-yl)-9H-pyrimido[4,5-b]indole-7-sulfonamide

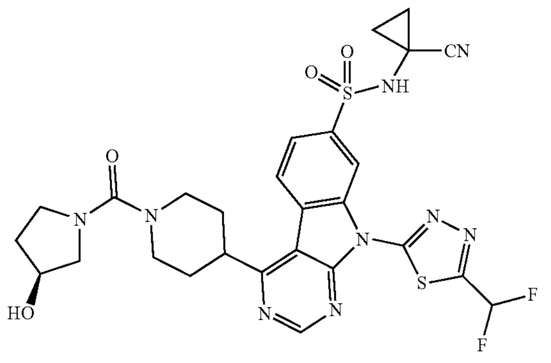 [SMILES: N#CC1(NS(=O)(=O)c2ccc3c4c(C5CCN(C(=O)N6CC[C@H](O)C6)CC5)ncnc4n(-c4nnc(C(F)F)s4)c3c2)CC1]

This compound was prepared as white solid by procedures analogous to those described for Example 129 Step 1-2 using (S)-1-(3-((tert-butyldimethylsilyl)oxy)pyrrolidine-1-carbonyl)-3-methyl-1H-imidazol-3-ium iodide (Intermediate 57) to replace (R)-1-(3-((tert-butyldimethylsilyl)oxy)pyrrolidine-1-carbonyl)-3-methyl-1H-imidazol-3-ium iodide (Intermediate 56) in Step 1. LCMS calc. for $C_{27}H_{28}F_2N_9O_4S_2$ $[M+H]^+$: m/z=644.2; Found: 644.2.

Example 131: (S)-9-(5-(Difluoromethyl)-1,3,4-thiadiazol-2-yl)-4-(1-(3-hydroxypyrrolidine-1-carbonyl)piperidin-4-yl)-N-(1-methylcyclopropyl)-9H-pyrimido[4,5-b]indole-7-sulfonamide

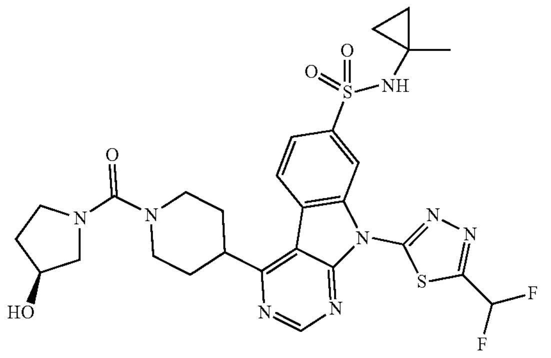 [SMILES: CC1(NS(=O)(=O)c2ccc3c4c(C5CCN(C(=O)N6CC[C@H](O)C6)CC5)ncnc4n(-c4nnc(C(F)F)s4)c3c2)CC1]

This compound was prepared as white solid by procedures analogous to those described for Example 129 Step 1-2 using 9-(5-(Difluoromethyl)-1,3,4-thiadiazol-2-yl)-N-(1-methylcyclopropyl)-4-(piperidin-4-yl)-9H-pyrimido[4,5-b]indole-7-sulfonamide (Example 93) and (S)-1-(3-((tert-butyldimethylsilyl)oxy)pyrrolidine-1-carbonyl)-3-methyl-1H-imidazol-3-ium iodide (Intermediate 57) in Step 1. LCMS calc. for $C_{27}H_{31}F_2N_8O_4S_2$ $[M+H]^+$: m/z=633.2; Found: 633.3.

Example 132: (R)-9-(5-(Difluoromethyl)-1,3,4-thiadiazol-2-yl)-4-(1-(3-hydroxypyrrolidine-1-carbonyl)piperidin-4-yl)-N-(1-methylcyclopropyl)-9H-pyrimido[4,5-b]indole-7-sulfonamide

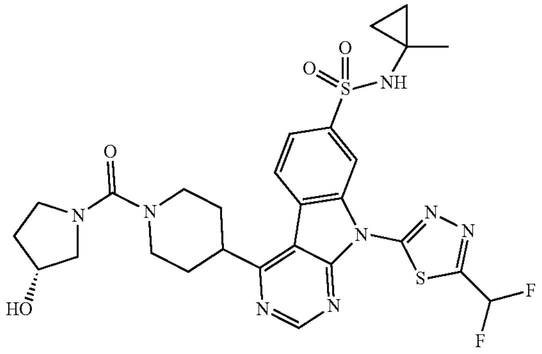 [SMILES: CC1(NS(=O)(=O)c2ccc3c4c(C5CCN(C(=O)N6CC[C@@H](O)C6)CC5)ncnc4n(-c4nnc(C(F)F)s4)c3c2)CC1]

This compound was prepared as white solid by procedures analogous to those described for Example 129 Step 1-2 using 9-(5-(Difluoromethyl)-1,3,4-thiadiazol-2-yl)-N-(1-methylcyclopropyl)-4-(piperidin-4-yl)-9H-pyrimido[4,5-b]indole-7-sulfonamide (Example 93) and (R)-1-(3-((tert-butyldimethylsilyl)oxy)pyrrolidine-1-carbonyl)-3-methyl-1H-imidazol-3-ium iodide (Intermediate 56) in Step 1. LCMS calc. for $C_{27}H_{31}F_2N_8O_4S_2$ $[M+H]^+$: m/z=633.2; Found: 633.3.

Example 133: 9-(5-(difluoromethyl)-1,3,4-thiadiazol-2-yl)-N-(1-methylcyclopropyl)-4-(1-(morpholine-4-carbonyl)piperidin-4-yl)-9H-pyrimido[4,5-b]indole-7-sulfonamide

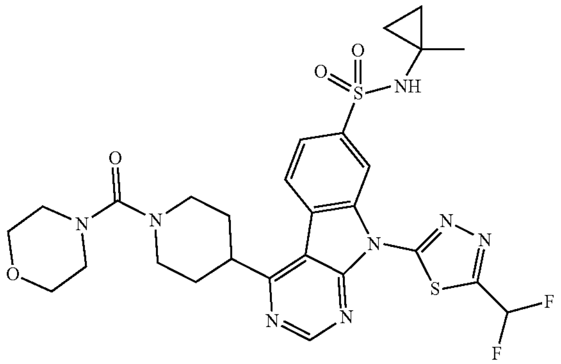 [SMILES: CC1(NS(=O)(=O)c2ccc3c4c(C5CCN(C(=O)N6CCOCC6)CC5)ncnc4n(-c4nnc(C(F)F)s4)c3c2)CC1]

To a solution of 9-(5-(difluoromethyl)-1,3,4-thiadiazol-2-yl)-N-(1-methylcyclopropyl)-4-(piperidin-4-yl)-9H-pyrimido[4,5-b]indole-7-sulfonamide (15 mg, 0.029 mmol, Example 93) in THF (1 mL) was added DIEA (9 mg, 0.07 mmol) and 3-methyl-1-(morpholine-4-carbonyl)-1H-imidazol-3-ium iodide (15 mg, 0.046 mmol, Intermediate 58). The reaction mixture was stirred at 25° C. for 16 h. The reaction mixture was concentrated under reduced pressure. The crude product was purified by prep-HPLC on a C18 column eluting with ACN/$H_2O$ (10-50%) to afford the title compound (9 mg, 50.0% yield) as a white solid. LCMS calc. for $C_{27}H_{31}F_2N_8O_4S_2$ $[M+H]^+$: m/z=633.3; Found: 633.2.

Example 134: (S)—N-(1-Cyanocyclopropyl)-9-(5-(difluoromethyl)-1,3,4-thiadiazol-2-yl)-4-(1-(3-methoxypyrrolidine-1-carbonyl)piperidin-4-yl)-9H-pyrimido[4,5-b]indole-7-sulfonamide

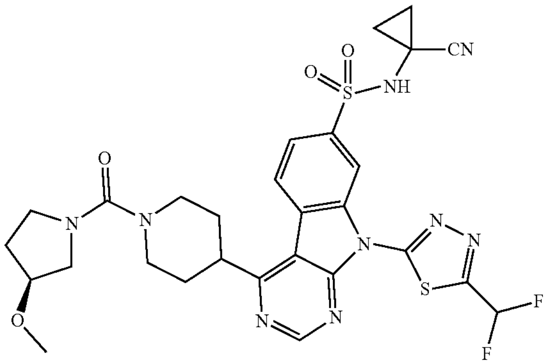 [SMILES: CO[C@H]1CCN(C(=O)N2CCC(c3ncnc4c3c3ccc(S(=O)(=O)NC5(C#N)CC5)cc3n4-c3nnc(C(F)F)s3)CC2)C1]

Step 1: 4-nitrophenyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carboxylate

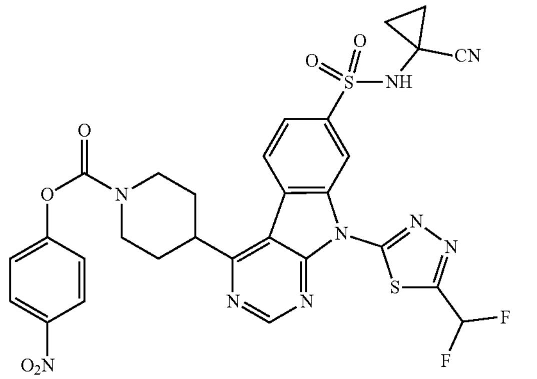 [SMILES: N#CC1(NS(=O)(=O)c2ccc3c4c(C5CCN(C(=O)Oc6ccc([N+](=O)[O-])cc6)CC5)ncnc4n(-c4nnc(C(F)F)s4)c3c2)CC1]

To a solution of N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (200 mg, 0.38 mmol, Example 87) in THF (2 mL) was added 4-nitrophenyl carbonochloridate (75 mg, 0.372 mmol). The reaction was cooled to 0° C., followed by dropwise addition of DIEA (120 mg, 0.93 mmol). The reaction mixture was stirred at 0° C. for 1 h., and concentrated under reduced pressure to afford the title compound (200 mg, 76.3% yield) as yellow oil. LCMS calc. for $C_{29}H_{24}F_2N_9O_6S_2$ $[M+H]^+$: m/z=696.1; Found: 696.2.

Step 2: (S)—N-(1-cyanocyclopropyl)-9-(5-(difluoromethyl)-1,3,4-thiadiazol-2-yl)-4-(1-(3-methoxypyrrolidine-1-carbonyl)piperidin-4-yl)-9H-pyrimido[4,5-b]indole-7-sulfonamide To a solution of 4-nitrophenyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carboxylate (50 mg, 0.072 mmol) in DIEA (0.5 mL) was added (S)-3- methoxypyrrolidine (0.3 mL). The reaction mixture was stirred at 90° C. for 12 h., and concentrated under reduced pressure. The residue was purified by prep-HPLC on a C18 column eluting with ACN/$H_2O$ (50-75%) to afford the title compound (20 mg, 47.3% yield) as a white solid. LCMS calc. for $C_{28}H_{30}F_2N_9O_4S_2$ $[M+H]^+$: m/z=658.2; Found: 658.3.

The compounds listed in Table 8 below were prepared by using 4-nitrophenyl 4-(7-(N-(1-cyanocyclopropyl)sulfamoyl)-9-(5-(difluoromethyl)-1,3,4-thiadiazol-2-yl)-9H-pyrimido[4,5-b]indol-4-yl)piperidine-1-carboxylate (Example 134 Step 1) and an appropriate amine (Int B) as the methods substantially analogous to those described for preparing Example 134 Step 2.

TABLE 8

Preparations of Examples (Ex)

| Ex # | Int B | Structure | Name | LCMS Calc./ Found |
|---|---|---|---|---|
| 135 | 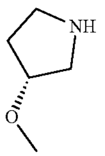 | 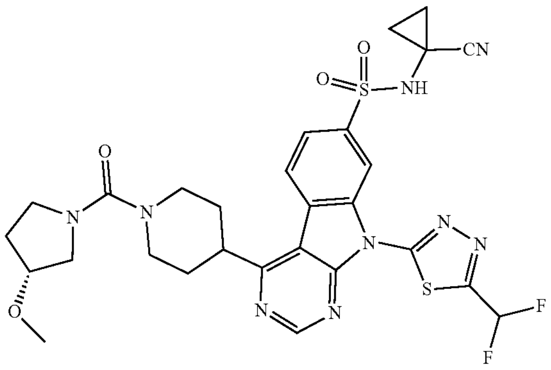 [SMILES: CO[C@@H]1CCN(C(=O)N2CCC(c3ncnc4c3c3ccc(S(=O)(=O)NC5(C#N)CC5)cc3n4-c3nnc(C(F)F)s3)CC2)C1] | (R)-N-(1-Cyanocyclopropyl)-9-(5-(difluoromethyl)-1,3,4-thiadiazol-2-yl)-4-(1-(3-methoxypyrrolidine-1-carbonyl)piperidin-4-yl)-9H-pyrimido [4,5-b]indole-7-sulfonamide | $[M + H]^+$ 658.2/658.2 |
| 136 | 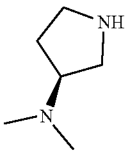 | 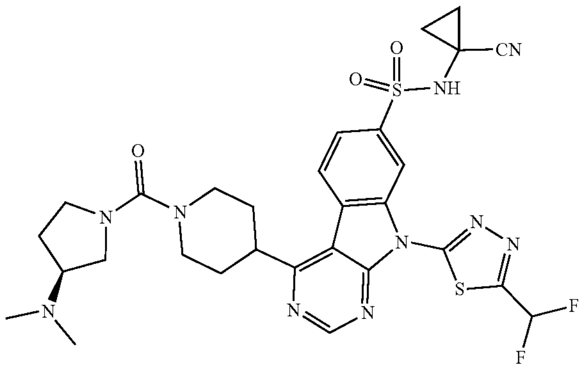 [SMILES: CN(C)[C@H]1CCN(C(=O)N2CCC(c3ncnc4c3c3ccc(S(=O)(=O)NC5(C#N)CC5)cc3n4-c3nnc(C(F)F)s3)CC2)C1] | (S)-N-(1-Cyanocyclopropyl)-9-(5-(difluoromethyl)-1,3,4-thiadiazol-2-yl)-4-(1-(3-(dimethylamino) pyrrolidine-1-carbonyl)piperidin-4-yl)-9H-pyrimido [4,5-b]indole-7-sulfonamide | $[M + H]^+$ 671.2/671.3 |
| 137 | 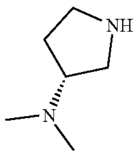 | 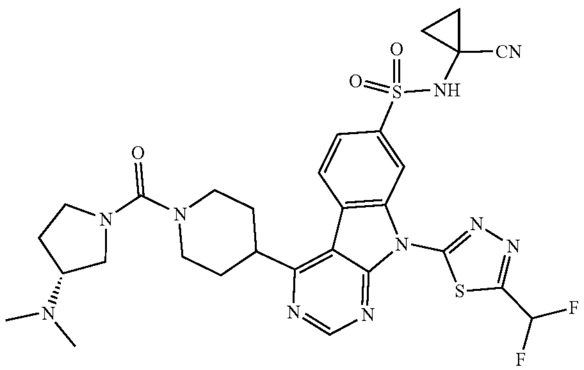 [SMILES: CN(C)[C@@H]1CCN(C(=O)N2CCC(c3ncnc4c3c3ccc(S(=O)(=O)NC5(C#N)CC5)cc3n4-c3nnc(C(F)F)s3)CC2)C1] | (R)-N-(1-Cyanocyclopropyl)-9-(5-(difluoromethyl)-1,3,4-thiadiazol-2-yl)-4-(1-(3-(dimethylamino) pyrrolidine-1-carbonyl)piperidin-4-yl)-9H-pyrimido[4,5-b] indole-7-sulfonamide | $[M + H]^+$ 671.2/671.3 |

TABLE 8-continued

Preparations of Examples (Ex)

| Ex # | Int B | Structure | Name | LCMS Calc./ Found |
|---|---|---|---|---|
| 138 | 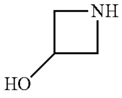 | 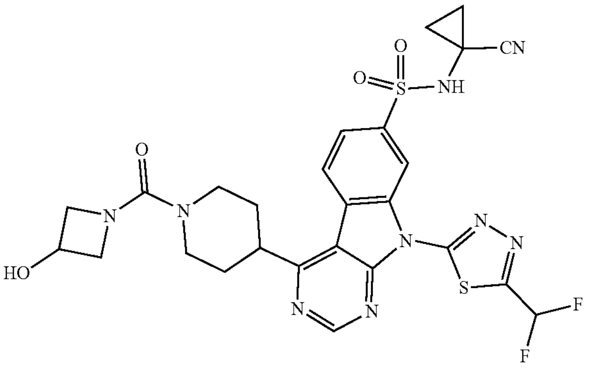 [SMILES: N#CC1(NS(=O)(=O)c2ccc3c4c(C5CCN(C(=O)N6CC(O)C6)CC5)ncnc4n(-c4nnc(C(F)F)s4)c3c2)CC1] | N-(1-cyanocyclo-propyl)-9-(5-(difluoromethyl)-1,3,4-thiadiazol-2-yl)-4-(1-(3-hydroxy-azetidine-1-carbonyl)piperidin-4-yl)-9H-pyrimido [4,5-b]indole-7-sulfonamide | [M + H]+ 630.2/630.2 |
| 139 | 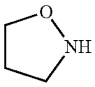 | 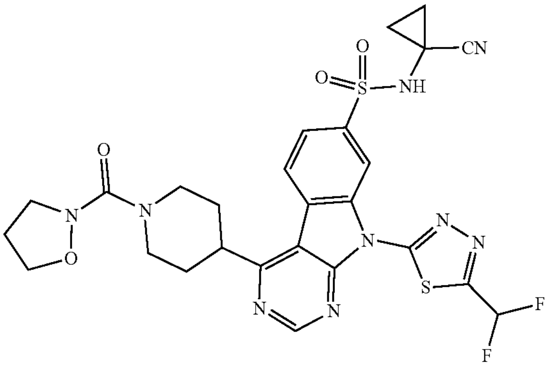 [SMILES: N#CC1(NS(=O)(=O)c2ccc3c4c(C5CCN(C(=O)N6CCCO6)CC5)ncnc4n(-c4nnc(C(F)F)s4)c3c2)CC1] | N-(1-cyanocyclo-propyl)-9-(5-(difluoromethyl)-1,3,4-thiadiazol-2-yl)-4-(1-isoxazolidine-2-carbonyl)piperidin-4-yl)-9H-pyrimido [4,5-b]indole-7-sulfonamide | [M + H]+ 630.2/630.4 |
| 140 | 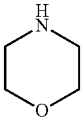 | 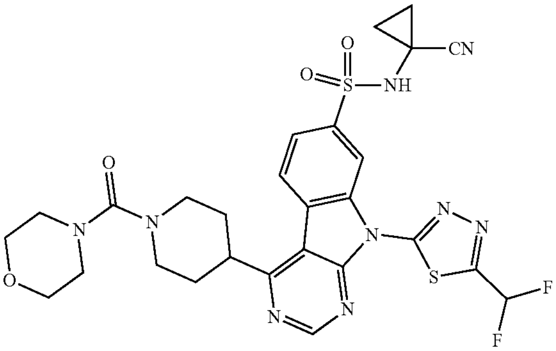 [SMILES: N#CC1(NS(=O)(=O)c2ccc3c4c(C5CCN(C(=O)N6CCOCC6)CC5)ncnc4n(-c4nnc(C(F)F)s4)c3c2)CC1] | N-(1-cyanocyclo-propyl)-9-(5-(difluoromethyl)-1,3,4-thiadiazol-2-yl)-4-(1-(morpholine-4-carbonyl)piperidin-4-yl)-9H-pyrimido [4,5-b]indole-7-sulfonamide | [M + H]+ 644.2/644.3 |
| 141 | 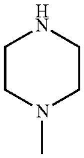 | 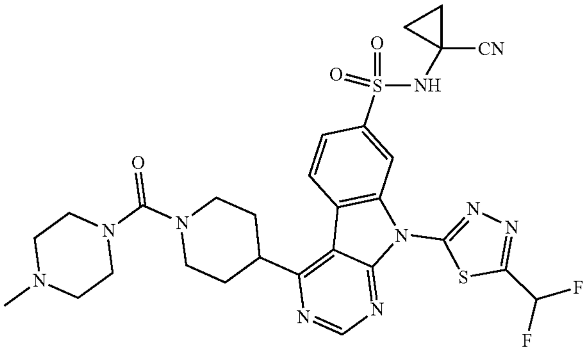 [SMILES: CN1CCN(C(=O)N2CCC(c3ncnc4c3c3ccc(S(=O)(=O)NC5(C#N)CC5)cc3n4-c3nnc(C(F)F)s3)CC2)CC1] | N-(1-cyanocyclo-propyl)-9-(5-(difluoromethyl)-1,3,4-thiadiazol-2-yl)-4-(1-(4-methylpiperazine-1-carbonyl)piperidin-4-yl)-9H-pyrimido [4,5-b]indole-7-sulfonamide | [M + H]+ 657.2/657.4 |

TABLE 8-continued

| Ex # | Int B | Structure | Name | LCMS Calc./ Found |
|---|---|---|---|---|
| Preparations of Examples (Ex) | | | | |
| 142 | 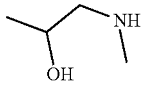 | 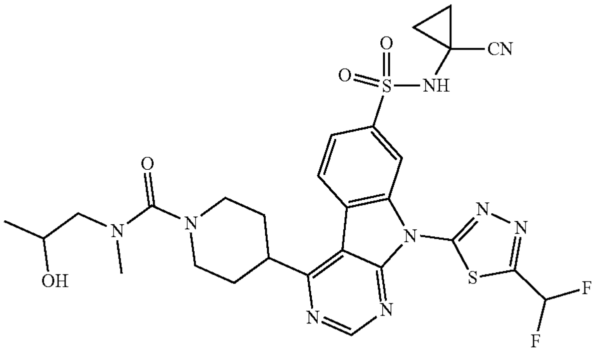 [SMILES: CC(O)CN(C)C(=O)N1CCC(c2ncnc3c2c2ccc(S(=O)(=O)NC4(C#N)CC4)cc2n3-c2nnc(C(F)F)s2)CC1] | 4-(7-(N-(1-cyanocyclo-propyl)sulfamoyl)-9-(5-(difluoromethyl)-1,3,4-thiadiazol-2-yl)-9H-pyrimido[4,5-b]indol-4-yl)-N-(2-hydroxypropyl)-N-methylpiperidine-1-carboxamide | [M + H]+ 646.2/646.2 |
| 143 | 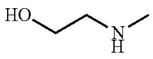 | 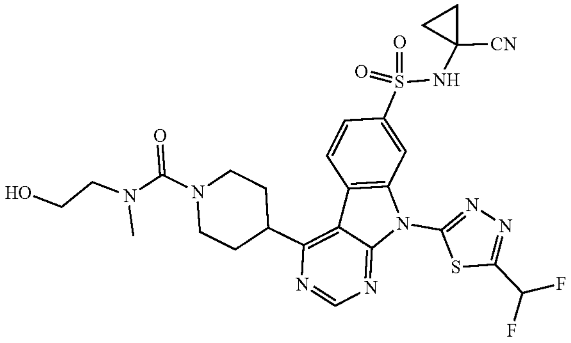 [SMILES: CN(CCO)C(=O)N1CCC(c2ncnc3c2c2ccc(S(=O)(=O)NC4(C#N)CC4)cc2n3-c2nnc(C(F)F)s2)CC1] | 4-(7-(N-(1-cyanocyclo-propyl)sulfamoyl)-9-(5-(difluoromethyl)-1,3,4-thiadiazol-2-yl)-9H-pyrimido[4,5-b]indol-4-yl)-N-(2-hydroxyethyl)-N-methylpiperidine-1-carboxamide | [M + H]+ 632.2/632.2 |
| 144 | 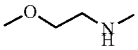 | 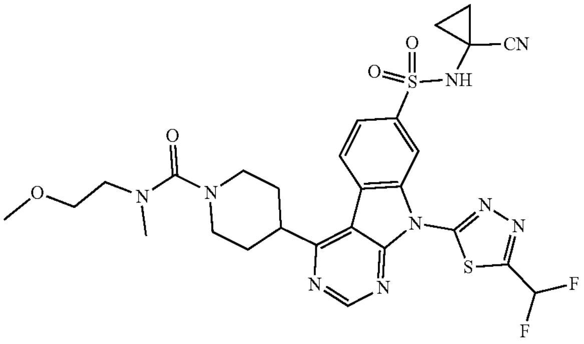 [SMILES: COCCN(C)C(=O)N1CCC(c2ncnc3c2c2ccc(S(=O)(=O)NC4(C#N)CC4)cc2n3-c2nnc(C(F)F)s2)CC1] | 4-(7-(N-(1-cyanocyclo-propyl)sulfamoyl)-9-(5-(difluoromethyl)-1,3,4-thiadiazol-2-yl)-9H-pyrimido[4,5-b]indol-4-yl)-N-(2-methoxyethyl)-N-methylpiperidine-1-carboxamide | [M + H]+ 646.2/646.5 |

Example 145: 4-(7-(N-(1-Cyanocyclopropyl)sulfamoyl)-9-(5-(difluoromethyl)-1,3,4-thiadiazol-2-yl)-9H-pyrimido[4,5-b]indol-4-yl)-N-methoxy-N-methylpiperidine-1-carboxamide

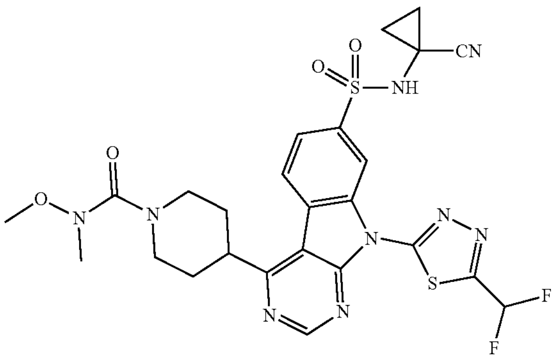 [SMILES: CON(C)C(=O)N1CCC(c2ncnc3c2c2ccc(S(=O)(=O)NC4(C#N)CC4)cc2n3-c2nnc(C(F)F)s2)CC1]

To a solution of N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (30 mg, 0.06 mmol, Example 87) and TEA (12 mg, 0.18 mmol) in N,N-dimethylformamide (0.5 mL) was added methoxy(methyl)carbamic chloride (15 mg, 0.12 mmol) at 0° C. The reaction mixture was stirred at r.t. for 1 h., poured into water (10 mL), and extracted with ethyl acetate (10 mL×3). The combined organic layers were washed with brine, dried over anhydrous $Na_2SO_4$, filtered and concentrated under reduced pressure. The residue was purified by Prep-HPLC eluting with ACN/$H_2O$ (10-95% with 10 mM $NH_4HCO_3$) to afford the title compound (4.7 mg, 13.4% yield). $^1H$ NMR: (400 MHz, DMSO-$d_6$) δ 9.55 (d, J=1.6 Hz, 1H), 9.50 (s, 1H), 9.31 (s, 1H), 8.71 (d, J=8.4 Hz, 1H), 8.10 (dd, J=8.3, 1.7 Hz, 1H), 7.71 (t, J=53.2 Hz, 1H), 4.16-3.95 (m, 3H), 3.59 (s, 3H), 3.28-3.25 (m, 2H), 2.86 (s, 3H), 2.06-1.87 (m, 4H), 1.45 (dd, J=8.4, 5.4 Hz, 2H), 1.29 (dd, J=8.4, 5.5 Hz, 2H). LCMS calc. for $C_{25}H_{26}F_2N_9O_4S_2$ $[M+H]^+$: m/z=618.2; Found: 618.2.

Example 146: N-(1-Cyanocyclopropyl)-9-(5-(difluoromethyl)-1,3,4-thiadiazol-2-yl)-4-(1-methylpiperidin-4-yl)-9H-pyrimido[4,5-b]indole-7-sulfonamide

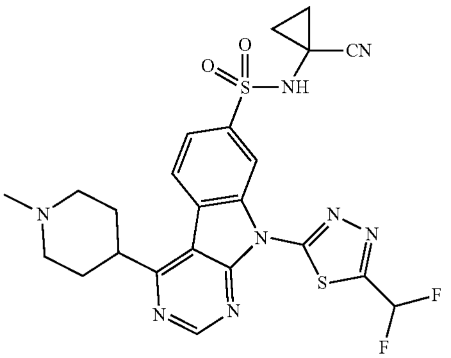 [SMILES: CN1CCC(c2ncnc3c2c2ccc(S(=O)(=O)NC4(C#N)CC4)cc2n3-c2nnc(C(F)F)s2)CC1]

To a mixture of N-(1-cyanocyclopropyl)-9-(5-(difluoromethyl)-1,3,4-thiadiazol-2-yl)-4-(piperidin-4-yl)-9H-pyrimido[4,5-b]indole-7-sulfonamide (20 mg, 0.04 mmol, Example 87) in THF (2 mL) and $H_2O$ (0.2 mL) was added $NaHCO_3$ (6.8 mg, 0.08 mmol), followed by addition of polyformaldehyde (1.8 mg, 0.06 mmol). The mixture was stirred at 25° C. for 30 min., sodium triacetoxyborohydride (12.9 mg, 0.06 mmol) was added. The reaction mixture was stirred at 25° C. for 1 h., diluted with $H_2O$ (1 mL), and extracted with EtOAc (3 mL). The organic layer was concentrated under reduced pressure. The residue was purified by prep-HPLC on a C18 column eluting with ACN/$H_2O$ (30-50%, with 0.05% TFA) to afford the title compound (0.3 mg, 1.5% yield) as a white solid. LCMS calc. for $C_{23}H_{23}F_2N_8O_2S_2$ $[M+H]^+$: m/z=545.1; Found: 545.2.

Example 147: N-(1-Cyanocyclopropyl)-9-(5-(difluoromethyl)-1,3,4-thiadiazol-2-yl)-4-(4-(2,2,2-trifluoroethyl)piperazin-1-yl)-9H-pyrimido[4,5-b]indole-7-sulfonamide

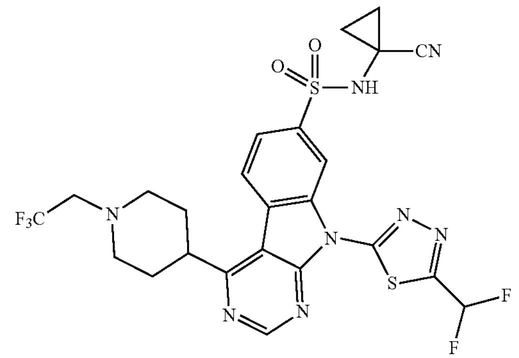 [SMILES: N#CC1(NS(=O)(=O)c2ccc3c4c(C5CCN(CC(F)(F)F)CC5)ncnc4n(-c4nnc(C(F)F)s4)c3c2)CC1]

To a solution of N-(1-cyanocyclopropyl)-9-(5-(difluoromethyl)-1,3,4-thiadiazol-2-yl)-4-(piperazin-1-yl)-9H-pyrimido[4,5-b]indole-7-sulfonamide (200 mg, 0.38 mmol, Example 87) in DMF (2 mL) was added 2,2,2-trifluoroethyl trifluoromethanesulfonate (79 mg, 0.34 mmol) and DBU (77 mg, 0.51 mmol). The reaction mixture was degassed and recharged with $N_2$ for 3 cycles, and stirred at 25° C. for 2 h. The mixture was concentrated under reduced pressure. The residue was purified by prep-HPLC eluting with ACN/$H_2O$ (30-50% with 0.05% TFA) to afford the title compound (75 mg, 32.6% yield) as a white solid. LCMS calc. for $C_{24}H_{22}F_5N_8O_2S_2$ $[M+H]^+$: m/z=613.1; Found: 613.2.

Example 148: 9-(5-(Difluoromethyl)-1,3,4-thiadiazol-2-yl)-6-fluoro-4-(1-isobutyrylpiperidin-4-yl)-N-(1-methylcyclopropyl)-9H-pyrimido[4,5-b]indole-7-sulfonamide

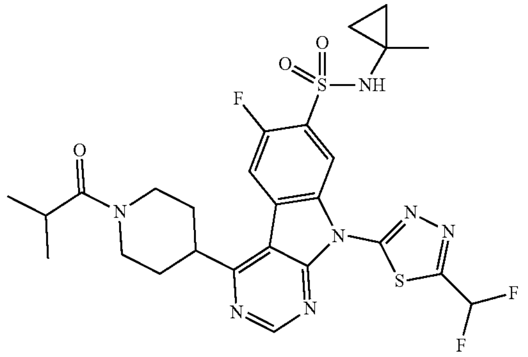 [SMILES: CC(C)C(=O)N1CCC(c2ncnc3c2c2cc(F)c(S(=O)(=O)NC4(C)CC4)cc2n3-c2nnc(C(F)F)s2)CC1]

Step 1: 6-fluoro-4-(1-isobutyryl-1,2,3,6-tetrahydropyridin-4-yl)-N-(1-methylcyclopropyl)-9H-pyrimido[4,5-b]indole-7-sulfonamide

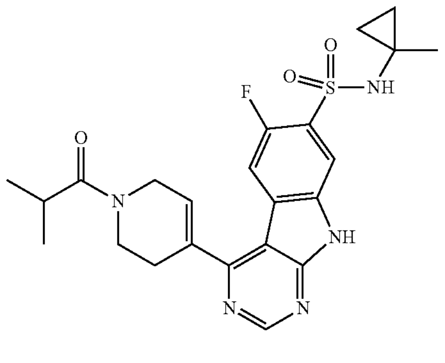 [SMILES: CC(C)C(=O)N1CC=C(c2ncnc3[nH]c4cc(S(=O)(=O)NC5(C)CC5)c(F)cc4c23)CC1]

A mixture of 4-chloro-6-fluoro-N-(1-methylcyclopropyl)-9H-pyrimido[4,5-b]indole-7-sulfonamide (280 mg, 0.79 mmol, Intermediate 4), 2-methyl-1-(4-(4,4,5,5-tetramethyl-1,3,2-dioxaborolan-2-yl)-3,6-dihydropyridin-1(2H)-yl)propan-1-one (330 mg, 1.19 mmol, Example 91 Step 3), $Pd(dppf)_2Cl_2$ (115 mg, 0.16 mmol) and sodium carbonate (335 mg, 3.16 mmol) in 1,4-dioxane (5 mL) and water (0.5 mL) was degassed and recharged with nitrogen for 3 cycles. The reaction mixture was stirred at 110° C. under $N_2$ for 2 h. After cooling, the mixture was poured into water (30 mL), and extracted with ethyl acetate (30 mL×3). The combined organic layers were washed with brine, dried over anhydrous $Na_2SO_4$, filtered and concentrated under reduced pressure. The residue was purified by flash chromatography on a silica gel column eluting with ethyl acetate/Hexanes (0-100%) to afford the title compound (140 mg, 37.4% yield). LCMS calc. for $C_{23}H_{27}FN_5O_3S$ $[M+H]^+$: m/z=472.2; Found: 472.1.

Step 2: 6-fluoro-4-(1-isobutyrylpiperidin-4-yl)-N-(1-methylcyclopropyl)-9H-pyrimido[4,5-b]indole-7-sulfonamide

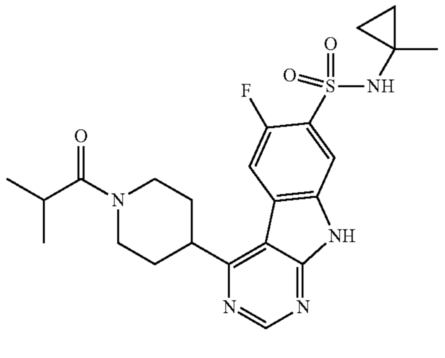 [SMILES: CC(C)C(=O)N1CCC(c2ncnc3[nH]c4cc(S(=O)(=O)NC5(C)CC5)c(F)cc4c23)CC1]

To a solution of 6-fluoro-4-(1-isobutyryl-1,2,3,6-tetrahydropyridin-4-yl)-N-(1-methylcyclopropyl)-9H-pyrimido[4,5-b]indole-7-sulfonamide (90 mg, 0.19 mmol) in methanol (5 mL) was added Pd/C (90 mg, 5% wet) under Ar. The mixture was degassed and purged with $H_2$ for 3 cycles. The reaction mixture was stirred at r.t. for 18 h. The solution was filtered and the filtrate was concentrated under reduced pressure. The residue was purified by flash chromatography on a silica gel column eluting with methanol/dichloromethane (0-15%) to afford the title compound (60 mg, 66.4% yield). LCMS calc. for $C_{23}H_{29}FN_5O_3S$ $[M+H]^+$: m/z=474.2; Found: 474.2.

Step 3: 9-(5-(difluoromethyl)-1,3,4-thiadiazol-2-yl)-6-fluoro-4-(1-isobutyrylpiperidin-4-yl)-N-(1-methylcyclopropyl)-9H-pyrimido[4,5-b]indole-7-sulfonamide This compound was prepared using procedures analogous to those described for Example 74 Step 2 using 6-fluoro-4-(1-isobutyrylpiperidin-4-yl)-N-(1-methylcyclopropyl)-9H-pyrimido[4,5-b]indole-7-sulfonamide and 2-bromo-5-(difluoromethyl)-1,3,4-thiadiazole to afford the title compound (23.2 mg, 30.1% yield) as white solid. $^1H$ NMR: (400 MHz, DMSO-$d_6$) δ 9.51 (d, J=6.3 Hz, 1H), 9.30 (s, 1H), 8.71 (s, 1H), 8.57 (d, J=10.2 Hz, 1H), 7.70 (t, J=53.2 Hz, 1H), 4.58 (d, J=12.1 Hz, 1H), 4.11-4.04 (m, 2H), 3.50-3.47 (m, 1H), 3.00-2.94 (m, 2H), 2.00-1.95 (m, 3H), 1.80-1.70 (m, 1H), 1.18 (s, 3H), 1.06-1.04 (m, 6H), 0.71-0.69 (m, 2H), 0.47-0.44 (m, 2H). LCMS calc. for $C_{26}H_{29}F_3N_7O_3S_2$ $[M+H]^+$: m/z=608.2; Found: 608.1.

Example 149: (2S)-4-(9-(5-(Difluoromethyl)-1,3,4-thiadiazol-2-yl)-6-fluoro-7-(N-(1-methylcyclopropyl)sulfamoyl)-9H-pyrimido[4,5-b]indol-4-yl)-N,N,2-trimethylpiperidine-1-carboxamide

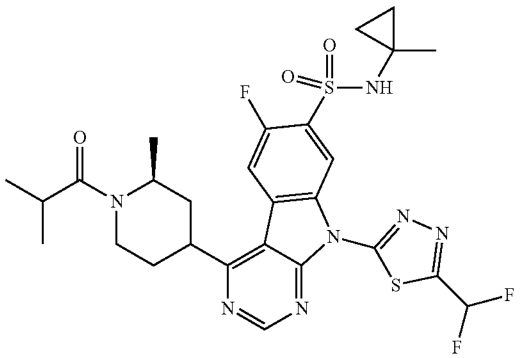 [SMILES: CC(C)C(=O)N1CCC(c2ncnc3c2c2cc(F)c(S(=O)(=O)NC4(C)CC4)cc2n3-c2nnc(C(F)F)s2)C[C@@H]1C]

Step 1: tert-butyl (S)-2-methyl-4-(((trifluoromethyl)sulfonyl)oxy)-3,6-dihydropyridine-1(2H)-carboxylate

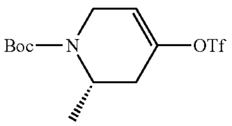 [SMILES: C[C@H]1CC(OS(=O)(=O)C(F)(F)F)=CCN1C(=O)OC(C)(C)C]

A solution of tert-butyl (S)-2-methyl-4-oxopiperidine-1-carboxylate (5 g, 23.4 mmol) in tetrahydrofuran (45 mL) was cooled to −78° C. and lithium hexamethyldisilazide (30.5 mL, 1 M solution in tetrahydrofuran) was added dropwise under nitrogen atmosphere. The resulting reaction was stirred for 30 min., and followed by addition of 1,1,1-trifluoro-N-phenyl-N-((trifluoromethyl) sulfonyl) methanesulfonamide (10.89 g, 30.5 mmol). The resulting solution was stirred at ambient temperature overnight. The mixture was poured into ice water (40 mL), and extracted with ethyl acetate (40 mL×3). The combined organic layers were dried over anhydrous $Na_2SO_4$, filtered and concentrated under reduced pressure. The residue was purified by flash chromatography on a silica gel column eluting with EtOAc/hexanes (0-50%) to afford the title compound (4.7 g, 58% yield). LCMS calc. for $C_8H_{11}F_3NO_5S$ [M−56+H]: m/z=290.0; Found: 290.0.

Step 2: tert-butyl (S)-2-methyl-4-(4,4,5,5-tetramethyl-1,3,2-dioxaborolan-2-yl)-3,6-dihydropyridine-1(2H)-carboxylate

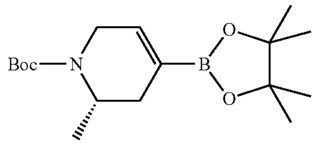 [SMILES: C[C@H]1CC(B2OC(C)(C)C(C)(C)O2)=CCN1C(=O)OC(C)(C)C]

A mixture of tert-butyl (S)-2-methyl-4-(((trifluoromethyl)sulfonyl)oxy)-3,6-dihydropyridine-1(2H)-carboxylate (4.7 g, 13.6 mmol), 4,4,4',4',5,5,5',5'-octamethyl-2,2'-bi(1,3,2-dioxaborolane) (5.2 g, 20.4 mmol), $Pd(dppf)_2Cl_2$ (987 mg, 1.36 mmol) and potassium acetate (2.7 g, 27.2 mmol) in dioxane (40 mL) was degassed and purged with nitrogen for 3 cycles, and then stirred at 90° C. for 2 h. The reaction was filtered and the filtrate was diluted with water (20 mL), and extracted with ethyl acetate (20 mL×3). The combined organic layers were dried over anhydrous $Na_2SO_4$, filtered and concentrated under reduced pressure. The residue was purified by flash chromatography on a silica gel column eluting with EtOAc/hexanes (0-30%) to afford the title compound (4.0 g, 90% yield). LCMS calc. for $C_{17}H_{31}BNO_4$ [M+H]: m/z=324.2; Found: 324.2.

Step 3: tert-butyl (S)-4-(6-fluoro-7-(N-(1-methylcyclopropyl)sulfamoyl)-9H-pyrimido[4,5-b]indol-4-yl)-2-methyl-3,6-dihydropyridine-1(2H)-carboxylate

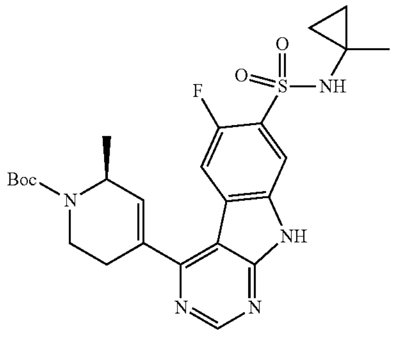 [SMILES: C[C@H]1C=C(c2ncnc3[nH]c4cc(S(=O)(=O)NC5(C)CC5)c(F)cc4c23)CCN1C(=O)OC(C)(C)C]

To a solution of 4-chloro-6-fluoro-N-(1-methylcyclopropyl)-9H-pyrimido[4,5-b]indole-7-sulfonamide (700 mg, 1.97 mmol), tert-butyl (S)-2-methyl-4-(4,4,5,5-tetramethyl-1,3,2-dioxaborolan-2-yl)-3,6-dihydropyridine-1(2H)-carboxylate (1.28 g, 3.9 mmol) in 1,4-dioxane/water=10/1 (16 mL/1.6 mL) was added $Pd(dppf)_2Cl_2$ (286 mg, 0.4 mmol) and sodium carbonate (627 mg, 5.9 mmol) at room temperature. The reaction mixture was stirred at 110° C. under $N_2$ for 2 h. The reaction mixture was poured into water (30 mL), and the mixture was extracted with ethyl acetate (30 mL×3). The combined organic layer was washed with brine (30 mL), dried over anhydrous $Na_2SO_4$, filtered and concentrated under reduced pressure. The crude product was purified by flash chromatography on a silica gel column eluting with EtOAc/hexanes (0-100%) to afford the title compound (430 mg, 42.3% yield). LCMS calc. for $C_{25}H_{29}FN_5O_4S$ $[M-H]^-$: m/z=514.1; Found: 514.1.

Step 4: tert-butyl (2S)-4-(6-fluoro-7-(N-(1-methylcyclopropyl)sulfamoyl)-9H-pyrimido[4,5-b]indol-4-yl)-2-methylpiperidine-1-carboxylate

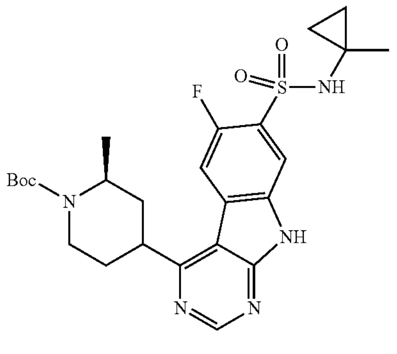 [SMILES: C[C@H]1CC(c2ncnc3[nH]c4cc(S(=O)(=O)NC5(C)CC5)c(F)cc4c23)CCN1C(=O)OC(C)(C)C]

To a solution of tert-butyl (S)-4-(6-fluoro-7-(N-(1-methylcyclopropyl)sulfamoyl)-9H-pyrimido[4,5-b]indol-4-yl)-2-methyl-3,6-dihydropyridine-1(2H)-carboxylate (430 mg, 0.83 mmol) in methanol (20 mL) was added Pd/C (400 mg, 10% wet) under Ar. The mixture was degassed and purged with $H_2$ for 3 cycles. The reaction mixture was stirred at r.t. for 72 h. And the solution was filtered and the filtrate was concentrated under reduced pressure. The crude product was purified by flash chromatography on a silica gel column eluting with methanol/dichloromethane (0-15%) to afford the title compound (280 mg, 65% yield). LCMS calc. for $C_{25}H_{31}FN_5O_4S$ $[M-H]^-$: m/z=516.3; Found: 516.3.

Step 5: tert-butyl (2S)-4-(9-(5-(difluoromethyl)-1,3,4-thiadiazol-2-yl)-6-fluoro-7-(N-(1-methylcyclopropyl)sulfamoyl)-9H-pyrimido[4,5-b]indol-4-yl)-2-methylpiperidine-1-carboxylate

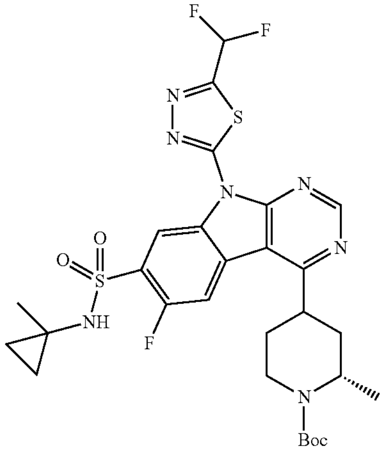 [SMILES: C[C@H]1CC(c2ncnc3c2c2cc(F)c(S(=O)(=O)NC4(C)CC4)cc2n3-c2nnc(C(F)F)s2)CCN1C(=O)OC(C)(C)C]

This compound was prepared using procedures analogous to those described for Example 74 Step 2 using tert-butyl (2S)-4-(6-fluoro-7-(N-(1-methylcyclopropyl)sulfamoyl)-9H-pyrimido[4,5-b]indol-4-yl)-2-methylpiperidine-1-carboxylate and 2-bromo-5-(difluoromethyl)-1,3,4-thiadiazole to afford the title compound as white solid. $^{1}$H NMR: (400 MHz, $CDCl_3$) δ 9.80 (d, J=6.2 Hz, 1H), 9.20 (s, 1H), 7.88 (d, J=9.6 Hz, 1H), 7.12 (t, J=53.6 Hz, 1H), 5.39 (s, 1H), 4.80-4.60 (m, 1H), 4.30-4.20 (m, 1H), 3.81 (t, J=12.2 Hz, 1H), 3.25-3.10 (m, 1H), 2.30-2.11 (m, 2H), 2.04-1.86 (m, 2H), 1.52 (s, 9H), 1.47 (d, J=6.8 Hz, 3H), 1.27 (s, 3H), 0.95-0.90 (m, 2H), 0.57 (d, J=1.0 Hz, 2H). LCMS calc. for $C_{24}H_{25}F_3N_7O_4S_2$ [M−56+H]$^+$: m/z=596.1; Found: 596.0.

Step 6: 9-(5-(difluoromethyl)-1,3,4-thiadiazol-2-yl)-6-fluoro-N-(1-methylcyclopropyl)-4-((2S)-2-methylpiperidin-4-yl)-9H-pyrimido[4,5-b]indole-7-sulfonamide

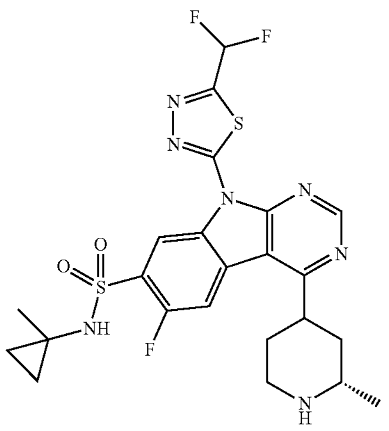 [SMILES: C[C@H]1CC(c2ncnc3c2c2cc(F)c(S(=O)(=O)NC4(C)CC4)cc2n3-c2nnc(C(F)F)s2)CCN1]

To a solution of tert-butyl (2S)-4-(9-(5-(difluoromethyl)-1,3,4-thiadiazol-2-yl)-6-fluoro-7-(N-(1-methylcyclopropyl)sulfamoyl)-9H-pyrimido[4,5-b]indol-4-yl)-2-methylpiperidine-1-carboxylate (175 mg, 0.27 mmol) in dichloromethane (2 mL) was added trifluoroacetic acid (2 mL). The reaction mixture was stirred at r.t. for 1 h., and concentrated under reduced pressure. The residue was purified by Prep-HPLC eluting with ACN/water (10-95% with 10 mM $NH_4HCO_3$) to afford the title compound (100 mg, 67.5% yield). $^{1}$H NMR: (400 MHz, $CDCl_3$) δ 9.80 (dd, J=6.2, 3.2 Hz, 1H), 9.22 (s, 1H), 7.91-7.84 (m, 1H), 7.13 (dt, J=53.6, 2.8 Hz, 1H), 5.50-5.35 (m, 1H), 4.10-3.80 (m, 1H), 3.58-3.42 (m, 2H), 3.20-3.11 (m, 1H), 2.26-2.02 (m, 4H), 1.54 (d, J=6.6 Hz, 3H), 1.33 (d, J=6.2 Hz, 3H), 0.93-0.89 (m, 2H), 0.59-0.57 (m, 2H). LCMS calc. for $C_{23}H_{25}F_3N_7O_2S_2$ [M+H]$^+$: m/z=552.1; Found: 552.2.

Step 7: (2S)-4-(9-(5-(difluoromethyl)-1,3,4-thiadiazol-2-yl)-6-fluoro-7-(N-(1-methylcyclopropyl)sulfamoyl)-9H-pyrimido[4,5-b]indol-4-yl)-N,N,2-trimethylpiperidine-1-carboxamide To a solution of 9-(5-(difluoromethyl)-1,3,4-thiadiazol-2-yl)-6-fluoro-N-(1-methylcyclopropyl)-4-((2S)-2-methylpiperidin-4-yl)-9H-pyrimido[4,5-b]indole-7-sulfonamide (15 mg, 0.03 mmol) and triethylamine (8.25 mg, 0.08 mmol) in dichloromethane (1 mL) was added dimethylcarbamic chloride (5 mg, 0.05 mmol) dropwise at 0° C. The reaction mixture was stirred at r.t. for 16 h., and concentrated under reduced pressure. The residue was purified by prep-HPLC eluting with ACN/water (10-95% with 1% $NH_4HCO_3$) to afford the title compound (5.26 mg, 31.0% yield). $^{1}$H NMR: (400 MHz, $CDCl_3$) δ 9.79 (d, J=6.4 Hz, 1H), 9.20 (s, 1H), 7.90 (d, J=9.6 Hz, 1H), 7.12 (t, J=53.7 Hz, 1H), 5.42 (s, 1H), 4.33-4.30 (m, 1H), 3.90-3.80 (m, 1H), 3.74 (d, J=13.2 Hz, 1H), 3.34 (t, J=2.0 Hz, 1H), 2.89 (s, 6H), 2.33-2.25 (m, 2H), 2.03-1.89 (m, 2H), 1.53 (d, J=6.8 Hz, 3H), 1.27 (s, 3H), 0.92 (d, J=4.4 Hz, 2H), 0.57 (d, J=1.4 Hz, 2H). LCMS calc. for $C_{26}H_{30}F_3N_8O_3S_2$[M+H]$^+$: m/z=623.2; Found: 623.1.

Example 150: N-(1-Cyanocyclopropyl)-9-(5-(difluoromethyl)-1,3,4-thiadiazol-2-yl)-4-((2S)-2-methylpiperidin-4-yl)-9H-pyrimido[4,5-b]indole-7-sulfonamide

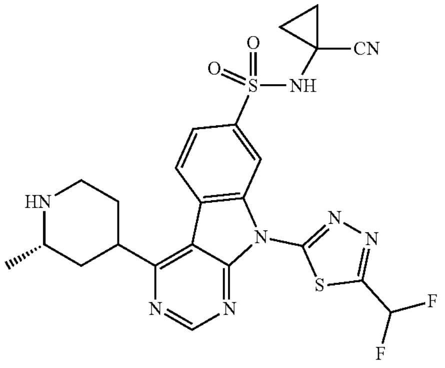 [SMILES: C[C@H]1CC(c2ncnc3c2c2ccc(S(=O)(=O)NC4(C#N)CC4)cc2n3-c2nnc(C(F)F)s2)CCN1]

Step 1: tert-butyl (S)-4-(7-(N-(1-cyanocyclopropyl)sulfamoyl)-9H-pyrimido[4,5-b]indol-4-yl)-2-methyl-3,6-dihydropyridine-1(2H)-carboxylate

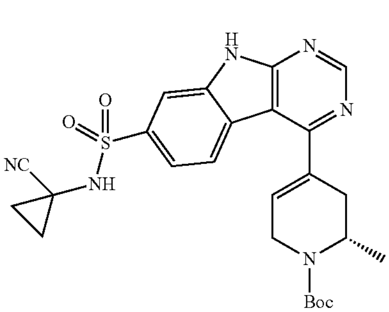 [SMILES: C[C@H]1CC(c2ncnc3[nH]c4cc(S(=O)(=O)NC5(C#N)CC5)ccc4c23)=CCN1C(=O)OC(C)(C)C]

This compound was prepared using procedures analogous to those described for Example 149 Step 3 using 4-chloro-N-(1-cyanocyclopropyl)-9H-pyrimido[4,5-b]indole-7-sulfonamide (Intermediate 1) and tert-butyl (S)-2-methyl-4-(4,4,5,5-tetramethyl-1,3,2-dioxaborolan-2-yl)-3,6-dihydropyridine-1(2H)-carboxylate (Example 150 Step 2). LCMS calc. for $C_{25}H_{27}N_6O_4S$ [M−H]$^-$: m/z=507.2; Found: 507.2.

Step 2: tert-butyl (S)-4-(7-(N-(1-cyanocyclopropyl) sulfamoyl)-9-(5-(difluoromethyl)-1,3,4-thiadiazol-2-yl)-9H-pyrimido[4,5-b]indol-4-yl)-2-methyl-3,6-dihydropyridine-1(2H)-carboxylate

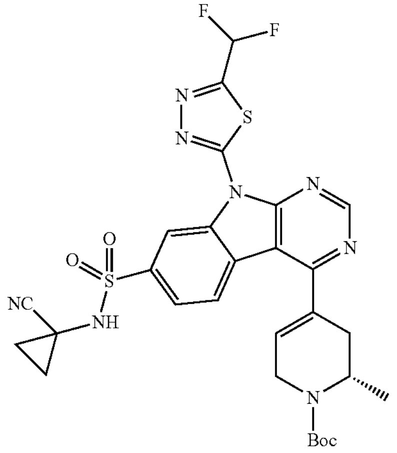 [SMILES: C[C@H]1CC(c2ncnc3c2c2ccc(S(=O)(=O)NC4(C#N)CC4)cc2n3-c2nnc(C(F)F)s2)=CCN1C(=O)OC(C)(C)C]

This compound was prepared using procedures analogous to those described for Example 74 Step 2 using tert-butyl (S)-4-(7-(N-(1-cyanocyclopropyl)sulfamoyl)-9H-pyrimido[4,5-b]indol-4-yl)-2-methyl-3,6-dihydropyridine-1(2H)-carboxylate and 2-bromo-5-(difluoromethyl)-1,3,4-thiadiazole to afford the title product as yellow solid. LCMS calc. for $C_{28}H_{27}F_2N_8O_4S_2$ $[M-H]^-$: m/z=641.2; Found: 641.2.

Step 3: tert-butyl (2S)-4-(7-(N-(1-cyanocyclopropyl)sulfamoyl)-9-(5-(difluoromethyl)-1,3,4-thiadiazol-2-yl)-9H-pyrimido[4,5-b]indol-4-yl)-2-methylpiperidine-1-carboxylate

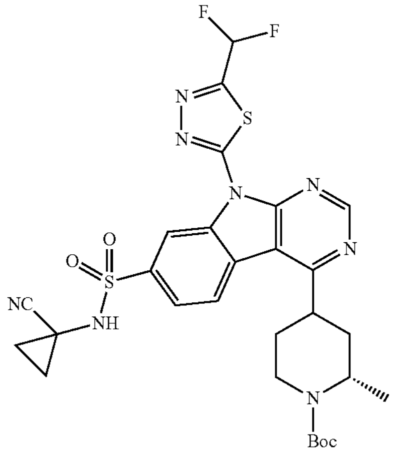 [SMILES: C[C@H]1CC(c2ncnc3c2c2ccc(S(=O)(=O)NC4(C#N)CC4)cc2n3-c2nnc(C(F)F)s2)CCN1C(=O)OC(C)(C)C]

To a solution of tert-butyl (S)-4-(7-(N-(1-cyanocyclopropyl)sulfamoyl)-9-(5-(difluoromethyl)-1,3,4-thiadiazol-2-yl)-9H-pyrimido[4,5-b]indol-4-yl)-2-methyl-3,6-dihydropyridine-1(2H)-carboxylate (100 mg, 0.156 mmol) in methanol/DCM (2.5:1, 9 mL) was added $Pd(OH)_2/C$ (100 mg, 10% wet) under Ar. The mixture was degassed and purged with $H_2$ for 3 cycles. The reaction mixture was stirred at r.t. for 18 h. The mixture was filtered and the filtrate was concentrated under reduced pressure. The crude product was dissolved in methanol/DCM (2.5:1, 9 mL), and $Pd(OH)_2/C$ (100 mg, 10% wet) was added under Ar. The above operation was repeated for three times. Then the solution was filtered and the filtrate was concentrated under reduced pressure. The crude product was purified by flash chromatography on a silica gel column eluting with methanol/dichloromethane (0-15%) to afford the title compound (5.2 mg, 5.1% yield). $^1H$ NMR: (400 MHz, DMSO-$d_6$) δ 9.54 (d, J=1.6 Hz, 1H), 9.32 (s, 1H), 8.54 (d, J=8.4 Hz, 1H), 8.10 (dd, J=8.3, 1.6 Hz, 1H), 7.71 (t, J=53.2 Hz, 1H), 4.14-3.94 (m, 2H), 3.80-3.76 (m, 1H), 3.59-3.48 (m, 1H), 2.18-1.92 (m, 4H), 1.47 (s, 9H), 1.45-1.41 (m, 2H), 1.30-1.25 (m, 2H), 1.13 (d, J=6.6 Hz, 3H). LCMS calc. for $C_{24}H_{23}F_2N_8O_4S_2$ $[M-56+H]^+$: m/z=589.1; Found: 589.1.

Step 4: N-(1-cyanocyclopropyl)-9-(5-(difluoromethyl)-1,3,4-thiadiazol-2-yl)-4-((2S)-2-methylpiperidin-4-yl)-9H-pyrimido[4,5-b]indole-7-sulfonamide This compound was prepared using procedures analogous to those described for Example 149 Step 6 using tert-butyl (2S)-4-(7-(N-(1-cyanocyclopropyl)sulfamoyl)-9-(5-(difluoromethyl)-1,3,4-thiadiazol-2-yl)-9H-pyrimido[4,5-b]indol-4-yl)-2-methylpiperidine-1-carboxylate and purified by flash chromatography on a silica gel column eluting with methanol/dichloromethane (0-15%) to afford the title product. $^1H$ NMR: (400 MHz, DMSO-$d_6$) δ 9.50 (s, 1H), 9.29 (s, 1H), 8.56 (d, J=8.4 Hz, 1H), 8.07 (d, J=7.4 Hz, 1H), 7.71 (t, J=53.2 Hz, 1H), 3.89-3.82 (m, 1H), 3.11-3.05 (m, 3H), 2.00-1.88 (m, 3H), 1.67 (dd, J=23.2, 10.6 Hz, 1H), 1.37-1.31 (m, 2H), 1.21-1.16 (m, 2H), 1.13 (d, J=6.0 Hz, 3H). LCMS calc. for $C_{23}H_{23}F_2N_8O_2S_2$ $[M+H]^+$: m/z=545.1; Found: 545.2.

Example 151: N-(1-Cyanocyclopropyl)-9-(5-(difluoromethyl)-1,3,4-thiadiazol-2-yl)-4-((2S)-1-isobutyryl-2-methylpiperidin-4-yl)-9H-pyrimido[4,5-b]indole-7-sulfonamide

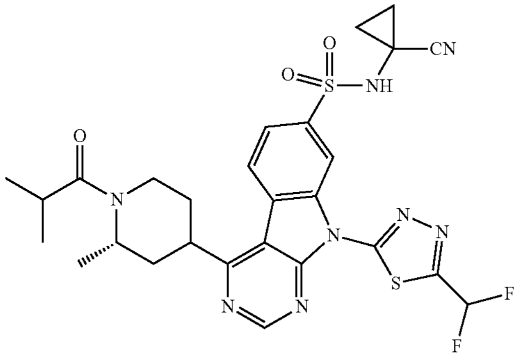 [SMILES: CC(C)C(=O)N1CCC(c2ncnc3c2c2ccc(S(=O)(=O)NC4(C#N)CC4)cc2n3-c2nnc(C(F)F)s2)C[C@@H]1C]

To a solution of isobutyric acid (6.3 mg, 0.072 mmol) and N,N-diisopropylethylamine (28 mg, 0.072 mmol) in DMF (0.5 mL) was added HATU (14 mg, 0.036 mmol) and N-(1-cyanocyclopropyl)-9-(5-(difluoromethyl)-1,3,4-thiadiazol-2-yl)-4-((2S)-2-methylpiperidin-4-yl)-9H-pyrimido[4,5-b]indole-7-sulfonamide (13 mg, 0.024 mmol, Example 150). The reaction mixture was stirred at r.t. for 2 h., poured into water (20 mL) and extracted with ethyl acetate (10 mL×3). The combined organic layers were washed with brine, dried over anhydrous $Na_2SO_4$, filtered and concentrated under reduced pressure. The residue was purified by Prep-HPLC eluting with ACN/water (10-95% with 1% $NH_4HCO_3$) to afford the title compound (5.84 mg, 39.8% yield). $^1H$ NMR: (400 MHz, DMSO-$d_6$) δ 9.54 (d, J=1.6 Hz, 2H), 9.33 (s, 1H), 8.45 (d, J=8.4 Hz, 1H), 8.12 (dd, J=8.3, 1.7 Hz, 1H), 7.71 (t, J=53.2 Hz, 1H), 4.43 (dd, J=14.4, 6.9 Hz, 1H), 4.13-3.81 (m, 2H), 3.61-3.42 (m, 1H), 2.92-2.89 (m, 1H), 2.34-2.15 (m, 3H), 2.06-1.98 (m, 1H), 1.45-1.42 (m, 2H), 1.29-1.25 (m, 2H), 1.13-1.03 (m, 9H). LCMS calc. for $C_{27}H_{29}F_2N_8O_3S_2$ [M+H]$^+$: m/z=615.2; Found: 615.3.

Example 152: 4-(9-(5-(Difluoromethyl)-1,3,4-thiadiazol-2-yl)-7-(N-(1-methylcyclopropyl)sulfamoyl)-9H-pyrimido[4,5-b]indol-4-yl)-N,N-dimethyl-3,6-dihydropyridine-1(2H)-carboxamide

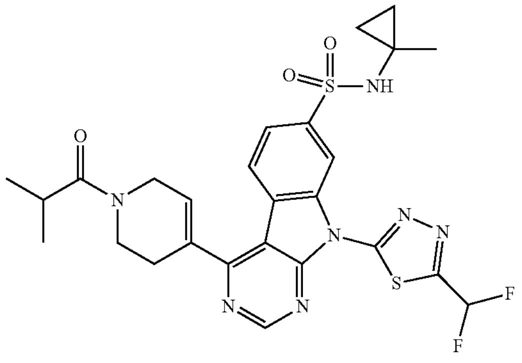 [SMILES: CC(C)C(=O)N1CC=C(c2ncnc3c2c2ccc(S(=O)(=O)NC4(C)CC4)cc2n3-c2nnc(C(F)F)s2)CC1]

Step 1: tert-butyl 4-(7-(N-(1-methylcyclopropyl)sulfamoyl)-9H-pyrimido[4,5-b]indol-4-yl)-3,6-dihydropyridine-1(2H)-carboxylate

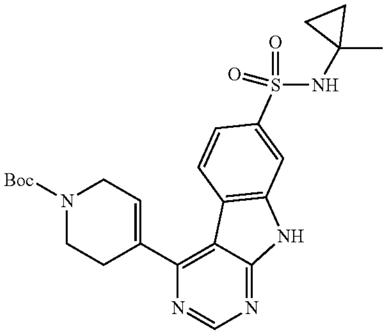 [SMILES: CC1(NS(=O)(=O)c2ccc3c(c2)[nH]c2ncnc(C4=CCN(C(=O)OC(C)(C)C)CC4)c23)CC1]

This compound was prepared using procedures analogous to those described for Example 91 Step 4 using 4-chloro-N-(1-methylcyclopropyl)-9H-pyrimido[4,5-b]indole-7-sulfonamide (Intermediate 2) and tert-butyl 4-(4,4,5,5-tetramethyl-1,3,2-dioxaborolan-2-yl)-3,6-dihydropyridine-1(2H)-carboxylate to afford the title product as a light yellow solid. LCMS calc. for $C_{24}H_{30}N_5O_4S$ [M+H]$^+$: m/z=484.2; Found: 484.2.

Step 2: N-(1-methylcyclopropyl)-4-(1,2,3,6-tetrahydropyridin-4-yl)-9H-pyrimido[4,5-b]indole-7-sulfonamide

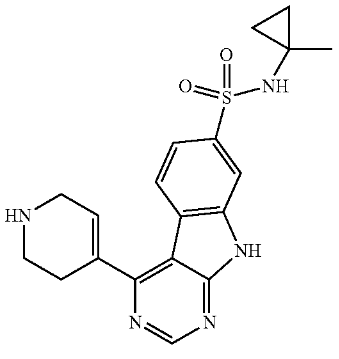

To a solution of tert-butyl 4-(7-(N-(1-methylcyclopropyl)sulfamoyl)-9H-pyrimido[4,5-b]indol-4-yl)-3,6-dihydropyridine-1(2H)-carboxylate (420 mg, 0.869 mmol) in MeOH (2 mL) was added HCl/MeOH (4 M, 2 mL) at 20° C. The mixture was stirred at 20° C. overnight. The mixture was concentrated under reduced pressure to afford the title compound (300 mg, 82.0% yield, HCl salt) as white solid. LCMS calc. for $C_{19}H_{22}N_5O_2S$ [M+H]$^+$: m/z=384.1; Found: 384.1.

Step 3: N,N-dimethyl-4-(7-(N-(1-methylcyclopropyl)sulfamoyl)-9H-pyrimido[4,5-b]indol-4-yl)-3,6-dihydropyridine-1(2H)-carboxamide

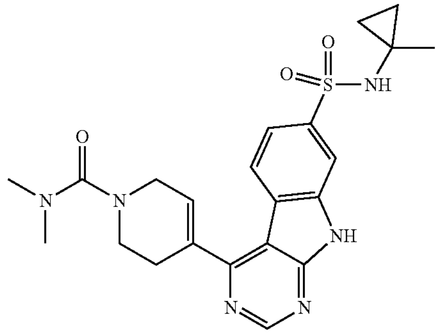

To a mixture of N-(1-methylcyclopropyl)-4-(1,2,3,6-tetrahydropyridin-4-yl)-9H-pyrimido[4,5-b]indole-7-sulfonamide (300 mg, 0.71 mmol) in ACN (6 mL) was added TEA (159 mg, 1.57 mmol) at 20° C. N,N-dimethylcarbamoyl chloride (42.2 mg, 0.393 mmol) was added to the above mixture at 0° C. The mixture was stirred at ambient temperature for 2 h. The mixture was poured into ice-water (10 mL) and extracted with ethyl acetate (5 mL×3). The combined organic layers were washed with brine, dried with anhydrous $Na_2SO_4$, filtered and concentrated under reduced pressure. The residue was purified by flash chromatography on a silica gel column eluting with EtOAc/PE (0-100%) to afford the title compound (180 mg, 55.6% yield) as white solid. LCMS calc. for $C_{22}H_{27}N_6O_3S$ [M+H]$^+$: m/z=455.2; Found: 455.2.

Step 4: 4-(9-(5-(difluoromethyl)-1,3,4-thiadiazol-2-yl)-7-(N-(1-methylcyclopropyl)sulfamoyl)-9H-pyrimido[4,5-b]indol-4-yl)-N,N-dimethyl-3,6-dihydropyridine-1(2H)-carboxamide This compound was prepared using procedures analogous to those described for Example 44 Step 2 using N,N-dimethyl-4-(7-(N-(1-methylcyclopropyl)sulfamoyl)-9H-pyrimido[4,5-b]indol-4-yl)-3,6-dihydropyridine-1(2H)-carboxamide and 2-bromo-5-(difluoromethyl)-1,3,4-thiadiazole to afford the title product as light yellow solid. $^1$H NMR: (400 MHz, DMSO-$d_6$) δ 9.51 (d, J=4.8 Hz, 1H), 9.29 (d, J=2.8 Hz, 1H), 8.53 (d, J=8.4 Hz, 1H), 8.45 (s, 1H), 7.99-7.97 (m, 1H), 7.72 (t, J=53.2 Hz, 1H), 6.65 (s, 1H), 4.10 (d, J=2.4 Hz, 2H), 3.53 (t, J=5.4 Hz, 2H), 2.85 (s, 6H), 2.82-2.80 (m, 2H), 1.13 (s, 3H), 0.67-0.65 (m, 2H), 0.43-0.40 (m, 2H). LCMS calc. for $C_{25}H_{27}F_2N_8O_3S_2$ $[M+H]^+$: m/z=589.2; Found: 589.1.

Example 153: 4-(9-(5-(Difluoromethyl)-1,3,4-thiadiazol-2-yl)-7-(N-(1-methylcyclopropyl)sulfamoyl)-9H-pyrimido[4,5-b]indol-4-yl)-N,N-dimethylpiperidine-1-carboxamide

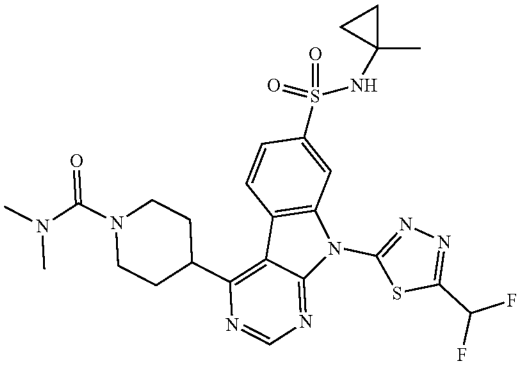

Step 1: N,N-dimethyl-4-(7-(N-(1-methylcyclopropyl)sulfamoyl)-9H-pyrimido[4,5-b]indol-4-yl)piperidine-1-carboxamide

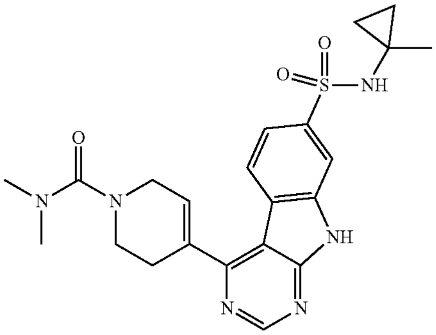

To a mixture of Pd/C (90 mg, 5% wet) in THF (9 mL) was added N,N-dimethyl-4-(7-(N-(1-methylcyclopropyl)sulfamoyl)-9H-pyrimido[4,5-b]indol-4-yl)-3,6-dihydropyridine-1(2H)-carboxamide (90 mg, 0.198 mmol, Example 152 Step 3) under Ar. The mixture was degassed and purged with $H_2$ for 3 cycles. The mixture was stirred at 20° C. overnight. The reaction mixture was filtered on celite and the filtrate was concentrated under reduced pressure. The residue was purified by flash chromatography on a silica gel column eluting with EtOAc/PE (0-100%) to afford the title compound as white solid. LCMS calc. for $C_{22}H_{29}N_6O_3S$ $[M+H]^+$: m/z=457.2; Found: 457.1.

Step 2: 4-(9-(5-(difluoromethyl)-1,3,4-thiadiazol-2-yl)-7-(N-(1-methylcyclopropyl)sulfamoyl)-9H-pyrimido[4,5-b]indol-4-yl)-N,N-dimethylpiperidine-1-carboxamide This compound was prepared using procedures analogous to those described for Example 44 Step 2 using N,N-dimethyl-4-(7-(N-(1-methylcyclopropyl)sulfamoyl)-9H-pyrimido[4,5-b]indol-4-yl)piperidine-1-carboxamide and 2-bromo-5-(difluoromethyl)-1,3,4-thiadiazole to afford the title compound as light yellow solid. $^1$H NMR: (400 MHz, DMSO-$d_6$) δ 9.51 (s, 1H), 9.29 (s, 1H), 8.63 (d, J=8.0 Hz, 1H), 8.46 (s, 1H), 8.07-8.04 (m, 1H), 7.71 (t, J=53.2 Hz, 1H), 3.92-3.90 (m, 1H), 3.75 (d, J=12.0 Hz, 2H), 3.17-3.11 (m, 2H), 2.80 (s, 6H), 2.01-1.96 (m, 4H), 1.12 (s, 3H), 0.68-0.65 (m, 2H), 0.43-0.41 (m, 2H). LCMS calc. for $C_{28}H_{29}F_2N_8O_3S_2$ $[M+H]^+$: m/z=591.2; Found: 591.2.

Example 154: (R)—N-(1-Cyanocyclopropyl)-9-(5-(difluoromethyl)-1,3,4-thiadiazol-2-yl)-4-(3-(hydroxymethyl)-4-isobutyrylpiperazin-1-yl)-9H-pyrimido[4,5-b]indole-7-sulfonamide

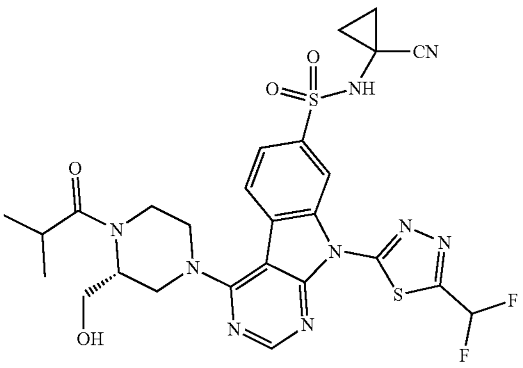

Step 1: tert-butyl (R)-3-(hydroxymethyl)-4-isobutyrylpiperazine-1-carboxylate

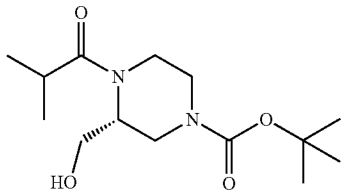 [SMILES: CC(C)C(=O)N1CCN(C(=O)OC(C)(C)C)C[C@@H]1CO]

To a mixture of tert-butyl (R)-3-(hydroxymethyl)piperazine-1-carboxylate (1 g, 4.62 mmol), $NaHCO_3$ (776 mg, 9.24 mmol) in THF (6 mL) and $H_2O$ (1 mL) was added isobutyryl chloride (744 mg, 6.93 mmol) dropwise at 0° C. The mixture was stirred at rt for 2 h. The reaction mixture was quenched with water (50 mL), extracted with EtOAc (50 mL×3). The combined organic layers were washed with brine, dried over anhydrous $Na_2SO_4$, filtered and concentrated under reduced pressure to afford tert-butyl (R)-3-(hydroxymethyl)-4-isobutyrylpiperazine-1-carboxylate (760 mg, 57% yield). LCMS calculated for $C_{14}H_{27}N_2O_4$ $[M+H]^+$: m/z=287.2; Found: 287.3.

Step 2: (R)-1-(2-(hydroxymethyl)piperazin-1-yl)-2-methylpropan-1-one

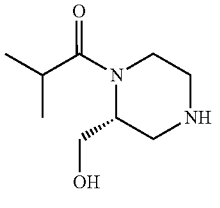

To a solution of tert-butyl (R)-3-(hydroxymethyl)-4-isobutyrylpiperazine-1-carboxylate (760 mg, 2.64 mmol) in DCM (5 mL) was added TFA (1 mL) and then stirred at r.t. for 2 h. The resulting mixture was evaporated under reduced pressure to afford (R)-1-(2-(hydroxymethyl)piperazin-1-yl)-2-methylpropan-1-one as TFA salt (900 mg) without further purification. LCMS calculated for $C_9H_{19}N_2O_2$ $[M+H]^+$: m/z=187.1; Found: 187.2.

Step 3: (R)—N-(1-cyanocyclopropyl)-4-(3-(hydroxymethyl)-4-isobutyrylpiperazin-1-yl)-9H-pyrimido[4,5-b]indole-7-sulfonamide

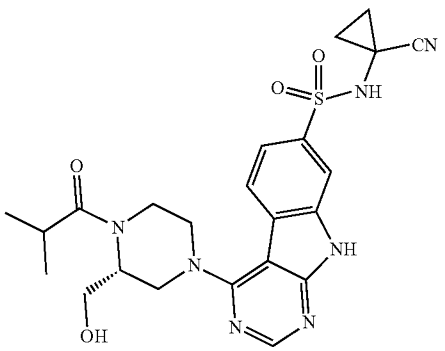 [SMILES: CC(C)C(=O)N1CCN(c2ncnc3[nH]c4cc(S(=O)(=O)NC5(C#N)CC5)ccc4c23)C[C@@H]1CO]

To a mixture of 4-chloro-N-(1-cyanocyclopropyl)-9H-pyrimido[4,5-b]indole-7-sulfonamide (300 mg, 0.86 mmol, Intermediate 1) and TEA (868.6 mg, 8.6 mmol) in DMAc (3 mL) was added (R)-1-(2-(hydroxymethyl)piperazin-1-yl)-2-methylpropan-1-one (643 mg, 3.45 mmol). The reaction mixture was stirred at 80° C. overnight, and concentrated under reduced pressure. The residue was purified by flash chromatography on a C18 column eluting with ACN/$H_2O$ (2%-22%) to afford the title compound (280 mg, 65.3% yield) as yellow solid. LCMS calculated for $C_{23}H_{28}N_7O_4S$ $[M+H]^+$: m/z=498.2; Found: 498.2.

Step 4: (R)—N-(1-cyanocyclopropyl)-9-(5-(difluoromethyl)-1,3,4-thiadiazol-2-yl)-4-(3-(hydroxymethyl)-4-isobutyrylpiperazin-1-yl)-9H-pyrimido[4,5-b]indole-7-sulfonamide A mixture of (R)—N-(1-cyanocyclopropyl)-4-(3-(hydroxymethyl)-4-isobutyrylpiperazin-1-yl)-9H-pyrimido[4,5-b]indole-7-sulfonamide (240 mg, 0.48 mmol), 2-bromo-5-(difluoromethyl)-1,3,4-thiadiazole (258.3 mg, 1.2 mmol), $Cs_2CO_3$ (471.4 mg, 0.9 mmol) and BrettphosPdG3 (20.3 mg, 0.024 mmol) in 1,4-dioxane (2 mL) was degassed and recharged with nitrogen for 3 cycles. The reaction mixture was stirred at 110° C. for 3 h. The reaction mixture was poured into water (20 mL), and extracted with DCM (30 mL×3). The combined organic layers were washed with brine, dried over anhydrous $Na_2SO_4$, filtered and concentrated under reduced pressure. The residue was purified by flash chromatography on a silica gel column eluting with EtOAc/PE (20-100%) to afford the crude product which was further purified by prep HPLC eluting with ACN/$H_2O$ (10-50% with 0.05% TFA) to afford the title compound (19.3 mg, 6.3% yield) as white solid. LCMS calc. for $C_{26}H_{28}F_2N_9O_4S_2$ $[M+H]^+$: m/z=632.2; Found: 632.2.

The compounds listed in Table 9 below were prepared by using an Intermediate 1 (Int A, sulfonamide derivative) and an appropriate amine derivative (Int B) in Step 3 as the methods substantially analogous to those described for preparing Example 154 Step 3-4.

TABLE 9

| Preparations of Examples (Ex) | | | | |
|---|---|---|---|---|
| Ex # | Int B | Structure | Name | LCMS Cacl./Found |
| 155 | 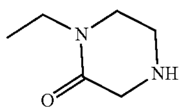 | 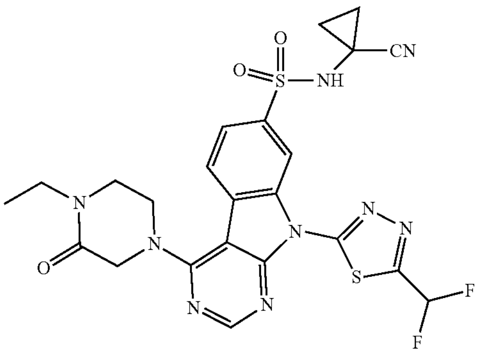 [SMILES: CCN1CCN(c2ncnc3c2c2ccc(S(=O)(=O)NC4(C#N)CC4)cc2n3-c2nnc(C(F)F)s2)CC1=O] | N-(1-cyanocyclopropyl)-9-(5-(difluoromethyl)-1,3,4-thiadiazol-2-yl)-4-(4-ethyl-3-oxopiperazin-1-yl)-9H-pyrimido[4,5-b]indole-7-sulfonamide | $[M + H]^+$ 574.1/574.2 |
| 156 | 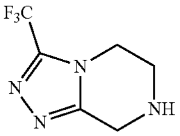 | 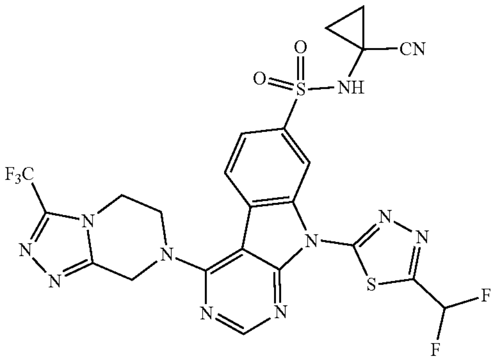 [SMILES: N#CC1(NS(=O)(=O)c2ccc3c4c(N5CCn6c(nnc6C(F)(F)F)C5)ncnc4n(-c4nnc(C(F)F)s4)c3c2)CC1] | N-(1-cyanocyclopropyl)-9-(5-(difluoromethyl)-1,3,4-thiadiazol-2-yl)-4-(3-(trifluoromethyl)-5,6-dihydro-[1,2,4]triazolo[4,3-a]pyrazin-7(8H)-yl)-9H-pyrimido[4,5-b]indole-7-sulfonamide | $[M - H]^-$ 636.1/636.2 |
| 157 | 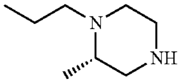 | 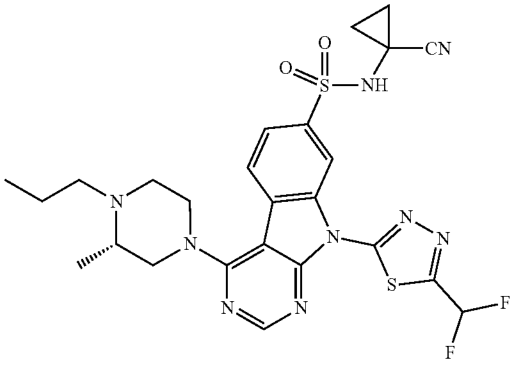 [SMILES: CCCN1CCN(c2ncnc3c2c2ccc(S(=O)(=O)NC4(C#N)CC4)cc2n3-c2nnc(C(F)F)s2)C[C@@H]1C] | (S)-N-(1-cyanocyclopropyl)-9-(5-(difluoromethyl)-1,3,4-thiadiazol-2-yl)-4-(3-methyl-4-propylpiperazin-1-yl)-9H-pyrimido[4,5-b]indole-7-sulfonamide | $[M + H]^+$ 588.2/588.3 |
| 158 | 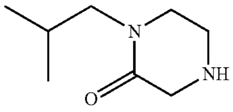 | 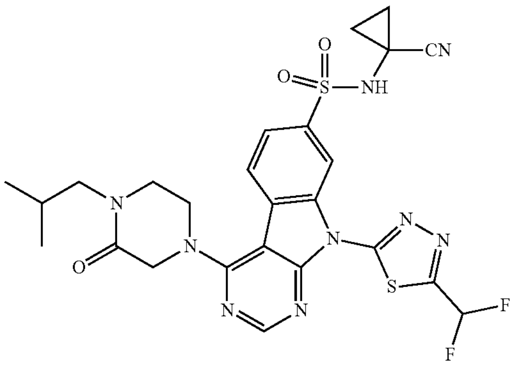 [SMILES: CC(C)CN1CCN(c2ncnc3c2c2ccc(S(=O)(=O)NC4(C#N)CC4)cc2n3-c2nnc(C(F)F)s2)CC1=O] | N-(1-cyanocyclopropyl)-9-(5-(difluoromethyl)-1,3,4-thiadiazol-2-yl)-4-(4-isobutyl-3-oxopiperazin-1-yl)-9H-pyrimido[4,5-b]indole-7-sulfonamide | $[M + H]^+$ 602.2/602.2 |

TABLE 9-continued

Preparations of Examples (Ex)

| Ex # | Int B | Structure | Name | LCMS Cacl./ Found |
|---|---|---|---|---|
| 159 | Int 59 | 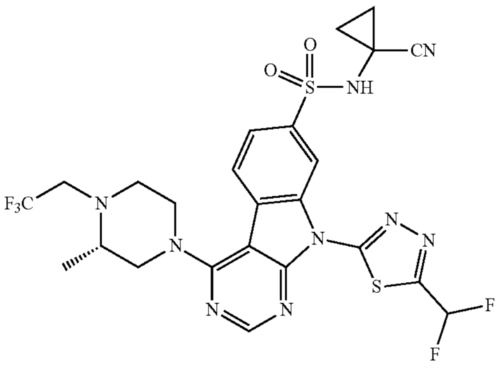 [SMILES: C[C@H]1CN(c2ncnc3c2c2ccc(S(=O)(=O)NC4(C#N)CC4)cc2n3-c2nnc(C(F)F)s2)CCN1CC(F)(F)F] | (S)-N-(1-cyanocyclopropyl)-9-(5-(difluoromethyl)-1,3,4-thiadiazol-2-yl)-4-(3-methyl-4-(2,2,2-trifluoroethyl) piperazin-1-yl)-9H-pyrimido[4,5-b] indole-7-sulfonamide | $[M + H]^+$ 628.1/628.2 |

Example 160: (S)—N-(1-Cyanocyclopropyl)-9-(5-(difluoromethyl)-1,3,4-thiadiazol-2-yl)-4-(hexahydropyrrolo[1,2-a]pyrazin-2(1H)-yl)-9H-pyrimido[4,5-b]indole-7-sulfonamide

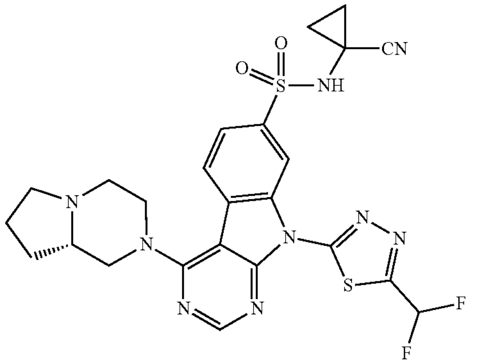

Step 1: (S)—N-(1-cyanocyclopropyl)-4-(hexahydropyrrolo[1,2-a]pyrazin-2(1H)-yl)-9H-pyrimido[4,5-b] indole-7-sulfonamide

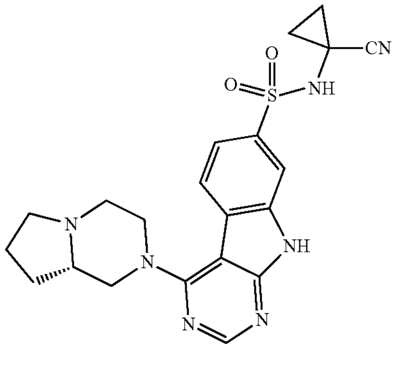 [SMILES: N#CC1(NS(=O)(=O)c2ccc3c(c2)[nH]c2ncnc(N4CCN5CCC[C@H]5C4)c23)CC1]

To a solution of (S)-octahydropyrrolo[1,2-a]pyrazine HCl salt (115 mg, 0.58 mmol) and triethylamine (190 mg, 1.8 mmol) in DMAc (1 mL) was added 4-chloro-N-(1-cyanocyclopropyl)-9H-pyrimido[4,5-b]indole-7-sulfonamide (100 mg, 0.29 mmol, Intermediate 1). The reaction mixture was stirred at 80° C. for 1 h., and cooled to r.t. The mixture was poured into water and extracted with DCM (10 mL×3). The combined organic layers were washed with brine, dried over anhydrous $Na_2SO_4$, filtered, and concentrated under reduced pressure. The residue was purified by flash chromatography on a silica gel column eluting with MeOH/DCM (0-10%) to afford (S)—N-(1-cyanocyclopropyl)-4-(hexahydropyrrolo[1,2-a]pyrazin-2(1H)-yl)-9H-pyrimido[4,5-b]indole-7-sulfonamide (100 mg, 79% yield) as brown solid. LCMS calc. for $C_{21}H_{24}N_7O_2S$ $[M+H]^+$: m/z=438.2; Found: 438.2.

Step 2: (S)—N-(1-cyanocyclopropyl)-9-(5-(difluoromethyl)-1,3,4-thiadiazol-2-yl)-4-(hexahydropyrrolo[1,2-a]pyrazin-2(1H)-yl)-9H-pyrimido[4,5-b] indole-7-sulfonamide To a solution of (S)—N-(1-cyanocyclopropyl)-4-(hexahydropyrrolo[1,2-a]pyrazin-2(1H)-yl)-9H-pyrimido[4,5-b] indole-7-sulfonamide (100 mg, 0.23 mmol) and 2-bromo-5-(difluoromethyl)-1,3,4-thiadiazole (74 mg, 0.35 mmol) in 1,4 dioxane (2 mL) was added CuI (26 mg, 0.14 mmol), (1R,2R)—$N^1$,$N^2$-dimethylcyclohexane-1,2-diamine (39 mg, 0.28 mmol) and CsF (104 mg, 0.68 mmol). The reaction mixture was stirred at 110° C. for overnight under nitrogen atmosphere. The mixture was cooled to r.t., poured into water, and extracted with DCM (100 mL×3). The combined organic layers were washed with brine, dried over anhydrous $Na_2SO_4$, filtered, and concentrated under reduced pressure. The residue was purified by flash chromatography on a silica gel column eluting with MeOH/DCM (0-8%) to afford the crude compound which was further purified by flash chromatography on a C18 column eluting with ACN/$H_2O$ (20%-70%) to afford the desired product (25 mg, 19% yield) as white solid. $^1H$ NMR: (400 MHz, DMSO-$d_6$) δ 10.81 (s, 1H), 10.45 (s, 1H), 9.47 (d, J=14.5 Hz, 2H), 8.89 (d, J=11.3 Hz, 1H), 8.12 (dd, J=45.9, 8.4 Hz, 2H), 7.70 (t, J=52.0 Hz, 1H), 4.61 (m, 1H), 4.23-3.94 (m, 3H), 3.89-3.41 (m, 5H), 2.30-1.61 (m, 4H), 1.58-1.36 (m, 2H), 1.34-1.05 (m, 2H). LCMS calc. for $C_{24}H_{24}F_2N_9O_2S_2$ $[M+H]^+$: m/z=572.1; Found: 572.2.

The compounds listed in Table 10 below were prepared by using an Intermediate 1 (Int A, sulfonamide derivative) and an appropriate amine derivative (Int B) as the methods substantially analogous to those described for preparing Example 160.

TABLE 10

Preparations of Examples (Ex)

| Ex # | Int B | Structure | Name | LCMS Cacl./ Found |
|---|---|---|---|---|
| 161 | 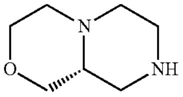 | 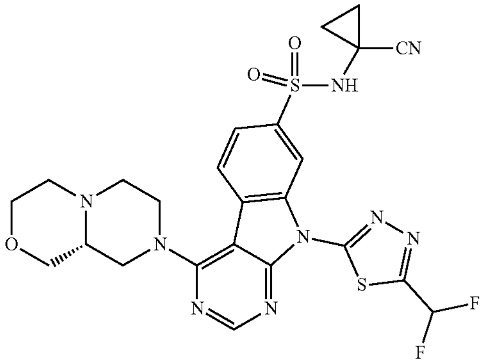 [SMILES: N#CC1(NS(=O)(=O)c2ccc3c4c(N5CCN6CCOC[C@H]6C5)ncnc4n(-c4nnc(C(F)F)s4)c3c2)CC1] | (R)-N-(1-cyanocyclopropyl)-9-(5-(difluoromethyl)-1,3,4-thiadiazol-2-yl)-4-(hexahydropyrazino [2,1-c][1,4]oxazin-8(1H)-yl)-9H-pyrimido[4,5-b] indole-7-sulfonamide | $[M + H]^+$ 588.1/588.2 |
| 162 | 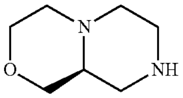 | 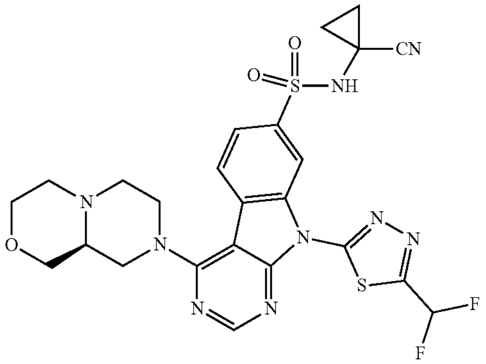 [SMILES: N#CC1(NS(=O)(=O)c2ccc3c4c(N5CCN6CCOC[C@@H]6C5)ncnc4n(-c4nnc(C(F)F)s4)c3c2)CC1] | (S)-N-(1-cyanocyclopropyl)-9-(5-(difluoromethyl)-1,3,4-thiadiazol-2-yl)-4-(hexahydropyrazino [2,1-c][1,4]oxazin-8(1H)-yl)-9H-pyrimido[4,5-b]indole-7-sulfonamide | $[M + H]^+$ 588.1/588.2 |
| 163 | 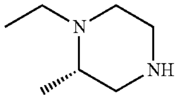 | 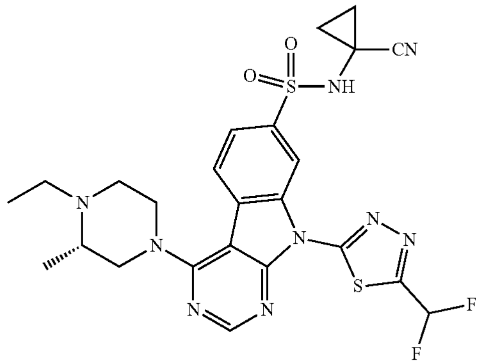 [SMILES: CCN1CCN(c2ncnc3c2c2ccc(S(=O)(=O)NC4(C#N)CC4)cc2n3-c2nnc(C(F)F)s2)C[C@@H]1C] | (S)-N-(1-cyanocyclopropyl)-9-(5-(difluoromethyl)-1,3,4-thiadiazol-2-yl)-4-(4-ethyl-3-methylpiperazin-1-yl)-9H-pyrimido [4,5-b]indole-7-sulfonamide | $[M + H]^+$ 574.2/574.2 |

TABLE 10-continued

| Preparations of Examples (Ex) | | | | |
|---|---|---|---|---|
| Ex # | Int B | Structure | Name | LCMS Cacl./ Found |
| 164 | 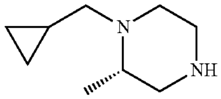 | 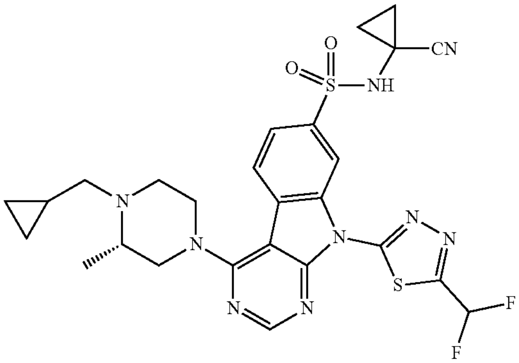 [SMILES: C[C@H]1CN(c2ncnc3c2c2ccc(S(=O)(=O)NC4(C#N)CC4)cc2n3-c2nnc(C(F)F)s2)CCN1CC1CC1] | (S)-N-(1-cyanocyclopropyl)-4-(4-(cyclopropylmethyl)-3-methylpiperazin-1-yl)-9-(5-(difluoromethyl)-1,3,4-thiadiazol-2-yl)-9H-pyrimido[4,5-b] indole-7-sulfonamide | $[M + H]^+$ 600.2/600.3 |
| 165 | 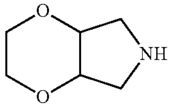 | 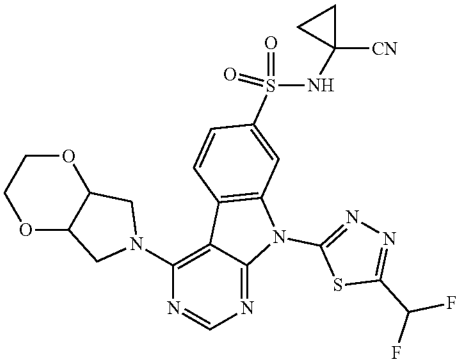 [SMILES: N#CC1(NS(=O)(=O)c2ccc3c4c(N5CC6OCCOC6C5)ncnc4n(-c4nnc(C(F)F)s4)c3c2)CC1] | N-(1-Cyanocyclopropyl)-9-(5-(difluoromethyl)-1,3,4-thiadiazol-2-yl)-4-(hexahydro-6H-[1,4] dioxino[2,3-c]pyrrol-6-yl)-9H-pyrimido[4,5-b] indole-7-sulfonamide | $[M + H]^+$ 575.1/575.0 |
| 166 | 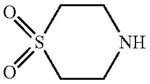 | 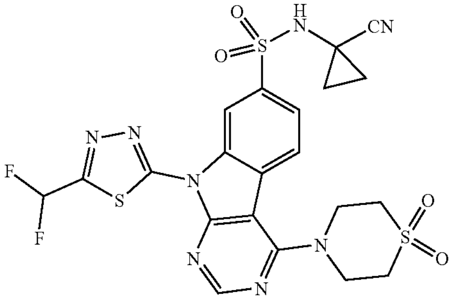 [SMILES: N#CC1(NS(=O)(=O)c2ccc3c4c(N5CCS(=O)(=O)CC5)ncnc4n(-c4nnc(C(F)F)s4)c3c2)CC1] | N-(1-cyanocyclopropyl)-9-(5-(difluoromethyl)-1,3,4-thiadiazol-2-yl)-4-(1,1-dioxidothiomorpholino)-9H-pyrimido[4,5-b] indole-7-sulfonamide | $[M - H]^-$ 579.1/579.1 |
| 167 | 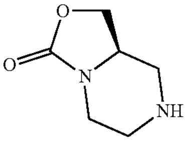 | 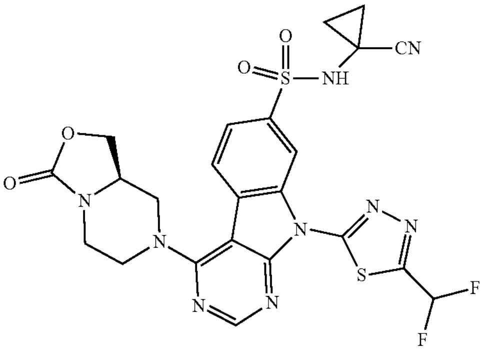 [SMILES: N#CC1(NS(=O)(=O)c2ccc3c4c(N5CCN6C(=O)OC[C@H]6C5)ncnc4n(-c4nnc(C(F)F)s4)c3c2)CC1] | (R)-N-(1-cyanocyclopropyl)-9-(5-(difluoromethyl)-1,3,4-thiadiazol-2-yl)-4-(3-oxotetrahydro-3H-oxazolo[3,4-a]pyrazin-7(1H)-yl)-9H-pyrimido [4,5-b]indole-7-sulfonamide | $[M + H]^+$ 588.1/588.2 |

Example 168: (R)—N-(1-Cyanocyclopropyl)-9-(5-(difluoromethyl)-1,3,4-thiadiazol-2-yl)-4-(4-oxo-hexahydropyrazino[2,1-c][1,4]oxazin-8(1H)-yl)-9H-pyrimido[4,5-b]indole-7-sulfonamide

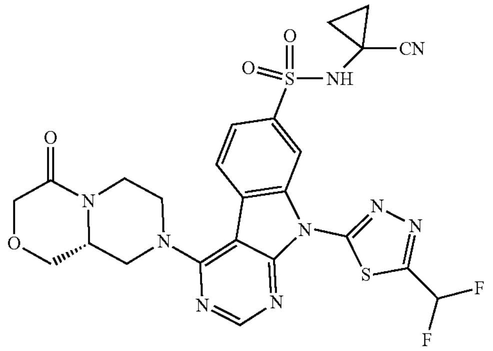 [SMILES: N#CC1(NS(=O)(=O)c2ccc3c4c(N5CCN6C(=O)COC[C@H]6C5)ncnc4n(-c4nnc(C(F)F)s4)c3c2)CC1]

Step 1: (R)—N-(1-cyanocyclopropyl)-4-(4-oxohexahydropyrazino[2,1-c][1,4]oxazin-8(1H)-yl)-9H-pyrimido[4,5-b]indole-7-sulfonamide

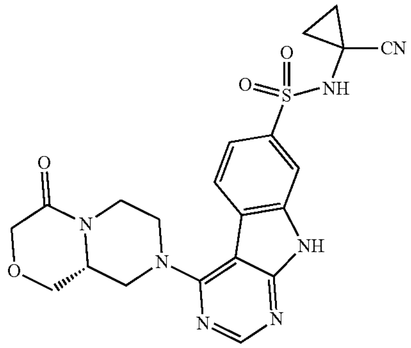 [SMILES: N#CC1(NS(=O)(=O)c2ccc3c(c2)[nH]c2ncnc(N4CCN5C(=O)COC[C@H]5C4)c23)CC1]

This compound was prepared using procedures analogous to those described for Example 160 Step 1 using 4-chloro-N-(1-cyanocyclopropyl)-9H-pyrimido[4,5-b]indole-7-sulfonamide (Intermediate 1) and (R)-hexahydropyrazino[2,1-c][1,4]oxazin-4(3H)-one hydrochloride. LCMS calc. for $C_{21}H_{22}N_7O_4S$ $[M+H]^+$: m/z=468.1; Found: 468.2.

Step 2: (R)—N-(1-cyanocyclopropyl)-9-(5-(difluoromethyl)-1,3,4-thiadiazol-2-yl)-4-(4-oxohexahydropyrazino[2,1-c][1,4]oxazin-8(1H)-yl)-9H-pyrimido[4,5-b]indole-7-sulfonamide A mixture of (R)—N-(1-cyanocyclopropyl)-4-(4-oxohexahydropyrazino[2,1-c][1,4]oxazin-8(1H)-yl)-9H-pyrimido[4,5-b]indole-7-sulfonamide (60 mg, 0.13 mmol), 2-bromo-5-(difluoromethyl)-1,3,4-thiadiazole (55 mg, 0.26 mmol), RuphosPdG3 (5.4 mg, 0.0064 mmol) and $K_3PO_4$ (55 mg, 0.26 mmol) in 1,4-dioxane (3 mL) was degassed and recharged with $N_2$ for three cycles. The mixture was stirred at 120° C. overnight under nitrogen atmosphere. After cooled to r.t., the mixture was concentrated under reduced pressure. The residue was purified by prep-HPLC eluting with ACN/1$H_2O$ (30-60%, 0.1% TFA) to afford the desired product (28.7 mg, 37.2% yield) as white solid. LCMS calc. for $C_{24}H_{22}F_2N_9O_4S_2$ $[M+H]^+$: m/z=602.1; Found: 602.2.

The compounds listed in Table 11 below were prepared by using an Intermediate 1 (Int A, sulfonamide derivative) and an appropriate amine derivative (Int B) as the methods substantially analogous to those described for preparing Example 168.

TABLE 11

Preparations of Examples (Ex)

| Ex # | Int B | Structure | Name | LCMS Cacl./ Found |
|---|---|---|---|---|
| 169 | 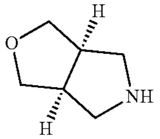 | 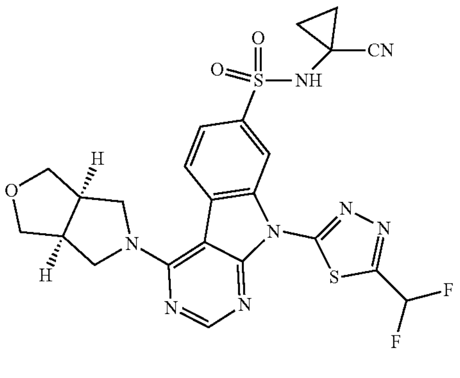 [SMILES: N#CC1(NS(=O)(=O)c2ccc3c4c(N5C[C@H]6COC[C@H]6C5)ncnc4n(-c4nnc(C(F)F)s4)c3c2)CC1] | N-(1-Cyanocyclopropyl)-9-(5-(difluoromethyl)-1,3,4-thiadiazol-2-yl)-4-((3aR,6aS)-tetrahydro-1H-furo[3,4-c]pyrrol-5(3H)-yl)-9H-pyrimido[4,5-b]indole-7-sulfonamide | $[M + H]^+$ 559.1/559.2 |

TABLE 11-continued

Preparations of Examples (Ex)

| Ex # | Int B | Structure | Name | LCMS Cacl./ Found |
|---|---|---|---|---|
| 170 | 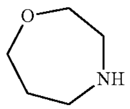 | 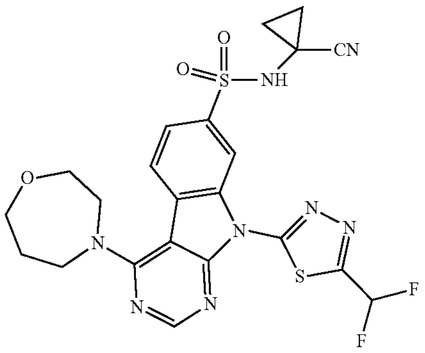 [SMILES: N#CC1(NS(=O)(=O)c2ccc3c4c(N5CCCOCC5)ncnc4n(-c4nnc(C(F)F)s4)c3c2)CC1] | N-(1-Cyanocyclo-propyl)-9-(5-(difluoromethyl)-1,3,4-thiadiazol-2-yl)-4-(1,4-oxazepan-4-yl)-9H-pyrimido[4,5-b]indole-7-sulfonamide | $[M + H]^+$ 547.1/547.2 |
| 171 | 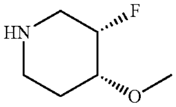 Int-60 | 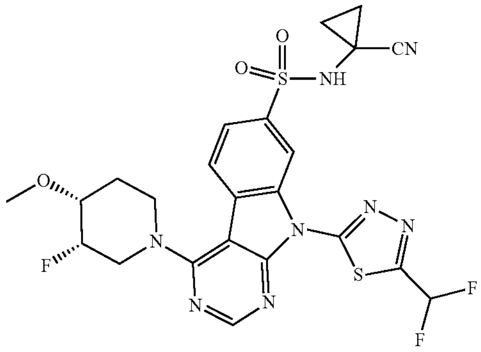 [SMILES: CO[C@@H]1CCN(c2ncnc3c2c2ccc(S(=O)(=O)NC4(C#N)CC4)cc2n3-c2nnc(C(F)F)s2)C[C@@H]1F] | N-(1-Cyanocyclo-propyl)-9-(5-(difluoromethyl)-1,3,4-thiadiazol-2-yl)-4-((3S,4R)-3-fluoro-4-methoxypiperidin-1-yl)-9H-pyrimido[4,5-b]indole-7-sulfonamide | $[M + H]^+$ 579.1/579.2 |
| 172 | 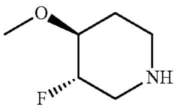 Int-61 | 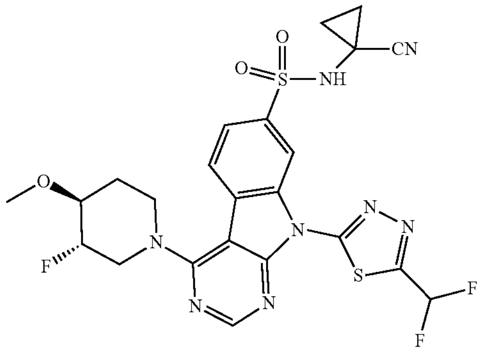 [SMILES: CO[C@H]1CCN(c2ncnc3c2c2ccc(S(=O)(=O)NC4(C#N)CC4)cc2n3-c2nnc(C(F)F)s2)C[C@@H]1F] | N-(1-cyanocyclo-propyl)-9-(5-(difluoromethyl)-1,3,4-thiadiazol-2-yl)-4-((3S,4S)-3-fluoro-4-methoxypiperidin-1-yl)-9H-pyrimido[4,5-b]indole-7-sulfonamide | $[M + H]^+$ 579.1/579.1 |
| 173 | 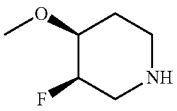 Int-62 | 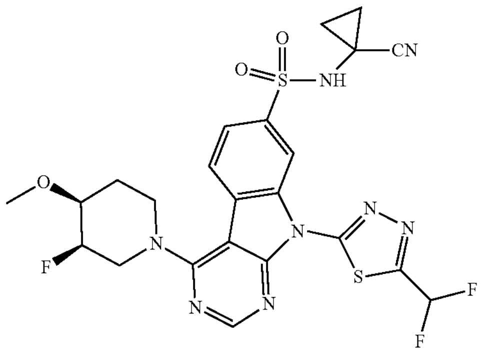 [SMILES: CO[C@H]1CCN(c2ncnc3c2c2ccc(S(=O)(=O)NC4(C#N)CC4)cc2n3-c2nnc(C(F)F)s2)C[C@H]1F] | N-(1-cyanocyclo-propyl)-9-(5-(difluoromethyl)-1,3,4-thiadiazol-2-yl)-4-((3R,4S)-3-fluoro-4-methoxypiperidin-1-yl)-9H-pyrimido[4,5-b]indole-7-sulfonamide | $[M + H]^+$ 579.1/579.1 |

TABLE 11-continued

| Preparations of Examples (Ex) | | | | |
|---|---|---|---|---|
| Ex # | Int B | Structure | Name | LCMS Cacl./ Found |
| 174 | 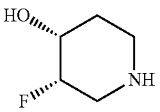 Int-63 | 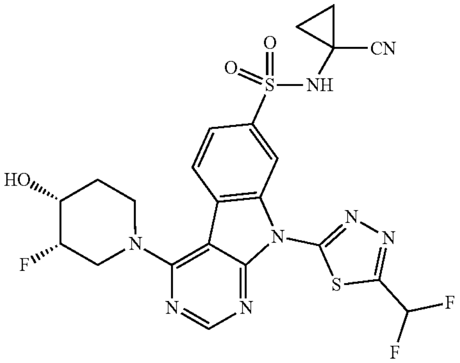 [SMILES: N#CC1(NS(=O)(=O)c2ccc3c4c(N5CC[C@@H](O)[C@@H](F)C5)ncnc4n(-c4nnc(C(F)F)s4)c3c2)CC1] | N-(1-cyanocyclo-propyl)-9-(5-(difluoromethyl)-1,3,4-thiadiazol-2-yl)-4-((3S,4R)-3-fluoro-4-hydroxypiperidin-1-yl)-9H-pyrimido[4,5-b] indole-7-sulfonamide | $[M + H]^+$ 565.1/565.1 |
| 175 | 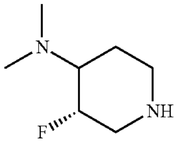 Int-64 | 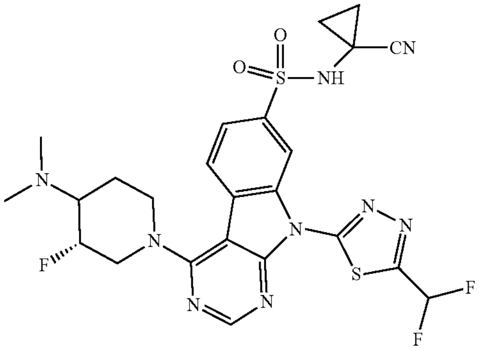 [SMILES: CN(C)C1CCN(c2ncnc3c2c2ccc(S(=O)(=O)NC4(C#N)CC4)cc2n3-c2nnc(C(F)F)s2)C[C@@H]1F] | N-(1-cyanocyclo-propyl)-9-(5-(difluoromethyl)-1,3,4-thiadiazol-2-yl)-4-((3S)-4-(dimethylamino)-3-fluoropiperidin-1-yl)-9H-pyrimido[4,5-b] indole-7-sulfonamide | $[M + H]^+$ 592.1/592.1 |
| 176 | 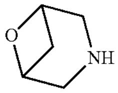 | 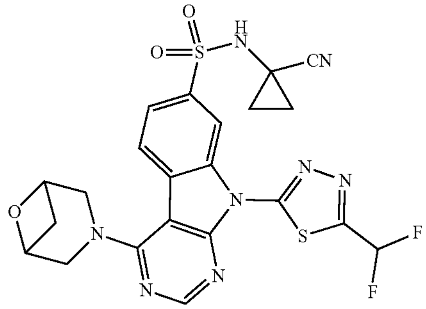 [SMILES: N#CC1(NS(=O)(=O)c2ccc3c4c(N5CC6CC(C5)O6)ncnc4n(-c4nnc(C(F)F)s4)c3c2)CC1] | 4-(6-oxa-3-azabicyclo [3.1.1]heptan-3-yl)-N-(1-cyanocyclopropyl)-9-(5-(difluoromethyl)-1,3,4-thiadiazol-2-yl)-9H-pyrimido[4,5-b] indole-7-sulfonamide | $[M + H]^+$ 545.1/545.1 |
| 177 | 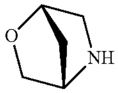 | 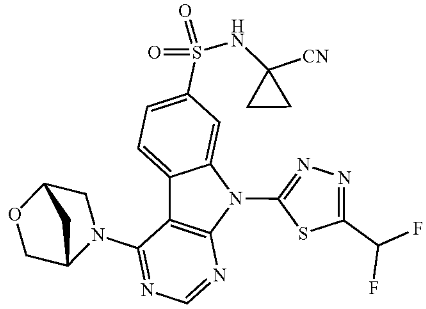 [SMILES: N#CC1(NS(=O)(=O)c2ccc3c4c(N5C[C@@H]6C[C@H]5CO6)ncnc4n(-c4nnc(C(F)F)s4)c3c2)CC1] | 4-((1S,4S)-2-oxa-5-azabicyclo[2.2.1]heptan-5-yl)-N-(1-cyanocyclo-propyl)-9-(5-(difluoromethyl)-1,3,4-thiadiazol-2-yl)-9H-pyrimido[4,5-b] indole-7-sulfonamide | $[M + H]^+$ 545.1/545.1 |

TABLE 11-continued

Preparations of Examples (Ex)

| Ex # | Int B | Structure | Name | LCMS Cacl./ Found |
|---|---|---|---|---|
| 178 | 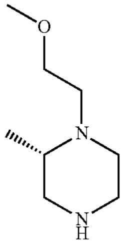 Int-65 | 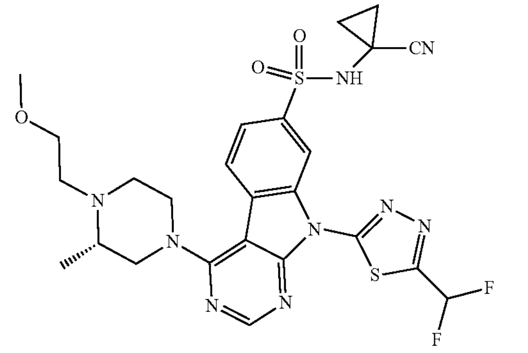 [SMILES: COCCN1CCN(c2ncnc3c2c2ccc(S(=O)(=O)NC4(C#N)CC4)cc2n3-c2nnc(C(F)F)s2)C[C@@H]1C] | (S)-N-(1-cyanocyclo-propyl)-9-(5-(difluoromethyl)-1,3,4-thiadiazol-2-yl)-4-(4-(2-methoxyethyl)-3-methylpiperazin-1-yl)-9H-pyrimido[4,5-b] indole-7-sulfonamide | $[M + H]^+$ 604.2/604.2 |
| 179 | 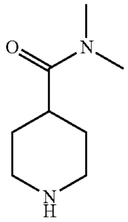 | 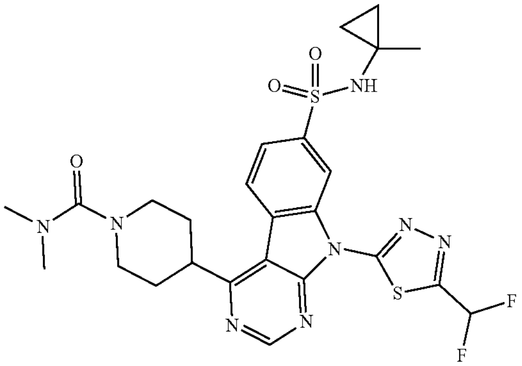 | 1-(7-(N-(1-Cyanocyclo-propyl)sulfamoyl)-9-(5-(difluoromethyl)-1,3,4-thiadiazol-2-yl)-9H-pyrimido[4,5-b] indol-4-yl)-N,N-dimethylpiperidine-4-carboxamide | $[M + H]^+$ 602.2/602.2 |
| 180 | 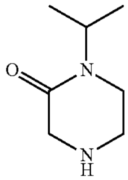 | 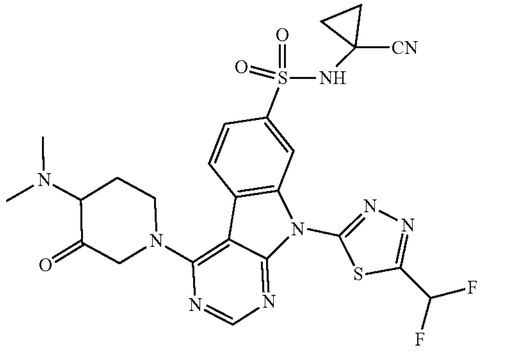 [SMILES: CN(C)C1CCN(c2ncnc3c2c2ccc(S(=O)(=O)NC4(C#N)CC4)cc2n3-c2nnc(C(F)F)s2)CC1=O] | N-(1-Cyanocyclo-propyl)-9-(5-(difluoromethyl)-1,3,4-thiadiazol-2-yl)-4-(4-isopropyl-3-oxopiperazin-1-yl)-9H-pyrimido[4,5-b] indole-7-sulfonamide | $[M + H]^+$ 588.1/588.2 |
| 181 | 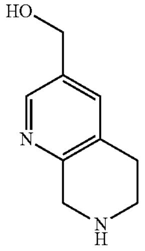 [SMILES: OCc1cnc2c(c1)CCNC2] Int-66 | 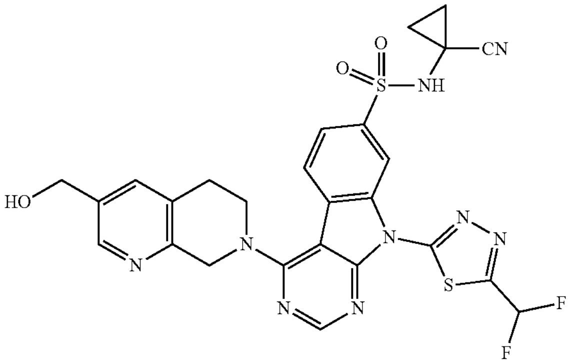 [SMILES: N#CC1(NS(=O)(=O)c2ccc3c4c(N5CCc6cc(CO)cnc6C5)ncnc4n(-c4nnc(C(F)F)s4)c3c2)CC1] | N-(1-Cyanocyclo-propyl)-9-(5-(difluoromethyl)-1,3,4-thiadiazol-2-yl)-4-(3-(hydroxymethyl)-5,8-dihydro-1,7-napthyridin-7(6H)-yl)-9H-pyrimido[4,5-b] indole-7-sulfonamide | $[M + H]^+$ 610.1/610.2 |

TABLE 11-continued

| Preparations of Examples (Ex) | | | | |
|---|---|---|---|---|
| Ex # | Int B | Structure | Name | LCMS Cacl./ Found |
| 182 | 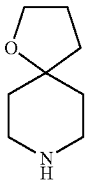 | 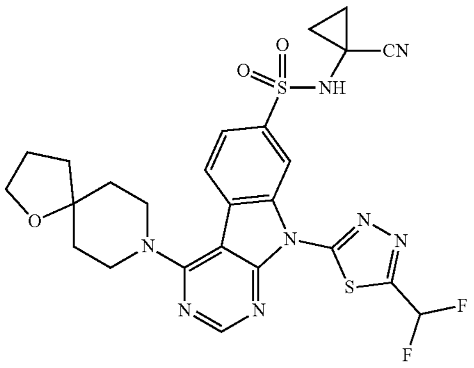 [SMILES: N#CC1(NS(=O)(=O)c2ccc3c4c(N5CCC6(CCCO6)CC5)ncnc4n(-c4nnc(C(F)F)s4)c3c2)CC1] | N-(1-Cyanocyclo-propyl)-9-(5-(difluoromethyl)-1,3,4-thiadiazol-2-yl)-4-(1-oxa-8-azaspiro[4.5] decan-8-yl)-9H-pyrimido[4,5-b] indole-7-sulfonamide | $[M + H]^+$ 587.1/587.2 |
| 183 | 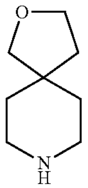 | 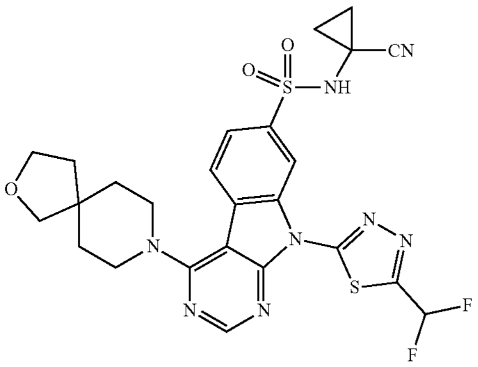 [SMILES: N#CC1(NS(=O)(=O)c2ccc3c4c(N5CCC6(CCOC6)CC5)ncnc4n(-c4nnc(C(F)F)s4)c3c2)CC1] | N-(1-Cyanocyclo-propyl)-9-(5-(difluoromethyl)-1,3,4-thiadiazol-2-yl)-4-(2-oxa-8-azaspiro[4.5] decan-8-yl)-9H-pyrimido[4,5-b] indole-7-sulfonamide | $[M + H]^+$ 587.1/587.0 |

TABLE 12

| $^1$H NMR data of Examples (Ex) | |
|---|---|
| Ex # | $^1$H NMR: (MHz, Solvent) δ |
| 111 | $^1$H NMR: (400 MHz, DMSO-$d_6$) δ 9.54 (d, J = 1.7 Hz, 1H), 9.30 (d, J = 1.6 Hz, 1H), 8.71 (d, J = 8.4 Hz, 1H), 8.09 (d, J = 8.3 Hz, 1H), 7.71 (t, J = 53.2 Hz, 1H), 4.75 (t, J = 6.6 Hz, 1H), 4.56-4.52 (m, 1H), 4.23-4.20 (m, 1H), 4.11-3.98 (m, 1H), 3.87-3.70 (m, 2H), 3.54-3.41 (m, 1H), 3.10-2.96 (m, 1H), 2.19-1.95 (m, 5H), 1.93-1.73 (m, 3H), 1.44 (dd, J = 8.3, 5.4 Hz, 2H), 1.27 (dd, J = 8.4, 5.4 Hz, 2H). |
| 112 | $^1$H NMR: (400 MHz, DMSO-$d_6$) δ 9.54 (s, 1H), 9.30 (s, 1H), 8.70 (d, J = 8.3 Hz, 1H), 8.09 (d, J = 8.3 Hz, 1H), 7.71 (t, J = 53.2 Hz, 1H), 4.63-4.58 (m, 1H), 4.46-4.38 (m, 1H), 4.03 (t, J = 11.7 Hz, 1H), 3.43 (t, J = 13.7 Hz, 1H), 3.24-3.21 (m, 2H), 3.02-2.98 (m, 2H), 2.28 (s, 3H), 2.18-1.91 (m, 4H), 1.80-1.75 (m, 4H), 1.44 (dd, J = 8.3, 5.4 Hz, 2H), 1.27 (dd, J = 8.3, 5.5 Hz, 2H). |
| 113 | $^1$H NMR: (400 MHz, DMSO-$d_6$) δ 9.55 (d, J = 1.6 Hz, 1H), 9.30 (s, 1H), 8.69 (d, J = 8.4 Hz, 1H), 8.10 (dd, J = 8.3, 1.7 Hz, 1H), 7.71 (t, J = 53.2 Hz, 1H), 4.77-4.66 (m, 4H), 4.63-4.55 (m, 1H), 4.26-4.17 (m, 1H), 4.06-3.98 (m, 1H), 3.60-3.56 (m, 2H), 3.06-3.03 (m, 1H), 2.06-1.97 (m, 3H), 1.89-1.80 (m, 1H), 1.44 (dd, J = 8.3, 5.4 Hz, 2H), 1.30-1.27 (m, 2H). |
| 114 | $^1$H NMR: (400 MHz, DMSO-$d_6$) δ 9.55 (d, J = 1.6 Hz, 1H), 9.52 (s, 1H), 9.31 (s, 1H), 8.72 (d, J = 8.4 Hz, 1H), 8.11 (dd, J = 8.3, 1.7 Hz, 1H), 7.71 (t, J = 53.2 Hz, 1H), 6.38 (s, 1H), 4.76-4.40 (m, 2H), 4.05 (s, 1H), 3.32-3.09 (m, 2H), 2.08-2.01 (m, 4H), 1.46 (dd, J = 8.4, 5.4 Hz, 2H), 1.29 (dd, J = 8.4, 5.5 Hz, 2H), 1.02-0.92 (m, 2H), 0.84-0.77 (m, 2H). |
| 115 | $^1$H NMR: (400 MHz, DMSO-$d_6$) δ 9.55 (s, 1H), 9.53 (s, 1H), 9.31 (s, 1H), 8.72 (d, J = 8.4 Hz, 1H), 8.10 (dd, J = 5.6, 4.2 Hz, 1H), 7.71 (t, J = 53.2 Hz, 1H), 4.60 (d, J = 13.0 Hz, 1H), 4.18 (d, J = 13.6 Hz, 1H), 4.05 (t, J = 11.8 Hz, 1H), 3.93-3.90 (m, 1H), 3.77-3.69 (m, 3H), 3.49-3.43 (m, 2H), 3.03 (t, J = 12.4 Hz, 1H), 2.11-1.90 (m, 5H), 1.90-1.79 (m, 1H), 1.48-1.44 (m, 2H), 1.31-1.29 (m, 2H). |
| 116 | $^1$H NMR: (400 MHz, DMSO-$d_6$) δ 9.56 (s, 1H), 9.53 (s, 1H), 9.31 (s, 1H), 8.72 (d, J = 8.4 Hz, 1H), 8.11 (dd, J = 8.4, 1.6 Hz, 1H), 7.71 (t, J = 53.2 Hz, 1H), 4.60 (d, J = 12.2 Hz, 1H), 4.19 (d, J = 14.6 Hz, 1H), 4.05 (t, J = 10.8 Hz, 1H), 3.93-3.90 (m, 1H), 3.77-3.69 (m, 3H), 3.49-3.43 (m, 2H), 3.03 (t, J = 12.6 Hz, 1H), 2.10-1.91 (m, 5H), 1.90-1.80 (m, 1H), 1.46-1.44 (m, 2H), 1.32-1.26 (m, 2H). |
| 117 | $^1$H NMR: (400 MHz, DMSO-$d_6$) δ 9.56 (s, 1H), 9.53 (s, 1H), 9.31 (s, 1H), 8.72 (d, J = 8.4 Hz, 1H), 8.11 (dt, J = 8.4, 1.6 Hz, 1H), 7.71 (t, J = 53.2 Hz, 1H), 4.54 (d, J = 12.6 Hz, 1H), 4.23-4.08 (m, 2H), 4.08-3.94 (m, 2H), 3.43-3.40 (m, 1H), 3.33 (s, 3H), 3.03 (t, J = 12.0 Hz, 1H), 2.03-1.99 (m, 3H), 1.85-1.81 (m, 1H), 1.48-1.44 (m, 2H), 1.32-1.28 (m, 2H). |
| 125 | $^1$H NMR: (400 MHz, $CD_3OD$) δ 9.56 (s, 1H), 9.14 (s, 1H), 8.50 (d, J = 8.4 Hz, 1H), 8.10 (d, J = 8.4 Hz, 1H), 7.36 (t, J = 53.6 Hz, 1H), 4.77-4.61 (m, 2H), 4.27-3.93 (m, 2H), 3.63 (t, J = 12.0 Hz, 1H), 3.51- |

TABLE 12-continued

| $^1$H NMR data of Examples (Ex) | |
|---|---|
| Ex # | $^1$H NMR: (MHz, Solvent) δ |
| | 3.40 (m, 1H), 3.23 (dd, J = 17.8, 9.21 Hz, 1H), 2.69-2.51 (m, 1H), 2.32-1.97 (m, 8H), 1.47 (t, J = 6.4 Hz, 2H), 1.40 (t, J = 6.4 Hz, 2H). |
| 138 | $^1$H NMR: (400 MHz, DMSO-$d_6$) δ 9.55 (d, J = 1.6 Hz, 1H), 9.51 (s, 1H), 9.30 (s, 1H), 8.68 (d, J = 8.4 Hz, 1H), 8.10 (dd, J = 8.3, 1.6 Hz, 1H), 7.71 (t, J = 53.2 Hz, 1H), 5.57 (d, J = 6.2 Hz, 1H), 4.40 (dd, J = 11.2, 5.1 Hz, 1H), 4.12-4.08 (m, 2H), 3.95-3.91 (, 3H), 3.70 (dd, J = 8.8, 4.8 Hz, 2H), 3.16 (t, J = 11.4 Hz, 2H), 2.01-1.76 (m, 4H), 1.45 (dd, J = 8.3, 5.4 Hz, 2H), 1.29 (dd, J = 8.3, 5.5 Hz, 2H). |
| 139 | $^1$H NMR: (400 MHz, DMSO-$d_6$) δ 9.52 (d, J = 1.4 Hz, 1H), 9.30 (s, 1H), 8.66 (d, J = 8.4 Hz, 1H), 8.38 (s, 1H), 8.08 (dd, J = 8.3, 1.5 Hz, 1H), 7.71 (t, J = 53.2 Hz, 1H), 4.25 (d, J = 13.2 Hz, 2H), 4.04-3.97 (m, 1H), 3.85 (t, J = 7.3 Hz, 2H), 3.48-3.45 (m, 4H), 2.20-2.13 (m, 2H), 2.02-1.94 (m, 4H), 1.41-1.34 (m, 2H), 1.23-1.19 (m, 2H). |
| 140 | $^1$H NMR: (400 MHz, DMSO-$d_6$) δ 9.55 (d, J = 1.4 Hz, 1H), 9.48 (s, 1H), 9.30 (s, 1H), 8.68 (d, J = 8.4 Hz, 1H), 8.10 (dd, J = 8.3, 1.4 Hz, 1H), 7.71 (t, J = 53.2 Hz, 1H), 3.98-3.89 (m, 1H), 3.80 (d, J = 12.9 Hz, 2H), 3.63-3.57 (m, 4H), 3.22-3.16 (m, 6H), 2.00-1.96 (m, 4H), 1.44 (dd, J = 8.2, 5.3 Hz, 2H), 1.28 (dd, J = 8.3, 5.5 Hz, 2H). |
| 141 | $^1$H NMR: (400 MHz, DMSO-$d_6$) δ 9.55 (d, J = 1.6 Hz, 1H), 9.30 (s, 1H), 8.68 (d, J = 8.4 Hz, 1H), 8.10 (dd, J = 8.3, 1.7 Hz, 1H), 7.71 (t, J = 53.2 Hz, 1H), 3.93 (dt, J = 15.2, 7.8 Hz, 1H), 3.77 (d, J = 12.8 Hz, 2H), 3.21-3.14 (m, 6H), 2.45-2.30 (m, 4H), 2.23 (s, 3H), 1.98-1.96 (m, 4H), 1.46 (dd, J = 8.4, 5.4 Hz, 2H), 1.29 (dd, J = 8.4, 5.5 Hz, 2H). |
| 142 | $^1$HNMR: (400 MHz, $CD_3OD$) δ 9.67 (d, J = 1.6 Hz, 1H), 9.17 (s, 1H), 8.52 (d, J = 8.4 Hz, 1H), 8.15 (dd, J = 8.3, 1.7 Hz, 1H), 7.35 (t, J = 53.6 Hz, 1H), 4.11-3.82 (m, 4H), 3.28 (s, 1H), 3.25-3.15 (m, 3H), 3.03 (s, 3H), 2.19-2.09 (m, 4H), 1.44 (dtd, J = 18.3, 7.0, 2.9 Hz, 4H), 1.17 (d, J = 6.3 Hz, 3H). |
| 143 | $^1$H NMR (400 MHz, DMSO-$d_6$) δ 9.55 (d, J = 1.6 Hz, 1H), 9.53 (s, 1H), 9.31 (s, 1H), 8.67 (d, J = 8.4 Hz, 1H), 8.10 (dd, J = 8.3, 1.7 Hz, 1H), 7.71 (t, J = 53.2 Hz, 1H), 4.73-4.70 (m, 1H), 3.90-3.80 (m, 1H), 3.75 (d, J = 12.8 Hz, 2H), 3.56 (q, J = 5.9 Hz, 2H), 3.23 (t, J = 6.0 Hz, 2H), 3.15-3.12 (m, 2H), 2.86 (s, 3H), 2.03-1.97 (m, 4H), 1.46-1.43 (m, 2H), 1.30-1.24 (m, 2H). |
| 144 | $^1$H NMR: (400 MHz, DMSO-$d_6$) δ 9.55 (d, J = 1.6 Hz, 1H), 9.52 (s, 1H), 9.31 (s, 1H), 8.68 (d, J = 8.4 Hz, 1H), 8.10 (dd, J = 8.3, 1.7 Hz, 1H), 7.71 (t, J = 53.2 Hz, 1H), 4.00-3.82 (m, 1H), 3.72 (d, J = 12.9 Hz, 2H), 3.50 (t, J = 5.7 Hz, 2H), 3.34-3.32 (m, 2H), 3.27 (s, 3H), 3.19-3.07 (m, 2H), 2.86 (s, 3H), 2.31-1.83 (m, 4H), 1.46-1.44 (m, 2H), 1.30-1.28 (m, 2H). |
| 163 | $^1$H NMR: (400 MHz, DMSO-$d_6$) δ 9.46 (d, J = 1.6 Hz, 1H), 9.39 (s, 1H), 8.73 (s, 1H), 8.07-8.02 (m, 2H), 7.68 (t, J = 53.2 Hz, 1H), 4.16-4.11 (m, 2H), 3.59-3.54 (m, 1H), 3.00-2.80 (m, 2H), 2.70-2.50 (m, 1H), 2.47-2.30 (m, 2H), 1.46-1.39 (m, 2H), 1.30-1.22 (m, 2H), 1.11-0.92 (m, 6H). |
| 165 | $^1$H NMR (400 MHz, DMSO-$d_6$) δ 9.50 (d, J = 1.8 Hz, 1H), 8.95 (s, 1H), 8.69 (s, 1H), 8.51 (d, J = 8.6 Hz, 1H), 7.95 (dd, J = 8.6, 1.8 Hz, 1H), 7.67 (t, J = 53.3 Hz, 1H), 4.35 (t, J = 4.2 Hz, 2H), 4.14 (d, J = 8.1 Hz, 2H), 4.06 (dd, J = 9.0, 5.9 Hz, 2H), 3.95 (dd, J = 8.6, 6.1 Hz, 2H), 3.62 (dd, J = 8.6, 5.5 Hz, 2H), 1.39 (dd, J = 8.2, 5.3 Hz, 2H), 1.24 (dd, J = 8.3, 5.3 Hz, 2H). |
| 177 | $^1$H NMR: (400 MHz, DMSO-$d_6$) δ 9.51 (d, J = 1.8 Hz, 1H), 9.37 (s, 1H), 8.71 (s, 1H), 8.27 (d, J= 8.4 Hz,, 1H), 7.96 (dd, J = 8.4 Hz, 1.8 Hz, 1H), 7.68 (d, JF-H = 51.4 Hz, 1H), 5.32 (s, 1H), 4.81 (s, 1H), 4.31 (d, J = 9.0 Hz, 1H), 3.96 (s, 2H), 3.65 (d, J = 9.0 Hz, 1H), 1.97-2.12 (m, 2H), 1.40-1.48 (m, 2H), 1.22-1.30 (m, 2H). |
| 182 | $^1$H NMR: (400 MHz, DMSO-$d_6$) δ ppm 9.47 (t, J = 1.3 Hz, 1H), 9.38 (s, 1H), 8.76-8.75 (m, 1H), 8.07-8.03 (m, 2H), 7.67 (t, J = 53.3 Hz, 1H), 3.98-3.82 (m, 2H), 3.79-3.75 (m, 4H), 1.95-1.91 (m, 2H), 1.80-1.74 (m, 6H), 1.45-1.41 (m, 2H), 1.29-1.25 (m, 2H). |
| 183 | $^1$H NMR: (400 MHz, DMSO-$d_6$) δ 9.48 (d, J = 1.6 Hz, 1H), 9.38 (s, 1H), 8.77 (t, J = 1.0 Hz, 1H), 8.09-8.01 (m, 2H), 7.68 (t, J = 53.3 Hz, 1H), 3.94-3.85 (m, 2H), 3.80-3.75 (m, 4H), 3.57 (s, 2H), 1.86 (t, J = 7.1 Hz, 2H), 1.76-1.73 (m, 4H), 1.45-1.39 (m, 2H), 1.29-1.25 (m, 2H). |

Example 184: (R)-9-(5-(Difluoromethyl)-1,3,4-thiadiazol-2-yl)-4-(hexahydropyrazino[2,1-c][1,4]oxazin-8(1H)-yl)-N-(1-methylcyclopropyl)-9H-pyrimido[4,5-b]indole-7-sulfonamide

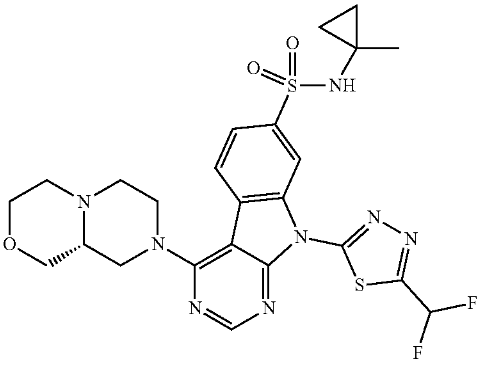 [SMILES: CC1(NS(=O)(=O)c2ccc3c4c(N5CCN6CCOC[C@H]6C5)ncnc4n(-c4nnc(C(F)F)s4)c3c2)CC1]

Step 1: (R)-4-(hexahydropyrazino[2,1-c][1,4]oxazin-8(1H)-yl)-N-(1-methylcyclopropyl)-9H-pyrimido[4,5-b]indole-7-sulfonamide

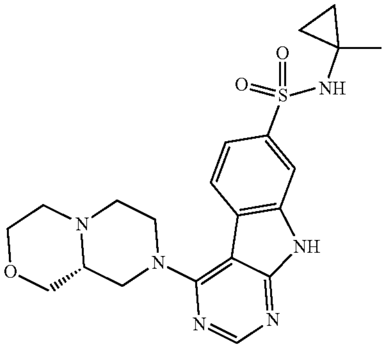 [SMILES: CC1(NS(=O)(=O)c2ccc3c(c2)[nH]c2ncnc(N4CCN5CCOC[C@H]5C4)c23)CC1]

This compound was prepared using procedures analogous to those described for Example 160 Step 1 using 4-chloro- N-(1-cyanocyclopropyl)-9H-pyrimido[4,5-b]indole-7-sulfonamide (Intermediate 2) and (R)-octahydropyrazino[2,1-c][1,4]oxazine. LCMS calc. for $C_{21}H_{27}N_6O_3S$ [M+H]$^+$: m/z=443.2; Found: 443.2.

Step 2: (R)-9-(5-(difluoromethyl)-1,3,4-thiadiazol-2-yl)-4-(hexahydropyrazino[2,1-c][1,4]oxazin-8(1H)-yl)-N-(1-methylcyclopropyl)-9H-pyrimido[4,5-b]indole-7-sulfonamide This compound was prepared using procedures analogous to those described for Example 165 Step 2 using (R)-4-(hexahydropyrazino[2,1-c][1,4]oxazin-8(1H)-yl)-N-(1-methylcyclopropyl)-9H-pyrimido[4,5-b]indole-7-sulfonamide and 2-bromo-5-(difluoromethyl)-1,3,4-thiadiazole to afford the desired product as white solid. LCMS calc. for $C_{24}H_{27}F_2N_8O_3S_2$ [M+H]$^+$: m/z=577.2; Found: 577.2.

Example 185: N-(1-Cyanocyclopropyl)-4-(4-(cyclopropanecarbonyl)piperazin-1-yl)-9-(5-methyl-1,3,4-thiadiazol-2-yl)-9H-pyrimido[4,5-b]indole-7-sulfonamide

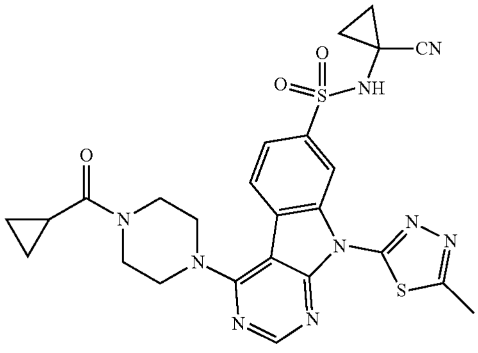 [SMILES: Cc1nnc(-n2c3cc(S(=O)(=O)NC4(C#N)CC4)ccc3c3c(N4CCN(C(=O)C5CC5)CC4)ncnc32)s1]

Step 1: N-(1-cyanocyclopropyl)-4-(4-(cyclopropanecarbonyl)piperazin-1-yl)-9H-pyrimido[4,5-b]indole-7-sulfonamide

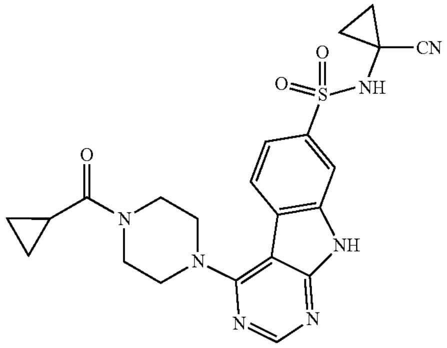 [SMILES: N#CC1(NS(=O)(=O)c2ccc3c(c2)[nH]c2ncnc(N4CCN(C(=O)C5CC5)CC4)c23)CC1]

This compound was prepared using procedures analogous to this described for Example 1 Step 1 using 4-chloro-N-(1-cyanocyclopropyl)-9H-pyrimido[4,5-b]indole-7-sulfonamide (Intermediate 1) and cyclopropyl(piperazin-1-yl)methanone. LCMS calc. for $C_{22}H_{22}N_7O_3S$ [M−H]$^-$: m/z=464.2; Found: 464.1.

Step 2: N-(1-cyanocyclopropyl)-4-(4-(cyclopropanecarbonyl)piperazin-1-yl)-9-(5-methyl-1,3,4-thiadiazol-2-yl)-9H-pyrimido[4,5-b]indole-7-sulfonamide This compound was prepared using procedures analogous to this described for Example 74 Step 2 using N-(1-cyanocyclopropyl)-4-(4-(cyclopropanecarbonyl)piperazin-1-yl)-9H-pyrimido[4,5-b]indole-7-sulfonamide and 2-bromo-5-methyl-1,3,4-thiadiazole to afford the title product as white solid. LCMS calc. for $C_{25}H_{26}N_9O_3S_2$[M+H]$^+$: m/z=564.2; Found: 564.2.

Example 186: N-(1-Cyanocyclopropyl)-4-(4-(cyclopropanecarbonyl)piperazin-1-yl)-9-(5-isopropyl-1,3,4-thiadiazol-2-yl)-9H-pyrimido[4,5-b]indole-7-sulfonamide

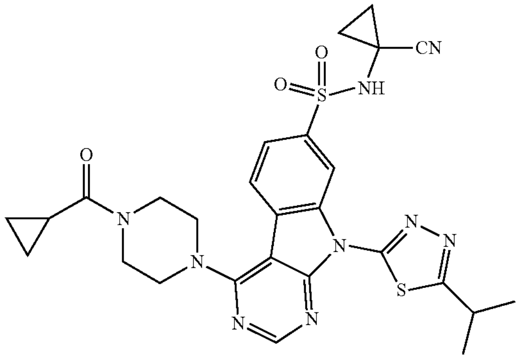 [SMILES: CC(C)c1nnc(-n2c3cc(S(=O)(=O)NC4(C#N)CC4)ccc3c3c(N4CCN(C(=O)C5CC5)CC4)ncnc32)s1]

Step 1: 2-bromo-5-isopropyl-1,3,4-thiadiazole

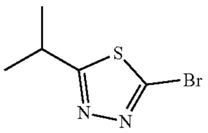

To a solution of 5-isopropyl-1,3,4-thiadiazol-2-amine (200 mg, 1.39 mmol) in ACN (2 mL) was added $CuBr_2$ (686.1 mg, 3.0 mmol) and isoamyl nitrite (360 mg, 3.0 mmol). The reaction mixture was stirred at rt for 2 h. The reaction mixture was poured into water (20 mL) and extracted with DCM (30 mL×3). The combined organic layers were washed with brine, dried over anhydrous $Na_2SO_4$, filtered and concentrated under reduced pressure. The residue was purified by flash chromatography on a silica gel column eluting with EtOAc/PE (0-11%) to afford 2-bromo-5-isopropyl-1,3,4-thiadiazole (280 mg, 99% yield) as a colorless oil. LCMS calculated for $C_5H_8BrN_2S$ [M+H]$^+$: m/z=207.0; Found: 207.0.

Step 2: N-(1-cyanocyclopropyl)-4-(4-(cyclopropanecarbonyl)piperazin-1-yl)-9-(5-isopropyl-1,3,4-thiadiazol-2-yl)-9H-pyrimido[4,5-b]indole-7-sulfonamide This compound was prepared using procedures analogous to this described for Example 74 Step 2 using N-(1-cyanocyclopropyl)-4-(4-(cyclopropanecarbonyl)piperazin-1-yl)-

9H-pyrimido[4,5-b]indole-7-sulfonamide (Example 170 Step 1) and 2-bromo-5-isopropyl-1,3,4-thiadiazole. LCMS calc. for $C_{27}H_{30}N_9O_3S_2$ [M+H]$^+$: m/z=592.2; Found: 592.2.

Example 187: N-(1-Cyanocyclopropyl)-4-(4-(cyclopropanecarbonyl)piperazin-1-yl)-9-(5-cyclopropyl-1,3,4-thiadiazol-2-yl)-9H-pyrimido[4,5-b]indole-7-sulfonamide

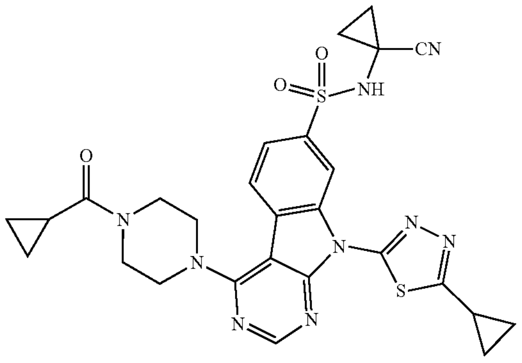 [SMILES: N#CC1(NS(=O)(=O)c2ccc3c4c(N5CCN(C(=O)C6CC6)CC5)ncnc4n(-c4nnc(C5CC5)s4)c3c2)CC1]

Step 1: 2-bromo-5-cyclopropyl-1,3,4-thiadiazole

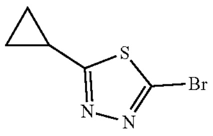

The compound was prepared using procedures analogous to those described for Example 186 Step 1 using 5-cyclopropyl-1,3,4-thiadiazol-2-amine to replace 5-isopropyl-1,3,4-thiadiazol-2-amine. LCMS calculated for $C_5H_6BrN_2S$ [M+H]$^+$: m/z=204.9; Found: 205.0.

Step 2: N-(1-cyanocyclopropyl)-4-(4-(cyclopropanecarbonyl)piperazin-1-yl)-9-(5-cyclopropyl-1,3,4-thiadiazol-2-yl)-9H-pyrimido[4,5-b]indole-7-sulfonamide This compound was prepared using procedures analogous to this described for Example 74 Step 2 using N-(1-cyanocyclopropyl)-4-(4-(cyclopropanecarbonyl)piperazin-1-yl)-9H-pyrimido[4,5-b]indole-7-sulfonamide (Example 170 Step 1) and 2-bromo-5-cyclopropyl-1,3,4-thiadiazole. LCMS calc. for $C_{27}H_{28}N_9O_3S_2$ [M+H]$^+$: m/z=590.2; Found: 590.2.

Example 188: N-(1-Cyanocyclopropyl)-4-(4-(cyclopropanecarbonyl)piperazin-1-yl)-9-(5-(trifluoromethyl)-1,3,4-thiadiazol-2-yl)-9H-pyrimido[4,5-b]indole-7-sulfonamide

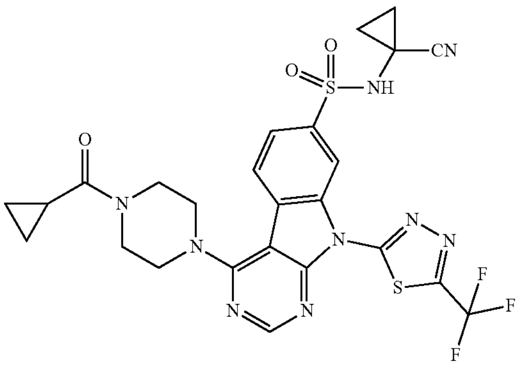 [SMILES: N#CC1(NS(=O)(=O)c2ccc3c4c(N5CCN(C(=O)C6CC6)CC5)ncnc4n(-c4nnc(C(F)(F)F)s4)c3c2)CC1]

Step 1: 2-bromo-5-(trifluoromethyl)-1,3,4-thiadiazole

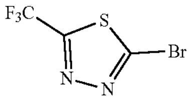

The Intermediate 105 was prepared using procedures analogous to those described for Example 186 Step 1 using 5-(trifluoromethyl)-1,3,4-thiadiazol-2-amine to replace 5-isopropyl-1,3,4-thiadiazol-2-amine. LCMS calculated for $C_3HBrF_3N_2S$ [M+H]$^+$: m/z=232.9; Found: 233.0.

Step 2: N-(1-cyanocyclopropyl)-4-(4-(cyclopropanecarbonyl)piperazin-1-yl)-9-(5-(trifluoromethyl)-1,3,4-thiadiazol-2-yl)-9H-pyrimido[4,5-b]indole-7-sulfonamide This compound was prepared using procedures analogous to this described for Example 154 Step 4 using N-(1-cyanocyclopropyl)-4-(4-(cyclopropanecarbonyl)piperazin-1-yl)-9H-pyrimido[4,5-b]indole-7-sulfonamide (Example 170 Step 1) and 2-bromo-5-(trifluoromethyl)-1,3,4-thiadiazole to afford the title product as white solid. LCMS calc. for $C_{25}H_{23}F_3N_9O_3S_2$ [M+H]$^+$: m/z=618.1; Found: 618.2.

Example 189: N-(1-Cyanocyclopropyl)-9-(5-(difluoromethyl)-1,3,4-thiadiazol-2-yl)-4-(4-hydroxypiperidin-1-yl)-9H-pyrimido[4,5-b]indole-7-sulfonamide

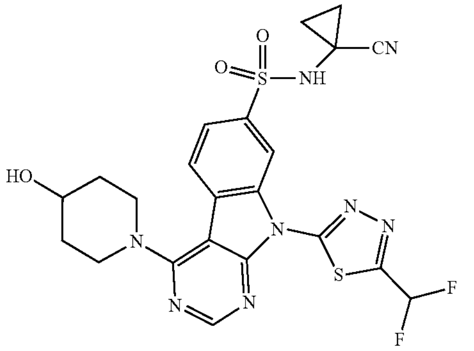 [SMILES: N#CC1(NS(=O)(=O)c2ccc3c4c(N5CCC(O)CC5)ncnc4n(-c4nnc(C(F)F)s4)c3c2)CC1]

Step 1: N-(1-cyanocyclopropyl)-4-(4-hydroxypiperidin-1-yl)-9H-pyrimido[4,5-b]indole-7-sulfonamide

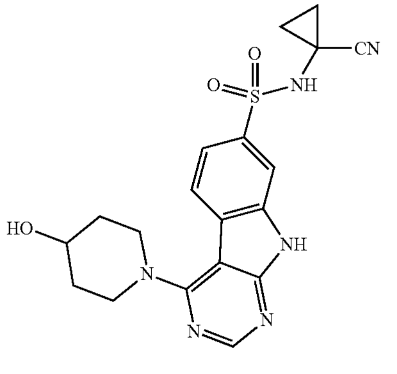 [SMILES: N#CC1(NS(=O)(=O)c2ccc3c(c2)[nH]c2ncnc(N4CCC(O)CC4)c23)CC1]

This compound was prepared using procedures analogous to this described for Example 1 Step 1 using 4-chloro-N-(1-cyanocyclopropyl)-9H-pyrimido[4,5-b]indole-7-sulfonamide (Intermediate 1) and piperidin-4-ol to afford the title product as yellow solid. LCMS calc. for $C_{19}H_{19}N_6O_3S$ $[M-H]^-$: m/z=411.1; Found: 411.1.

Step 2: N-(1-cyanocyclopropyl)-9-(5-(difluoromethyl)-1,3,4-thiadiazol-2-yl)-4-(4-hydroxypiperidin-1-yl)-9H-pyrimido[4,5-b]indole-7-sulfonamide This compound was prepared using procedures analogous to this described for Example 44 Step 2 using N-(1-cyanocyclopropyl)-4-(4-hydroxypiperidin-1-yl)-9H-pyrimido[4,5-b]indole-7-sulfonamide and 2-bromo-5-(difluoromethyl)-1,3,4-thiadiazole to afford the title product as light yellow solid. $^1H$ NMR: (400 MHz, DMSO-$d_6$) δ 9.49 (s, 1H), 9.39 (s, 1H), 8.79 (s, 1H), 8.10-8.06 (m, 2H), 7.69 (t, J=53.2 Hz, 1H), 4.80 (d, J=4.0 Hz, 1H), 4.15-4.11 (m, 2H), 3.91-3.87 (m, 1H), 3.61-3.53 (m, 2H), 2.08-1.89 (m, 2H), 1.67-1.55 (m, 2H), 1.46-1.42 (m, 2H), 1.30-1.27 (m, 2H). LCMS calc. for $C_{22}H_{21}F_2N_8O_3S_2[M+H]^+$: m/z=547.1; Found: 547.1.

Example 190: 9-(5-(Difluoromethyl)-1,3,4-thiadiazol-2-yl)-4-((3R,5S)-4-isobutyryl-3,5-dimethylpiperazin-1-yl)-N-(1-methylcyclopropyl)-9H-pyrimido[4,5-b]indole-7-sulfonamide

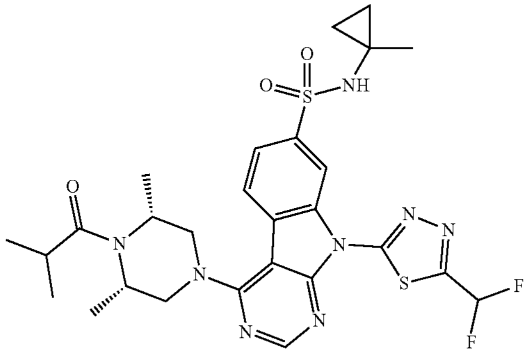 [SMILES: CC(C)C(=O)N1[C@H](C)CN(c2ncnc3c2c2ccc(S(=O)(=O)NC4(C)CC4)cc2n3-c2nnc(C(F)F)s2)C[C@@H]1C]

Step 1: 4-((3R,5S)-4-isobutyryl-3,5-dimethylpiperazin-1-yl)-N-(1-methylcyclopropyl)-9H-pyrimido[4,5-b]indole-7-sulfonamide

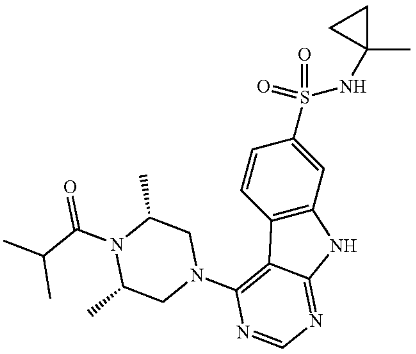 [SMILES: CC(C)C(=O)N1[C@H](C)CN(c2ncnc3[nH]c4cc(S(=O)(=O)NC5(C)CC5)ccc4c23)C[C@@H]1C]

This compound was prepared using procedures analogous to this described for Example 1 Step 1 using 4-chloro-N-(1-methylcyclopropyl)-9H-pyrimido[4,5-b]indole-7-sulfonamide (Intermediate 2) and 1-((2S,6R)-2,6-dimethylpiperazin-1-yl)-2-methylpropan-1-one (Intermediate 38) to afford the title product as white solid. LCMS calc. for $C_{24}H_{31}N_6O_3S$ $[M-H]^-$: m/z=483.2; Found: 483.0.

Step 2: 9-(5-(difluoromethyl)-1,3,4-thiadiazol-2-yl)-4-((3R,5S)-4-isobutyryl-3,5-dimethylpiperazin-1-yl)-N-(1-methylcyclopropyl)-9H-pyrimido[4,5-b]indole-7-sulfonamide This compound was prepared using procedures analogous to this described for Example 44 Step 2 using 4-((3R,5S)-4-isobutyryl-3,5-dimethylpiperazin-1-yl)-N-(1-methylcyclopropyl)-9H-pyrimido[4,5-b]indole-7-sulfonamide and 2-bromo-5-(difluoromethyl)-1,3,4-thiadiazole to afford the title product as yellow solid. $^1H$ NMR: (400 MHz, DMSO-$d_6$) δ 9.46 (d, J=1.6 Hz, 1H), 8.77 (s, 1H), 8.35 (s, 1H), 8.18 (d, J=8.4 Hz, 1H), 7.96 (d, J=8.0 Hz, 1H), 7.68 (t, J=53.2 Hz, 1H), 4.70 (s, 1H), 4.35 (d, J=12.8 Hz, 3H), 3.75 (s, 2H), 2.87-2.83 (m, 1H), 1.22-1.14 (m, 6H), 1.13 (s, 3H), 1.06-

1.05 (m, 6H), 0.67-0.64 (m, 2H), 0.42-0.40 (m, 2H). LCMS calc. for $C_{27}H_{33}F_2N_8O_3S_2$ $[M+H]^+$: m/z=619.2; Found: 619.2.

Example 191: N-(1-Cyanocyclopropyl)-9-(5-(difluoromethyl)-1,3,4-thiadiazol-2-yl)-4-(4-hydroxy-4-(trifluoromethyl) piperidin-1-yl)-9H-pyrimido [4,5-b]indole-7-sulfonamide

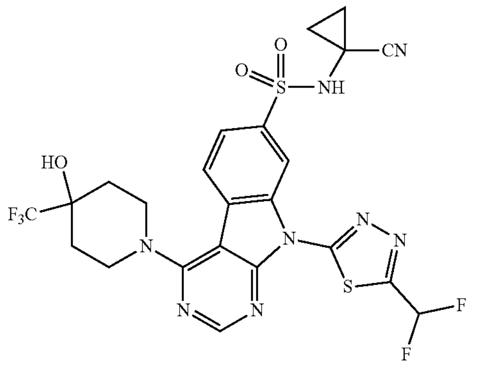 [SMILES: N#CC1(NS(=O)(=O)c2ccc3c4c(N5CCC(O)(C(F)(F)F)CC5)ncnc4n(-c4nnc(C(F)F)s4)c3c2)CC1]

Step 1: N-(1-cyanocyclopropyl)-4-(4-hydroxy-4-(trifluoromethyl) piperidin-1-yl)-9H-pyrimido [4,5-b]indole-7-sulfonamide

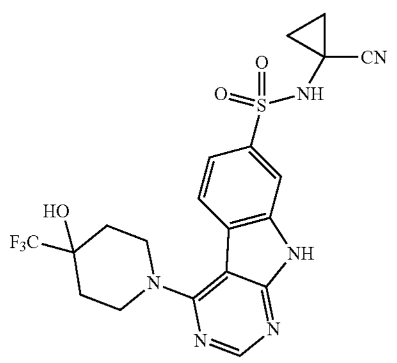 [SMILES: N#CC1(NS(=O)(=O)c2ccc3c(c2)[nH]c2ncnc(N4CCC(O)(C(F)(F)F)CC4)c23)CC1]

This compound was prepared using procedures analogous to this described for Example 1 Step 1 using 4-chloro-N-(1-cyanocyclopropyl)-9H-pyrimido[4,5-b]indole-7-sulfonamide (Intermediate 1) and 4-(trifluoromethyl) piperidin-4-ol to afford the title product as white solid. LCMS calc. for $C_{20}H_{20}F_3N_6O_3S$ $[M+H]^+$: m/z=481.1; Found: 481.2.

Step 2: N-(1-cyanocyclopropyl)-9-(5-(difluoromethyl)-1,3,4-thiadiazol-2-yl)-4-(4-hydroxy-4-(trifluoromethyl) piperidin-1-yl)-9H-pyrimido [4,5-b]indole-7-sulfonamide This compound was prepared using procedures analogous to this described for Example 44 Step 2 using N-(1-cyanocyclopropyl)-4-(4-hydroxy-4-(trifluoromethyl)piperidin-1-yl)-9H-pyrimido[4,5-b]indole-7-sulfonamide and 2-bromo-5-(difluoromethyl)-1,3,4-thiadiazole to afford the title product as white solid. $^1$H NMR: (400 MHz, DMSO-$d_6$) δ 9.48 (s, 1H), 9.40 (s, 1H), 8.82 (s, 1H), 8.14-8.12 (m, 1H), 8.07-8.05 (m, 1H), 7.68 (t, J=53.2 Hz, 1H), 6.29 (s, 1H), 4.29 (d, J=12.8 Hz, 2H), 3.60-3.54 (m, 2H), 1.96-1.85 (m, 4H), 1.44-1.42 (m, 2H), 1.29-1.27 (m, 2H). LCMS calc. for $C_{23}H_{20}F_5N_8O_3S_2$ $[M+H]^+$: m/z=615.1; Found: 615.1.

Example 192: (R)—N-(1-Cyanocyclopropyl)-9-(5-(difluoromethyl)-1,3,4-thiadiazol-2-yl)-4-(hexahydropyrazino[2,1-c][1,4]oxazin-8(1H)-yl)-2-methyl-9H-pyrimido[4,5-b]indole-7-sulfonamide

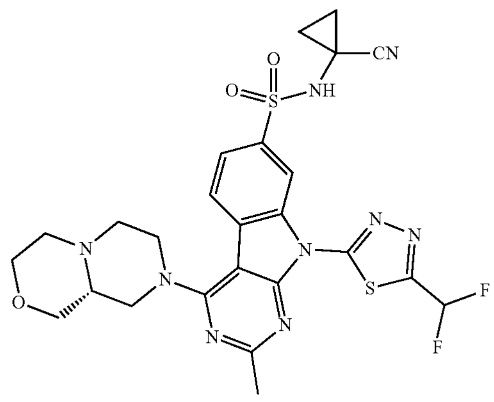

Step 1: N-(1-cyanocyclopropyl)-2-methyl-4-oxo-4,9-dihydro-3H-pyrimido[4,5-b]indole-7-sulfonamide

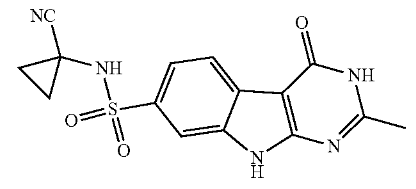 [SMILES: Cc1nc2[nH]c3cc(S(=O)(=O)NC4(C#N)CC4)ccc3c2c(=O)[nH]1]

A mixture of 2-amino-6-(N-(1-cyanocyclopropyl)sulfamoyl)-1H-indole-3-carboxamide (400 mg, 1.25 mmol, Intermediate 1 Step 2) and p-toluenesulfonic acid (108 mg, 0.63 mmol) in triethyl orthoformate (10 mL) was stirred at 90° C. for 72 h. The reaction solution was cooled and filtered. The filter cake was collected and purified by prep-TLC (MeOH/DCM=10/1) to afford the title compound (250 mg, 58.1% yield) as brown solid. LCMS calc. for $C_{15}H_{14}N_5O_3S$ $[M+H]^+$: m/z=344.1; Found: 344.1.

Step 2: 4-chloro-N-(1-cyanocyclopropyl)-2-methyl-9H-pyrimido[4,5-b]indole-7-sulfonamide

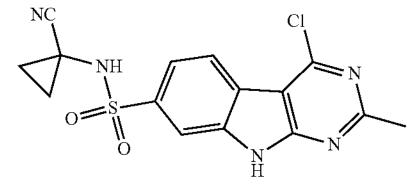 [SMILES: Cc1nc(Cl)c2c(n1)[nH]c1cc(S(=O)(=O)NC3(C#N)CC3)ccc12]

A mixture of N-(1-cyanocyclopropyl)-2-methyl-4-oxo-4,9-dihydro-3H-pyrimido[4,5-b]indole-7-sulfonamide (250 mg, 0.73 mmol) in $POCl_3$ (1 mL) and MeCN (3 mL) was stirred under reflux for 15 h. The reaction mixture was concentrated under reduced pressure. The crude product was slurried in MTBE (5 mL) at r.t. to afford the title compound (170 mg, 64.8% yield) as brown solid. LCMS calc. for $C_{15}H_{13}ClN_5O_2S$ $[M+H]^+$: m/z=362.0; Found: 362.1.

Step 3: (R)—N-(1-cyanocyclopropyl)-4-(hexahydropyrazino[2,1-c][1,4]oxazin-8(1H)-yl)-2-methyl-9H-pyrimido[4,5-b]indole-7-sulfonamide

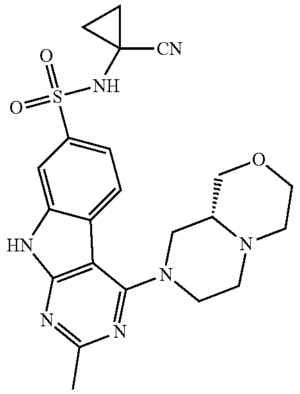 [SMILES: Cc1nc(N2CCN3CCOC[C@H]3C2)c2c(n1)[nH]c1cc(S(=O)(=O)NC3(C#N)CC3)ccc12]

A mixture of 4-chloro-N-(1-cyanocyclopropyl)-2-methyl-9H-pyrimido[4,5-b]indole-7-sulfonamide (120 mg, 0.33 mmol), (R)-octahydropyrazino[2,1-c][1,4]oxazine (71 mg, 0.50 mmol) and TEA (101 mg, 1.0 mmol) in MeCN (10 mL) was stirred at 75° C. for 12 h. The reaction mixture was concentrated under reduced pressure. The crude product was purified by prep-TLC eluting with (MeOH/DCM=1:10) to afford the title compound (45 mg, 29.0% yield). LCMS calc. for $C_{22}H_{26}N_7O_3S$ $[M+H]^+$: m/z=468.2; Found: 468.2.

Step 4: (R)—N-(1-cyanocyclopropyl)-9-(5-(difluoromethyl)-1,3,4-thiadiazol-2-yl)-4-(hexahydropyrazino[2,1-c][1,4]oxazin-8(1H)-yl)-2-methyl-9H-pyrimido[4,5-b]indole-7-sulfonamide This compound was prepared using procedures analogous to this described for Example 165 Step 2 using (R)—N-(1-cyanocyclopropyl)-4-(hexahydropyrazino[2,1-c][1,4]oxazin-8(1H)-yl)-2-methyl-9H-pyrimido[4,5-b]indole-7-sulfonamide and 2-bromo-5-(difluoromethyl)-1,3,4-thiadiazole to afford the desired product as white solid. LCMS calc. for $C_{25}H_{26}F_2N_9O_3S_2$ $[M+H]^+$: m/z=602.2; Found: 602.2.

Example 193: N-(1-Cyanocyclopropyl)-9-(5-(difluoromethyl)-1,3,4-thiadiazol-2-yl)-4-((2R,5S)-2,4,5-trimethylpiperazin-1-yl)-9H-pyrimido[4,5-b]indole-7-sulfonamide

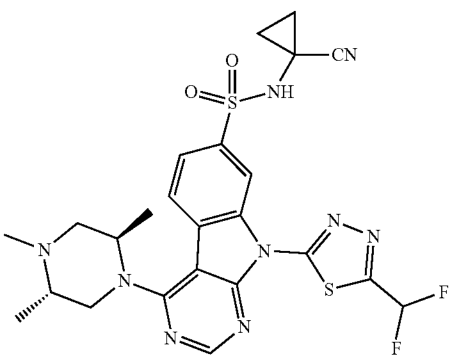 [SMILES: C[C@@H]1CN(C)[C@@H](C)CN1c1ncnc2c1c1ccc(S(=O)(=O)NC3(C#N)CC3)cc1n2-c1nnc(C(F)F)s1]

Step 1: tert-butyl (2S,5R)-4-(7-(N-(1-cyanocyclopropyl)sulfamoyl)-9H-pyrimido[4,5-b]indol-4-yl)-2,5-dimethylpiperazine-1-carboxylate

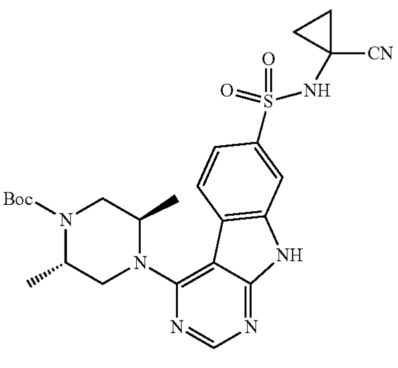 [SMILES: C[C@@H]1CN(C(=O)OC(C)(C)C)[C@@H](C)CN1c1ncnc2[nH]c3cc(S(=O)(=O)NC4(C#N)CC4)ccc3c12]

This compound was prepared using procedures analogous to this described for Example 160 Step 1 using 4-chloro-N-(1-cyanocyclopropyl)-9H-pyrimido[4,5-b]indole-7-sulfonamide (Intermediate 1) and tert-butyl (2S,5R)-2,5-dimethylpiperazine-1-carboxylate to afford the title product. LCMS calc. for $C_{25}H_{32}N_7O_4S$ [M+H]$^+$: m/z=526.2; Found: 526.3.

Step 2: tert-butyl (2S,5R)-4-(7-(N-(1-cyanocyclopropyl)sulfamoyl)-9-(5-(difluoromethyl)-1,3,4-thiadiazol-2-yl)-9H-pyrimido[4,5-b]indol-4-yl)-2,5-dimethylpiperazine-1-carboxylate

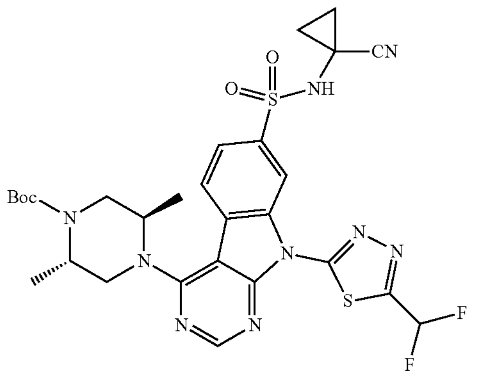 [SMILES: C[C@@H]1CN(C(=O)OC(C)(C)C)[C@@H](C)CN1c1ncnc2c1c1ccc(S(=O)(=O)NC3(C#N)CC3)cc1n2-c1nnc(C(F)F)s1]

This compound was prepared using procedures analogous to this described for Example 74 Step 2 using tert-butyl (2S,5R)-4-(7-(N-(1-cyanocyclopropyl)sulfamoyl)-9H-pyrimido[4,5-b]indol-4-yl)-2,5-dimethylpiperazine-1-carboxylate and 2-bromo-5-(difluoromethyl)-1,3,4-thiadiazole to afford the title product as white solid. LCMS calc. for $C_{28}H_{32}F_2N_9O_4S_2$ [M+H]$^+$: m/z=660.2; Found: 660.1.

Step 3: N-(1-cyanocyclopropyl)-9-(5-(difluoromethyl)-1,3,4-thiadiazol-2-yl)-4-((2R,5S)-2,5-dimethylpiperazin-1-yl)-9H-pyrimido[4,5-b]indole-7-sulfonamide

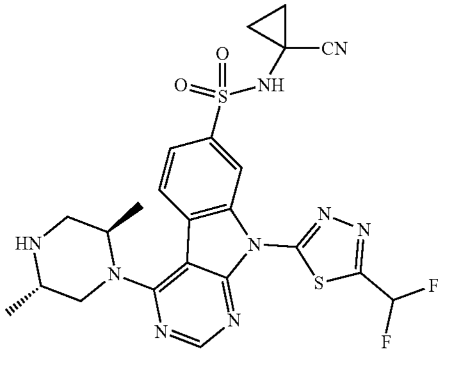 [SMILES: C[C@@H]1CN[C@@H](C)CN1c1ncnc2c1c1ccc(S(=O)(=O)NC3(C#N)CC3)cc1n2-c1nnc(C(F)F)s1]

This compound was prepared using procedures analogous to this described for Example 74 Step 3 using tert-butyl (2S,5R)-4-(7-(N-(1-cyanocyclopropyl)sulfamoyl)-9-(5-(difluoromethyl)-1,3,4-thiadiazol-2-yl)-9H-pyrimido[4,5-b]indol-4-yl)-2,5-dimethylpiperazine-1-carboxylate. LCMS calc. for $C_{23}H_{24}F_2N_9O_2S_2$ [M+H]$^+$: m/z=560.1; Found: 560.1.

Step 4: N-(1-cyanocyclopropyl)-9-(5-(difluoromethyl)-1,3,4-thiadiazol-2-yl)-4-((2R,5S)-2,4,5-trimethylpiperazin-1-yl)-9H-pyrimido[4,5-b]indole-7-sulfonamide To a solution of N-(1-cyanocyclopropyl)-9-(5-(difluoromethyl)-1,3,4-thiadiazol-2-yl)-4-((2R,5S)-2,5-dimethylpiperazin-1-yl)-9H-pyrimido[4,5-b]indole-7-sulfonamide (45 mg, 0.08 mmol), formaldehyde (3 mg, 0.10 mmol) and acetic acid (5.7 mg, 0.10 mmol) in THF/MeOH (8:1, 0.4 mL) was added sodium triacetoxyborohydride (20.2 mg, 0.10 mmol). The reaction mixture was stirred at r.t. for 3 h. The reaction mixture was poured into water (30 mL), and extracted with ethyl acetate (5 mL×3). The combined organic layers were washed with brine, dried over anhydrous $Na_2SO_4$, filtered and concentrated under reduced pressure. The crude product was purified by prep-HPLC eluting with $MeCN/H_2O$ (10-80% with 10 mM $NH_4HCO_3$) to afford the desired product (20 mg, 26% yield over two steps). $^1H$ NMR: (400 MHz, DMSO-$d_6$) δ 9.49 (d, J=1.2 Hz, 1H), 9.41 (s, 1H), 8.89 (s, 1H), 8.13-8.07 (m, 2H), 7.69 (t, J=53.2 Hz, 1H), 4.47-4.45 (m, 1H), 3.85-3.81 (m, 1H), 3.35-3.32 (m, 1H), 3.01-2.97 (m, 1H), 2.86-2.83 (m, 1H), 2.39 (dd, J=11.7, 5.5 Hz, 1H), 2.28 (s, 3H), 1.45-1.42 (m, 2H), 1.35-1.30 (m, 3H), 1.29-1.23 (m, 2H), 0.84 (d, J=6.4 Hz, 3H). LCMS calc. for $C_{24}H_{26}F_2N_9O_2S_2$ [M+H]$^+$: m/z=574.2; Found: 574.1.

Example 194: 4-(9-(5-(Difluoromethyl)-1,3,4-thiadiazol-2-yl)-7-(N-(1-methylcyclopropyl)sulfamoyl)-9H-pyrido[2,3-b]indol-4-yl)-N,N-dimethyl-3,6-dihydropyridine-1(2H)-carboxamide

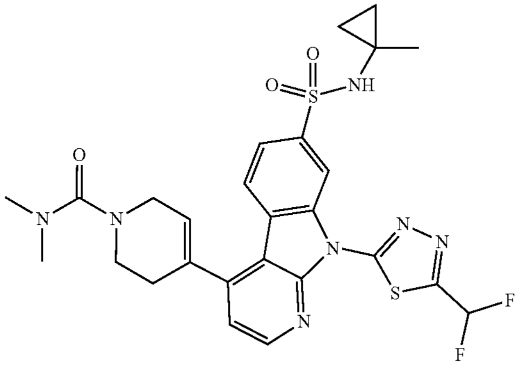 [SMILES: CN(C)C(=O)N1CC=C(c2ccnc3c2c2ccc(S(=O)(=O)NC4(C)CC4)cc2n3-c2nnc(C(F)F)s2)CC1]

Step 1: tert-butyl 4-(7-(N-(1-methylcyclopropyl)sulfamoyl)-9H-pyrido[2,3-b]indol-4-yl)-3,6-dihydropyridine-1(2H)-carboxylate

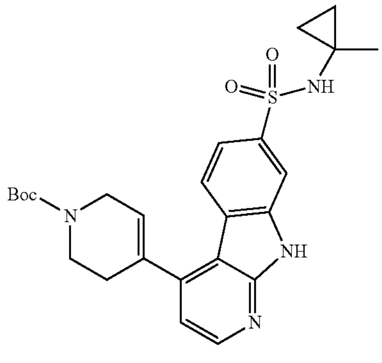 [SMILES: CC1(NS(=O)(=O)c2ccc3c(c2)[nH]c2nccc(C4=CCN(C(=O)OC(C)(C)C)CC4)c23)CC1]

This compound was prepared using procedures analogous to this described for Example 84 Step 1 using 4-bromo-N-(1-methylcyclopropyl)-9H-pyrido[2,3-b]indole-7-sulfonamide (Intermediate 6) and tert-butyl 4-(4,4,5,5-tetramethyl-1,2-oxaborolan-2-yl)-3,6-dihydropyridine-1(2H)-carboxylate to afford the title product as white solid. $^1$H NMR: (400 MHz, DMSO-$d_6$) δ 12.3 (s, 1H), 8.46 (d, J=4.8 Hz, 1H), 8.09-8.14 (m, 2H), 7.95 (d, J=1.6 Hz, 1H), 7.58 (dd, J=8.4, 1.6 Hz, 1H), 7.10 (d, J=5.2 Hz, 1H), 6.11 (s, 1H), 4.12 (s, 2H), 3.73 (t, J=5.2 Hz, 2H), 2.54 (s, 2H), 1.48 (s, 9H), 1.04 (s, 3H), 0.61-0.58 (m, 2H), 0.37-0.34 (m, 2H). LCMS calc. for $C_{25}H_{31}N_4O_4S$ $[M+H]^+$: m/z=483.2; Found: 483.3.

Step 2: N-(1-methylcyclopropyl)-4-(1,2,3,6-tetrahydropyridin-4-yl)-9H-pyrido[2,3-b]indole-7-sulfonamide (HCl)

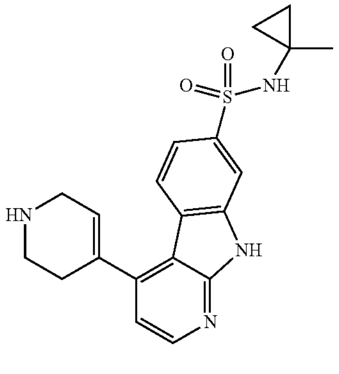 [SMILES: CC1(NS(=O)(=O)c2ccc3c(c2)[nH]c2nccc(C4=CCNCC4)c23)CC1]

To a solution of tert-butyl 4-(7-(N-(1-methylcyclopropyl)sulfamoyl)-9H-pyrido[2,3-b]indol-4-yl)-3,6-dihydropyridine-1(2H)-carboxylate (300 mg, 0.622 mmol) in MeOH (3 mL) was added HCl/MeOH (4 M, 2 mL). The reaction mixture was stirred at 20° C. overnight. The mixture was concentrated under reduced pressure to afford the title compound (220 mg, 84.5% yield, HCl salt) as a white solid. LCMS calc. for $C_{20}H_{23}N_4O_2S$ $[M+H]^+$: m/z=383.2; Found: 383.1.

Step 3: N,N-dimethyl-4-(7-(N-(1-methylcyclopropyl)sulfamoyl)-9H-pyrido[2,3-b]indol-4-yl)-3,6-dihydropyridine-1(2H)-carboxamide

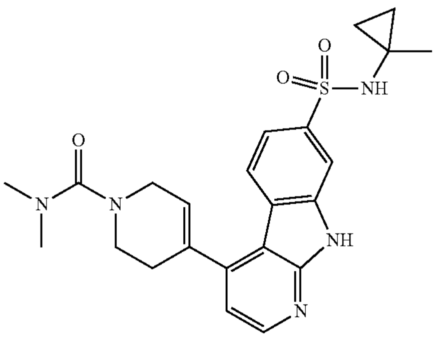

To a mixture of N-(1-methylcyclopropyl)-4-(1,2,3,6-tetrahydropyridin-4-yl)-9H-pyrido[2,3-b]indole-7-sulfonamide HCl salt (220 mg, 0.525 mmol) and dimethylcarbamic chloride (28.2 mg, 0.263 mmol) in ACN (2 mL) was added TEA (106 mg, 1.05 mmol) at 20° C.

The mixture was stirred at 20° C. overnight. The reaction mixture was quenched with $H_2O$ (20 mL) at 0-5° C., and extracted with EtOAc. The combined organic layers were washed with brine, dried over anhydrous $Na_2SO_4$, filtered and concentrated under reduced pressure. The residue was purified by flash chromatography on a silica gel column eluting with MeOH/DCM (0-10%) to afford the title compound (160 mg, 67.2% yield) as light yellow solid. $^1$H NMR: (400 MHz, DMSO-$d_6$) δ 12.3 (s, 1H), 8.46 (d, J=4.8 Hz, 1H), 8.16 (d, J=8.4 Hz, 1H), 8.09 (s, 1H), 7.95 (s, 1H), 7.58 (dd, J=8.4, 1.6 Hz, 1H), 7.09 (d, J=8.0 Hz, 1H), 6.10 (s, 1H), 3.98 (d, J=2.4 Hz, 2H), 3.53 (t, J=5.2 Hz, 2H), 2.84 (s, 6H), 2.58 (s, 2H), 1.04 (s, 3H), 0.63-0.58 (m, 2H), 0.37-0.34 (m, 2H). LCMS calc. for $C_{23}H_{28}N_5O_3S$ $[M+H]^+$: m/z=454.2; Found: 454.2.

Step 4: 4-(9-(5-(difluoromethyl)-1,3,4-thiadiazol-2-yl)-7-(N-(1-methylcyclopropyl)sulfamoyl)-9H-pyrido[2,3-b]indol-4-yl)-N,N-dimethyl-3,6-dihydropyridine-1(2H)-carboxamide This compound was prepared using procedures analogous to this described for Example 44 Step 2 using N,N-dimethyl-4-(7-(N-(1-methylcyclopropyl)sulfamoyl)-9H-pyrido[2,3-b]indol-4-yl)-3,6-dihydropyridine-1(2H)-carboxamide and 2-bromo-5-(difluoromethyl)-1,3,4-thiadiazole to afford the title product as brown solid. $^1$H NMR: (400 MHz, DMSO-$d_6$) δ 9.51 (s, 1H), 8.72 (d, J=5.2 Hz, 1H), 8.38-8.33 (m, 2H), 7.93-7.91 (m, 1H), 7.68 (t, J=53.2 Hz, 1H), 7.48 (d, J=5.2 Hz, 1H), 6.19 (s, 1H), 4.01 (d, J=2.8 Hz, 2H), 3.57 (t, J=5.6 Hz, 2H), 2.85 (s, 6H), 2.62 (s, 2H), 1.11 (d, J=6.0 Hz, 3H), 0.67-0.64 (m, 2H), 0.43-0.40 (m, 2H). LCMS calc. for $C_{26}H_{28}F_2N_7O_3S_2$ $[M+H]^+$: m/z=588.2; Found: 588.2.

Example 195: 4-(9-(5-(Difluoromethyl)-1,3,4-thiadiazol-2-yl)-7-(N-(1-methylcyclopropyl)sulfamoyl)-9H-pyrido[2,3-b]indol-4-yl)-N,N-dimethylpiperidine-1-carboxamide

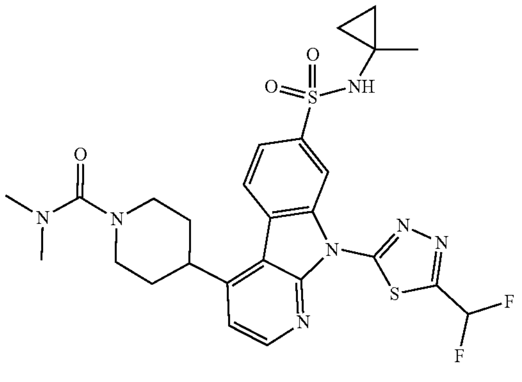 [SMILES: CN(C)C(=O)N1CCC(c2ccnc3c2c2ccc(S(=O)(=O)NC4(C)CC4)cc2n3-c2nnc(C(F)F)s2)CC1]

Step 1: N,N-dimethyl-4-(7-(N-(1-methylcyclopropyl)sulfamoyl)-9H-pyrido[2,3-b]indol-4-yl)piperidine-1-carboxamide

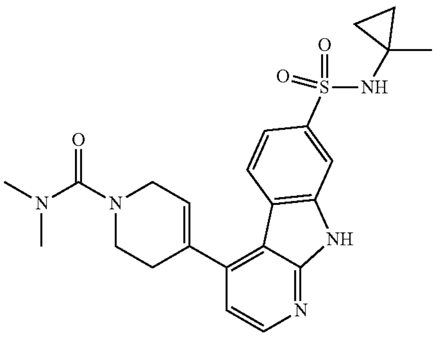

A solution of N,N-dimethyl-4-(7-(N-(1-methylcyclopropyl)sulfamoyl)-9H-pyrido[2,3-b]indol-4-yl)-3,6-dihydropyridine-1(2H)-carboxamide (60 mg, 0.132 mmol, Example 184 Step 3) in THF (15 mL) was added to Pd/C (300 mg, 5% wet) at 20° C. under Ar. The mixture was degassed and purged with $H_2$ for 3 cycles. The mixture was stirred at 30° C. overnight under $H_2$. The mixture was filtered, and the filter cake was washed with THF (50 mL×2). The combined filtrate was concentrated under reduced pressure. The residue was purified by flash chromatography on a silica gel column eluting with MeOH/DCM (0-30%) to afford the title compound (45 mg, 74.7% yield) as white solid. $^1H$ NMR: (400 MHz, DMSO-$d_6$) δ 12.3 (s, 1H), 8.46 (d, J=4.8 Hz, 1H), 8.32 (d, J=8.0 Hz, 1H), 8.11 (s, 1H), 7.97 (s, 1H), 7.66 (dd, J=8.4, 1.6 Hz, 1H), 7.19 (d, J=5.2 Hz, 1H), 3.77-3.70 (m, 3H), 3.11 (t, J=12 Hz, 2H), 2.79 (s, 6H), 1.98 (d, J=12.0 Hz, 2H), 1.82-1.76 (m, 2H), 1.04 (s, 3H), 0.62-0.59 (m, 2H), 0.37-0.34 (m, 2H). LCMS calc. for $C_{23}H_{30}N_5O_3S$ $[M+H]^+$: m/z=456.2; Found: 456.2.

Step 2: 4-(9-(5-(difluoromethyl)-1,3,4-thiadiazol-2-yl)-7-(N-(1-methylcyclopropyl)sulfamoyl)-9H-pyrido[2,3-b]indol-4-yl)-N,N-dimethylpiperidine-1-carboxamide This compound was prepared using procedures analogous to this described for Example 44 Step 2 using N,N-dimethyl-4-(7-(N-(1-methylcyclopropyl)sulfamoyl)-9H-pyrido[2,3-b]indol-4-yl)piperidine-1-carboxamide and 2-bromo-5-(difluoromethyl)-1,3,4-thiadiazole to afford the title product as off-white solid. $^1H$ NMR: (400 MHz, DMSO-$d_6$) δ 9.55 (s, 1H), 8.72 (d, J=5.2 Hz, 1H), 8.54 (d, J=8.8 Hz, 1H), 8.40 (s, 1H), 8.00 (d, J=7.2 Hz, 1H), 7.68 (t, J=53.2 Hz, 1H), 7.59 (d, J=5.2 Hz, 1H), 3.81-3.46 (m, 3H), 3.15 (t, J=12.0 Hz, 2H), 2.80 (s, 6H), 2.01-1.87 (m, 2H), 1.85-1.79 (m, 2H), 1.11 (s, 3H), 0.67-0.65 (m, 2H), 0.42-0.39 (m, 2H). LCMS calc. for $C_{26}H_{30}F_2N_7O_3S_2[M+H]^+$: m/z=590.2; Found: 590.2.

Example 196: N-(1-Cyanocyclopropyl)-9-(5-(difluoromethyl)-1,3,4-thiadiazol-2-yl)-4-(1-isobutyryl-1,2,3,6-tetrahydropyridin-4-yl)-9H-pyrido[2,3-b]indole-7-sulfonamide

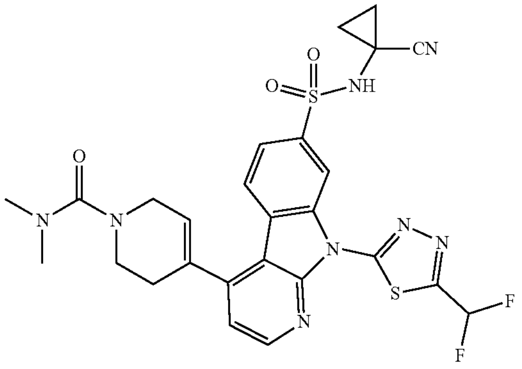 [SMILES: CN(C)C(=O)N1CC=C(c2ccnc3c2c2ccc(S(=O)(=O)NC4(C#N)CC4)cc2n3-c2nnc(C(F)F)s2)CC1]

Step 1: N-(1-cyanocyclopropyl)-4-(1-isobutyryl-1,2,3,6-tetrahydropyridin-4-yl)-9H-pyrido[2,3-b]indole-7-sulfonamide

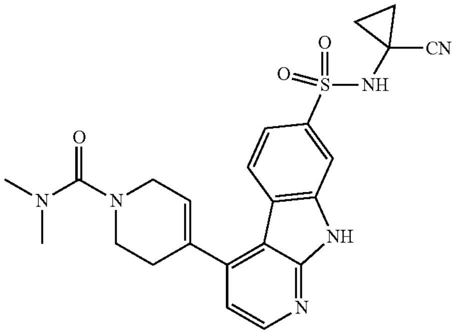

This compound was prepared using procedures analogous to this described for Example 84 Step 1 using 4-bromo-N-(1-cyanocyclopropyl)-9H-pyrido[2,3-b]indole-7-sulfonamide (Intermediate 5) and 2-methyl-1-[4-(4,4,5,5-tetramethyl-1,3,2-dioxaborolan-2-yl)-3,6-dihydro-2H-pyridin-1-yl]propan-1-one (Example 91 Step 3) to afford the title product as off-white solid. $^1H$ NMR: (400 MHz, DMSO-$d_6$) δ 12.4 (s, 1H), 9.14 (s, 1H), 8.49 (d, J=8.0 Hz, 1H), 8.20 (t, J=8.0 Hz, 1H), 8.00 (s, 1H), 7.62 (d, J=8.0 Hz, 1H), 7.12 (d, J=4.0 Hz, 1H), 6.14 (s, 1H), 4.31 (d, J=49.2 Hz, 2H), 3.90-3.87 (m, 2H), 3.04-2.99 (m, 1H), 2.56 (d, J=44.0 Hz, 2H), 1.42-1.38 (m, 2H), 1.25-1.22 (m, 2H), 1.09 (d, J=6.4 Hz, 6H). LCMS calc. for $C_{24}H_{26}N_5O_3S$ $[M+H]^+$: m/z=464.2; Found: 464.2.

Step 2: N-(1-cyanocyclopropyl)-9-(5-(difluoromethyl)-1,3,4-thiadiazol-2-yl)-4-(1-isobutyryl-1,2,3,6-tetrahydropyridin-4-yl)-9H-pyrido[2,3-b]indole-7-sulfonamide This compound was prepared using procedures analogous to this described for Example 74 Step 2 using N-(1-cyanocyclopropyl)-4-[1-(2-methylpropanoyl)-3,6-dihydro-2H-pyridin-4-yl]-9H-pyrido[2,3-b]indole-7-sulfonamide and 2-bromo-5-(difluoromethyl)-1,3,4-thiadiazole to afford the title product as light yellow solid. $^{1}$H NMR: (400 MHz, DMSO-$d_6$) δ 9.56 (s, 1H), 9.43 (s, 1H), 8.75 (d, J=4.0 Hz, 1H), 8.39 (d, J=4.0 Hz, 1H), 7.97 (d, J=12.0 Hz, 1H), 7.69 (t, J=53.2 Hz, 1H), 7.52 (d, J=4.0 Hz, 1H), 6.22 (s, 1H), 4.41-4.29 (m, 2H), 3.94-3.91 (m, 2H), 3.04-3.00 (m, 1H), 2.63-2.50 (m, 2H), 1.42-1.40 (m, 2H), 1.26-1.24 (m, 2H), 1.10 (d, J=6.4 Hz, 6H). LCMS calc. for $C_{27}H_{26}F_2N_7O_3S_2$ $[M+H]^+$: m/z=598.2; Found: 598.2.

Example 197: N-(1-Cyanocyclopropyl)-9-(5-(difluoromethyl)-1,3,4-thiadiazol-2-yl)-4-(1-isobutyrylpiperidin-4-yl)-9H-pyrido[2,3-b]indole-7-sulfonamide

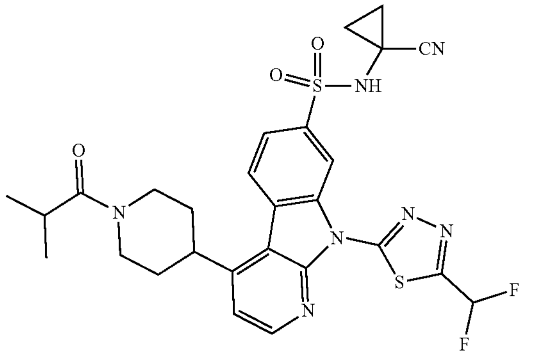 [SMILES: CC(C)C(=O)N1CCC(c2ccnc3c2c2ccc(S(=O)(=O)NC4(C#N)CC4)cc2n3-c2nnc(C(F)F)s2)CC1]

Step 1: N-(1-cyanocyclopropyl)-4-(1-isobutyrylpiperidin-4-yl)-9H-pyrido[2,3-b]indole-7-sulfonamide

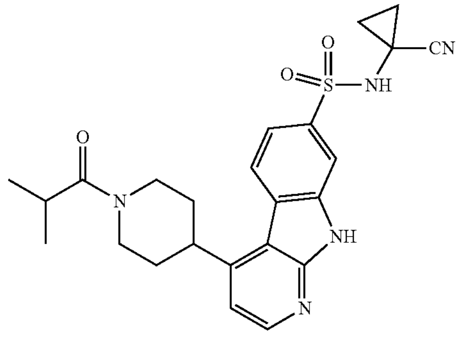 [SMILES: CC(C)C(=O)N1CCC(c2ccnc3[nH]c4cc(S(=O)(=O)NC5(C#N)CC5)ccc4c23)CC1]

This compound was prepared using procedures analogous to this described for Example 185 Step 1 using N-(1-cyanocyclopropyl)-4-(1-isobutyryl-1,2,3,6-tetrahydropyridin-4-yl)-9H-pyrido[2,3-b]indole-7-sulfonamide (Example 186 Step 1) to afford the title product as white solid. LCMS calc. for $C_{24}H_{28}N_5O_3S$ $[M+H]^+$: m/z=466.2; Found: 466.1.

Step 2: N-(1-cyanocyclopropyl)-9-(5-(difluoromethyl)-1,3,4-thiadiazol-2-yl)-4-(1-isobutyrylpiperidin-4-yl)-9H-pyrido[2,3-b]indole-7-sulfonamide This compound was prepared using procedures analogous to this described for Example 44 Step 2 using N-(1-cyanocyclopropyl)-4-(1-isobutyrylpiperidin-4-yl)-9H-pyrido[2,3-b]indole-7-sulfonamide and 2-bromo-5-(difluoromethyl)-1,3,4-thiadiazole to afford the title product as light yellow solid. $^{1}$H NMR: (400 MHz, DMSO-$d_6$) δ 9.61 (s, 1H), 9.38 (s, 1H), 8.74 (d, J=4.0 Hz, 1H), 8.63 (d, J=4.0 Hz, 1H), 8.07-8.04 (m, 1H), 7.69 (t, J=53.2 Hz, 1H), 7.61 (d, J=5.2 Hz, 1H), 4.69 (d, J=12.0 Hz, 1H), 4.20 (d, J=12.4 Hz, 1H), 3.92 (t, J=12.0 Hz, 1H), 3.48 (t, J=12.0 Hz, 1H), 3.00-2.93 (m, 2H), 2.10-2.07 (m, 2H), 1.82-1.65 (m, 2H), 1.46-1.43 (m, 2H), 1.31-1.29 (m, 2H), 1.08-1.05 (m, 6H). LCMS calc. for $C_{27}H_{28}F_2N_7O_3S_2$ $[M+H]^+$: m/z=600.2; Found: 600.2.

Example 198: N-(1-Cyanocyclopropyl)-9-(5-(difluoromethyl)-1,3,4-thiadiazol-2-yl)-4-(4-methylpiperazin-1-yl)-9H-pyrido[2,3-b]indole-7-sulfonamide

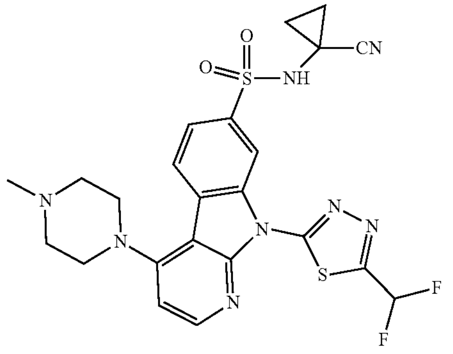 [SMILES: CN1CCN(c2ccnc3c2c2ccc(S(=O)(=O)NC4(C#N)CC4)cc2n3-c2nnc(C(F)F)s2)CC1]

Step 1: N-(1-cyanocyclopropyl)-4-(4-methylpiperazin-1-yl)-9H-pyrido[2,3-b]indole-7-sulfonamide

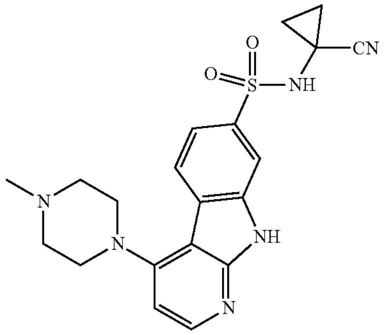 [SMILES: CN1CCN(c2ccnc3[nH]c4cc(S(=O)(=O)NC5(C#N)CC5)ccc4c23)CC1]

To a solution of 4-bromo-N-(1-cyanocyclopropyl)-9H-pyrido[2,3-b]indole-7-sulfonamide (250 mg, 0.639 mmol, Intermediate 5) and 1-methylpiperazine (102 mg, 1.02 mmol) in dioxane (5 mL) was added t-BuXPhosPdG3 (40.6 mg, 0.05 mmol) and $Cs_2CO_3$ (333 mg, 1.02 mmol) at 20° C. under $N_2$. The mixture was degassed and recharged with $N_2$ for three cycles, and stirred at 120° C. for 12 h. The reaction solution was cooled to r.t., diluted with MeOH (2 mL) and then filtered with diatomite. The filtrate was concentrated under reduced pressure. The residue was purified by prep-HPLC on a C18 column eluting with ACN/water (25%-55%, 0.1% TFA)) to afford the title product (68.0 mg, 21.0% yield, TFA salt) as white solid. $^{1}$H NMR: (400 MHz, DMSO-$d_6$) δ 12.4 (s, 1H), 9.84 (s, 1H), 9.16 (s, 1H), 8.44 (d, J=4.0 Hz, 1H), 8.05-8.00 (m, 2H), 7.72 (d, J=8.0 Hz, 1H), 6.97 (d, J=4.0 Hz, 1H), 3.90-3.65 (m, 6H), 3.32-3.22 (m, 2H), 2.97 (s, 3H), 1.36-1.34 (m, 2H), 1.29-1.25 (m, 2H). LCMS calc. for $C_{20}H_{23}N_6O_2S$ $[M+H]^+$: m/z=411.2; Found: 411.1.

Step 2: N-(1-cyanocyclopropyl)-9-(5-(difluoromethyl)-1,3,4-thiadiazol-2-yl)-4-(4-methylpiperazin-1-yl)-9H-pyrido[2,3-b]indole-7-sulfonamide This compound was prepared using procedures analogous to this described for Example 44 Step 2 using N-(1-cyanocyclopropyl)-4-(4-methylpiperazin-1-yl)-9H-pyrido[2,3-b]indole-7-sulfonamide and 2-bromo-5-(difluoromethyl)-1,3,4-thiadiazole to afford the title product as yellow solid. $^1$H NMR: (400 MHz, DMSO-$d_6$) δ 10.3-10.2 (m, 1H), 9.17 (d, J=8.0 Hz, 1H), 9.07 (s, 1H), 8.17 (s, 1H), 7.95 (d, J=8.0 Hz, 1H), 7.72 (d, J=8.4 Hz, 1H), 7.68 (t, J=53.2 Hz, 1H), 7.20 (d, J=8.0 Hz, 1H), 4.40-4.01 (m, 2H), 3.72-3.71 (m, 2H), 3.49-3.14 (m, 4H), 2.93 (s, 3H), 1.40-1.37 (m, 2H), 1.30-1.23 (m, 2H). LCMS calc. for $C_{23}H_{23}F_2N_8O_2S_2$ $[M+H]^+$: m/z=545.1; Found: 545.1.

Example 199: (R)—N-(1-Cyanocyclopropyl)-9-(5-(difluoromethyl)-1,3,4-thiadiazol-2-yl)-4-(3-methylmorpholino)-9H-pyrimido[4,5-b]indole-7-sulfonamide

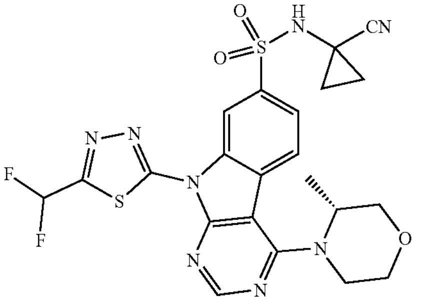 [SMILES: C[C@@H]1COCCN1c1ncnc2c1c1ccc(S(=O)(=O)NC3(C#N)CC3)cc1n2-c1nnc(C(F)F)s1]

Step 1: (R)—N-(1-cyanocyclopropyl)-4-(3-methylmorpholino)-9H-pyrimido[4,5-b]indole-7-sulfonamide

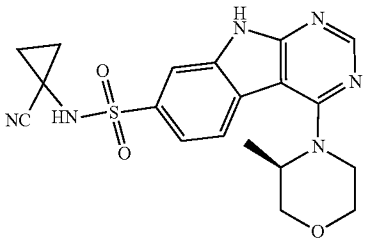 [SMILES: C[C@@H]1COCCN1c1ncnc2[nH]c3cc(S(=O)(=O)NC4(C#N)CC4)ccc3c12]

A mixture of 4-chloro-N-(1-cyanocyclopropyl)-9H-pyrimido[4,5-b]indole-7-sulfonamide (4.0 g, 11.6 mmol, Intermediate 1), (R)-3-methylmorpholine (3.55 g, 34.8 mmol) and $Et_3N$ (5.82 mg, 57.6 mmol) in DMF (40 mL) was stirred at 70° C. for 60 h. After concentrated under reduced pressure, the residue was purified by flash chromatography on a C18 column eluting with MeCN/$H_2O$ (50-75% with 0.05% TFA) to afford the title compound (3.9 g, 82% yield) as a brown solid. LCMS calc. for $C_{19}H_{21}N_6O_3S$ $[M+H]^+$: m/z=413.1; found: 413.1.

Step 2: (R)—N-(1-cyanocyclopropyl)-9-(5-(difluoromethyl)-1,3,4-thiadiazol-2-yl)-4-(3-methylmorpholino)-9H-pyrimido[4,5-b]indole-7-sulfonamide A mixture of (R)—N-(1-cyanocyclopropyl)-4-(3-methylmorpholino)-9H-pyrimido[4,5-b]indole-7-sulfonamide (3.9 g, 9.5 mmol), 2-bromo-5-(difluoromethyl)-1,3,4-thiadiazole (5.1 g, 23.7 mmol), CuI (1.45 g, 7.6 mmol), (1R,2R)—$N^1$,$N^2$-dimethylcyclohexane-1,2-diamine (2.18 g, 15.2 mmol) and CsF (5.79 g, 38.1 mmol) in dioxane (40 mL) was degassed and recharged with $N_2$ for 3 cycles. The mixture was stirred at 110° C. for 5 h. After cooled to r.t., the reaction mixture was diluted with $H_2O$ (100 mL), extracted with EA (100 mL×3). The combined organic layers were washed with brine, dried over $Na_2SO_4$, filtered and then concentrated under reduced pressure. The residue was purified by flash chromatography on a silica gel column eluting with DCM/EA (25-45%) to afford the title compound (2.1 g, 40% yield) as white solid. $^1$H NMR: (400 MHz, DMSO-$d_6$) δ 9.40 (d, J=1.2 Hz, 1H), 9.38 (s, 1H), 8.71 (s, 1H), 8.00 (dd, J=8.0 Hz, J=1.2 Hz, 1H), 7.94 (d, J=8.0 Hz, 1H), 7.67 (d, $J_{F-H}$=56.0 Hz, 1H), 4.56-4.70 (m, 1H), 4.01 (d, J=12.0 Hz, 1H), 3.75-3.90 (m, 4H), 3.63-3.70 (m, 1H), 1.40-1.50 (m, 5H), 1.25-1.30 (m, 2H). LCMS calc. for $C_{22}H_{21}F_2N_8O_3S_2$ $[M+H]^+$: m/z=547.1; Found: 547.1.

Example 200: N-(1-Cyanocyclopropyl)-9-(5-(difluoromethyl)-1,3,4-thiadiazol-2-yl)-4-((2S,5R)-2,5-dimethylmorpholino)-9H-pyrimido[4,5-b]indole-7-sulfonamide

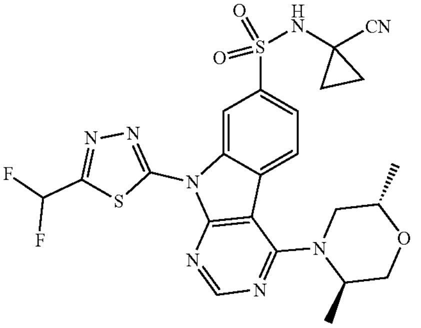 [SMILES: C[C@@H]1CO[C@@H](C)CN1c1ncnc2c1c1ccc(S(=O)(=O)NC3(C#N)CC3)cc1n2-c1nnc(C(F)F)s1]

Step 1: N-(1-cyanocyclopropyl)-4-((2S,5R)-2,5-dimethylmorpholino)-9H-pyrimido[4,5-b]indole-7-sulfonamide

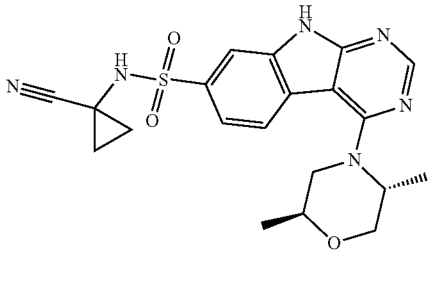 [SMILES: C[C@@H]1CO[C@@H](C)CN1c1ncnc2[nH]c3cc(S(=O)(=O)NC4(C#N)CC4)ccc3c12]

A mixture of 4-chloro-N-(1-cyanocyclopropyl)-9H-pyrimido[4,5-b]indole-7-sulfonamide (200 mg, 0.58 mmol, Intermediate 1), (2S,5R)-2,5-dimethylmorpholine (100 mg, 0.86 mmol) and TEA (291 mg, 2.9 mmol) in ACN (1.5 mL) was stirred at 80° C. for 3 days. After cooled to r.t., the mixture was filtered to afford the title compound (180 mg, 73% yield) as white solid. LCMS calc. for $C_{20}H_{23}N_6O_3S$. $[M+H]^+$: m/z=427.2; Found: 427.1.

Step 2: N-(1-cyanocyclopropyl)-9-(5-(difluoromethyl)-1,3,4-thiadiazol-2-yl)-4-((2S,5R)-2,5-dimethylmorpholino)-9H-pyrimido[4,5-b]indole-7-sulfonamide A mixture of N-(1-cyanocyclopropyl)-4-((2S,5R)-2,5-dimethylmorpholino)-9H-pyrimido[4,5-b]indole-7-sulfonamide (160 mg, 0.38 mmol), 2-bromo-5-(difluoromethyl)-1,3,4-thiadiazole (161 mg, 0.75 mmol), RuPhos Pd G3 (16 mg, 0.02 mmol) and $K_3PO_4$ (159 mg, 0.75 mmol) in dioxane (2 mL) was degassed and recharged with $N_2$ for 3 cycles. The reaction mixture was stirred at 120° C. for 12 h. under $N_2$, and then concentrated under reduced pressure. The residue was purified by flash chromatography on a silica gel column eluting with DCM/EA (0-15%) to afford a crude product which was further purified by Prep-HPLC on a C18 column eluting with MeCN/$H_2O$ (40-70%) to afford the title compound (50.1 mg, 24% yield) as yellow solid. LCMS calc. for $C_{23}H_{23}F_2N_8O_3S_2$ $[M+H]^+$: m/z=561.1; Found: 561.1.

Example 201: 4-(8-Oxa-3-azabicyclo[3.2.1]octan-3-yl)-N-(1-cyanocyclopropyl)-9-(5-(difluoromethyl)-1,3,4-thiadiazol-2-yl)-9H-pyrimido[4,5-b]indole-7-sulfonamide

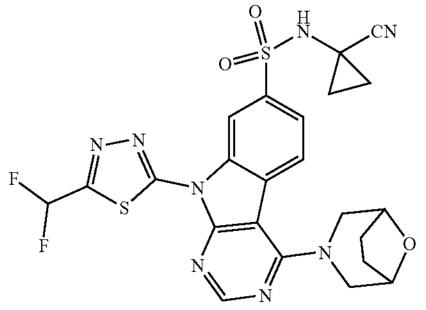 [SMILES: N#CC1(NS(=O)(=O)c2ccc3c4c(N5CC6CCC(C5)O6)ncnc4n(-c4nnc(C(F)F)s4)c3c2)CC1]

Step 1: 4-(8-oxa-3-azabicyclo[3.2.1]octan-3-yl)-N-(1-cyanocyclopropyl)-9H-pyrimido[4,5-b]indole-7-sulfonamide

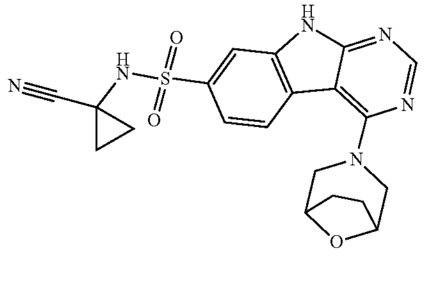 [SMILES: N#CC1(NS(=O)(=O)c2ccc3c(c2)[nH]c2ncnc(N4CC5CCC(C4)O5)c23)CC1]

This compound was prepared using procedures analogous to this described for Example 200 Step 1 using 4-chloro-N-(1-cyanocyclopropyl)-9H-pyrimido[4,5-b]indole-7-sulfonamide (Intermediate 1) and 8-oxa-3-azabicyclo[3.2.1]octane hydrochloride to afford the title product as brown solid. LCMS calc. for $C_{20}H_{21}N_6O_3S$. $[M+H]^+$: m/z=425.1; Found: 425.1.

Step 2: 4-(8-oxa-3-azabicyclo[3.2.1]octan-3-yl)-N-(1-cyanocyclopropyl)-9-(5-(difluoromethyl)-1,3,4-thiadiazol-2-yl)-9H-pyrimido[4,5-b]indole-7-sulfonamide This compound was prepared using procedures analogous to this described for Example 200 Step 2 using 4-(8-oxa-3-azabicyclo[3.2.1]octan-3-yl)-N-(1-cyanocyclopropyl)-9H-pyrimido[4,5-b]indole-7-sulfonamide and 2-bromo-5-(difluoromethyl)-1,3,4-thiadiazole to afford the title product as white solid. LCMS calc. for $C_{23}H_{21}F_2N_8O_3S_2$ $[M+H]^+$: m/z=559.1; Found: 559.1.

Example 202: 4-((1R,4R)-2-Oxa-5-azabicyclo[2.2.1]heptan-5-yl)-N-(1-cyanocyclopropyl)-9-(5-(difluoromethyl)-1,3,4-thiadiazol-2-yl)-9H-pyrimido[4,5-b]indole-7-sulfonamide

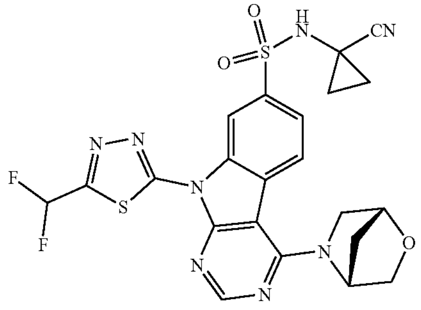 [SMILES: N#CC1(NS(=O)(=O)c2ccc3c4c(N5C[C@H]6C[C@@H]5CO6)ncnc4n(-c4nnc(C(F)F)s4)c3c2)CC1]

Step 1: 4-((1R,4R)-2-oxa-5-azabicyclo[2.2.1]heptan-5-yl)-N-(1-cyanocyclopropyl)-9H-pyrimido[4,5-b]indole-7-sulfonamide

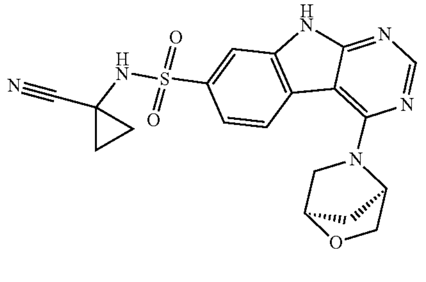 [SMILES: N#CC1(NS(=O)(=O)c2ccc3c(c2)[nH]c2ncnc(N4C[C@H]5C[C@@H]4CO5)c23)CC1]

This compound was prepared using procedures analogous to this described for Example 200 Step 1 using 4-chloro-N-(1-cyanocyclopropyl)-9H-pyrimido[4,5-b]indole-7-sulfonamide (Intermediate 1) and (1R,4R)-2-oxa-5-azabicyclo[2.2.1]heptane hydrochloride to afford the title product as brown solid. LCMS calc. for $C_{19}H_{19}N_6O_3S$. $[M+H]^+$: m/z=411.1; Found: 411.1.

Step 2: 4-((1R,4R)-2-oxa-5-azabicyclo[2.2.1]heptan-5-yl)-N-(1-cyanocyclopropyl)-9-(5-(difluoromethyl)-1,3,4-thiadiazol-2-yl)-9H-pyrimido[4,5-b]indole-7-sulfonamide This compound was prepared using procedures analogous to this described for Example 200 Step 2 using 4-((1R,4R)-2-oxa-5-azabicyclo[2.2.1]heptan-5-yl)-N-(1-cyanocyclopropyl)-9H-pyrimido[4,5-b]indole-7-sulfonamide and 2-bromo-5-(difluoromethyl)-1,3,4-thiadiazole to afford the title product as white solid. LCMS calc. for $C_{22}H_{19}F_2N_8O_3S_2$ $[M+H]^+$: m/z=545.1; Found: 545.1.

Example 203: (R)—N-(1-Cyanocyclopropyl)-9-(5-(difluoromethyl)-1,3,4-thiadiazol-2-yl)-4-(3-(fluoromethyl)-4-methylpiperazin-1-yl)-9H-pyrimido[4,5-b]indole-7-sulfonamide

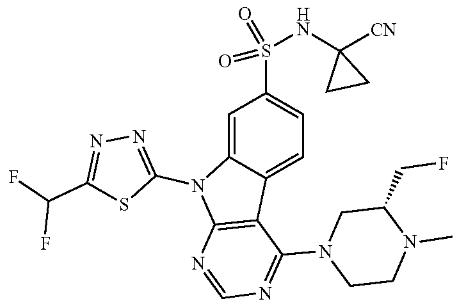

Step 1. tert-butyl (R)-3-(hydroxymethyl)-4-methylpiperazine-1-carboxylate

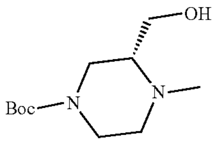 [SMILES: CN1CCN(C(=O)OC(C)(C)C)C[C@@H]1CO]

To a mixture of tert-butyl (R)-3-(hydroxymethyl)piperazine-1-carboxylate (500 mg, 2.31 mmol), sodium acetate (303 mg, 3.70 mmol) and paraformaldehyde (375 mg, 4.16 mmol) in MeOH (12 mL) was sodium cyanoborohydride (218 mg, 3.47 mmol). The mixture was stirred at r.t. for 1 h., sat. aq. $NaHCO_3$ was added. The mixture was extracted with DCM (50 mL). The organic phase was dried over anhydrous $Na_2SO_4$, filtered and concentrated under reduced pressure. The residue was purified by flash chromatography on a silica gel column eluting with DCM/MeOH (0-10%) to afford tert-butyl (R)-3-(hydroxymethyl)-4-methylpiperazine-1-carboxylate (488 mg, purity: 75%, 92% yield) as yellow oil. LCMS calc. for $C_{11}H_{23}N_2O_3$ $[M+H]^+$: m/z=231.1. Found: 231.6.

Step 2. tert-butyl (R)-3-(fluoromethyl)-4-methylpiperazine-1-carboxylate

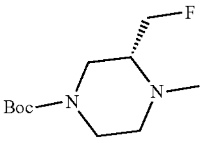 [SMILES: CN1CCN(C(=O)OC(C)(C)C)C[C@@H]1CF]

To a solution of tert-butyl (R)-3-(hydroxymethyl)-4-methylpiperazine-1-carboxylate (488 mg, 2.12 mmol) in DCM (6 mL) was added dropwise a solution of DAST (2.05 g, 12.72 mmol) in DCM (3 mL) at −65° C. under nitrogen. The mixture was stirred at ambient temperature overnight. The reaction mixture was cooled to 5° C., and cold water was added dropwise while the temperature was maintained at 10° C. The mixture was adjusted to pH 9.0 with aqueous sodium hydroxide, and extracted with DCM (30 mL×3). The combined organic layers were washed with water, dried over $Na_2SO_4$, and concentrated to afford the crude tert-butyl (R)-3-(fluoromethyl)-4-methylpiperazine-1-carboxylate (210 mg, 0.91 mmol) which was used directly in the next step without purification. LCMS calc. for $C_{11}H_{22}FN_2O_2$$[M+H]^+$: m/z=233.2. Found: 233.3.

Step 3. (R)-2-(fluoromethyl)-1-methylpiperazine

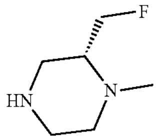

A solution of crude tert-butyl (R)-3-(fluoromethyl)-4-methylpiperazine-1-carboxylate (210 mg, 0.91 mmol) in HCl (4.0 M in dioxane, 2 mL) was stirred at r.t. for 2 h. The precipitate was filtered and washed with ethyl acetate (2 mL) to afford (R)-2-(fluoromethyl)-1-methylpiperazine (105 mg, 0.80 mmol) as HCl salt, which was used in the next step. LCMS calc. for $C_6H_{14}FN_2$ $[M+H]^+$: m/z=133.1. Found: 133.3.

Step 4. (R)—N-(1-cyanocyclopropyl)-4-(3-(fluoromethyl)-4-methylpiperazin-1-yl)-9H-pyrimido[4,5-b]indole-7-sulfonamide

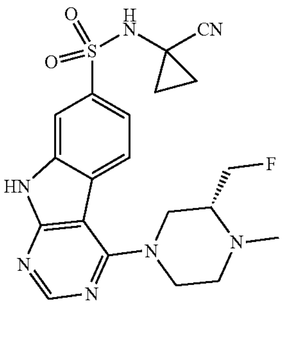 [SMILES: CN1CCN(c2ncnc3[nH]c4cc(S(=O)(=O)NC5(C#N)CC5)ccc4c23)C[C@@H]1CF]

A mixture of 4-chloro-N-(1-cyanocyclopropyl)-9H-pyrimido[4,5-b]indole-7-sulfonamide (200 mg, 0.58 mmol, Intermediate 1), (R)-2-(fluoromethyl)-1-methylpiperazine (105 mg crude, 0.80 mmol) and DIPEA (0.2 mL, 1.16 mmol) in DMF (2 mL) was stirred at 100° C. for 4 h. The mixture was concentrated. The residue was purified by prep-HPLC on a C18 column eluting with $CH_3CN/H_2O$ (45%-60% with 0.1% $NH_4HCO_3$) to give (R)—N-(1-cyanocyclopropyl)-4-(3-(fluoromethyl)-4-methylpiperazin-1-yl)-9H-pyrimido[4,5-b]indole-7-sulfonamid (170 mg, 60% purity, 43.5% yield) as yellow solid. LCMS calc. for $C_{20}H_{23}FN_7O_2S$ $[M+H]^+$: m/z=444.2, Found: 444.7.

Step 5. (R)—N-(1-cyanocyclopropyl)-9-(5-(difluoromethyl)-1,3,4-thiadiazol-2-yl)-4-(3-(fluoromethyl)-4-methylpiperazin-1-yl)-9H-pyrimido[4,5-b]indole-7-sulfonamide To a solution of (R)—N-(1-cyanocyclopropyl)-4-(3-(fluoromethyl)-4-methylpiperazin-1-yl)-9H-pyrimido[4,5-b]indole-7-sulfonamide (170 mg, 0.38 mmol, 60% purity) in DMF (2 mL) was added 2-bromo-5-(difluoromethyl)-1,3,4-thiadiazole (325 mg, 1.52 mmol) and $Cs_2CO_3$ (372 mg, 1.14 mmol). The mixture was stirred at 60° C. for 2 h. The reaction was purified by prep-HPLC on a C18 column eluting with $CH_3CN/H_2O$ (45%-60% with 0.1% $NH_4HCO_3$) to afford the product which was further purified by flash chromatography on a silica gel column eluting with DCM/MeOH (0-6%) to afford the title product (7.54 mg, 5.7% yield) as white solid. $^1H$ NMR (400 MHz, DMSO-$d_6$) δ ppm 9.49 (d, J=1.4 Hz, 1H), 9.41 (s, 1H), 8.82 (s, 1H), 8.11 (d, J=8.5 Hz, 1H), 8.04 (dd, J=8.4, 1.5 Hz, 1H), 7.68 (t, J=53.2 Hz, 1H), 4.72-4.61 (m, 1H), 4.59-4.50 (m, 1H), 4.36 (d, J=12.6 Hz, 1H), 4.17 (d, J=11.9 Hz, 1H), 3.59-3.50 (m, 2H), 2.95 (d, J=11.9 Hz, 1H), 2.59-2.54 (m, 1H), 2.40 (d, J=11.4 Hz, 1H), 2.34 (s, 3H), 1.43 (dd, J=8.3, 5.4 Hz, 2H), 1.27 (d, J=6.0 Hz, 2H). LCMS calc. for $C_{23}H_{23}F_3N_9O_2S_2$ $[M+H]^+$: m/z=578.1, Found: 577.8.

Example 204: (R)—N-(1-Cyanocyclopropyl)-9-(5-(difluoromethyl)-1,3,4-thiadiazol-2-yl)-4-(3-(methoxymethyl)-4-methylpiperazin-1-yl)-9H-pyrimido[4,5-b]indole-7-sulfonamide

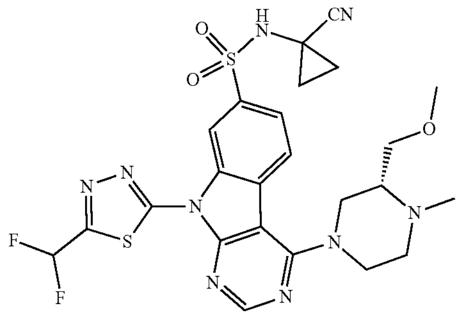

Step 1. tert-butyl (R)-3-(methoxymethyl)-4-methylpiperazine-1-carboxylate

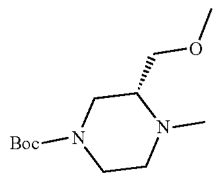 [SMILES: COC[C@H]1CN(C(=O)OC(C)(C)C)CCN1C]

tert-Butyl (R)-3-(hydroxymethyl)-4-methylpiperazine-1-carboxylate (380 mg, 1.65 mmol, Example 203 Step 1) was added to a suspension of sodium hydride (132 mg, 3.3 mmol, 60% in mineral oil) in THF (8 mL) at 0° C. under $N_2$. The mixture was stirred at 0° C. for 5 min., and iodomethane (469 mg, 3.3 mmol) was added. The reaction mixture was stirred at ambient temperature for 4 h., diluted with water (10 mL) and extracted with ethyl acetate (30 mL×3). The combined organic layers were washed with brine, dried over $Na_2SO_4$, filtered and concentrated to afford tert-butyl (R)-3-(methoxymethyl)-4-methylpiperazine-1-carboxylate (95 mg) which was used directly in the next step without further purification. LCMS calc. for $Cl_2H_{25}N_2O_3$ $[M+H]^+$: m/z=245.2; Found: 245.6.

Step 3. (R)-2-(methoxymethyl)-1-methylpiperazine

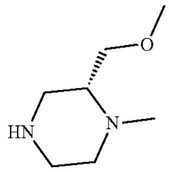

tert-Butyl (R)-3-(methoxymethyl)-4-methylpiperazine-1-carboxylate (95 mg, 0.39 mmol) was treated with HCl (2 mL, 4.0 M in dioxane) at r.t. for 2 h. The mixture was filtered and the solid was washed with ethyl acetate to afford the crude product (R)-2-(methoxymethyl)-1-methylpiperazine (60 mg) as HCl salt which was directly used in the next step. LCMS calc. for $C_7H_{17}N_2O$ $[M+H]^+$: m/z=145.1; Found: 145.4.

Step 4. (R)—N-(1-cyanocyclopropyl)-4-(3-(methoxymethyl)-4-methylpiperazin-1-yl)-9H-pyrimido[4,5-b]indole-7-sulfonamide

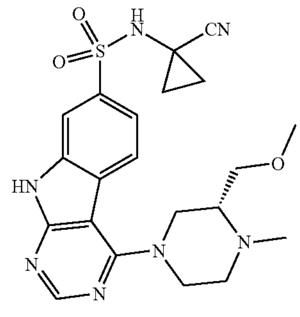 [SMILES: COC[C@H]1CN(c2ncnc3[nH]c4cc(S(=O)(=O)NC5(C#N)CC5)ccc4c23)CCN1C]

This compound was prepared using procedures analogous to this described for Example 203 Step 4 using 4-chloro-N-(1-cyanocyclopropyl)-9H-pyrimido[4,5-b]indole-7-sulfonamide (Intermediate 1) and (R)-2-(methoxymethyl)-1-methylpiperazine to afford the title product as a yellow solid. LCMS for $C_{21}H_{26}N_7O_3S$ $[M+H]^+$: m/z=456.2; Found: 456.2 Step 5. (R)—N-(1-cyanocyclopropyl)-9-(5-(difluoromethyl)-1,3,4-thiadiazol-2-yl)-4-(3-(methoxymethyl)-4-methylpiperazin-1-yl)-9H-pyrimido[4,5-b]indole-7-sulfonamide

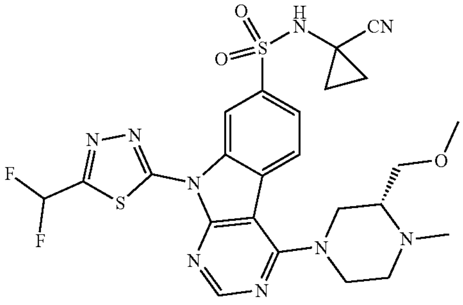 [SMILES: COC[C@H]1CN(c2ncnc3c2c2ccc(S(=O)(=O)NC4(C#N)CC4)cc2n3-c2nnc(C(F)F)s2)CCN1C]

This compound was prepared using procedures analogous to this described for Example 203 Step 5 using (R)—N-(1-cyanocyclopropyl)-4-(3-(methoxymethyl)-4-methylpiperazin-1-yl)-9H-pyrimido[4,5-b]indole-7-sulfonamide and 2-bromo-5-(difluoromethyl)-1,3,4-thiadiazole to afford the title product as white solid. $^1H$ NMR (400 MHz, DMSO-$d_6$) δ ppm 9.49 (d, J=1.7 Hz, 1H), 9.40 (s, 1H), 8.80 (s, 1H), 8.10 (d, J=8.5 Hz, 1H), 8.03 (dd, J=8.4, 1.7 Hz, 1H), 7.68 (t, J=53.3 Hz, 1H), 4.40 (d, J=12.6 Hz, 1H), 4.18 (d, J=10.7 Hz, 1H), 3.63 (dd, J=9.8, 4.1 Hz, 1H), 3.51 (t, J=10.9 Hz, 1H), 3.26 (s, 3H), 3.19 (dd, J=13.2, 10.1 Hz, 1H), 2.92 (dt, J=4.9, 2.7 Hz, 1H), 2.44 (s, 2H), 2.36 (d, J=8.9 Hz, 1H), 2.29 (s, 3H), 1.45-1.41 (m, 2H), 1.29-1.26 (m, 2H). LCMS for $C_{24}H_{26}F_2N_9O_3S_2$ $[M+H]^+$: m/z=590.1; Found: 590.0.

Example 205: (S)—N-(1-Cyanocyclopropyl)-4-(4-(cyanomethyl)-3-methylpiperazin-1-yl)-9-(5-(difluoromethyl)-1,3,4-thiadiazol-2-yl)-9H-pyrimido[4,5-b]indole-7-sulfonamide

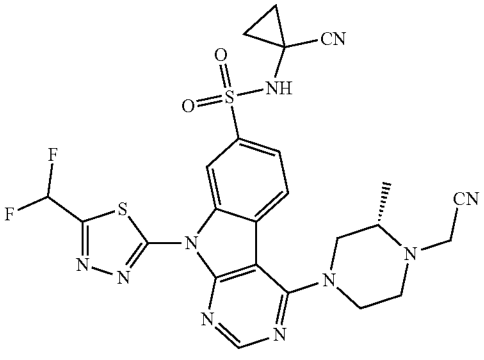

Step 1: tert-butyl (S)-4-(cyanomethyl)-3-methylpiperazine-1-carboxylate

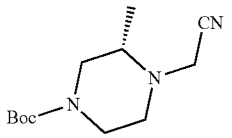 [SMILES: C[C@H]1CN(C(=O)OC(C)(C)C)CCN1CC#N]

To (R)-tert-butyl 2-methylpiperazine-1-carboxylate (500 mg, 2.50 mmol) in THF (12 mL) was added tetramethylguanidine (0.46 mL, 3.62 mmol) at 0° C. (ice-water bath). Bromoacetonitrile (0.21 mL, 3.00 mmol, 1.4 eq) was added. The mixture was then stirred at r.t. for 16 h., and diluted EtOAc (30 mL). The mixture was washed with water and brine, dried over a phase separating column. The solvent was removed under reduced pressure. The crude compound was purified by flash chromatography on a silica gel column eluting with 0-50% ethyl acetate in PE to afford the title compound (479 mg, 2.00 mmol, 80.1% yield) as a colorless oil.

Step 2: (S)-2-(2-methylpiperazin-1-yl)acetonitrile

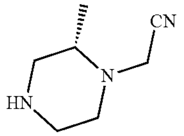

A solution of tert-butyl (S)-4-(cyanomethyl)-3-methylpiperazine-1-carboxylate (479 mg, 2.00 mmol, 1.0 eq) in HCl (4.0 M in dioxane, 5 mL) was stirred at room temperature for 2 h. The reaction was monitored by LCMS. After completion of the reaction, the mixture was filtered and the solid was washed with ethyl acetate (10 mL) to afford the crude product (420 mg, 3.02 mmol) as an HCl salt, which was used in the next step. LCMS calc. for $C_7H_{14}N_3[M+H]^+$: m/z=140.1; Found: 140.2.

Step 3: (S)—N-(1-cyanocyclopropyl)-4-(4-(cyanomethyl)-3-methylpiperazin-1-yl)-9H-pyrimido[4,5-b]indole-7-sulfonamide

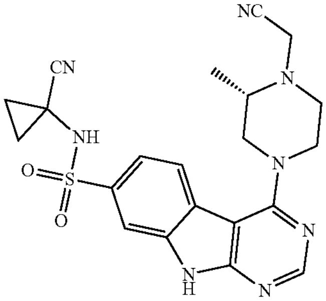 [SMILES: C[C@H]1CN(c2ncnc3[nH]c4cc(S(=O)(=O)NC5(C#N)CC5)ccc4c23)CCN1CC#N]

This compound was prepared using procedures analogous to this described for Example 203 Step 4 using 4-chloro-N-(1-cyanocyclopropyl)-9H-pyrimido[4,5-b]indole-7-sulfonamide (Intermediate 1) and (S)-2-(2-methylpiperazin-1-yl) acetonitrile to afford product as yellow solid. LCMS calc. for $C_{21}H_{22}N_8O_2S$ [M+H]$^+$: m/z=451.2; Found: 451.8.

Step 4: (S)—N-(1-cyanocyclopropyl)-4-(4-(cyanomethyl)-3-methylpiperazin-1-yl)-9-(5-(difluoromethyl)-1,3,4-thiadiazol-2-yl)-9H-pyrimido[4,5-b] indole-7-sulfonamide This compound was prepared using procedures analogous to this described for Example 203 Step 5 using (S)—N-(1-cyanocyclopropyl)-4-(4-(cyanomethyl)-3-methylpiperazin-1-yl)-9H-pyrimido[4,5-b]indole-7-sulfonamide and 2-bromo-5-(difluoromethyl)-1,3,4-thiadiazole to afford the title product as yellow solid. $^1H$ NMR (400 MHz, DMSO-$d_6$) δ ppm 9.49 (s, 1H), 8.83 (s, 1H), 8.09 (t, J=6.8 Hz, 2H), 7.95 (s, 1H), 7.62 (d, J=53.2 Hz, 1H), 4.30 (dd, J=13.6, 4.2 Hz, 2H), 4.05 (d, J=17.8 Hz, 1H), 3.92-3.77 (m, 1H), 3.56 (t, J=11.2 Hz, 1H), 3.13 (dd, J=13.0, 10.4 Hz, 1H), 2.97 (d, J=11.4 Hz, 1H), 2.55 (dd, J=9.3, 6.8 Hz, 2H), 1.45-1.39 (m, 2H), 1.27 (dd, J=8.3, 5.4 Hz, 2H), 1.10 (d, J=6.2 Hz, 3H). LCMS calc. for $C_{24}H_{23}F_2N_{10}O_2S_2$ [M+H]$^+$: m/z=585.1; Found: 585.2.

Example 206: N-(1-Cyanocyclopropyl)-4-((3S)-4-(diethylamino)-3-fluoropiperidin-1-yl)-9-(5-(difluoromethyl)-1,3,4-thiadiazol-2-yl)-9H-pyrimido[4,5-b] indole-7-sulfonamide

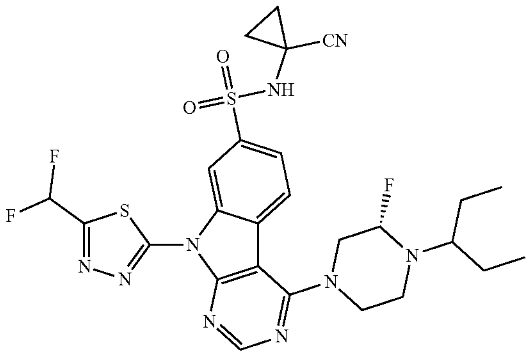 [SMILES: CCC(CC)N1CCN(c2ncnc3c2c2ccc(S(=O)(=O)NC4(C#N)CC4)cc2n3-c2nnc(C(F)F)s2)C[C@@H]1F]

Step 1: (3S)—N,N-diethyl-3-fluoropiperidin-4-amine

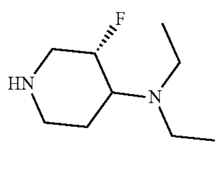

This compound was prepared by procedures analogous to those described for Intermediate 64 Step 1-3 using diethylamine solution (2.0 M in THF) to replace dimethylamine solution (2.0 M in THF) in Step 1. LCMS calc. for $C_9H_{20}FN_2$ [M+H]$^+$: m/z=175.2; Found: 175.1.

Step 2: N-(1-cyanocyclopropyl)-4-((3S)-4-(diethylamino)-3-fluoropiperidin-1-yl)-9H-pyrimido[4,5-b] indole-7-sulfonamide

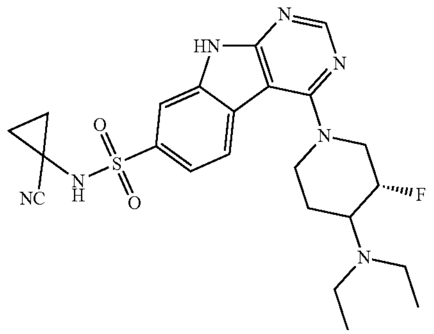 [SMILES: CCN(CC)C1CCN(c2ncnc3[nH]c4cc(S(=O)(=O)NC5(C#N)CC5)ccc4c23)C[C@@H]1F]

A mixture of 4-chloro-N-(1-cyanocyclopropyl)-9H-pyrimido[4,5-b]indole-7-sulfonamide (200 mg, 0.58 mmol, Intermediate 1), (3S)—N,N-diethyl-3-fluoropiperidin-4-amine (150 mg, 0.86 mmol) and $Et_3N$ (291 mg, 2.88 mmol) in DMF (4 mL) was stirred at 60° C. for 8 h. After concentrated under reduced pressure, the residue was purified by flash chromatography on a C18 column eluting with $MeCN/H_2O$ (55-65% with 0.05% TFA) to afford the title compound (56 mg, 80% yield) as an off-white solid. LCMS calc. for $C_{23}H_{29}FN_7O_2S$ [M+H]$^+$: m/z=486.2; Found: 486.2.

Step 3: N-(1-cyanocyclopropyl)-4-((3S)-4-(diethylamino)-3-fluoropiperidin-1-yl)-9-(5-(difluoromethyl)-1,3,4-thiadiazol-2-yl)-9H-pyrimido[4,5-b] indole-7-sulfonamide A mixture of N-(1-cyanocyclopropyl)-4-((3S)-4-(diethylamino)-3-fluoropiperidin-1-yl)-9H-pyrimido[4,5-b]indole-7-sulfonamide (50 mg, 0.1 mmol), RuPhos Pd G3 (9 mg, 0.01 mmol), 2-bromo-5-(difluoromethyl)-1,3,4-thiadiazole (43 mg, 0.2 mmol) and $K_3PO_4$ (42 mg, 0.2 mmol) in dioxane (1 mL) was degassed and recharged with $N_2$ for 3 cycles, and then stirred at 110° C. for 4 h. After cooled to 25° C., the reaction mixture was diluted with $H_2O$ (10 mL) and extracted with EA (10 mL×3). The combined organic layers were washed with brine, dried over $Na_2SO_4$, filtered and concentrated under reduced pressure. The residue was purified by prep-HPLC on a C18 column eluting with MeCN/$H_2O$ (55-70% with 0.05% TFA) to afford the title compound (6.0 mg, 10% yield) as a light yellow solid. LCMS calc. for $C_{26}H_{29}F_3N_9O_2S_2$ [M+H]$^+$: m/z=620.2; Found: 620.2.

Example 207: N-(1-Cyanocyclopropyl)-9-(5-(difluoromethyl)-1,3,4-thiadiazol-2-yl)-4-((3S)-3-fluoro-4-(pyrrolidin-1-yl)piperidin-1-yl)-9H-pyrimido[4,5-b]indole-7-sulfonamide

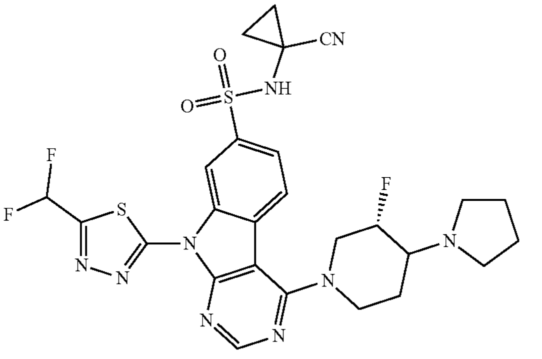

Step 1: (3S)-3-fluoro-4-(pyrrolidin-1-yl)piperidine

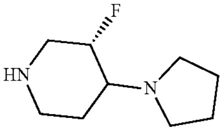 [SMILES: F[C@H]1CNCCC1N1CCCC1]

This compound was prepared by procedures analogous to those described for Intermediate 64 Step 1-3 using pyrrolidine to replace dimethylamine solution (2.0 M in THF) in Step 1. LCMS calc. for $C_9H_{48}FN_2$ [M+H]$^+$: m/z=173.1; Found: 173.1.

Step 2: N-(1-cyanocyclopropyl)-4-((3S)-3-fluoro-4-(pyrrolidin-1-yl)piperidin-1-yl)-9H-pyrimido[4,5-b]indole-7-sulfonamide

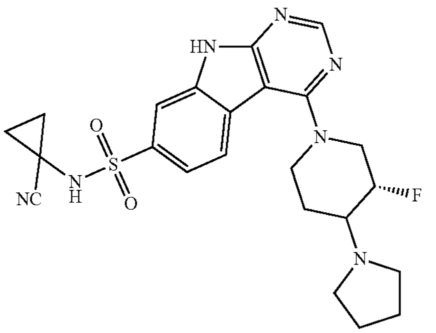 [SMILES: N#CC1(NS(=O)(=O)c2ccc3c(c2)[nH]c2ncnc(N4CCC(N5CCCC5)[C@@H](F)C4)c23)CC1]

This compound was prepared by procedures analogous to those described for Example 206 Step 2 using 4-chloro-N-(1-cyanocyclopropyl)-9H-pyrimido[4,5-b]indole-7-sulfonamide (Intermediate 1) and (3S)-3-fluoro-4-(pyrrolidin-1-yl)piperidine to afford the title product as an off-white solid. LCMS calc. for $C_{23}H_{27}FN_7O_2S$ [M+H]$^+$: m/z=484.2; Found: 484.2.

Step 3: N-(1-cyanocyclopropyl)-9-(5-(difluoromethyl)-1,3,4-thiadiazol-2-yl)-4-((3S)-3-fluoro-4-(pyrrolidin-1-yl)piperidin-1-yl)-9H-pyrimido[4,5-b]indole-7-sulfonamide This compound was prepared by procedures analogous to those described for Example 206 Step 3 using N-(1-cyanocyclopropyl)-4-((3S)-3-fluoro-4-(pyrrolidin-1-yl)piperidin-1-yl)-9H-pyrimido[4,5-b]indole-7-sulfonamide and 2-bromo-5-(difluoromethyl)-1,3,4-thiadiazole to afford the title product as a white solid. LCMS calc. for $C_{26}H_{27}F_3N_9O_2S_2$ [M+H]$^+$: m/z=618.2; Found: 618.2.

Example 208: 4-((3S)-4-(Azetidin-1-yl)-3-fluoropiperidin-1-yl)-N-(1-cyanocyclopropyl)-9-(5-(difluoromethyl)-1,3,4-thiadiazol-2-yl)-9H-pyrimido[4,5-b]indole-7-sulfonamide

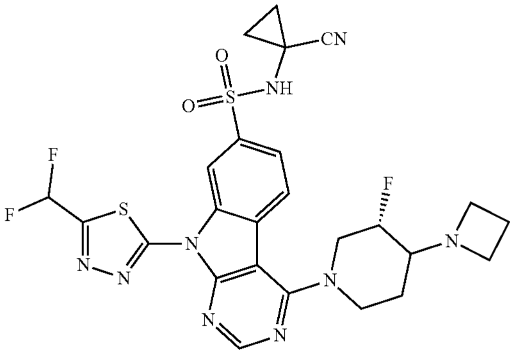

Step 1: (3S)-4-(azetidin-1-yl)-3-fluoropiperidine

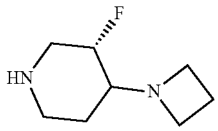 [SMILES: F[C@H]1CNCCC1N1CCC1]

This compound was prepared by procedures analogous to those described for Intermediate 64 Step 1-3 using azetidine to replace dimethylamine solution (2.0 M in THF) in Step 1. LCMS calc. for $C_8H_{16}FN_2$ [M+H]$^+$: m/z=159.1; Found: 159.1.

Step 2: 4-((3S)-4-(azetidin-1-yl)-3-fluoropiperidin-1-yl)-N-(1-cyanocyclopropyl)-9H-pyrimido[4,5-b]indole-7-sulfonamide

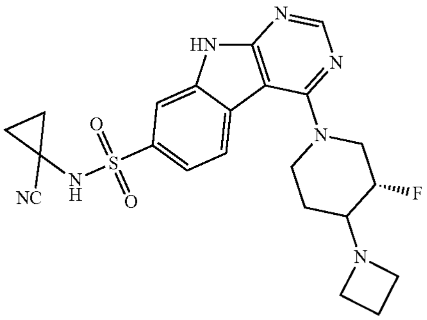 [SMILES: N#CC1(NS(=O)(=O)c2ccc3c(c2)[nH]c2ncnc(N4CCC(N5CCC5)[C@@H](F)C4)c23)CC1]

This compound was prepared by procedures analogous to those described for Example 206 Step 2 using 4-chloro-N-(1-cyanocyclopropyl)-9H-pyrimido[4,5-b]indole-7-sulfonamide (Intermediate 1) and (3S)-4-(azetidin-1-yl)-3-fluoropiperidine to afford the title product as an off-white solid. LCMS calc. for $C_{22}H_{25}FN_7O_2S$ $[M+H]^+$: m/z=470.2; Found: 470.2.

Step 3: 4-((3S)-4-(azetidin-1-yl)-3-fluoropiperidin-1-yl)-N-(1-cyanocyclopropyl)-9-(5-(difluoromethyl)-1,3,4-thiadiazol-2-yl)-9H-pyrimido[4,5-b]indole-7-sulfonamide This compound was prepared by procedures analogous to those described for Example 206 Step 3 using 4-((3S)-4-(azetidin-1-yl)-3-fluoropiperidin-1-yl)-N-(1-cyanocyclopropyl)-9H-pyrimido[4,5-b]indole-7-sulfonamide and 2-bromo-5-(difluoromethyl)-1,3,4-thiadiazole to afford the title product as a white solid. LCMS calc. for $C_{25}H_{25}F_3N_9O_2S_2$ $[M+H]^+$: m/z=604.1; Found: 604.1.

Example 209: N-(1-Cyanocyclopropyl)-9-(5-(difluoromethyl)-1,3,4-thiadiazol-2-yl)-4-((3S)-3-fluoro-4-morpholinopiperidin-1-yl)-9H-pyrimido[4,5-b]indole-7-sulfonamide

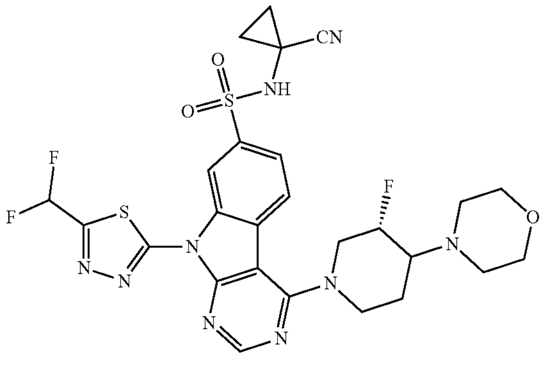

Step 1: 4-((3S)-3-fluoropiperidin-4-yl)morpholine

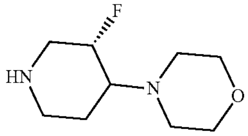 [SMILES: F[C@H]1CNCCC1N1CCOCC1]

This compound was prepared by procedures analogous to those described for Intermediate 64 Step 1-3 using morpholine to replace dimethylamine solution (2.0 M in THF) in Step 1. LCMS calc. for $C_9H_{18}FN_2O$ $[M+H]^+$: m/z=189.1; Found: 189.1.

Step 2: N-(1-cyanocyclopropyl)-4-((3S)-3-fluoro-4-morpholinopiperidin-1-yl)-9H-pyrimido[4,5-b]indole-7-sulfonamide

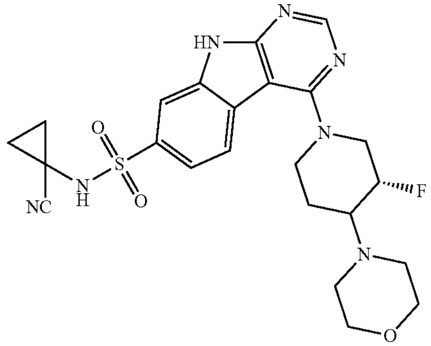 [SMILES: N#CC1(NS(=O)(=O)c2ccc3c(c2)[nH]c2ncnc(N4CCC(N5CCOCC5)[C@@H](F)C4)c23)CC1]

This compound was prepared by procedures analogous to those described for Example 206 Step 2 using 4-chloro-N-(1-cyanocyclopropyl)-9H-pyrimido[4,5-b]indole-7-sulfonamide (Intermediate 1) and 4-((3S)-3-fluoropiperidin-4-yl)morpholine to afford the title product as a white solid. LCMS calc. for $C_{23}H_{27}FN_7O_3S$ $[M+H]^+$: m/z=500.2; Found: 500.2.

Step 3: N-(1-cyanocyclopropyl)-9-(5-(difluoromethyl)-1,3,4-thiadiazol-2-yl)-4-((3S)-3-fluoro-4-morpholinopiperidin-1-yl)-9H-pyrimido[4,5-b]indole-7-sulfonamide This compound was prepared by procedures analogous to those described for Example 206 Step 3 using N-(1-cyanocyclopropyl)-4-((3S)-3-fluoro-4-morpholinopiperidin-1-yl)-9H-pyrimido[4,5-b]indole-7-sulfonamide (100 mg, 0.2 mmol) and 2-bromo-5-(difluoromethyl)-1,3,4-thiadiazole to afford the title product as a white solid. LCMS calc. for $C_{26}H_{27}F_3N_9O_3S_2$ $[M+H]^+$: m/z=634.2; found: 634.2.

Example 210: 4-(3-Oxa-8-azabicyclo[3.2.1]octan-8-yl)-N-(1-cyanocyclopropyl)-9-(5-(difluoromethyl)-1,3,4-thiadiazol-2-yl)-9H-pyrimido[4,5-b]indole-7-sulfonamide

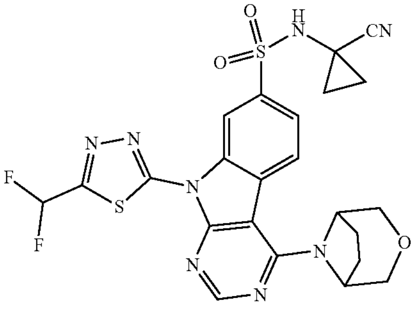 [SMILES: N#CC1(NS(=O)(=O)c2ccc3c4c(N5C6CCC5COC6)ncnc4n(-c4nnc(C(F)F)s4)c3c2)CC1]

Step 1: 4-(3-oxa-8-azabicyclo[3.2.1]octan-8-yl)-N-(1-cyanocyclopropyl)-9H-pyrimido[4,5-b]indole-7-sulfonamide

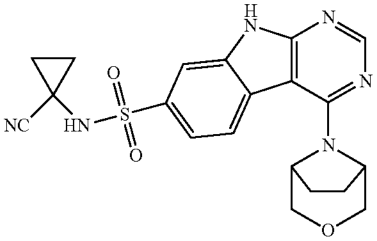 [SMILES: N#CC1(NS(=O)(=O)c2ccc3c(c2)[nH]c2ncnc(N4C5CCC4COC5)c23)CC1]

This compound was prepared by procedures analogous to those described for Example 206 Step 2 using 4-chloro-N-(1-cyanocyclopropyl)-9H-pyrimido[4,5-b]indole-7-sulfonamide (Intermediate 1) and 3-oxa-8-azabicyclo[3.2.1]octane hydrochloride to afford the title product as a brown solid. LCMS calc. for $C_{20}H_{21}N_6O_3S$ $[M+H]^+$: m/z=425.1; Found: 425.1.

Step 2: 4-(3-oxa-8-azabicyclo[3.2.1]octan-8-yl)-N-(1-cyanocyclopropyl)-9-(5-(difluoromethyl)-1,3,4-thiadiazol-2-yl)-9H-pyrimido[4,5-b]indole-7-sulfonamide A mixture of 4-(3-oxa-8-azabicyclo[3.2.1]octan-8-yl)-N-(1-cyanocyclopropyl)-9H-pyrimido[4,5-b]indole-7-sulfonamide (520 mg, 1.22 mmol), 2-bromo-5-(difluoromethyl)-1,3,4-thiadiazole (660 mg, 3.1 mmol), CuI (145 mg, 0.76 mmol), (1R,2R)—$N^1$,$N^2$-dimethylcyclohexane-1,2-diamine (218 mg, 1.52 mmol) and CsF (730 mg, 4.8 mmol) in dioxane (5 mL) was degassed and recharged with $N_2$ for 3 cycles. The mixture was stirred at 110° C. for 5 h. After cooled to r.t., the reaction mixture was diluted with $H_2O$ (40 mL), extracted with EA (50 mL×3). The combined organic layers were washed with brine, dried over $Na_2SO_4$, filtered and then concentrated under reduced pressure. The residue was purified by flash chromatography on a silica gel column eluting with EA/DCM (55-75%) to afford the title compound (122 mg) as a white solid. LCMS calc. for $C_{23}H_{21}F_2N_8O_3S_2$ $[M+H]^+$: m/z=559.1; found: 559.1.

Intermediate 1: 4-Chloro-N-(1-cyanocyclopropyl)-9H-pyrimido[4,5-b]indole-7-sulfonamide

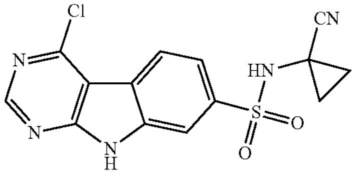 [SMILES: N#CC1(NS(=O)(=O)c2ccc3c(c2)[nH]c2ncnc(Cl)c23)CC1]

Step 1: 4-chloro-N-(1-cyanocyclopropyl)-3-nitrobenzenesulfonamide

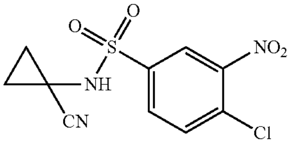 [SMILES: N#CC1(NS(=O)(=O)c2ccc(Cl)c([N+](=O)[O-])c2)CC1]

To a mixture of 1-aminocyclopropane-1-carbonitrile hydrochloride (55.6 g, 469 mmol), pyridine (500 mL) and DMAP (19.1 g, 156 mmol) in MeCN (500 mL) was added 4-chloro-3-nitrobenzenesulfonyl chloride (100 g, 391 mmol) at 0-5° C. The resulting mixture was then stirred at r.t. for 2 h. The reaction mixture was poured into ice-water (500 mL), and adjusted to pH ~3 with aq. HCl solution (1 N) at 0-5° C. The aqueous phase was extracted with EtOAc (300 mL×3). The combined organic layers were washed with brine (500 mL), dried over anhydrous $Na_2SO_4$, filtered and concentrated under reduced pressure. The residue was triturated with MTBE (100 mL) at 20° C. for 2 h. The solid formed was collected by filtration and dried in vacuum to afford 4-chloro-N-(1-cyanocyclopropyl)-3-nitrobenzenesulfonamide (75 g, 63.6% yield) as yellow solid. LCMS calc. for $C_{10}H_7ClN_3O_4S$ $[M-H]^-$: m/z=300.0. Found: 300.0. $^1$H NMR: (400 MHz, DMSO-$d_6$) δ 9.54 (s, 1H), 8.51 (s, 1H), 8.09-8.14 (m, 2H), 1.47-1.51 (m, 2H), 1.31-1.35 (m, 2H)

Step 2: 2-amino-6-(N-(1-cyanocyclopropyl)sulfamoyl)-1H-indole-3-carboxamide

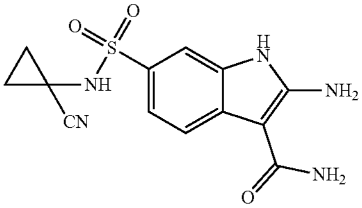 [SMILES: N#CC1(NS(=O)(=O)c2ccc3c(C(N)=O)c(N)[nH]c3c2)CC1]

To a solution of 2-cyanoacetamide (41.8 g, 497 mmol) in DMF (750 mL) was added NaH (39.8 g, 994 mmol, 60% in mineral oil) at 0° C. The mixture was stirred at 0° C. for 30 min., and 4-chloro-N-(1-cyanocyclopropyl)-3-nitrobenzenesulfonamide (75.0 g, 249 mmol) was added at 0° C. The mixture was stirred at 20° C. for 1 h. The reaction was poured into ice-water (500 mL) in portions, and adjusted to pH-3 with conc. HCl solution (12 N) at 0-5° C. To the solution was added DMF (750 mL), followed by addition of $FeCl_3$ (120 g, 744 mmol) at 20° C. The mixture was heated to 60° C., and Zn (162 g, 2.48 mol) was added in small portions. The mixture was stirred and then heated at 100° C. for 2 h. LCMS showed the reaction was completed. After cooling, the reaction mixture was filtered on celite. The filtrate was extracted with DCM (500 mL×6). The combined organic layers were dried over anhydrous $Na_2SO_4$, filtered and concentrated in vacuum. The residue was purified by flash chromatography on a silica gel column eluting with PE/EtOAc (0-100%) to afford 2-amino-6-(N-(1-cyanocyclopropyl)sulfamoyl)-1H-indole-3-carboxamide (30.0 g, 18.9% yield) as yellow foam. LCMS calc. for $C_{13}H_{12}N_5O_3S$ $[M-H]^-$: m/z=318.1. Found: 318.0.

Step 3: N-(1-cyanocyclopropyl)-4-oxo-4,9-dihydro-3H-pyrimido[4,5-b]indole-7-sulfonamide

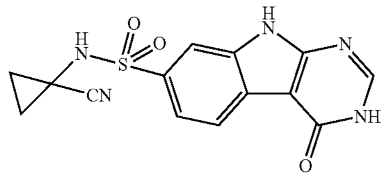 [SMILES: N#CC1(NS(=O)(=O)c2ccc3c(c2)[nH]c2nc[nH]c(=O)c23)CC1]

To a mixture of 2-amino-6-(N-(1-cyanocyclopropyl)sulfamoyl)-1H-indole-3-carboxamide (28.0 g, 87.7 mmol) in trimethoxymethane (560 mL) was added aq. HCl (12 N, 161 mL) at 20° C. The mixture was stirred at 60° C. for 1 h. LCMS showed the starting material was consumed completely. The reaction mixture was filtered. The filter cake was dried in vacuum to afford N-(1-cyanocyclopropyl)-4-oxo-4,9-dihydro-3H-pyrimido[4,5-b]indole-7-sulfonamide (20.0 g, 69.3% yield) as yellow solid. $^1H$ NMR: (400 MHz, DMSO-$d_6$) δ 12.7 (s, 1H), 12.5 (s, 1H), 9.07 (s, 1H), 8.24 (s, 1H), 8.17 (d, J=8.0 Hz, 1H), 7.96 (s, 1H), 7.71 (d, J=10.0 Hz, 1H), 1.37-1.42 (m, 2H), 1.22-1.27 (m, 2H). LCMS calc. for $C_{14}H_0N_5O_3S$ $[M-H]^-$: m/z=328.1; Found: 328.1.

Step 4: 4-chloro-N-(1-cyanocyclopropyl)-9H-pyrimido[4,5-b]indole-7-sulfonamide

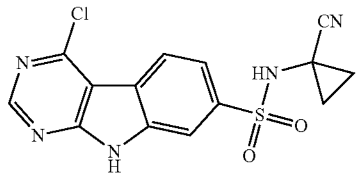 [SMILES: N#CC1(NS(=O)(=O)c2ccc3c(c2)[nH]c2ncnc(Cl)c23)CC1]

A mixture of N-(1-cyanocyclopropyl)-4-oxo-4,9-dihydro-3H-pyrimido[4,5-b]indole-7-sulfonamide (18.0 g, 54.7 mmol) in $POCl_3$ (720 mL) was stirred at 100° C. for 16 hrs. LCMS showed the starting material was consumed completely. The mixture was concentrated under reduced pressure. The residue was purified by flash chromatography on a silica gel column eluting with PE/EtOAc (0-100%) to afford 4-chloro-N-(1-cyanocyclopropyl)-9H-pyrimido[4,5-b]indole-7-sulfonamide (10.0 g, 47.3% yield) as light yellow solid. LCMS calc. for $C_{14}H_9ClN_5O_2S$ $[M-H]^-$: m/z=346.0; Found: 345.9.

Intermediate 2: 4-Chloro-N-(1-methylcyclopropyl)-9H-pyrimido[4,5-b]indole-7-sulfonamide

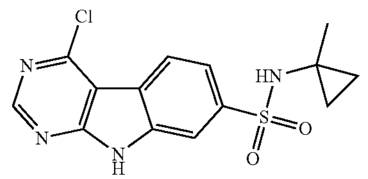 [SMILES: CC1(NS(=O)(=O)c2ccc3c(c2)[nH]c2ncnc(Cl)c23)CC1]

This compound was prepared using procedures analogous to those described for Intermediate 1 using 1-methylcyclopropan-1-amine to replace 1-aminocyclopropane-1-carbonitrile hydrochloride in step 1. LCMS calc. for $C_{14}H_{12}C_1N_4O_2S$ $[M-H]^-$: m/z=335.0; Found: 334.9.

Intermediate 3: 4-chloro-6-fluoro-N-(1-methylcyclopropyl)-9H-pyrimido[4,5-b]indole-7-sulfonamide

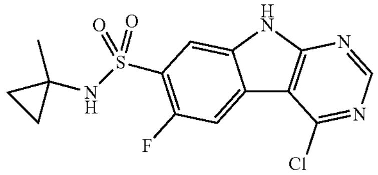 [SMILES: CC1(NS(=O)(=O)c2cc3[nH]c4ncnc(Cl)c4c3cc2F)CC1]

Step 1:4-chloro-2-fluoro-N-(1-methylcyclopropyl)-5-nitrobenzenesulfonamide

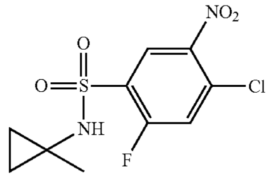 [SMILES: CC1(NS(=O)(=O)c2cc([N+](=O)[O-])c(Cl)cc2F)CC1]

To a solution of 4-chloro-2-fluoro-5-nitrobenzenesulfonyl chloride (9.0 g, 33.0 mmol, Intermediate 4 Step 1) in acetonitrile (135 mL) was added a solution of 1-methylcyclopropan-1-amine hydrochloride (3.53 g, 33.0 mmol) in acetonitrile (45 mL) at −10° C. The reaction mixture was stirred at this temperature for 5 min. before poured into water (300 mL). The mixture was extracted with EtOAc (100 mL×3). The organic layer was washed with brine (60 mL), dried over $Na_2SO_4$, filtered and concentrated under reduced pressure. The residue was purified by flash chromatography on a silica gel column eluting with EtOAc/hexanes (0-15%) to afford the title compound (5.8 g, 57% yield). LCMS calc. for $C_{10}H_9ClFN_2O_4S$ $[M-H]^-$: m/z=307.0; Found: 307.0.

Step 2: 2-cyano-2-(5-fluoro-4-(N-(1-methylcyclopropyl)sulfamoyl)-2-nitrophenyl)acetamide

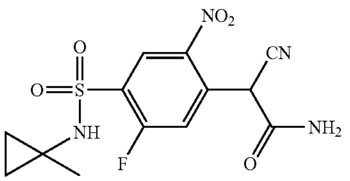 [SMILES: CC1(NS(=O)(=O)c2cc([N+](=O)[O-])c(C(C#N)C(N)=O)cc2F)CC1]

To a solution of 2-cyanoacetamide (3.71 g, 44.2 mmol) and potassium tert-butoxide (7.43 g, 66.3 mmol) in tetrahydrofuran (30 mL) was added 4-chloro-2-fluoro-5-nitrobenzenesulfonyl chloride (6.8 g, 22.1 mmol) at −15° C. The reaction mixture was stirred at r.t. for 2 h. The mixture was poured into water (150 mL), and extracted with EtOAc (50 mL×3). The organic layer was washed with brine (40 mL), dried over $Na_2SO_4$, filtered and concentrated under reduced pressure. The residue was purified by flash chromatography on a silica gel column eluting with EtOAc/hexanes (0-80%) to afford the title compound (3.0 g, 39% yield). LCMS calc. for $C_{13}H_{12}FN_4O_5S$ [M−H]: m/z=355.0; Found: 355.0.

Step 3: 2-amino-5-fluoro-6-(N-(1-methylcyclopropyl)sulfamoyl)-1H-indole-3-carboxamide

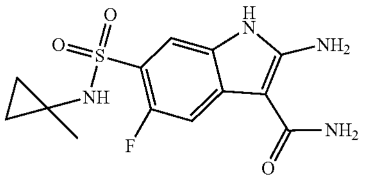 [SMILES: CC1(NS(=O)(=O)c2cc3[nH]c(N)c(C(N)=O)c3cc2F)CC1]

To a solution of 2-cyano-2-(5-fluoro-4-(N-(1-methylcyclopropyl)sulfamoyl)-2-nitrophenyl)acetamide (3.0 g, 8.4 mmol) in ethanol/$H_2O$ (v:v=1:1, 30 mL) was added ammonium chloride (4.55 g, 84.3 mmol) and Fe (4.72 g, 84.3 mmol). The reaction mixture was stirred at 70° C. for 3 h. The mixture was filtered and the filtrate was poured into water (90 mL). The mixture was extracted with EtOAc (30 mL×3). The organic layer was washed with brine (30 mL), dried over $Na_2SO_4$, filtered and concentrated under reduced pressure. The crude product was purified by flash chromatography on a silica gel column eluting with EtOAc/hexanes (0-100%) to afford the title compound (2.0 g, 72% yield). LCMS calc. for $C_{13}H_{16}FN_4O_3S$ $[M+H]^+$: m/z=327.2; Found: 327.2 Step 4: 6-fluoro-N-(1-methylcyclopropyl)-4-oxo-4,9-dihydro-3H-pyrimido[4,5-b]indole-7-sulfonamide

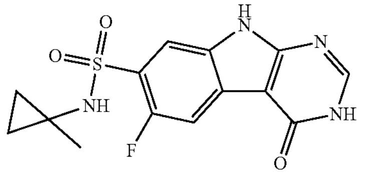 [SMILES: CC1(NS(=O)(=O)c2cc3[nH]c4nc[nH]c(=O)c4c3cc2F)CC1]

A mixture of 2-amino-5-fluoro-6-(N-(1-methylcyclopropyl)sulfamoyl)-1H-indole-3-carboxamide (1550 mg, 4.75 mmol), and p-toluenesulfonic acid (163.6 mg, 0.95 mmol) in trimethoxymethane (15 mL) was stirred at r.t. for 2 h. The reaction mixture was poured into water (60 mL), then the solution was filtered. The filtrate was concentrated under reduced pressure to afford the title compound (1.24 g, 77% yield). LCMS calc. for $C_{14}H_{14}FN_4O_3S$ $[M+H]^+$: m/z=337.1; Found: 337.1.

Step 5: 4-chloro-6-fluoro-N-(1-methylcyclopropyl)-9H-pyrimido[4,5-b]indole-7-sulfonamide

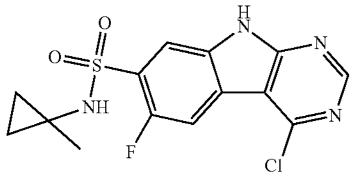 [SMILES: CC1(NS(=O)(=O)c2cc3[nH]c4ncnc(Cl)c4c3cc2F)CC1]

6-Fluoro-N-(1-methylcyclopropyl)-4-oxo-4,9-dihydro-3H-pyrimido[4,5-b]indole-7-sulfonamide (1.6 g, 4.76 mmol) in phosphoryl trichloride (50 mL) was stirred at 120° C. for 2 h. The reaction mixture was poured into ice-water (200 mL), and extracted with EtOAc (50 mL×3). The combined organic layers were washed with brine (50 mL), dried over $Na_2SO_4$, filtered and concentrated under reduced pressure. The crude product was purified by flash chromatography on a silica gel column eluting with EtOAc/Hexanes (0-60%) to afford the title compound (0.68 g, 40% yield). LCMS calc. for $C_{14}H_{13}C_1FN_4O_2S$ $[M+H]^+$: m/z=355.1; Found: 355.1.

Intermediate 4: 4-Chloro-N-(1-cyanocyclopropyl)-6-fluoro-9H-pyrimido[4,5-b]indole-7-sulfonamide

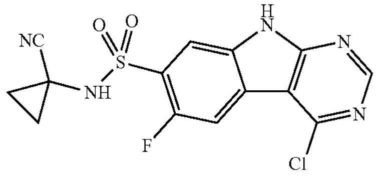 [SMILES: N#CC1(NS(=O)(=O)c2cc3[nH]c4ncnc(Cl)c4c3cc2F)CC1]

Step 1: 4-chloro-2-fluoro-5-nitrobenzenesulfonyl chloride

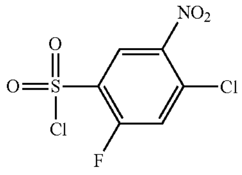 [SMILES: O=[N+]([O-])c1cc(S(=O)(=O)Cl)c(F)cc1Cl]

A solution of 2-chloro-4-fluoro-1-nitrobenzene (100 g, 569.7 mmol) in chlorosulfonic acid (200 mL) was stirred at 120° C. for 16 h. After cooled to r.t., the reaction mixture was added dropwise to ice water (2000 mL), extracted with EtOAc (200 mL×2), washed with saturated $NaHCO_3$ aq. to pH 6-7 below 10° C. The combined organic layers were dried over $Na_2SO_4$, filtered and concentrated. The residue was triturated with PE (300 mL) at 20° C. for 12 h. The solid was collected by filtration to afford the title compound (35.0 g, 22.4% yield) as light-yellow solid. $^1$H NMR: (400 MHz, $CDCl_3$) δ 8.61 (d, J=6.8 Hz, 1H), 7.63 (d, J=8.4 Hz, 1H).

Step 2: 4-Chloro-N-(1-cyanocyclopropyl)-6-fluoro-9H-pyrimido[4,5-b]indole-7-sulfonamide This compound was prepared using procedures analogous to those described for Intermediate 3 using 1-aminocyclopropane-1-carbonitrile hydrochloride to replace 1-methylcyclopropan-1-amine hydrochloride in Step 1. $^1$H NMR: (400 MHz, DMSO-$d_6$) δ 13.27 (s, 1H), 9.61 (s, 1H), 8.92 (s, 1H), 8.29 (d, J=10.0 Hz, 2H), 8.09 (d, J=6.0 Hz, 2H), 1.44-1.48 (m, 2H), 1.26-1.30 (m, 2H).

Intermediate 5: 4-Bromo-N-(1-cyanocyclopropyl)-9H-pyrido[2,3-b]indole-7-sulfonamide

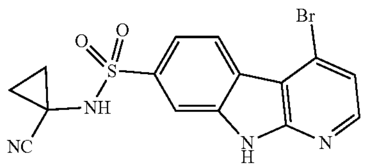 [SMILES: N#CC1(NS(=O)(=O)c2ccc3c(c2)[nH]c2nccc(Br)c23)CC1]

Step 1: 3-benzylsulfanylaniline

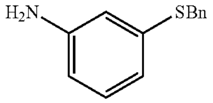

To a solution of NaOH (8.95 g, 224 mmol) in $H_2O$ (20 mL) was added a solution of 3-aminobenzenethiol (20.0 g, 160 mmol) in EtOH (80 mL), follow by addition of a solution of benzyl chloride (20.8 g, 165 mmol) in EtOH (20 mL). The reaction mixture was stirred at 20° C. for 3 h. The solid was removed by filtration. The filtrate was poured into $H_2O$ (200 mL) at 0-5° C., and extracted with DCM (50 mL×3). The combined organic layers were washed with brine (200 mL), dried over $Na_2SO_4$, filtered and concentrated under reduced pressure. The residue was triturated with PE (100 mL) at 20° C. for 30 min. The solid was collected by filtration and dried in an oven under vacuum to afford the title compound (22.0 g, 64.0% yield) as a white solid. $^1$H NMR: (400 MHz, $CDCl_3$) δ 7.22-7.27 (m, 5H), 7.01 (t, J=8.0 Hz, 1H), 6.76 (d, J=12.0 Hz, 1H), 6.67 (s, 1H), 6.54 (d, J=8.0 Hz, 1H), 4.07 (s, 2H), 3.67 (s, 2H). LCMS calc. for $C_{13}H_{14}NS$ $[M+H]^+$: m/z=216.1; Found: 215.9.

Step 2: N-(3-benzylsulfanylphenyl)-3-bromo-pyridin-2-amine

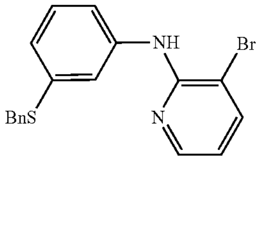

A mixture of 3-benzylsulfanylaniline (20.0 g, 92.9 mmol), 2,3-dibromopyridine (17.6 g, 74.3 mmol), $PPh_3$ (2.44 g, 9.29 mmol), t-BuONa (10.7 g, 111 mmol) and $Pd(OAc)_2$ (1.04 g, 4.64 mmol) in o-xylene (300 mL) was degassed and recharged with $N_2$ for three cycles, and stirred for 5 min. at 20° C. under nitrogen atmosphere. The resulting mixture was then stirred at 120° C. for 4 h. The mixture was concentrated under reduced pressure. The residue was purified by flash chromatography on a silica gel column eluting with EtOAc/PE (0-50%) to afford the title compound (19.0 g, 55.1% yield) as a yellow solid. $^1$H NMR: (400 MHz, $CDCl_3$) δ 8.08 (d, J=8.0 Hz, 1H), 7.66 (d, J=8.0 Hz, 1H), 7.61 (t, J=1.0 Hz, 1H), 7.20-7.33 (m, 7H), 6.92 (d, J=8.0 Hz, 2H), 6.58 (dd, J=4.0 Hz, 1H), 4.14 (s, 2H).

Step 3: 7-benzylsulfanyl-9H-pyrido[2,3-b]indole

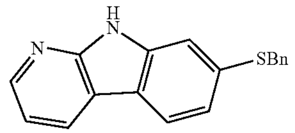

To a solution of N-(3-benzylsulfanylphenyl)-3-bromo-pyridin-2-amine (16.5 g, 44.4 mmol) and DBU (13.5 g, 88.9 mmol) in o-xylene (410 mL) and DMA (410 mL) was added $PCy_3 \cdot HBF_4$ (8.18 g, 22.2 mmol) and $Pd(OAc)_2$ (2.49 g, 11.1 mmol) at 20° C. under $N_2$. The reaction mixture was degassed and recharged with $N_2$ for three cycles, and stirred at 145° C. for 12 h. After cooled to r.t., the reaction mixture was quenched with $H_2O$ (2 L) at 0~5° C., and stirred at 20° C. for 30 min. The solid formed was collected by filtration and washed with MeCN (30 mL). The crude product was triturated with MeOH (80 mL) at 20° C. for 1 h., filtered and dried in an oven under vacuum to afford the title compound (5.4 g, 41.9% yield) as a yellow solid. $^1$H NMR: (400 MHz, DMSO-$d_6$) δ 11.8 (s, 1H), 8.44 (dd, J=8.0 Hz, 2H), 8.07 (d, J=8.0 Hz, 1H), 7.17-7.41 (m, 8H), 4.32 (s, 2H).

Step 4: 9H-pyrido[2,3-b]indole-7-sulfonyl chloride

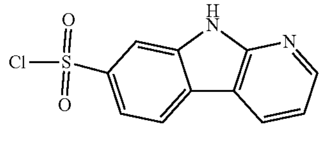 [SMILES: O=S(=O)(Cl)c1ccc2c(c1)[nH]c1ncccc12]

To a solution of 7-benzylsulfanyl-9H-pyrido[2,3-b]indole (5.20 g, 17.9 mmol) in MeCN (52 mL) was added AcOH (5.2 mL), $H_2O$ (2.6 mL) and 1,3-dichloro-5,5-dimethylimidazolidine-2,4-dione (5.29 g, 26.9 mmol) at 0~5° C. under $N_2$. The reaction mixture was stirred at 0~5° C. for 2 h., and quenched with $H_2O$ (100 mL) at 0~5° C. The resulting mixture was extracted with EtOAc (30 mL×3). The combined organic layers were washed with brine (50 mL), dried over $Na_2SO_4$, filter and concentrated under reduced pressure to afford the title compound (4.20 g, 87.9% yield) as a yellow solid, which was directly used to next step without further purification. LCMS calc. for $C_{11}H_8ClN_2O_2S$ $[M+H]^+$: m/z=267.0; Found: 266.9.

Step 5: N-(1-cyanocyclopropyl)-9H-pyrido[2,3-b]indole-7-sulfonamide

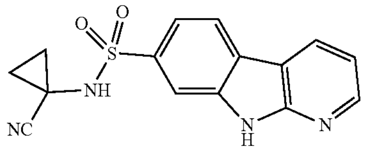 [SMILES: N#CC1(NS(=O)(=O)c2ccc3c(c2)[nH]c2ncccc23)CC1]

To a solution of 1-aminocyclopropanecarbonitrile HCl salt (3.64 g, 30.7 mmol) in MeCN (20 mL) and pyridine (19.6 g, 248 mmol) was added DMAP (751 mg, 6.15 mmol) and 9H-pyrido[2,3-b]indole-7-sulfonyl chloride (4.1 g, 15.4 mmol) at 0-5° C. The resulting mixture was stirred at 20° C. for 1 h., and quenched with $H_2O$ (50 mL) at 0-5° C. The mixture was extracted with EtOAc (20 mL×3). The combined organic layers were washed with brine (30 mL), dried over $Na_2SO_4$, filtered and concentrated under reduced pressure. The crude product was triturated with EtOAc (20 mL) at 25° C. for 1 h. The solid was collected by filtration and dried in an oven under vacuum to afford the title compound (3.50 g, 72.9% yield) as a yellow solid. $^1H$ NMR: (400 MHz, DMSO-$d_6$) δ 12.3 (s, 1H), 9.11 (s, 1H), 8.67 (d, J=8.0 Hz, 1H), 8.55 (d, J=8.0 Hz, 1H), 8.43 (d, J=8.0 Hz, 1H), 8.00 (s, 1H), 7.69 (d, J=8.0 Hz, 1H), 7.31 (dd, J=4.0 Hz, 1H), 1.39-1.42 (m, 2H), 1.24-1.28 (m, 2H). LCMS calc. for $C_{15}H_{13}N_4O_2S$ $[M+H]^+$: m/z=313.1; Found: 313.0.

Step 6: N-(1-cyanocyclopropyl)-1-oxido-9H-pyrido[2,3-b]indol-1-ium-7-sulfonamide

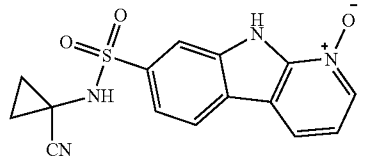 [SMILES: N#CC1(NS(=O)(=O)c2ccc3c(c2)[nH]c2c3ccc[n+]2[O-])CC1]

To a solution of N-(1-cyanocyclopropyl)-9H-pyrido[2,3-b]indole-7-sulfonamide (3.50 g, 11.2 mmol) in THF (52 mL) was added m-CPBA (11.4 g, 56.0 mmol, 85.0% purity) at 20° C. The resulting mixture was stirred at 20° C. for 12 h. The reaction mixture was quenched with saturated $Na_2SO_3$ aq. (100 mL) at 0-5° C. The solid formed was collected by filtration, and triturated with MeOH (20 mL) at 20° C. for 30 min. The solid was collected by filtration and dried in an oven under vacuum to afford the title compound (2.5 g, 68.0% yield) as a yellow solid. $^1H$ NMR: (400 MHz, DMSO-$d_6$) δ 13.1 (s, 1H), 9.21 (s, 1H), 8.47-8.50 (m, 2H), 8.31 (d, J=8.0 Hz, 1H), 8.07 (s, 1H), 7.76 (d, J=8.0 Hz, 1H), 7.33 (dd, J=4.0 Hz, 1H), 1.40-1.43 (m, 2H), 1.25-1.28 (m, 2H). LCMS calc. for $C_{15}H_{13}N_4O_3S$ $[M+H]^+$: m/z=329.1; Found: 329.1.

Step 7: 4-bromo-N-(1-cyanocyclopropyl)-9H-pyrido[2,3-b]indole-7-sulfonamide

To a solution of N-(1-cyanocyclopropyl)-1-oxido-9H-pyrido[2,3-b]indol-1-ium-7-sulfonamide (2.00 g, 6.09 mmol) in DMF (30.0 mL) was added $POBr_3$ (3.49 g, 12.2 mmol) at 0~5° C. under $N_2$. The resulting mixture was stirred at 20° C. for 2 h., and then quenched with $H_2O$ (100 mL) at 0-5° C. The solid formed was collected by filtration, and triturated with MeOH (15 mL) at 20° C. for 30 min., filtered again, and dried in an oven under vacuum to afford the title compound (1.00 g, 42.0% yield) as an off-white solid. $^1H$ NMR: (400 MHz, DMSO-$d_6$) δ 12.7 (s, 1H), 9.22 (s, 1H), 8.69 (d, J=8.0 Hz, 2H), 8.41 (d, J=4.0 Hz, 1H), 8.05 (s, 1H), 7.79 (dd, J=4.0 Hz, 1H), 7.60 (d, J=4.0 Hz, 1H), 1.40-1.44 (m, 2H), 1.25-1.29 (m, 2H). LCMS calc. for $C_{15}H_{12}BrN_4O_2S$ $[M+H]^+$: m/z=391.0; Found: 391.0.

Intermediate 6: 4-Bromo-N-(1-methylcyclopropyl)-9H-pyrido[2,3-b]indole-7-sulfonamide

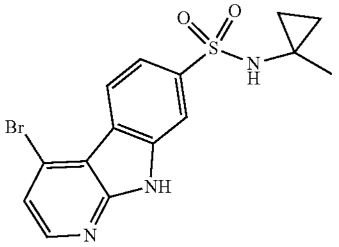 [SMILES: CC1(NS(=O)(=O)c2ccc3c(c2)[nH]c2nccc(Br)c23)CC1]

This compound was prepared as an off-white solid using procedures analogous to those described for Intermediate 5 Step 5-7 using 1-methylcyclopropanamine HCl salt to replace 1-aminocyclopropanecarbonitrile HCl salt in Step 5. $^1H$ NMR: (400 MHz, DMSO-$d_6$) δ 12.6 (s, 1H), 8.64 (d, J=8.0 Hz, 1H), 8.39 (d, J=5.2 Hz, 1H), 8.16 (s, 1H), 8.00 (s, 1H), 7.75 (dd, J=8.4, 1.6 Hz, 1H), 7.58 (d, J=5.2 Hz, 1H), 1.03 (s, 3H), 0.62-0.59 (m, 2H), 0.38-0.35 (m, 2H). LCMS calc. for $C_{15}H_{15}BrN_3O_2S$ $[M+H]^+$: m/z=380.0; Found: 380.0.

Intermediate 10: (1-Methylcyclobutyl)(piperazin-1-yl)methanone

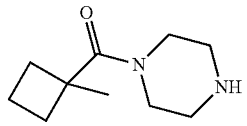

Step 1: tert-butyl 4-(1-methylcyclobutane-1-carbonyl)piperazine-1-carboxylate

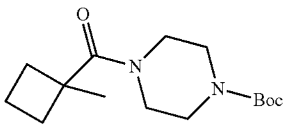 [SMILES: CC(C)(C)OC(=O)N1CCN(C(=O)C2(C)CCC2)CC1]

To a solution of tert-butyl piperazine-1-carboxylate (1.00 g, 4.49 mmol) in DMF (5.00 mL) was added 1-methylcyclobutanecarboxylic acid (0.615 g, 5.39 mmol) and TBTU (1.73 g, 5.39 mmol) and DIPEA (2.90 g, 22.5 mmol). The mixture was stirred at r.t. overnight. The reaction mixture was diluted with $H_2O$ (30 mL) and extracted with MTBE (50 mL×3). The combined organic layers were washed with brine (4 mL×2), dried over $Na_2SO_4$, filtered and concentrated under reduced pressure, and the crude product (0.5 g) was obtained as a white solid, which was used in the next step without purification. LCMS calc. for $C_{11}H_{19}N_2O_3$ $[M-56+H]^+$: m/z=227.1; Found: 227.0.

Step 2: (1-methylcyclobutyl)(piperazin-1-yl)methanone

A mixture of tert-butyl 4-(1-methylcyclobutane-1-carbonyl)piperazine-1-carboxylate (0.500 g, 1.77 mmol) and HCl/MeOH (1.2 mL, 4 M) in MeOH (1.0 mL) was stirred at r.t. for 2 h. The reaction mixture was concentrated under reduced pressure. The crude product was triturated with EtOAc (1.0 mL) at r.t. for 2 h. The solid was collected by filtration to afford the title compound as HCl salt (0.250 g, 64.5% yield) as a white solid. $^1H$ NMR: (400 MHz, DMSO-$d_6$) δ 9.14 (s, 2H), 3.48-3.63 (m, 4H), 3.05-3.08 (m, 4H), 2.38-2.50 (m, 3H), 1.92-1.95 (m, 1H), 1.80-1.81 (m, 2H), 1.61-1.63 (m, 1H), 1.35 (s, 3H). LCMS calc. for $C_{10}H_{19}N_2O$ $[M+H]^+$: m/z=183.1; Found: 183.2.

The following Intermediates listed in Table 12 were prepared by using an appropriate amine and an acid as the methods analogous to those described for preparing Intermediate 10.

TABLE 12

Preparations of Intermediates (Int)

| Int # | Structure | Name | $[M + H]^+$: Calc./Found and/or $^1$HNMR |
|---|---|---|---|
| 11 | 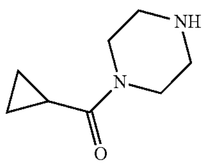 [SMILES: O=C(C1CC1)N1CCNCC1] | cyclopropyl (piperazin-1-yl) methanone | $^1H$ NMR: (400 MHz, DMSO-$d_6$) δ 9.47 (s, 1H), 3.91 (s, 2H), 3.68 (s, 2H), 3.08 (s, 4H), 0.75 (t, J = 4.0 Hz, 4H). |
| 12 | 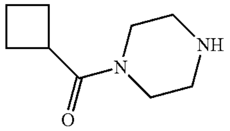 [SMILES: O=C(C1CCC1)N1CCNCC1] | cyclobutyl (piperazin-1-yl) methanone | $^1H$ NMR: (400 MHz, DMSO-$d_6$) δ 9.88 (s, 1H), 9.53 (s, 2H), 3.63-3.67 (m, 2H), 3.53-3.58 (m, 2H), 3.35-3.39 (m, 1H), 3.00-3.03 (m, 4H), 2.06-2.20 (m, 4H), 1.81-1.90 (m, 1H), 1.65-1.76 (m, 1H). |
| 13 | 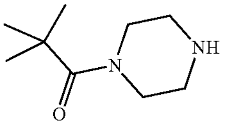 | 2,2-dimethyl-1-(piperazin-1-yl) propan-1-one | $[M + H]^+$: 171.1/171.2. |
| 14 | 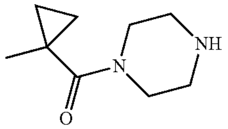 | (1-methylcyclopropyl) (piperazin-1-yl)methanone | $^1H$ NMR: (400 MHz, DMSO-$d_6$) δ 9.48 (s, 2H), 5.48 (s, 1H), 3.75 (s, 4H), 3.07 (s, 4H), 1.22 (s, 3H), 0.82-0.84 (m, 2H), 0.52-0.55 (m, 2H). |
| 15 | 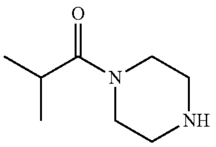 | 2-methyl-1-(piperazin-1-yl)propan-1-one | $^1H$ NMR: (400 MHz, DMSO-$d_6$) δ 9.41 (s, 2H), 3.70 (d, J = 21.2 Hz, 4H), 3.05 (d, J = 12.8 Hz, 4H), 2.85-2.89 (m, 1H), 0.99 (d, J = 6.8 Hz, 6H). |
| 16 | 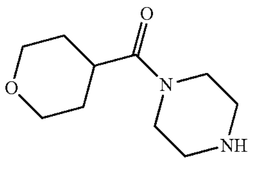 [SMILES: O=C(C1CCOCC1)N1CCNCC1] | piperazin-1-yl (tetrahydro-2H-pyran-4-yl)methanone | $^1H$ NMR: (400 MHz, DMSO-$d_6$) δ 9.29 (s, 2H), 3.82-3.86 (m, 2H), 3.70 (d, J = 33.2 Hz, 4H), 3.36-3.39 (m, 3H), 3.04-3.07 (m 4H), 2.85-2.92 (m, 1H), 1.53-1.62 (m, 4H). |
| 17 | 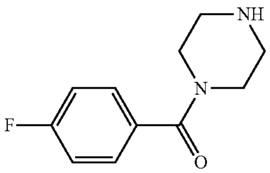 [SMILES: O=C(c1ccc(F)cc1)N1CCNCC1] | (4-fluorophenyl) (piperazin-1-yl)methanone | $^1H$ NMR: (400 MHz, DMSO-$d_6$) δ 9.37 (s, 2H), 7.52-7.56 (m, 2H), 7.28-7.32 (m, 2H), 3.68 (s, 4H), 3.14 (s, 4H). $[M + H]^+$: m/z = 209.1/209.1. |

TABLE 12-continued

| Preparations of Intermediates (Int) | | | |
|---|---|---|---|
| Int # | Structure | Name | $[M + H]^+$: Calc./Found and/or $^1$HNMR |
| 18 | 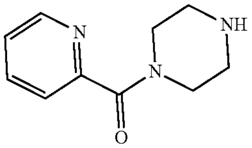 [SMILES: O=C(c1ccccn1)N1CCNCC1] | piperazin-1-yl (pyridin-2-yl)methanone | $^1$H NMR: (400 MHz, DMSO-$d_6$) δ 9.53 (s, 2H), 8.61-8.63 (m, 1H), 7.97-8.01 (m, 1H), 7.67-7.70 (m, 1H), 7.53-7.58 (m, 1H), 3.89 (s, 2H), 3.71 (s, 2H), 3.18 (s, 2H), 3.10 (s, 2H). $[M + H]^+$: 192.1/192.2. |
| 19 | 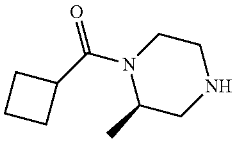 | (R)-cyclobutyl(2-methylpiperazin-1-yl)methanone | $^1$H NMR: (400 MHz, DMSO-$d_6$) δ 4.70 (s, 1H), 4.14-4.38 (m, 1H), 3.65 (d, J = 12.4 Hz, 1H), 3.14 (d, J = 12.8 Hz, 2H), 2.99 (s, 1H), 2.82 (s, 1H), 1.93-2.08 (m, 4H), 1.86-1.90 (m, 1H), 1.75 (s, 1H), 1.11-1.31 (m, 3H). |
| 20 | 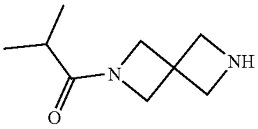 | 2-methyl-1-(2,6-diazaspiro[3.3] heptan-2-yl)propan-1-one | $[M + H]^+$: 169.1/169.0. |
| 21 | 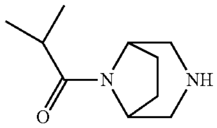 | 1-(3,8-diazabicyclo [3.2.1]octan-8-yl)-2-methylpropan-1-one | $[M + H]^+$: 183.1/183.0. |
| 22 | 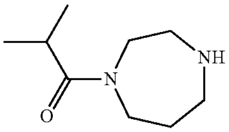 | 1-(1,4-diazepan-1-yl)-2-methylpropan-1-one | $[M + H]^+$: 171.1/171.0 |
| 23 | 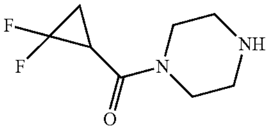 [SMILES: O=C(C1CC1(F)F)N1CCNCC1] | (2,2-difluorocyclopropyl) (piperazin-1-yl)methanone | $[M + H]^+$: 191.1/191.0 |
| 24 | 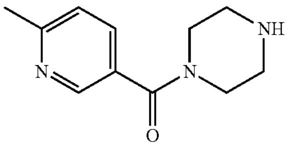 | (6-methylpyridin-3-yl)(piperazin-1-yl)methanone | $^1$H NMR (400 MHz, DMSO-$d_6$) δ 9.66-9.76 (m, 2H), 8.83 (d, J = 1.6 Hz, 1H), 8.29 (d, J = 8.4 Hz, 1H), 7.79 (d, J = 8.0 Hz, 1H), 3.60-3.85 (m, 4H), 3.15 (s, 4H), 2.70 (s, 3H). |
| 25 | 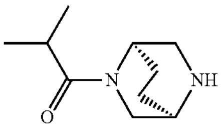 | 1-((1R,4R)-2,5-diazabicyclo[2.2.2] octan-2-yl)-2-methylpropan-1-one | $[M + H]^+$: 183.1/183.1 |
| 26 | 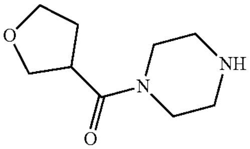 [SMILES: O=C(C1CCOC1)N1CCNCC1] | piperazin-1-yl (tetrahydrofuran-3-yl)methanone | $[M + H]^+$: 185.1/185.0 |
| 27 | 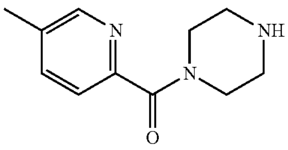 | (5-methylpyridin-2-yl)(piperazin-1-yl)methanone | $^1$H NMR: (400 MHz, DMSO-$d_6$) δ 9.57-9.67 (m, 1H), 8.50 (s, 1H), 7.87 (d, J = 6.4 Hz, 1H), 7.64 (d, J = 8.0 Hz, 1H), 3.88 (s, 2H), 3.75 (s, 2H), 3.15 (d, J = 26.4 Hz, 4H), 2.38 (s, 3H). |

TABLE 12-continued

| Preparations of Intermediates (Int) | | | |
|---|---|---|---|
| Int # | Structure | Name | $[M + H]^+$: Calc./Found and/or $^1$HNMR |
| 28 | 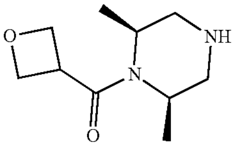 | ((2S,6R)-2,6-dimethylpiperazin-1-yl)(oxetan-3-yl)methanone | $[M + H]^+$: 199.1/199.2 |
| 29 | 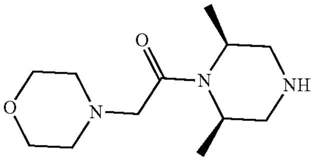 [SMILES: C[C@@H]1CNC[C@H](C)N1C(=O)CN1CCOCC1] | 1-((2S,6R)-2,6-dimethylpiperazin-1-yl)-2-morpholinoethan-1-one | $[M + H]^+$: 242.2/242.6 |
| 30 | 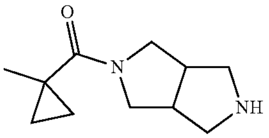 | (hexahydropyrrolo [3,4-c]pyrrol-2(1H)-yl)(1-methylcyclopropyl) methanone | $[M + H]^+$: 195.1/195.0 |

Intermediate 31: N-Ethyl-N-methylpiperazine-1-carboxamide

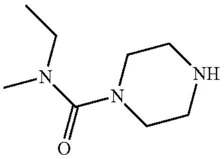

Step 1: tert-butyl 4-(ethyl(methyl)carbamoyl)piperazine-1-carboxylate

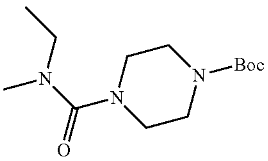 [SMILES: CCN(C)C(=O)N1CCN(C(=O)OC(C)(C)C)CC1]

To a solution of tert-butyl piperazine-1-carboxylate (3.00 g, 13.5 mmol) in DMF (21 mL) was added N-ethyl-N-methyl-carbamoyl chloride (1.97 g, 16.2 mmol) and DIPEA (8.70 g, 67.4 mmol). The mixture was stirred at r.t. overnight. The reaction mixture was diluted with $H_2O$ (100 mL) and extracted with MTBE (80 mL×3). The combined organic layers were washed with brine, dried over $Na_2SO_4$, filtered and concentrated under reduced pressure. The residue was purified by flash chromatography on a silica gel column eluting with EtOAc/PE (2-100%) to afford the title product (1.3 g, 35.5% yield) as a white solid. LCMS calc. for $C_9H_{18}N_3O_3$ $[M-56+H]^+$: m/z=216.2; Found: 216.1.

Step 2: N-ethyl-N-methylpiperazine-1-carboxamide

This compound was prepared as HCl salt using procedures analogous to those described for Intermediate 10 Step 2. $^1$H NMR: (400 MHz, DMSO-$d_6$) δ 3.49 (s, 1H), 3.25-3.28 (m, 4H), 3.11-3.16 (m, 2H), 3.06 (s, 4H), 2.76 (s, 3H), 1.05 (d, J=7.2 Hz, 3H). LCMS calc. for $C_8H_{18}N_3O$ $[M+H]^+$: m/z=172.1; Found: 171.9.

The following Intermediates listed in Table 13 were prepared by using an appropriate amine and an acyl chloride as the methods analogous to those described for preparing Intermediate 31.

TABLE 13

| Preparations of Intermediates (Int) | | | |
|---|---|---|---|
| Int # | Structure | Name | $[M + H]^+$: Cacl./Found and/or $^1$HNMR |
| 32 | 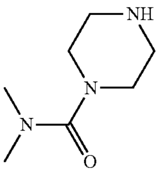 | N,N-dimethylpiperazine-1-carboxamide | $^1$H NMR: (400 MHz, DMSO-$d_6$) δ 9.16 (s, 2H), 3.27-3.30 (m, 4H), 3.06 (s, 4H), 2.76 (s, 6H). |

TABLE 13-continued

Preparations of Intermediates (Int)

| Int # | Structure | Name | [M + H]$^+$: Cacl./Found and/or $^1$HNMR |
|---|---|---|---|
| 33 | 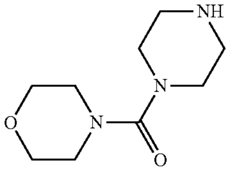 [SMILES: O=C(N1CCNCC1)N1CCOCC1] | morpholino(piperazin-1-yl)methanone | $^1$H NMR: (400 MHz, DMSO-$d_6$) δ 9.26 (s, 2H), 3.83 (s, 4H), 3.39 (t, J = 4.8 Hz, 4H), 3.17 (t, J = 4.4 Hz, 4H), 3.06 (s, 4H). [M + H]$^+$: 200.1/200.0. |
| 34 | 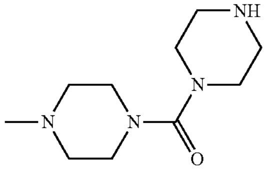 | (4-methylpiperazin-1-yl)(piperazin-1-yl)methanone | $^1$H NMR: (400 MHz, DMSO-$d_6$) δ 12.7 (s, 1H)., 9.24 (s, 2H), 3.67-3.70 (m, 2H), 3.55 (s, 2H), 3.38-3.44 (m, 8H), 3.08-3.09 (m, 4H). |
| 35 | 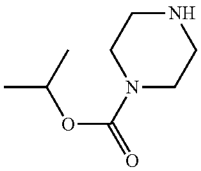 | isopropyl piperazine-1-carboxylate | $^1$H NMR: (400 MHz, DMSO-$d_6$) δ 9.30-9.36 (m, 2H), 4.76-4.83 (m, 1H), 3.58 (s, 4H), 3.06 (s, 4H), 1.19-1.21 (m, 6H). |
| 36 | 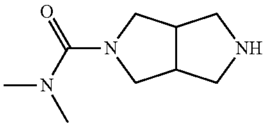 | N,N-dimethylhexahydropyrrolo[3,4-c]pyrrole-2(1H)-carboxamide | [M + H]$^+$: 184.1/183.7 |
| 37 | 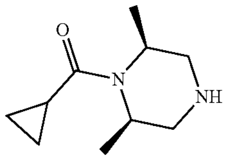 | cyclopropyl((2S,6R)-2,6-dimethylpiperazin-1-yl)methanone | [M + H]$^+$: 183.1/183.1 |
| 38 | 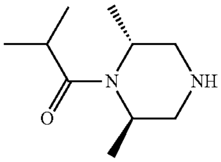 | 1-((2R,6R)-2,6-dimethylpiperazin-1-yl)-2-methylpropan-1-one | [M + H]$^+$: 185.2/185.0 |
| 39 | 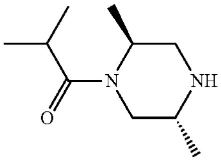 | 1-((2S,5R)-2,5-dimethylpiperazin-1-yl)-2-methylpropan-1-one | [M + H]$^+$: 185.2/185.0 |
| 40 | 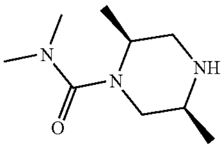 | 1-((2S,5S)-2,5-dimethylpiperazin-1-yl)-2-methylpropan-1-one | [M + H]$^+$: 185.2/185.0 |
| 41 | 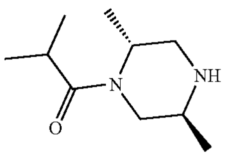 | 1-((2R,5S)-2,5-dimethylpiperazin-1-yl)-2-methylpropan-1-one | [M + H]$^+$: 185.2/184.9 |

TABLE 13-continued

Preparations of Intermediates (Int)

| Int # | Structure | Name | $[M + H]^+$: Cacl./Found and/or $^1$HNMR |
|---|---|---|---|
| 42 | 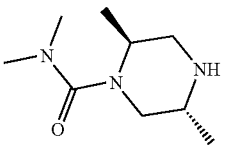 | (2S,5R)-N,N,2,5-tetramethylpiperazine-1-carboxamide | $^1$H NMR: (400 MHz, $CDCl_3$) δ 3.76 (s, 1H), 3.44-3.06 (m, 6H), 2.91 (s, 6H), 2.87 (s, 3H), 1.32 (s, 3H) |
| 43 | 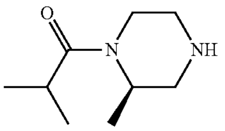 | (R)-2-methyl-1-(2-methylpiperazin-1-yl)propan-1-one | $^1$H NMR (400 MHz, $CD_3OD$) δ 4.15 (s, 1H), 3.36 (d, J = 12.8 Hz, 2H), 3.26-3.28 (m, 3H), 2.87-2.94 (m, 2H), 1.08 (d, J = 6.8 Hz, 9H). |
| 44 | 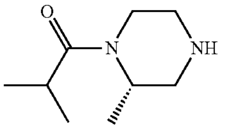 | (S)-2-methyl-1-(2-methylpiperazin-1-yl)propan-1-one | $^1$H NMR (400 MHz, $CD_3OD$) δ 4.15 (s, 1H), 3.34-3.40 (m, 2H), 3.20-3.23 (m, 2H), 3.04-3.09 (m, 1H), 2.90-2.97 (m, 2H), 1.10-1.13 (m, 9H) |
| 45 | 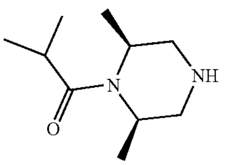 | 1-((2S,6R)-2,6-dimethylpiperazin-1-yl)-2-methylpropan-1-one | $[M + H]^+$: 185.2/185.0 |
| 47 | 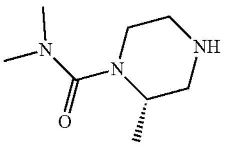 | (S)-N,N,2-trimethylpiperazine-1-carboxamide | $^1$H NMR (400 MHz, $CD_3OD$) δ 3.85-3.94 (m, 1H), 3.35-3.44 (m, 2H), 3.24-3.29 (m, 2H), 3.14-3.20 (m, 2H), 2.90 (s, 6H), 1.32 (d, J = 7.2 Hz, 3H). |

Intermediate 48: 1-(cyclopropylmethyl)piperazin-2-one

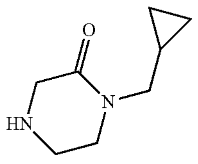 [SMILES: O=C1CNCCN1CC1CC1]

Step 1: tert-butyl 4-(cyclopropylmethyl)-3-oxopiperazine-1-carboxylate

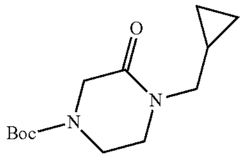 [SMILES: CC(C)(C)OC(=O)N1CCN(CC2CC2)C(=O)C1]

To a solution of tert-butyl 3-oxopiperazine-1-carboxylate (1.00 g, 4.99 mmol) in THF (20 mL) was added t-BuOK solution (1 M in THF, 7.49 mL). The reaction mixture was stirred at 20° C. for 20 min., followed by addition of (bromomethyl)cyclopropane (1.01 g, 7.49 mmol) at 0° C. The mixture was stirred at 20° C. for 2 h. The reaction mixture was diluted with $H_2O$ (30 mL), extracted with EtOAc (50 mL×3). The combined organic layers were washed with brine (40 mL×2), dried over $Na_2SO_4$, filtered and concentrated under reduced pressure to afford the title compound (800 mg) as a white oil. LCMS calc. for $C_{91}H_{15}N_2O_3$ $[M-56+H]^+$: m/z=199.2; Found: 198.9.

Step 2: 1-(cyclopropylmethyl)piperazin-2-one

This compound was prepared as HCl salt using procedures analogous to those described for Intermediate 10 Step 2. LCMS calc. for $C_8H_{15}N_2O$ $[M+H]^+$: m/z=155.1; Found: 154.8.

Intermediate 49: Piperazin-1-yl(pyrrolidin-1-yl)methanone

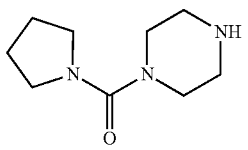 [SMILES: O=C(N1CCCC1)N1CCNCC1]

Step 1: tert-butyl 4-(1H-imidazole-1-carbonyl)piperazine-1-carboxylate

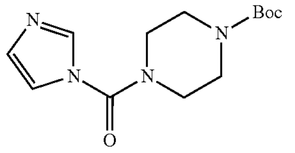 [SMILES: CC(C)(C)OC(=O)N1CCN(C(=O)n2ccnc2)CC1]

To a solution of tert-butyl piperazine-1-carboxylate (2.0 g, 10.7 mmol) in DCM (20.0 mL) was added TEA (1.20 g, 11.8 mmol) and CDI (1.74 g, 10.7 mmol) at 0° C. under $N_2$. The reaction mixture was stirred at 20° C. for 12 h. The mixture was diluted with $H_2O$ (20.0 mL), extracted with DCM (20.0 mL). The organic layer was washed with brine (20.0 mL), dried over $Na_2SO_4$, filtered and concentrated to afford the title compound (2.50 g, 83.0% yield) as white solid. $^1H$ NMR: (400 MHz, DMSO-$d_6$) δ 8.03 (s, 1H), 7.47 (s, 1H), 7.04 (s, 1H), 3.43-3.49 (m, 8H), 1.41 (s, 9H).

Step 2: 1-(4-(tert-butoxycarbonyl)piperazine-1-carbonyl)-3-methyl-1H-imidazol-3-ium iodide

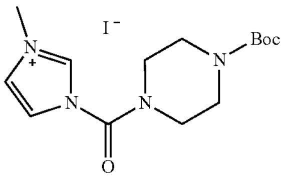 [SMILES: C[n+]1ccn(C(=O)N2CCN(C(=O)OC(C)(C)C)CC2)c1 ; [I-]]

To a solution of tert-butyl 4-(1H-imidazole-1-carbonyl)piperazine-1-carboxylate (2.00 g, 7.13 mmol) in MeCN (20.0 mL) was added MeI (4.05 g, 28.5 mmol) at 20° C. The reaction mixture was stirred at 20° C. for 12 h. The mixture was concentrated to afford the title compound (2.50 g, 83.0% yield) as white solid. $^1H$ NMR: (400 MHz, $CD_3OD$) δ 9.44 (s, 0.39H), 7.93 (d, J=2.4 Hz, 1H), 7.72 (d, J=2.0 Hz, 1H), 4.03 (s, 3H), 3.58-3.68 (m, 8H), 1.48 (s, 9H).

Step 3: tert-butyl 4-(pyrrolidine-1-carbonyl)piperazine-1-carboxylate

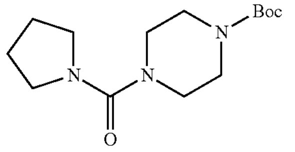 [SMILES: CC(C)(C)OC(=O)N1CCN(C(=O)N2CCCC2)CC1]

To a solution of 1-(4-(tert-butoxycarbonyl)piperazine-1-carbonyl)-3-methyl-1H-imidazol-3-ium iodide (1.00 g, 2.37 mmol) and TEA (719 mg, 7.10 mmol) in DCM (10.0 mL) was added pyrrolidine (337 mg, 4.74 mmol). The reaction mixture was stirred at 20° C. for 12 h. The mixture was diluted with $H_2O$ (20.0 mL), extracted with DCM (10.0 mL). The organic layer was washed with brine (10.0 mL), dried over $Na_2SO_4$, filtered and concentrated to afford the title compound (0.65 g, 96.9% yield) as off-white solid. $^1H$ NMR: (400 MHz, DMSO-$d_6$) δ 3.24-3.32 (m, 8H), 3.08-3.13 (m, 4H), 1.72-1.76 (m, 4H), 1.40 (s, 9H).

Step 4: piperazin-1-yl(pyrrolidin-1-yl)methanone

This compound was prepared as HCl salt using procedures analogous to those described for Intermediate 10 Step 2. $^1H$ NMR: (400 MHz, DMSO-$d_6$) δ 9.39 (s, 2H), 7.44 (br.s, 2H), 3.34-3.38 (m, 4H), 3.25-3.29 (m, 4H), 3.02-3.06 (m, 4H), 1.73-1.77 (m, 4H).

Intermediate 50: Azetidin-1-yl(piperazin-1-yl)methanone

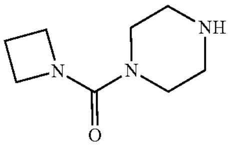 [SMILES: O=C(N1CCC1)N1CCNCC1]

This compound was prepared using procedures analogous to those described for Intermediate 49 Step 1-4 using azetidine to replace pyrrolidine to afford the title compound as white solid. $^1H$ NMR: (400 MHz, DMSO-$d_6$) δ 9.51 (d, J=1.2 Hz, 1H), 9.42 (s, 2H), 6.71 (s, 5H), 3.66-3.57 (m, 2H), 3.55-3.52 (m, 4H), 3.14 (d, J=6.8 Hz, 2H), 3.03 (d, J=15.2 Hz, 4H), 1.90-1.83 (m, 2H).

Intermediate 51: N-Methyl-N-(2,2,2-trifluoroethyl)piperazine-1-carboxamide

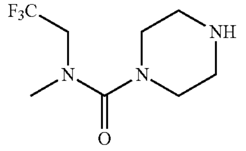

Step 1: tert-butyl 4-((2,2,2-trifluoroethyl)carbamoyl)piperazine-1-carboxylate

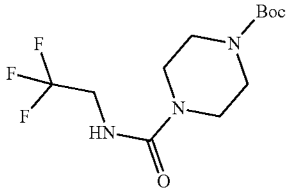 [SMILES: CC(C)(C)OC(=O)N1CCN(C(=O)NCC(F)(F)F)CC1]

This compound was prepared using procedures analogous to those described for Intermediate 49 Step 1-3 using 2,2,2-trifluoroethan-1-amine to replace pyrrolidine to afford the title compound as white solid. $^1H$ NMR: (400 MHz, DMSO-$d_6$) δ 3.87-3.93 (m, 2H), 3.37 (s, 7H), 3.16-3.19 (m, 1H), 1.47 (s, 9H).

Step 2: tert-butyl 4-(methyl(2,2,2-trifluoroethyl) carbamoyl)piperazine-1-carboxylate

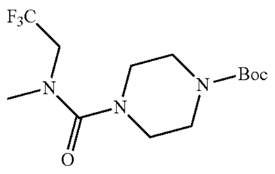 [SMILES: CN(CC(F)(F)F)C(=O)N1CCN(C(=O)OC(C)(C)C)CC1]

To a solution of tert-butyl 4-((2,2,2-trifluoroethyl)carbamoyl)piperazine-1-carboxylate (0.40 g, 1.28 mmol) in THF (2 mL) was added NaH (309 mg, 7.71 mmol, 60% in mineral oil) at 0~5° C., followed by addition of Mel (1.09 g, 7.71 mmol) at 0~5° C. The reaction mixture was stirred at 20~25° C. for 12 h., and poured into ice-water (10 mL). The resulting mixture was extracted with EtOAc (5 mL×3). The combined organic phase was washed with brine (10 mL), dried over anhydrous $Na_2SO_4$, filtered and concentrated under reduced pressured. The residue was purified by flash chromatography on a silica gel column eluting with EtOAc/PE (0-100%) to afford the title compound (0.12 g, 28.7% yield) as white solid. $^1H$ NMR: (400 MHz, $CDCl_3$) δ 3.91-3.94 (m, 2H), 3.43-3.46 (m, 4H), 3.24-3.26 (m, 4H), 3.01 (s, 3H), 1.46 (s, 9H).

Step 3: N-methyl-N-(2,2,2-trifluoroethyl)piperazine-1-carboxamide

This compound was prepared as HCl salt using procedures analogous to those described for Intermediate 10 Step 2. LCMS calc. for $C_8H_{15}F_3N_3O$ $[M+H]^+$: m/z=226.1; Found: 225.6.

Intermediate 52: 4-Methoxy-4-(trifluoromethyl)piperidine

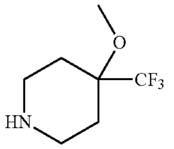

Step 1: tert-butyl 4-hydroxy-4-(trifluoromethyl) piperidine-1-carboxylate

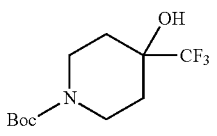

To a solution of 4-(trifluoromethyl)piperidin-4-ol (1.20 g, 7.09 mmol) in DCM (12 mL) was added $Boc_2O$ (1.86 g, 8.51 mmol, 1.96 mL) and TEA (1.44 g, 14.2 mmol) at 20~25° C. The reaction mixture was stirred at 20~25° C. for 12 h. The mixture was concentrated under reduced pressure. The residue was purified by flash chromatography on a silica gel column eluting with EtOAc/PE (0-10%) to afford the title compound (1.30 g, 68.1% yield) as white solid. $^1H$ NMR (400 MHz, DMSO-$d_6$) δ 6.01 (s, 1H), 3.94 (d, J=8.0 Hz, 2H), 3.01 (s, 2H), 1.70 (d, J=8.0 Hz, 2H), 1.54-1.62 (m, 2H), 1.46 (s, 9H).

Step 2: tert-butyl 4-methoxy-4-(trifluoromethyl) piperidine-1-carboxylate

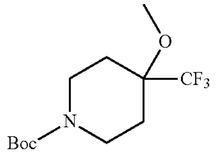 [SMILES: COC1(C(F)(F)F)CCN(C(=O)OC(C)(C)C)CC1]

To a solution of tert-butyl 4-hydroxy-4-(trifluoromethyl) piperidine-1-carboxylate (1.30 g, 4.83 mmol) in THF (13 mL) was added NaH (386 mg, 9.66 mmol, 60% in mineral oil) at 0~5° C., followed by the addition of iodomethane (1.37 g, 9.66 mmol) at 0~5° C. The rection mixture was stirred at 20~25° C. for 12 h. The mixture was poured into ice-water (20 mL), extracted with EtOAc (10 mL×3). The combined organic phase was washed with brine (30 mL), dried with $Na_2SO_4$, filtered and concentrated under reduced pressure. The residue was purified by flash chromatography on a silica gel column eluting with EtOAc/PE (0-100%) to afford the title compound (700 mg, 51.2% yield) as yellow oil. $^1H$ NMR (400 MHz, DMSO-$d_6$) δ 3.89 (d, J=8.0 Hz, 2H), 3.37 (s, 3H), 2.86 (s, 2H), 1.92 (d, J=16.0 Hz, 2H), 1.52-1.60 (m, 2H), 1.41 (s, 9H).

Step 3: 4-methoxy-4-(trifluoromethyl)piperidine

This compound was prepared as HCl salt using procedures analogous to those described for Intermediate 10 step 2. $^1H$ NMR (400 MHz, DMSO-$d_6$) δ 9.24 (s, 2H), 3.37 (s, 3H), 3.25 (d, J=16.0 Hz, 2H), 2.90 (s, 2H), 2.02-2.07 (m, 4H).

Intermediate 53: 2-Piperazin-1-ylpyrimidine

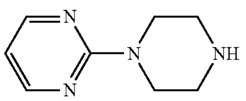 [SMILES: c1cnc(N2CCNCC2)nc1]

Step 1: tert-butyl 4-pyrimidin-2-ylpiperazine-1-carboxylate

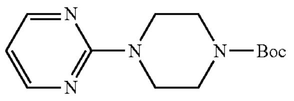 [SMILES: CC(C)(C)OC(=O)N1CCN(c2ncccn2)CC1]

To a solution of tert-butyl piperazine-1-carboxylate (5.0 g, 22.5 mmol) in EtOH (25 mL) was added TEA (4.54 g, 44.9 mmol) and 2-bromopyrimidine (3.93 g, 24.7 mmol). The reaction mixture was stirred at 50° C. for 16 h. The mixture was concentrated under reduced pressure to afford the title compound (4.0 g, 67.4% yield) as a yellow oil. $^1$H NMR: (400 MHz, $CDCl_3$) δ 8.34 (d, J=4.4 Hz, 2H), 6.54 (t, J=4.4 Hz, 1H), 3.83 (t, J=5.2 Hz, 4H), 3.52 (t, J=5.6 Hz, 4H), 1.51 (s, 9H). LCMS calc. for $C_{13}H_{21}N_4O_2$ $[M+H]^+$: m/z=265.2; Found: 265.2.

Step 2: 2-piperazin-1-ylpyrimidine

To a solution of tert-butyl 4-pyrimidin-2-ylpiperazine-1-carboxylate (2.00 g, 7.57 mmol) in MeOH (10 mL) was added HCl/MeOH (4M, 10 mL). The reaction mixture was stirred at 20° C. for 12 h. The reaction mixture was concentrated under reduced pressure to afford the title compound (0.9 g, 72.4% yield) as a white solid. $^1$H NMR: (400 MHz, $D_2O$) δ 8.50 (d, J=5.2 Hz, 2H), 6.96 (d, J=4.8 Hz, 1H), 4.04 (t, J=4.8 Hz, 4H), 3.36 (t, J=5.6 Hz, 4H). LCMS calc. for $C_8H_{13}N_4[M+H]^+$: m/z=165.1; Found: 165.0.

Intermediate 54: 3-(Piperazin-1-yl)pyridazine

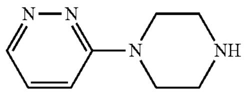 [SMILES: c1cnnc(N2CCNCC2)c1]

This compound was prepared as HCl salt using procedures analogous to those described for Intermediate 53 by using 6-chloropyridazine to replace 2-bromopyrimidine in Step 1. $^1$H NMR: (400 MHz, $D_2O$) δ 8.72 (dd, J=14.4, 6.0 Hz, 1H), 7.85-8.04 (m, 2H), 4.00 (t, J=5.2 Hz, 4H), 3.42 (t, J=5.6 Hz, 4H). LCMS calc. for $C_8H_{13}N_4[M+H]^+$: 165.1; Found: 165.2.

Intermediate 55: 2-(Piperazin-1-yl)thiazole

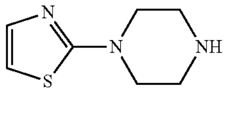 [SMILES: c1csc(N2CCNCC2)n1]

This compound was prepared as HCl salt using procedures analogous to those described for Intermediate 53 by using 2-chlorothiazole to replace 2-bromopyrimidine in Step 1. $^1$H NMR: (400 MHz, DMSO-$d_6$) 7.24 (d, J=4.4 Hz, 1H), 6.97 (d, J=4.4 Hz, 1H), 3.87 (t, J=5.2 Hz, 4H), 3.44 (t, J=5.6 Hz, 4H). LCMS calc. for $C_7H_{12}N3S$ $[M+H]^+$: 170.1; Found: 170.0.

Intermediate 56: (R)-1-(3-((tert-Butyldimethylsilyl) oxy)pyrrolidine-1-carbonyl)-3-methyl-1H-imidazol-3-ium iodide

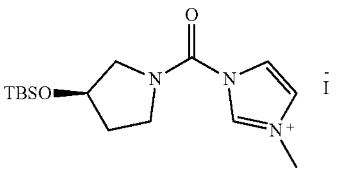

Step 1: (R)-3-((tert-butyldimethylsilyl)oxy)pyrrolidine

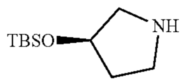

To a solution of (R)-pyrrolidin-3-ol (1 g, 11.5 mmol) in DCM (20 mL) was added DIPEA (2.2 g, 17.0 mmol), followed by addition of a solution of tert-butylchlorodimethylsilane (1.9 g, 12.6 mmol) in DCM (5 mL). The reaction mixture was stirred at 0-5° C. for 1 h, then stirred at rt for 1 h. The reaction mixture was quenched with $H_2O$ (10 mL), the organic layer was collected and the aqueous layer was extracted with DCM (20 mL×2). The combined organic layers were washed with brine (10 mL), dried over anhydrous $Na_2SO_4$, filtered and concentrated under reduced pressure to afford the title compound (1.8 g, 78% yield) as light yellow oil. LCMS calc. for $C_{10}H_{24}NOSi$ $[M+H]^+$: m/z=202.2; Found: 202.2.

Step 2: (R)-(3-((tert-butyldimethylsilyl)oxy)pyrrolidin-1-yl)(1H-imidazol-1-yl)methanone

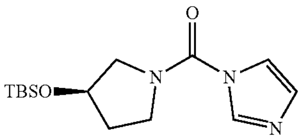 [SMILES: CC(C)(C)[Si](C)(C)O[C@@H]1CCN(C(=O)n2ccnc2)C1]

To a solution of (R)-3-((tert-butyldimethylsilyl)oxy)pyrrolidine (1.8 g, 8.9 mmol) in THF (50 mL) was added DIPEA (1.7 g, 13.2 mmol) and CDI (1.6 g, 9.9 mmol). The reaction mixture was stirred at rt for 1.5 h. The reaction mixture was concentrated under reduced pressure, the crude product was purified by flash chromatography on a silica column eluting with EtOAc/PE (30-100%) to afford the title compound (590 mg, 22.6% yield) as colorless oil. LCMS calc. for $C_{14}H_{26}N_3O_2Si$ $[M+H]^+$: m/z=296.2; Found: 296.3.

Step 3: (R)-1-(3-((tert-butyldimethylsilyl)oxy)pyrrolidine-1-carbonyl)-3-methyl-1H-imidazol-3-ium iodide To a solution of (R)-(3-((tert-butyldimethylsilyl)oxy)pyrrolidin-1-yl)(1H-imidazol-1-yl)methanone (590 mg, 2 mmol) in ACN (10 mL) was added iodomethane (1.1 g, 7.96 mmol). The reaction mixture was stirred at rt overnight. The reaction mixture was concentrated under reduced pressure to afford the title compound (610 mg, 69.9% yield) as light yellow solid. LCMS calc. for $C_{15}H_{28}IN_3O_2Si$ $[M]^+$: m/z=310.2; Found: 310.3.

Intermediate 57: (S)-1-(3-((tert-Butyldimethylsilyl)oxy)pyrrolidine-1-carbonyl)-3-methyl-1H-imidazol-3-ium iodide

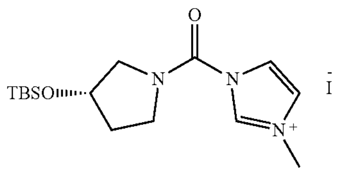

The Intermediate 78 was prepared using procedures analogous to those described for Intermediate 56 using (S)-pyrrolidin-3-ol to replace (R)-pyrrolidin-3-ol. LCMS calc. for $C_{15}H_{28}IN_3O_2Si$ $[M]^+$: m/z=310.2; Found: 310.3.

Intermediate 58: 3-Methyl-1-(morpholine-4-carbonyl)-1H-imidazol-3-ium iodide

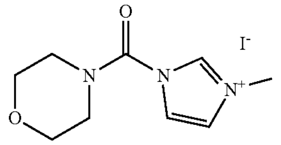

The Intermediate 81 was prepared using procedures analogous to those described for Intermediate 56 Step 2-3 using morpholino to replace (R)-3-((tert-butyldimethylsilyl)oxy)pyrrolidine. LCMS calc. for $C_9H_{14}$N302+$[M]^+$: m/z=196.1; Found: 196.1.

Intermediate 59: (S)-2-methyl-1-(2,2,2-trifluoroethyl)piperazine

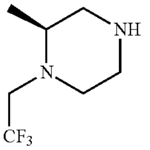

Step 1: tert-butyl (S)-3-methyl-4-(2,2,2-trifluoroethyl)piperazine-1-carboxylate

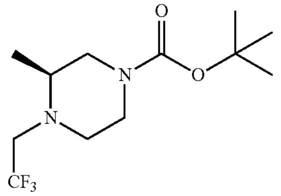 [SMILES: C[C@H]1CN(C(=O)OC(C)(C)C)CCN1CC(F)(F)F]

To a mixture of tert-butyl (S)-3-methylpiperazine-1-carboxylate (1 g, 5.0 mmol) and DBU (2.28 g, 15.0 mmol) in DMF (10 mL) was added 2,2,2-trifluoroethyl trifluoromethanesulfonate (2.32 mg, 10.0 mmol) dropwise at r.t. The mixture was stirred at 80° C. overnight. The reaction mixture was quenched with water (50 mL) and extracted with EtOAc (50 mL×3). The combined organic layers were washed with brine (80 mL), dried over anhydrous $Na_2SO_4$, filtered and concentrated under reduced pressure. The residue was purified by flash chromatography on a silica gel column eluting with EtOAc/PE (5-20%) to afford tert-butyl (S)-3-methyl-4-(2,2,2-trifluoroethyl)piperazine-1-carboxylate (560 mg, 20% yield). LCMS calculated for $Cl_2H_{22}F_3N_2O_2[M+H]^+$: m/z=283.2; Found: 283.2.

Step 2: (S)-2-methyl-1-(2,2,2-trifluoroethyl)piperazine

To a solution of tert-butyl tert-butyl (S)-3-methyl-4-(2,2,2-trifluoroethyl)piperazine-1-carboxylate (560 mg, 1.98 mmol) in DCM (10 mL) was added TFA (2 mL). The mixture was stirred at r.t. for 5 h. The resulting mixture was evaporated under reduced pressure to afford (S)-2-methyl-1-(2,2,2-trifluoroethyl)piperazine as TFA salt (650 mg) without further purification. LCMS calc. for $C_7H_{14}F_3N_2$ $[M+H]^+$: m/z=183.1; Found: 183.2.

Intermediate 60: (3S,4R)-3-fluoro-4-methoxypiperidine

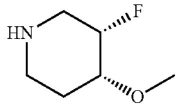

Step 1: tert-butyl (3S,4R)-3-fluoro-4-methoxypiperidine-1-carboxylate

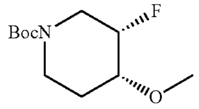

To a solution of tert-butyl (3S,4R)-3-fluoro-4-hydroxypiperidine-1-carboxylate (200 mg, 0.913 mmol) in THF (3.0 mL) was added NaH (109.6 mg, 1.83 mmol, 60% in mineral oil) and stirred for 30 min. $CH_3I$ (194.5 mg, 1.37 mmol) was added. The reaction mixture was stirred at 25° C. for 2 h. The mixture was quenched with $H_2O$, and extracted with EtOAc. The organic layer was dried over anhydrous $Na_2SO_4$, filtered and concentrated to give the title compound 212.6 mg as light yellow oil.

Step 2: (3S,4R)-3-fluoro-4-methoxypiperidine

To a solution of tert-butyl (3S,4R)-3-fluoro-4-methoxypiperidine-1-carboxylate (212.6 mg, 0.912 mmol) in DCM (5 mL) was added TFA (2.5 mL). The reaction mixture was stirred at 25° C. for 1 h. The mixture was concentrated under reduced pressure to afford the title compound (120 mg, 57.1%, TFA salt) as light yellow oil. LCMS calc. for $C_6H_{13}FNO$ $[M+H]^+$: m/z=134.1; Found: 134.1.

Intermediate 61: (3S,4S)-3-fluoro-4-methoxypiperidine

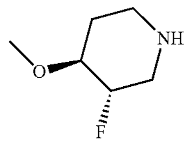

Step 1: tert-butyl (3S,4S)-3-fluoro-4-methoxypiperidine-1-carboxylate

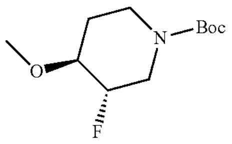 [SMILES: CO[C@H]1CCN(C(=O)OC(C)(C)C)C[C@@H]1F]

To a solution of tert-butyl (3S,4S)-3-fluoro-4-hydroxypiperidine-1-carboxylate (500 mg, 2.3 mmol) in THF (10 mL) was added portion of NaH (137 mg, 3.4 mmol, 60% in mineral oil) at 0° C. The mixture was stirred at 0° C. for 30 min, and then $CH_3I$ (388 mg, 2.7 mmol) was added at 0° C. The resulting mixture was stirred at room temperature for 2 h., quenched by water (10 mL), and then extracted with ethyl acetate (10 mL×3). The organic layer was washed with brine, dried over $Na_2SO_4$, filtered and concentrated under reduced pressure to afford the title compound (500 mg, 94% yield) as yellow oil. LCMS calc. for $C_{11}H_{21}FNO_3$ $[M+H]^+$: m/z=234.1; found: 234.1.

Step 2: (3S,4S)-3-fluoro-4-methoxypiperidine

To a solution of tert-butyl (3S,4S)-3-fluoro-4-methoxypiperidine-1-carboxylate (500 mg, 2.14 mmol) in DCM (5 mL) was added HCl solution (5 mL, 20 mmol, 4.0 M in 1,4-dioxane). The reaction mixture was stirred at r.t. for 5 h., and concentrated under reduced pressure to afford the title compound (200 mg, 80% yield) as white solid. LCMS calc. for $C_6H_{13}FNO$ $[M+H]^+$: m/z=134.1; Found: 134.1.

Intermediate 62: (3R,4S)-3-fluoro-4-methoxypiperidine

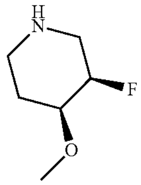

Step 1: tert-butyl (3R,4S)-3-fluoro-4-methoxypiperidine-1-carboxylate

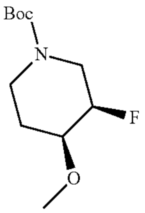 [SMILES: CO[C@H]1CCN(C(=O)OC(C)(C)C)C[C@H]1F]

To a solution of tert-butyl (3R,4S)-3-fluoro-4-hydroxypiperidine-1-carboxylate (500 mg, 2.3 mmol) in THF (10 mL) was added portion of NaH (137 mg, 3.4 mmol, 60% in mineral oil) at 0° C. The mixture was stirred at 0° C. for 30 min, then $CH_3I$ (388 mg, 2.7 mmol) was added at 0° C. The resulting mixture was stirred at r.t. for 2 h., quenched by water (10 mL), and then extracted with ethyl acetate (10 mL×3). The organic layer was washed with brine, dried over $Na_2SO_4$, filtered and concentrated under reduced pressure to afford the title compound (500 mg, 94% yield) as yellow oil. LCMS calc. for $C_{11}H_{21}FNO_3$ $[M+H]^+$: m/z=234.1; Found: 234.1.

Step 2: (3R,4S)-3-fluoro-4-methoxypiperidine

To a solution of tert-butyl (3R,4S)-3-fluoro-4-methoxypiperidine-1-carboxylate (500 mg, 2.14 mmol) in DCM (5 mL) was added HCl solution (4.0 M in 1,4-dioxane, 5 mL). The reaction mixture was stirred at r.t. for 5 h. The reaction mixture was concentrated under reduced pressure to afford the title compound (200 mg, 80% yield) as white solid. LCMS calc. for $C_6H_{13}FNO$ $[M+H]^+$: m/z=134.1; Found: 134.1.

Intermediate 63: (3S,4R)-3-fluoropiperidin-4-ol

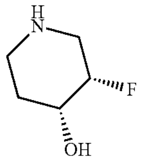

To a solution of tert-butyl (3S,4R)-3-fluoro-4-hydroxypiperidine-1-carboxylate (1.0 g, 2.14 mmol) in DCM (10 mL) was added HCl solution (4M in 1,4-dioxane, 10 mL). The reaction mixture was stirred at r.t. for 3 h., and concentrated under reduced pressure to afford the title compound (500 mg, 92% yield) as white solid. LCMS calc. for $C_5H_{11}FNO$ $[M+H]^+$: m/z=120.1; Found: 120.1.

Intermediate 64: (3S)-3-fluoro-N,N-dimethylpiperidin-4-amine

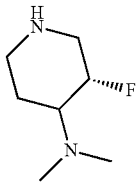

Step 1: tert-butyl (S)-3-fluoro-4-oxopiperidine-1-carboxylate

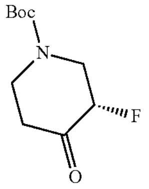

To a solution of tert-butyl (3S,4R)-3-fluoro-4-hydroxypiperidine-1-carboxylate (1.0 g, 4.6 mmol) in DCM (10 mL) was added Dess-Martin periodinane (1.16 g, 5.5 mmol). The reaction mixture was stirred at r.t. for 8 h. After concentrated under reduced pressure, the residue was purified by flash chromatography on a silica gel column eluting with DCM/EA (30-50%) to afford the title compound (500 mg, 51% yield) as white solid. LCMS calc. for $C_{10}H_{17}FNO_3$ $[M+H]^+$: m/z=218.1; Found: 218.1.

Step 2: tert-butyl (3S)-4-(dimethylamino)-3-fluoropiperidine-1-carboxylate

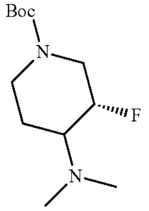

To a solution of tert-butyl (S)-3-fluoro-4-oxopiperidine-1-carboxylate (500 mg, 2.30 mmol) in DCM (10 mL) was added dimethylamine solution (2.3 mL, 4.6 mmol, 2.0 M in THF). The reaction mixture was stirred at r.t. for 30 min., $NaBH(OAc)_3$ (976 mg, 4.60 mmol) was added, and then stirred at r.t. for additional 2 h. The mixture was quenched with water (10 mL) and extracted with ethyl acetate (10 mL×3). The organic layer was washed with brine dried over $Na_2SO_4$, filtered and concentrated under reduced pressure to afford the title compound (300 mg, 51% yield) as yellow oil. LCMS calc. for $Cl_2H_{24}FN_2O_2[M+H]^+$: m/z=247.2; Found: 247.2.

Step 3: (3S)-3-fluoro-N,N-dimethylpiperidin-4-amine

To a solution of tert-butyl (3S)-4-(dimethylamino)-3-fluoropiperidine-1-carboxylate (300 mg, 1.22 mmol) in DCM (3 mL) was added HCl solution (3 mL, 12 mmol, 4M in 1,4-dioxane). The reaction mixture was stirred at room temperature for 3 h. The reaction mixture was concentrated under reduced pressure to give the title compound (130 mg, 73% yield) as a yellow solid. LCMS calc. for $C_7H_{15}FN_2$ $[M+H]^+$: m/z=147.2; Found: 147.2.

Intermediate 65: (S)-1-(2-Methoxyethyl)-2-methylpiperazine

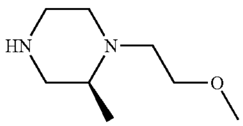

Step 1: tert-butyl (S)-4-(2-methoxyacetyl)-3-methylpiperazine-1-carboxylate

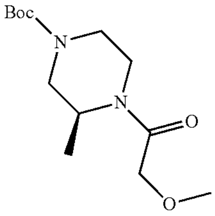 [SMILES: COCC(=O)N1CCN(C(=O)OC(C)(C)C)C[C@@H]1C]

A mixture of 2-methoxyacetic acid (0.9 g, 10 mmol), tert-butyl (S)-3-methylpiperazine-1-carboxylate (2.0 g, 10 mmol), HATU (4.56 g, 12 mmol) and TEA (1.51 g, 15 mmol) in DMF (20 mL) was stirred at r.t. overnight. The reaction mixture was quenched with water (100 mL), extracted with EA (80 mL×3). The combined organic layers were washed with brine, dried over $Na_2SO_4$, filtered and concentrated under reduced pressure. The residue was purified by flash chromatography on a silica gel column eluting with EtOAc/PE (50-80%) to afford the title compound (1.8 g, 66% yield) as a white solid. LCMS calc. for $C_{13}H_{25}N_2O_4$ $[M+H]^+$: m/z=273.2; Found: 273.2.

Step 2: tert-butyl (S)-4-(2-methoxyethyl)-3-methylpiperazine-1-carboxylate

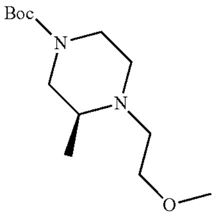 [SMILES: COCCN1CCN(C(=O)OC(C)(C)C)C[C@@H]1C]

A solution of tert-butyl (S)-4-(2-methoxyacetyl)-3-methylpiperazine-1-carboxylate (544 mg, 2.0 mmol) in $BH_3$-THF complex solution (10 mL, 10 mmol, 1.0M in THF) was stirred at 60° C. for 5 h. After cooled to 0° C., the reaction mixture was quenched with MeOH (10 mL) followed by aq. $Na_2CO_3$ (2.0 M, 50 mL), and then extracted with EtOAc (40 mL×3). The combined organic layers were washed with brine, dried over $Na_2SO_4$, filtered and then concentrated under reduced pressure to afford the title compound (500 mg, 95%). LCMS calc. for $C_{13}H_{27}N_2O_3$ $[M+H]^+$: m/z=259.2; Found: 259.2.

Step 3: (S)-1-(2-methoxyethyl)-2-methylpiperazine

To a solution of tert-butyl (R)-3-oxotetrahydro-3H-oxazolo[3,4-a]pyrazine-7(1H)-carboxylate (500 mg, 1.94 mmol) in DCM (5 mL) was added HCl solution (4M in 1,4-dioxane, 5 mL). The reaction mixture was stirred at r.t. for 2 h., and concentrated under reduced pressure to afford the title compound (300 mg, 98% yield) as white solid. LCMS calc. for $C_8H_{19}N20$ $[M+H]^+$: m/z=159.1; Found: 159.2.

Intermediate 66: (5,6,7,8-tetrahydro-1,7-naphthyridin-3-yl)methanol

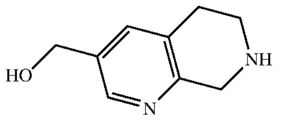 [SMILES: OCc1cnc2c(c1)CCNC2]

To a solution of 7-(tert-butyl) 3-methyl 5,8-dihydro-1,7-naphthyridine-3,7(6H)-dicarboxylate (500 mg, 1.7 mmol) in THF (10 mL) was added $BH_3$ in THF (6.8 mL, 6.8 mmol, 1M). The reaction mixture was stirred at 70° C. for 12 h. The mixture was quenched with MeOH (5 mL), and concentrated under reduced pressure. The residue was diluted with THF (5 mL), followed by addition of 4N HCl (7 mL). The mixture was stirred at r.t. for 6 h., then concentrated under reduced pressure to afford the title compound (510 mg, HCl salt) as light yellow oil which was directly used in next step. LCMS calc. for $C_9H_{13}N20$ $[M+H]^+$: m/z=165.1; Found: 165.2.

Example A: Biological Assays

PARG Enzymatic Activity Assay

HTRF assay was used to measure the ability of compounds to inhibit the activity of PARG in vitro. C-terminal His6-tag PARG expressed in *E. coli* was purified and stored at −80° C. in aliquots. Assay measurements were performed with 1×buffer comprising 50 mM Tris pH 7.4, 0.1 mg/mL BSA, 3 mM EDTA, 0.4 mM EGTA, 1 mM DTT, 50 mM KCl and 0.01% Tween 20. Compounds dissolved in DMSO were plated into a 384-well assay plate (PerkinElmer, Catalog #: 6008280) in duplicate using a dispenser (Labcyte, Echo 665), and tested on a 10-point 4-fold serial dilution. Add 5 μL Enzyme mix [hPARG (C-terminal His6-tag, 4.2 μM), 65 pM final] to the test wells. The plates were covered and left to incubate for 60 minutes at RT before the addition of 5 μL substrate mix [biotinylated-NAD ribosylated PARP1 (6.1 μM), 8 nM final] to initiate reaction. After incubating 10 minutes at RT, add 2.5 μL Streptavidin-Eu cryptate (Cisbio, Catalog #: 610SAKLA) and 2.5 μL Mab anti 6HIS-XL665 (Cisbio, Catalog #: 61HISXLA) to the plate, and incubate for 60 minutes at RT. Read on a multimode plate reader (PerkinElmer, Envision 2015) in time-resolved fluorescence (TRF) mode, with excitation at 337 nm and emission at both 620 nm and 665 nm. Average HTRF signal of high control (Wells with 1% DMSO) was calculated and as Vehicle Control (VC). Average HTRF signal of low control (no Enzyme) was calculated and as Positive control (PC).

$$\% \text{ Inhibition} = \left(\text{Signal}_{cmpd} - \text{Signal}_{Ave\_VC}\right) / \left(\text{Signal}_{Ave\_PC} - \text{Signal}_{Ave\_VC}\right) \times 100.$$

$IC_{50}$ values were determined by fitting the data to the standard 4 parameters with Hill Slope using GraphPad Prism software.

The compounds of the disclosure were found to be inhibitors of PARG according to the above-described assay. $IC_{50}$ data is proved below in Table 14: a "+" denotes an $IC_{50}$ value of >1 μM, a "++" denotes an $IC_{50}$ value of 0.1 μM<$IC_{50}$≤1 μM, and a "+++" denotes an $IC_{50}$ value of ≤0.1 μM.

Cell Viability Assay

Cell viability studies were conducted in Kuramochi cell line. Cells were maintained in RPMI (Hyclone, Catalog #: SH3080901B) supplemented with 10% v/v FBS (AusGeneX, Catalog #: FBS500-S), 1% v/v Penicillin Streptomycin (Gibco, Catalog #: 15140122). Cells were seeded in 96-well plates (PerkinElmer, Catalog #: 6005680) at a density of 400 cells/well. Compounds dissolved in DMSO were plated in duplicate using a multichannel pipette, and tested on a 9-point 3-fold serial dilution. Cells were incubated for 7 days in a 37° C. active humidified incubator at 5% $CO_2$. Cell viability was measured using the Cell Titer-Glo reagent (Promega, Catalog #: G7573) as manufacturer's instructions. Luminescence signal was measured with a multimode plate reader (Perkin Elmer, Envision 2105 or BMG, ClarioStar Plus). Average values of DMSO treated wells in a plate was calculated and as high control (HC). Average values of only medium in a plate was calculated and as low control (LC).

$$\% \text{ inhibition} = \left(\text{Signal}_{Ave\_HC} - \text{Signal}_{cmpd}\right) / \left(\text{Signal}_{Ave\_HC} - \text{Signal}_{Ave\_LC}\right) \times 100.$$

$IC_{50}$ values were determined by fitting the data to the standard 4 parameters with Hill Slope using GraphPad Prism software. $IC_{50}$ data is proved below in Table 14: a "+" denotes an $IC_{50}$ value of >1 μM, a "++" denotes an $IC_{50}$ value of 0.1 μM<$IC_{50}$≤1 μM, and a "+++" denotes an $IC_{50}$ value of ≤0.1 μM.

TABLE 14

| Ex. # | PARG enzymatic activity ($IC_{50}$) | PARG Cell viability ($IC_{50}$) |
|---|---|---|
| 1 | +++ | ++ |
| 2 | +++ | +++ |
| 3 | +++ | +++ |
| 4 | +++ | ++ |
| 5 | +++ | ++ |
| 6 | +++ | +++ |
| 7 | +++ | +++ |
| 8 | +++ | +++ |
| 9 | +++ | ++ |
| 10 | +++ | +++ |
| 11 | +++ | +++ |
| 12 | +++ | +++ |
| 13 | ++ | ++ |
| 14 | +++ | +++ |
| 15 | ++ | ++ |

TABLE 14-continued

| Ex. # | PARG enzymatic activity ($IC_{50}$) | PARG Cell viability ($IC_{50}$) |
|---|---|---|
| 16 | ++ | ++ |
| 17 | ++ | ++ |
| 18 | ++ | ++ |
| 19 | +++ | ++ |
| 20 | +++ | +++ |
| 21 | +++ | ++ |
| 22 | +++ | ++ |
| 23 | +++ | ++ |
| 24 | +++ | ++ |
| 25 | +++ | ++ |
| 26 | +++ | +++ |
| 27 | +++ | ++ |
| 28 | +++ | ++ |
| 29 | +++ | +++ |
| 30 | +++ | ++ |
| 31 | ++ | ++ |
| 32 | +++ | ++ |
| 33 | +++ | +++ |
| 34 | +++ | +++ |
| 35 | +++ | +++ |
| 36 | +++ | ++ |
| 37 | +++ | +++ |
| 38 | +++ | ++ |
| 39 | +++ | +++ |
| 40 | +++ | +++ |
| 41 | +++ | +++ |
| 42 | +++ | +++ |
| 43 | +++ | ++ |
| 44 | +++ | +++ |
| 45 | +++ | +++ |
| 46 | +++ | +++ |
| 47 | +++ | ++ |
| 48 | +++ | +++ |
| 49 | +++ | +++ |
| 50 | +++ | +++ |
| 51 | +++ | ++ |
| 52 | ++ | ++ |
| 53 | +++ | +++ |
| 54 | ++ | ++ |
| 55 | +++ | +++ |
| 56 | +++ | +++ |
| 57 | ++ | ++ |
| 58 | +++ | +++ |
| 59 | +++ | +++ |
| 60 | ++ | ++ |
| 61 | +++ | +++ |
| 62 | +++ | +++ |
| 63 | +++ | +++ |
| 64 | +++ | +++ |
| 65 | +++ | ++ |
| 66 | +++ | +++ |
| 67 | +++ | ++ |
| 68 | +++ | ++ |
| 69 | +++ | +++ |
| 70 | +++ | +++ |
| 71 | +++ | ++ |
| 72 | ++ | ++ |
| 73 | +++ | +++ |
| 74 | +++ | +++ |
| 75 | +++ | +++ |
| 76 | +++ | +++ |
| 77 | +++ | +++ |
| 78 | +++ | ++ |
| 79 | +++ | +++ |
| 80 | ++ | ++ |
| 81 | +++ | +++ |
| 82 | +++ | +++ |
| 83 | +++ | ++ |
| 84 | +++ | +++ |
| 85 | +++ | +++ |
| 86 | +++ | ++ |
| 87 | +++ | ++ |
| 88 | +++ | +++ |
| 89 | +++ | +++ |
| 90 | +++ | +++ |
| 91 | +++ | +++ |
| 92 | +++ | +++ |
| 93 | +++ | +++ |
| 94 | +++ | +++ |
| 95 | +++ | +++ |
| 96 | +++ | +++ |
| 97 | +++ | +++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 104 | +++ | ++ |
| 105 | +++ | +++ |
| 106 | +++ | +++ |
| 107 | +++ | +++ |
| 108 | +++ | +++ |
| 109 | +++ | +++ |
| 110 | +++ | +++ |
| 111 | +++ | +++ |
| 112 | +++ | ++ |
| 113 | +++ | +++ |
| 114 | +++ | ++ |
| 115 | +++ | +++ |
| 116 | +++ | +++ |
| 117 | +++ | +++ |
| 118 | +++ | +++ |
| 119 | +++ | +++ |
| 120 | +++ | +++ |
| 121 | +++ | +++ |
| 122 | +++ | +++ |
| 123 | +++ | +++ |
| 124 | +++ | ++ |
| 125 | +++ | ++ |
| 126 | +++ | ++ |
| 127 | +++ | ++ |
| 128 | +++ | ++ |
| 129 | +++ | ++ |
| 130 | +++ | ++ |
| 131 | +++ | +++ |
| 132 | +++ | +++ |
| 133 | +++ | +++ |
| 134 | +++ | +++ |
| 135 | +++ | +++ |
| 136 | +++ | +++ |
| 137 | +++ | ++ |
| 138 | +++ | ++ |
| 139 | +++ | +++ |
| 140 | +++ | +++ |
| 141 | +++ | ++ |
| 142 | +++ | +++ |
| 143 | +++ | ++ |
| 144 | +++ | +++ |
| 145 | +++ | +++ |
| 146 | +++ | +++ |
| 147 | +++ | +++ |
| 148 | +++ | +++ |
| 149 | +++ | +++ |
| 150 | +++ | ++ |
| 151 | +++ | +++ |
| 152 | +++ | +++ |
| 153 | +++ | +++ |
| 154 | +++ | +++ |
| 155 | +++ | +++ |
| 156 | +++ | +++ |
| 157 | +++ | +++ |
| 158 | +++ | +++ |
| 159 | +++ | ++ |
| 160 | +++ | +++ |
| 161 | +++ | +++ |
| 162 | +++ | +++ |
| 163 | ++ | +++ |
| 164 | +++ | +++ |
| 165 | ++ | ++ |
| 166 | +++ | ++ |
| 167 | +++ | +++ |
| 168 | +++ | +++ |
| 169 | +++ | +++ |

TABLE 14-continued

| Ex. # | PARG enzymatic activity ($IC_{50}$) | PARG Cell viability ($IC_{50}$) |
|---|---|---|
| 170 | +++ | +++ |
| 171 | +++ | +++ |
| 172 | +++ | +++ |
| 173 | +++ | +++ |
| 174 | +++ | +++ |
| 175 | +++ | +++ |
| 176 | +++ | +++ |
| 177 | +++ | +++ |
| 178 | +++ | +++ |
| 179 | +++ | +++ |
| 180 | +++ | +++ |
| 181 | +++ | ++ |
| 182 | +++ | +++ |
| 183 | +++ | +++ |
| 184 | +++ | ++ |
| 185 | ++ | ++ |
| 186 | ++ | ++ |
| 187 | | |
| 188 | +++ | ++ |
| 189 | +++ | +++ |
| 190 | +++ | +++ |
| 191 | +++ | +++ |
| 192 | ++ | +++ |
| 193 | +++ | +++ |
| 194 | ++ | ++ |
| 195 | +++ | ++ |
| 196 | +++ | ++ |
| 197 | +++ | ++ |
| 198 | +++ | +++ |
| 199 | +++ | +++ |
| 200 | +++ | +++ |
| 201 | +++ | +++ |
| 202 | +++ | +++ |
| 203 | +++ | +++ |
| 204 | +++ | +++ |
| 205 | +++ | +++ |
| 206 | +++ | +++ |
| 207 | +++ | +++ |
| 208 | +++ | +++ |
| 209 | +++ | +++ |
| 210 | +++ | +++ |

Although the present disclosure has been comprehensively described through its embodiments, it is worth noting that various changes and modifications are obvious to those skilled in the art. Such changes and modifications should be included in the scope of the appended claims of the present disclosure.

What is claimed is:

1. A compound of Formula (I), or a pharmaceutically acceptable salt, stereoisomer, solvate, N-oxide, tautomer, isotopic variant, or deuterated compound thereof;

(I)

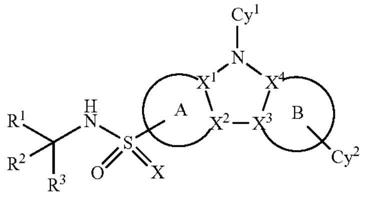

wherein:

$X^1$ is C;

$X^2$ is N or C;

$X^3$ is N or C;

$X^4$ is C;

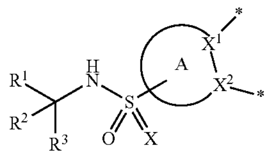

is

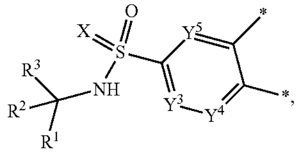

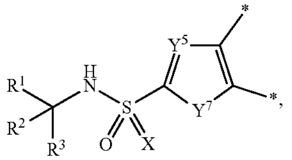

or

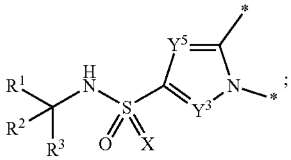

;

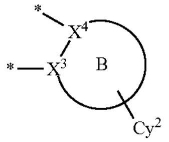

is

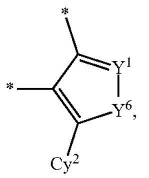

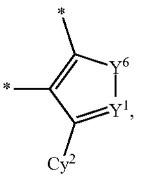

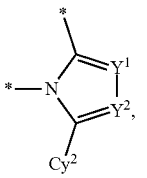

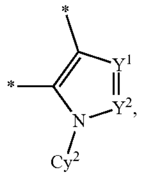

or

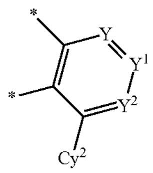

;

each X is independently O or $NR^5$;

Y is N or $CR^{15}$;

each $Y^1$ is independently N or $CR^6$;

each $Y^2$ is independently N or $CR^7$;

each $Y^3$ is independently N or $CR^8$;

$Y^4$ is N or $CR^4$;

each $Y^5$ is independently N or $CR^4$;

each $Y^6$ is independently S, O, or $NR^{14}$;

$Y^7$ is S, O, or $NR^{16}$;

$Cy^1$ is 5-10 membered heteroaryl optionally substituted by 1, 2, 3, 4, or 5 substituents, each of which is independently $R^9$;

each $Cy^2$ is independently $C_6$-$C_{10}$ aryl, $C_3$-$C_{10}$ cycloalkyl, 5-10 membered heteroaryl, or 4-14 membered heterocycloalkyl; wherein the $C_6$-$C_{10}$ aryl, $C_3$-$C_{10}$ cycloalkyl, 5-10 membered heteroaryl, and 4-14 membered heterocycloalkyl are each optionally substituted by 1, 2, 3, 4, or 5 substituents, each of which is independently $R^{10}$;

$R^1$, $R^2$, and $R^3$ are each independently H, D, CN, $C_1$-$C_3$ alkyl, $C_2$-$C_3$ alkenyl, $C_2$-$C_3$ alkynyl, $C_3$-$C_7$cycloalkyl, or 4-7 membered heterocycloalkyl; wherein the $C_1$-$C_3$ alkyl, $C_2$-$C_3$ alkenyl, $C_2$-$C_3$ alkynyl, $C_3$-$C_7$ cycloalkyl, and 4-7 membered heterocycloalkyl are each optionally substituted by 1-5 substituents, each independently selected from D, halo, CN, OH, $C_1$-$C_6$ alkyl, $C_1$-$C_6$ haloalkyl, —O—$C_1$-$C_6$ alkyl, and —O$C_1$-$C_6$ haloalkyl;

or $R^2$ and $R^3$ together with the carbon atom to which they are attached form $C_3$-$C_7$ cycloalkyl or 4-7 membered heterocycloalkyl; wherein the $C_3$-$C_7$ cycloalkyl and 4-7 membered heterocycloalkyl are each optionally substituted by 1, 2, 3, or 4 substituents, each independently selected from D, halo, CN, $NO_2$, oxo, OH, $C_1$-$C_6$ alkyl, $C_1$-$C_6$ haloalkyl, —O—$C_1$-$C_6$ alkyl, and—O$C_1$-$C_6$ haloalkyl;

each $R^4$ is independently H, D, halo, OH, CN, $NO_2$, $SF_5$, $C_1$-$C_3$ alkyl, $C_2$-$C_3$ alkenyl, $C_2$-$C_3$ alkynyl, —O—$C_1$-$C_3$ alkyl, or $NR^CR^D$; wherein the $C_1$-$C_3$ alkyl, $C_2$-$C_3$ alkenyl, and $C_2$-$C_3$ alkynyl are each optionally substituted with halogen or CN;

$R^5$ is H, D, CN, $OR^B$, or $C_1$-$C_4$ alkyl optionally substituted with at least one of $R^{5A}$; wherein each $R^{5A}$ is independently D, F, CI, CN, $NH_2$, OH, —O—$C_1$-$C_6$ alkyl, —O$C_1$-$C_6$ haloalkyl, optionally substituted $C_3$-$C_7$ cycloalkyl, or optionally substituted 4-7 membered heterocycloalkyl; wherein the optionally substituted substituent is selected from D, halo, CN, OH, $C_1$-$C_4$ alkyl, $C_1$-$C_4$ haloalkyl, —O—$C_1$-$C_4$ alkyl, or —O$C_1$-$C_4$ haloalkyl;

or $R^1$ and $R^5$ together with the atoms to which they are attached form 5-7 membered partially saturated heterocycloalkyl optionally substituted by 1, 2, 3, or 4 substituents, each independently selected from D, halogen, CN, $CF_3$, $NO_2$, oxo, OH, $C_1$-$C_6$ alkyl, $C_1$-$C_6$ haloalkyl, —O—$C_1$-$C_6$ alkyl, and —O$C_1$-$C_6$ haloalkyl;

$R^6$, $R^7$ and $R^{15}$ are each independently H, D, halogen, CN, $NO_2$, $C_1$-$C_6$ alkyl, $C_1$-$C_6$ haloalkyl, $C_2$-$C_6$ alkenyl, $C_2$-$C_6$ alkynyl, $OR^A$, $SR^A$, $SF_5$, $NHOR^A$, $C(O)OR^A$, $C(O)R^B$, $C(O)NR^CR^D$, $OC(O)NR^CR^D$, $NR^CR^D$, NRCC(O)$R^B$, NRCC(O)$NR^CR^D$, NRCC(O)$OR^A$, $NR^CS(O)_2R^B$, $B(OR^C)(OR^D)$, $C(=NR^C)NR^CR^D$, $NR^DC(=NR^C)NR^CR^D$, $NR^DC(=NR^C)R^B$, $P(O)R^ER^F$, $P(O)OR^EOR^F$, $OP(O)OR^EOR^F$, $S(O)(=NR^B)R^B$, $S(O)R^B$, $S(O)NR^CR^D$, $S(O)_2R^B$, $S(O)_2NR^CR^D$, $NR^CS(O)_2NR^CR^D$, or $NR^CS(O)(=NR^B)R^B$; wherein the $C_1$-$C_6$ alkyl, $C_2$-$C_6$ alkenyl, and $C_2$-$C_6$ alkynyl are each optionally substituted with 1, 2, or 3 substituents, each of which is independently $R^{11}$;

$R^8$ is H, D, CN, halo, OH, $NH_2$, $C_1$-$C_3$ alkyl, $C_1$-$C_3$ haloalkyl, —O—$C_1$-$C_3$ alkyl, —O$C_1$-$C_3$ haloalkyl, $C_1$-$C_3$ cyanoalkyl, or $SF_5$;

each $R^9$ is independently H, D, halo, $C_1$-$C_6$ alkyl, $C_2$-$C_6$ alkenyl, $C_2$-$C_6$ alkynyl, $C_1$-$C_6$ haloalkyl, O$C_1$-$C_6$ alkyl, O$C_1$-$C_6$ haloalkyl, O$C_3$-$C_7$ cycloalkyl, $C_3$-$C_7$ cycloalkyl, CN, $NO_2$, $N_3$, or $SF_5$; wherein the $C_1$-$C_6$ alkyl, $C_2$-$C_6$ alkenyl, $C_2$-$C_6$ alkynyl, and $C_3$-$C_7$ cycloalkyl are each optionally substituted with 1, 2, or 3 substituents, each of which is independently $R^{11}$;

each $R^{10}$ is independently H, D, halo, CN, $NO_2$, $N_3$, oxo, $C_1$-$C_6$ alkyl, $C_2$-$C_6$ alkenyl, $C_2$-$C_6$ alkynyl, $OR^A$, $SR^A$, $SF_5$, $NR^COR^A$, $C(O)R^B$, $C(=S)R^B$, $C(O)NR^CR^D$, $C(O)N(R^C)OR^A$, $C(O)OR^A$, $OC(O)R^B$, $OC(O)NR^CR^D$, $NR^CR^D$, NRCC(O)$R^D$, NRCC(O)$NR^CR^D$, NRCC(O)$OR^A$, $B(OR^C)(OR^D)$, $C(=NR^C)NR^CR^D$, $NR^DC(=NR^C)NR^CR^D$, $NR^DC(=NR^C)R^B$, $SiR^GR^HR^I$, $P(O)R^ER^F$, $P(O)OR^EOR^F$, $OP(O)OR^EOR^F$, $S(O)(=NR^B)R^B$, $S(O)R^B$, $S(O)NR^CR^D$, $S(O)_2R^B$, $NR^CS(O)_2R^B$, $S(O)_2NR^CR^D$, $NR^CS(O)_2NR^CR^D$, $NR^CS(O)(=NR^B)R^B$, $Cy^3$, $C_1$-$C_6$ alkyl-$Cy^3$, $OCy^3$, or O—$C_1$-$C_6$ alkyl-$Cy^3$; wherein the $C_1$-$C_6$ alkyl, $C_2$-$C_6$ alkenyl, and $C_2$-$C_6$ alkynyl are each optionally substituted with 1, 2, 3, 4, or 5 substituents, each of which is independently $R^{11}$; or two $R^{10}$ together with the atom(s) to which they are attached form oxo, $C_3$-$C_{10}$ cycloalkyl, or 4-10 membered heterocycloalkyl; wherein the $C_3$-$C_{10}$ cycloalkyl 4-10 membered heterocycloalkyl are each optionally substituted by 1, 2, or 3 substituents, each independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$-cyanoalkyl, CN, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)(OR^d)$, $C(=NR^c)NR^cR^d$, $NR^cC(=NR^c)NR^cR^d$, $NR^cC(=NR^c)R^b$, $OP(O)OR^eOR^f$, $P(O)OR^eOR^f$, $S(O)(=NR^b)R^b$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, $NR^cS(O)(=NR^b)R^b$, and $Cy^4$; wherein $Cy^4$ is $C_6$-$C_{10}$ aryl, $C_3$-$C_{10}$ cycloalkyl, 5-10 membered heteroaryl, or 4-10 membered heterocycloalkyl; wherein the $C_6$-$C_{10}$ aryl, $C_3$-$C_{10}$ cycloalkyl, 5-10 membered heteroaryl, and 4-10 membered heterocycloalkyl are each optionally substituted by 1, 2, 3, or 4 substituents, each independently selected from D, halo, CN, $NO_2$, OH, oxo, $NH_2$, NH$C_1$-$C_4$ alkyl, N($C_1$-$C_4$ alkyl)$_2$, $C_1$-$C_3$ alkyl, $C_1$-$C_3$ haloalkyl, O$C_1$-$C_3$ alkyl, O$C_1$-$C_3$ haloalkyl, O$C_2$-$C_3$ alkylOH, O$C_2$-$C_3$ alkyl-O—$C_1$-$C_6$ alkyl, and $SF_5$;

each $Cy^3$ is independently $C_6$-$C_{10}$ aryl, $C_3$-$C_{10}$ cycloalkyl, 5-10 membered heteroaryl, or 4-10 membered heterocycloalkyl; wherein the $C_6$-$C_{10}$ aryl, $C_3$-$C_{10}$ cycloalkyl, 5-10 membered heteroaryl, and 4-10 membered heterocycloalkyl are each optionally substituted with 1, 2, 3, 4, or 5 substituents, each of which is independently $R^{12}$;

each $R^{11}$ is independently selected from H, D, halo, CN, $NO_2$, $N_3$, $C_1$-$C_6$ alkyl, $C_2$-$C_6$ alkenyl, $C_2$-$C_6$ alkynyl, $C_1$-$C_6$ haloalkyl, O$C_1$-$C_6$ alkylOH, O$C_1$-$C_6$ alkyl-O—$C_1$-$C_6$ alkyl, $OR^{a1}$, $SR^{a1}$, $SF_5$, $NHOR^{a1}$, $C(O)R^{b1}$, $C(O)NR^{c1}R^{d1}$, $C(O)OR^{a1}$, $OC(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b1}$, $P(O)OR^{e1}OR^{f1}$, $OP(O)OR^{e1}OR^{f1}$, $S(O)(=NR^{b1})R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl, wherein the $C_6$-$C_{10}$ aryl, $C_3$-$C_{10}$ cycloalkyl, 5-10 membered heteroaryl, and 4-10 membered heterocycloalkyl are each optionally substituted by 1, 2, 3, 4, or 5 substituents, each independently selected from D, halo, CN, $NO_2$, $NH_2$, NH$C_1$-$C_4$ alkyl, N($C_1$-$C_4$ alkyl)$_2$, $C_1$-$C_3$ alkyl, $C_1$-$C_3$ haloalkyl, O$C_1$-$C_3$ alkyl, O$C_1$-$C_3$ haloalkyl, O$C_2$-$C_3$ alkylOH, O$C_2$-$C_3$ alkyl-O—$C_1$-$C_6$ alkyl, and $SF_5$;

each $R^{12}$ is independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$ alkylOH, $C_1$-$C_6$ alkyl-O—$C_1$-$C_6$ alkyl, CN, $NO_2$, $N_3$, $OR^{a1}$, $SR^{a1}$, $SF_5$, $NHOR^{a1}$, $C(O)R^{b1}$, $C(O)NR^{c1}R^{d1}$, $C(O)OR^{c1}$, $OC(O)R^{b1}$, $OC(O)NR^{c1}R^{d1}$, $NR^{e1}R^{d1}$, $NR^{c1}C(O)R^{b1}$, $NR^{c1}C(O)NR^{c1}R^{d1}$, $NR^{c1}C(O)OR^{a1}$, $B(OR^{c1})(OR^{d1})$, $C(=NR^{c1})NR^{c1}R^{d1}$, $NR^{d1}C(=NR^{c1})NR^{c1}R^{d1}$, $NR^{d1}C(=NR^{c1})R^{b1}$, $P(O)R^{e1}R^{f1}$, $P(O)OR^{e1}OR^{f1}$, $OP(O)OR^{e1}OR^{f1}$, $S(O)(=NR^{b1})R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})R^{b1}$, $C_6$-$C_{10}$ aryl, $C_3$-$C_{10}$ cycloalkyl, 5-10 membered heteroaryl, and 4-10 membered heterocycloalkyl; wherein the $C_6$-$C_{10}$ aryl, $C_3$-$C_{10}$ cycloalkyl, 5-10 membered heteroaryl, and 4-10 membered heterocycloalkyl are each substituted by 1, 2, 3, 4, or 5 substituents, each independently selected from D, halo, CN, $NO_2$, $NH_2$, $NHC_1$-$C_4$ alkyl, N($C_1$-$C_4$ alkyl)$_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, and $SF_5$;

each $R^{13}$ is independently H, D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_1$-$C_4$ alkylOH, $OC_1$-$C_4$ alkyl-O—$C_1$-$C_4$ alkyl, $OC_1$-$C_4$ alkyl-O—$C_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, optionally substituted $C_3$-$C_7$ cycloalkyl, optionally substituted 4-7 membered heterocycloalkyl, $SF_5$, $OR^a$, $SR^a$, C(O)$R^b$, OC(O)$NR^cR^d$, $NR^cR^d$, $NR^c$C(O)$R^b$, $NR^c$C(O)$NR^cR^d$, $NR^c$C(O)$OR^a$, S(O)$R^b$, S(O)$NR^cR^d$, S(O)$_2R^b$, $NR^c$S(O)$_2R^b$, S(O)$_2NR^cR^d$, $NR^c$S(O)$_2$ $NR^cR^d$, or B($OR^c$) ($OR^d$); wherein the optionally substituted substituent is selected from D, halo, CN, OH, $C_1$-$C_4$ alkyl, $C_1$-$C_4$ haloalkyl, —O—$C_1$-$C_4$ alkyl, and —$OC_1$-$C_4$ haloalkyl;

$R^{14}$ and $R^{16}$ are each independently H, D, $C_1$-$C_6$ alkyl, $C_1$-$C_6$ haloalkyl, $C_2$-$C_6$ alkenyl, $C_2$-$C_6$ alkynyl, $C_1$-$C_6$ alkyl-OH, $C_1$-$C_6$ alkyl-CN, or $C_1$-$C_6$ alkyl-O—$C_1$-$C_6$ alkyl;

each $R^A$ is independently H, D, $C_1$-$C_6$ alkyl, $C_2$-$C_4$ alkenyl, $C_2$-$C_4$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_4$ alkenyl, $C_2$-$C_4$ alkynyl, $C_3$-$C_{10}$ cycloalkyl, 4-10 membered heterocyclalkyl, $C_6$-$C_{10}$ aryl, 5-10 membered heteroaryl, arylalkyl, heteroarylalkyl, cycloalkylalkyl, and heterocycloalkylalkyl are each optionally substituted with 1, 2, 3, 4, or 5 substituents, each independently selected from D, OH, CN, halo, $C_1$-$C_4$ alkyl, $NO_2$, oxo, $OR^a$, $SR^a$, $SF_5$, $NHOR^a$, C(O)$R^b$, C(O)$NR^cR^d$, C(O)$OR^a$, OC(O)$R^b$, OC(O)$NR^cR^d$, $NR^cR^d$, $NR^c$C(O)$R^b$, $NR^c$C(O)$NR^cR^d$, $NR^c$C(O)$OR^a$, B($OR^c$) ($OR^d$), C(=$NR^c$)$NR^cR^d$, $NR^c$C(=$NR^c$)$NR^cR^d$, $NR^c$C(=$NR^c$) $R^b$, P(O)$R^eR^f$, P(O)$OR^eOR^f$, OP(O)$OR^eOR^f$, S(O)$R^b$, S(O)$NR^cR^d$, S(O)$_2R^b$, $NR^c$S(O)$_2R^b$, S(O)$_2NR^cR^d$, $NR^c$S(O)$_2NR^cR^d$, and $NR^c$S(O)(=$NR^b$)$R^b$;

each $R^B$ is independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, and heterocycloalkylalkyl are each optionally substituted with 1, 2, 3, 4, or 5 substituents, each of which is independently $R^{13}$;

each $R^C$ and $R^D$ is independently H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_7$cycloalkyl, 4-7 membered heterocycloalkyl, phenyl, 5-6 membered heteroaryl, arylalkyl, heteroarylalkyl, cycloalkylalkyl, and heterocycloalkylalkyl are each optionally substituted with 1, 2, 3, 4, or 5 substituents, each independently selected from D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, $SF_5$, OC(O)$NR^cR^d$, $NR^cR^d$, $NR^c$C(O)$R^b$, S(O)$NR^cR^d$, S(O)$_2R^b$, $NR^c$S(O)$_2R^b$, S(O)$_2NR^cR^d$, $NR^c$S(O)$_2NR^cR^d$, and B($OR^c$)($OR^d$);

or $R^C$ and $R^D$ together with the N atom to which they are attached form 4-7 membered heterocycloalkyl optionally substituted with 1, 2, 3, 4, or 5 substituents, each independently selected from D, OH, oxo, CN, —$NH_2$, —NH($C_1$-$C_4$ alkyl), —N($C_1$-$C_4$ alkyl)$_2$, halo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_2$-$C_4$ alkylOH, $OC_2$-$C_4$ alkyl-O—$C_1$-$C_4$ alkyl, and $OC_2$-$C_4$ alkyl-O—$C_1$-$C_4$ haloalkyl;

each $R^a$ and $R^{a1}$ is independently H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, and 4-7 membered heterocycloalkyl are each optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, and $C_1$-$C_4$ haloalkoxy;

each $R^b$ and $R^{b1}$ is independently H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, 4-7 membered heterocycloalkyl, arylalkyl, heteroarylalkyl, cycloalkylalkyl, or heterocycloalkylalkyl; wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, 4-7 membered heterocycloalkyl, arylalkyl, heteroarylalkyl, cycloalkylalkyl, and heterocycloalkylalkyl are each optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_6$-$C_{10}$ aryl, $C_3$-$C_{10}$ cycloalkyl, 5-10 membered heteroaryl, and 4-10 membered heterocycloalkyl;

each $R^c$ and $R^d$ is independently H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl; wherein the $C_1$-4 alkyl, $C_2$-4 alkenyl, $C_{2-4}$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, C(O)$OR^a$1, C(O)$R^{b1}$ S(O)$_2R^{b1}$, $C_1$-$C_4$ alkyl-O—$C_1$-$C_4$ alkyl, and $C_1$-$C_4$ alkyl-O—$C_1$-$C_4$ alkyl-O—;

or $R^c$ and $R^d$ together with the N atom to which they are attached form 4-7 membered heterocycloalkyl optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkoxy-$C_1$-$C_4$ alkyl, and $C_1$-$C_4$ alkoxy-$C_1$-$C_4$ alkoxy;

each $R^{c1}$ and $R^{d1}$ is independently H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, or heterocycloalkylalkyl; wherein the $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, and heterocycloalkylalkyl are each optionally substituted with 1, 2, or 3 substituents, each independently selected from D, OH, CN, $—NH_2$, $—NH(C_1$-$C_4$ alkyl), $—N(C_1$-$C_4$ alkyl$)_2$, halo, $C_1$-$C_4$ alkyl, $C_1$-$C_4$ alkoxy, $C_1$-$C_4$ haloalkyl, and $C_1$-$C_4$ haloalkoxy;

or $R^{c1}$ and $R^{d1}$ together with the N atom to which they are attached form 4-7 membered heterocycloalkyl optionally substituted with 1, 2, or 3 substituents, each independently selected from D, OH, CN, $—NH_2$, $—NH(C_1$-$C_4$ alkyl), $—N(C_1$-$C_4$ alkyl$)_2$, halo, $C_1$-$C_4$ alkyl, $C_1$-$C_4$ alkoxy, $C_1$-$C_4$ haloalkyl, and $C_1$-4 haloalkoxy;

each $R^E$, $R^e$, and $R^{e1}$ is independently H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 3-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl;

each $R^F$, $R^f$, and $R^{f1}$ is independently H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl; and each $R^G$, $R^H$, and $R^I$ is independently $C_1$-$C_4$ alkyl or phenyl.

2. The compound of claim 1, wherein the compound is a compound having the structure of Formula (Ia), (Ib), (Ic), (Id), (Ie), (If), (Ig), (Ih), (Ii), (Ij), (Ik), (Il), (Im), (In), (Io), (Ip), or (Iq):

(Ia)

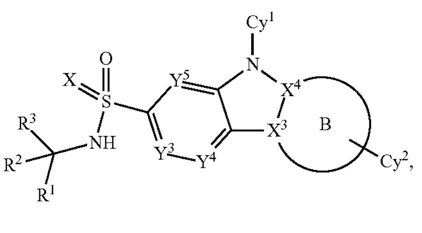

(Ib)

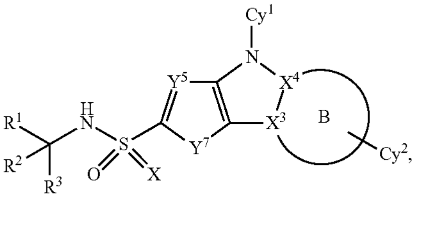

-continued (Ic)

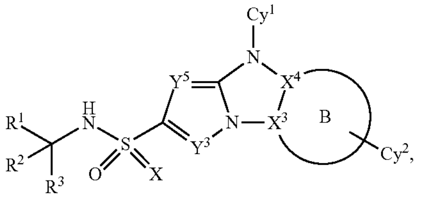

(Id)

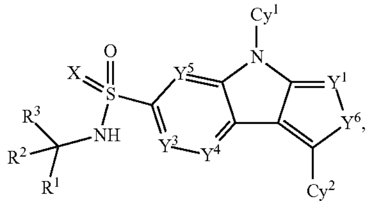

(Ie)

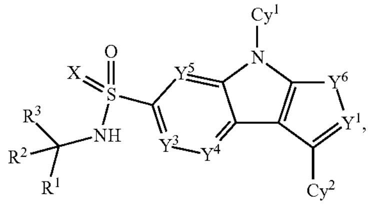

(If)

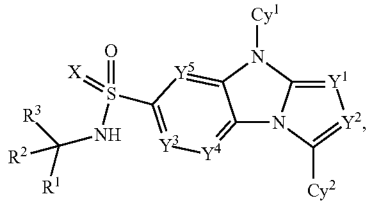

(Ig)

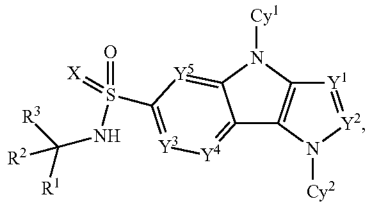

(Ih)

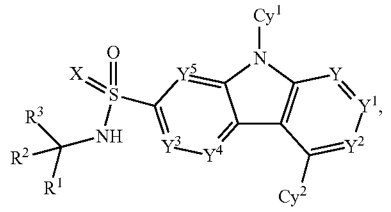

(Ii)

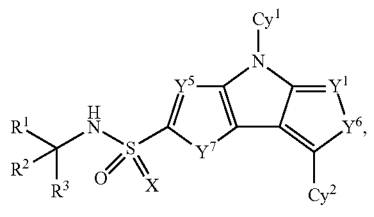

-continued (Ij)

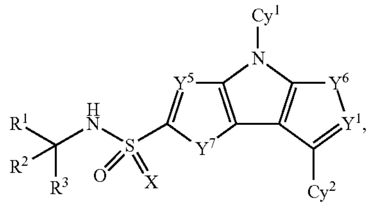

(Ik)

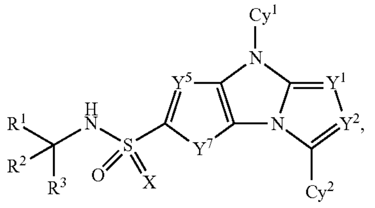

(Il)

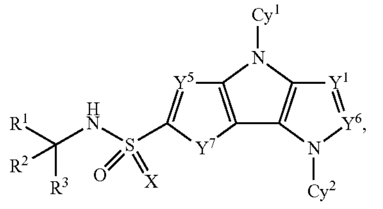

(Im)

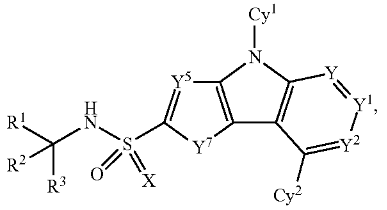

(In)

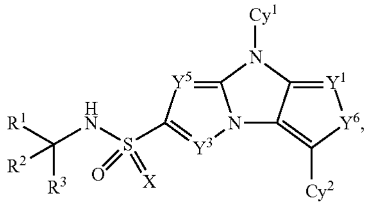

(Io)

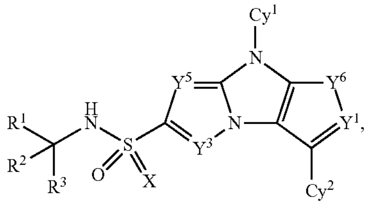

(Ip)

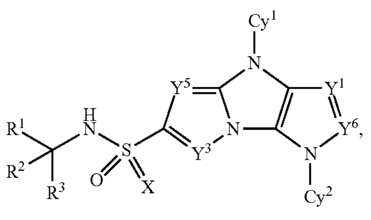

or

-continued (Iq)

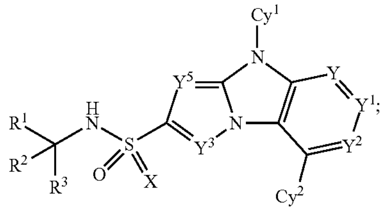

or a pharmaceutically acceptable salt, stereoisomer, solvate, N-oxide, tautomer, isotopic variant, or deuterated compound thereof.

3. The compound or a pharmaceutically acceptable salt, stereoisomer, solvate, N-oxide, tautomer, isotopic variant, or deuterated compound thereof of claim 1, wherein the compound is a compound having the structure of Formula (II):

(II)

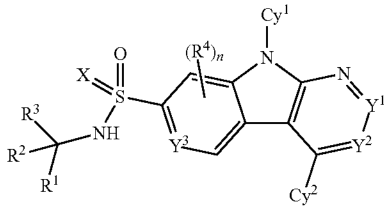

wherein,

X is O or $NR^5$;

$Y^1$ is N or $CR^6$;

$Y^2$ is N, or $CR^7$, and at most one of $Y^1$ or $Y^2$ is N;

$Y^3$ is N, or $CR^8$;

n is an integer of 0, 1, or 2;

$Cy^1$ is 5-10 membered heteroaryl optionally substituted by 1, 2, 3, 4, or 5 substituents, each of which is independently $R^9$;

$Cy^2$ is $C_6$-$C_{10}$ aryl, $C_3$-$C_{10}$ cycloalkyl, 5-10 membered heteroaryl, or 4-14 membered heterocycloalkyl, wherein the $C_6$-$C_{10}$ aryl, $C_3$-$C_{10}$ cycloalkyl, 5-10 membered heteroaryl, and 4-14 membered heterocycloalkyl are each optionally substituted by 1, 2, 3, 4, or 5 substituents, each of which is independently $R^{10}$;

$R^1$, $R^2$, and $R^3$ are each independently H, D, CN, $C_1$-$C_3$ alkyl, $C_2$-$C_3$ alkenyl, $C_2$-$C_3$ alkynyl, $C_3$-$C_7$cycloalkyl, or 4-7 membered heterocycloalkyl, wherein the $C_1$-$C_3$ alkyl, $C_2$-$C_3$ alkenyl, $C_2$-$C_3$ alkynyl, $C_3$-$C_7$ cycloalkyl, and 4-7 membered heterocycloalkyl are each optionally substituted by 1, 2, 3, 4, or 5 substituents, each independently selected from D, halo, CN, OH, —O—$C_1$-$C_6$ alkyl, and —$OC_1$-$C_6$ haloalkyl;

or $R^2$ and $R^3$ together with the carbon atom to which they are attached form $C_3$-$C_7$ cycloalkyl or 4-7 membered heterocycloalkyl, wherein the $C_3$-$C_7$ cycloalkyl and 4-7 membered heterocycloalkyl are each optionally substituted by 1, 2, 3, or 4 substituents, each independently selected from D, halo, CN, $NO_2$, oxo, OH, —O—$C_1$-$C_6$ alkyl, and —$OC_1$-$C_6$ haloalkyl;

each $R^4$ is independently H, D, halo, OH, CN, $NO_2$, $SF_5$, $C_1$-$C_3$ alkyl, $C_2$-$C_3$ alkenyl, $C_2$-$C_3$ alkynyl, —O—$C_1$-$C_3$ alkyl, or $NR^CR^D$; wherein the $C_1$-$C_3$ alkyl, $C_2$-$C_3$ alkenyl, and $C_2$-$C_3$ alkynyl are each optionally substituted with halogen or CN;

$R^5$ is H, D, CN, $OR^B$, or $C_1$-$C_4$ alkyl optionally substituted with at least one of $R^{5A}$, wherein each $R^{5A}$ is independently D, F, Cl, CN, $NH_2$, OH, —O—$C_1$-$C_6$ alkyl, —$OC_1$-$C_6$ haloalkyl, optionally substituted $C_3$-$C_7$ cycloalkyl, or optionally substituted 4-7 membered heterocycloalkyl; wherein the optionally substituted substituent is selected from D, halo, CN, OH, $C_1$-$C_4$ alkyl, $C_1$-$C_4$ haloalkyl, —O—$C_1$-$C_4$ alkyl, and —$OC_1$-$C_4$ haloalkyl;

or $R^1$ and $R^5$ together with the atoms to which they are attached form 5-7 membered partially saturated heterocycloalkyl optionally substituted by 1, 2, 3, or 4 substituents, each independently selected from D, halogen, CN, $CF_3$, $NO_2$, oxo, OH, —O—$C_1$-$C_6$ alkyl, and —$OC_1$-$C_6$ haloalkyl;

$R^6$ and $R^7$ are each independently H, D, halogen, CN, $NO_2$, $C_1$-$C_6$ alkyl, $C_1$-$C_6$ haloalkyl, $C_2$-$C_6$ alkenyl, $C_2$-$C_6$ alkynyl, $OR^A$, $SR^A$, $SF_5$, $NHOR^A$, $C(O)OR^A$, $C(O)R^B$, $C(O)NR^CR^D$, $OC(O)NR^CR^D$, $NR^CR^D$, NRCC(O)$R^B$, NRCC(O)$NR^CR^D$, NRCC(O)$OR^A$, $NR^CS(O)_2R^B$, $B(OR^C)(OR^D)$, $C(=NR^C)NR^CR^D$, $NR^DC(=NR^C)NR^CR^D$, $NR^DC(=NR^C)$ $R^B$, $P(O)R^ER^F$, $P(O)OR^EOR^F$, $OP(O)OR^EOR^F$, $S(O)(=NR^B)$ $R^B$, $S(O)R^B$, $S(O)NR^CR^D$, $S(O)_2R^B$, $S(O)_2NR^CR^D$, $NR^CS(O)_2NR^CR^D$, or $NR^CS(O)(=NR^B)$ $R^B$; wherein the $C_1$-$C_6$ alkyl, $C_2$-$C_6$ alkenyl, and $C_2$-$C_6$ alkynyl are each optionally substituted with 1, 2, or 3 substituents, each of which is independently $R^{11}$;

$R^8$ is H, D, CN, halo, OH, $NH_2$, $C_1$-$C_3$ alkyl, $C_1$-$C_3$ haloalkyl, —O—$C_1$-$C_3$ alkyl, —$OC_1$-$C_3$ haloalkyl, $C_1$-$C_3$ cyanoalkyl, or $SF_5$;

each $R^9$ is independently H, D, halo, $C_1$-$C_6$ alkyl, $C_2$-$C_6$ alkenyl, $C_2$-$C_6$ alkynyl, $C_1$-$C_6$ haloalkyl, $C_3$-$C_7$ cycloalkyl, $OC_1$-$C_6$ alkyl, $OC_1$-$C_6$ haloalkyl, $OC_3$-$C_7$ cycloalkyl, CN, $NO_2$, $N_3$, or $SF_5$; wherein the $C_1$-$C_6$ alkyl, $C_2$-$C_6$ alkenyl, $C_2$-$C_6$ alkynyl, and $C_3$-$C_7$ cycloalkyl are each optionally substituted with 1, 2, or 3 substituents, each of which is independently $R^{11}$;

each $R^{10}$ is independently H, D, halo, CN, $NO_2$, $N_3$, oxo, $C_1$-$C_6$ alkyl, $C_2$-$C_6$ alkenyl, $C_2$-$C_6$ alkynyl, $OR^A$, $SR^A$, $SF_5$, $NR^COR^A$, $C(O)R^B$, $C(=S)$ $R^B$, $C(O)NR^CR^D$, $C(O)N(R^C)$ $OR^A$, $C(O)OR^A$, $OC(O)R^B$, $OC(O)NR^CR^D$, $NR^CR^D$, NRCC(O)$R^D$, NRCC(O)$NR^CR^D$, NRCC(O)$OR^A$, $B(OR^C)(OR^D)$, $C(=NR^C)NR^CR^D$, $NR^DC(=NR^C)NR^CR^D$, $NR^DC(=NR^C)$ $R^B$, $SiR^GR^HR^I$, $P(O)R^ER^F$, $P(O)OR^EOR^F$, $OP(O)OR^EOR^F$, $S(O)(=NR^B)$ $R^B$, $S(O)R^B$, $S(O)NR^CR^D$, $S(O)_2R^B$, $NR^CS(O)_2R^B$, $S(O)_2NR^CR^D$, $NR^CS(O)_2NR^CR^D$, $NR^CS(O)(=NR^B)$ $R^B$, $Cy^3$, $C_1$-$C_6$ alkyl-$Cy^3$, $OCy^3$, or O—$C_1$-$C_6$ alkyl-$Cy^3$; wherein the $C_1$-$C_6$ alkyl, $C_2$-$C_6$ alkenyl, and $C_2$-$C_6$ alkynyl are each optionally substituted with 1, 2, 3, 4, or 5 substituents, each of which is independently $R^{11}$; or two $R^{10}$ together with the atoms to which they are attached form oxo, $C_3$-$C_{10}$ cycloalkyl, or 4-10 membered heterocycloalkyl, wherein the $C_3$-$C_{10}$ cycloalkyl and 4-10 membered heterocycloalkyl are each optionally substituted by 1, 2, or 3 substituents, each independently selected from D, halo, $C_1$-$C_6$ alkyl, $C_2$-$C_6$ alkenyl, $C_2$-$C_6$ alkynyl, $C_1$-$C_6$ haloalkyl, $C_1$-$C_6$ cyanoalkyl, CN, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)$ $(OR^d)$, $C(=NR^c)NR^cR^d$, $NR^cC(=NR^c)NR^cR^d$, $NR^cC(=NR^c)$ $R^b$, $OP(O)OR^eOR^f$, $P(O)OR^eOR^f$, $S(O)(=NR^b)$ $R^b$, $S(O)R^b$, $S(O)NR^cR^d$, $S(O)_2R^b$, $NR^cS(O)_2R^b$, $S(O)_2NR^cR^d$, $NR^CS(O)_2NR^cR^d$, $NR^cS(O)(=NR^b)$ $R^b$, and $Cy^4$; wherein $Cy^4$ is $C_6$-$C_{10}$ aryl, $C_3$-$C_{10}$ cycloalkyl, 5-10 membered heteroaryl, or 4-10 membered heterocycloalkyl, wherein the $C_6$-$C_{10}$ aryl, $C_3$-$C_{10}$ cycloalkyl, 5-10 membered heteroaryl, and 4-10 membered heterocycloalkyl are each optionally substituted by 1, 2, 3, or 4 substituents, each independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, and $SF_5$;

each $Cy^3$ is independently $C_6$-$C_{10}$ aryl, $C_3$-$C_{10}$ cycloalkyl, 5-10 membered heteroaryl, or 4-10 membered heterocycloalkyl; wherein the $C_6$-$C_{10}$ aryl, $C_3$-$C_{10}$ cycloalkyl, 5-10 membered heteroaryl, and 4-10 membered heterocycloalkyl are each optionally substituted with 1, 2, 3, 4, or 5 substituents, each of which is independently $R^{12}$;

each $R^{11}$ is independently H, D, halo, CN, $NO_2$, $N_3$, $C_1$-$C_6$ alkyl, $C_2$-$C_6$ alkenyl, $C_2$-$C_6$ alkynyl, $C_1$-$C_6$ haloalkyl, $OC_1$-$C_6$ alkylOH, $OC_1$-$C_6$ alkyl-O—$C_1$-$C_6$ alkyl, $OR^{a1}$, $SR^{a}1$, $SF_5$, $NHOR^{a1}$, $C(O)R^{b1}$, $C(O)NR^{c1}R^{d1}$, $C(O)OR^{a1}$, $OC(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $B(OR^{c1})$ $(OR^{d1})$, $C(=NR^{c1})NR^{c1}R^{d1}$, $NR^{d1}C(=NR^{c1})NR^{c1}R^{d1}$, $NR^{d1}C(=NR^{c1})$ $R^{b1}$, $P(O)OR^{e1}OR^{f1}$, $OP(O)OR^{e1}OR^{f1}$, $S(O)(=NR^{b1})$ $R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})$ $R^{b1}$, $C_6$-$C_{10}$ aryl, $C_3$-$C_{10}$ cycloalkyl, 5-10 membered heteroaryl, or 4-10 membered heterocycloalkyl, wherein the $C_6$-$C_{10}$ aryl, $C_3$-$C_{10}$ cycloalkyl, 5-10 membered heteroaryl, and 4-10 membered heterocycloalkyl are each optionally substituted with 1, 2, 3, 4, or 5 substituents, each independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, and $SF_5$;

each $R^{12}$ is independently D, halo, $C_1$-$C_6$ alkyl, $C_2$-$C_6$ alkenyl, $C_2$-$C_6$ alkynyl, $C_1$-$C_6$ haloalkyl, $C_1$-$C_6$ alkylOH, $C_1$-$C_6$ alkyl-O—$C_1$-$C_6$ alkyl, CN, $NO_2$, $N_3$, $OR^{a1}$, $SR^{a1}$, $SF_5$, $NHOR^{a}1$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{e1}C(O)OR^{a1}$, $B(OR^{c1})$ $(OR^{d1})$, $C(=NR^{c1})NR^{c1}R^{d1}$, $NR^{d1}C(=NR^{c1})NR^{c1}R^{d1}$, $NR^{d1}C(=NR^{c1})$ $R^{b1}$, $P(O)R^{e1}R^{f1}$, $P(O)OR^{e1}OR^{f1}$, $OP(O)OR^{e1}OR^{f1}$, $S(O)(=NR^{b1})$ $R^{b1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $NR^{c1}S(O)_2NR^{c1}R^{d1}$, $NR^{c1}S(O)(=NR^{b1})$ $R^{b1}$, $C_6$-$C_{10}$ aryl, $C_3$-$C_{10}$ cycloalkyl, 5-10 membered heteroaryl, and 4-10 membered heterocycloalkyl, wherein the $C_6$-$C_{10}$ aryl, $C_3$-$C_{10}$ cycloalkyl, 5-10 membered heteroaryl, or 4-10 membered heterocycloalkyl are each optionally substituted, each independently selected from D, halo, CN, $NO_2$, $NH_2$, $NHC_1$-$C_4$ alkyl, $N(C_1$-$C_4$ alkyl$)_2$, $C_1$-$C_3$ alkyl, $C_1$-$C_3$ haloalkyl, $OC_1$-$C_3$ alkyl, $OC_1$-$C_3$ haloalkyl, $OC_2$-$C_3$ alkylOH, $OC_2$-$C_3$ alkyl-O—$C_1$-$C_6$ alkyl, and $SF_5$;

each $R^A$ is independently H, D, $C_1$-$C_6$ alkyl, $C_2$-$C_4$ alkenyl, $C_2$-$C_4$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_4$ alkenyl, $C_2$-$C_4$ alkynyl, $C_3$-$C_{10}$ cycloalkyl, 4-10 membered heterocyclalkyl, $C_6$-$C_{10}$ aryl, 5-10 membered heteroaryl, arylalkyl, heteroarylalkyl, cycloalkylalkyl, and heterocycloalkylalkyl are each optionally substituted with 1, 2, 3, 4, or 5 substituents, each independently selected from D, OH, CN, halo, $C_1$-$C_4$ alkyl, $NO_2$, oxo, $OR^a$, $SR^a$, $SF_5$, $NHOR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $B(OR^c)$ $(OR^d)$, $C(=NR^c)NR^cR^d$, $NR^cC(=NR^c)NR^cR^d$, $NR^cC(=NR^c)$ $R^b$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, and $NR^cS(O)(=NR^b)R^b$;

each $R^B$ is independently H, D, $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_{10}$ cycloalkyl, 4-10 membered heterocycloalkyl, $C_6$-$C_{10}$ aryl, 5-10 membered heteroaryl, arylalkyl, heteroarylalkyl, cycloalkylalkyl, and heterocycloalkylalkyl are each optionally substituted with 1, 2, 3, 4, or 5 substituents, each of which is independently $R^{13}$;

each $R^{13}$ is independently H, D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, optionally substituted $C_3$-$C_7$ cycloalkyl, optionally substituted 4-7 membered heterocycloalkyl, $SF_5$, $OR^a$, $SR^a$, $C(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, $S(O)_2NR^cR^d$, $NR^cS(O)_2NR^cR^d$, or $B(OR^c)$ $(OR^d)$; wherein the optionally substituted substituent is selected from D, halo, CN, OH, $C_1$-$C_4$ alkyl, $C_1$-$C_4$ haloalkyl, —O—$C_1$-$C_4$ alkyl, and —$OC_1$-$C_4$ haloalkyl;

each $R^C$ and $R^D$ is independently H, D, $C_1$-$C_6$ alkyl, $C_2$-$C_6$ alkenyl, $C_2$-$C_6$ alkynyl, $C_3$-$C_7$ cycloalkyl, 4-7 membered heterocycloalkyl, phenyl, 5-6 membered heteroaryl, arylalkyl, heteroarylalkyl, cycloalkylalkyl, or heterocycloalkylalkyl; wherein the $C_1$-$C_6$ alkyl, $C_2$-$C_6$ alkenyl, $C_2$-$C_6$ alkynyl, $C_3$-$C_7$cycloalkyl, 4-7 membered heterocycloalkyl, phenyl, 5-6 membered heteroaryl, arylalkyl, heteroarylalkyl, cycloalkylalkyl, and heterocycloalkylalkyl are each optionally substituted with 1, 2, 3, 4, or 5 substituents, each independently selected from D, OH, CN, halo, oxo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $C_1$-$C_4$ alkyl-O—$C_1$-$C_4$ alkyl, $C_1$-$C_4$ alkyl-O—$C_1$-$C_4$ haloalkyl, $OC_2$-$C_4$ alkylOH, $OC_2$-$C_4$ alkyl-O—$C_1$-$C_4$ alkyl, $OC_2$-$C_4$ alkyl-O—$C_1$-$C_4$ haloalkyl, $SF_5$, $OC(O)NR^cR^d$, $NR^cR^d$, $NR^cC(O)R^b$, $S(O)NR^cR^d$, $S(O)_2R^b$, $NR^cS(O)_2R^b$, $S(O)_2NR^cR^d$, $NR^cS(O)_2$ $NR^cR^d$, and $B(OR^c)$ $(OR^d)$;

or $R^C$ and $R^D$ together with the N atom to which they are attached form 4-7 membered heterocycloalkyl optionally substituted with 1, 2, 3, 4, or 5 substituents, each independently selected from D, OH, oxo, CN, —$NH_2$, —NH($C_1$-$C_4$ alkyl), —N($C_1$-$C_4$ alkyl)$_2$, halo, $C_1$-$C_4$ alkyl, $C_1$-$C_4$ haloalkyl, $C_1$-$C_4$ cyanoalkyl, $OC_1$-$C_4$ alkyl, $OC_1$-$C_4$ haloalkyl, $OC_2$-$C_4$ alkylOH, $OC_2$-$C_4$ alkyl-O—$C_1$-$C_4$ alkyl, and $OC_2$-$C_4$ alkyl-O—$C_1$-$C_4$ haloalkyl;

each $R^a$ and $R^{a1}$ is independently H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, or 4-7 membered heterocycloalkyl, wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, and 4-7 membered heterocycloalkyl are each optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, and $C_1$-$C_4$ haloalkoxy;

each $R^b$ and $R^{b1}$ is independently H, D, $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, 4-7 membered heterocycloalkyl, arylalkyl, heteroarylalkyl, cycloalkylalkyl, and heterocycloalkylalkyl; wherein the $C_1$-$C_4$ alkyl, $C_2$-$C_4$ alkenyl, $C_2$-$C_4$ alkynyl, phenyl, $C_3$-$C_7$ cycloalkyl, 5-6 membered heteroaryl, 4-7 membered heterocycloalkyl, arylalkyl, heteroarylalkyl, cycloalkylalkyl, and heterocycloalkylalkyl are each optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_6$-$C_{10}$ aryl, $C_3$-$C_{10}$ cycloalkyl, 5-10 membered heteroaryl, and 4-10 membered heterocycloalkyl;

each $R^c$ and $R^d$ is independently H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl; wherein the $C_{1-4}$ alkyl, $C_{2-4}$ alkenyl, $C_{2-4}$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkyl-O—$C_1$-$C_4$ alkyl, and $C_1$-$C_4$ alkyl-O—$C_1$-$C_4$ alkyl-O—;

or $R^c$ and $R^d$ together with the N atom to which they are attached form 4-7 membered heterocycloalkyl optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, $C_1$-$C_4$ haloalkoxy, $C_1$-$C_4$ hydroxyalkyl, $C_1$-$C_4$ cyanoalkyl, $C_6$-$C_{10}$ aryl, 5-10 membered heteroaryl, $C(O)OR^{a1}$, $C(O)R^{b1}$, $S(O)_2R^{b1}$, $C_1$-$C_4$ alkoxy-$C_1$-$C_4$ alkyl, and $C_1$-$C_4$ alkoxy-$C_1$-$C_4$ alkoxy;

each $R^{c1}$ and $R^{d1}$ is independently H, D, $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, or heterocycloalkylalkyl; wherein the $C_1$-$C_4$ alkyl, $C_1$-$C_4$ haloalkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, 4-10 membered heterocycloalkyl, arylalkyl, heteroarylalkyl, cycloalkylalkyl, and heterocycloalkylalkyl are each optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, and $C_1$-$C_4$ haloalkoxy;

or $R^{c1}$ and $R^{d1}$ together with the N atom to which they are attached form 4-7 membered heterocycloalkyl optionally substituted with 1, 2, or 3 substituents, each independently selected from D, OH, CN, —$NH_2$, —NH($C_1$-$C_4$ alkyl), —N($C_1$-$C_4$ alkyl)$_2$, halo, $C_1$-$C_4$ alkyl, $C_1$-$C_4$ alkoxy, $C_1$-$C_4$ haloalkyl, and $C_1$-4 haloalkoxy;

each $R^E$, $R^e$, and $R^{e1}$ is independently H, D, $C_1$-$C_4$ alkyl, $C_1$-$C_4$ haloalkyl, $C_2$-$C_4$ alkenyl, ($C_1$-$C_4$ alkoxy)-$C_1$-$C_4$ alkyl, $C_2$-$C_4$ alkynyl, $C_6$-$C_{10}$ aryl, 5-10 membered heteroaryl, $C_3$-$C_{10}$ cycloalkyl, 3-10 membered heterocycloalkyl, $C_6$-$C_{10}$ aryl-$C_1$-$C_4$ alkyl, $C_3$-$C_{10}$ cycloalkyl-$C_1$-$C_4$ alkyl, 5-10 membered heteroaryl-$C_1$-$C_4$ alkyl, or 4-10 membered heterocycloalkyl-$C_1$-$C_4$ alkyl;

each $R^F$, $R^f$, and $R^{f1}$ is independently H, D, $C_1$-$C_4$ alkyl, $C_2$-$C_4$ alkenyl, $C_2$-$C_4$ alkynyl, $C_6$-$C_{10}$ aryl, 5-10 membered heteroaryl, $C_3$-$C_{10}$ cycloalkyl, or 4-10 membered heterocycloalkyl; and each $R^G$, $R^H$, and $R^I$ is independently $C_1$-$C_4$ alkyl or phenyl.

4. The compound or a pharmaceutically acceptable salt, stereoisomer, solvate, N-oxide, tautomer, isotopic variant, or deuterated compound thereof of claim 1, wherein $Cy^1$ is

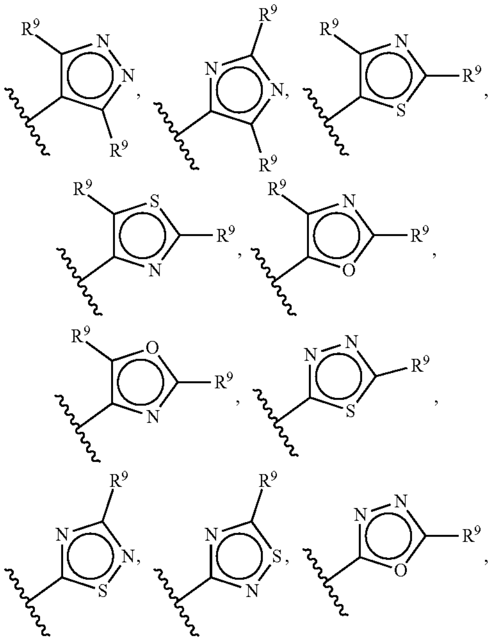

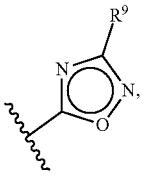

or

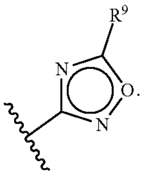

5. The compound or a pharmaceutically acceptable salt, stereoisomer, solvate, N-oxide, tautomer, isotopic variant, or deuterated compound thereof of claim 1, wherein $Cy^2$ is

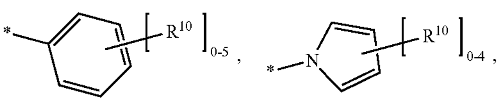

-continued

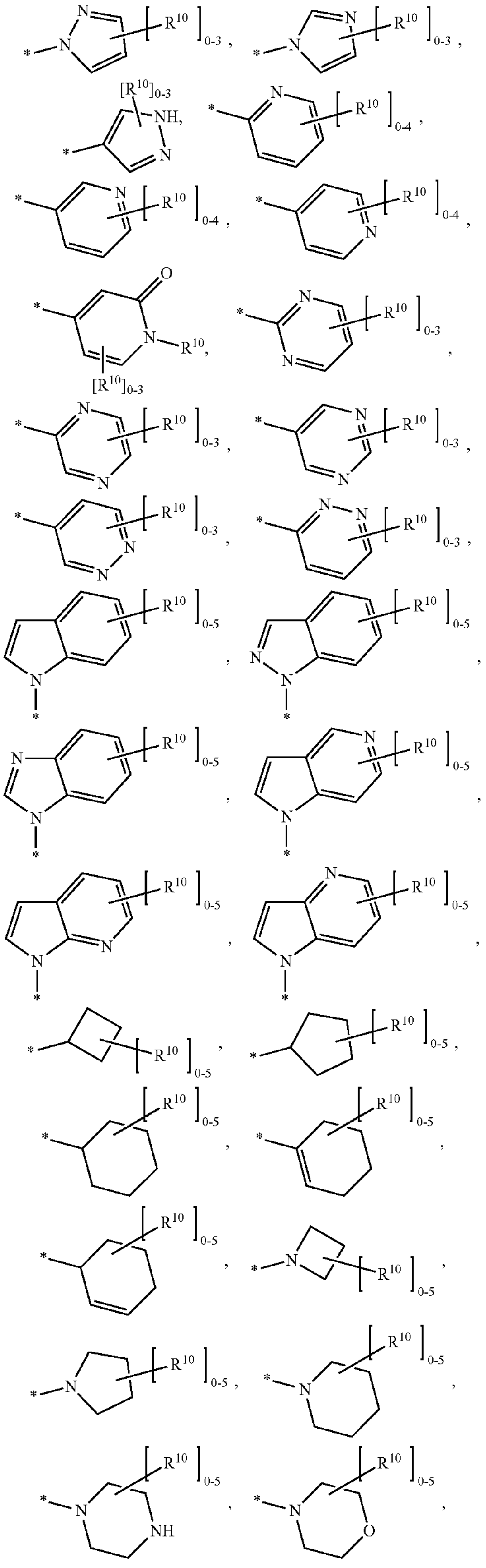

-continued
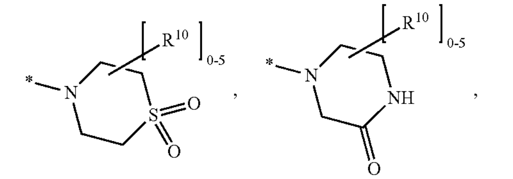
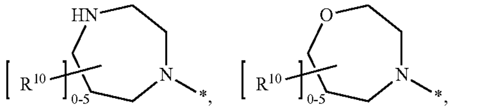
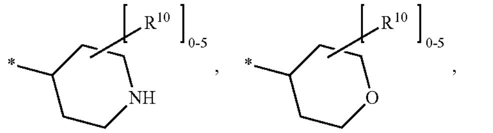
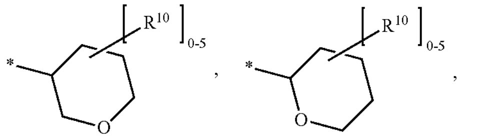
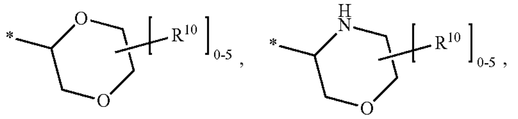
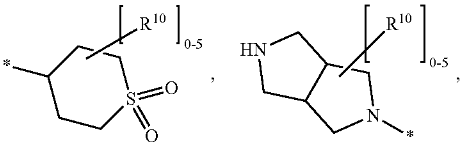
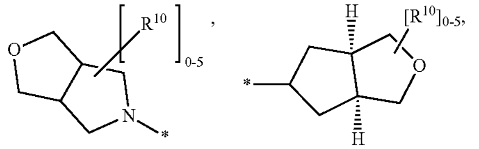
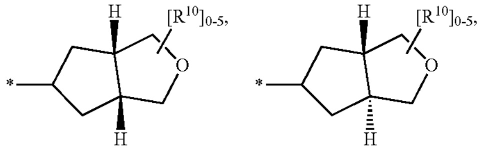
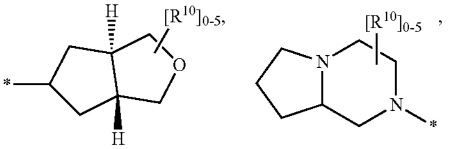
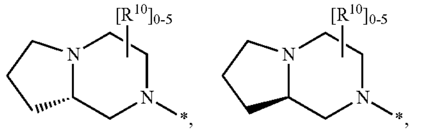
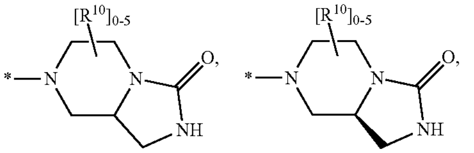
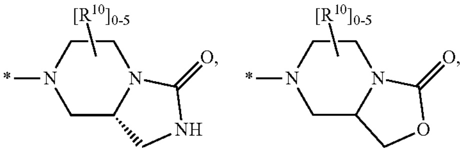
-continued
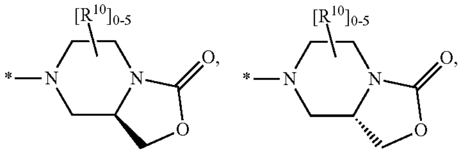
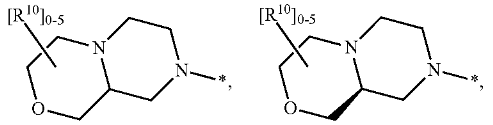
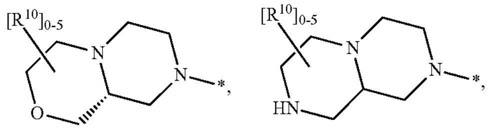
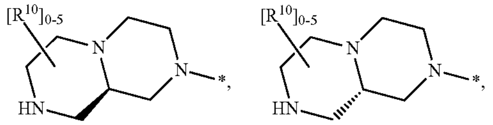
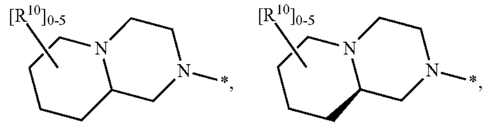
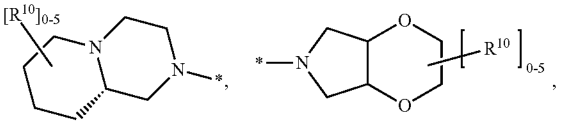
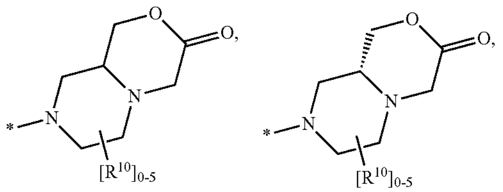
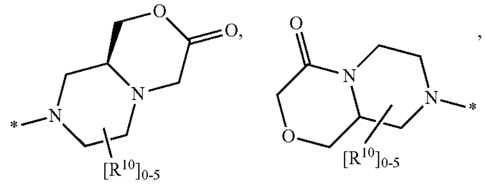
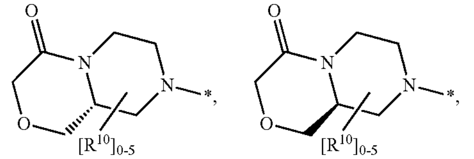
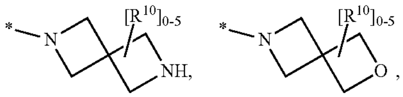
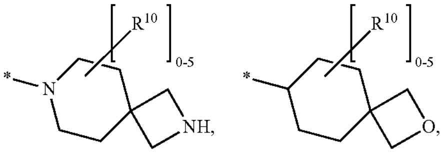
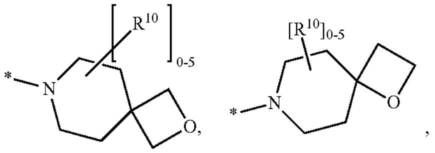

-continued

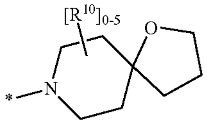

,

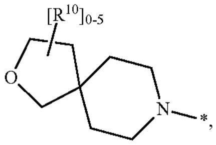

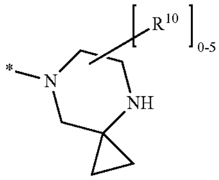

,

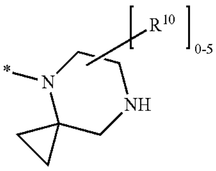

,

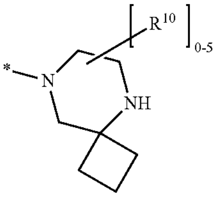

,

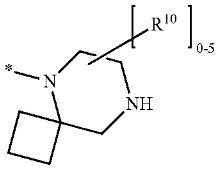

,

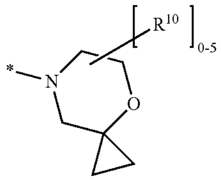

,

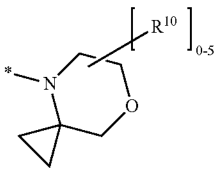

,

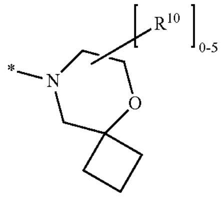

,

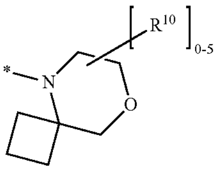

,

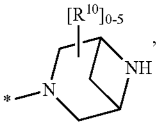

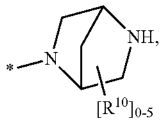

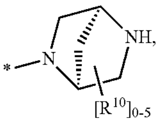

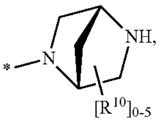

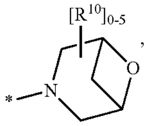

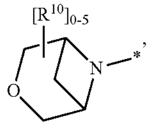

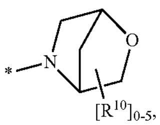

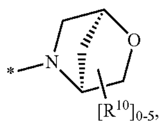

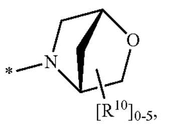

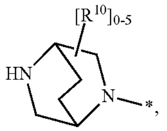

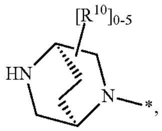

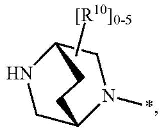

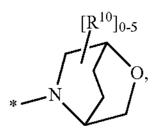

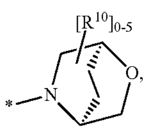

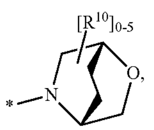

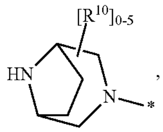

,

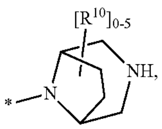

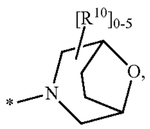

-continued

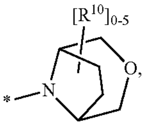

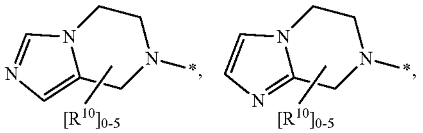

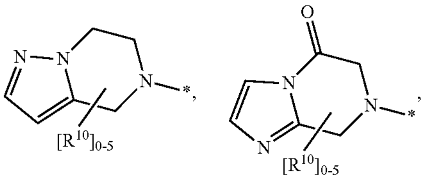

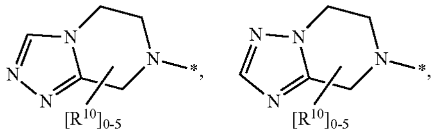

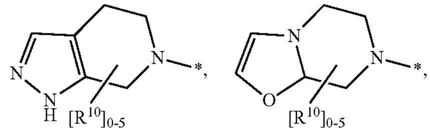

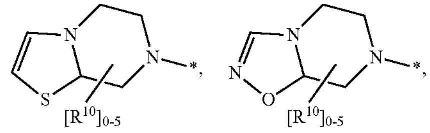

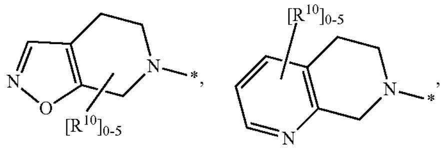

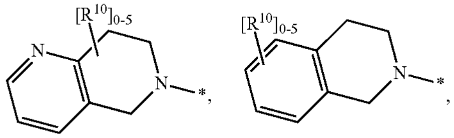

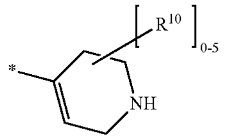

,

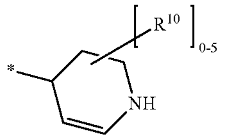

,

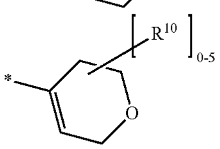

, or

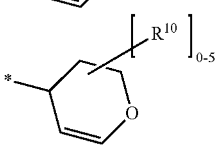

.

6. The compound or a pharmaceutically acceptable salt, stereoisomer, solvate, N-oxide, tautomer, isotopic variant, or deuterated compound thereof of claim 1, wherein each $R^1$ is independently H, D, CN, or $C_1$-$C_3$ alkyl optionally substituted by 1-5 substituents, each independently selected from D, halo, CN, OH, $C_1$-$C_6$ alkyl, $C_1$-$C_6$ haloalkyl, —O—$C_1$-$C_6$ alkyl, and —O$C_1$-$C_6$ haloalkyl.

7. The compound or a pharmaceutically acceptable salt, stereoisomer, solvate, N-oxide, tautomer, isotopic variant, or deuterated compound thereof of claim 1, wherein each $R^2$ and $R^3$ is independently H, D, CN, or $C_1$-$C_3$ alkyl optionally substituted by 1-5 substituents, each independently selected from D, halo, CN, OH, $C_1$-$C_6$ alkyl, $C_1$-$C_6$ haloalkyl, —O—$C_1$-$C_6$ alkyl, and —O$C_1$-$C_6$ haloalkyl.

8. The compound or a pharmaceutically acceptable salt, stereoisomer, solvate, N-oxide, tautomer, isotopic variant, or deuterated compound thereof of claim 1, wherein $R^2$ and $R^3$ together with the carbon atom to which they are attached form $C_3$-$C_6$ cycloalkyl or 4-6 membered heterocycloalkyl, wherein the $C_3$-$C_6$ cycloalkyl and 4-6 membered heterocycloalkyl are each optionally substituted by 1, 2, 3, or 4 substituents, each independently selected from D, halo, CN, $NO_2$, oxo, OH, OMe, $OCF_3$, and OEt.

9. The compound or a pharmaceutically acceptable salt, stereoisomer, solvate, N-oxide, tautomer, isotopic variant, or deuterated compound thereof of claim 1, wherein the compound is a compound having the structure of Formula (IIA):

(IIA)

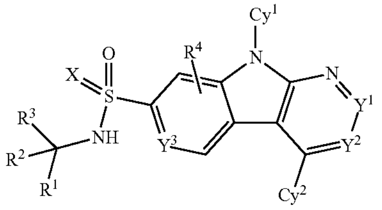

or pharmaceutically acceptable salt, stereoisomer, solvate, N-oxide, tautomer, isotopic variant, or deuterated compound thereof.

10. The compound or a pharmaceutically acceptable salt, stereoisomer, solvate, N-oxide, tautomer, isotopic variant, or deuterated compound thereof of claim 1, wherein the compound is a compound having the structure of Formula (IIa) or (IIb):

(IIa)

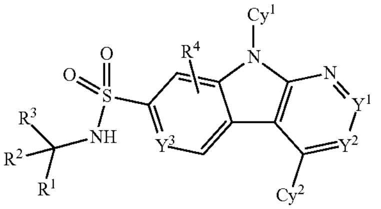

or (IIb)

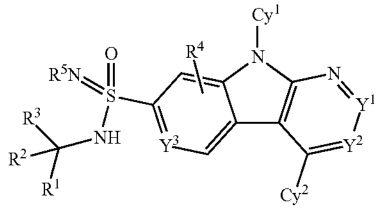

or pharmaceutically acceptable salt, stereoisomer, solvate, N-oxide, tautomer, isotopic variant, or deuterated compound thereof.

11. The compound of claim 1, wherein the compound is a compound having the structure of Formula (IIIa) or (IIIb):

(IIIa)

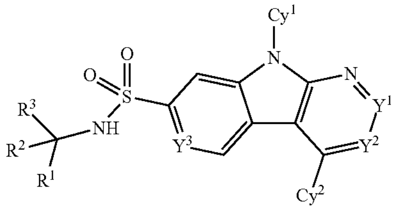

or

-continued (IIIb)

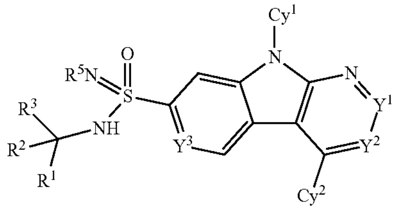

or pharmaceutically acceptable salt, stereoisomer, solvate, N-oxide, tautomer, isotopic variant, or deuterated compound thereof.

12. The compound of claim 1, wherein the compound is a compound having the structure of Formula (IV):

(IV)

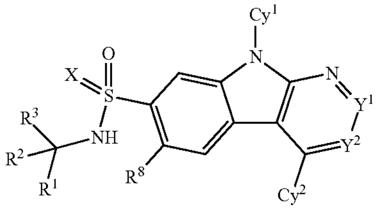

or pharmaceutically acceptable salt, stereoisomer, solvate, N-oxide, tautomer, isotopic variant, or deuterated compound thereof.

13. The compound of claim 1, wherein the compound is a compound having the structure of Formula (IVa) or (IVb):

(IVa)

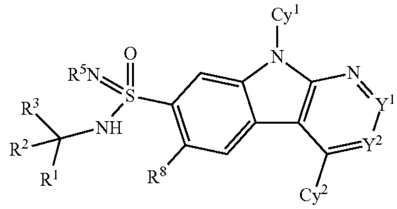

or (IVb)

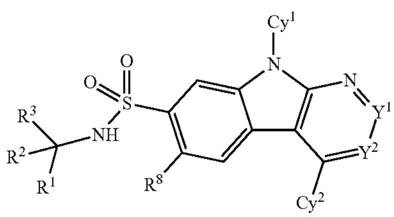

or pharmaceutically acceptable salt, stereoisomer, solvate, N-oxide, tautomer, isotopic variant, or deuterated compound thereof.

14. The compound of claim 1, wherein the compound is a compound having the structure of Formula (Va), (Vb), or (Vc):

(Va)

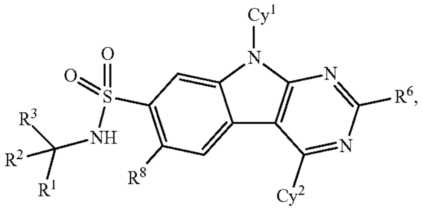

(Vb)

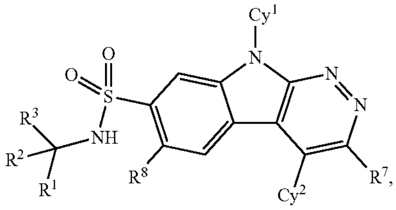

or (Vc)

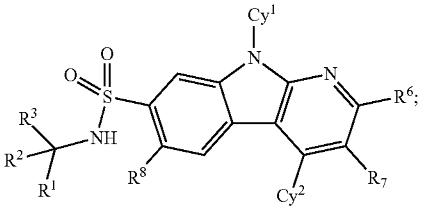

or pharmaceutically acceptable salt, stereoisomer, solvate, N-oxide, tautomer, isotopic variant, or deuterated compound thereof.

15. The compound of claim 1, wherein the compound is a compound having the structure of Formula (VI):

(VI)

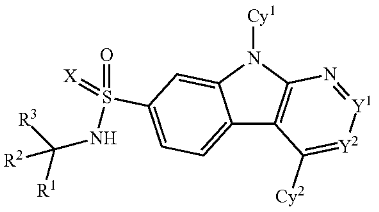

or pharmaceutically acceptable salt, stereoisomer, solvate, N-oxide, tautomer, isotopic variant, or deuterated compound thereof; wherein $Cy^1$ is 5 membered heteroaryl having 1, 2, 3, or 4 heteroatoms, each independently selected from N, O, and S; and wherein the 5 membered heteroaryl is optionally substituted by 1, 2, 3, or 4 $R^9$.

16. The compound of claim 1, wherein the compound is a compound having the structure of Formula (VIa) or (VIb):

(VIa)

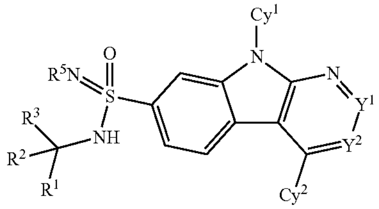

or (VIb)

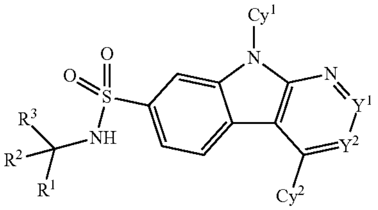

or pharmaceutically acceptable salt, stereoisomer, solvate, N-oxide, tautomer, isotopic variant, or deuterated compound thereof; wherein each $Cy^1$ is independently 5 membered heteroaryl having 1, 2, 3, or 4 heteroatoms, each independently selected from N, O, and S; and wherein, the 5 membered heteroaryl optionally substituted by 1, 2, 3, or 4 $R^9$.

17. The compound of claim 1, wherein the compound is a compound having the structure of Formula (VII):

(VII)

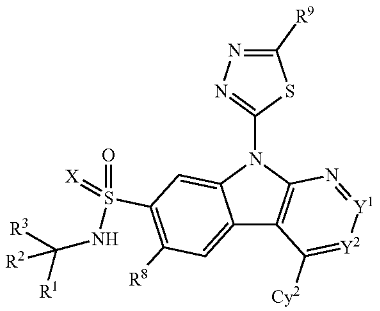

or pharmaceutically acceptable salt, stereoisomer, solvate, N-oxide, tautomer, isotopic variant, or deuterated compound thereof.

18. The compound of claim 1, wherein the compound is a compound having the structure of Formula (VIIa) or (VIIb):

(VIIa)

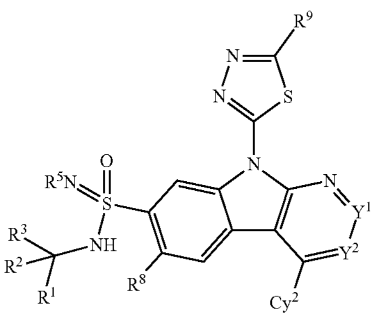

or

-continued (VIIb)

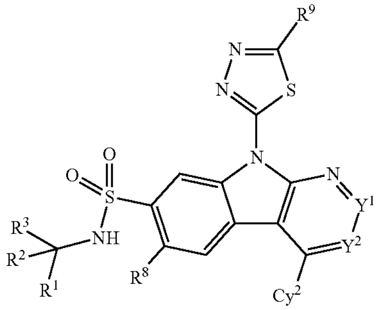

or pharmaceutically acceptable salt, stereoisomer, solvate, N-oxide, tautomer, isotopic variant, or deuterated compound thereof.

19. The compound of claim 1, wherein the compound is a compound having the structure of Formula (VIIIa), (VIIIb), or (VIIIc):

(VIIIa)

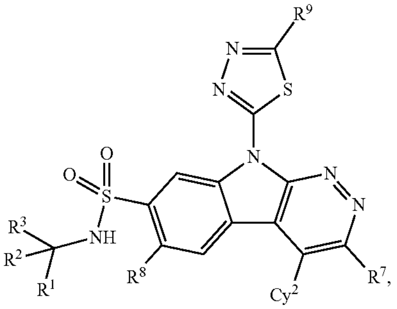

(VIIIb)

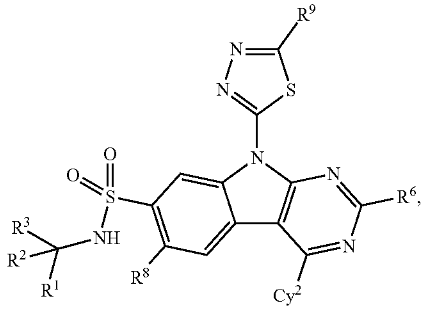

or (VIIIc)

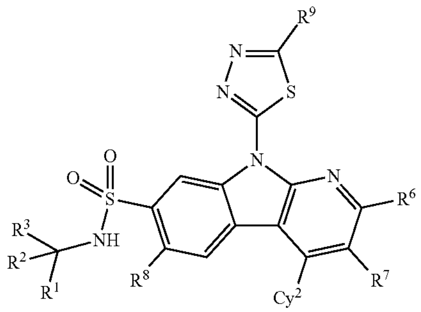

or pharmaceutically acceptable salt, stereoisomer, solvate, N-oxide, tautomer, isotopic variant, or deuterated compound thereof.

20. The compound of claim 1, wherein the compound is a compound having the structure of Formula (IXa), (IXb), or (IXc):

(IXa)

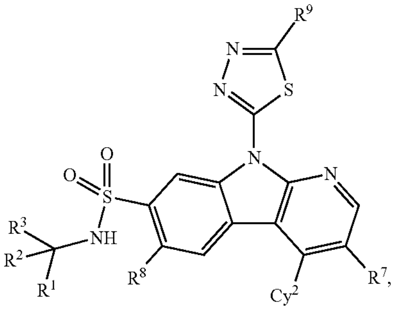

(IXb)

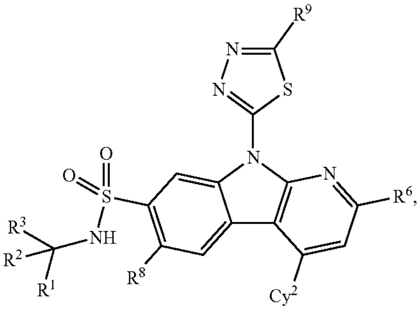

or (IXc)

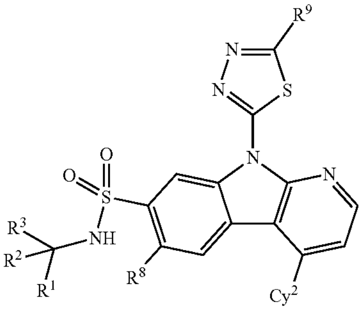

or pharmaceutically acceptable salt, stereoisomer, solvate, N-oxide, tautomer, isotopic variant, prodrug, or deuterated compound thereof.

21. The compound of claim 1, wherein the compound is a compound having the structure of Formula (Xa) or (Xb):

(Xa)

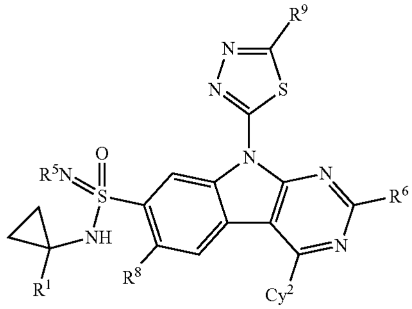

or

-continued
(Xb)
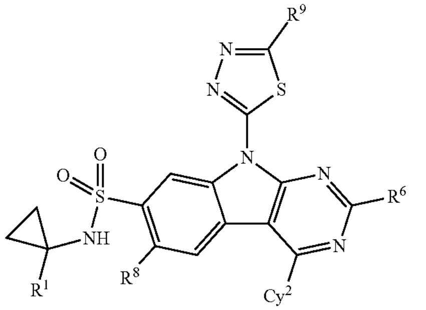
or pharmaceutically acceptable salt, stereoisomer, solvate, N-oxide, tautomer, isotopic variant, or deuterated compound thereof.
22. The compound of claim 1, wherein the compound is:
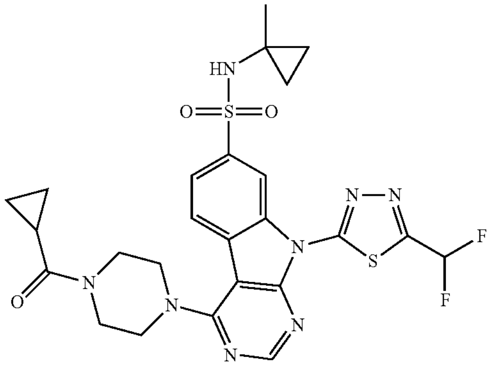
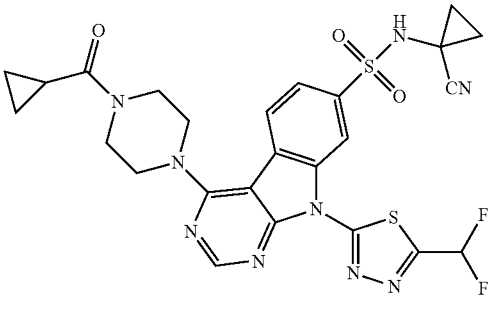
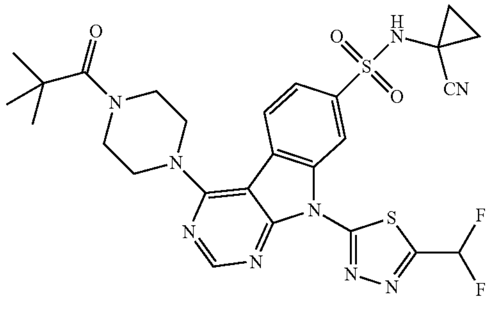
-continued
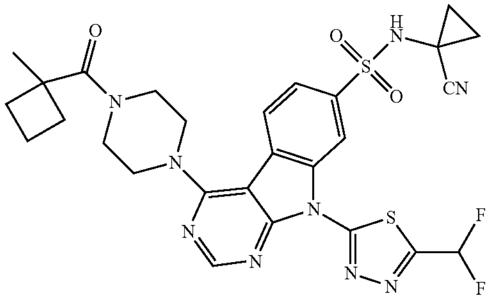
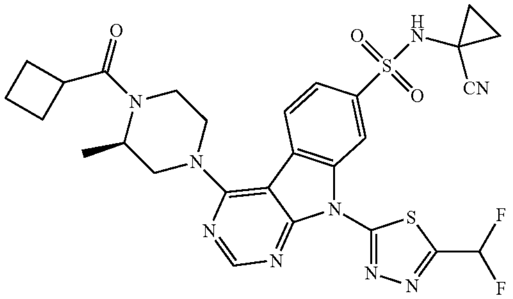
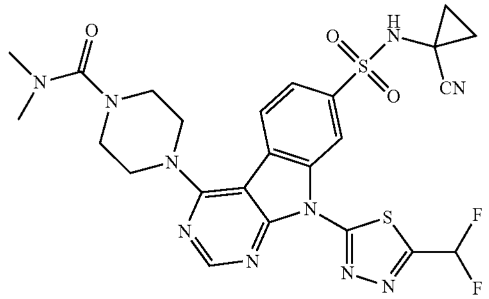
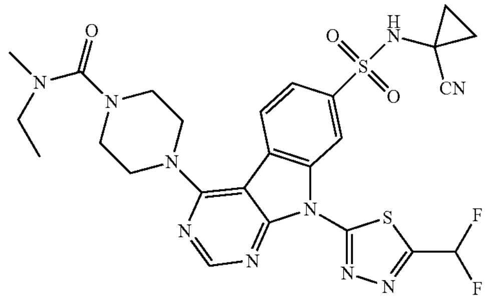
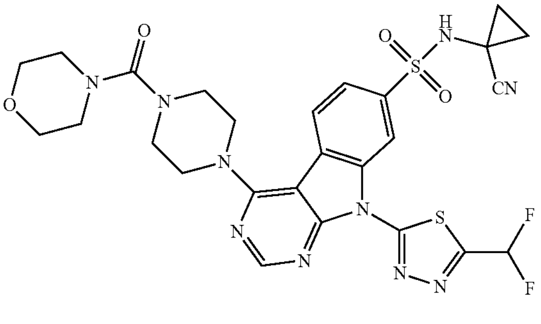

-continued
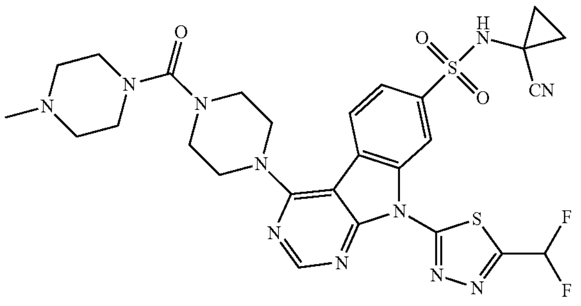
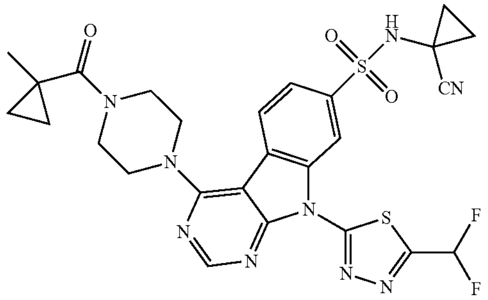
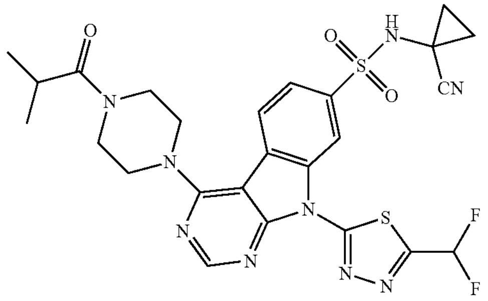
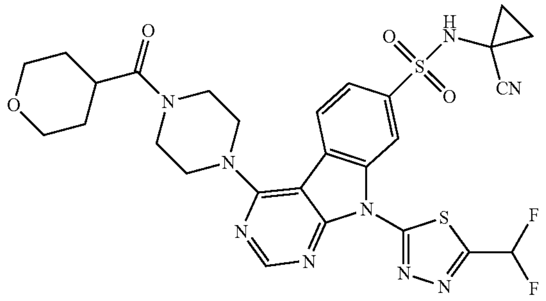
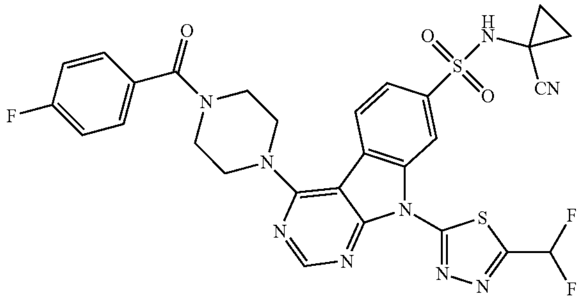
-continued
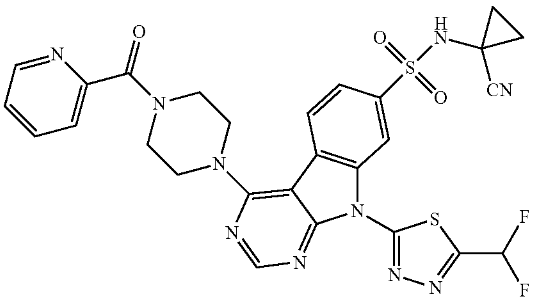
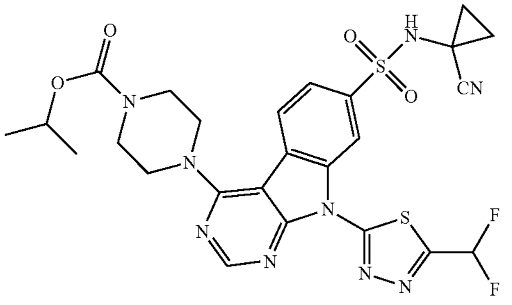
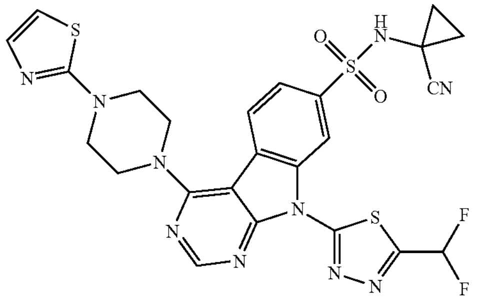
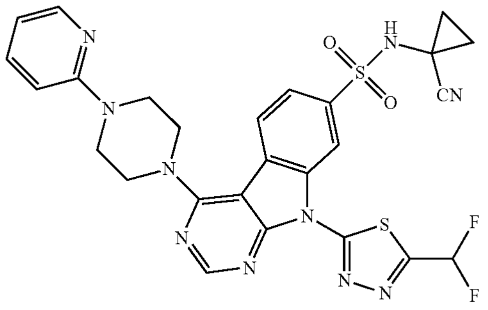
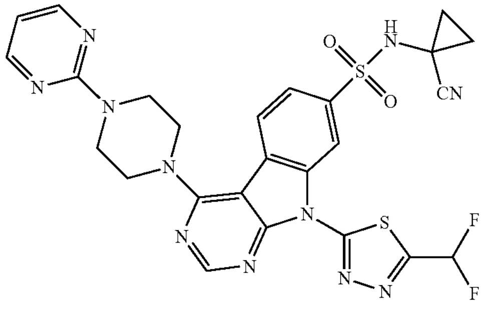

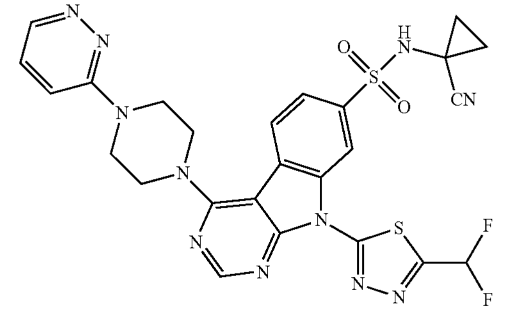
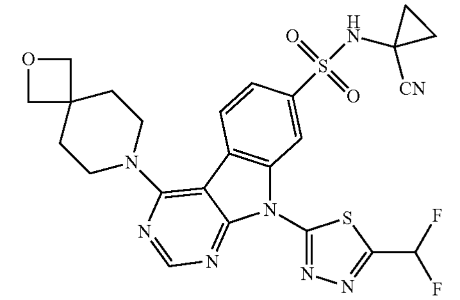
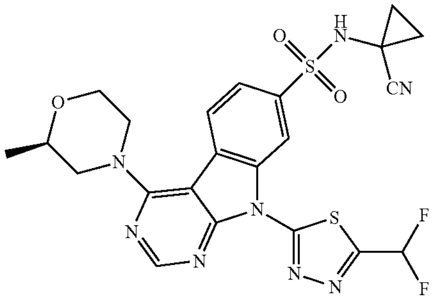
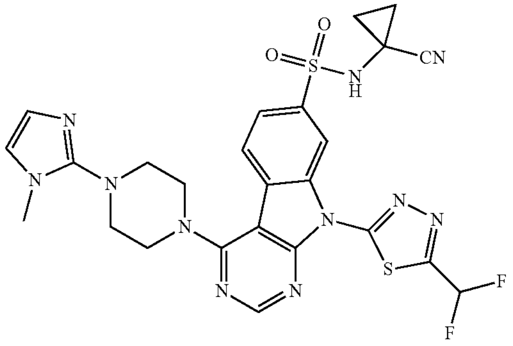
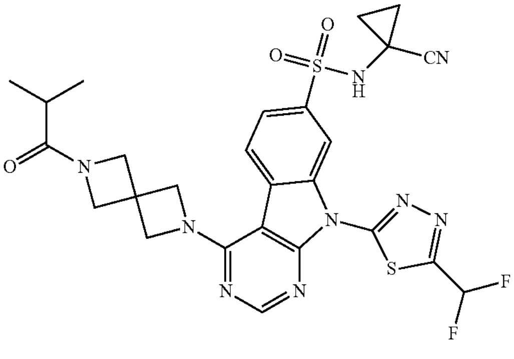
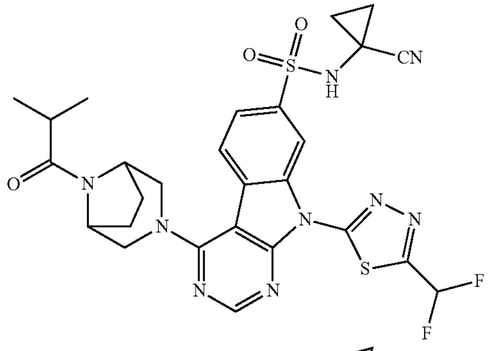
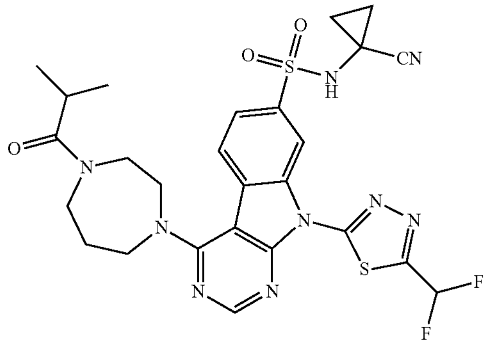
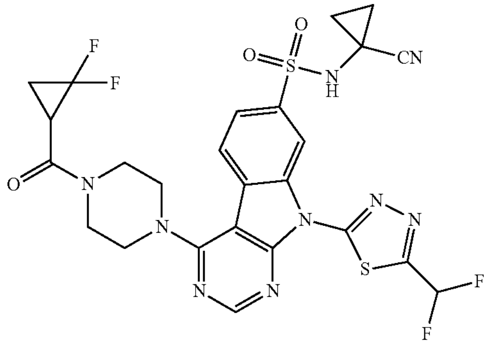
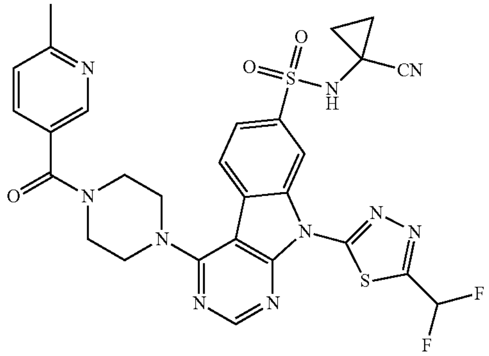
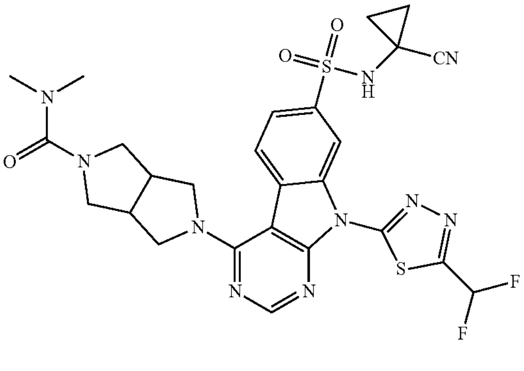

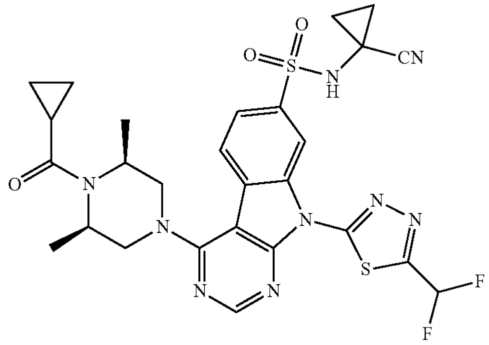
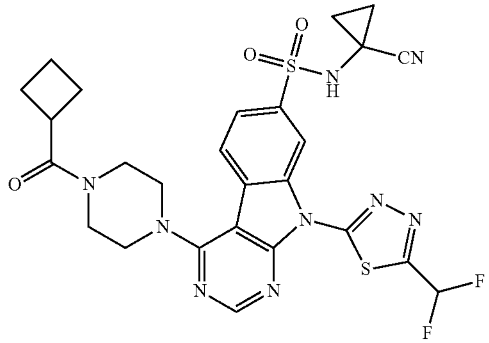
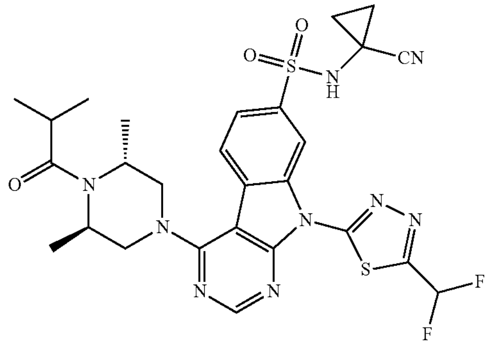
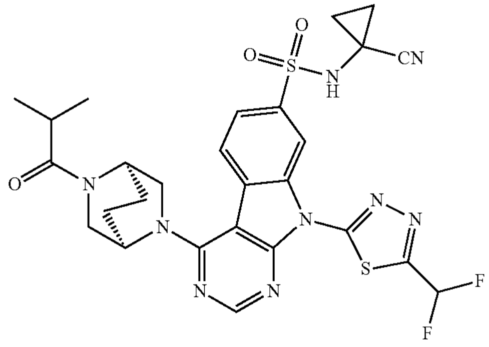
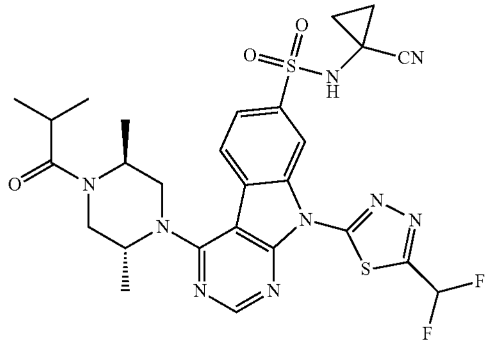
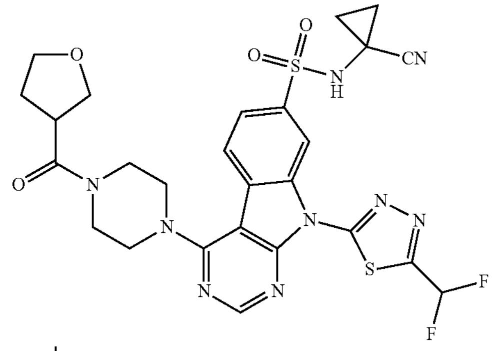
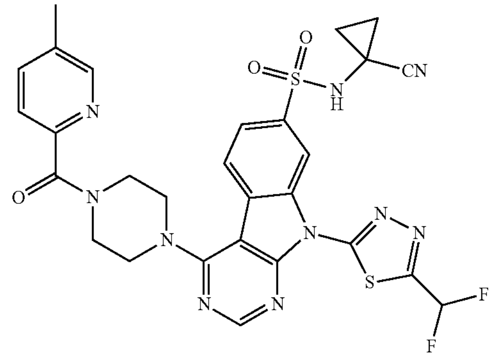
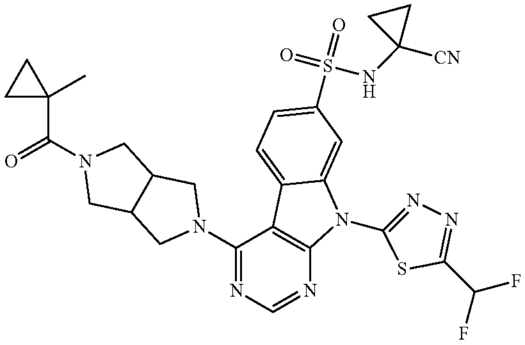
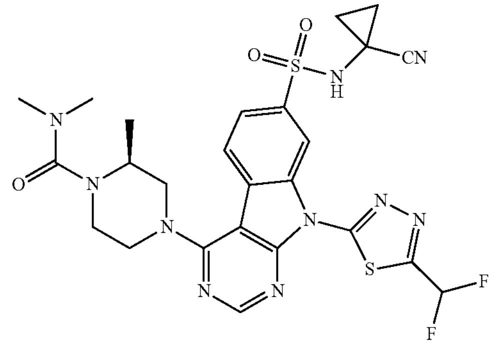
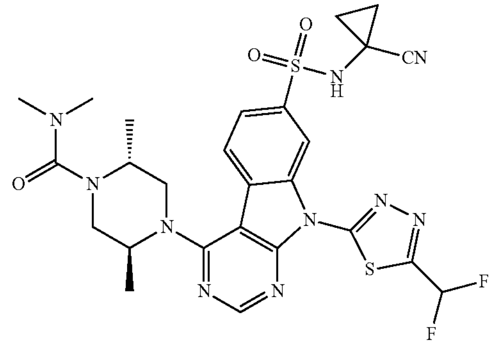

-continued
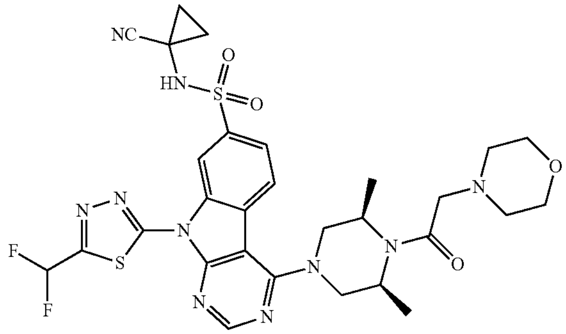
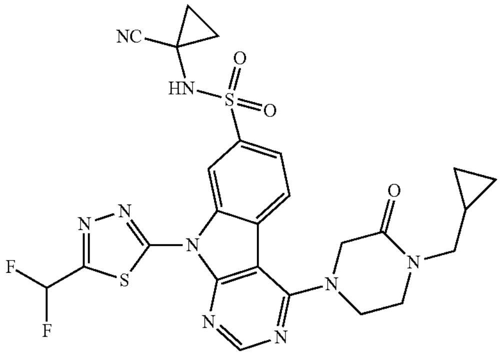
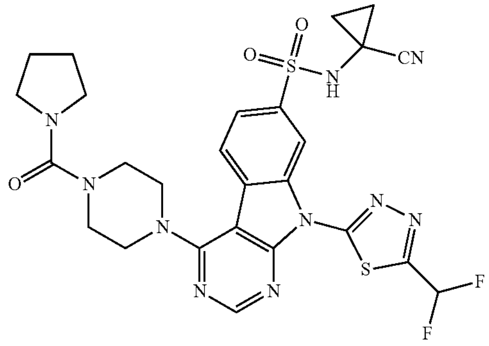
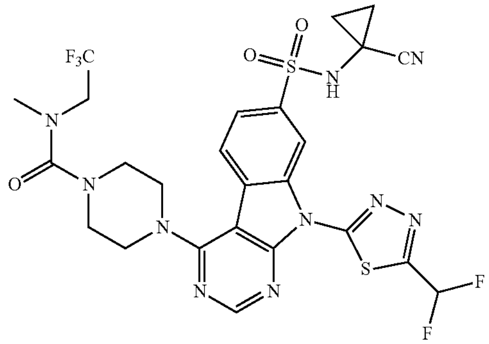
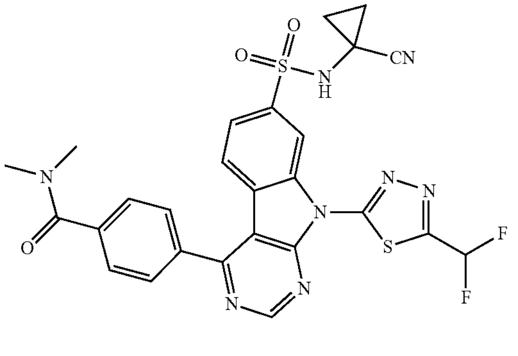
-continued
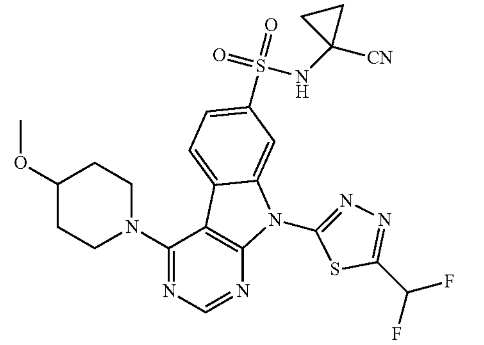
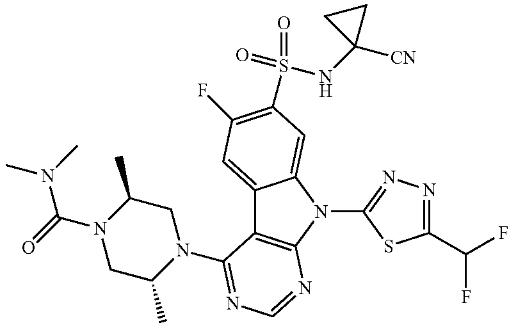
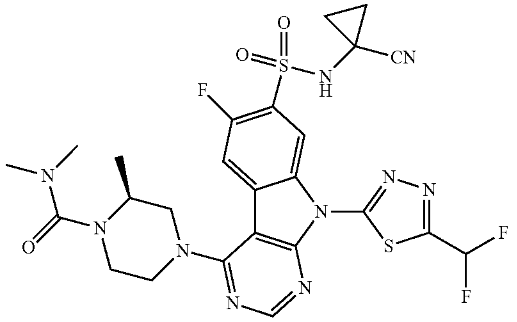
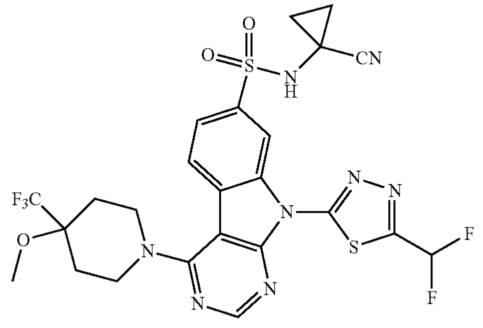
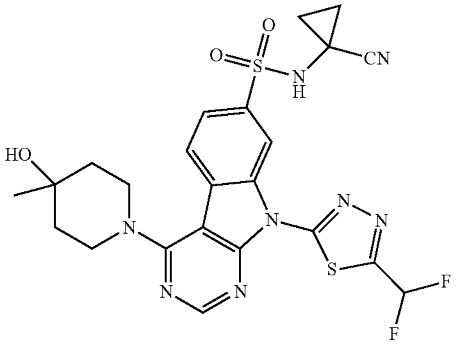

-continued
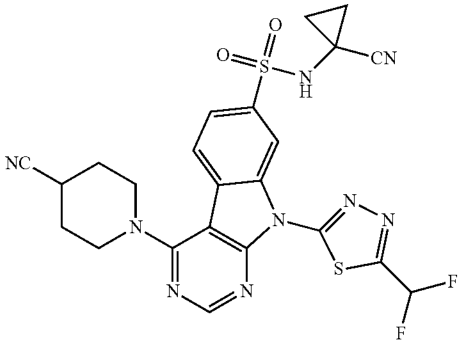
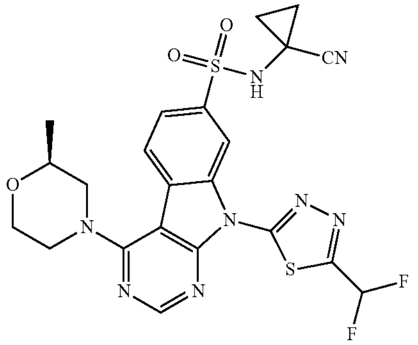
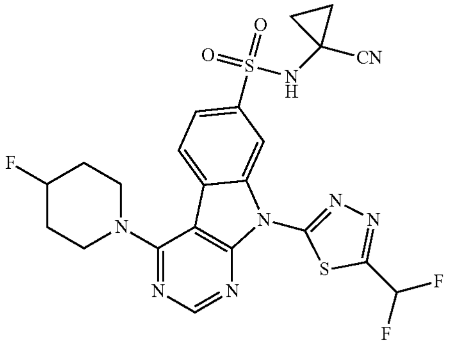
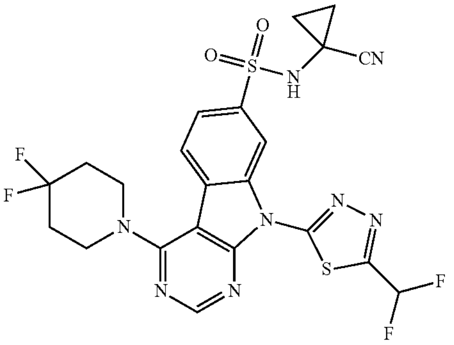
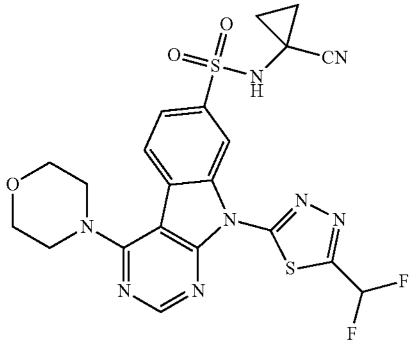
-continued
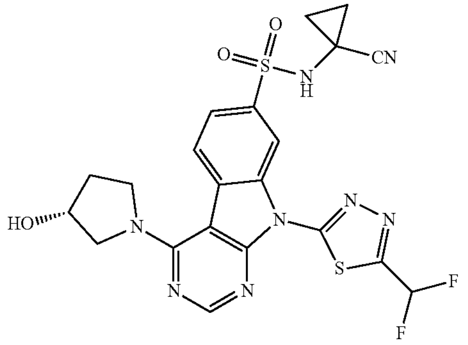
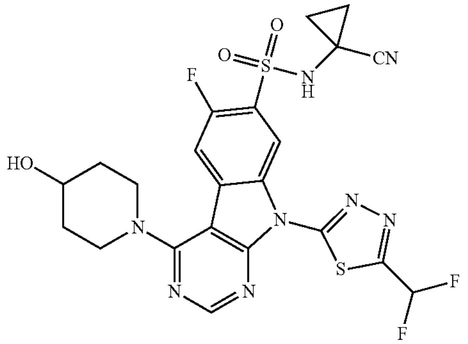
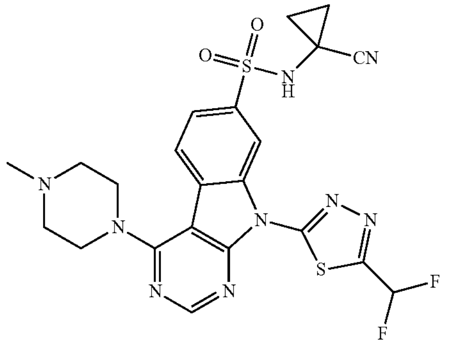
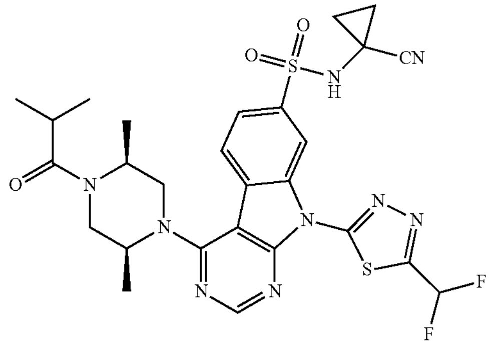
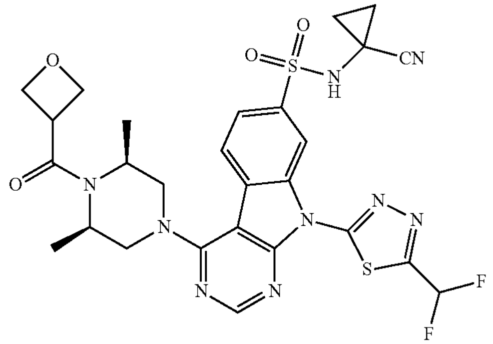

-continued
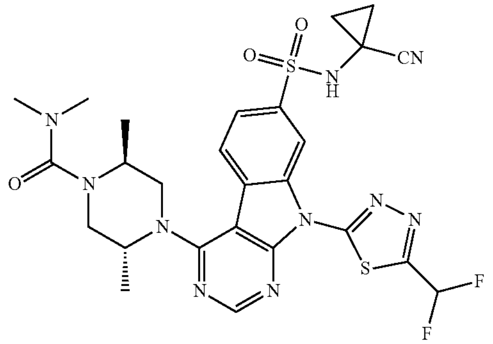
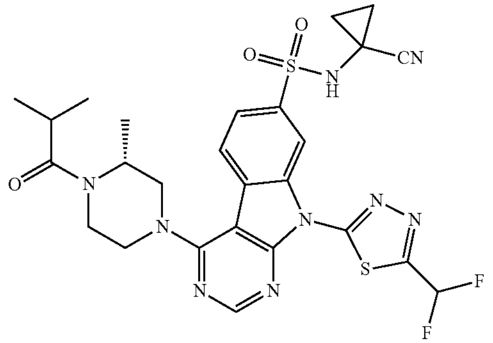
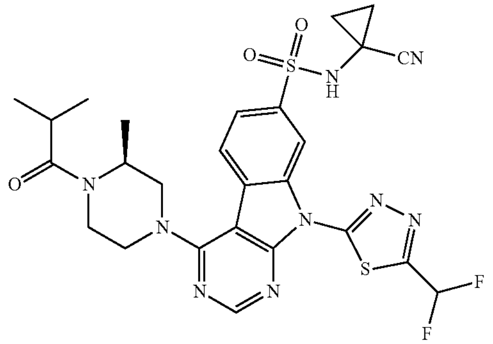
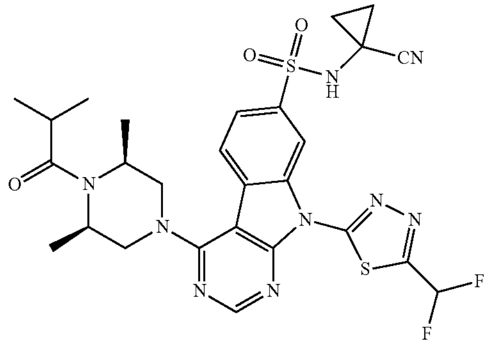
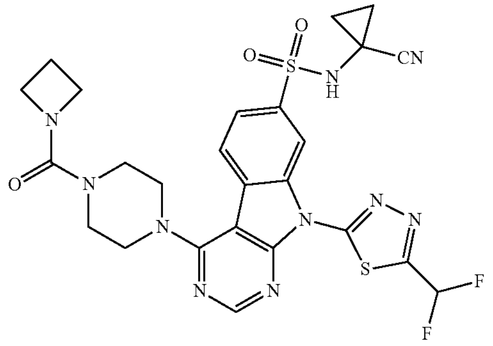
-continued
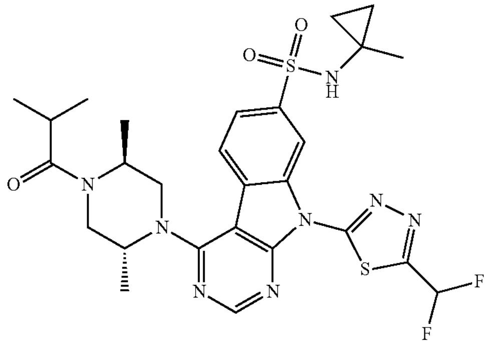
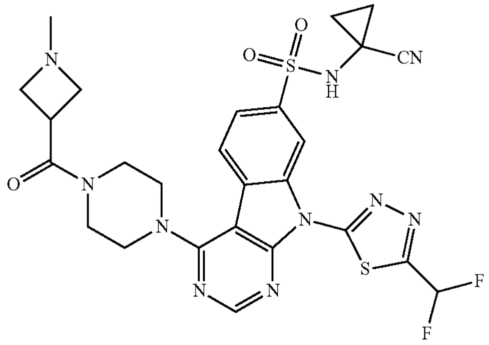
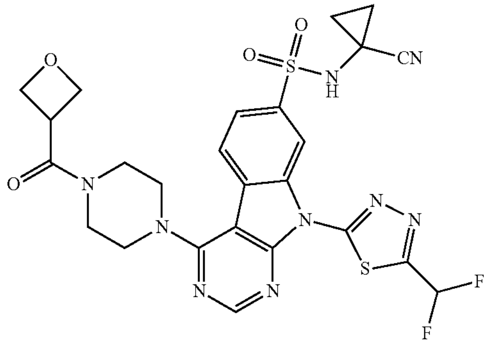
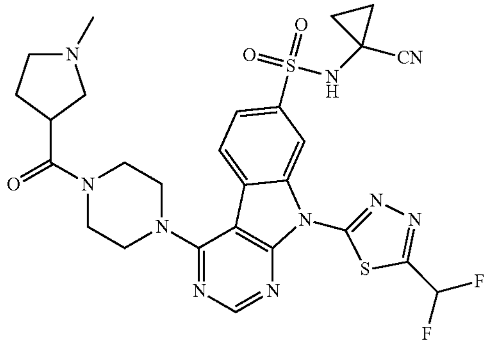
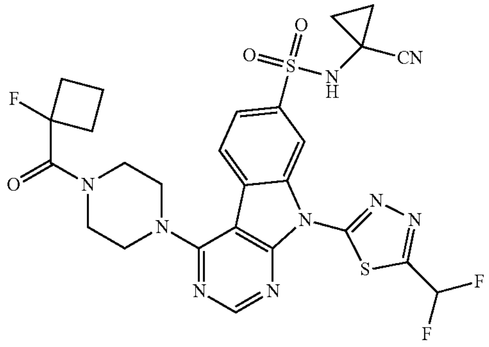

-continued
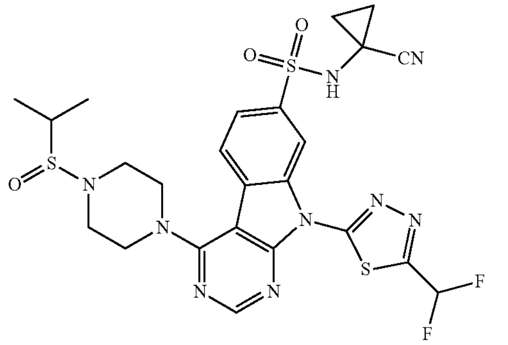
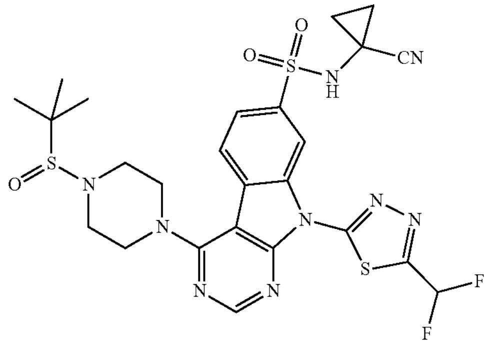
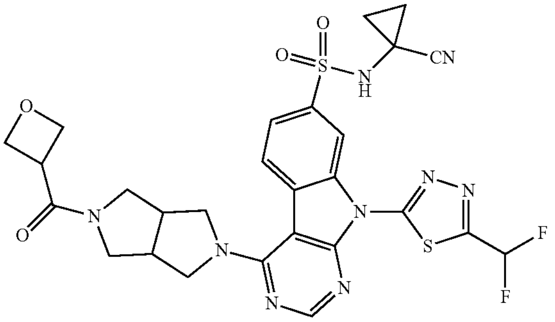
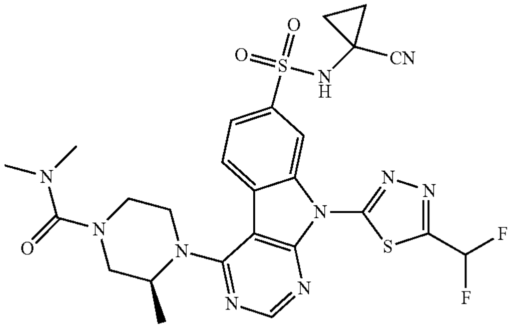
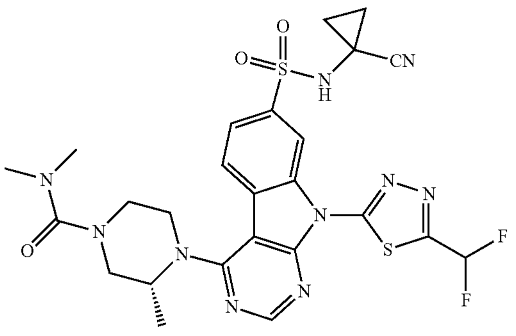
-continued
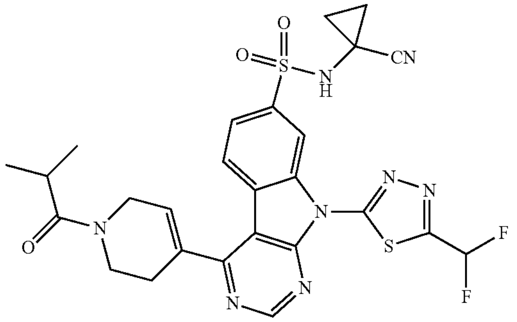
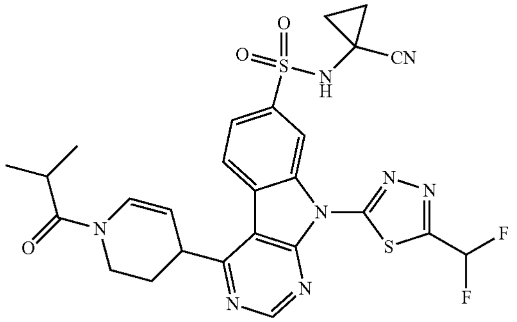
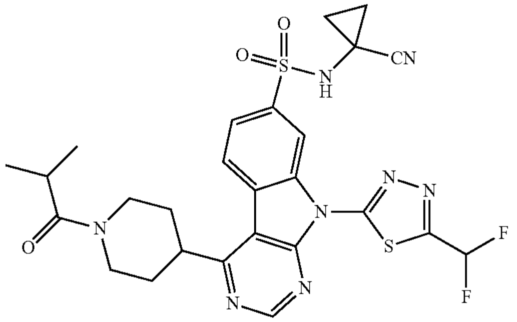
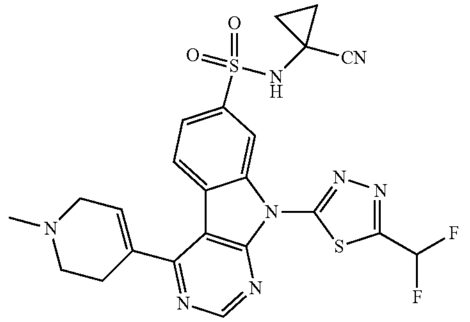
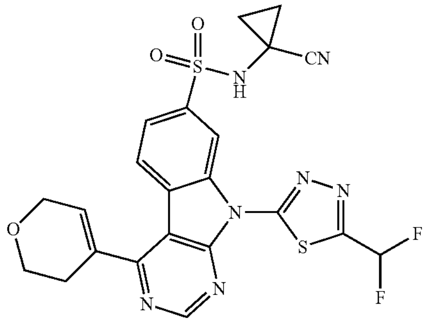

-continued
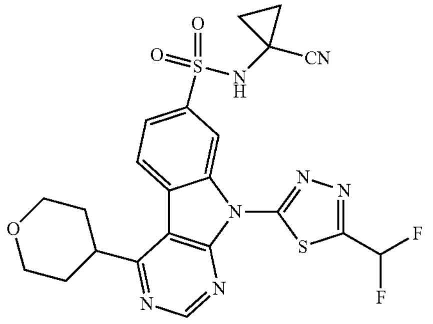
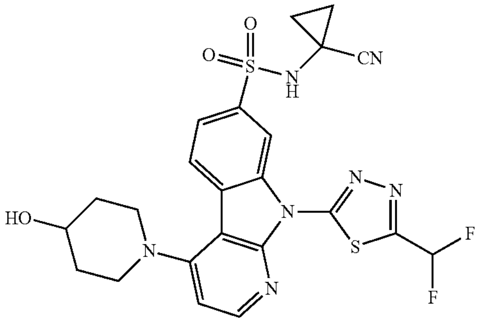
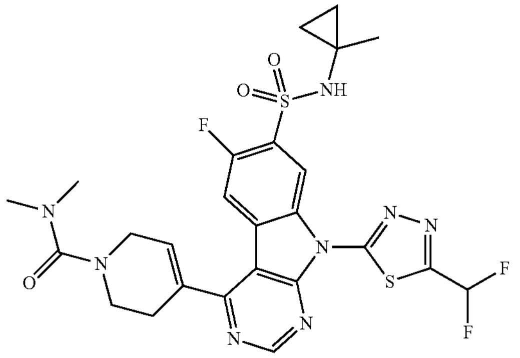
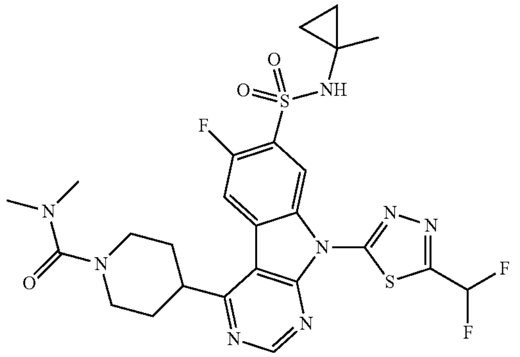
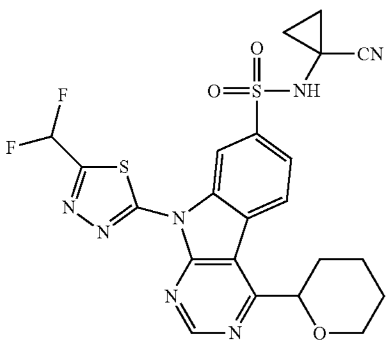
-continued
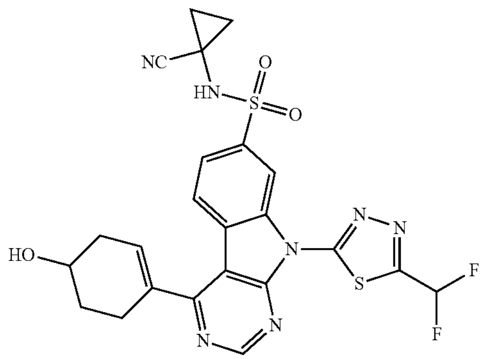
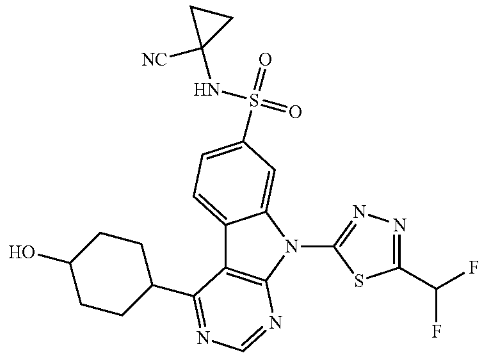
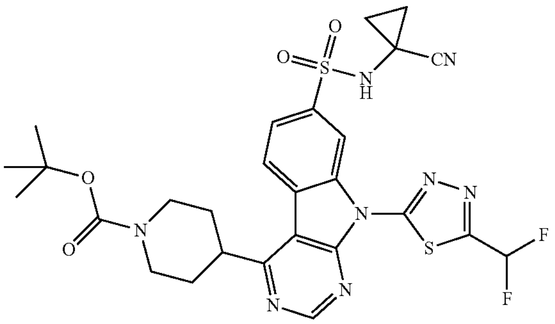
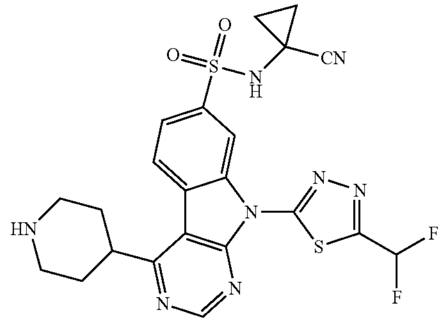
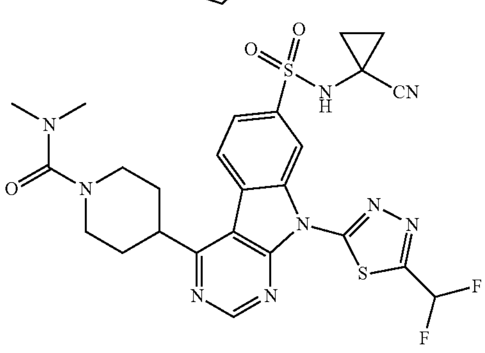

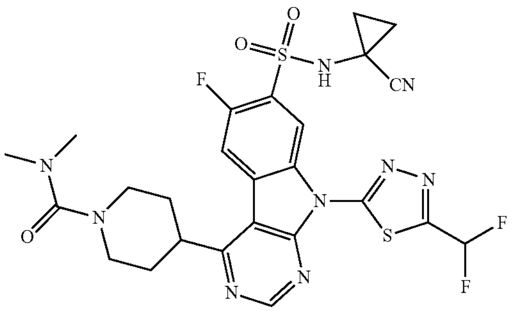
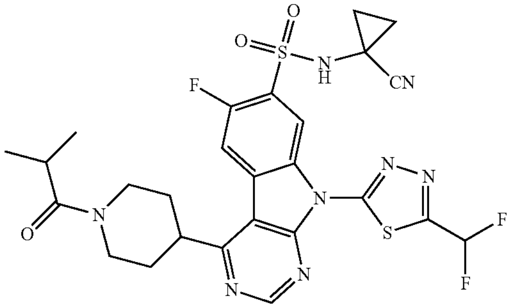
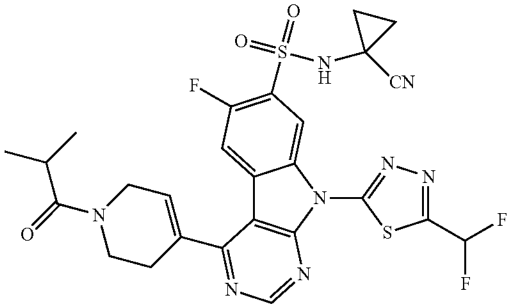
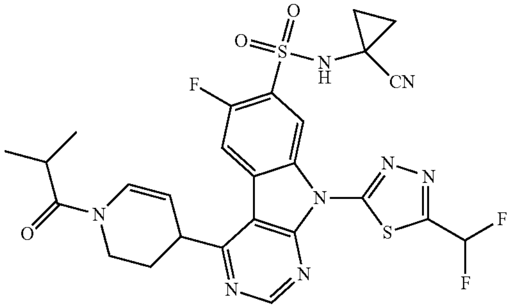
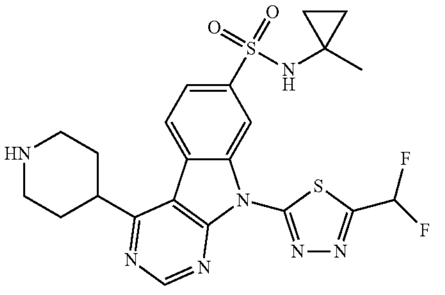
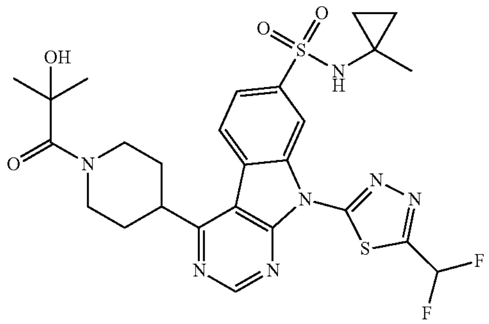
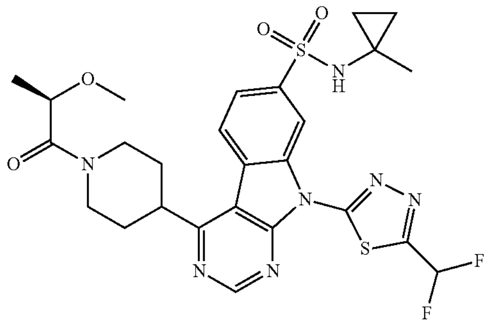
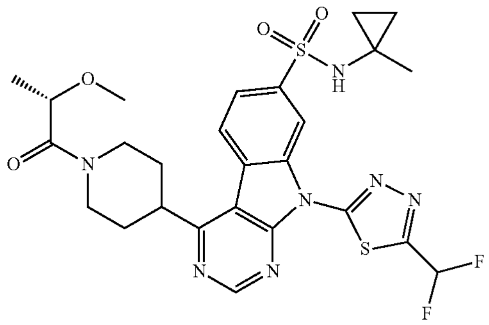
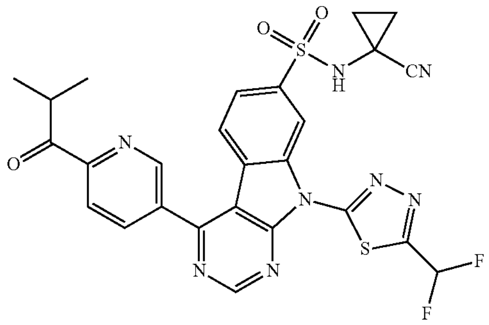
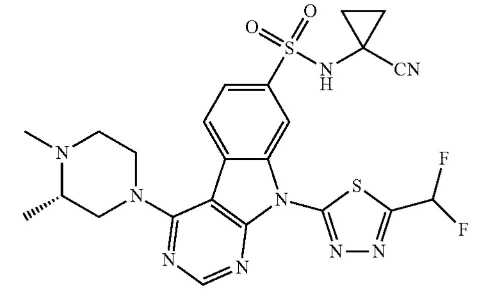

-continued
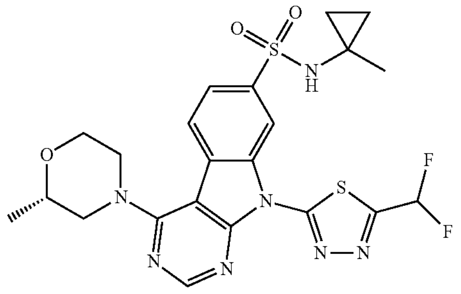
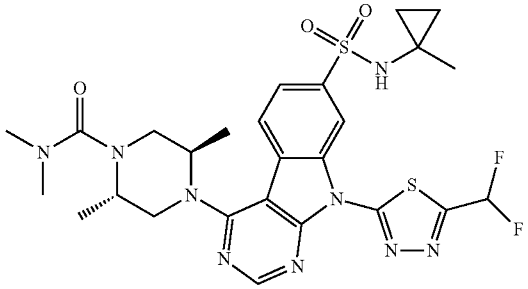
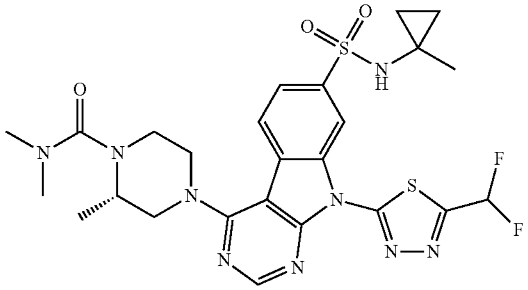
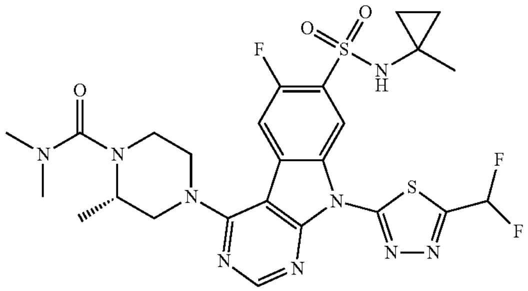
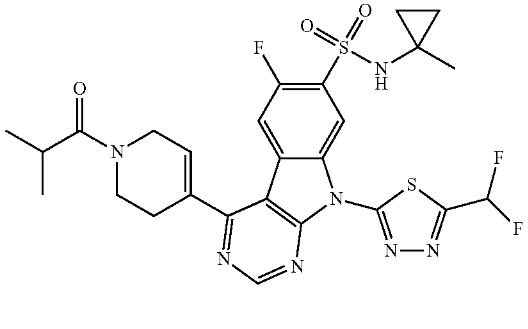
-continued
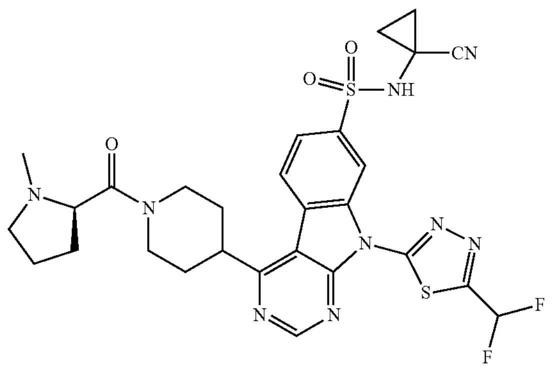
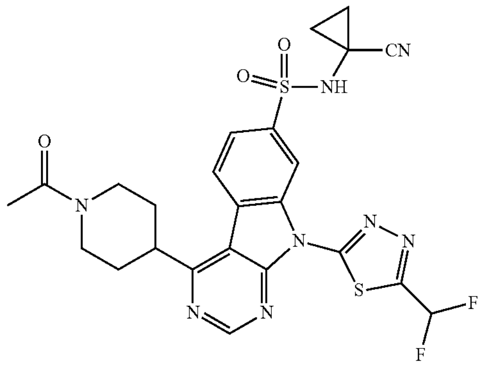
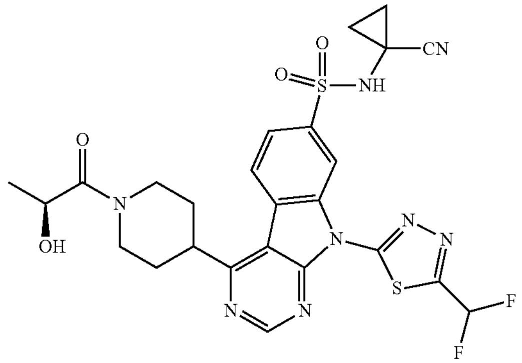
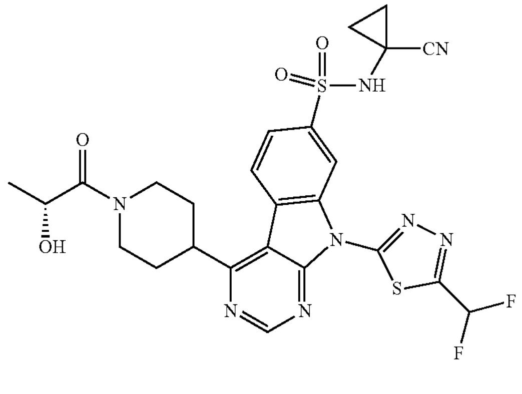

-continued
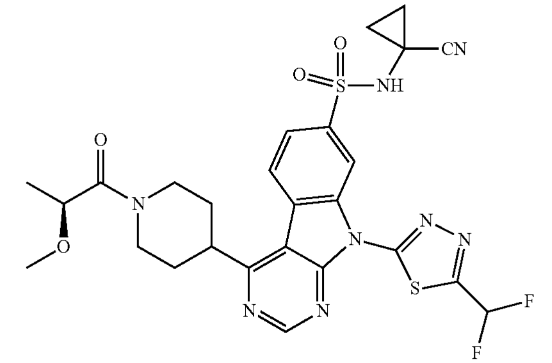
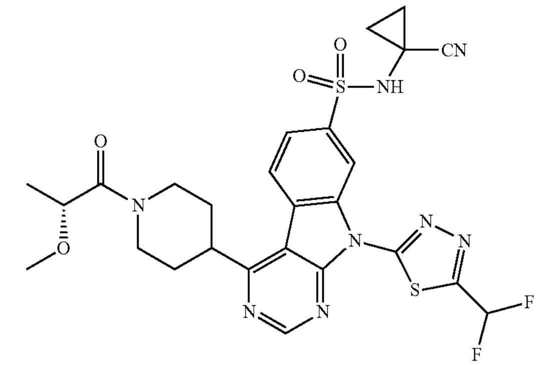
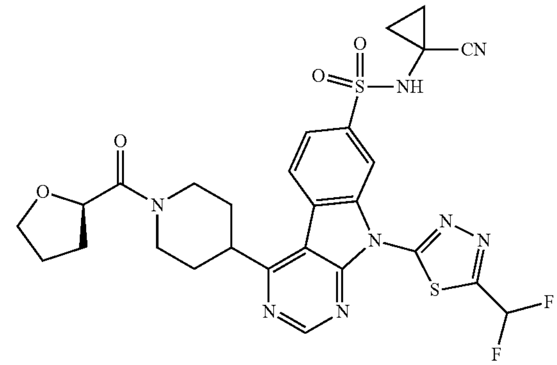
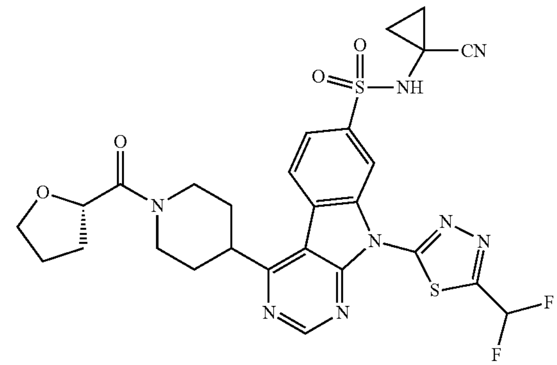
-continued
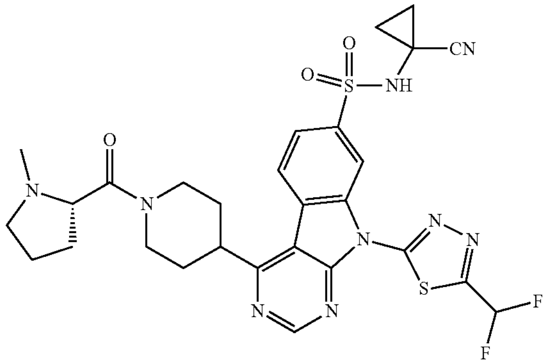
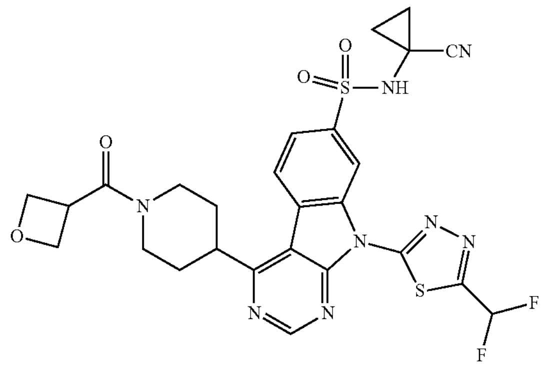
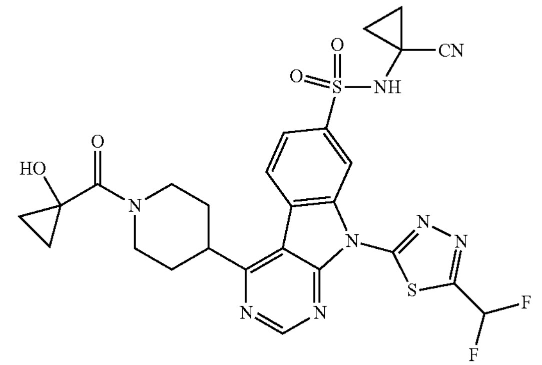
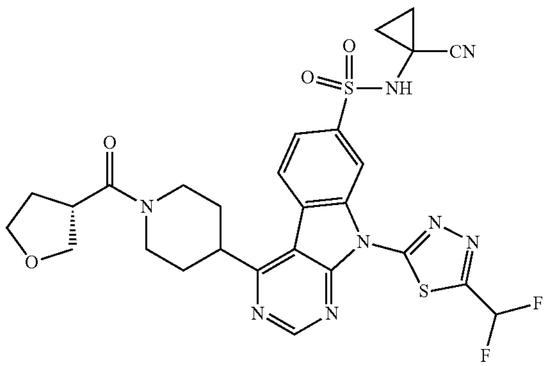

-continued
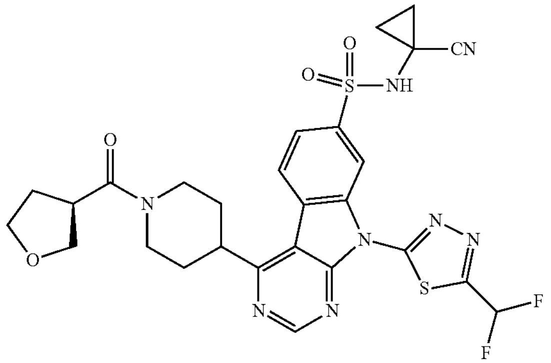
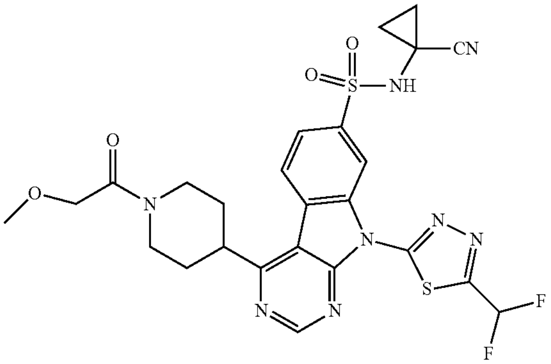
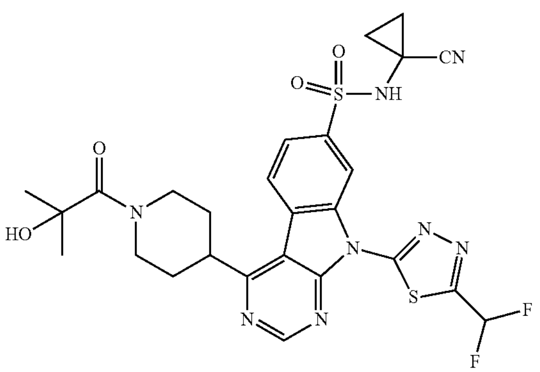
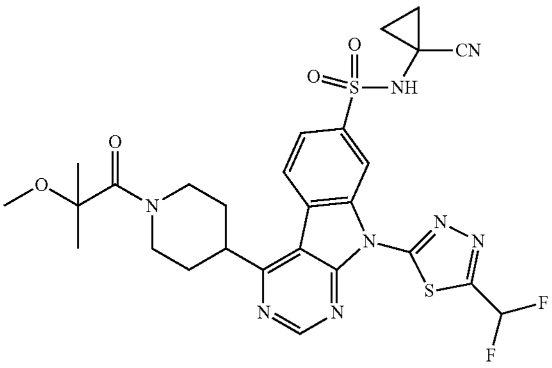
-continued
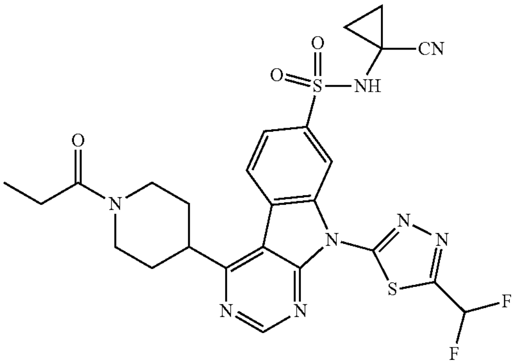
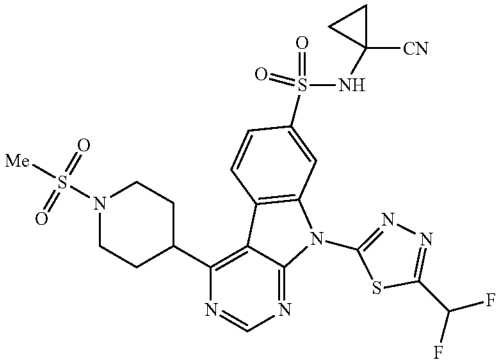
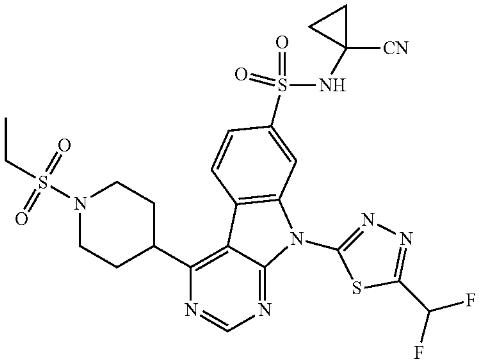
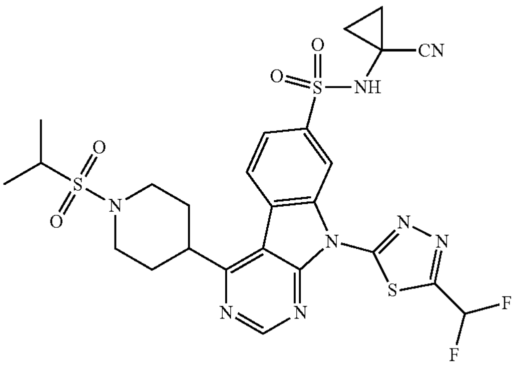

-continued
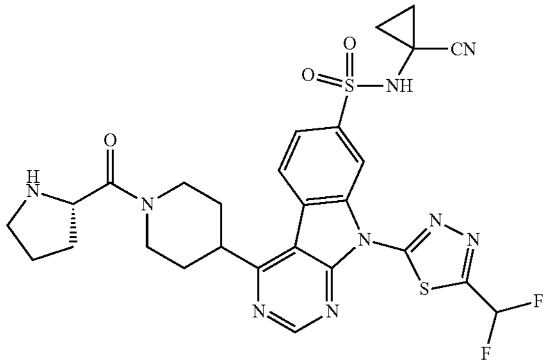
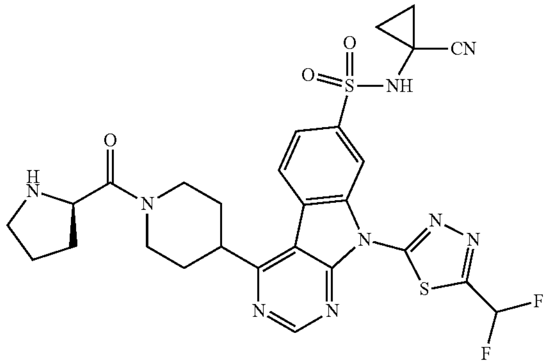
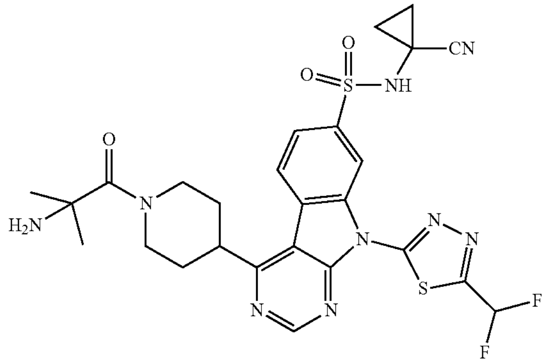
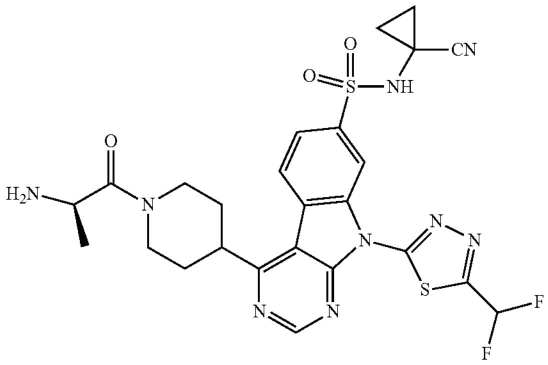
-continued
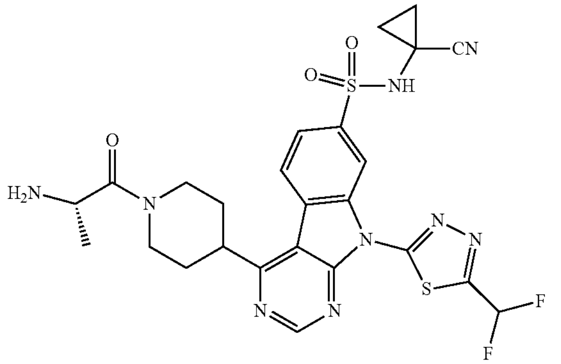
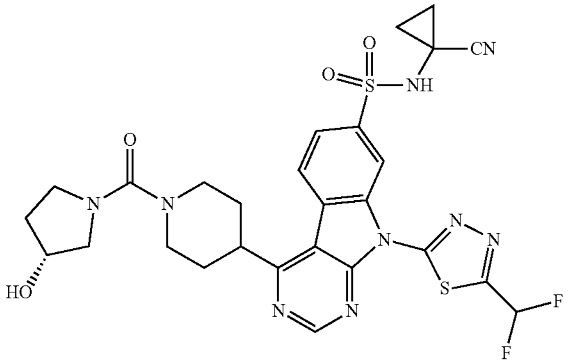
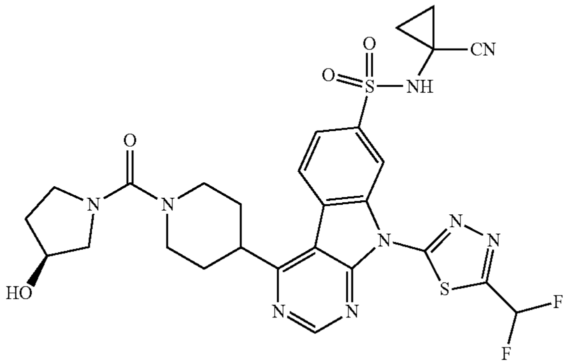
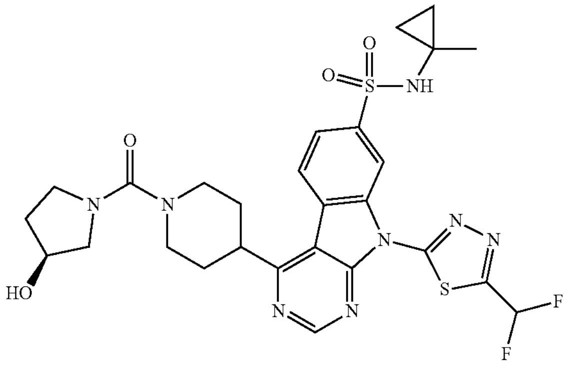

-continued
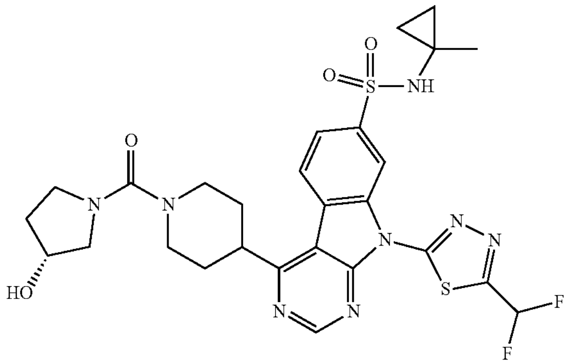
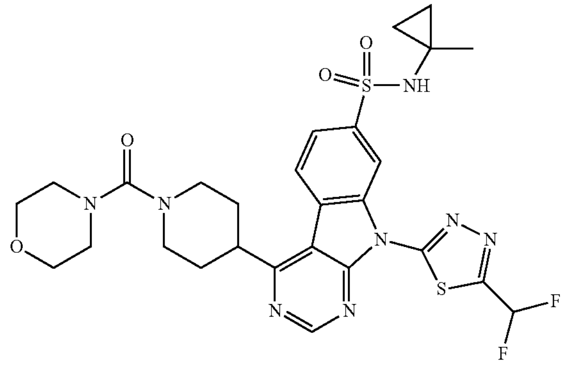
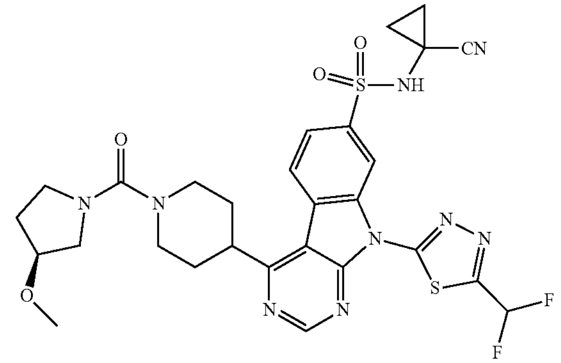
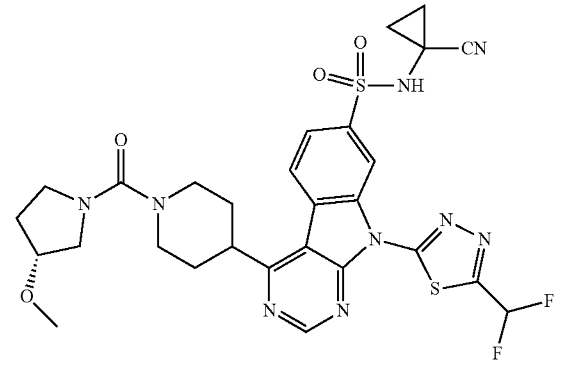
-continued
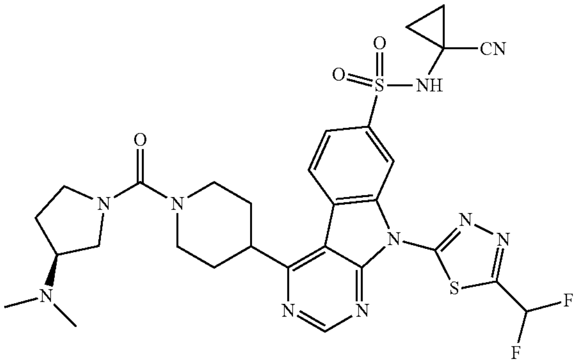
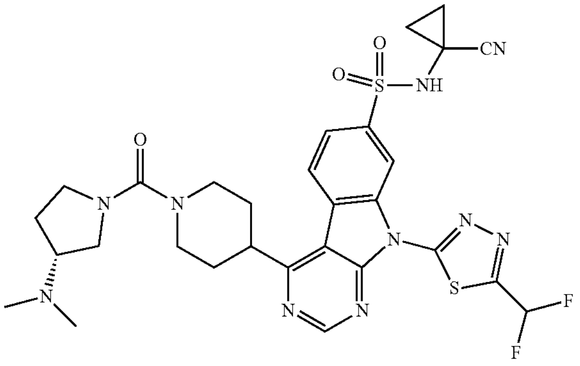
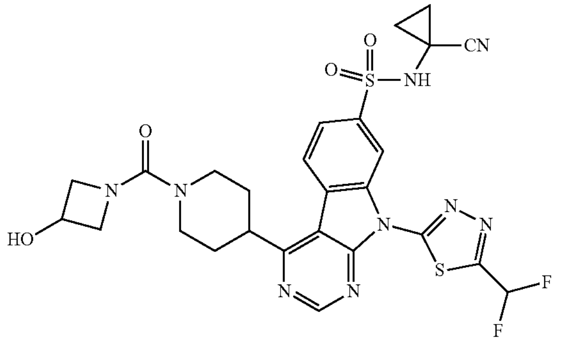
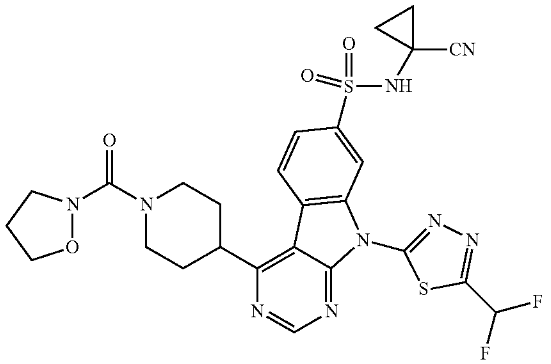

-continued
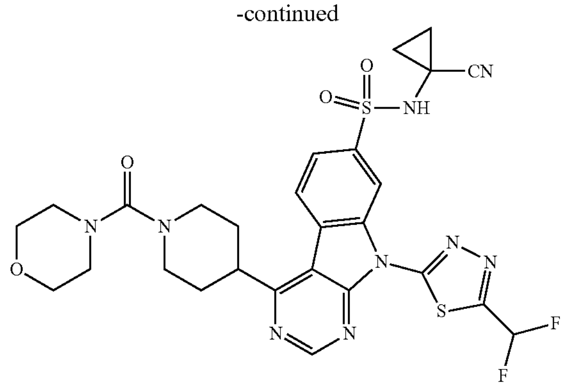
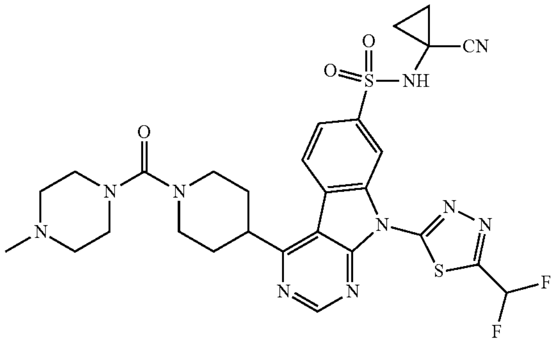
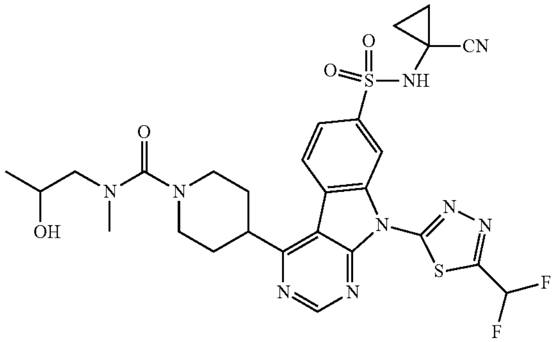
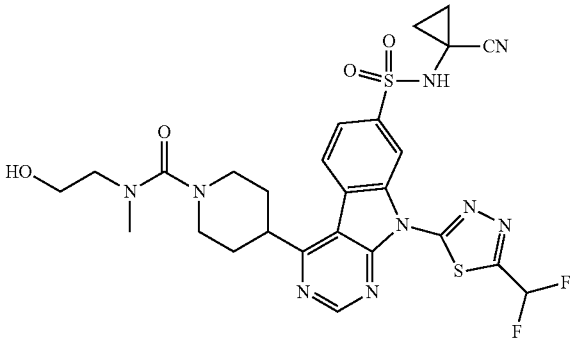
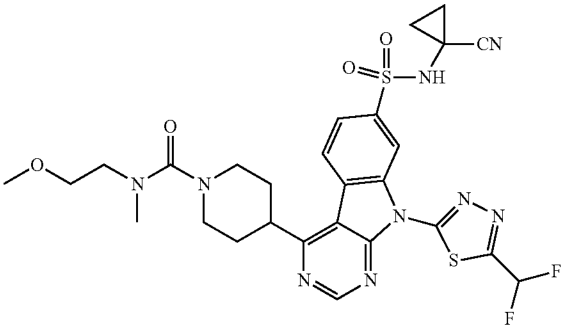
-continued
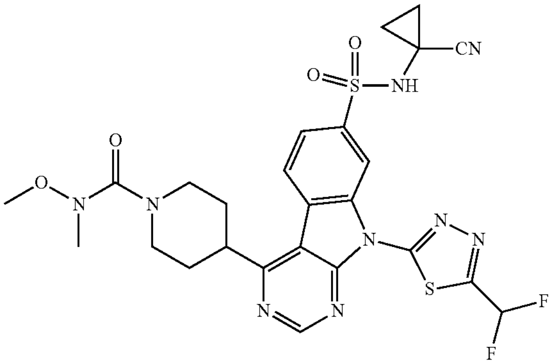
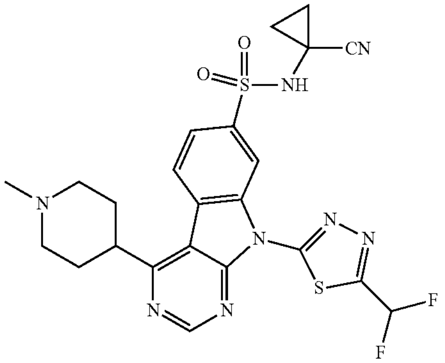
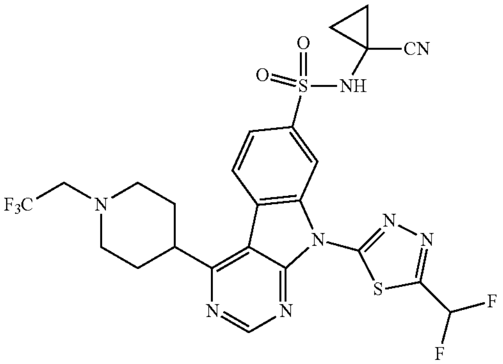
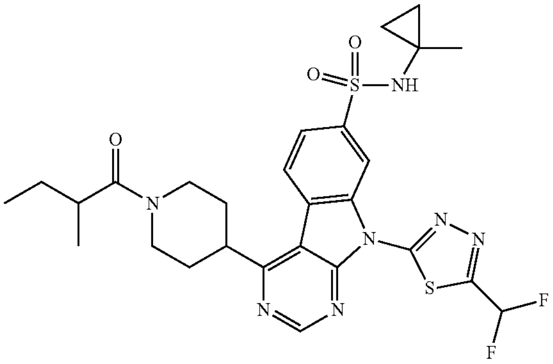

-continued
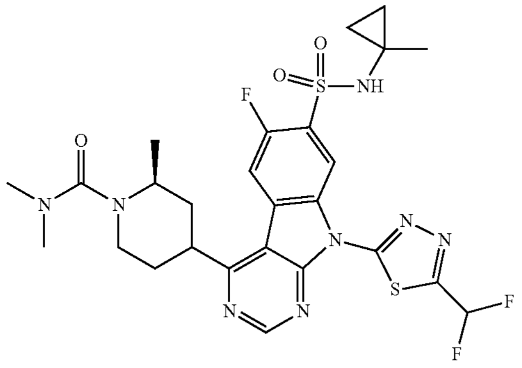
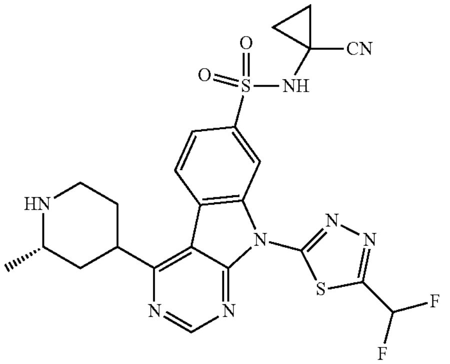
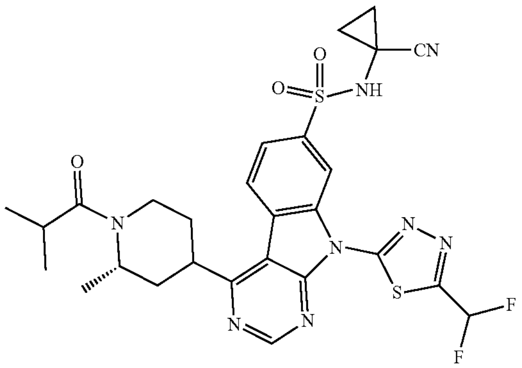
-continued
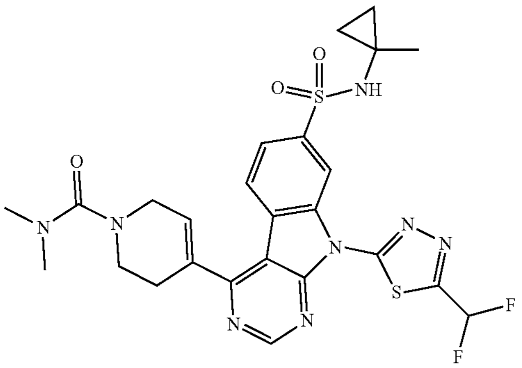
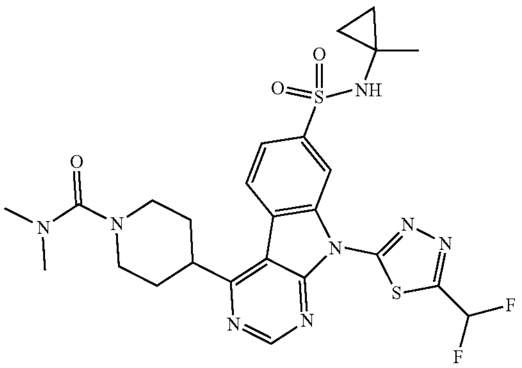
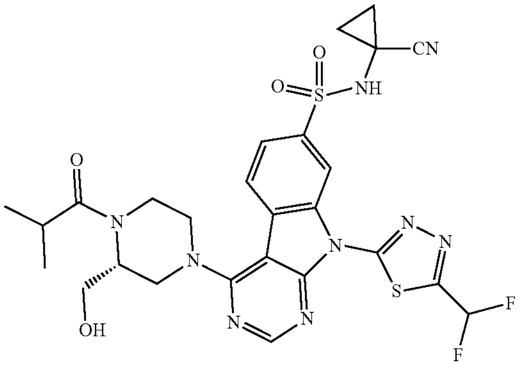
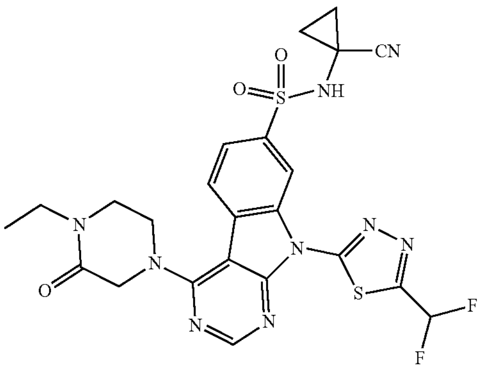

-continued
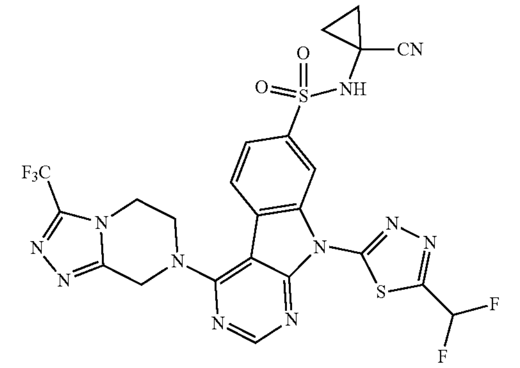
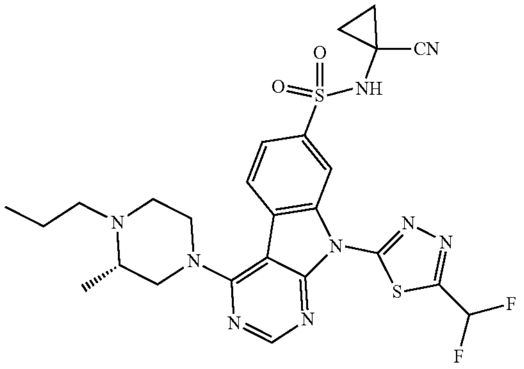
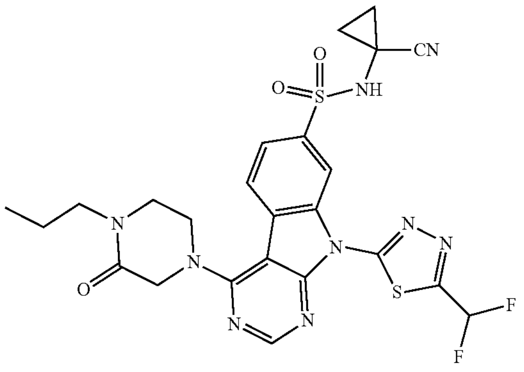
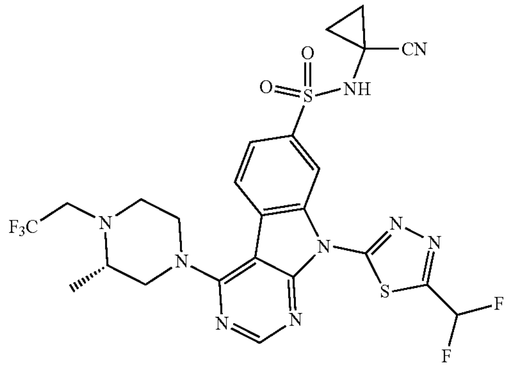
-continued
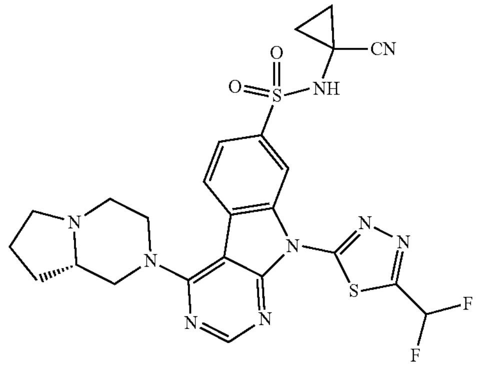
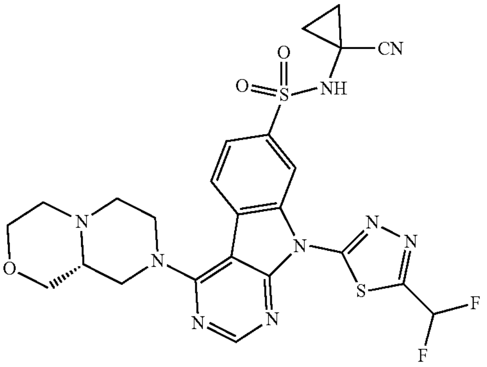
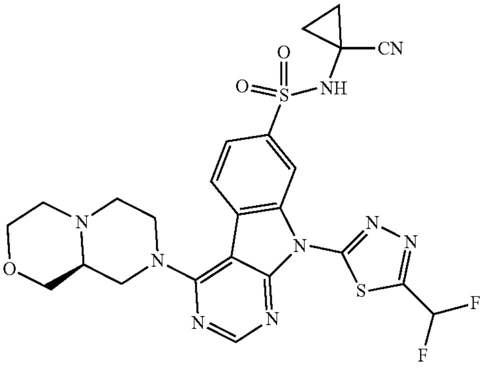
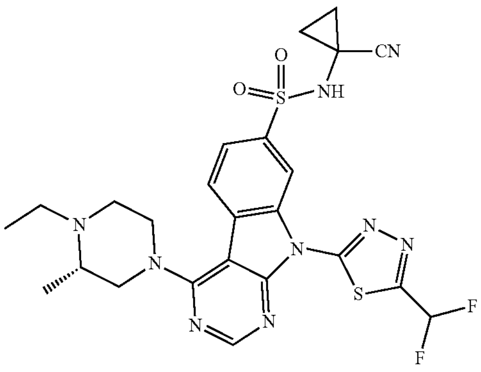

-continued
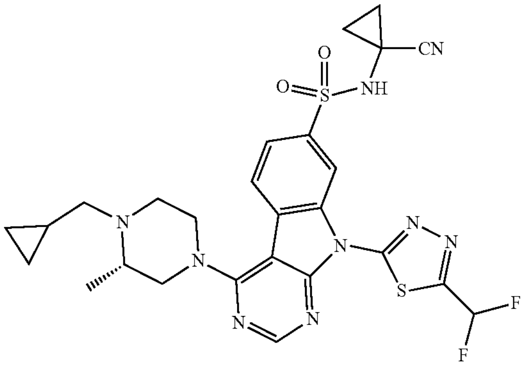
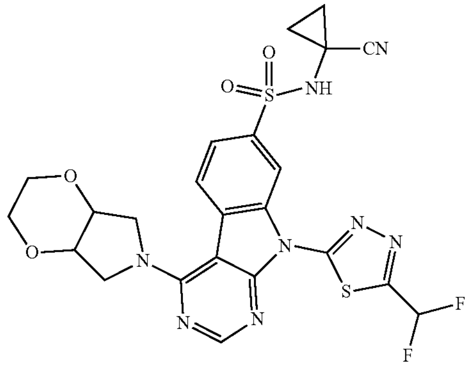
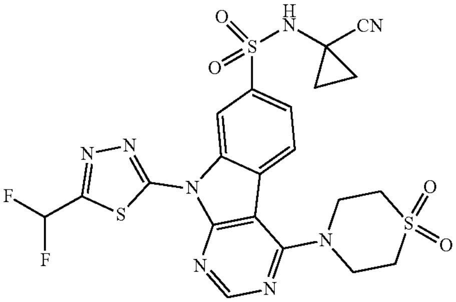
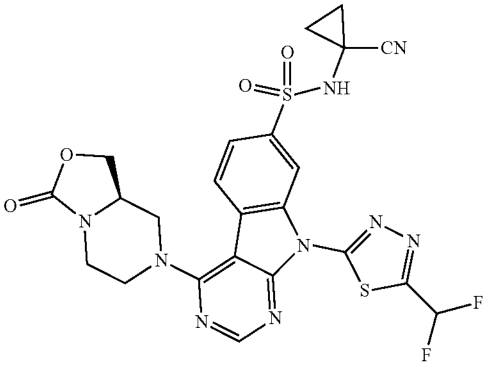
-continued
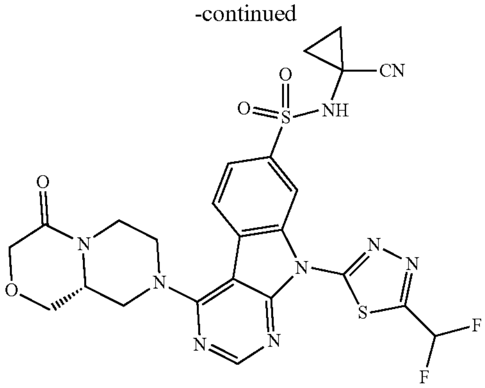
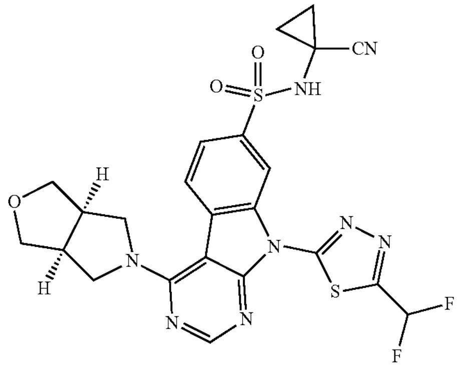
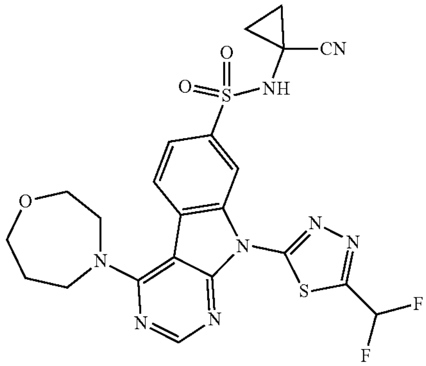
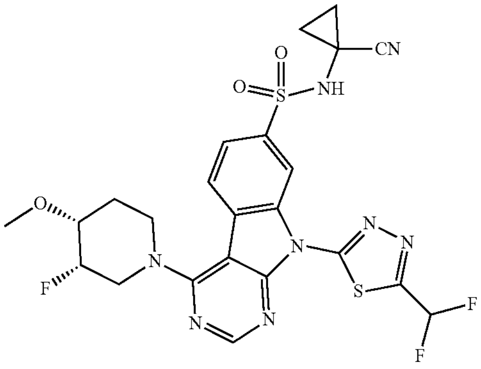

-continued
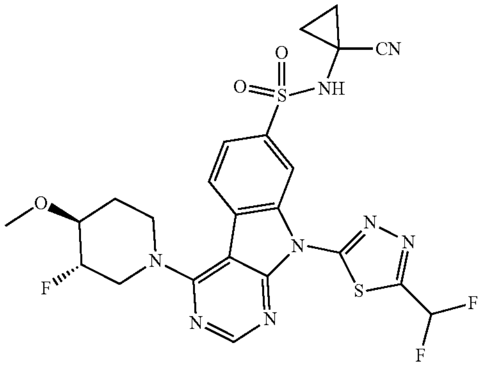
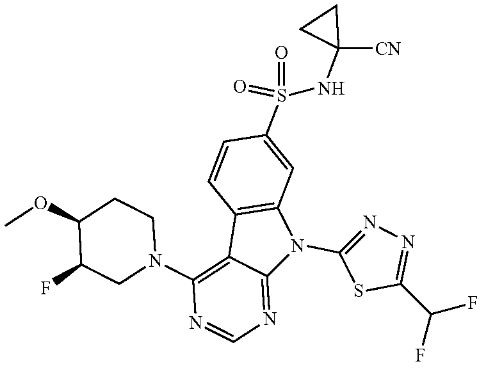
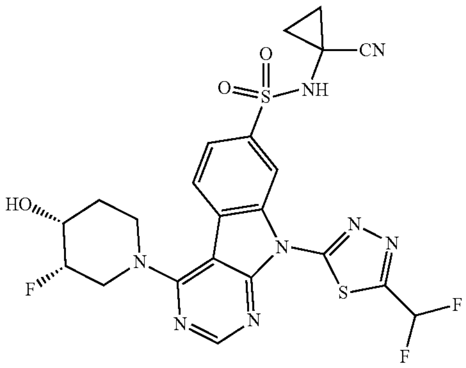
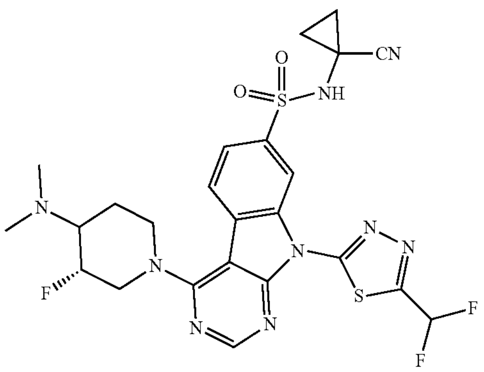
-continued
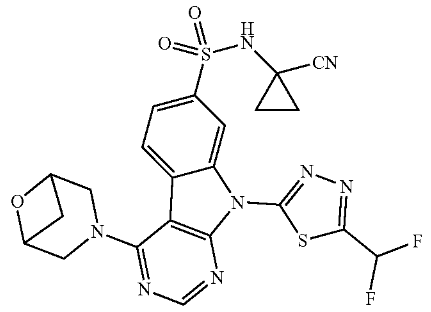
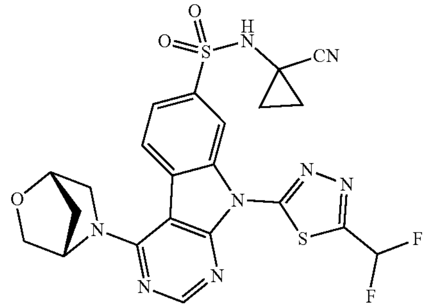
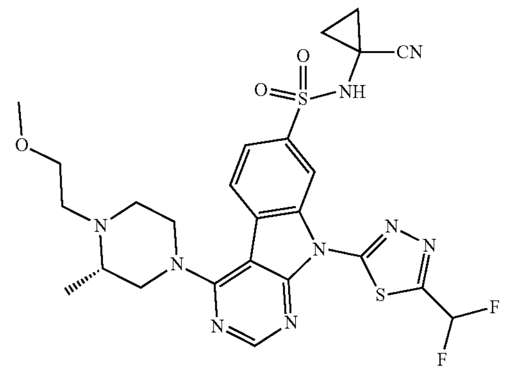
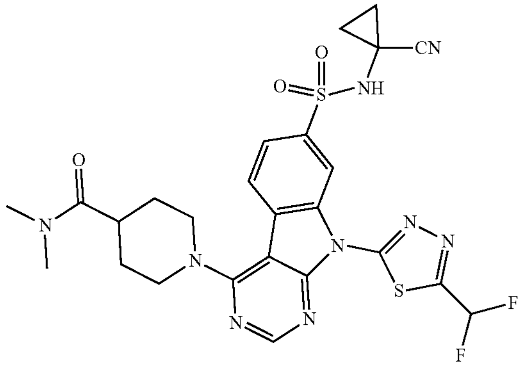
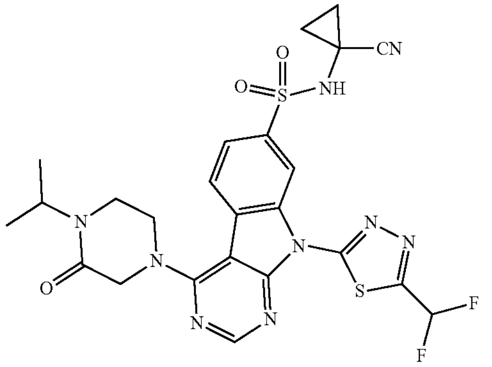

-continued
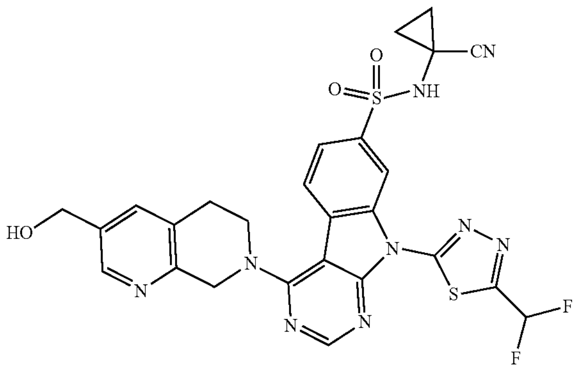
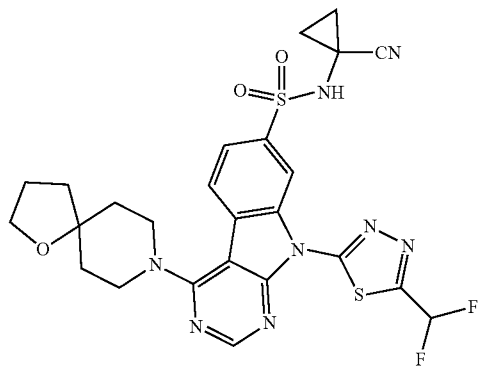
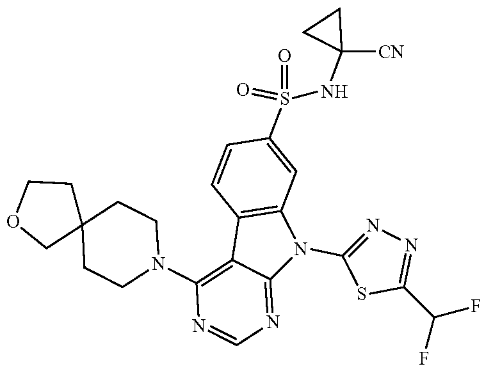
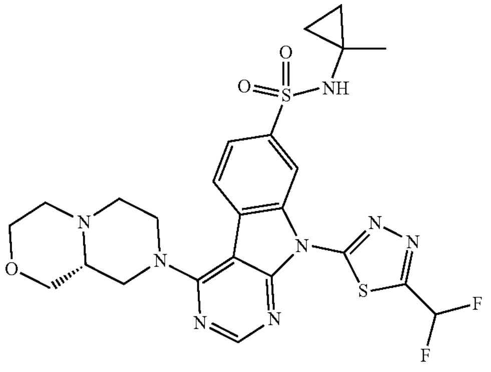
-continued
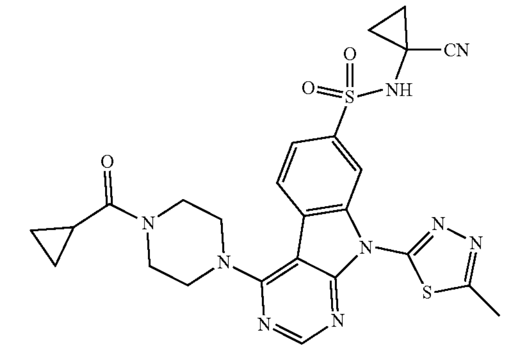
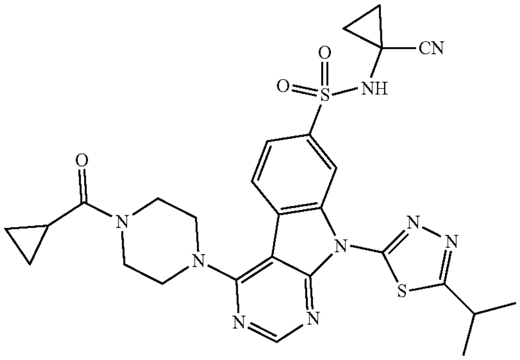
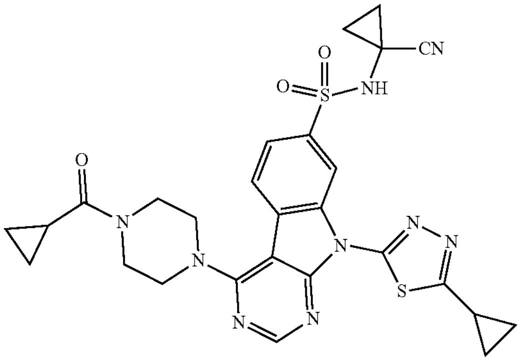
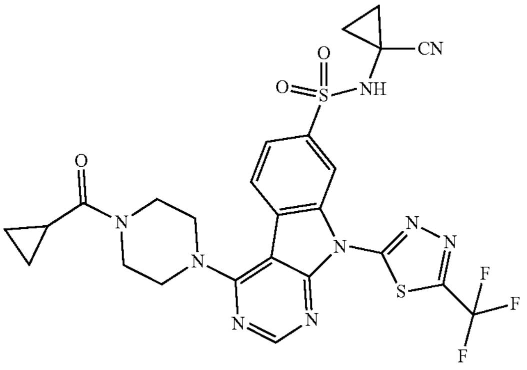

-continued
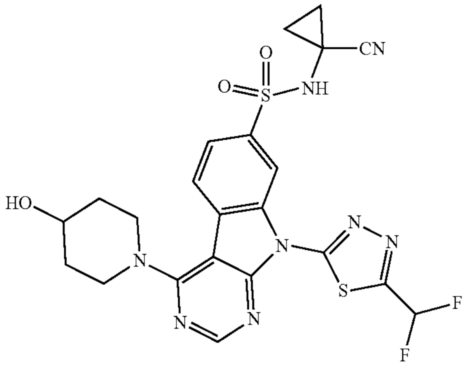
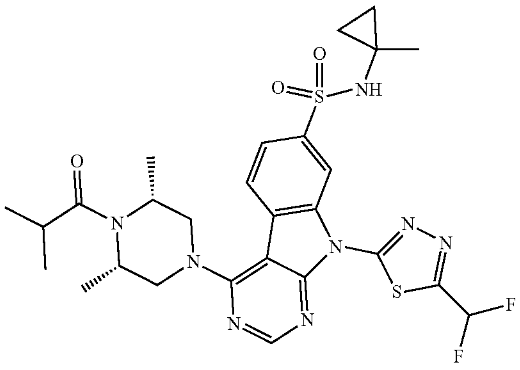
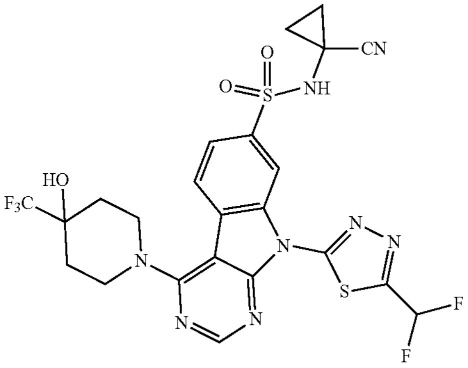
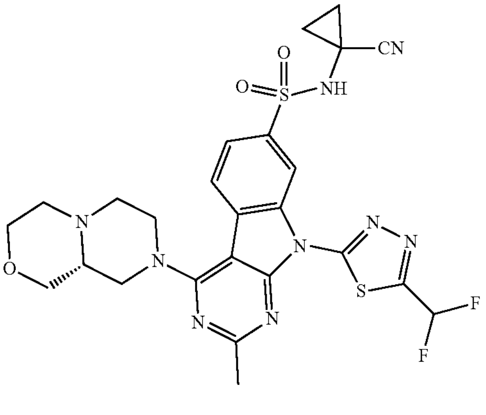
-continued
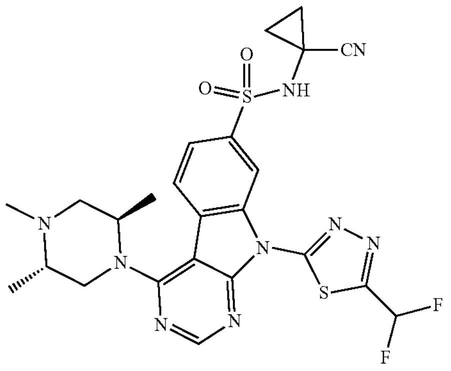
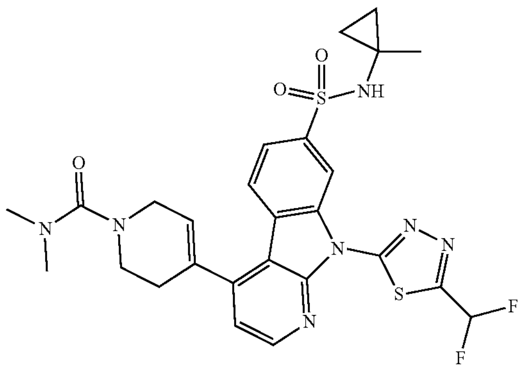
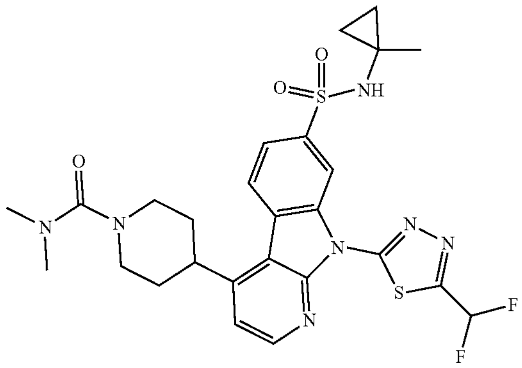
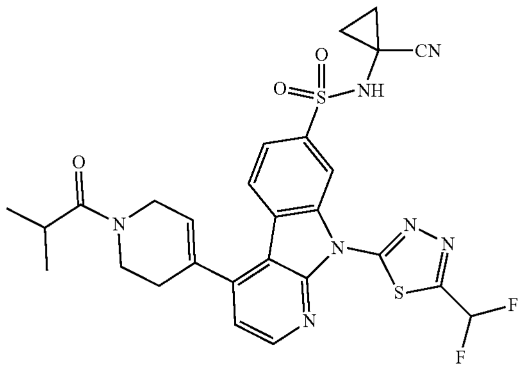

-continued
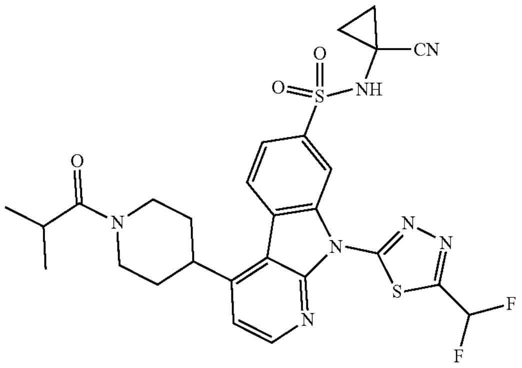
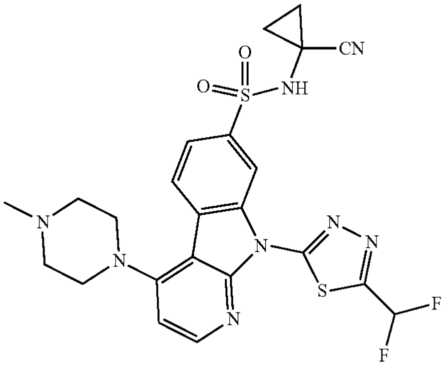
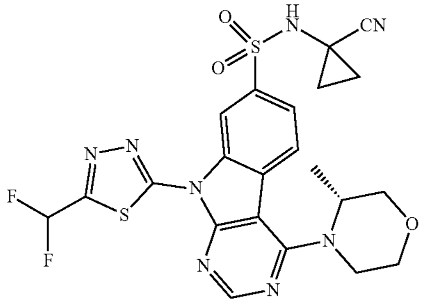
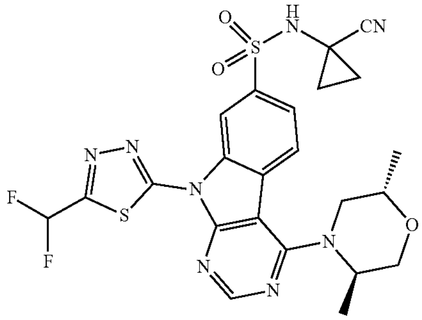
-continued
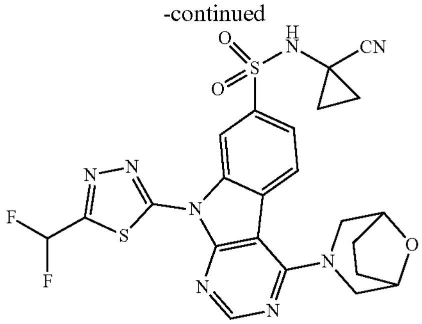
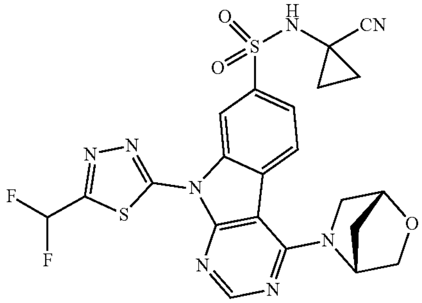
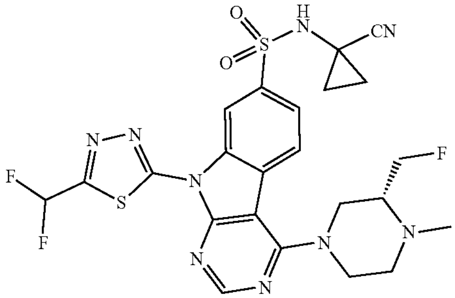
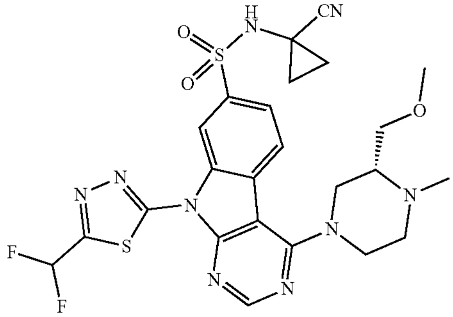
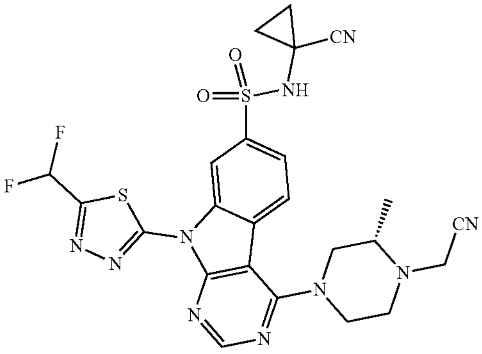

-continued
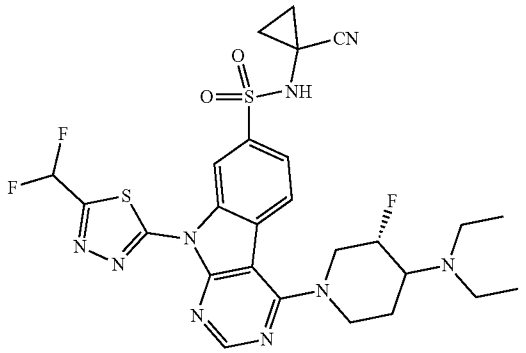
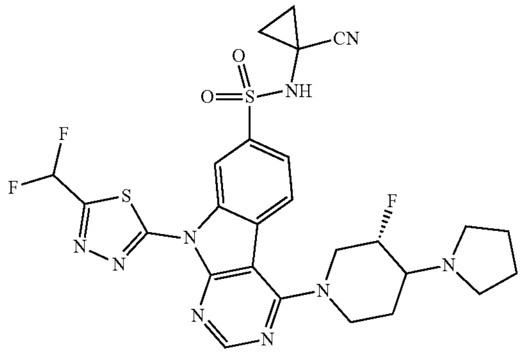
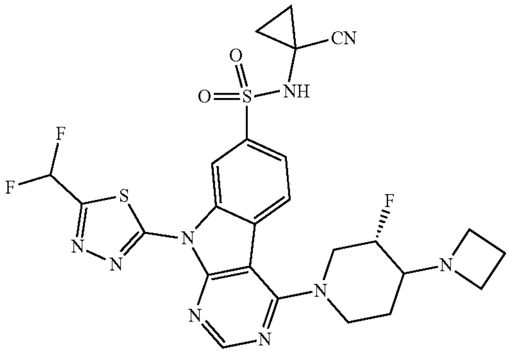
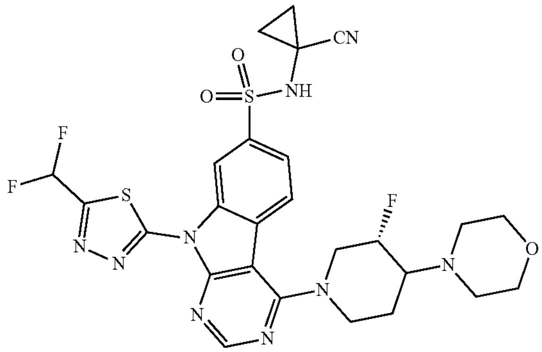
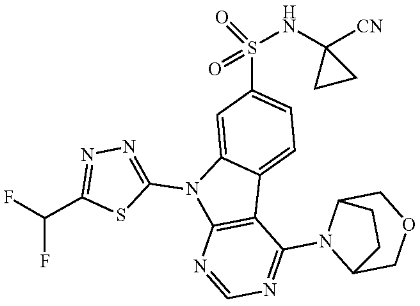
-continued
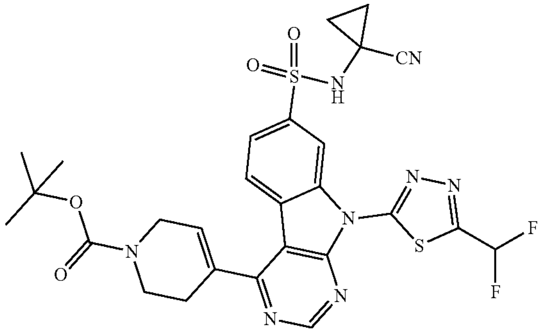
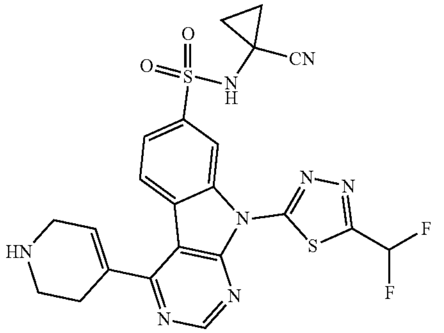
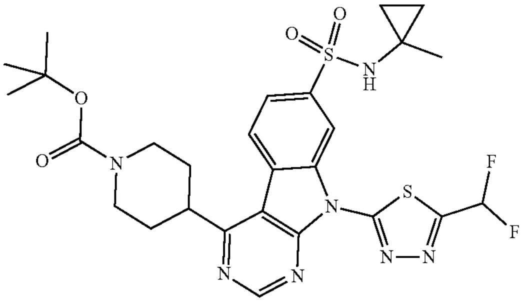
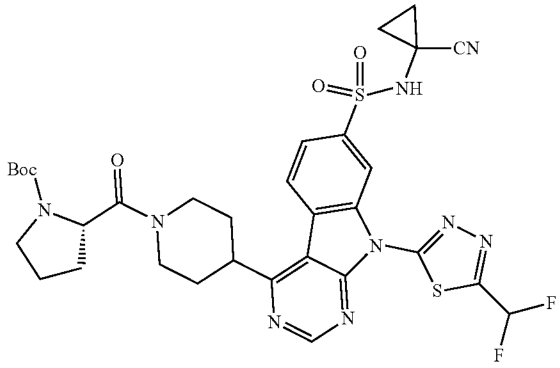
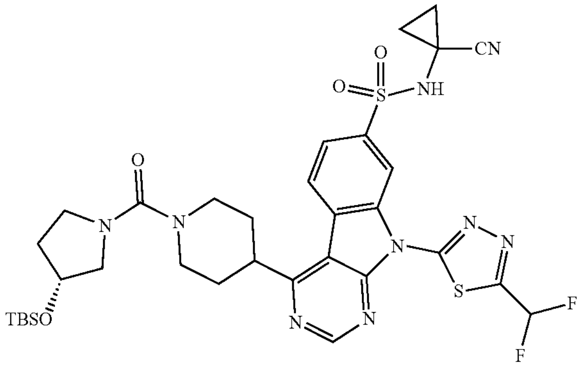

-continued
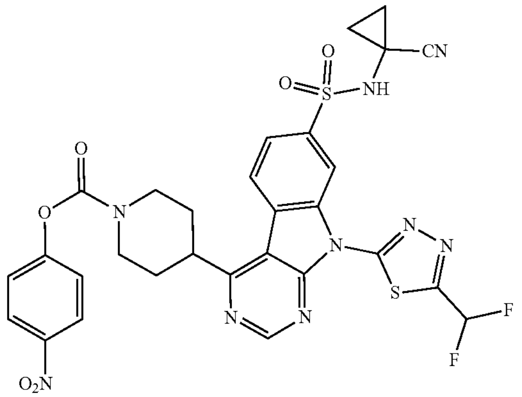
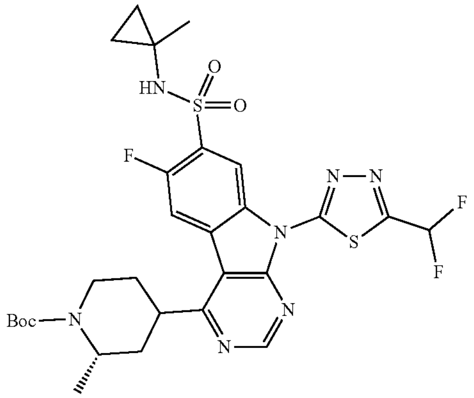
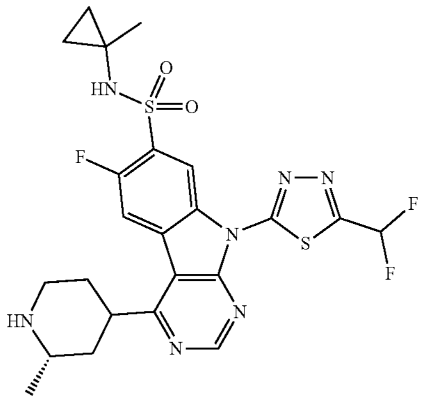
-continued
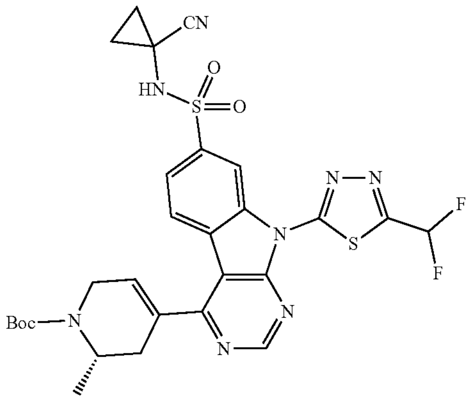
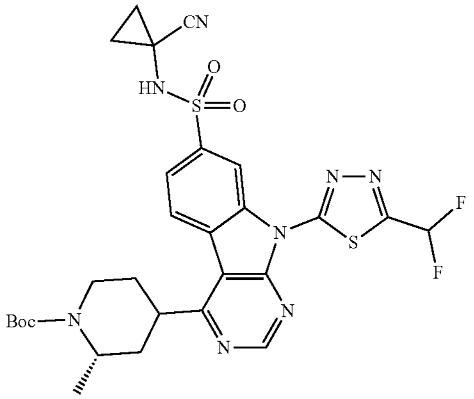
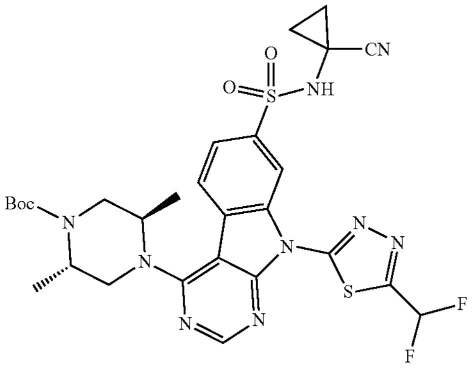
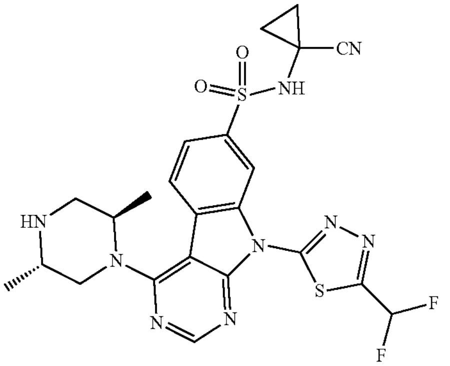

-continued
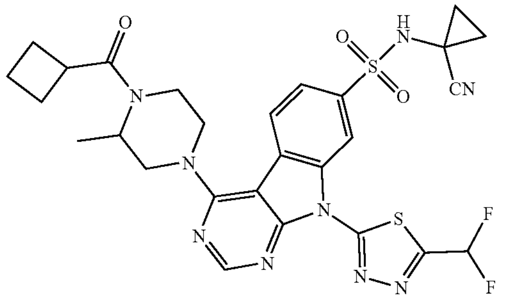
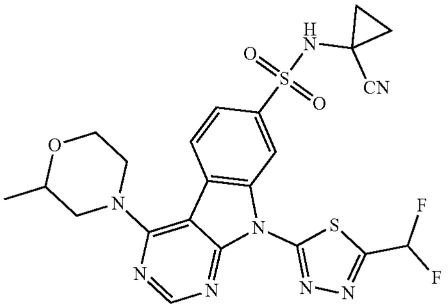
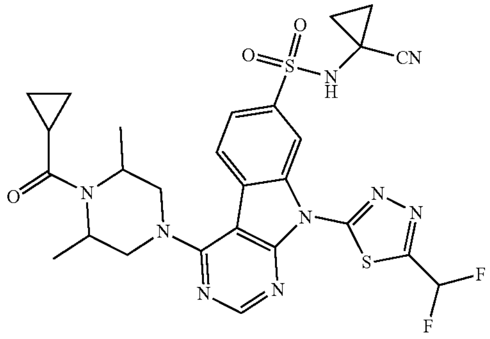
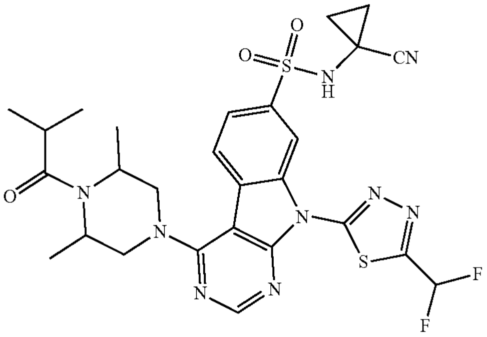
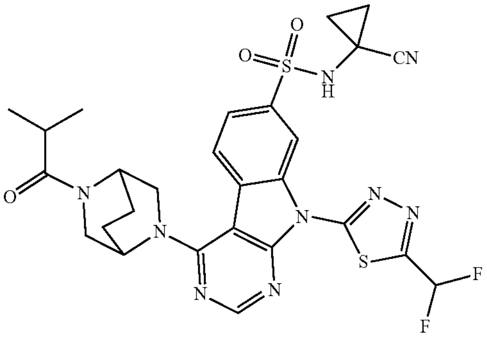
-continued
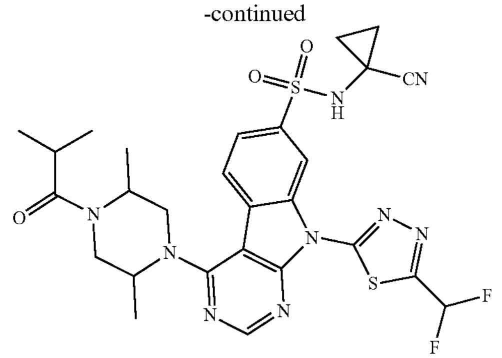
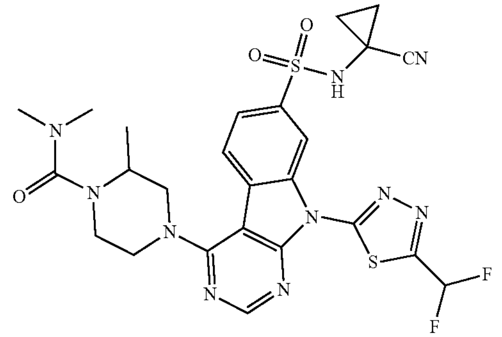
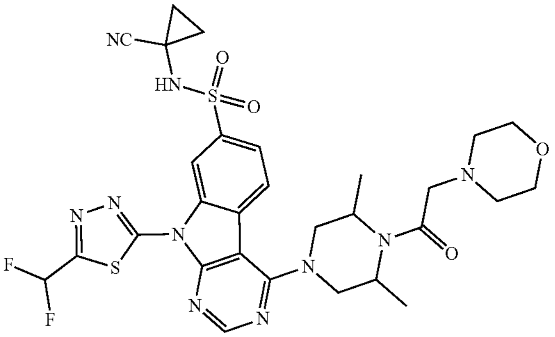
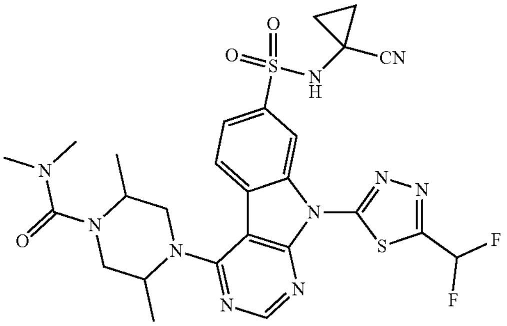
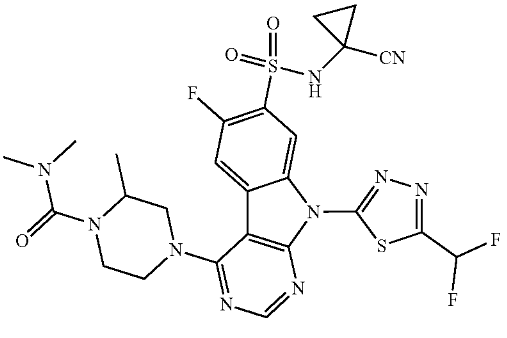

-continued
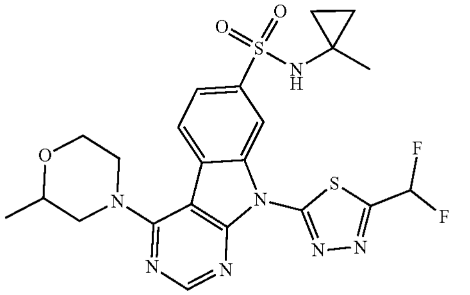
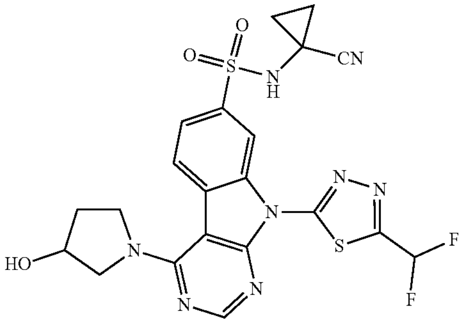
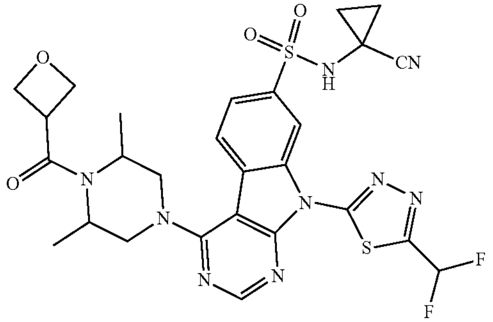
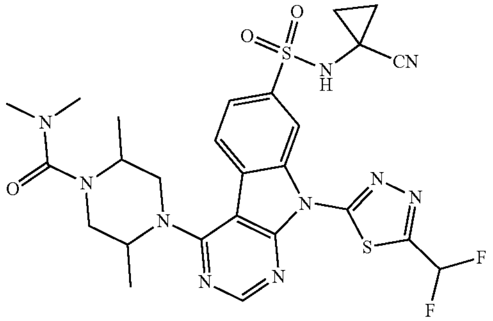
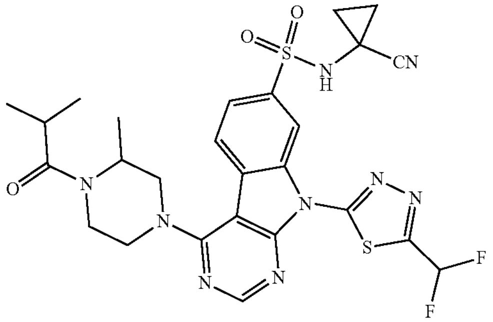
-continued
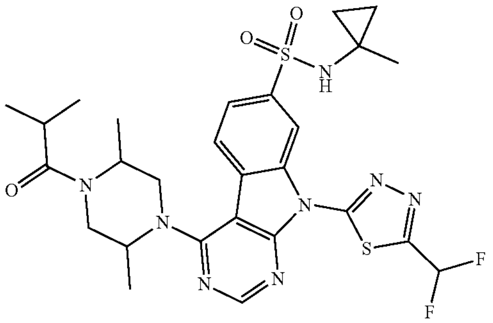
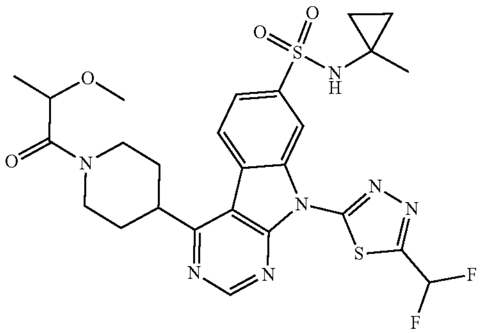
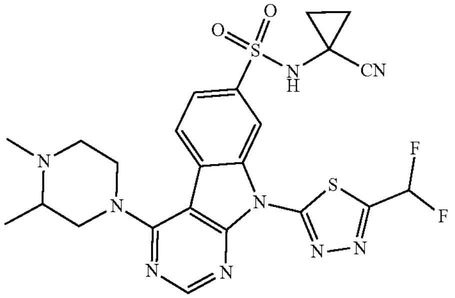
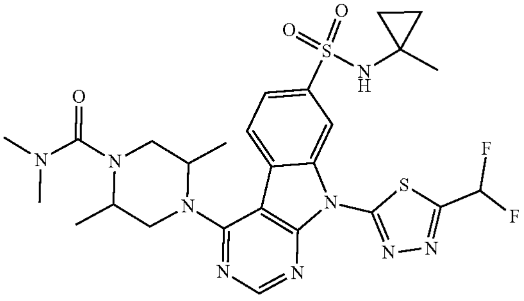
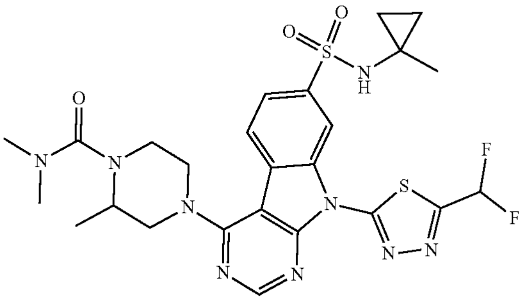

-continued
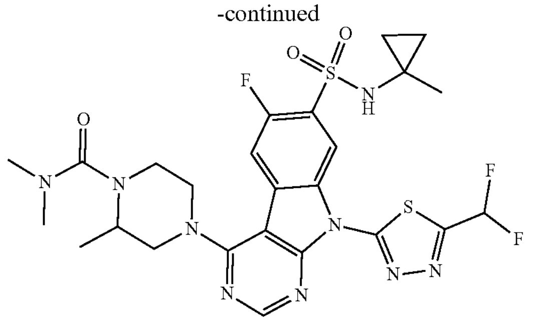
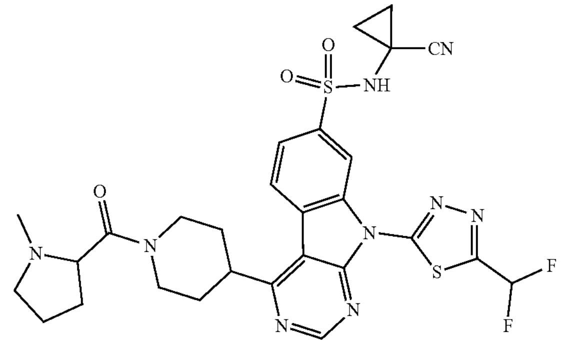
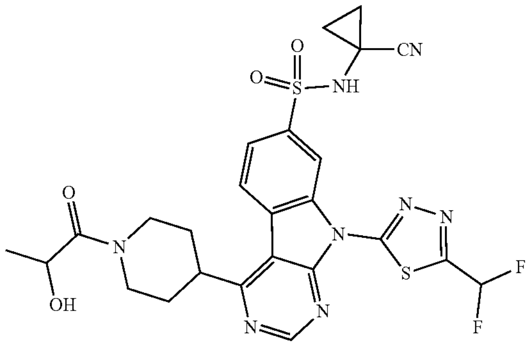
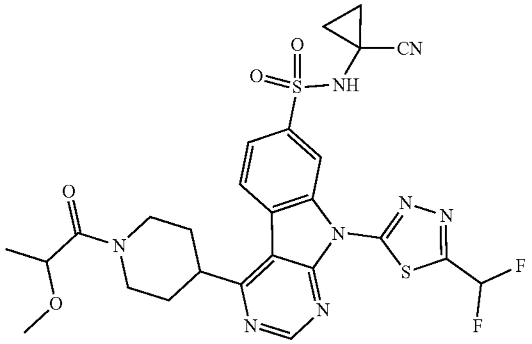
-continued
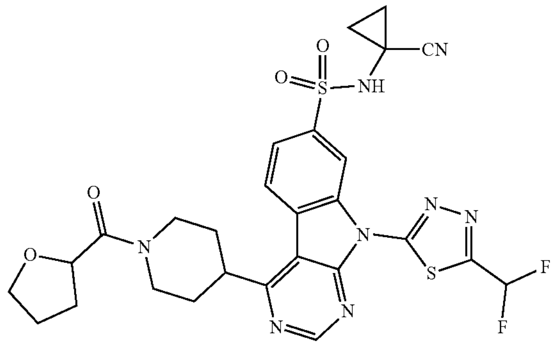
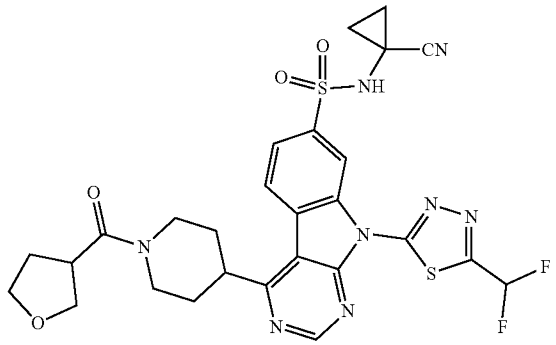
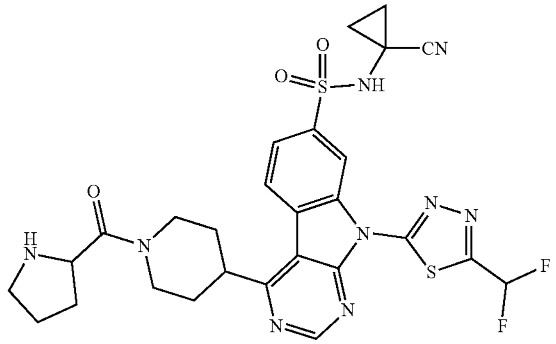
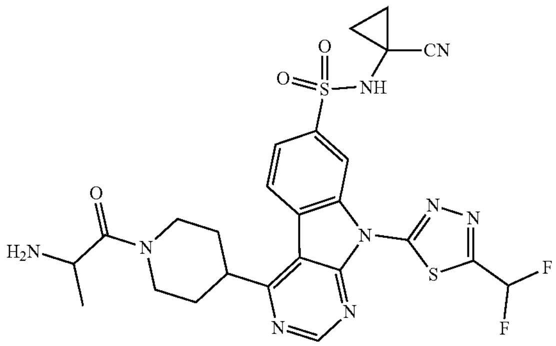

-continued
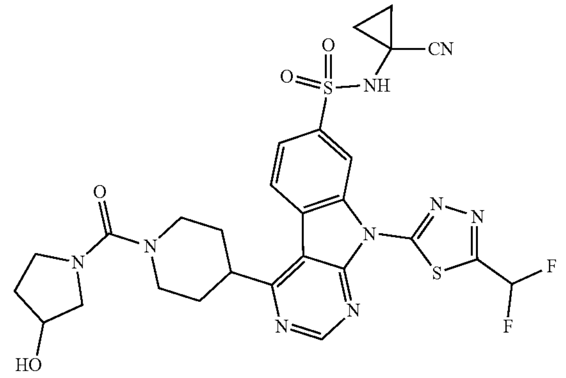
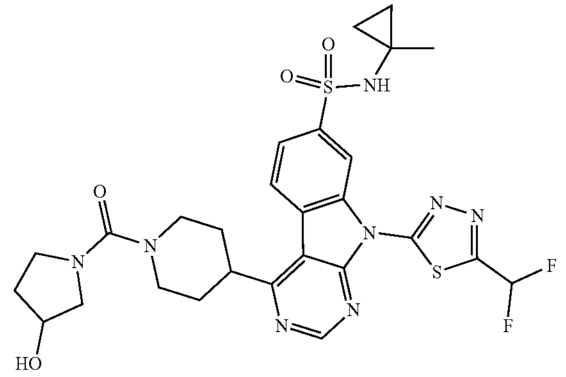
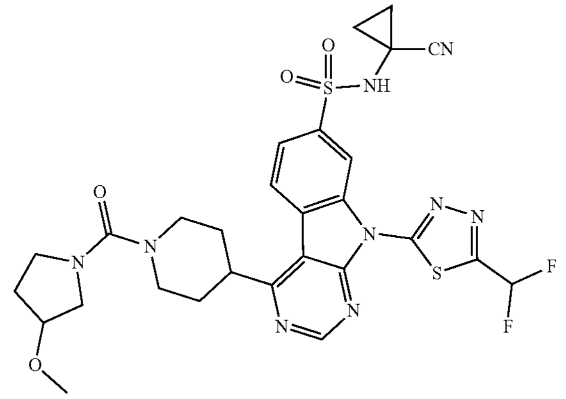
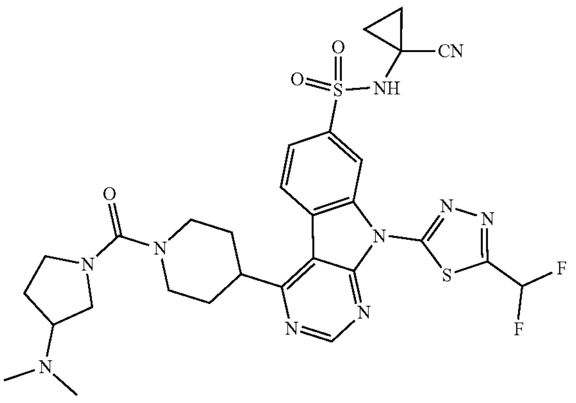
-continued
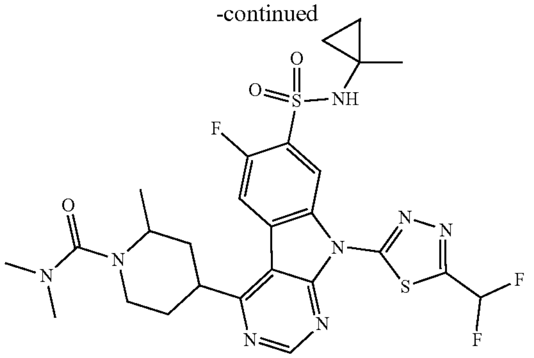
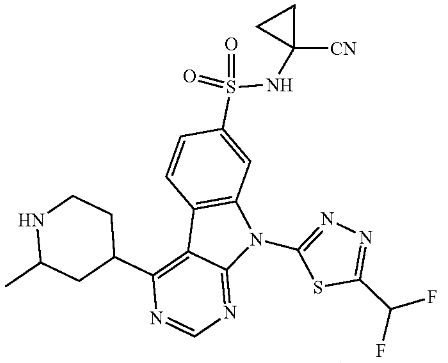
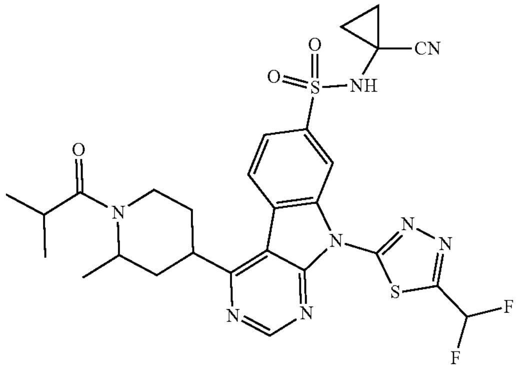
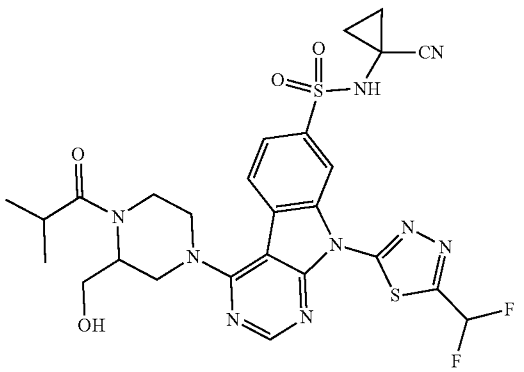

-continued
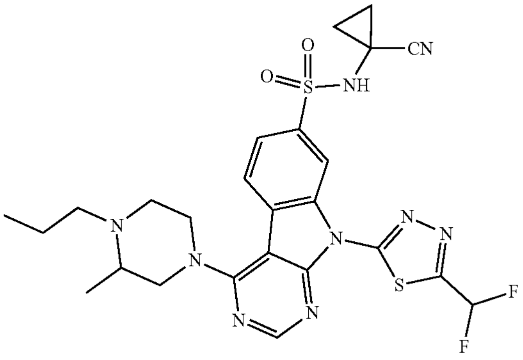
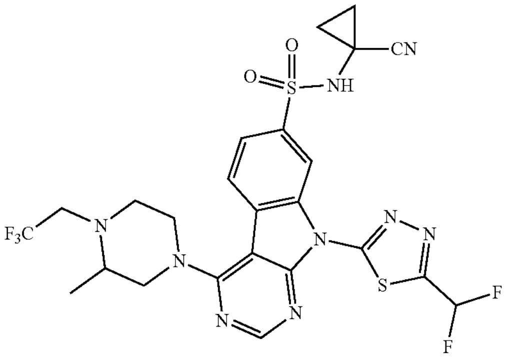
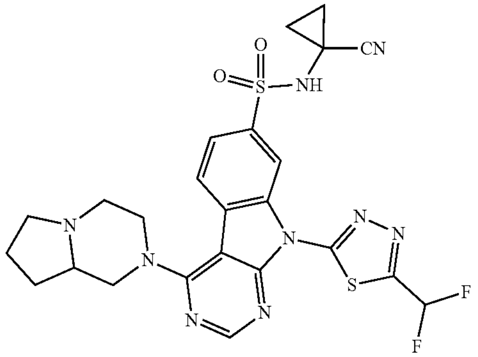
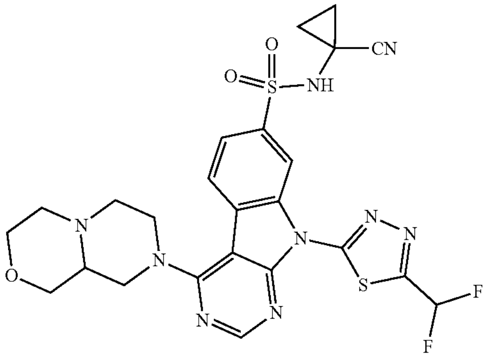
-continued
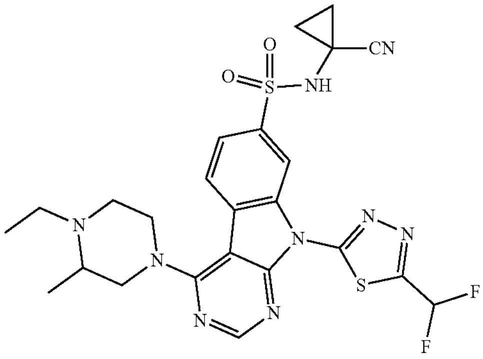
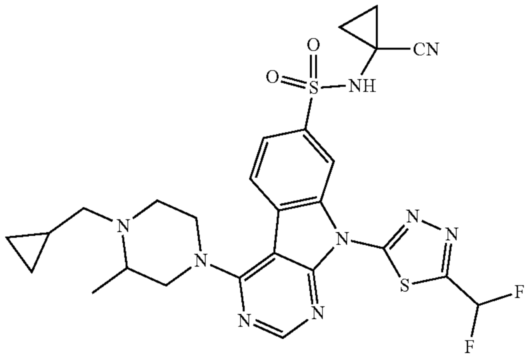
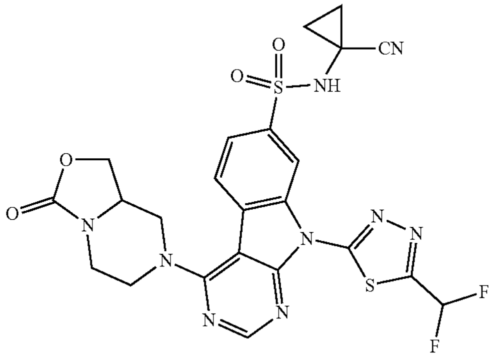
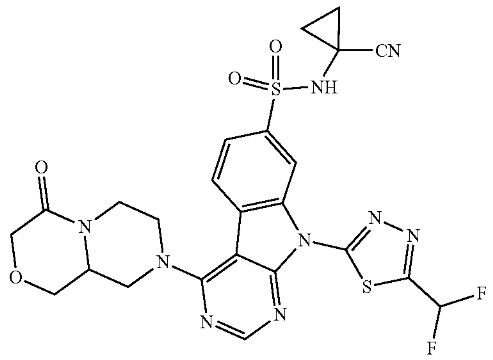

-continued
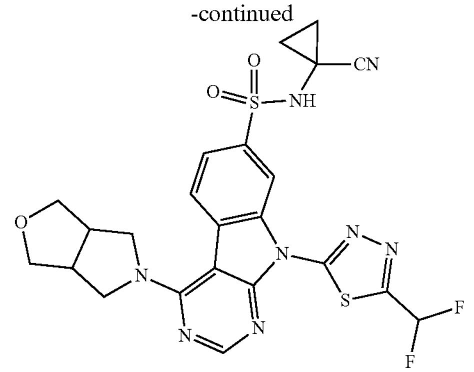
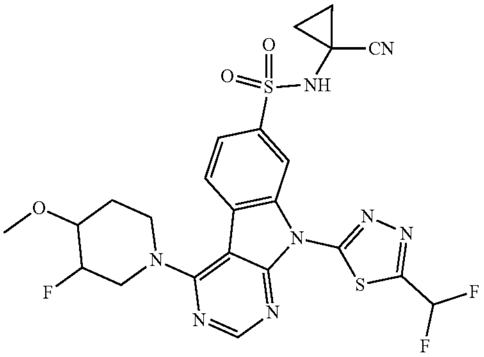
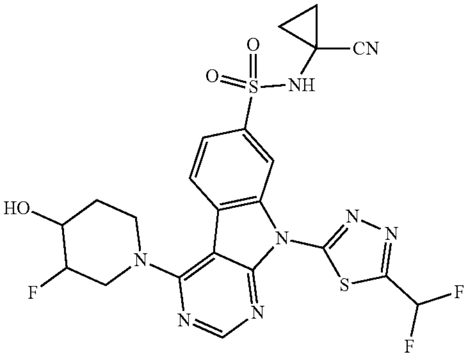
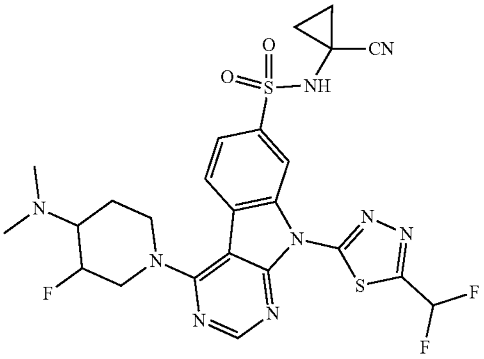
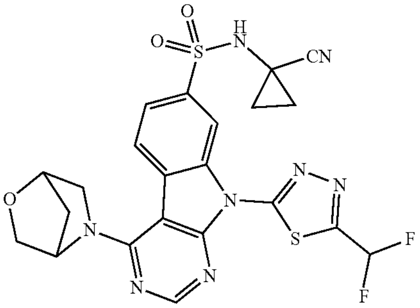
-continued
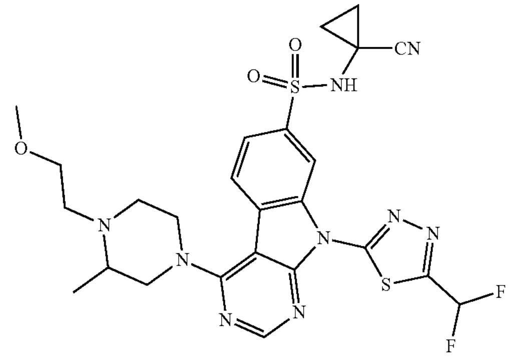
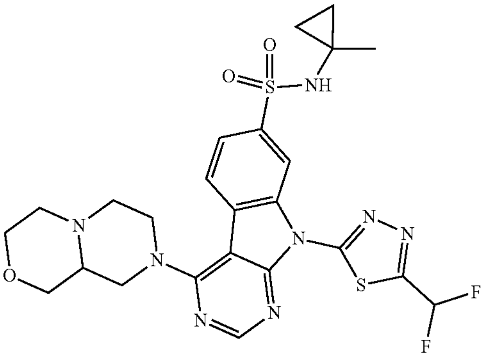
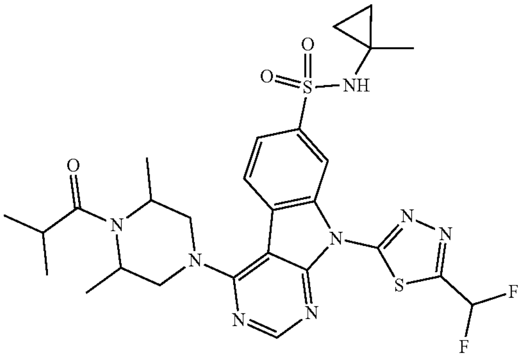
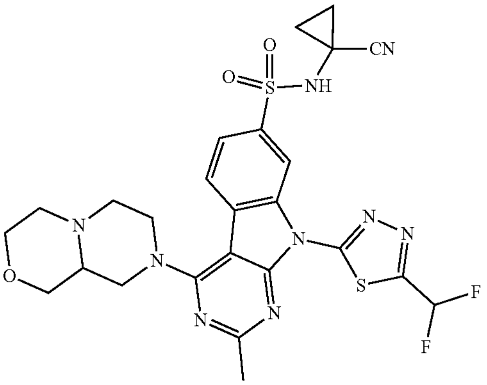

-continued
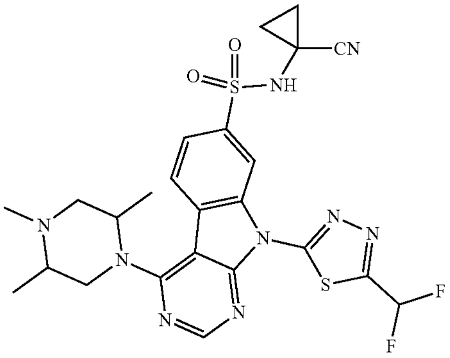
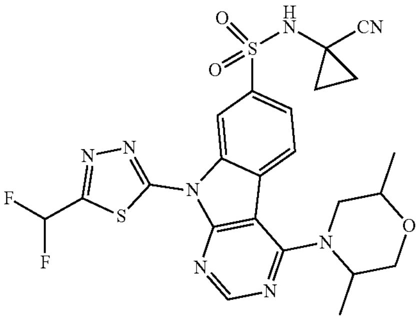
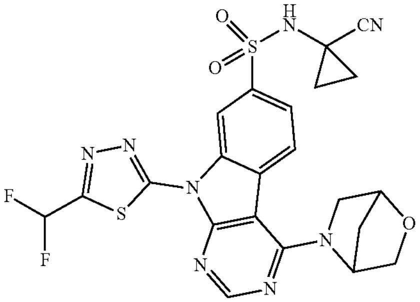
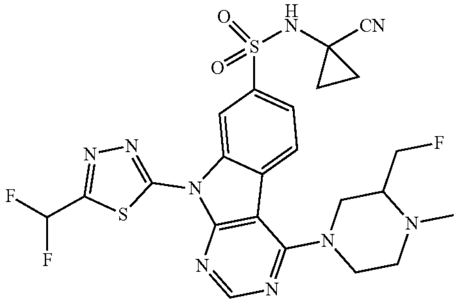
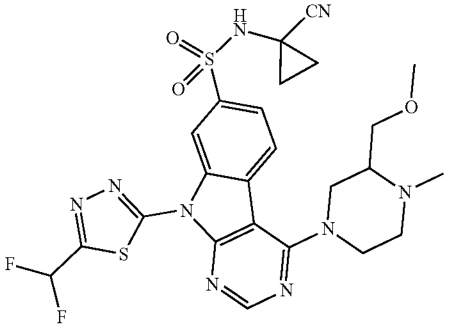
-continued
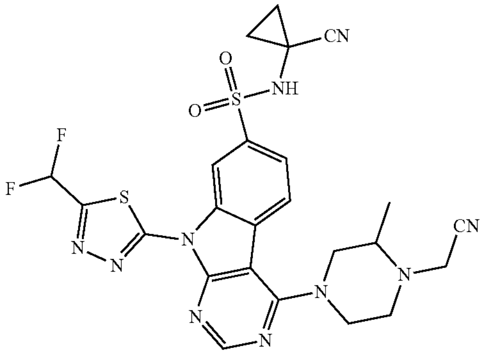
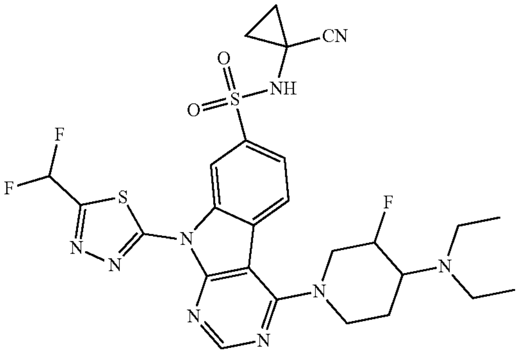
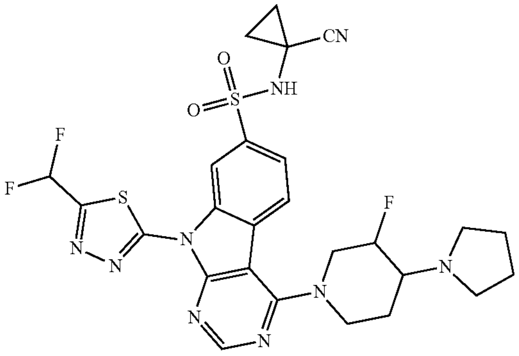
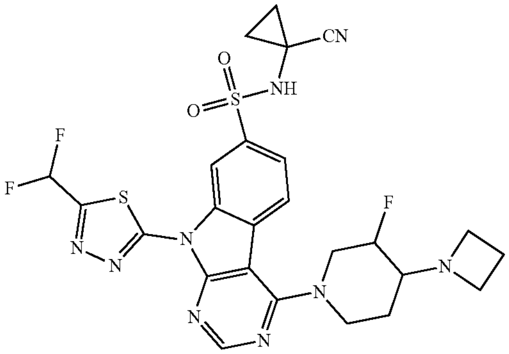

-continued
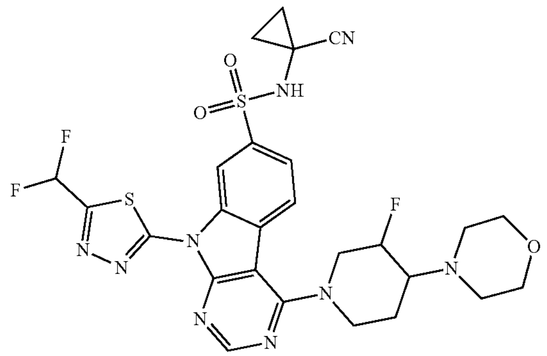
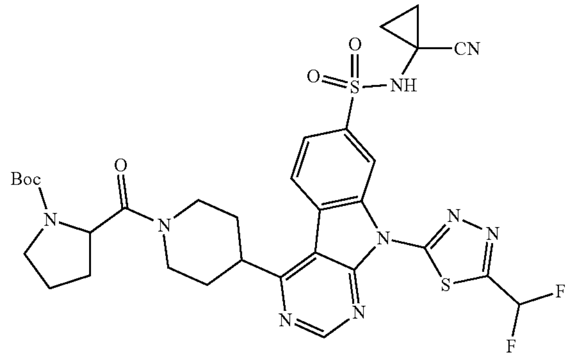
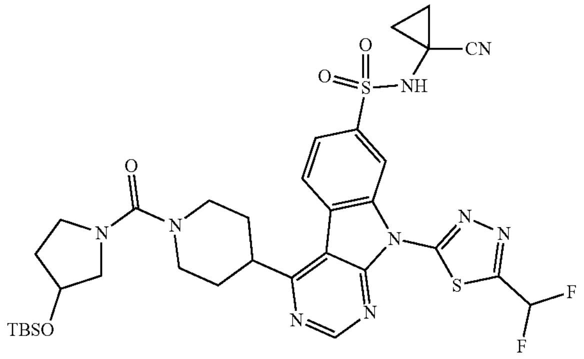
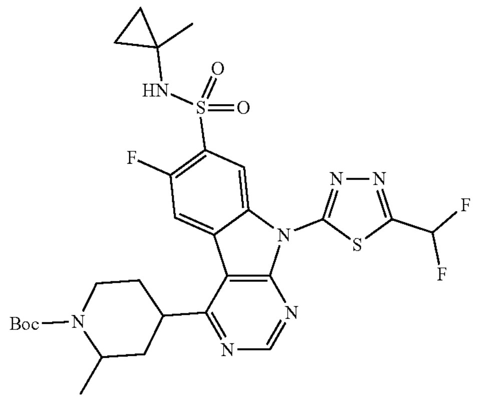
-continued
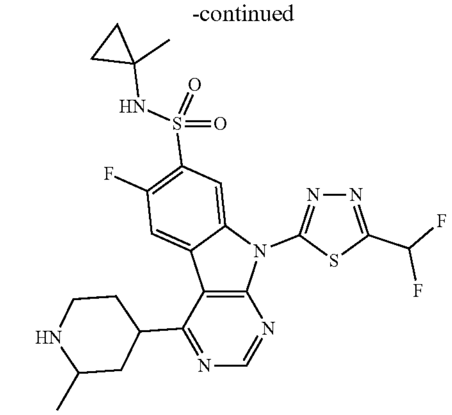
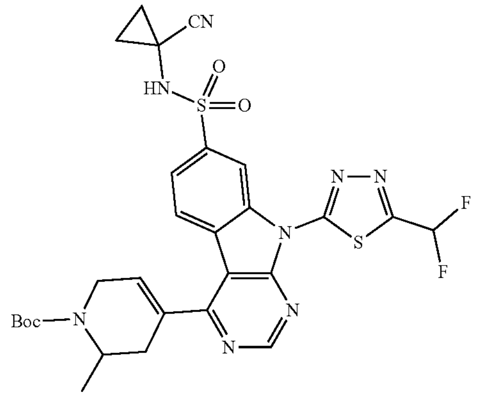
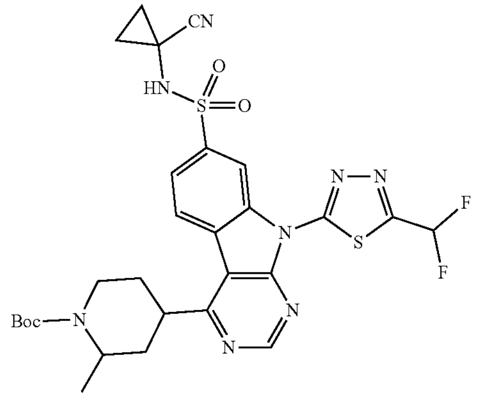

-continued

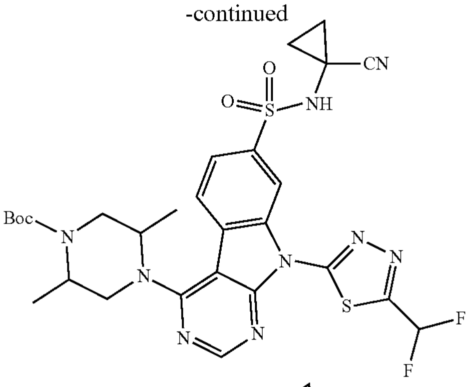

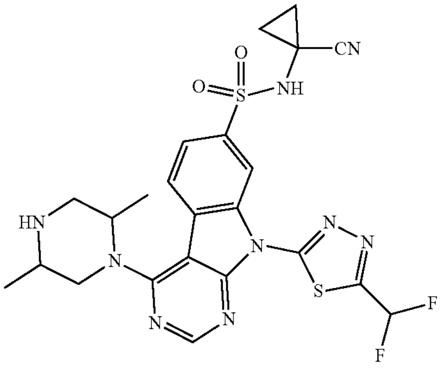

or pharmaceutically acceptable salt, stereoisomer, solvate, N-oxide, tautomer, isotopic variant, or deuterated compound thereof.

23. A pharmaceutical composition comprising the compound of claim 1, or a pharmaceutically acceptable salt, stereoisomer, solvate, N-oxide tautomer, isotopic variant, or deuterated compound thereof; and at least one pharmaceutically acceptable carrier or excipient.

24. A method of inhibiting PARG, comprising administering to a patient in need thereof the compound of claim 1, or a pharmaceutically acceptable salt, stereoisomer, solvate, N-oxide, tautomer, isotopic variant, or deuterated compound thereof.

25. A method of treating cancer, comprising administering to a patient in need thereof a therapeutically effective amount of the compound of claim 1, or a pharmaceutically acceptable salt, stereoisomer, solvate, N-oxide, tautomer, isotopic variant, or deuterated compound thereof.

26. The method of claim 25, wherein the cancer is breast, ovarian, gastric, prostate, pancreatic, uterine, cervical, endometrial, lung, brain, bile duct and hematological cancer.

* * * * *